United States Patent
Abela et al.

(10) Patent No.: US 11,453,655 B2
(45) Date of Patent: *Sep. 27, 2022

(54) MODULATOR OF THE CYSTIC FIBROSIS TRANSMEMBRANE CONDUCTANCE REGULATOR, PHARMACEUTICAL COMPOSITIONS, METHODS OF TREATMENT, AND PROCESS FOR MAKING THE MODULATOR

(71) Applicant: Vertex Pharmaceuticals Incorporated, Boston, MA (US)

(72) Inventors: Alexander Russell Abela, San Diego, CA (US); Timothy Alcacio, San Diego, CA (US); Corey Anderson, San Diego, CA (US); Paul Timothy Angell, Carlsbad, CA (US); Minson Baek, San Diego, CA (US); Jeremy J. Clemens, San Diego, CA (US); Thomas Cleveland, San Marcos, CA (US); Lori Ann Ferris, Wilmington, MA (US); Peter Diederik Jan Grootenhuis, Del Mar, CA (US); Raymond Stanley Gross, Poway, CA (US); Anton V. Gulevich, San Diego, CA (US); Sara Sabina Hadida Ruah, La Jolla, CA (US); Clara Kuang-Ju Hsia, San Diego, CA (US); Robert M. Hughes, San Diego, CA (US); Pramod Virupax Joshi, San Diego, CA (US); Ping Kang, San Diego, CA (US); Ali Keshavarz-Shokri, San Diego, CA (US); Haripada Khatuya, San Diego, CA (US); Paul John Krenitsky, San Diego, CA (US); Jason McCartney, Cardiff by the Sea, CA (US); Mark Thomas Miller, San Diego, CA (US); Prasuna Paraselli, San Diego, CA (US); Fabrice Jean Denis Pierre, La Jolla, CA (US); Yi Shi, Natick, MA (US); Muna Shrestha, Belmont, MA (US); David Andrew Siesel, San Diego, CA (US); Kathy Stavropoulos, Quincy, MA (US); Andreas P. Termin, Encinitas, CA (US); Fredrick F. Van Goor, San Diego, CA (US); Johnny Uy, San Diego, CA (US); Timothy John Young, San Diego, CA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 5 days.

This patent is subject to a terminal disclaimer.

(21) Appl. No.: 16/994,875

(22) Filed: Aug. 17, 2020

(65) Prior Publication Data
US 2021/0047295 A1 Feb. 18, 2021

Related U.S. Application Data

(62) Division of application No. 15/836,627, filed on Dec. 8, 2017, now Pat. No. 10,793,547.
(Continued)

(51) Int. Cl.
*C07D 401/04* (2006.01)
*C07D 401/14* (2006.01)
(Continued)

(52) U.S. Cl.
CPC ............ *C07D 401/14* (2013.01); *A61P 11/00* (2018.01); *C07D 231/20* (2013.01);
(Continued)

(58) Field of Classification Search
CPC .................................................. C07D 401/14
(Continued)

(56) References Cited

U.S. PATENT DOCUMENTS 1,117,936 A * 11/1914 West .................. D04B 9/46
66/48
5,410,061 A 4/1995 Gilmore et al.
(Continued)

FOREIGN PATENT DOCUMENTS

AU 2013231151 A1 10/2013
AU 2013270464 A1 1/2014
(Continued)

OTHER PUBLICATIONS

"A CFTR corrector (lumacaftor) and a CFTR potentiator (ivacaftor) for treatment of patients with cystic fibrosis who have a phe508del CFTR mutation: a phase 2 randomised controlled trial", Boyle, M., The Lancet Respiratory Medicine (Jul. 1, 2014) Retrieved from the Internet: https://www-clinicalkeycom-ez03.infotrieve.com/#!/content/playContent/1-s2.0S2213260014701328?returnurl=null&referrer=null.
(Continued)

*Primary Examiner* — Nizal S Chandrakumar
(74) *Attorney, Agent, or Firm* — Finnegan, Henderson, Farabow, Garrett & Dunner, LLP

(57) ABSTRACT

Compounds of Formula (I):

(Continued)

pharmaceutically acceptable salts thereof, deuterated derivatives of any of the foregoing, and metabolites of any of the foregoing are disclosed. Pharmaceutical compositions comprising the same, methods of treating cystic fibrosis using the same, and methods for making the same are also disclosed. Also disclosed are solid state forms of Compound 1 and salts and solvates thereof.

8 Claims, 30 Drawing Sheets

Related U.S. Application Data

(60) Provisional application No. 62/432,537, filed on Dec. 9, 2016.

(51) Int. Cl.
  *C07D 471/14* (2006.01)
  *A61P 11/00* (2006.01)
  *C07D 498/14* (2006.01)
  *C07D 231/20* (2006.01)

(52) U.S. Cl.
  CPC ......... *C07D 401/04* (2013.01); *C07D 471/14* (2013.01); *C07D 498/14* (2013.01); *C07B 2200/13* (2013.01)

(58) Field of Classification Search
  USPC ....................................................... 514/267
  See application file for complete search history.

(56) References Cited

U.S. PATENT DOCUMENTS

| | | | |
|---|---|---|---|
| 6,441,004 B1 | 8/2002 | Faull et al. | |
| 6,787,651 B2 | 9/2004 | Stolle et al. | |
| 6,949,572 B2 | 9/2005 | Bertinato et al. | |
| 6,979,692 B2 | 12/2005 | Bertinato et al. | |
| 7,368,573 B2 | 5/2008 | Bertinato et al. | |
| 8,058,299 B2 | 11/2011 | Bolin et al. | |
| 9,663,508 B2 | 5/2017 | Bregman et al. | |
| 9,782,408 B2 | 10/2017 | Miller et al. | |
| 9,981,910 B2 | 5/2018 | Altenbach et al. | |
| 10,118,916 B2 | 11/2018 | Altenbach et al. | |
| 10,131,670 B2 | 11/2018 | Strohbach et al. | |
| 10,138,227 B2 | 11/2018 | Altenbach et al. | |
| 10,208,053 B2 | 2/2019 | Strohbach et al. | |
| 10,258,624 B2 | 4/2019 | Miller et al. | |
| 10,570,115 B2 | 2/2020 | Alcacio et al. | |
| 10,654,829 B2 | 5/2020 | Dhamankar et al. | |
| 10,793,547 B2 * | 10/2020 | Abela ................. | C07D 401/04 |
| 11,155,533 B2 | 10/2021 | Dhamankar et al. | |
| 11,186,566 B2 | 11/2021 | Alcacio et al. | |
| 11,253,509 B2 | 2/2022 | Chen et al. | |
| 2002/0055631 A1 | 5/2002 | Augeri et al. | |
| 2002/0086887 A1 | 7/2002 | Augeri et al. | |
| 2004/0006237 A1 | 1/2004 | Dolitzky et al. | |
| 2005/0171185 A1 | 8/2005 | Yamasaki et al. | |
| 2005/0197376 A1 | 9/2005 | Kayakiri et al. | |
| 2010/0160322 A1 | 6/2010 | Bruncko et al. | |
| 2010/0227888 A1 | 9/2010 | Hadida Ruah et al. | |
| 2011/0165118 A1 | 7/2011 | Chan et al. | |
| 2013/0072483 A1 | 3/2013 | Wenge et al. | |
| 2013/0267493 A1 | 10/2013 | Bhattacharya et al. | |
| 2013/0317000 A1 | 11/2013 | Chowdhury et al. | |
| 2013/0317001 A1 | 11/2013 | Andrez et al. | |
| 2014/0080825 A1 | 3/2014 | Hadida-Ruah et al. | |
| 2014/0296200 A1 | 10/2014 | Brown et al. | |
| 2015/0320736 A1 | 11/2015 | Phenix et al. | |
| 2015/0322002 A1 | 11/2015 | Dehnhardt et al. | |
| 2018/0099932 A1 | 4/2018 | Altenbach et al. | |
| 2018/0141954 A1 | 5/2018 | Strohbach et al. | |
| 2018/0170938 A1 | 6/2018 | Strohbach et al. | |
| 2018/0244611 A1 | 8/2018 | Altenbach et al. | |
| 2018/0244640 A1 | 8/2018 | Altenbach et al. | |
| 2019/0055220 A1 | 2/2019 | Bear et al. | |
| 2019/0077784 A1 | 3/2019 | Altenbach et al. | |
| 2019/0153000 A1 | 5/2019 | Munoz et al. | |
| 2019/0240197 A1 | 8/2019 | Chu et al. | |
| 2019/0269683 A1 | 9/2019 | Miller et al. | |
| 2020/0138798 A1 | 5/2020 | Chen et al. | |
| 2020/0171015 A1 | 6/2020 | Haseltine et al. | |
| 2020/0283405 A1 | 9/2020 | Alcacio et al. | |
| 2020/0369608 A1 | 11/2020 | Angell et al. | |
| 2020/0392109 A1 | 12/2020 | Dhamankar et al. | |
| 2021/0032272 A1 | 2/2021 | Abela et al. | |
| 2021/0047295 A1 | 2/2021 | Abela et al. | |
| 2021/0052584 A1 | 2/2021 | Miller et al. | |
| 2021/0069174 A1 | 3/2021 | Chu et al. | |
| 2021/0113547 A1 | 4/2021 | Chen et al. | |
| 2021/0139514 A1 | 5/2021 | Abela et al. | |
| 2021/0228489 A1 | 7/2021 | Dokou et al. | |
| 2021/0246117 A1 | 8/2021 | Angell et al. | |

FOREIGN PATENT DOCUMENTS

| | | |
|---|---|---|
| CA | 2145473 A1 | 9/1995 |
| EA | 011074 B1 | 12/2008 |
| EP | 0 194 599 A2 | 9/1986 |
| EP | 0 673 930 A1 | 9/1995 |
| EP | 1 318 978 B1 | 2/2006 |
| JP | 10-114654 A | 5/1998 |
| WO | WO 96/03380 A1 | 2/1996 |
| WO | WO 96/22022 A1 | 7/1996 |
| WO | WO 97/18712 A1 | 5/1997 |
| WO | WO 97/22586 A1 | 6/1997 |
| WO | WO 98/08818 A1 | 3/1998 |
| WO | WO 98/31226 A1 | 7/1998 |
| WO | WO 99/16744 A1 | 4/1999 |
| WO | WO 99/37153 A1 | 7/1999 |
| WO | WO 99/41238 A1 | 8/1999 |
| WO | WO 00/76969 A1 | 12/2000 |
| WO | WO 01/08487 A1 | 2/2001 |
| WO | WO 01/15533 A1 | 3/2001 |
| WO | WO 01/39597 A2 | 6/2001 |
| WO | WO 02/15902 A1 | 2/2002 |
| WO | WO 02/24636 A2 | 3/2002 |
| WO | WO 02/30895 A1 | 4/2002 |
| WO | WO 02/085120 A2 | 10/2002 |
| WO | WO 02/096883 A1 | 12/2002 |
| WO | WO 03/002533 A1 | 1/2003 |
| WO | WO 03/022050 A1 | 3/2003 |
| WO | WO 03/028458 A1 | 4/2003 |
| WO | WO 03/043423 A1 | 5/2003 |
| WO | WO 03/043655 A1 | 5/2003 |
| WO | WO 03/101959 A1 | 12/2003 |
| WO | WO 03/103394 A2 | 12/2003 |
| WO | WO 2004/021788 A1 | 3/2004 |
| WO | WO 2004/021987 A2 | 3/2004 |
| WO | WO 2004/037798 A1 | 5/2004 |
| WO | WO 2004/039753 A2 | 5/2004 |
| WO | WO 2004/043939 A1 | 5/2004 |
| WO | WO 2004/046141 A1 | 6/2004 |
| WO | WO 2004/056775 A1 | 7/2004 |
| WO | WO 2004/056777 A1 | 7/2004 |
| WO | WO 2004/078114 A2 | 9/2004 |
| WO | WO 2004/085420 A1 | 10/2004 |
| WO | WO 2004/111014 A1 | 12/2004 |
| WO | WO 2005/049018 A1 | 6/2005 |
| WO | WO 2005/054191 A1 | 6/2005 |
| WO | WO 2005/070006 A2 | 8/2005 |
| WO | WO 2005/075435 A1 | 8/2005 |
| WO | WO 2005/080373 A1 | 9/2005 |
| WO | WO 2005/085216 A1 | 9/2005 |
| WO | WO 2005/099705 A2 | 10/2005 |
| WO | WO 2005/108369 A1 | 11/2005 |
| WO | WO 2006/002421 A2 | 1/2006 |
| WO | WO 2006/030807 A1 | 3/2006 |
| WO | WO 2006/039212 A2 | 4/2006 |
| WO | WO 2006/065204 A1 | 6/2006 |
| WO | WO 2006/066968 A1 | 6/2006 |
| WO | WO 2006/067392 A2 | 6/2006 |

(56) References Cited

FOREIGN PATENT DOCUMENTS

| | | |
|---|---|---|
| WO | WO 2007/019397 A2 | 2/2007 |
| WO | WO 2007/021982 A2 | 2/2007 |
| WO | WO 2007/053641 A2 | 5/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/113327 A2 | 10/2007 |
| WO | WO 2007/117715 A2 | 10/2007 |
| WO | WO 2007/134279 A2 | 11/2007 |
| WO | WO 2008/005457 A2 | 1/2008 |
| WO | WO 2008/100867 A2 | 8/2008 |
| WO | WO 2008/127399 A2 | 10/2008 |
| WO | WO 2008/141385 A1 | 11/2008 |
| WO | WO 2009/006315 A1 | 1/2009 |
| WO | WO 2009/027730 A1 | 3/2009 |
| WO | WO 2009/032116 A1 | 3/2009 |
| WO | WO 2009/038683 A2 | 3/2009 |
| WO | WO 2009/064848 A1 | 5/2009 |
| WO | WO 2009/071947 A2 | 6/2009 |
| WO | WO 2009/073757 A1 | 6/2009 |
| WO | WO 2009/076142 A2 | 6/2009 |
| WO | WO 2009/127822 A2 | 10/2009 |
| WO | WO 2009/138758 A2 | 11/2009 |
| WO | WO 2010/003444 A2 | 1/2010 |
| WO | WO 2010/007116 A2 | 1/2010 |
| WO | WO 2010/019239 A2 | 2/2010 |
| WO | WO 2010/022307 A2 | 2/2010 |
| WO | WO 2010/025295 A2 | 3/2010 |
| WO | WO 2010/048526 A2 | 4/2010 |
| WO | WO 2010/053471 A1 | 5/2010 |
| WO | WO 2010/054138 A2 | 5/2010 |
| WO | WO 2010/065824 A2 | 6/2010 |
| WO | WO 2010/078103 A1 | 7/2010 |
| WO | WO 2010/083441 A2 | 7/2010 |
| WO | WO 2010/102758 A2 | 9/2010 |
| WO | WO 2010/108155 A1 | 9/2010 |
| WO | WO 2010/108162 A1 | 9/2010 |
| WO | WO 2010/110231 A1 | 9/2010 |
| WO | WO 2010/123822 A1 | 10/2010 |
| WO | WO 2010/138588 A2 | 12/2010 |
| WO | WO 2011/019413 A1 | 2/2011 |
| WO | WO 2011/068560 A1 | 6/2011 |
| WO | WO 2011/072241 A1 | 6/2011 |
| WO | WO 2011/102514 A1 | 8/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/127290 A2 | 10/2011 |
| WO | WO 2011/128251 A1 | 10/2011 |
| WO | WO 2011/133751 A2 | 10/2011 |
| WO | WO 2011/133951 A1 | 10/2011 |
| WO | WO 2011/150016 A1 | 12/2011 |
| WO | WO 2012/027247 A2 | 3/2012 |
| WO | WO 2012/027731 A2 | 3/2012 |
| WO | WO 2012/052540 A1 | 4/2012 |
| WO | WO 2012/087938 A1 | 6/2012 |
| WO | WO 2012/089721 A1 | 7/2012 |
| WO | WO 2012/089722 A2 | 7/2012 |
| WO | WO 2012/102297 A1 | 8/2012 |
| WO | WO 2012/110519 A1 | 8/2012 |
| WO | WO 2012/116960 A1 | 9/2012 |
| WO | WO 2012/139891 A1 | 10/2012 |
| WO | WO 2012/166415 A1 | 12/2012 |
| WO | WO 2012/170061 A1 | 12/2012 |
| WO | WO 2013/033068 A1 | 3/2013 |
| WO | WO 2013/037955 A1 | 3/2013 |
| WO | WO 2013/038373 A1 | 3/2013 |
| WO | WO 2013/041602 A1 | 3/2013 |
| WO | WO 2013/070961 A1 | 5/2013 |
| WO | WO 2013/082102 A1 | 6/2013 |
| WO | WO 2013/112804 A1 | 8/2013 |
| WO | WO 2013/118805 A1 | 8/2013 |
| WO | WO 2013/130669 A1 | 9/2013 |
| WO | WO 2013/158121 A1 | 10/2013 |
| WO | WO 2013/177224 A1 | 11/2013 |
| WO | WO 2013/185112 A1 | 12/2013 |
| WO | WO 2013/185202 A1 | 12/2013 |
| WO | WO 2014/008458 A2 | 1/2014 |
| WO | WO 2014/014841 A1 | 1/2014 |
| WO | WO 2014/017093 A1 | 1/2014 |
| WO | WO 2014/028381 A1 | 2/2014 |
| WO | WO 2014/028968 A1 | 2/2014 |
| WO | WO 2014/039714 A2 | 3/2014 |
| WO | WO 2014/047427 A2 | 3/2014 |
| WO | WO 2014/071122 A1 | 5/2014 |
| WO | WO 2014/071247 A1 | 5/2014 |
| WO | WO 2014/071378 A1 | 5/2014 |
| WO | WO 2014/086723 A1 | 6/2014 |
| WO | WO 2014/086739 A1 | 6/2014 |
| WO | WO 2014/086751 A1 | 6/2014 |
| WO | WO 2014/096388 A2 | 6/2014 |
| WO | WO 2014/109858 A1 | 7/2014 |
| WO | WO 2014/144100 A2 | 9/2014 |
| WO | WO 2014/152013 A1 | 9/2014 |
| WO | WO 2014/152018 A1 | 9/2014 |
| WO | WO 2014/180562 A1 | 11/2014 |
| WO | WO 2014/181287 A1 | 11/2014 |
| WO | WO 2014/190199 A1 | 11/2014 |
| WO | WO 2015/010832 A1 | 1/2015 |
| WO | WO 2015/031608 A1 | 3/2015 |
| WO | WO 2015/069287 A1 | 5/2015 |
| WO | WO 2015/073231 A1 | 7/2015 |
| WO | WO 2015/160787 A1 | 10/2015 |
| WO | WO 2016/057730 A1 | 2/2016 |
| WO | WO 2016/057572 A1 | 4/2016 |
| WO | WO 2016/081556 A1 | 5/2016 |
| WO | WO 2016/105484 A1 | 6/2016 |
| WO | WO 2016/105485 A2 | 6/2016 |
| WO | WO 2016/128529 A1 | 8/2016 |
| WO | WO 2016/160945 A1 | 10/2016 |
| WO | WO 2017/053455 A1 | 3/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/223188 A1 | 12/2017 |
| WO | WO 2018/064632 A1 | 4/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 |
| WO | WO 2018/116185 A1 | 6/2018 |
| WO | WO 2018/127130 A1 | 7/2018 |
| WO | WO 2018/183367 A1 | 10/2018 |
| WO | WO 2018/201126 A1 | 11/2018 |
| WO | WO 2018/227049 A1 | 12/2018 |
| WO | WO 2019/010092 A1 | 1/2019 |
| WO | WO 2019/018353 A1 | 1/2019 |
| WO | WO 2019/018395 A1 | 1/2019 |
| WO | WO 2019/028228 A1 | 2/2019 |
| WO | WO 2019/071078 A1 | 4/2019 |
| WO | WO 2019/079760 A1 | 4/2019 |
| WO | WO 2019/113089 A1 | 6/2019 |
| WO | WO 2019/113476 A1 | 6/2019 |
| WO | WO 2019/152940 A1 | 8/2019 |
| WO | WO 2019/026075 A1 | 10/2019 |
| WO | WO 2019/191620 A1 | 10/2019 |
| WO | WO 2019/195739 A1 | 10/2019 |
| WO | WO 2019/200246 A1 | 10/2019 |
| WO | WO 2020/214921 A1 | 10/2020 |
| WO | WO 2020/242935 A1 | 12/2020 |
| WO | WO 2021/030552 A1 | 2/2021 |
| WO | WO 2021/030554 A1 | 2/2021 |
| WO | WO 2021/030555 A1 | 2/2021 |
| WO | WO 2021/030556 A1 | 2/2021 |

OTHER PUBLICATIONS

Garg, V. et al. "Pharmacokinetic and Drug-Drug Interaction Profiles of the Combination of Tezacaftor/Ivacaftor", Clinical and Translational Science—CTS, vol. 12, No. 3, Jan. 29, 2019 (Jan. 29, 2019), pp. 267-275, XP055719490, US ISSN: 1752-8054, DOI: 10.1111/cts.12610.

(56) References Cited

OTHER PUBLICATIONS

International Patent Application No. PCT/US2020/028699: International Search Report and Written Opinion, dated Jul. 20, 2020 (9 pages).
International Patent Application No. PCT/US2020/034199: International Search Report and Written Opinion, dated Aug. 11, 2020 (15 pages).
Kieltsch, I. et al. Laureates: Awards and Honors SCS Fall Meeting 2007 260 Recent Advances in Electrophilic CF 3—Transfer Using Hypervalent Iodine(III) Reagents 11, A Chimia Chimia Schweizerische Chemische Gesellschaft ISSN, vol. 62, No. 62, Jan. 1, 2008 (Jan. 1, 2008), pp. 260-263, XP055591571, DOI: 10.2533/chimia.2008.260.
Montemayor, Kristina et al. "Unmasking catamenial hemoptysis in the era of CFTR modulator therapy", Journal of Cystic Fibrosis, Elsevier, NL, vol. 19, No. 4, Jan. 24, 2020 (Jan. 24, 2020), XP086202454, ISSN: 1569-1993, DOI: 10.1016/J.JCF.2020.01.005 [retrieved on Jan. 24, 2020].
NCT03029455 "A Study to Evaluate Safety and Pharmacokinetics of VX-659 in Healthy Subjects and in Adults With Cystic Fibrosis". Vertex Pharmaceuticals Incorporated, Retrieved from the Internet: https://clinicaltrials.gov/ct2/show/study/NCT03029455.
Qun, C. et al. "Synthesis of 3,3,3-trifluoro-2,2-dimethylpropionic acid", Huaxue Shi Ji—Chemical Reagents, Beijing : Huaxue Huaxue Shi Ji Keji Qingbao Zhongxinzhan, CN, vol. 38, No. 4, Jan. 1, 2016 (Jan. 1, 2016), pp. 386-388, XP009513488, ISSN: 0258-3283, DOI: 10.13822/J.CNKI.HXSJ.2016.04.026.
Tsong-Long H. et al. "Synthesis and pharmacological characterization of 2-aminobenzaldehyde oxime analogs as dual inhibitors of neutrophil elastase and proteinase 3", Bioorganic & Medicinal Chemistry, vol. 23, No. 5, Jan. 16, 2015, pp. 1123-1134, XP029199003.
"Vertex Provides Update on Ongoing Phase 3 Program for VX-661 in Combination with Ivacaftor for the Treatment of Cystic Fibrosis" (Aug. 15, 2016) Retrieved from the Internet: https://www.businesswire.com/news/home/20160815006099/en/Vertex-Update-Ongoing-Phase-3-Program-VX-661.
Anilkumar, G.N. et al. (2011) "II. Novel HCV NS5B polymerase inhibitors: Discovery of indole C2 acyl sulfonamides" *Biogranic & Medicinal Chemistry Letters*, 22(1):713-717.
Atzrodt J, Derdau V, Fey T, Zimmermann J. "The Renaissance of H/D Exchange" Angew. Chem. Int. Ed. 2007: 46, 7744-7765.
Atzrodt J, Derdau V, Kerr W, Reid M. "C—H functionalization for hydrogen isotope exchange" Angew. Chem. Int. Ed. 2018: 57, 3022-3047.
Belikov, V.G., (2007) *Farmatsevticheskaya khimiya (Pharmaceutical Chemistry)*, Moscow: MEDpress-inform, pp. 27-29.
Borhade, S.R. et al. (2013) "Synthesis of Novel Aryl and Heteroaryl Acyl Sulfonimidamides via Pd-Catalyzed Carbonylation Using a Nongaseous Precursor" *Organic Lett*, 15(5):1056-1059.
Braman, V.; Liu, J. F.; Harbeson, S.; Uttamsingh, V.; Bridson, G.; Wu, L.; Shipley, J. E. "Preliminary Clinical Outcomes for CTP-354, a Novel Subtype-Selective GABA(A) Modulator" Presented at the American Neurological Association (ANA) 2014 Annual Meeting, Baltimore, MD, Oct. 12-14, 2014.
Byrn, S. et al. (1995) "Pharmaceutical solids: A strategic approach to regulatory considerations," (12): 945-954.
Caira, M. R. (1998) "Crystalline Polymorphism of Organic Compounds," *Topics in Current Chemistry*, 163-208.
Cargnin S, Serafini M, Pirali T. "A primer of deuterium in drug design" Future Med. Chem. 2019; 11(16): 2039-2042.
Chen, Y. (Jan. 26, 2016) "N-Monoacylation of Sulfonimidamides" *Synthesis*, 48(7):1019-1028.
Czeskis B, Elmore, CS, Haight A, Hesk D, Maxwell BD, Miller SA, Raglione T, Schildknegt K, Traverse JF, Wang P. "Deuterated active pharmaceutical ingredients: A science-based proposal for synthesis, analysis, and control. Part 1: Framing the problem" J. Label. Compd. Radiopharm. 2019, 62: 690-694. DOI: 10.1002/jlcr.3743.
Dao HT, Li C, Michaudel Q, Maxwell BD, Baran PS. J. Am. Chem. Soc. 2015; 137, 8046-8049.

Database Caplus, Accession No. 1965:51408. Abstract of French Patent No. FR M2868, filed Nov. 23, 1964, by Roussel-UCLAF [online]. Retrieved Jan. 6, 2017 (1 page).
Database Caplus, Accession No. 1965:51409. Abstract of German Patent No. DE 1182243, filed Nov. 26, 1964, by Badische Anilin & Soda-Fabrik A.G. [online]. Retrieved Jan. 6, 2017 (2 pages).
Database Pubchem, CID: 20050716. Compound Summary, 1-[2-[[2-[(2-Amino-3-methylbutanoyl)amino]-3-methylpentanoyl]amino]-3-phenylpropanoyl]pyrrolidine-2-carboxylic acid. NIH, U.S. National Library of Medicine, National Center for Biotechnology Information; Modify Date: Nov. 30, 2019. [online]. Retrieved from https://pubchem.ncbi.nlm.nih.gov/compound/20050716, on Dec. 3, 2019 (7 pages).
Database Pubchem, CID: 20091118. Compound Summary, [4-(5-Hexylpyrimidin-2-yl)phenyl] 2-methoxypropanoate. NIH, U.S. National Library of Medicine, National Center for Biotechnology Information; Modify Date: Nov. 30, 2019. [online]. Retrieved from https://pubchem.ncbi.nlm.nih.gov/compound/20091118, on Dec. 3, 2019 (9 pages).
Database Pubchem, CID: 20120819. Compound Summary, 4-(Cyclopentyloxy)-3-fluorobenzene-1-sulfonyl chloride. NIH, U.S. National Library of Medicine, National Center for Biotechnology Information; Modify Date: Nov. 30, 2019. [online]. Retrieved from https://pubchem.ncbi.nlm.nih.gov/compound/20120819, on Dec. 3, 2019 (8 pages).
Database Pubchem, CID: 2545578. Compound Summary, T5339296. NIH, U.S. National Library of Medicine, National Center for Biotechnology Information; Modify Date: Jan. 16, 2016. [online]. Retrieved from https://pubchem.ncbi.nlm.nih.gov/compound/2545578, on Jan. 22, 2016 (9 pages).
Database Pubchem, CID: 44419393. Compound Summary, CHEMBL374189. NIH, U.S. National Library of Medicine, National Center for Biotechnology Information; Modify Date: Jan. 16, 2016. [online]. Retrieved from https://pubchem.ncbi.nlm.nih.gov/compound/44419393, on Jan. 22, 2016 (11 pages).
Database Pubchem, CID: 49774135. Compound Summary, SCHEMBL13395127. NIH, U.S. National Library of Medicine, National Center for Biotechnology Information; Modify Date: Jan. 16, 2016 [online], Retrieved from https://pubchem.ncbi.nlm.nih.gov/compound/49774135, on Jan. 22, 2016 (10 pages).
Database Pubchem, CID: 58132855. Compound Summary, SCHEMBL831192. NIH, U.S. National Library of Medicine, National Center for Biotechnology Information, PubChem Open Chemistry Database; Modify Date: Jan. 16, 2016 [online]. Retrieved from: https://pubchem.ncbi.nlm.nih.gov/compound/58132855, on Jan. 22, 2016 (10 pages).
Dorwald, F. A. (2006) "Side Reactions in Organic Synthesis" Wiley: VCH, Weinheim p. IX of Preface p. 1-15.
Gant TG. "Using Deuterium in Drug Discovery: Leaving the Label in the Drug" J Med. Chem. 2014; 57(9): 3595-3611.
Halford B. "The deuterium switcheroo" Chemical & Engineering News 2016; 94(27), 32-36.
Hopkins, C.R. et al. (2006) "Design and synthesis of novel N-sulfonyl-2-indole carboxamides as potent PPAR-gamma binding agents with potential application to the treatment of osteoporosis" Bioorganic & Medicinal Chemistry Letters, 16(21):5659-5663.
International Patent Application No. PCT/US2015/54316: International Search Report and Written Opinion, dated Feb. 5, 2016 (11 pages).
International Patent Application No. PCT/US2017/025381: International Search Report and Written Opinion, dated Jun. 6, 2017 (11 pages).
International Patent Application No. PCT/US2017/054611: International Search Report and Written Opinion, dated Jan. 3, 2018 (10 pages).
International Patent Application No. PCT/US2017/065425: International Search Report and Written Opinion, dated Feb. 27, 2018 (10 pages).
International Patent Application No. PCT/US2018/036610: International Search Report and Written Opinion, dated Sep. 19, 2018 (9 pages).

(56) References Cited

OTHER PUBLICATIONS

International Patent Application No. PCT/US2018/040427: International Search Report and Written Opinion, dated Oct. 9, 2018 (15 pages).
International Patent Application No. PCT/US2018/042415: International Search Report and Written Opinion, dated Oct. 31, 2018 (12 pages).
International Patent Application No. PCT/US2018/042486: International Search Report and Written Opinion, dated Nov. 7, 2018 (13 pages).
International Patent Application No. PCT/US2018/044963: International Search Report and Written Opinion, dated Sep. 25, 2018 (15 pages).
International Patent Application No. PCT/US2018/056772: International Search Report and Written Opinion, dated Jan. 29, 2019 (13 pages).
International Patent Application No. PCT/US2018/063871: International Search Report and Written Opinion, dated Feb. 25, 2019 (16 pages).
International Patent Application No. PCT/US2019/016537: International Search Report and Written Opinion, dated Apr. 23, 2019 (13 pages).
International Patent Application No. PCT/US2018/064522: International Search Report and Written Opinion, dated Jun. 25, 2019 (21 pages).
International Patent Application No. PCT/US2019/018042: International Search Report and Written Opinion, dated Apr. 17, 2019 (10 pages).
International Patent Application No. PCT/US2019/024890: International Search Report and Written Opinion, dated Jun. 17, 2019 (13 pages).
International Patent Application No. PCT/US2019/026075: International Search Report and Written Opinion, dated Jun. 17, 2019 (13 pages).
International Patent Application No. PCT/US2019/027202: International Search Report and Written Opinion, dated Jun. 17, 2019 (10 pages).
Jain, B.C. et al. (1947) "Studies in Sulphanilamides. Part XIII. Reaction With Dicarboxylic Acids. Some New N1- and N4-Acyl and Heterocycic Derivatives" *Journal of the Indian Chemical Society*, 24:173-176.
Kettle, J.G. et al. (2004) "N-Benzylindole-2-carboxylic acids: potent functional antagonists of the CCR2b chemokine receptor" *Bioorganic & Medicinal Chemistry Letters*, 14(2): 405-408.
Lai, J.T. et al. (1980) "Rearrangement of 2,2,6,6-tetramethyl-4-piperidone in phase-transfer catalyzed reactions," *Journal of Organic Chemistry*, 45(8):1513-1514.
Liu, J. F. et al. "CTP-354: A Novel Deuterated Subtype-Selective GABA(A) Modulator for Treatment of Neuropathic Pain, Spasticity and Anxiety Disorders" Presented at the American College of Neuropsychopharmacology (ACNP) 51st Annual Meeting, Hollywood, FL, Dec. 2-6, 2012.
Matter, H. et al. (2002) "Design and Quantitative Structure-Activity Relationship of 3-Amidinobenzyl-1H-indole-2-carboxamides as Potent, Nonchiral, and Selective Inhibitors of Blood Coagulation Factor Xa" *Journal of Medicinal Chemistry*, 45(13):2749-2769.
Maxwell BD, Tran SB, Lago M, Li J, and Bonacorsi Jr SJ. "The syntheses of [14C]BMS-823778 for use in a human ADME clinical study and of [13CD313CD2]BMT-094817, a stable-isotope labeled standard of a newly detected human metabolite" J. Label. Compd. Radiopharm. 2016; 59, 255-259.
Norman, P. (2014) "Novel picolinamide-based cystic fibrosis transmembrane regulator modulators: evaluation of WO2013038373, WO2013038376, WO2013038381, WO2013038386, and WO2013038390," *Expert Opinion on Therapeutic Patents*, 24(7):829-837.
Notman, N. (2016) "2Heavy drugs gaining momentum" [online] Retrieved from the internet: https://www.chemistryworld.com/features/2heavy-drugs-gaining-momentum/1010186.article, on Oct. 7, 2019.

Passarella, D. et al. (2001) "Cyclodimerization of indol-2-ylacetylenes. An example of intermolecular enyne-alkyne cycloaddition" *Journal of the Chemical Society, Perkin Transactions 1*, 127-129.
Pirali T, Serafini M, Cargnin S, Genazzani AA. "Applications of Deuterium in Medicinal Chemistry" J Med. Chem. 2019; 62(11): 5276-5297.
Rosebraugh, C.J. (2015) "Highlights of Presecribing Information for Orkambi," [online] Retrieved from the Internet: https://www.accessdata.fda.gov/drugsatfda_docs/label/2015/206038Orig1s000lbl.pdf, on Aug. 24, 2017.
Schmidt C. "First deuterated drug approved" Nat. Biotechnol. 2017, 35, 493-494.
Silverman, R. (2004) The Organic Chemistry of Drug Design and Drug Action, Elsevier, pp. 29-32.
Soloducho, J. (1989) "Synthesis of Some Pyrido [2,3-c][1,2,6]triazinone Derivatives" *Journal für Pracktische Chemie*, 331(3):503-506.
Tullis, E. et al. (2018) "Preliminary safety and efficacy of triple-combination CFTR modulator regimens," *Respirology*, 23(51):33.
U.S. Appl. No. 16/620,265, filed Dec. 6, 2019, by Chen et al.
U.S. Appl. No. 16/625,028, filed Dec. 20, 2019, by Chu et al.
U.S. Appl. No. 16/625,028, filed Jan. 17, 2020, by Haseltine et al.
U.S. Appl. No. 16/635,346, filed Jan. 30, 2020, by Angell et al.
U.S. Appl. No. 16/836,155, filed Mar. 31, 2020, by Miller et al.
Uttamsingh, V. et al. (2016) "WS13.6 CTP-656 tablet confirmed superiority of pharmacokinetic profile relative to Kalydeco in Phase I clinical studies" *Journal of Cystic Fibrosis*, 15:S22.
Venkatesh, S. et al. (2000) "Role of the development scientist in compound lead selection and optimization" *J. Pharm. Sci.* 89(2), 145-154.
Verado, G. et al. (1999) "Reductive One Batch Synthesis of N-Substituted Pyrrolidines from Primary Amines and 2,5-Dimethoxytetrahydrofuran" *Synthesis*, (1):74-79.
Vertex Pharmaceuticals, Inc. (Mar. 28, 2017) "Two Phase 3 Studies of the Tezacaftor/Ivacaftor Combination Treatment Met Primary Endpoints with Statistically Significant Improvements in Lung Function (FEV1) in People With Cystic Fibrosis" [online] Retrieved from the Internet: http://investors.vrtx.com/static-files/f15217ac-4a8b-436a-9215-79144ec2e59b, on Oct. 10, 2019.
Vertex Pharmaceuticals, Inc. (Jul. 18, 2017) "Vertex Announces Positive Phase 1 & Phase 2 Data from Three Different Triple Combination Regimens in People with Cystic Fibrosis Who Have One F508del Mutation and One Minimal Function Mutation (F508del/Min)", Retrieved from the Internet: URL: http://investors.vrtx.com/news-releases/news-release-details/vertex/announces-positive-phase-1-phase-2-data-three-different [retrieved on Mar. 27, 2019].
Vertex Pharmaceuticals, Inc. (Nov. 3, 2017) "Vertex announces presentations of data at North American Cystic Fibrosis Conference that Demonstrate Important Progress Toward Goal of Helping All People with CF," Health and Medicine Week, vol. 3, p. 196.
Vodak, D. (2014) "Design and Development of HPMCAS-Based Spray-Dried Dispersions," 303-322.
Wainwright, C.E. et al. (2015) "Lumacaftor-Ivacaftor in Patients with Cystic Fibrosis Homozygous for Phe508del CFTR," *The New England Journal of Medicine*, 373(3):220-231.
Winn, M. et al. (1993) "2-(Alkylamino)nicotinic Acid and Analogs. Potent Angiotensin II Antagonists" *Journal of Medicinal Chemistry*, 36(18):2676-2688.
Yarnell AT. "Heavy-Hydrogen Drugs Turn Heads, Again" Chemical & Engineering News 2009; 87(25), 36-39.
Bhattacharya, S. et al. (2009) Polymorphism in Pharmaceutical Solids: Thermoanalytical and Crystallographic Methods (Brittain H. ed., 2d ed. Informa Healthcare USA, Inc. 2009) 318-335.
Brown et al. (2006) "On scaffolds and hopping in medicinal Chemistry," Mini-reviews in medicinal chemistry, vol. 6, 11(13), 1217-1229.
Chemical Abstracts Service, CAS Registry No. 204017-11-8. CA Index Name: 1H-Indole-2-carboxamide, 1-[[2,4-bis(trifluoromethyl)phenyl]methyl]-2,3-dihydro-N-(phenylsulfonyl)-. Entered STN: Apr. 12, 1998.

(56) References Cited

OTHER PUBLICATIONS

Chemical Abstracts Service, CAS Registry No. 220678-97-7. CA Index Name: 1H-Indole-2-carboxamide, 1-[(3,4-dichlorophenyl)methyl]-N-(phenylsulfonyl)-. Entered STN: Mar. 24, 1999.
Chemical Abstracts Service, CAS Registry No. 220678-99-9. CA Index Name: 1H-Indole-2-carboxamide, 1-[(3,4-dichlorophenyl)methyl]-N-[(3,5-dimethyl-4-isoxazolyl)sulfonyl]-. Entered STN: Mar. 24, 1999.
Chemical Abstracts Service, CAS Registry No. 412005-98-2. CA Index Name: 1H-Indole-2-carboxamide, 3-(4-methoxyphenyl)-N-(phenylsulfonyl)-1-[[3-(trifluoromethyl)phenyl]methyl]-. Entered STN: May 7, 2002.
Chemical Abstracts Service, CAS Registry No. 895575-67-4. CA Index Name: 1H-Indole-2-carboxamide,1-[(3-chlorophenyl)methyl]-4-nitro-N-(2-thienylsulfonyl)-. Jun. 30, 2006.
Chemical Abstracts Service, CAS Registry No. 895575-68-5. CA Index Name: 1H-Indole-2-carboxamide,4-amino-1-[(3-chlorophenyl)methyl]-N-(2-thienylsulfonyl)-. Jul. 23, 2006.
European Patent Application No. 15849396.5 (Patent No. 3203840): Notice of Opposition by Elkington and Fife, LLP, May 5, 2021 (19 pages).
Ghose et al. (1999) Knowledge-based approach in designing combinatorial or medicinal chemistry libraries for drug discovery—qualitive and quantitative characterization of known drug databases, *J. Comb. Chem.* 1(1), 55-68.
Ivanisevic, I. (2011) "Uses of X-Ray Powder Diffraction in the Pharmaceutical Industry," Pharm. Form. Qual. 30-33.
Kola et al. (2004) "Can the pharmaceutical industry reduce attrition rates?" Nature Reviews Drug Discovery, 3(8), 711-715.
Shih et al. (2010) "Pyrazole compound BPR1P0034 with potent and selective anti-influenza virus activity" Journal of Biomedical Science, 17:13.
Soloducho, J. et al. "Synthesis of Some Pyrido[3,2g][1,2,5]triazocine Derivatives," *Polish Journal of Chemistry*, vol. 59, No. 10-12, Jan. 1, 1985, pp. 1115-1120.
Table 2 : List of the mutations or SNP tested in this study (https://www.jmdjournal.org/cms/10.2353/jmoldx.2008.080056/attachment/2286a276-d0b2-4a8a-83f8-8273bef9a761/mmc1.doc). Accessed Jan. 25, 2021.
U.S. Appl. No. 17/475,606, filed Sep. 15, 2021, by Chu et al.
U.S. Appl. No. 17/505,699, filed Oct. 20, 2021, by Alcacio et al.
Walters et al. (2002) "Prediction of 'drug-likeness'," Advanced Drug Delivery Reviews, 54(3), 255-271.

\* cited by examiner

FIG. 7

| Mutation cDNA Name | Mutation Protein Name | Mutation Legacy Name |
|---|---|---|
| c.1A>G | p.? (unknown) | M1V |
| c.54-5940_273+10250del21kb | pSer18ArgfsX16 | CFTRdele2,3 |
| c.91C>T | p.Arg31Cys | R31C |
| c.115C>T | p.Gln39X | Q39X |
| c.137C>A | p.Ala46Asp | A46D |
| c.165-1G>A | No protein name | 297-1G->A |
| c.166G>A | p.Glu56Lys | E56K |
| c.174_175insA | p.Arg59LysfsX10 | 306insA |
| c.178G>T | p.Glu60X | E60X |
| c.200C>T | p.Pro67leu | P67L |
| c.220C>T | p.Arg74Trp | R74W |
| c.223C>T | p.Arg75X | R75X |
| c.224G>A | p.Arg75Gln | R75Q |
| c.254G>A | p.Gly85Glu | G85E |
| c.262_263delTT | p.Leu88IlefsX22 | 394delTT |
| c.273+1G>A | No protein name | 405+1G->A |
| c.274-1G>A | No protein name | 406-1G->A |
| c.274G>A | p.Glu92Lys | E92K |
| c.274G>T | p.Glu92X | E92X |
| c.292C>T | p.Gln98X | Q98X |
| c.313delA | p.Ile105SerfsX2 | 444delA |
| c.325_327delTATinsG | p.Tyr109GlyfsX4 | 457TAT->G |
| c.328G>C | p.Asp110His | D110H |
| c.349C>T | p.Arg117Cys | R117C |
| c.350G>A | p.Arg117His | R117H |
| c.366T>A | p.Tyr122X | Y122X |
| c.442delA | p.Ile148LeufsX5 | 574delA |
| c.443T>C | p.Ile148Thr | I148T |

FIG. 7 (continued)

| Mutation cDNA Name | Mutation Protein Name | Mutation Legacy Name |
|---|---|---|
| c.489+1G>T | No protein name | 621+1G->T |
| c.531delT | p.Ile177MetfsX12 | 663delT |
| c.532G>A | p.Gly178Glu | G178R |
| c.543_546delTAGT | p.Leu183PhefsX5 | 675del4 |
| c.579+1G>T | No protein name | 711+1G->T |
| c.579+3A>G | No protein name | 711+3A->G |
| c.579+5G>A | No protein name | 711+5G->A |
| c.580-1G>T | No protein name | 712-1G->T |
| C.595OT | p.His199Tyr | H199Y |
| C.613CM | p.Pro205Ser | P205S |
| c.617T>G | p.Leu206Trp | L206W |
| C.658OT | p.Gln220X | Q220X |
| c.580T>G | p.Leu227Arg | L227R |
| c.720_741delAGGGAGAATGATGATGAAGTAC | p.Gly241GlufsX13 | 852del22 |
| c.828C>A | p.Cys276X | C276X |
| c.948delT | p.Phe316LeufsX12 | 1078delT |
| c.988G>T | p.Gly330X | G330X |
| c.1000C>T | p.Arg334Trp | R334W |
| c.1007T>A | p.Ile336Lys | I336K |
| c.1013C>T | p.Thr338Ile | T338I |
| c.1021T>C | p.Ser341Pro | S341P |
| c.1022_1023insTC | p.Phe342HisfsX28 | 1154insTC |
| c.1040G>A | p.Arg347His | R347H |
| c.1040G>C | p.Arg347Pro | R347P |
| c.1055G>A | p.Arg352Gln | R352Q |
| c.[1075C>A; 1079C>A] | p.[Gln359Lys;Thr360Lys] | Q359K/T360K |
| c.1081delT | p.Trp361GlyfsX8 | 1213delT |
| c.1116+1G>A | No protein name | 1248+1G->A |

FIG. 7 (continued)

| Mutation cDNA Name | Mutation Protein Name | Mutation Legacy Name |
|---|---|---|
| c.1127_1128insA | p.Gln378AlafsX4 | 1259insA |
| c.1153_1154insAT | p.Asn386IlefsX3 | 1288insTA |
| c.1202G>A or c.1203G>A | p.Trp401X | W401X |
| c.1209+1G>A | No protein name | 1341+1G->A |
| c.1210-12[5] | No protein name | 5T |
| c.1210-12(7] | No protein name | 7T |
| c.1240C>T | p.Gln414X | Q414X |
| c.1329_1330insAGAT | p.Ile444ArgfsX3 | 1461ins4 |
| c.1340delA | p.Lys447ArgfsX2 | 1471delA |
| c.1364C>A | p.Ala455Glu | A455E |
| c.1393-1G>A | No protein name | 1525-1G->A |
| c.1397C>A or c.1397C>G | p.Ser466X | S466X |
| c.1400T>C | p.Leu467Pro | L467P |
| c.1408A>G | p.Met470Val | M470V |
| c.1418delG | p.Gly473GlufsX54 | 1548delG |
| c.1466C>A | p.Ser489X | S489X |
| c.1475C>T | p.Ser492Phe | S492F |
| c.1477C>T | p.Gln493X | Q493X |
| c.1519_1521delATC | 'p.Ile507del | I507del |
| c.1521_1523delCTT | p.Phe508del | F508del |
| c.1545_1546delTA | p.Tyr515X | 1677delTA |
| c.1558G>T | p.Val520Phe | V520F |
| c.1573C>T | p.Gln525X | Q525X |
| c.1585-8G>A | No protein name | 1717-8G->A |
| c.1585-1G>A | No protein name | 1717-1G->A |
| c.1624G>T | p.Gly542X | G542X |
| c.1645A>C or c.1G47T>G | p.Ser549Arg | S549R |
|  |  |  |

FIG. 7 (continued)

| Mutation cDNA Name | Mutation Protein Name | Mutation Legacy Name |
|---|---|---|
| c.1646G>A | p.Ser549Asn | S549N |
| c.1650delA | p.Gly551ValfsX8 | 1782delA |
| c.1651G>A | p.Gly551Ser | G551S |
| c.1652G>A | p.Gly551Asp | G551D |
| c.1654C>T | p.Gln552X | Q552X |
| c.1657C>T | p.Arg553X | R553X |
| c.1673T>C | p.Leu558Ser | L558S |
| c.1675G>A | p.Ala559Thr | A559T |
| c.1679G>A | p.Arg560Lys | R560K |
| c.1679G>C | p.Arg560Thr | R560T |
| c.1679+1G>C | No protein name | 1811+1G->C |
| c.1679+1.6kbA>G | No protein name | 1811+1.6kbA->G |
| c.1680-1G>A | No protein name | 1812-1G->A |
| c.1682C>A | p.Ala561Glu | A561E |
| c.1692delA | p.Asp565MetfsX7 | 1824delA |
| c.1705T>G | p.Tyr569Asp | Y569D |
| c.1727G>C | p.Gly576Ala | G576A |
| c.1736A>G | p.Asp579Gly | D579G |
| c.1753G>T | p.Glu585X | E585X |
| c.1766+1G>A | No protein name | 1898+1G->A |
| c.1766+1G>C | No protein name | 1898+1G->C |
| c.1766+3A>G | No protein name | 1898+3A->G |
| c.1841A>G | p.Asp614Gly | D614G |
| c.1923_1931del9ins | pSer641ArgfsX5 | 2055del9->A |
| c.1973_1985del13insAGAAA | p.Arg658 LysfsX4 | 2105-2117del13insAGAAA |
| c.1986_1989delAACT | p.Thr663ArgfsX8 | 2118del4 |
| c.2002C>T | p.Arg668Cys | R668C |
| c.2012delT | p.Leu671X | 2143delT |

FIG. 7 (continued)

| Mutation cDNA Name | Mutation Protein Name | Mutation Legacy Name |
|---|---|---|
| c.2051_2052delAAinsG | p.Lys684SerfsX38 | 2183AA->G+ |
| c.2051_2052delAAinsG | p.Lys684SerfsX38 | 2183delAA->G# |
| c.2052_2053insA | p.Gln685ThrfsX4 | 2184insA |
| c.2052delA | p.Lys684AsnfsX38 | 2184delA |
| c.2125O>T | p.Arg709X | R709X |
| c.2128A>T | p.Lys710X | K710X |
| c.2175_2176insA | p.Glu726ArgfsX4 | 2307insA |
| c.2195T>G | p.Leu732X | L732X |
| c.2215delG | p.Val739TyrfsX16 | 2347delG |
| c.2260G>A | p.Val754Met | V754M |
| c.2290C>T | p.Arg764X | R764X |
| c.2353C>T | p.Arg785X | R785X |
| c.2374C>T | p.Arg792X | R792X |
| c.2424_2425insAT | p.Ser809IlefsX13 | 2556insAT |
| c.2453delT | p.Leu818TrpfsX3 | 2585delT |
| c.2462_2463delGT | p.Ser821ArgfsX4 | No legacy name |
| c.2464G>T | p.Glu822X | E822X |
| c.2490+1G>A | No protein name | 2622+1G->A |
| c.2491G>T | p.Glu831X | E831X |
| c.2537G>A or c.2538G>A | p.Trp846X | W846X |
| c.2547O>A | p.Tyr849X | Y849X |
| c.2551C>T | p.ArgSSIX | R851X |
| c.2583delT | p.Phe861LeufsX3 | 2711delT |
| c.2657+2_2657+3insA | No protein name | 2789+2insA |
| c.2657+5G>A | No protein name | 2789+5G->A |
| c.2658-1G>C | No protein name | 2790-1G->C |
| c.2668C>T | p.Gln890X | Q890X |
| c.2735C>A | p.Ser912X | S912X |

FIG. 7 (continued)

| Mutation cDNA Name | Mutation Protein Name | Mutation Legacy Name |
|---|---|---|
| c.2737_2738insG |  | 2869insG |
| c.2739T>A | p.Tyr913X | Y913X |
| c.2764_2765insAG | p.Val922GlufsX2 | 2896insAG |
| c.2780T>C | p.Leu927Pro | L927P |
| c.2834C>T | p.Ser945Leu | S945L |
| c.2875delG | p.Ala959HisfsX9 | 3007delG |
| c.2908G>C | p.Gly970Arg | G970R |
| c.2930C>T | p.Ser977Phe | S977F |
| c.2988G>A | No protein name | 3120G->A |
| c.2988+1G>A | No protein name | 3120+1G->A |
| c.2989-977_3367+248del | No protein name | 3121-977_3499+248del2515 |
| c.2989-1G>A | No protein name | 3121-1G->A |
| c.2991G>C | p.Leu997Phe | L997F |
| c.3002_3003delTG | p.Val1001AspfsX45 | 3132delTG |
| c.3080T>C | p.Ile1027Thr | I1027T |
| c.3140-26A>G | No protein name | 3272-26A->G |
| c.3154T>G | p.Phe1052Val | F1052V |
| c.3160C>G | p.His1054Asp | H1054D |
| c.3181G>C | p.Gly1061Arg | G1061R |
| c.3194T>C | p.Leu1065Pro | L1065P |
| c.3196C>T | p.Arg1066Cys | R1066C |
| c.3197G>A | p.Arg1066His | R1066H |
| c.3205G>A | p.Gly1069Arg | G1069R |
| c.3208C>T | p.Arg1070Trp | R1070W |
| c.3209G>A | p.Arg1070Gln | R1070Q |
| c.3222T>A | p.Phe1074Leu | F1074L |
| c.3230T>C | p.Leu1077Pro | L1077P |
| c.3266G>A | p.Trp1089X | W1089X |

FIG. 7 (continued)

| Mutation cDNA Name | Mutation Protein Name | Mutation Legacy Name |
|---|---|---|
| c.3276C>A or c.3276C>G | p.Tyr1092X | Y1092X |
| c.3302T>A | p.Met1101Lys | M1101K |
| c.3310G>T | p.Glu1104X | E1104X |
| c.3454G>C | p.Asp1152His | D1152H |
| c.3472C>T | p.Arg1158X | R1158X |
| c.3484C>T | p.Arg1162X | R1162X |
| c.3485G>T | p.Arg1162Leu | R1162L |
| c.3528delC | p.Lys1177SerfsX15 | 3659delC |
| c.3535_3536insTCAA | p.Thr1179IlefsX17 | 3667ins4 |
| c.3587C>G | p.Ser1196X | S1196X |
| c.3605delA | p.Asp1202AlafsX9 | 3737delA |
| c.3611G>A or c.3612G>A | p.Trp1204X | W1204X |
| c.3659delC | p.Thr1220LysfsX8 | 3791delC |
| c.3691delT | p.Ser1231ProfsX4 | 3821delT |
| c.3700A>G | p.Ile1234Val | I1234V |
| c.3705T>G | p.Ser1235Arg | S1235R |
| c.3717+12191C>T | No protein name | 3849+10kbC->T |
| c.3715-1G>A | No protein name | 3850-1G->A |
| c.3731G>A | p.Gly1244Glu | G1244E |
| c.3744delA | p.Lys1250ArgfsX9 | 3876delA |
| c.3752G>A | p.Ser1251Asn | S1251N |
| c.3763T>C | p.Ser1255Pro | S1255P |
| c.37640A | p.Ser1255X | S1255X |
| c.3773_3774insT | p.Leu1258PhefsX7 | 3905insT |
| c.3808G>A | p.Asp1270Asn | D1270N |
| c.3346G>A | p.Trp12S2X | W1282X |

FIG. 7 (continued)

| Mutation cDNA Name | Mutation Protein Name | Mutation Legacy Name |
|---|---|---|
| c.3873+1G>A | No protein name | 4005+1G->A |
| c.3883delA | p.Ile1295PhefsX3 | 4015delA |
| c.3884_3885insT | p.Ser1297PhefsX5 | 4016insT |
| c.3909C>G | p.Asn1303Lys | N1303K |
| c.3937C>T | p.Gln1313X | Q1313X |
| c.3964-78_4242+577del | NULL | CFTRdele22,23 |
| c.4046G>A | p.Gly1349Asp | G1349D |
| c.4077_4080delTGTTinsAA | No protein name | 4209TGTT->AA |
| c.4111G>T | p.Glu1371X | E1371X |
| c.4196_4197delTC | p.Cys1400X | 4326delTC |
| c.4234C>T | p.Gln1412X | Q1412X |
| c.4242+1G>T | No protein name | 4374+1G->T |
| c.4251delA | p.Glu1418ArgfsX14 | 4382delA |
| c.4296_4297insGA | p.Ser1435GlyfsX14 | 4428insGA |

MODULATOR OF THE CYSTIC FIBROSIS TRANSMEMBRANE CONDUCTANCE REGULATOR, PHARMACEUTICAL COMPOSITIONS, METHODS OF TREATMENT, AND PROCESS FOR MAKING THE MODULATOR

Disclosed herein is a modulator of Cystic Fibrosis Transmembrane Conductance Regulator (CFTR), pharmaceutical compositions containing the modulator, methods of treatment of cystic fibrosis, and a process for making the modulator.

Cystic fibrosis (CF) is a recessive genetic disease that affects approximately 70,000 children and adults worldwide. Despite progress in the treatment of CF, there is no cure.

In patients with CF, mutations in CFTR endogenously expressed in respiratory epithelia lead to reduced apical anion secretion causing an imbalance in ion and fluid transport. The resulting decrease in anion transport contributes to enhanced mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on only 322 of these identified mutations, with sufficient evidence to define 281 mutations as disease causing. The most prevalent disease-causing mutation is a deletion of phenylalanine at position 508 of the CFTR amino acid sequence, and is commonly referred to as the F508del mutation. This mutation occurs in approximately 70% of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the $Na^+$-$K^+$-ATPase pump and Cl— channels expressed on the basolateral surface of the cell. Secondary active transport of chloride from the luminal side leads to the accumulation of intracellular chloride, which can then passively leave the cell via Cl⁻ channels, resulting in a vectorial transport. Arrangement of $Na^+/2Cl^-/K^+$ co-transporter, $Na^+$-$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Accordingly, there is a need for novel treatments of CFTR mediated diseases.

Disclosed herein are novel compounds, including compounds of Formulae (I)-(VI) and pharmaceutically acceptable salts thereof. For example, compounds of Formula (I) can be depicted as:

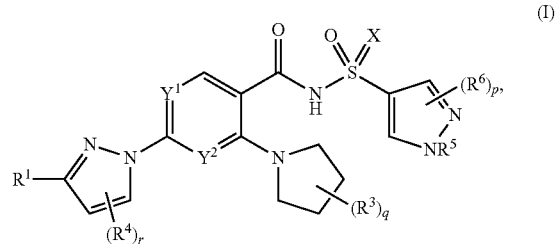

a pharmaceutically acceptable salt thereof, or a deuterated derivative of any of the foregoing,
wherein:
one of $Y^1$ and $Y^2$ is N and the other is CH;
X is chosen from O, NH, and $N(C_1-C_4$ alkyl) groups;
$R^1$ is —$(C(R^2)_2)_k$—O—$(C(R^2)_2)_m R^7$,
each $R^2$ is independently chosen from hydrogen; halogens; cyano; hydroxy; $C_1$-$C_2$ alkoxy groups; and $C_1$-$C_2$ alkyl groups optionally substituted with one or more substituents each independently chosen from halogens, hydroxy, and $C_{3-5}$ cycloalkyl groups optionally substituted with one or more substituents each independently chosen from $C_1$-$C_2$ alkyl groups, halogenated $C_1$-$C_2$ alkyl groups, and halogens;
each $R^3$ is independently chosen from $C_1$-$C_4$ alkyl groups optionally substituted with one or more hydroxy groups, or optionally two geminal $R^3$, together with the carbon atom to which they are attached, form a $C_{3-4}$ cycloalkyl;
each $R^4$ is independently chosen from halogens;
$R^5$ is chosen from hydrogen and $C_1$-$C_4$ alkyl groups;
each $R^6$ is independently chosen from halogens, cyano, hydroxy, hydroxymethyl, $C_1$-$C_2$ alkoxy groups, $C_1$-$C_2$ alkyl groups, and halogenated $C_1$-$C_2$ alkyl groups;

R[7] is chosen from hydrogen; halogens; cyano; $C_1$-$C_2$ alkyl groups optionally substituted with one or more substituents each independently chosen from halogens and hydroxy; and $C_3$-$C_{10}$ cycloalkyl groups optionally substituted with one or more substituents each independently chosen from $C_1$-$C_2$ alkyl groups, halogenated $C_1$-$C_2$ alkyl groups, and halogens;

k is 0 or 1;
r is 0 or 1;
m is 0, 1, 2, or 3;
p is 0, 1, or 2; and
q is 0, 1, 2, 3, 4, 5, 6, 7, or 8.

Also disclosed herein are pharmaceutical compositions comprising at least one of the novel compounds disclosed herein and/or at least one pharmaceutically acceptable salt thereof, which compositions may further include at least one additional active pharmaceutical ingredient and/or at least one carrier. Also disclosed are methods of treating the CFTR-mediated disease cystic fibrosis comprising administering at least one of the novel compounds disclosed herein and/or at least one pharmaceutically acceptable salt thereof, optionally as part of a pharmaceutical composition comprising at least one additional component, to a subject in need thereof.

Also disclosed are methods of treating the CFTR-mediated disease cystic fibrosis comprising administering at least one of the novel compounds disclosed herein and/or at least one pharmaceutically acceptable salt thereof, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound II), and N-[2,4-bis(1,1-dimethylethyl)-5-hydroxyphenyl]-1,4-dihydro-4-oxoquinoline-3-carboxamide (Compound III), optionally as part of at least one pharmaceutical composition comprising at least one additional component, to a patient in need thereof.

Also disclosed herein is Compound 1:

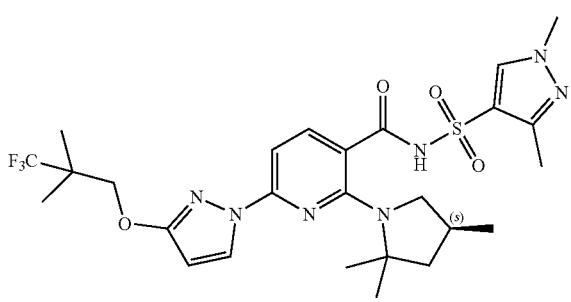 [SMILES: Cc1nn(C)cc1S(=O)(=O)NC(=O)c1ccc(-n2ccc(OCC(C)(C)C(F)(F)F)n2)nc1N1C[C@@H](C)CC1(C)C]

N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide Also disclosed herein are pharmaceutical compositions of Compound 1, and forms thereof, which may include at least one additional active pharmaceutical ingredient and at least one carrier, and methods of treating the CFTR-mediated disease cystic fibrosis, comprising administering Compound 1 to a subject in need thereof. A process of making Compound 1 is also disclosed.

BRIEF DESCRIPTION OF THE DRAWINGS

FIG. 7 is a representative list of CFTR mutations.

DEFINITIONS

Figure 1:
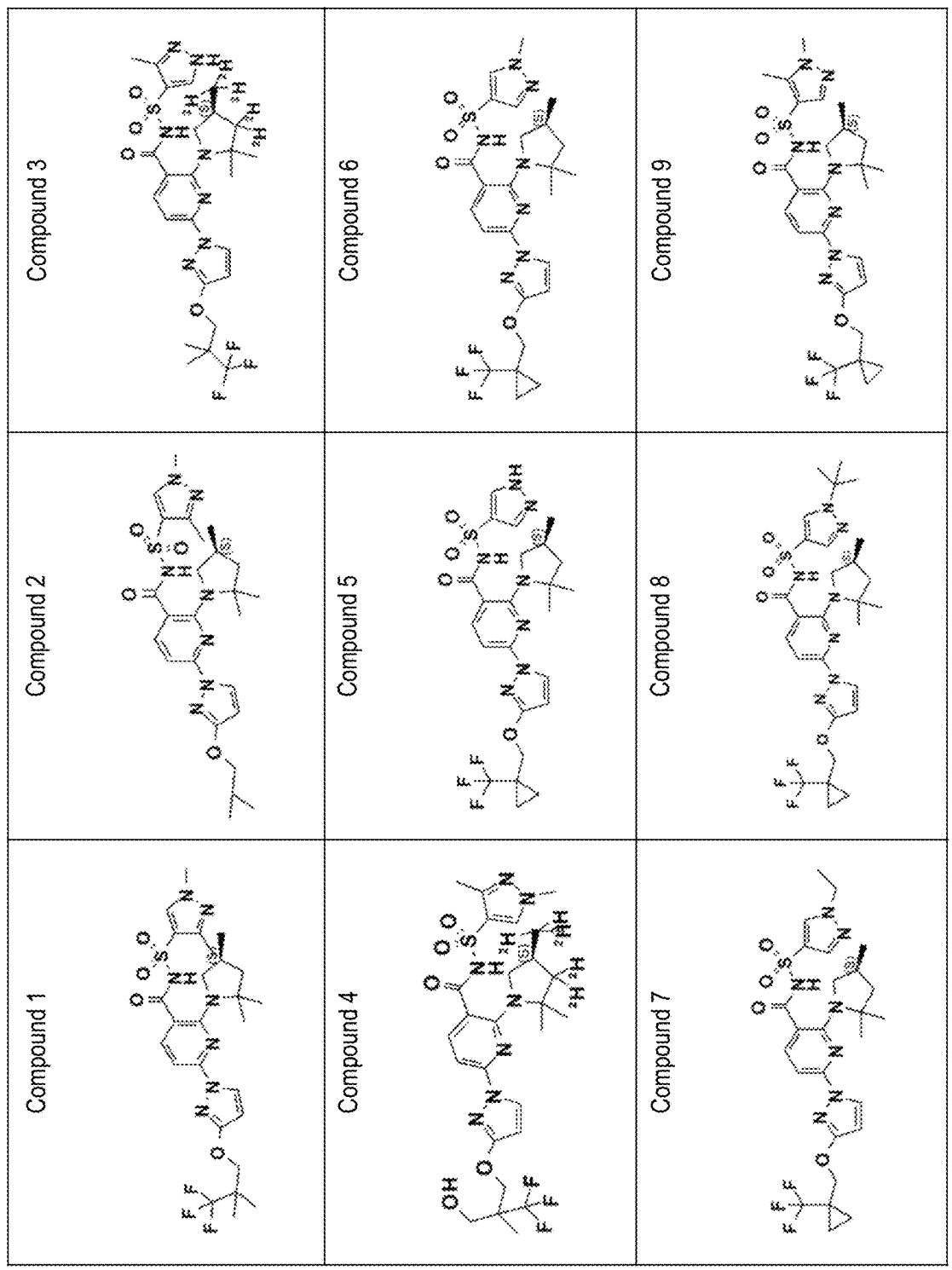
FIG. 1 shows the structures of non-limiting examples of novel compounds disclosed herein.
Figure 1:
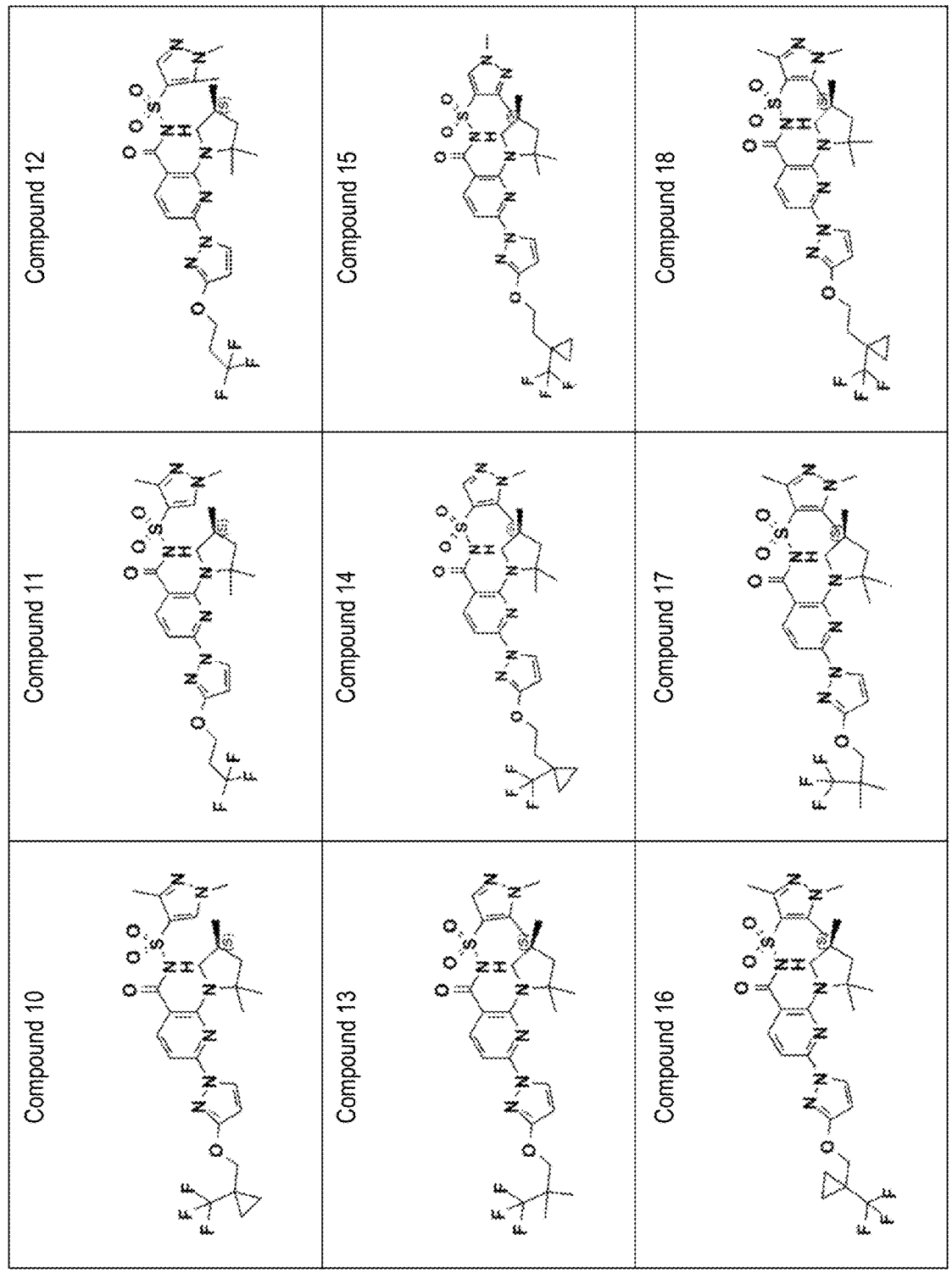
Figure 1:
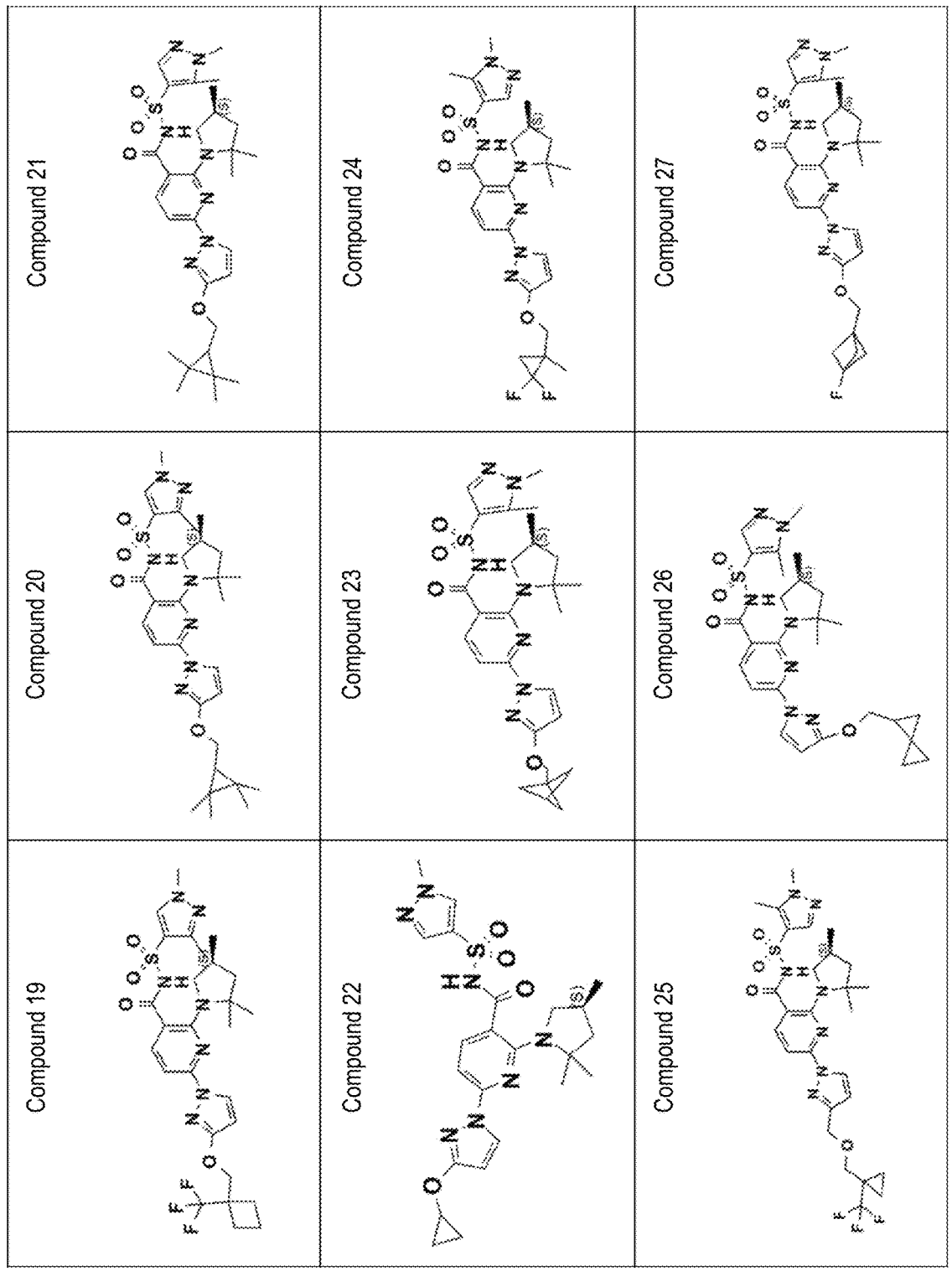
Figure 1:
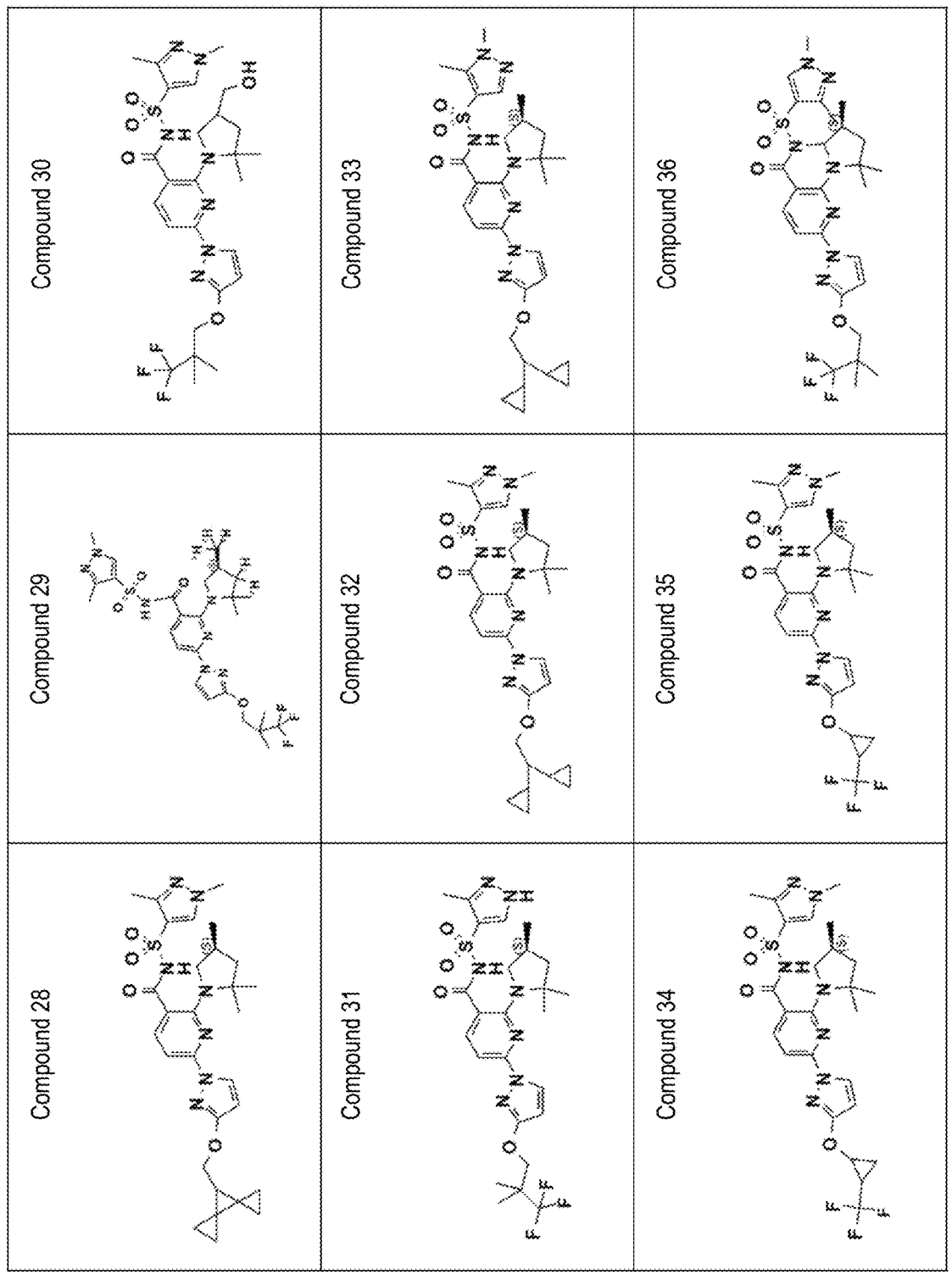
Figure 1:
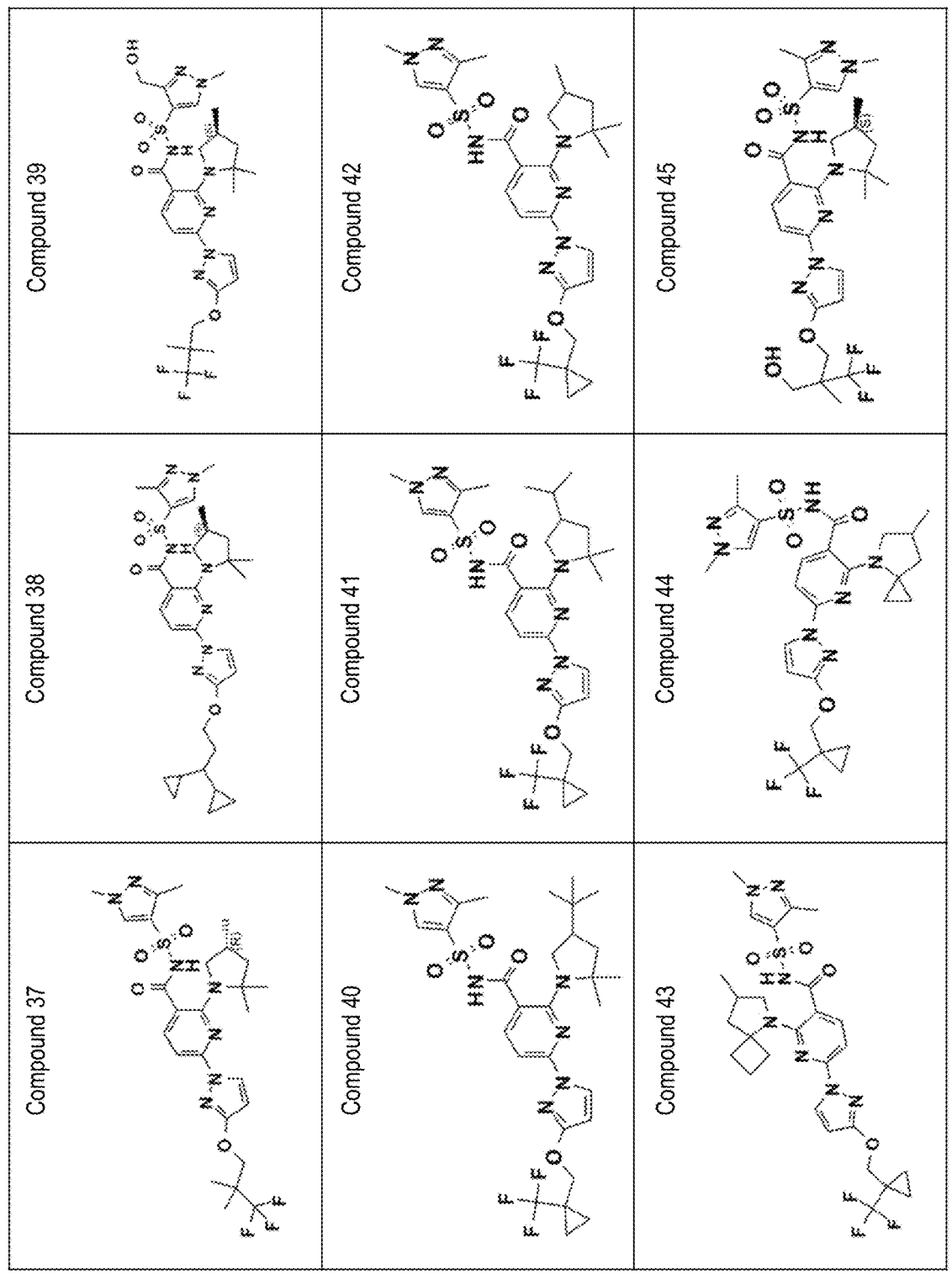
Figure 1:
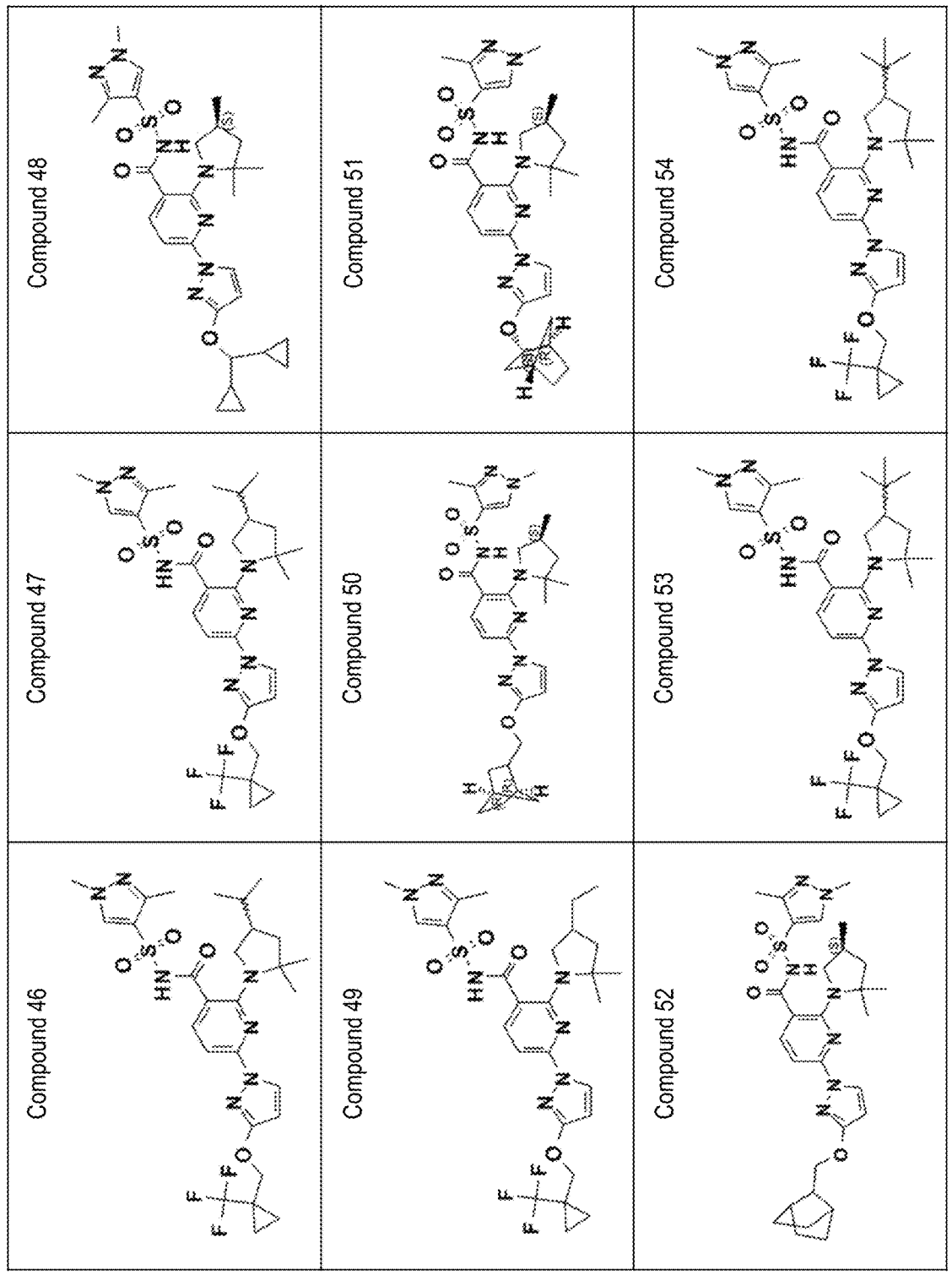
Figure 1:
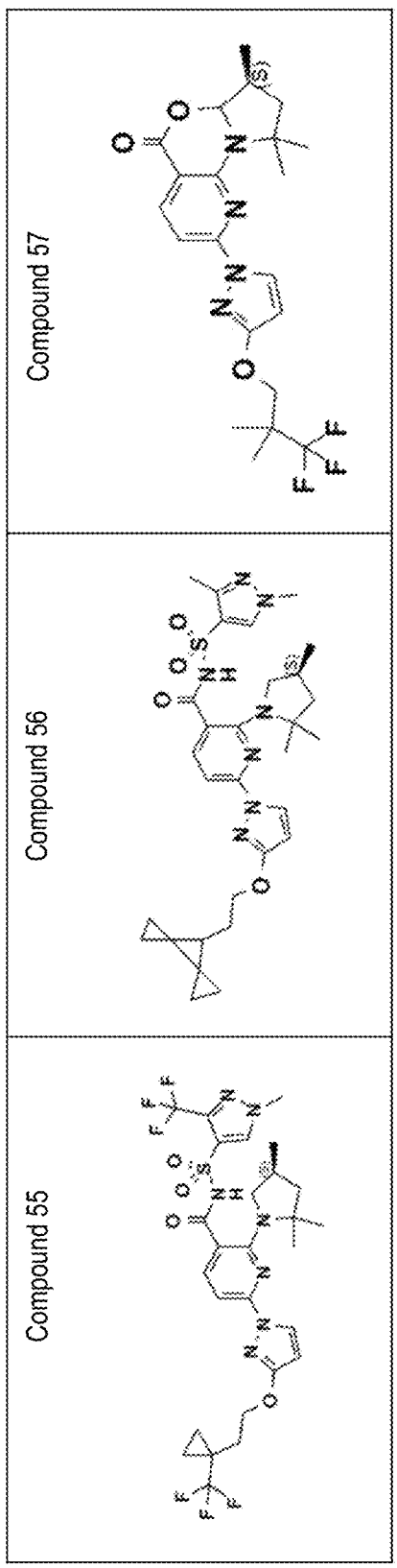

As used herein, the term "alkyl" refers to a saturated, branched or unbranched aliphatic hydrocarbon containing carbon atoms (such as, for example, 1, 2, 3, 4, 5, 6, 7, 8, 9, 10, 11, 12, 13, 14, 15, 16, 17, 18, 19, or 20 carbon atoms). Alkyl groups may be substituted or unsubstituted.

The term "alkoxy" as used herein refers to an alkyl or cycloalkyl covalently bonded to an oxygen atom. Alkoxy groups may be substituted or unsubstituted.

As used herein, "cycloalkyl" refers to a cyclic, bicyclic, tricyclic, or polycyclic non-aromatic hydrocarbon groups having 3 to 12 carbons (such as, for example 3-10 carbons). "Cycloalkyl" groups encompass monocyclic, bicyclic, tricyclic, bridged, fused, and spiro rings, including mono Spiro and dispiro rings. Non-limiting examples of cycloalkyl groups are cyclopropyl, cyclobutyl, cyclopentyl, cyclohexyl, adamantyl, norbornyl, and dispiro[2.0.2.1]heptane. Cycloalkyl groups may be substituted or unsubstituted.

"Substituted," whether preceded by the term "optionally" or not, indicates that at least one hydrogen of the "substituted" group is replaced by a substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position.

As used herein, "deuterated derivative(s)" means the same chemical structure, but with one or more hydrogen atoms replaced by a deuterium atom.

As used herein, "CFTR" means cystic fibrosis transmembrane conductance regulator.

As used herein, "mutations" can refer to mutations in the CFTR gene or the CFTR protein. A "CFTR gene mutation" refers to a mutation in the CFTR gene, and a "CFTR protein mutation" refers to a mutation in the CFTR protein. A genetic defect or mutation, or a change in the nucleotides in a gene in general results in a mutation in the CFTR protein translated from that gene, or a frame shift(s).

The term "F508del" refers to a mutant CFTR protein which is lacking the amino acid phenylalanine at position 508.

As used herein, a patient who is "homozygous" for a particular gene mutation has the same mutation on each allele.

As used herein, a patient who is "heterozygous" for a particular gene mutation has this mutation on one allele, and a different mutation on the other allele.

As used herein, the term "modulator" refers to a compound that increases the activity of a biological compound such as a protein. For example, a CFTR modulator is a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that facilitates the processing and trafficking of CFTR to increase the amount of CFTR at the cell surface. Compounds of Formulae (I), (II), (III), (IV), (V), and (VI), and Compound II, and their pharmaceutically acceptable salts thereof disclosed herein are CFTR correctors.

As used herein, the term "CFTR potentiator" refers to a compound that increases the channel activity of CFTR protein located at the cell surface, resulting in enhanced ion transport. Compound III disclosed herein is a CFTR potentiator.

As used herein, the term "active pharmaceutical ingredient" ("API") refers to a biologically active compound.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. Pharmaceutically acceptable salts are well known in the art. For example, S. M. Berge, et al. describe pharmaceutically acceptable salts in detail in *J. Pharmaceutical Sciences*, 1977, 66, 1-19.

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order. Amorphous solids are generally isotropic, i.e. exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See, US 2004/0006237 for a comparison of XRPDs of an amorphous material and crystalline material.

As used herein, the term "substantially amorphous" refers to a solid material having little or no long range order in the position of its molecules. For example, substantially amorphous materials have less than 15% crystallinity (e.g., less than 10% crystallinity or less than 5% crystallinity). It is also noted that the term 'substantially amorphous' includes the descriptor, 'amorphous', which refers to materials having no (0%) crystallinity.

As used herein, the term "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase); or alternatively, an amorphous drug (dispersed phase) in an amorphous polymer (continuous phase). In some embodiments, a solid dispersion includes the polymer constituting the dispersed phase, and the drug constitute the continuous phase. Or, a solid dispersion includes the drug constituting the dispersed phase, and the polymer constituting the continuous phase.

The terms "patient" and "subject" are used interchangeably and refer to an animal including humans.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment, and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement of CF or its symptoms or lessening the severity of CF or its symptoms in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent.

Each of compounds of Formulae (I), (II), (III), (IV), (V), and (VI), and Compounds II, III, IV, and pharmaceutically acceptable salts thereof, and their deuterated derivatives described herein independently can be administered once daily, twice daily, or three times daily. In some embodiments, at least one compound chosen from Compounds of Formulae (I), (II), (III), (IV), (V), and (VI), and pharmaceutically acceptable salts thereof, and their deuterated derivatives is administered once daily. In some embodiments, at least one compound chosen from Compounds of Formulae (I), (II), (III), (IV), (V), and (VI), and pharmaceutically acceptable salts thereof, and their deuterated derivatives are administered twice daily. In some embodiments, at least one compound chosen from Compound II and pharmaceutically acceptable salts thereof is administered once daily. In some embodiments, at least one compound chosen from Compound II and pharmaceutically acceptable salts thereof is administered twice daily. In some embodiments, at least one compound chosen from Compound III and pharmaceutically acceptable salts thereof is administered once daily. In some embodiments, at least one compound chosen from Compound III and pharmaceutically acceptable salts thereof is administered twice daily. In some embodiments, at least one compound chosen from Compound IV and pharmaceutically acceptable salts thereof is administered once daily. In some embodiments, at least one compound chosen from Compound IV and pharmaceutically acceptable salts thereof is administered twice daily. In some embodiments, a deuterated derivative of Compound II, III, and/or IV or a pharmaceutically acceptable salt thereof is employed in any one of these embodiments.

In some embodiments, 10 mg to 1,500 mg of a compound disclosed herein, a pharmaceutically acceptable salt thereof, or a deuterated derivative of such compound or salt are administered daily.

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form. For example, "10 mg of at least one compound chosen from compounds of Formula (I) and pharmaceutically acceptable salts thereof" includes 10 mg of a compound of Formula (I) and a concentration of a pharmaceutically acceptable salt of compounds of Formula (I) equivalent to 10 mg of compounds of Formula (I).

As stated above, disclosed herein are compounds of Formula (I):

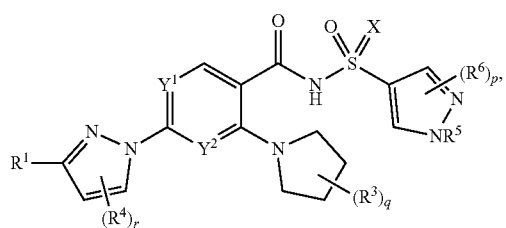

(I)

pharmaceutically acceptable salts thereof, and deuterated derivatives of any of the foregoing,
wherein:
one of $Y^1$ and $Y^2$ is N and the other is CH;
X is chosen from O, NH, and $N(C_1\text{-}C_4$ alkyl) groups;
$R^1$ is $-(C(R^2)_2)_k-O-(C(R^2)_2)_m R^7$,
each $R^2$ is independently chosen from hydrogen, halogens, cyano, hydroxyl, $C_1\text{-}C_2$ alkoxyl groups, and $C_1\text{-}C_2$ alkyl groups optionally substituted with one or more substituents each independently chosen from halogens, hydroxyl, and $C_{3\text{-}5}$ cycloalkyl groups optionally substituted with one or more substituents each independently chosen from $C_1\text{-}C_2$ alkyl groups, halogenated $C_1\text{-}C_2$ alkyl groups, and halogens;
each $R^3$ is independently chosen from $C_1\text{-}C_4$ alkyl groups optionally substituted with one or more hydroxyl groups, or optionally two geminal $R^3$, together with the carbon atom to which they are attached, form a $C_{3\text{-}4}$ cycloalkyl;
each $R^4$ is independently chosen from halogens;
$R^5$ is chosen from hydrogen and $C_1\text{-}C_4$ alkyl groups;
each $R^6$ is independently chosen from halogens, cyano, hydroxyl, hydroxymethyl, $C_1\text{-}C_2$ alkoxyl groups, $C_1\text{-}C_2$ alkyl groups, and halogenated $C_1\text{-}C_2$ alkyl groups;
$R^7$ is chosen from hydrogen, halogens, cyano, $C_1\text{-}C_2$ alkyl groups optionally substituted with one or more substituents each independently chosen from halogens and hydroxyl, and $C_3\text{-}C_{10}$ cycloalkyl groups optionally substituted with one or more substituents each independently chosen from $C_1\text{-}C_2$ alkyl groups, halogenated $C_1\text{-}C_2$ alkyl groups, and halogens;
k is 0 or 1;
r is 0 or 1;
m is 0, 1, 2, or 3;
p is 0, 1, or 2; and
q is 0, 1, 2, 3, 4, 5, 6, 7, or 8.

Also disclosed herein are compounds of Formula (II):

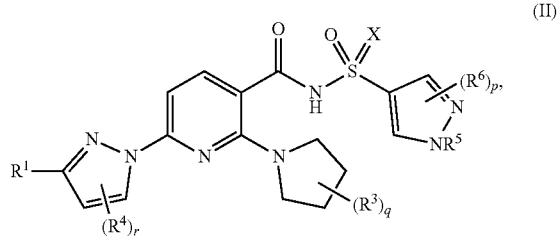

(II)

pharmaceutically acceptable salts thereof, and deuterated derivatives of any of the foregoing,
wherein:
X is chosen from O, NH, and $N(C_1\text{-}C_4$ alkyl) groups;
$R^1$ is $-(C(R^2)_2)_k-O-(C(R^2)_2)_m R^7$,
each $R^2$ is independently chosen from hydrogen, halogens, cyano, hydroxyl, $C_1\text{-}C_2$ alkoxyl groups, and $C_1\text{-}C_2$ alkyl groups optionally substituted with one or more substituents each independently chosen from halogens, hydroxyl, and $C_{3\text{-}5}$ cycloalkyl groups optionally substituted with one or more substituents each independently chosen from $C_1\text{-}C_2$ alkyl groups, halogenated $C_1\text{-}C_2$ alkyl groups, and halogens;
each $R^3$ is independently chosen from $C_1\text{-}C_4$ alkyl groups optionally substituted with one or more hydroxyl groups, or optionally two geminal $R^3$, together with the carbon atom to which they are attached, form a $C_{3\text{-}4}$ cycloalkyl;
each $R^4$ is independently chosen from halogens;
$R^5$ is chosen from hydrogen and $C_1\text{-}C_4$ alkyl groups;

each $R^6$ is independently chosen from halogens, cyano, hydroxyl, hydroxymethyl, $C_1$-$C_2$ alkoxyl groups, $C_1$-$C_2$ alkyl groups, and halogenated $C_1$-$C_2$ alkyl groups;

$R^7$ is chosen from hydrogen halogens, cyano, $C_1$-$C_2$ alkyl groups optionally substituted with one or more substituents each independently chosen from halogens and hydroxy, and $C_3$-$C_{10}$ cycloalkyl groups optionally substituted with one or more substituents each independently chosen from $C_1$-$C_2$ alkyl groups, halogenated $C_1$-$C_2$ alkyl groups, and halogens;

k is 0 or 1;
r is 0 or 1;
m is 0, 1, 2, or 3;
p is 0, 1, or 2; and
q is 0, 1, 2, 3, 4, 5, 6, 7, or 8.

Encompassed within the scope of Formulae (I) and (II) are compounds comprising an

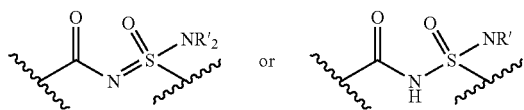

group (where R' is H or $C_1$-$C_4$ alkyl), i.e., wherein X is chosen from NH and N($C_1$-$C_4$ alkyl) groups and pharmaceutically acceptable salts thereof, and deuterated derivatives of any of the foregoing. In some embodiments, a compound having any one of the structural formulae shown in FIG. 1 but one of the (S=O) group of the sulfonamide group in each formula is replaced with NH or NR', or a pharmaceutically acceptable salt thereof, or a deuterated derivative of any of the foregoing is encompassed, either as an isomeric mixture or enantioenriched (e.g., >90% ee, >95% ee, or >98% ee) isomers.

Also disclosed herein are compounds of Formula (III):

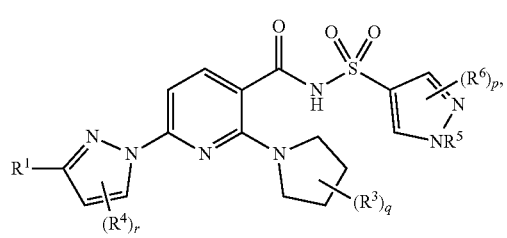

(III)

pharmaceutically acceptable salts thereof, and deuterated derivatives of any of the foregoing,
wherein:

$R^1$ is —$(C(R^2)_2)_k$—O—$(C(R^2)_2)_m R^7$, each $R^2$ is independently chosen from hydrogen; halogens; cyano; hydroxy; $C_1$-$C_2$ alkoxy groups; and $C_1$-$C_2$ alkyl groups optionally substituted with one or more substituents each independently chosen from halogens, hydroxy, and $C_{3-5}$ cycloalkyl groups optionally substituted with one or more substituents each independently chosen from $C_1$-$C_2$ alkyl groups, halogenated $C_1$-$C_2$ alkyl groups, and halogens;

each $R^3$ is independently chosen from $C_1$-$C_4$ alkyl groups optionally substituted with one or more hydroxy groups, or optionally two geminal $R^3$, together with the carbon atom to which they are attached, form a $C_{3-4}$ cycloalkyl;

each $R^4$ is independently chosen from halogens;
$R^5$ is chosen from hydrogen and $C_1$-$C_4$ alkyl groups;
each $R^6$ is independently chosen from halogens, cyano, hydroxy, hydroxymethyl, $C_1$-$C_2$ alkoxy groups, $C_1$-$C_2$ alkyl groups, and halogenated $C_1$-$C_2$ alkyl groups;

$R^7$ is chosen from hydrogen, halogens, cyano, $C_1$-$C_2$ alkyl groups optionally substituted with one or more substituents each independently chosen from halogens and hydroxy, and $C_3$-$C_{10}$ cycloalkyl groups optionally substituted with one or more substituents each independently chosen from $C_1$-$C_2$ alkyl groups, halogenated $C_1$-$C_2$ alkyl groups, and halogens;

k is 0 or 1;
r is 0 or 1;
m is 0, 1, 2, or 3;
p is 0, 1, or 2; and
q is 0, 1, 2, 3, 4, 5, 6, 7, or 8.

In some embodiments, in compounds of Formulae (I), (II), and (III), pharmaceutically acceptable salts thereof, and/or deuterated derivatives of any of the foregoing:

each $R^2$ is independently chosen from hydrogen and $C_1$-$C_2$ alkyl groups;
$R^5$ is chosen from hydrogen and $C_1$-$C_2$ alkyl groups; and
each $R^6$ is independently chosen from $C_1$-$C_2$ alkyl groups.

In some embodiments, in compounds of Formulae (I), (II), and (III), pharmaceutically acceptable salts thereof, and/or deuterated derivatives of any of the foregoing:

$R^1$ is —O—$(CH_2)(C(R^2)_2)_{(m-1)} R^7$, $R^7$ is independently chosen from $C_1$-$C_2$ alkyl groups optionally substituted with one or more substituents each independently chosen from halogens, hydroxyl, and $C_3$-$C_{10}$ cycloalkyl groups optionally substituted with one or more substituents each independently chosen from $C_1$-$C_2$ alkyl groups, halogenated $C_1$-$C_2$ alkyl groups, and halogens, and each $R^2$ is independently chosen from $C_1$-$C_2$ alkyl groups, OH, $C_1$-$C_2$ alkoxyl groups, and halogens;

$R^4$ is H; and
q is 0, 1, 2, 3, or 4.

In some embodiments, in compounds of Formulae (I), (II), and (III), pharmaceutically acceptable salts thereof, and/or deuterated derivatives of any of the foregoing, r is 0.

Also disclosed herein are compounds of Formula (IV):

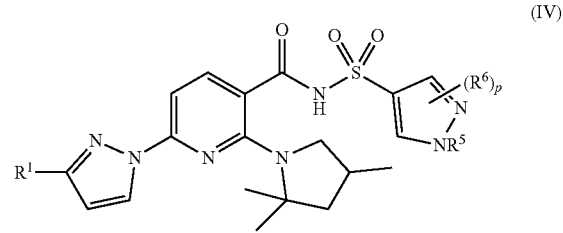

(IV)

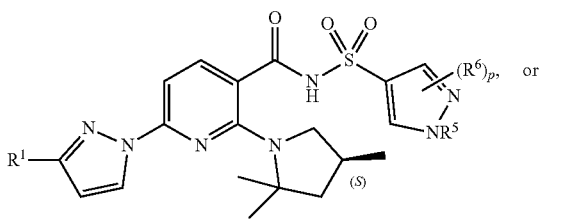

(V)

or

-continued (VI)

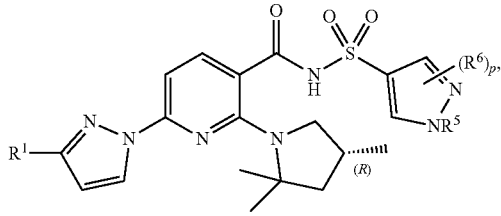

pharmaceutically acceptable salts of any of the foregoing, and deuterated derivatives of any of the foregoing, wherein:

$R^1$ is —O—$(CH_2)(C(R^2)_2)_{(m-1)}R^7$, each $R^2$ is independently chosen from $C_1$-$C_2$ alkyl groups, OH, $C_1$-$C_2$ alkoxy groups, and halogens;

$R^7$ is chosen from $C_1$-$C_2$ alkyl groups optionally substituted with one or more substituents each independently chosen from halogens, and $C_3$-$C_{10}$ cycloalkyl groups optionally substituted with one or more substituents each independently chosen from $C_1$-$C_2$ alkyl groups, halogenated $C_1$-$C_2$ alkyl groups, and halogens $R^5$ is chosen from hydrogen and $C_1$-$C_2$ alkyl groups;

each $R^6$ is independently chosen from $C_1$-$C_2$ alkyl groups; and p is 0, 1, or 2.

In some embodiments, p is 0 or 1. In some embodiments, p is 0.

In some embodiments, in compounds of Formulae (I), (II), (III), (IV), (V), and (VI), and pharmaceutically acceptable salts thereof, each $R^2$ is independently chosen from $CH_3$, OH, F, and $OCH_3$. In some embodiments, p is 0 or 1. In some embodiments, p is 0.

In some embodiments, in compounds of Formulae (I), (II), (III), (IV), (V), and (VI), and pharmaceutically acceptable salts thereof, p is 1; $R^5$ is methyl; and $R^6$ is methyl.

In some embodiments, in compounds of Formulae (I), (II), (III), (IV), (V), and (VI), and pharmaceutically acceptable salts thereof, $R^7$ is a cyclopropyl group. In some embodiments, $R^7$ is a cyclopropyl group substituted with a halogenated $C_1$ alkyl group. In some embodiments, $R^7$ is a cyclopropyl group substituted with one or more halogens. In some embodiments, $R^7$ is a cyclopropyl group substituted with one or more $C_1$ alkyl groups. In some embodiments, $R^7$ is a cyclopropyl group substituted with one or more halogens and one or more $C_1$ alkyl groups. In some embodiments, $R^7$ is a $CF_3$ group. In some embodiments, $R^7$ is chosen from $C_4$ cycloalkyl groups optionally substituted with one or more substituents each independently chosen from $C_1$-$C_2$ alkyl groups, halogenated $C_1$-$C_2$ alkyl groups, and halogens. In some embodiments, $R^7$ is chosen from $C_5$ cycloalkyl groups optionally substituted with one or more substituents each independently chosen from $C_1$-$C_2$ alkyl groups, halogenated $C_1$-$C_2$ alkyl groups, and halogens. In some embodiments, $C_5$ cycloalkyl groups are bicyclic.

In some embodiments, $R^7$ is chosen from $C_7$ cycloalkyl groups optionally substituted with one or more substituents each independently chosen from $C_1$-$C_2$ alkyl groups, halogenated $C_1$-$C_2$ alkyl groups, and halogens. In some embodiments, $C_7$ cycloalkyl groups are bicyclic. In some embodiments, $C_7$ cycloalkyl groups are tricyclic.

Also disclosed herein are compounds having a formula chosen from any one of the formulae depicted in FIG. 1 and pharmaceutically acceptable salts thereof.

Also disclosed herein is a compound having the following formula:

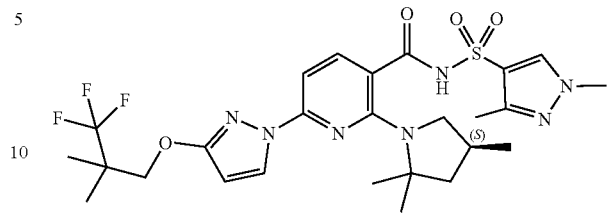

a pharmaceutically acceptable salt thereof, or a deuterated derivative of any of the foregoing.

Also disclosed herein is a compound having the following formula:

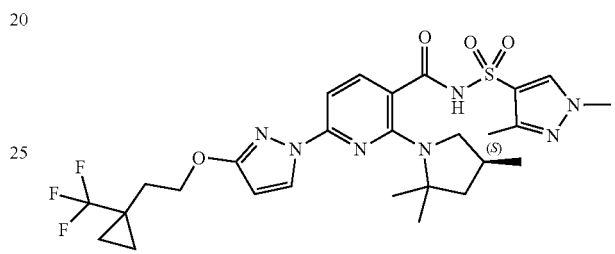

a pharmaceutically acceptable salt thereof, or a deuterated derivative of any of the foregoing.

Also disclosed herein is a compound having the following formula:

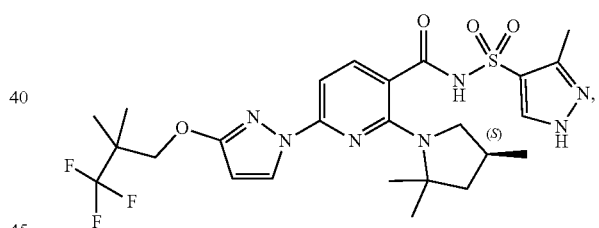

a pharmaceutically acceptable salt thereof, or a deuterated derivative of any of the foregoing.

Also disclosed herein is a compound having the following formula:

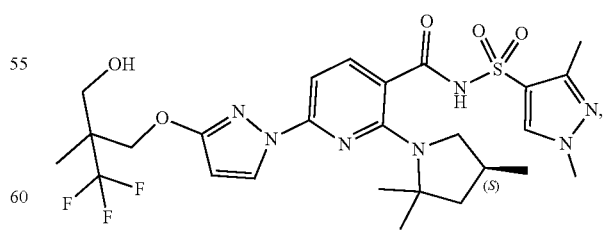

a pharmaceutically acceptable salt thereof, or a deuterated derivative of any of the foregoing.

Also disclosed herein is a compound having the following formula:

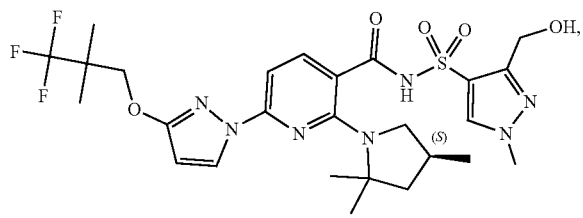

a pharmaceutically acceptable salt thereof, or a deuterated derivative of any of the foregoing.

Also disclosed herein is a compound having the following formula:

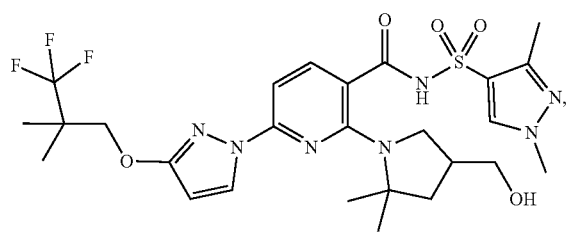 [SMILES: Cc1nn(C)cc1S(=O)(=O)NC(=O)c1ccc(-n2ccc(OCC(C)(C)C(F)(F)F)n2)nc1N1CC(CO)CC1(C)C]

a pharmaceutically acceptable salt thereof, or a deuterated derivative of any of the foregoing.

Also disclosed herein is a compound having the following formula:

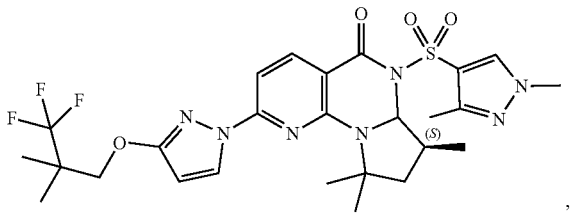

a pharmaceutically acceptable salt thereof, or a deuterated derivative of any of the foregoing.

Also disclosed herein is a compound having the following formula:

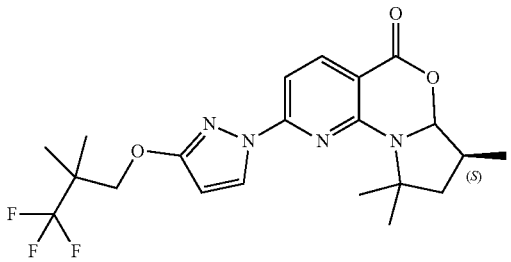

a pharmaceutically acceptable salt thereof, or a deuterated derivative of any of the foregoing.

Also disclosed herein is a compound having the following formula:

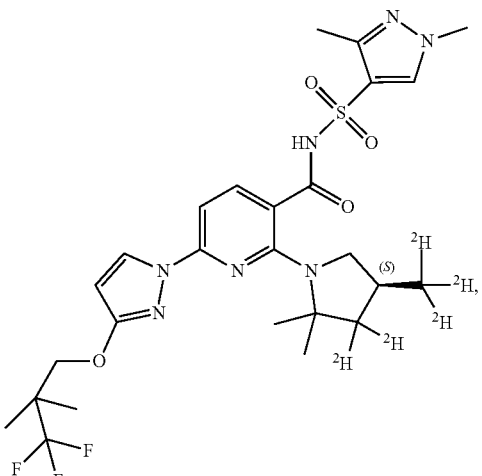

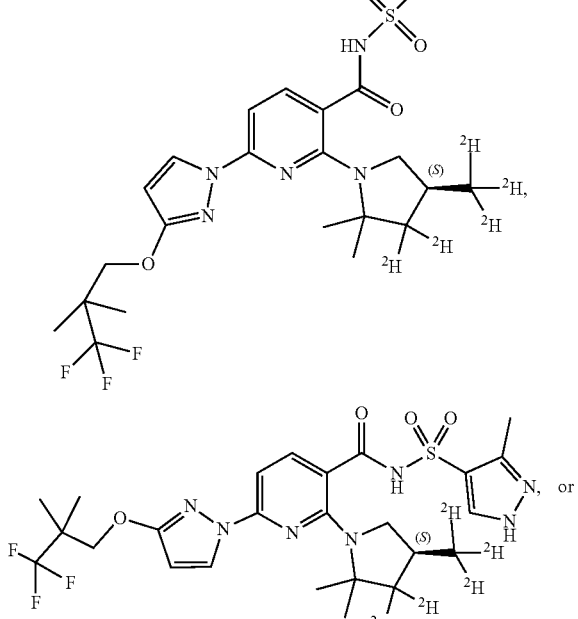

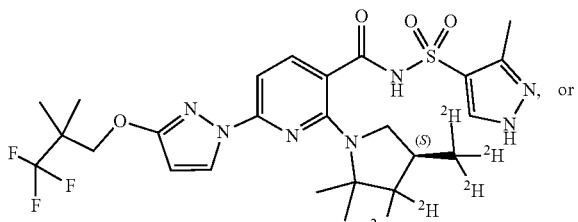

a pharmaceutically acceptable salt thereof, or a deuterated derivative of any of the foregoing.

Also disclosed herein is a compound having any one of the following formulae:

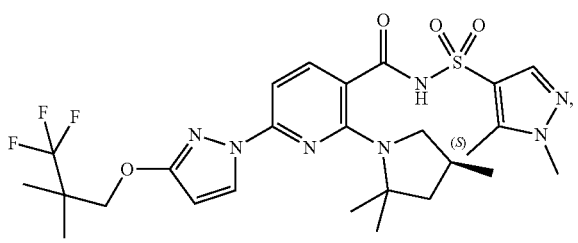

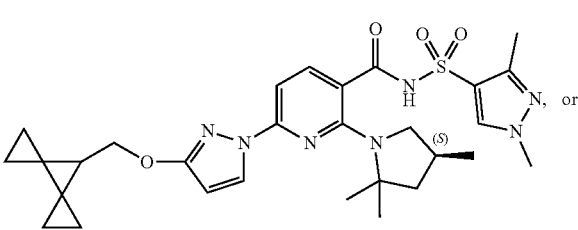

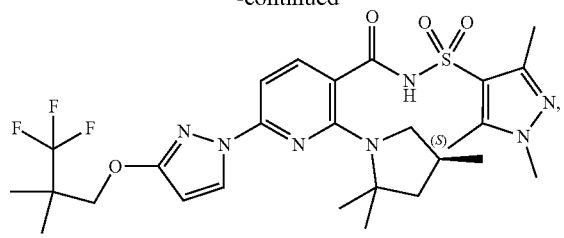
a pharmaceutically acceptable salt thereof, or a deuterated derivative of any of the foregoing.
Also disclosed herein is a compound having any one of the following formulae:
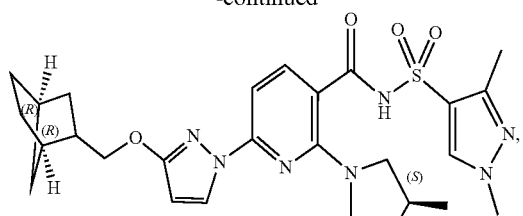
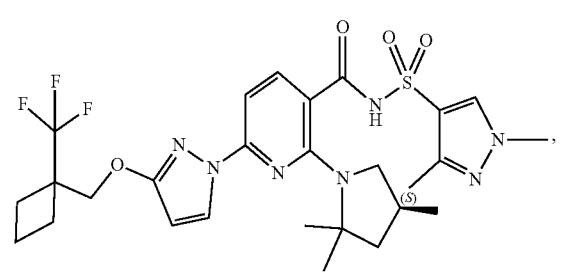
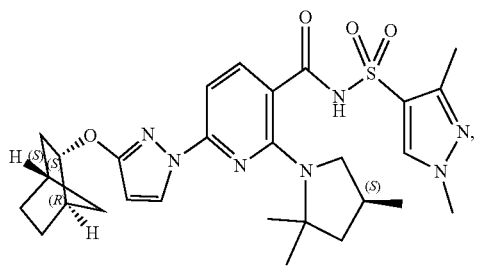
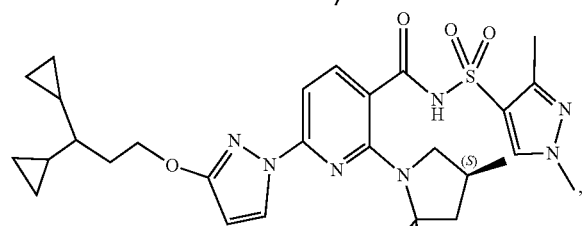
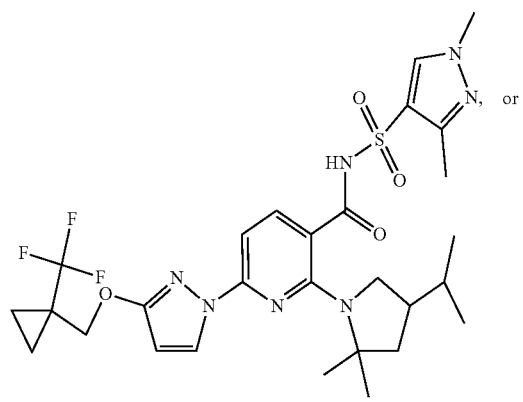
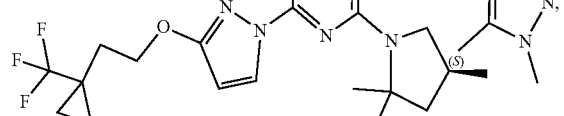
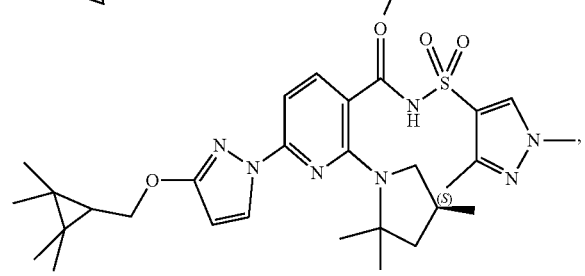
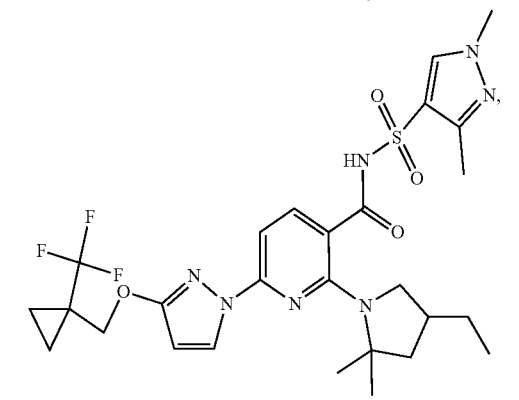
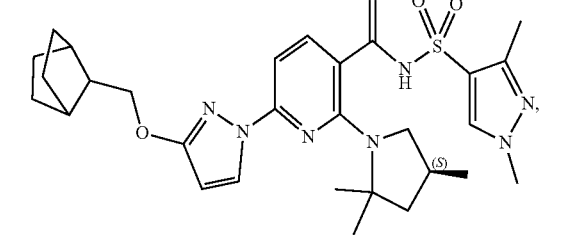
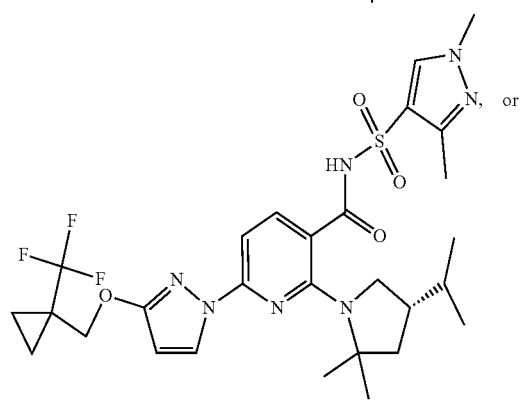

-continued

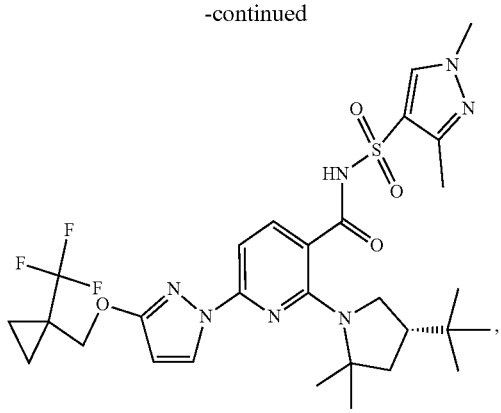

a pharmaceutically acceptable salt thereof, or a deuterated derivative of any of the foregoing.

Suitable pharmaceutically acceptable salts are, for example, those disclosed in S. M. Berge, et al. *J. Pharmaceutical Sciences*, 1977, 66, 1-19. For example, Table 1 of that article provides the following pharmaceutically acceptable salts:

TABLE 1

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable salts derived from appropriate acids include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

In some embodiments, at least one compound chosen from the novel compounds disclosed herein, pharmaceutically acceptable salts thereof, and deuterated derivatives of the foregoing is administered in combination with at least one compound chosen from Compound II, pharmaceutically acceptable salts thereof, and deuterated derivatives of the foregoing. In some embodiments, at least one compound chosen from the novel compounds disclosed herein, pharmaceutically acceptable salts thereof, and deuterated derivatives of the foregoing is administered in combination with at least one compound chosen from Compound III and pharmaceutically acceptable salts thereof. In some embodiments, at least one compound chosen from the novel compounds disclosed herein, pharmaceutically acceptable salts thereof, and deuterated derivatives of the foregoing is administered in combination with at least one compound chosen from Compound IV and pharmaceutically acceptable salts thereof. In some embodiments, at least one compound chosen from the novel compounds disclosed herein, pharmaceutically acceptable salts, and deuterated derivatives of the foregoing thereof is administered in combination with Compounds II or a pharmaceutically acceptable salt or deuterated derivative thereof and at least one compound chosen from Compound III, pharmaceutically acceptable salts thereof, and deuterated derivatives of any of the foregoing. In some embodiments, at least one compound chosen from the novel compounds disclosed herein, pharmaceutically acceptable salts, and deuterated derivatives of any of the foregoing thereof is administered in combination with at least one compound chosen from Compound III, pharmaceutically acceptable salts thereof, and deuterated derivatives of any of the foregoing and at least one compound chosen from Compound IV, pharmaceutically acceptable salts thereof, and deuterated derivatives of any of the foregoing.

In some embodiments, at least one novel compound (and/or at least one pharmaceutically acceptable salt thereof and/or at least one deuterated derivative of such compound or salt) can be administered in combination with at least one additional active pharmaceutical ingredient. In some embodiments, at least one additional active pharmaceutical ingredient is chosen from:

(a) Compound II:

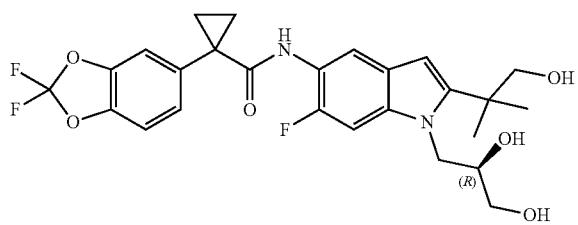

and pharmaceutically acceptable salts thereof.

A chemical name for Compound II is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide;

(b) Compound III:

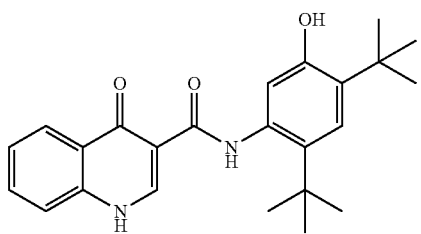 [SMILES: CC(C)(C)c1cc(C(C)(C)C)c(NC(=O)c2c[nH]c3ccccc3c2=O)cc1O]

and pharmaceutically acceptable salts thereof.

A chemical name for Compound III is N-(5-hydroxy-2,4-di-tert-butyl-phenyl)-4-oxo-1H-quinoline-3-carboxamide; and (c) Compound IV:

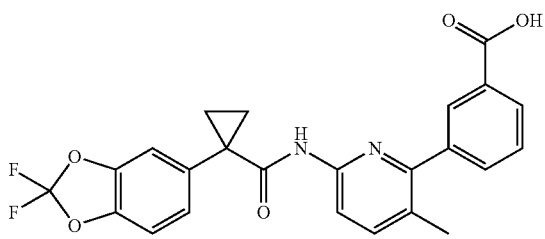 [SMILES: Cc1ccc(NC(=O)C2(c3ccc4c(c3)OC(F)(F)O4)CC2)nc1-c1cccc(C(=O)O)c1]

and pharmaceutically acceptable salts thereof.

A chemical name for Compound IV is 3-(6-(1-(2,2-difluorobenzo[d][1,3]dioxol-5-yl)cyclopropanecarboxamido)-3-methylpyridin-2-yl)benzoic acid. In some embodiments, Compound 1 and/or a pharmaceutically acceptable salt thereof can be administered in combination with Compound II and/or a pharmaceutically acceptable salt thereof. In some embodiments, Compound 1 and/or a pharmaceutically acceptable salt thereof can be administered in combination with Compound III and/or a pharmaceutically acceptable salt thereof. In some embodiments, Compound 1 and/or a pharmaceutically acceptable salt thereof can be administered in combination with Compound IV and/or a pharmaceutically acceptable salt thereof. In some embodiments Compound 1 and/or a pharmaceutically acceptable salt thereof can be administered in combination with Compounds II and/or a pharmaceutically acceptable salt thereof and Compound III and/or a pharmaceutically acceptable salt thereof. In some embodiments Compound 1 and/or a pharmaceutically acceptable salt thereof can be administered in combination with Compounds II and/or a pharmaceutically acceptable salt thereof and Compound IV and/or a pharmaceutically acceptable salt thereof.

In one aspect, the disclosure features a pharmaceutical composition comprising Compound 1 and/or a pharmaceutically acceptable salt thereof, and a pharmaceutically acceptable carrier.

In one aspect, the disclosure features a pharmaceutical composition comprising Compound 1 and/or a pharmaceutically acceptable salt thereof, Compound II and/or a pharmaceutically acceptable salt thereof, and a pharmaceutically acceptable carrier.

In one aspect, the disclosure features a pharmaceutical composition comprising Compound 1 and/or a pharmaceutically acceptable salt thereof, Compound III and/or a pharmaceutically acceptable salt thereof, and a pharmaceutically acceptable carrier.

In one aspect, the disclosure features a pharmaceutical composition comprising Compound 1 and/or a pharmaceutically acceptable salt thereof, Compound II and/or a pharmaceutically acceptable salt thereof, Compound III and/or a pharmaceutically acceptable salt thereof, and a pharmaceutically acceptable carrier.

Any of the novel compounds disclosed herein, such as for example, compounds of Formula (I), (II), (III), (IV), (V), or (VI), and their pharmaceutically acceptable salts thereof, and deuterated derivatives of such compounds and salts can be comprised in a single pharmaceutical composition or separate pharmaceutical compositions in combination with other additional active pharmaceutical ingredient(s) (e.g., Compound II, III, or IV, or its pharmaceutically acceptable salt thereof, or a deuterated derivative of such Compound or salt). Such pharmaceutical compositions can be administered once daily or multiple times daily, such as twice daily. In some embodiments, the disclosure features a pharmaceutical composition comprising at least one compound chosen from any of the compounds disclosed herein and pharmaceutically acceptable salts thereof, and at least one pharmaceutically acceptable carrier.

In some embodiments, the disclosure features a pharmaceutical composition comprising at least one compound chosen from the novel compounds disclosed herein and pharmaceutically acceptable salts thereof, at least one compound chosen from Compound II and pharmaceutically acceptable salts thereof, and at least one pharmaceutically acceptable carrier.

In some embodiments, the disclosure features a pharmaceutical composition comprising at least one compound chosen from the novel compounds disclosed herein and pharmaceutically acceptable salts thereof, at least one compound chosen from Compound III and pharmaceutically acceptable salts thereof, and at least one pharmaceutically acceptable carrier.

In some embodiments, the disclosure features a pharmaceutical composition comprising at least one compound chosen from the novel compounds disclosed herein and pharmaceutically acceptable salts thereof, at least one compound chosen from Compound II and pharmaceutically acceptable salts thereof, at least one compound chosen from Compound III and pharmaceutically acceptable salts thereof, and at least one pharmaceutically acceptable carrier.

In some embodiments, the disclosure features a pharmaceutical composition comprising at least one compound chosen from the novel compounds disclosed herein and pharmaceutically acceptable salts thereof, at least one compound chosen from Compound III and pharmaceutically acceptable salts thereof, at least one compound chosen from Compound IV and pharmaceutically acceptable salts thereof, and at least one pharmaceutically acceptable carrier.

In some embodiments, pharmaceutical compositions disclosed herein comprise at least one additional active pharmaceutical ingredient. In some embodiments, the at least one additional active pharmaceutical ingredient is a CFTR modulator. In some embodiments, the at least one additional active pharmaceutical ingredient is a CFTR corrector. In some embodiments, the at least one additional active pharmaceutical ingredient is a CFTR potentiator. In some embodiments, the pharmaceutical composition comprises (i) a compound of Formulae (I), (II), (III), (IV), (V), or (VI), or a pharmaceutically acceptable salt thereof, or a deuterated derivative of such compound or salt; and (ii) at least two additional active pharmaceutical ingredients, one of which is a CFTR corrector and one of which is a CFTR potentiator.

In some embodiments, at least one additional active pharmaceutical ingredient is selected from mucolytic agents, bronchodialators, antibiotics, anti-infective agents, and anti-inflammatory agents.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure, including a pharmaceutical composition comprising combinations described previously, can be employed in combination therapies; that is, the compositions can be administered concurrently with, prior to, or subsequent to, at least one additional active pharmaceutical ingredient or medical procedures.

Pharmaceutical compositions comprising these combinations are useful for treating cystic fibrosis.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and anti-oxidants.

In some embodiments, the methods of the disclosure employ administering to a patient in need thereof at least one compound chosen from any of the compounds disclosed herein and pharmaceutically acceptable salts thereof, and at least one compound chosen from Compound II, Compound III, Compound IV, and pharmaceutically acceptable salts of any of the foregoing.

Any suitable pharmaceutical compositions known in the art can be used for the novel compounds disclosed herein, Compound II, Compound III, Compound IV, and pharmaceutically acceptable salts thereof. Some exemplary pharmaceutical compositions for Compound 1 and its pharmaceutically acceptable salts are described in the Examples. Some exemplary pharmaceutical compositions for Compound II and its pharmaceutically acceptable salts can be found in WO 2011/119984 and WO 2014/015841, all of which are incorporated herein by reference. Some exemplary pharmaceutical compositions for Compound III and its pharmaceutically acceptable salts can be found in WO 2007/134279, WO 2010/019239, WO 2011/019413, WO 2012/027731, and WO 2013/130669, all of which are incorporated herein by reference. Some exemplary pharmaceutical compositions for Compound IV and its pharmaceutically acceptable salts can be found in WO 2010/037066, WO 2011/127241, WO 2013/112804, and WO 2014/071122, all of which are incorporated herein by reference.

In some embodiments, a pharmaceutical composition comprising at least one compound chosen from the novel compounds disclosed herein and pharmaceutically acceptable salts thereof is administered with a pharmaceutical composition comprising Compound II and Compound III. Pharmaceutical compositions comprising Compound II and Compound III are disclosed in PCT Publication No. WO 2015/160787, incorporated herein by reference. An exemplary embodiment is shown in the following Table 2:

TABLE 2

Exemplary Tablet Comprising 100 mg of Compound II and 150 mg of Compound III.

| | Ingredient | Amount per tablet (mg) |
|---|---|---|
| Intra-granular | Compound II SDD (spray dried dispersion) (80 wt % Compound II, 20 wt % HPMC) | 125 |

TABLE 2-continued

Exemplary Tablet Comprising 100 mg of Compound II and 150 mg of Compound III.

| | Ingredient | Amount per tablet (mg) |
|---|---|---|
| | Compound III SDD (80 wt % Compound III, 19.5 wt % HPMCAS-HG; 0.5 wt % sodium lauryl sulfate) | 187.5 |
| | Microcrystalline cellulose | 131.4 |
| | Croscarmellose Sodium | 29.6 |
| | Total | 473.5 |
| Extra-granular | Microcrystalline cellulose | 112.5 |
| | Magnesium Stearate | 5.9 |
| | Total | 118.4 |
| Total uncoated Tablet | | 591.9 |
| Film coat | Opadry | 17.7 |
| Total coated Tablet | | 609.6 |

In some embodiments, a pharmaceutical composition comprising at least one compound chosen from the novel compounds disclosed herein and pharmaceutical salts thereof is administered with a pharmaceutical composition comprising Compound III. Pharmaceutical compositions comprising Compound III are disclosed in PCT Publication No. WO 2010/019239, incorporated herein by reference. An exemplary embodiment is shown in the following Table 3:

TABLE 3

Ingredients for Exemplary Tablet of Compound III.

| Tablet Formulation | Percent Dose % Wt./Wt. | Dose (mg) | Batch (g) |
|---|---|---|---|
| Compound III SDD (80 wt % Compound III, 19.5 wt % HPMCAS-HG; 0.5 wt % sodium lauryl sulfate) | 34.09% | 187.5 | 23.86 |
| Microcrystalline cellulose | 30.51% | 167.8 | 21.36 |
| Lactose | 30.40% | 167.2 | 21.28 |
| Sodium croscarmellose | 3.000% | 16.50 | 2.100 |
| SLS | 0.500% | 2.750 | 0.3500 |
| Colloidal silicon dioxide | 0.500% | 2.750 | 0.3500 |
| Magnesium stearate | 1.000% | 5.500 | 0.7000 |
| Total | 100% | 550 | 70 |

Additional pharmaceutical compositions comprising Compound III are disclosed in PCT Publication No. WO 2013/130669, incorporated herein by reference. Exemplary mini-tablets (~2 mm diameter, ~2 mm thickness, each mini-tablet weighing about 6.9 mg) was formulated to have approximately 50 mg of Compound III per 26 mini-tablets and approximately 75 mg of Compound III per 39 mini-tablets using the amounts of ingredients recited in Table 4, below.

TABLE 4

Ingredients for mini-tablets for 50 mg and 75 mg potency

| Tablet Formulation | Percent Dose % Wt./Wt. | Dose (mg) 50 mg potency | Dose (mg) 75 mg potency | (Batch g) |
|---|---|---|---|---|
| Compound III SDD (80 wt % Compound III, 19.5 wt % HPMCAS-HG; 0.5 wt % sodium lauryl sulfate) | 35 | 62.5 | 93.8 | 1753.4 |
| Mannitol | 13.5 | 24.1 | 36.2 | 675.2 |
| Lactose | 41 | 73.2 | 109.8 | 2050.2 |
| Sucralose | 2.0 | 3.6 | 5.4 | 100.06 |
| Croscarmellose sodium | 6.0 | 10.7 | 16.1 | 300.1 |
| Colloidal silicon dioxide | 1.0 | 1.8 | 2.7 | 50.0 |
| Magnesium stearate | 1.5 | 2.7 | 4.0 | 74.19 |
| Total | 100 | 178.6 | 268 | 5003.15 |

In some embodiments, the pharmaceutical compositions are a tablet. In some embodiments, the tablets are suitable for oral administration.

The compounds, pharmaceutically acceptable salts thereof, and deuterated analogs of any of the foregoing, and pharmaceutical compositions, of this disclosure, either in monotherapies or in combo-therapies are useful for treating cystic fibrosis.

In some embodiments, disclosed herein are methods of treating, lessening the severity of, or symptomatically treating cystic fibrosis in a patient comprising administering an effective amount of a compound, pharmaceutically acceptable salt thereof, or a deuterated analog of any of the foregoing; or a pharmaceutical composition, of this disclosure to a patient, such as a human, wherein said patient has cystic fibrosis. In some embodiments, the patient has F508del/minimal function (MF) genotypes, F508del/F508del genotypes, F508del/gating genotypes, or F508del/residual function (RF) genotypes.

Patients with an F508del/minimal function genotype are defined as patients that are heterozygous F508del-CFTR with a second CFTR allele containing a mutation that is predicted to result in a CFTR protein with minimal function and that is not expected to respond to Compound II, Compound III, or the combination of Compound II and Compound III. These CFTR mutations were defined using 3 major sources:

biological plausibility for the mutation to respond (i.e., mutation class)
    evidence of clinical severity on a population basis (per CFTR2 patient registry; accessed on 15 Feb. 2016)
        average sweat chloride >86 mmol/L, and
        prevalence of pancreatic insufficiency (PI) >50%
    in vitro testing
        mutations resulting in baseline chloride transport <10% of wild-type CFTR were considered minimal function
        mutations resulting in chloride transport <10% of wild-type CFTR following the addition of Compound II and/or Compound III were considered nonresponsive.

Patients with an F508del/residual function genotype are defined as patients that are heterozygous F508del-CFTR with a second CFTR allele that contains a mutation that results in reduced protein quantity or function at the cell surface which can produce partial CFTR activity. CFTR gene mutations known to result in a residual function phenotype include in some embodiments, a CFTR residual function mutation selected from 2789+5G→A, 3849+10kbC→T, 3272-26A→G, 711+3A→G, E56K, P67L, R74W, D110E, D110H, R117C, L206W, R347H, R352Q, A455E, D579G, E831X, S945L, S977F, F1052V, R1070W, F1074L, D1152H, D1270N, E193K, and K1060T. In some embodiments, the CFTR residual function mutation is selected from R117H, S1235R, I1027T, R668C, G576A, M470V, L997F, R75Q, R1070Q, R31C, D614G, G1069R, R1162L, E56K, A1067T, E193K, or K1060T. In some embodiments, the CFTR residual function mutation is selected from R117H, S1235R, I1027T, R668C, G576A, M470V, L997F, R75Q, R1070Q, R31C, D614G, G1069R, R1162L, E56K, or A1067T.

Patients with an F508del/gating mutation genotype are defined as patients that are heterozygous F508del-CFTR with a second CFTR allele that contains a mutation associated with a gating defect and clinically demonstrated to be responsive to Compound III. Examples of such mutations include: G178R, S549N, S549R, G551D, G551S, G1244E, S1251N, S1255P, and G1349D.

In some embodiments, the methods of treating, lessening the severity of, or symptomatically treating cystic fibrosis disclosed herein are each independently produces an increase in chloride transport above the baseline chloride transport of the patient.

In some embodiments, in the methods of treating, lessening the severity of, or symptomatically treating cystic fibrosis disclosed herein, the patient is heterozygous for F508del, and the other CFTR mutation is any CF-causing mutation. In some embodiments, the paient is heterozygous for F508del, and the other CFTR mutation is any CF-causing mutation, and is expected to be and/or is responsive to any of the novel compounds disclosed herein, such as Compound 1, Compound II, Compound III and/or Compound IV genotypes based on in vitro and/or clinical data. In some embodiments, the paient is heterozygous for F508del, and the other CFTR mutation is any CF-causing mutation, and is expected to be and/or is responsive to any combinations of (i) the novel compounds disclosed herein, such as Compound 1, and (ii) Compound II, and/or Compound III and/or Compound IV genotypes based on in vitro and/or clinical data.

In some embodiments, in the methods of treating, lessening the severity of, or symptomatically treating cystic fibrosis disclosed herein, the patient possesses a CFTR mutation selected from any of the mutations listed in Table 5.

TABLE 5

| CFTR Mutations |
|---|
| 078delT |
| 444delA |
| 297-1G → A |
| 1078delT |
| 1123\4V |
| 1154insTC |
| 1119delA |
| 1161delC |
| 1138insG |
| 1213delT |
| 1248+1G→A |
| 1249-1G→A |

TABLE 5-continued

| CFTR Mutations |
|---|
| 124del23bp |
| 1259insA |
| 1288insTA |
| 1341+1G->A |
| 1342-2A->C |
| 1461ins4 |
| 1471delA |
| 1497delGG |
| 1507del |
| 1525-1G→A |
| 1525-2A→G |
| 1548delG |
| 1577delTA |
| 1609del CA |
| 1677delTA |
| 1716G/A |
| 1717-1G→A |
| 1717-8G→A |
| 1782delA |
| 1811+1G->C |
| 1811+1.6kbA→G |
| 1811+1G→C |
| 1812-1G->A |
| 1898+1G->A |
| 1812-1G→A |
| 1824delA |
| 182delT |
| 185+1G→T |
| 1898+1G->T |
| 1898+1G→A |
| 1898+1G→C |
| 1898+3A->G |
| 1898+5G->T |
| 1924del7 |
| 1949del84 |
| 2043delG |
| 2055del9→A |
| 2105-2117del13insAGAAA |
| 2118del14 |
| 2143delT |
| 2183AA→G$^a$ |
| 2183delAA→G |
| 2184delA |
| 2184insA |
| 2307insA |
| 2347delG |
| 2556insAT |
| 2585delT |
| 2594delGT |
| 2622+1G->A |
| 2659delC |
| 2711delT |
| 271delT |
| 2721del11 |
| 2732insA |
| 2789+2insA |
| 2789+5G→A |
| 2790-1G→C |
| 2790-1G->C |
| 2869insG |
| 2896insAG |
| 2942insT |
| 2957delT |
| 296+1G→A |
| 2991del32 |
| 3007delG |
| 3028delA |
| 3040G→C |
| 306insA |
| 306insA |
| 1138insG |
| 3120G→A |
| 3120 + 1G → A |
| 3121-1G→A |
| 3121-2A→G |
| 3121-977_3499+248 del2515 |

TABLE 5-continued

| CFTR Mutations |
|---|
| 3132delTG |
| 3141del9 |
| 3171delC |
| 3195del6 |
| 3199del6 |
| 3272-26A->G |
| 3500-2A→G |
| 3600+2insT |
| 365-366insT |
| 3659delC |
| 3667ins4 |
| 3737delA |
| 3791delC |
| 3821delT |
| 3849+10kbC→T |
| 3849+lOkbC->T |
| 3850-1G→A |
| 3850-3T->G |
| 3850-lG->A |
| 3876delA |
| 3878delG |
| 3905InsT |
| 394delTT |
| 4005+1G->A |
| 4005+2T->C |
| 4005+1G->A |
| 4005+lG->A |
| 4010del4 |
| 4015delA |
| 4016insT |
| 4021dupT |
| 4040delA |
| 405+1G→A |
| 405+3A→C |
| 405+lG->A |
| 406-1G→A |
| 406-lG->A |
| 4209TGTT->A |
| 4209TGTT→AA |
| 4279insA |
| 4326delTC |
| 4374+1G→T |
| 4374+lG->T |
| 4382delA |
| 4428insGA |
| 442delA |
| 457TAT→G |
| 541delC |
| 574delA |
| 5T |
| 621+1G→T |
| 621+3A->G |
| 663delT |
| 663delT |
| 675del4 |
| 711+1G→T |
| 711+1G→T |
| 711+3A→G |
| 711+5G→A |
| 712-1G->T |
| 7T |
| 852del22 |
| 935delA |
| 991del5 |
| A1006E |
| A120T |
| A234D |
| A349V |
| A455E |
| A460 |
| A613T |
| A46D |
| A46Db |
| A559T |
| A559Tb |
| A561E |
| C276X |
| C524R |

TABLE 5-continued

| CFTR Mutations |
|---|
| C524X |
| CFTRdel2,3 |
| CFTRdele22-23 |
| D110E |
| D110H |
| D1152H |
| D1270N |
| D192G |
| D443Y |
| D513G |
| D579G |
| D614G |
| D836Y |
| D924N |
| D979V |
| E1104X |
| E116K |
| E1371X |
| E193K |
| E193X |
| E403D |
| E474K |
| E56K |
| E585X |
| E588V |
| E60K |
| E60X |
| E822K |
| E822X |
| E831X |
| E92K |
| E92X |
| F10165 |
| F1052V |
| F1074L |
| F1099L |
| F191V |
| F311del |
| F311L |
| F508C |
| F508del |
| F575Y |
| G1061R |
| G1069R |
| G1244E |
| G1249R |
| G126D |
| G1349D |
| G149R |
| G178R |
| G194R |
| G194V |
| G27R |
| G27X |
| G314E |
| G330X |
| G458V |
| G463V |
| G480C |
| G542X |
| G550X |
| G551D |
| G551S |
| G576A |
| G622D |
| G628R |
| G628R(G->A) |
| G673X |
| G85E |
| G91R |
| G970D |
| G970R |
| G970R |
| H1054D |
| H1085P |
| H1085R |
| H1375P |
| H139R |

TABLE 5-continued

| CFTR Mutations |
|---|
| H199R |
| H199Y |
| H609R |
| H939R |
| I336K |
| I1005R |
| I1027T |
| I1234V |
| I1269N |
| I1366N |
| I148T |
| I175V |
| I3336K |
| I502T |
| I506S |
| I506T |
| I507del |
| I507del |
| I601F |
| I618T |
| I807M |
| I980K |
| IVS14b+5G->A |
| K710X |
| K710X |
| K710X |
| L102R |
| L1065P |
| L1077P |
| L1077Pb |
| L1254X |
| L1324P |
| L1335P |
| L138ins |
| L1480P |
| L15P |
| L165S |
| L206W |
| L218X |
| L227R |
| L320V |
| L346P |
| L453S |
| L467P |
| L467Pb |
| L558S |
| L571S |
| L732X |
| L927P |
| L967S |
| L997F |
| M1101K |
| M1101R |
| M152V |
| M1T |
| M1V |
| M265R |
| M470V |
| M952I |
| M952T |
| N1303K |
| P205S |
| P574H |
| P5L |
| P67L |
| P750L |
| P99L |
| Q1100P |
| Q1291H |
| Q1291R |
| Q1313X |
| Q1382X |
| Q1411X |
| Q1412X |
| Q220X |
| Q237E |
| Q237H |
| Q290X |

TABLE 5-continued

| CFTR Mutations |
|---|
| Q359K/T360K |
| Q39X |
| Q414 |
| Q414X |
| Q452P |
| Q493X |
| Q525X |
| Q552X |
| Q685X |
| Q890X |
| Q890X |
| Q98R |
| Q98X |
| R1066C |
| R1066H |
| R1066M |
| R1070Q |
| R1070W |
| R1102X |
| R1158X |
| R1162L |
| R1162X |
| R117C |
| R117G |
| R117H |
| R117L |
| R117P |
| R1283M |
| R1283S |
| R170H |
| R258G |
| R31C |
| R31L |
| R334L |
| R334Q |
| R334W |
| R347H |
| R347L |
| R347P |
| R352Q |
| R352W |
| R516G |
| R553Q |
| R553X |
| R560K |
| R560S |
| R560T |
| R668C |
| R709X |
| R74W |
| R751L |
| R75Q |
| R75X |
| R764X |
| R785X |
| R792G |
| R792X |
| R851X |
| R933G |
| S1118F |
| S1159F |
| S1159P |
| S1196X |
| S1235R |
| S1251N |
| S1255P |
| S1255X |
| S13F |
| S341P |
| S434X |
| S466X |
| S489X |
| S492F |
| S4X |
| S549N |
| S549R |
| S549R(A->C) |
| S549R(T->G) |

TABLE 5-continued

CFTR Mutations

S589N
S737F
S912L
S912X
S945L
S977F
T1036N
T1053I
T1246I
T338I
T604I
V1153E
V1240G
V1293G
V201M
V232D
V456A
V456F
V520F
V562I
V754M
W1089X
W1098C
W1098R
W1098X
W1204X
W1282R
W1282X
W361R
W401X
W496X
W57G
W57R
W57X
W846X
Y1014C
Y1032C
Y1092X
Y109N
Y122X
Y161D
Y161S
Y563D
Y563N
Y569C
Y569D
Y569Db
Y849X
Y913C
Y913X

[a] Also known as 2183delAA→G.

In some embodiments, in the methods of treating, lessening the severity of, or symptomatically treating cystic fibrosis disclosed herein, the patient possesses a CFTR mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, 621+3A→G, 1949del84, 3141del9, 3195del6, 3199del6, 3905InsT, 4209TGTT→A, ΔI006E, A120T, A234D, A349V, A613T, C524R, D192G, D443Y, D513G, D836Y, D924N, D979V, E116K, E403D, E474K, E588V, E60K, E822K, F1016S, F1099L, F191V, F311del, F311L, F508C, F575Y, G1061R, G1249R, G126D, G149R, G194R, G194V, G27R, G314E, G458V, G463V, G480C, G622D, G628R, G628R(G→A), G91R, G970D, H1054D, H1085P, H1085R, H1375P, H139R, H199R, H609R, H939R, I1005R, I1234V, I1269N, I1366N, I175V, I502T, I506S, I506T, I601F, I618T, I807M, 1980K, L102R, L1324P, L1335P, L138ins, L1480P, L15P, L165S, L320V, L346P, L453S, L571S, L967S, M1101R, M152V, M1T, M1V, M265R, M952I, M952T, P574H, P5L, P750L, P99L, Q1100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352W, R516G, R553Q, R751L, R792G, R933G, S1118F, S1159F, S1159P, S13F, S549R(A→C), S549R(T→G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C.

In some embodiments, the patient has at least one combination mutation chosen from: G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G.

In some embodiments, the patient has at least one combination mutation chosen from: 1949del84, 3141del9, 3195del6, 3199del6, 3905InsT, 4209TGTT→A, ΔI006E, A120T, A234D, A349V, A613T, C524R, D192G, D443Y, D513G, D836Y, D924N, D979V, E116K, E403D, E474K, E588V, E60K, E822K, F1016S, F1099L, F191V, F311del, F311L, F508C, F575Y, G1061R, G1249R, G126D, G149R, G194V, G27R, G314E, G458V, G463V, G480C, G622D, G628R, G628R(G→A), G91R, G970D, H1054D, H1085P, H1085R, H1375P, H139R, H199R, H609R, H939R, I1005R, I1234V, I1269N, I1366N, I175V, I502T, I506S, I506T, I601F, I618T, I807M, 1980K, L102R, L1324P, L1335P, L138ins, L1480P, L15P, L165S, L320V, L346P, L453S, L571S, L967S, M1101R, M152V, M1T, M1V, M265R, M952I, M952T, P574H, P5L, P750L, P99L, Q1100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352W, R516G, R553Q, R751L, R792G, R933G, S1118F, S1159F, S1159P, S13F, S549R(A→C), S549R(T→G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C.

In some embodiments, in the methods of treating, lessening the severity of, or symptomatically treating cystic fibrosis disclosed herein, the patient possesses a CFTR mutation G551D. In some embodiments, the patient is homozygous for the G551D mutation. In some embodiments, the patient is heterozygous for the G551D mutation. In some embodiments, the patient is heterozygous for the G551D mutation, having the G551D mutation on one allele and any other CF-causing mutation on the other allele. In some embodiments, the patient is heterozygous for the G551D genetic mutation on one allele and the other CF-causing mutation on the other allele is any one of F508del, G542X, N1303K, W1282X, R117H, R553X, 1717-1G→A, 621+1G→T, 2789+5G→A, 3849+10kbC→T, R1162X, G85E, 3120+1G→A, ΔI507, 1898+1G→A, 3659delC, R347P, R560T, R334W, A455E, 2184delA, or 711+1G→T. In some embodiments, the patient is heterozygous for the G551D mutation, and the other CFTR mutation is F508del. In some embodiments, the patient is heterozygous for the G551D mutation, and the other CFTR mutation is R117H.

In some embodiments, in the methods of treating, lessening the severity of, or symptomatically treating cystic fibrosis disclosed herein, the patient possesses a CFTR mutation F508del. In some embodiments, the patient is homozygous for the F508del mutation. In some embodiments, the patient is heterozygous for the F508del mutation wherein the patient has the F508del mutation on one allele and any CF-causing mutation on the other allele. In some embodiments, the patient is heterozygous for F508del, and the other CFTR mutation is any CF-causing mutation, including, but not limited to G551D, G542X, N1303K, W1282X, R117H, R553X, 1717-1G→A, 621+1G→T, 2789+5G→A, 3849+10kbC→T, R1162X, G85E, 3120+1G→A, ΔI507, 1898+1G→A, 3659delC, R347P, R560T, R334W, A455E, 2184delA, or 711+1G→T. In some embodiments, the patient is heterozygous for F508del, and the other CFTR mutation is G551D. In some embodiments, the patient is heterozygous for F508del, and the other CFTR mutation is R117H.

In some embodiments, the patient has at least one combination mutation chosen from:
(i) D443Y; G576A; R668C,
(ii) F508C; S1251N,
(iii) G576A; R668C,
(iv) G970R; M470V,
(v) R74W; D1270N,
(vi) R74W; V201M, and
(vii) R74W; V201M; D1270N.

In some embodiments, in the methods of treating, lessening the severity of, or symptomatically treating cystic fibrosis disclosed herein, the patient possesses a CFTR mutation selected from G178R, G551S, G970R, G1244E, S1255P, G1349D, S549N, S549R, S1251N, E193K, F1052V and G1069R. In some embodiments, the patient possesses a CFTR mutation selected from G178R, G551S, G970R, G1244E, S1255P, G1349D, S549N, S549R and S1251N. In some embodiments, the patient possesses a CFTR mutation selected from E193K, F1052V and G1069R. In some embodiments, the method produces an increase in chloride transport relative to baseline chloride transport of the patient of the patient.

In some embodiments, in the methods of treating, lessening the severity of, or symptomatically treating cystic fibrosis disclosed herein, the patient possesses a CFTR mutation selected from R117C, D110H, R347H, R352Q, E56K, P67L, L206W, A455E, D579G, S1235R, S945L, R1070W, F1074L, D110E, D1270N and D1152H.

In some embodiments, the patient possesses a CFTR mutation selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G. In some embodiments, the patient possesses a CFTR mutation selected from 1717-1G→A, 1811+1.6kbA→G, 2789+5G→A, 3272-26A→G and 3849+10kbC→T. In some embodiments, the patient possesses a CFTR mutation selected from 2789+5G→A and 3272-26A→G.

In some embodiments, in the methods of treating, lessening the severity of, or symptomatically treating cystic fibrosis disclosed herein, the patient possesses a CFTR mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and CFTR mutations selected from F508del, R117H, and G551D.

In some embodiments, in the methods of treating, lessening the severity of, or symptomatically treating cystic fibrosis disclosed herein, the patient possesses a CFTR mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, 621+3A→G, and a CFTR mutation selected from F508del, R117H, and G551D; and a CFTR mutations selected from F508del, R117H, and G551D.

In some embodiments, the patient possesses a CFTR mutation selected from G178R, G551S, G970R, G1244E, S1255P, G1349D, S549N, S549R, S1251N, E193K, F1052V and G1069R, and a CFTR mutation selected from F508del, R117H, and G551D. In some embodiments, the patient possesses a CFTR mutation selected from G178R, G551S, G970R, G1244E, S1255P, G1349D, S549N, S549R and S1251N, and a CFTR mutation selected from F508del, R117H, and G551D. In some embodiments, the patient possesses a CFTR mutation selected from E193K, F1052V and G1069R, and a CFTR mutation selected from F508del, R1711, and G551D.

In some embodiments, the patient possesses a CFTR mutation selected from R117C, D110H, R347H, R352Q, E56K, P67L, L206W, A455E, D579G, S1235R, S945L, R1070W, F1074L, D110E, D1270N and D1152H, and a CFTR mutation selected from F508del, R117H, and G551D.

In some embodiments, the patient possesses a CFTR mutation selected from 1717-1G→A, 621+1G→T, 3120+1G→A, 1898+1G→A, 711+1G→T, 2622+1G→A, 405+

1G→A, 406-1G→A, 4005+1G→A, 1812-1G→A, 1525-1G→A, 712-1G→T, 1248+1G→A, I341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a CFTR mutation selected from F508del, R1171-1, and G551D. In some embodiments, the patient possesses a CFTR mutation selected from 1717-1G→A, 1811+1.6kbA→G, 2789+5G→A, 3272-26A→G and 3849+10kbC→T, and a CFTR mutation selected from F508del, R117H, and G551D. In some embodiments, the patient possesses a CFTR mutation selected from 2789+5G→A and 3272-26A→G, and a CFTR mutation selected from F508del, R117H.

In some embodiments, the patient is heterozygous having a CF-causing mutation on one allele and a CF-causing mutation on the other allele. In some embodiments, the patient is heterozygous for F508del, and the other CFTR-causing mutation is any CF-causing mutation, including, but not limited to F508del on one CFTR allele and a CFTR mutation on the second CFTR allele that is associated with minimal CFTR function, residual CFTR function, or a defect in CFTR channel gating activity. In some embodiments, the CF-causing mutation is selected from Table 5. In some embodiments, the CF-causing mutation is selected from Table 6. In some embodiments, the CF-causing mutation is selected from Table 7.

In some embodiments, the patient is heterozygous having a CFTR mutation on one CFTR allele selected from the mutations listed in the table from FIG. 7 and a CFTR mutation on the other CFTR allele is selected from the CFTR mutations listed in Table 6:

TABLE 6

| CFTR Mutations |
|---|
| Q39X |
| W57X |
| E60X |
| R75X |
| E92X |
| Q98X |
| Y122X |
| L218X |
| Q220X |
| C276X |
| Q290X |
| G330X |
| W401X |
| Q414X |
| S434X |
| S466X |
| S489X |
| Q493X |
| W496X |
| Q525X |
| G542X |
| Q552X |
| R553X |
| E585X |
| G673X |
| R709X |
| K710X |
| L732X |
| R764X |
| R785X |
| R792X |
| E822X |
| W846X |
| R851X |

TABLE 6-continued

| CFTR Mutations |
|---|
| Q890X |
| S912X |
| W1089X |
| Y1092X |
| E1104X |
| R1158X |
| R1162X |
| S1196X |
| W1204X |
| S1255X |
| W1282X |
| Q1313X |
| 621+1G→T |
| 711+1G→T |
| 711+5G→A |
| 712-1G→T |
| 405+1G→A |
| 405+3A→C |
| 406-1G→A |
| 621+1G→T |
| 1248+1G→A |
| 1341+1G→A |
| 1717-1G→A |
| 1811+1.6kbA→G |
| 1811+1G→C |
| 1812-1G→A |
| 1898+1G→A |
| 2622+1G→A |
| 3120+1G→A |
| 3120G→A |
| 3850-1G→A |
| 4005+1G→A |
| 4374+1G→T |
| 663delT |
| 2183AA→G |
| CFTRdel2,3 |
| 3659delC |
| 394delTT |
| 2184insA |
| 3905insT |
| 2184delA |
| 1078delT |
| 1154insTC |
| 2183delAA→G |
| 2143delT |
| 1677delTA |
| 3876delA |
| 2307insA |
| 4382delA |
| 4016insT |
| 2347delG |
| 3007delG |
| 574delA |
| 2711delT |
| 3791delC |
| CFTRdele22-23 |
| 457TAT→G |
| 2043delG |
| 2869insG |
| 3600+2insT |
| 3737delA |
| 4040delA |
| 541delC |
| A46D |
| T338I |
| R347P |
| L927P |
| G85E |
| S341P |
| L467P |
| I507del |
| V520F |
| A559T |
| R560T |
| R560S |
| A561E |
| Y569D |
| L1065P |

TABLE 6-continued

| CFTR Mutations |
|---|
| R1066C |
| R1066M |
| L1077P |
| H1085R |
| M1101K |
| N1303K |
| 3849+10kbC→T |
| 3272-26A→G |
| 711+3A→G |
| E56K |
| P67L |
| R74W |
| D110E |
| D110H |
| R117C |
| L206W |
| R347H |
| R352Q |
| A455E |
| D579G |
| E831X |
| S945L |
| S977F |
| F1052V |
| R1070W |
| F1074L |
| D1152H |
| D1270N |
| G178R |
| S549N |
| S549R |
| G551D |
| G551S |
| G1244E |
| S1251N |
| S1255P |
| G1349D |

TABLE 7

CFTR Mutations

| Criteria | Mutation | | | | |
|---|---|---|---|---|---|
| Truncation mutations % PI >50% and/or SwCl⁻ >86 mmol/L no full-length protein | S4X | C276X | G542X | R792X | E1104X |
| | G27X | Q290X | G550X | E822X | R1158X |
| | Q39X | G330X | Q552X | W846X | R1162X |
| | W57X | W401X | R553X | Y849X | S1196X |
| | E60 | Q414X | E585X | R851X | W1204X |
| | R75X | S434X | G673X | Q890X | L1254X |
| | E92X | S466X | Q685X | S912X | S1255X |
| | Q98X | S489X | R709X | Y913X | W1282X |
| | Y122X | Q493X | K710X | W1089X | Q1313X |
| | E193X | W496X | L732X | Y1092X | E1371X |
| | L218X | C524X | R764X | W1098X | Q1382X |
| | Q220X | Q525X | R785X | R1102X | Q1411X |
| Splice mutations % PI >50% and/or SwCl⁻ >86 mmol/L no or little mature mRNA | 185+1G→T | 711+5G→A | 1717-8G→A | 2622+1G→A | 3121-1G→A |
| | 296+1G→A | 712-1G→T | 1717-1G→A | 2790-1G→C | 3500-2A→G |
| | 405+1G→A | 1248+1G→A | 1811+1G→C | 3040G→C | 3600+2insT |
| | 405+3A→C | 1249-1G→A | 1811+1.6kbA→G (G970R) | 3850-1G→A |
| | 406-1G→A | 1341+1G→A | 1812-1G→A | 3120G→A | 4005+1G→A |
| | 621+1G→T | 1525-2A→G | 1898+1G→A | 3120+1G→A | 4374+1G→T |
| | 711+1G→T | 1525-1G→A | 1898+1G→C | 3121-2A→G | |
| Small (≤3 nucleotide) insertion/deletion (ins/del) frameshift mutations % PI >50% and/or SwCl⁻ >86 mmol/L garbled and/or truncated protein | 182delT | 1119delA | 1782delA | 2732insA | 3876delA |
| | 306insA | 1138insG | 1824delA | 2869insG | 3878delG |
| | 365-366insT | 1154insTC | 2043delG | 2896insAG | 3905insT |
| | 394delTT | 1161delC | 2143delT | 2942insT | 4016insT |
| | 442delA | 1213delT | 2183AA→G ᵃ | 2957delT | 4021dupT |
| | 444delA | 1259insA | 2184delA | 3007delG | 4040delA |
| | 457TAT→G | 1288insTA | 2184insA | 3028delA | 4279insA |
| | 541delC | 1471delA | 2307insA | 3171delC | 4326delTC |
| | 574delA | 1497delGG | 2347delG | 3659delC | |
| | 663delT | 1548delG | 2585delT | 3737delA | |
| | 935delA | 1609del CA | 2594delGT | 3791delC | |
| | 1078delT | 1677delTA | 2711delT | 3821delT | |
| Non-small (>3 nucleotide) insertion/deletion (ins/del) frameshift mutations % PI >50% and/or SwCl⁻ >86 mmol/L garbled and/or truncated protein | CFTRdele2, 3 | 1461ins4 | | 2991del32 | |
| | CFTRdele22, 23 | 1924del7 | | 3667ins4 | |
| | 124del23bp | 2055del9→A | | 4010del4 | |
| | 852del22 | 2105-2117del13insAGAAA | | 4209TGTT→AA | |
| | 991del5 | 2721del11 | | | |
| Class II, III, IV mutations not responsive to Compound III alone or in combination with Compound II or Compound IV % PI >50% and/or SwCl⁻ >86 mmol/L | A46Dᵇ | V520F | Y569Dᵇ | N1303K | |
| | G85E | A559Tᵇ | L1065P | | |
| | R347P | R560T | R1066C | | |
| | L467Pᵇ | R560S | L1077Pᵇ | | |
| | I507del | A561E | M1101K | | |

TABLE 7-continued

CFTR Mutations

| Criteria | Mutation |
|---|---|
| AND Not responsive in vitro to Compound III alone or in combination with Compound II or Compound IV | |

Note:
% PI: percentage of F508del-CFTR heterozygous patients in the CFTR2 patient registry who are pancreatic insufficient;
SwCl⁻: mean sweat chloride of F508del-CFTR heterozygous patients in the CFTR2 patient registry
$^a$ Also known as 2183delAA→G.
$^b$Unpublished data.

Table 7 above includes certain exemplary CFTR minimal function mutations, which are detectable by an FDA-cleared genotyping assay, but does not include an exhaustive list.

In some embodiments, the patient is: with F508del/MF (F/MF) genotypes (heterozygous for F508del and an MF mutation not expected to respond to CFTR modulators, such as Compound III); with F508del/F508del (F/F) genotype (homozygous for F508del); and/or with F508del/gating (F/G) genotypes (heterozygous for F508del and a gating mutation known to be CFTR modulator-responsive (e.g., Compound III-responsive). In some embodiments, the patient with F508del/MF (F/MF) genotypes has a MF mutation that is not expected to respond to Compound II, Compound III, and both of Compound II and Compound III. In some embodiments, the patient with F508del/MF (F/MF) genotypes has any one of the MF mutations in Table 7.

In some embodiments, the patient is heterozygous for F508del, and the other CFTR genetic mutation is any CF-causing mutation, including truncation mutations, splice mutations, small (≤3 nucleotide) insertion or deletion (ins/del) frameshift mutations; non-small (>3 nucleotide) insertion or deletion (ins/del) frameshift mutations; and Class II, III, IV mutations not responsive to Compound III alone or in combination with Compound II or Compound IV.

In some embodiments, the patient is heterozygous for F508del, and the other CFTR genetic mutation is a truncation mutation. In some specific embodiments, the truncation mutation is a truncation mutation listed in Table 7.

In some embodiments, the patient is heterozygous for F508del, and the other CFTR genetic mutation is a splice mutation. In some specific embodiments, the splice mutation is a splice mutation listed in Table 7.

In some embodiments, the patient is heterozygous for F508del, and the other CFTR genetic mutation is a small (≤3 nucleotide) insertion or deletion (ins/del) frameshift mutation. In some specific embodiments, the small (≤3 nucleotide) insertion or deletion (ins/del) frameshift mutation is a small (≤β nucleotide) insertion or deletion (ins/del) frameshift mutation listed in Table 7.

In some embodiments, the patient is heterozygous for F508del, and the other CFTR genetic mutation is any CF-causing mutation expected to be and/or is responsive to, based on in vitro and/or clinical data, any combination of (i) a novel compound chosen from those disclosed herein (e.g., compounds of Formula (I), (II), (III), (IV), (V), or (VI), and pharmaceutically acceptable salts thereof, and their deuterated derivatives), and (ii) Compound II, and/or Compound III, and/or Compound IV.

In some embodiments, the patient is heterozygous for F508del, and the other CFTR genetic mutation is any CF-causing mutation expected to be and/or is responsive, based on in vitro and/or clinical data, to the triple combination of a novel compound chosen from those disclosed herein (e.g., compounds of Formula (I), (II), (III), (IV), (V), or (VI), and pharmaceutically acceptable salts thereof, and their deuterated derivatives), and Compound II, and Compound III.

In some embodiments, the patient is heterozygous for F508del, and the other CFTR genetic mutation is a non-small (>3 nucleotide) insertion or deletion (ins/del) frameshift mutation. In some specific embodiments, the non-small (>3 nucleotide) insertion or deletion (ins/del) frameshift mutation is a non-small (>3 nucleotide) insertion or deletion (ins/del) frameshift mutation listed in Table 6.

In some embodiments, the patient is heterozygous for F508del, and the other CFTR genetic mutation is a Class II, III, IV mutations not responsive to Compound III alone or in combination with Compound II or Compound IV. In some embodiments, the Class II, III, IV mutations not responsive to Compound III alone or in combination with Compound II or Compound IV is a Class II, III, IV mutations not responsive to Compound III alone or in combination with Compound II or Compound IV listed in Table 7.

In some embodiments, the patient is heterozygous for F508del, and the other CFTR genetic mutation is any mutation listed in Table 7.

In some embodiments, the patient is heterozygous for F508del, and the other CFTR genetic mutation is any mutation, but other than F508del, listed in Table 5, 6, 7, and FIG. 7.

In some embodiments, the patient is heterozygous for F508del, and the other CFTR genetic mutation is any mutation listed in Table 5. In some embodiments, the patient is heterozygous for F508del, and the other CFTR genetic mutation is any mutation listed in Table 6. In some embodiments, the patient is heterozygous for F508del, and the other CFTR genetic mutation is any mutation listed in Table 7. In some embodiments, the patient is heterozygous for F508del, and the other CFTR genetic mutation is any mutation listed in FIG. 7.

In some embodiments, the patient is homozygous for F508del.

In some embodiments, the patient is heterozygous having one CF-causing mutation on one CFTR allele selected from the mutations listed in the table from FIG. 7 and another CF-causing mutation on the other CFTR allele is selected from the CFTR mutations listed in Table 7.

In some embodiments, the composition disclosed herein is useful for treating, lessening the severity of, or symptomatically treating cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected for patients that are heterozygous or homozygous for a variety of different mutations, including patients heterozygous for the most common mutation, F508del, as well as other mutations such as the G551D mutation, or the R117H mutation. In some embodiments, compositions disclosed herein are useful for treating, lessening the severity of, or symptomatically treating cystic fibrosis in patients who exhibit little to no residual CFTR activity. In some embodiments, compositions disclosed herein are useful for treating, lessening the severity of, or symptomatically treating cystic fibrosis in patients who exhibit little to no residual CFTR activity in the apical membrane of respiratory epithelia.

In some embodiments, the compositions disclosed herein are useful for treating or lessening the severity of cystic fibrosis in patients who exhibit residual CFTR activity using pharmacological methods. Such methods increase the amount of CFTR present at the cell surface, thereby inducing a hitherto absent CFTR activity in a patient or augmenting the existing level of residual CFTR activity in a patient.

In some embodiments, the compositions disclosed herein are useful for treating or lessening the severity of cystic fibrosis in patients with certain genotypes exhibiting residual CFTR activity.

In some embodiments, compositions disclosed herein are useful for treating, lessening the severity of, or symptomatically treating cystic fibrosis in patients within certain clinical phenotypes, e.g., a mild to moderate clinical phenotype that typically correlates with the amount of residual CFTR activity in the apical membrane of epithelia. Such phenotypes include patients exhibiting pancreatic sufficiency.

In some embodiments, the compositions disclosed herein are useful for treating, lessening the severity of, or symptomatically treating patients diagnosed with pancreatic sufficiency, idiopathic pancreatitis and congenital bilateral absence of the vas deferens, or mild lung disease wherein the patient exhibits residual CFTR activity.

In some embodiments, this disclosure relates to a method of augmenting or inducing anion channel activity in vitro or in vivo, comprising contacting the channel with a composition disclosed herein. In some embodiments, the anion channel is a chloride channel or a bicarbonate channel. In some embodiments, the anion channel is a chloride channel.

The exact amount of a pharmaceutical composition required will vary from subject to subject, depending on the species, age, and general condition of the subject, the severity of the disease, the particular agent, its mode of administration, and the like. The compounds of this disclosure may be formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of this disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, such as a mammal, and even further such as a human.

In some embodiments, the disclosure also is directed to methods of treatment using isotope-labelled compounds of the afore-mentioned compounds, which have the same structures as disclosed herein except that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

The isotope-labelled compounds and salts can be used in a number of beneficial ways. They can be suitable for medicaments and/or various types of assays, such as substrate tissue distribution assays. For example, tritium ($^{3}H$)- and/or carbon-14 ($^{14}C$)-labelled compounds are particularly useful for various types of assays, such as substrate tissue distribution assays, due to relatively simple preparation and excellent detectability. For example, deuterium ($^{2}H$)-labelled ones are therapeutically useful with potential therapeutic advantages over the non-$^{2}H$-labelled compounds. In general, deuterium ($^{2}H$)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^{2}H$)-labelled ones. In some specific embodiments, the isotope-labelled compounds and salts are deuterium ($^{2}H$)-labelled, wherein one or more hydrogen atoms therein have been replaced by deuterium. In chemical structures, deuterium is represented as "$^{2}H$" or "D."

The deuterium ($^{2}H$)-labelled compounds and salts can manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2$-$7$ are typical. For a further discussion, see S. L. Harbeson and R. D. Tung, *Deuterium In Drug Discovery and Development*, Ann. Rep. Med. Chem. 2011, 46, 403-

417; and T. G. Gant "Using deuterium in drug discovery: leaving the label in the drug" J. Med. Chem. 2014, 57, 3595-3611, relevant portions of which are independently incorporated herein by reference.

The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

One of ordinary skill in the art would understand that deuteration of one or more metabolically labile positions on a compound or active metabolite may lead to improvement of one or more superior DMPK properties while maintaining biological activity as compared to the corresponding hydrogen analogs. The superior DMPK property or properties may have an impact on the exposure, half-life, clearance, metabolism, and/or even food requirements for optimal absorption of the drug product. Deuteration may also change the metabolism at other non-deuterated positions of the deuterated compound.

In some embodiments, the disclosure includes deuterated derivatives of the novel compounds disclosed herein and of their pharmaceutically acceptable salts. Non-limiting examples of deuterated compounds are disclosed in FIG. 1.

In some embodiments, Compound III' as used herein includes the deuterated compound disclosed in U.S. Pat. No. 8,865,902 (which is incorporated herein by reference), and CTP-656.

In some embodiments, Compound III' is:

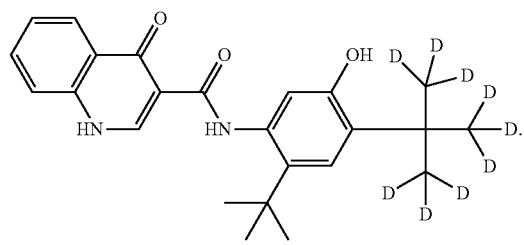

Exemplary embodiments of the disclosure include: The novel compounds disclosed herein (e.g., compounds of Formulae (I)-(VI), pharmaceutically acceptable salts thereof, and deuterated derivatives of any of the foregoing, including the compounds in FIG. 1 and those specifically depicted herein) can be prepared by suitable methods known in the art. For example, they can be prepared in accordance with procedures described in WO 2016/057572 and by the exemplary syntheses described below in the Examples. For example, deuterated derivatives of the novel compounds of Formulae (I)-(VI) and pharmaceutically acceptable salts thereof can be prepared in a similar manner as those for compounds of Formulae (I)-(VI) and pharmaceutically acceptable salts thereof by employing intermediates and/or reagents where one or more hydrogen atoms are replaced with deuterium. For example, see T. G. Gant "Using deuterium in drug discovery: leaving the label in the drug," J. Med. Chem. 2014, 57, 3595-3611, the relevant portions of which are incorporated herein by reference.

In some embodiments, compounds of Formulae (X), (III), (IV), (V), and (VI) and pharmaceutically acceptable salts thereof, and deuterated derivatives of any of the foregoing are prepared as depicted in Schemes 1-2, wherein the variables therein are each and independently are as those for Formula (I), (II), (III), (IV), (V), or (VI) above, and wherein each $R^a$ is independently chosen from $C_1$-$C_4$ alkyl groups; and each $X^a$ is independently chosen from F or $C_1$. Suitable condition(s) known in the art can be employed for each step depicted in the schemes. In some embodiments, each $X^a$ for Formulae (B), (C), (D), (F), (B-1), (C-1), (D-1), and (F-1) in Schemes 2-4 is independently Cl. In some embodiments, each X' for Formulae (D), (L), (O), and (P) in Scheme 6 is independently F. In some embodiments, r in Formulae (X), (B), (C), (D), and (F) is independently 0.

In some embodiments, as shown in Scheme 1, the methods comprise reacting a compound of Formula (F) or a salt thereof with a compound of Formula (G) or a salt thereof to generate a compound of Formula (X), a pharmaceutically acceptable salt thereof, or a deuterated derivative of any of the foregoing.

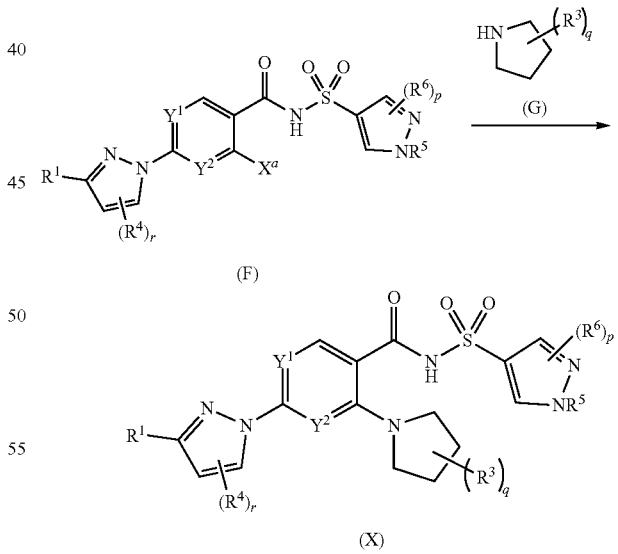

In some embodiments, in said Formulae (F), (G) and (X):
one of $Y^1$ and $Y^2$ is N and the other is CH;
$R^1$ is —$(C(R^2)_2)_k$—O—$(C(R^2)_2)_m R^7$,
each $R^2$ is independently chosen from hydrogen; halogens; cyano; hydroxy; $C_1$-$C_2$ alkoxy groups; and $C_1$-$C_2$ alkyl groups optionally substituted with one or more substituents each independently chosen from halogens, hydroxy, and $C_{3-5}$ cycloalkyl groups optionally substituted with one or more substituents each independently chosen from $C_1$-$C_2$ alkyl groups, halogenated $C_1$-$C_2$ alkyl groups, and halogens;

each $R^3$ is independently chosen from $C_1$-$C_4$ alkyl groups optionally substituted with one or more hydroxy groups, or optionally two geminal $R^3$, together with the carbon atom to which they are attached, form a $C_{3-4}$ cycloalkyl;

each $R^4$ is independently chosen from halogens;

$R^5$ is chosen from hydrogen and $C_1$-$C_4$ alkyl groups;

each $R^6$ is chosen from halogens, cyano, hydroxy, hydroxymethyl, $C_1$-$C_2$ alkoxy groups, $C_1$-$C_2$ alkyl groups, and halogenated $C_1$-$C_2$ alkyl groups;

$R^7$ is chosen from hydrogen, halogens, cyano, $C_1$-$C_2$ alkyl groups optionally substituted with one or more substituents each independently chosen from halogens and hydroxy, and $C_3$-$C_{10}$ cycloalkyl groups optionally substituted with one or more substituents each independently chosen from $C_1$-$C_2$ alkyl groups, halogenated $C_1$-$C_2$ alkyl groups, and halogens;

$X^a$ is F or Cl;

k is 0 or 1;

r is 0 or 1;

m is 0, 1, 2, or 3;

p is 0, 1, or 2; and q is 0, 1, 2, 3, 4, 5, 6, 7, or 8.

In some embodiments, r in Formula (X) is 0.

Any suitable conditions, such as those for a nucleophilic reaction of amine, known in the art can be used. In some embodiments, the reaction depicted in Scheme 1 is performed in the presence of a base, such as a metal carbonate (e.g., $Na_2CO_3$ or $K_2CO_3$).

In some embodiments, compounds of Formula (X), pharmaceutically acceptable salts thereof, or deuterated derivatives of any of the foregoing, wherein $Y^2$ is N and $Y^1$ is CH in each of Formulae (F), (G) and (X), are prepared by the methods in Scheme 1. In some embodiments, a salt of a compound of Formula (G) is employed. In some embodiments, an HCl salt of a compound of Formula (G) is employed.

A compound of Formula (F) or a salt thereof and a compound of Formula (G) or a salt thereof can be prepared by any suitable method known in the art, for example, those in WO 2016/57572 and those in the exemplary syntheses described below in the Examples.

In some embodiments, as shown in Scheme 2, a compound of Formula (F), a pharmaceutically acceptable salt thereof, or a deuterated derivative of any of the foregoing is prepared by a method that comprises reacting a compound of Formula (D) or a salt thereof with a compound of Formula (E) or a salt thereof. In some embodiments, compounds of Formula (D), salts thereof, or deuterated derivatives of any of the foregoing are prepared by a method that comprises reacting a compound of Formula (A) or a salt thereof with a compound of Formula (B) or a salt thereof to generate a compound of Formula (C) or a salt thereof; and hydrolyzing the —C(O)OR$^a$ of compound of Formula (C) to generate a compound of Formula (D) or a salt thereof. Any suitable conditions known in the art can be used for steps (a), (b), and (c) of Scheme 2 below, such as those for a coupling reaction between carboxylic acid and sulfonamide or those for an acylation of sulfonamide for step (a), those for hydrolysis of ester for step (b), and those for a nucleophilic reaction of amine for step (c).

In some embodiments, step (a) of Scheme 2 below is performed in the presence of a base. In some specific embodiments, step (a) is performed in the presence of a non-nucleophilic base. In some embodiments, in step (a), the reaction of a compound of Formula (D) or a salt thereof with a compound of Formula (E) or a salt thereof comprises reacting a compound of Formula (D) or a salt thereof with a coupling reagent, such as carbonyl diimidazole (CDI), and subsequently with a compound of Formula (E) or a salt thereof in the presence of a base, such as a non-nucleophilic base. In some embodiments, a compound of Formula (D) or a salt thereof is reacted with CDI prior to the reaction with a compound of Formula (E) or a salt thereof, and then subsequently with a compound of Formula (E) or a salt thereof in the presence of a base, such as DBU (1,8-diazabicyclo(5.4.0)undec-7-ene).

In some embodiments, step (b) of Scheme 2 below is performed in the presence of a base. In some embodiments, step (b) is performed in the presence of an aqueous base, such as aqueous hydroxide. In some embodiments, step (b) is performed in the presence of an aqueous metal hydroxide, such as aqueous NaOH. In some embodiments, step (b) of Scheme 2 below is performed in the presence of an acid. In some embodiments, step (b) is performed in the presence of an aqueous acid, such as an aqueous HCl.

In some embodiments, step (c) of Scheme 2 below is performed in the presence of a base. In some embodiments, step (c) is performed in the presence of a metal carbonate (e.g., $Na_2CO_3$ or $K_2CO_3$).

Scheme 2

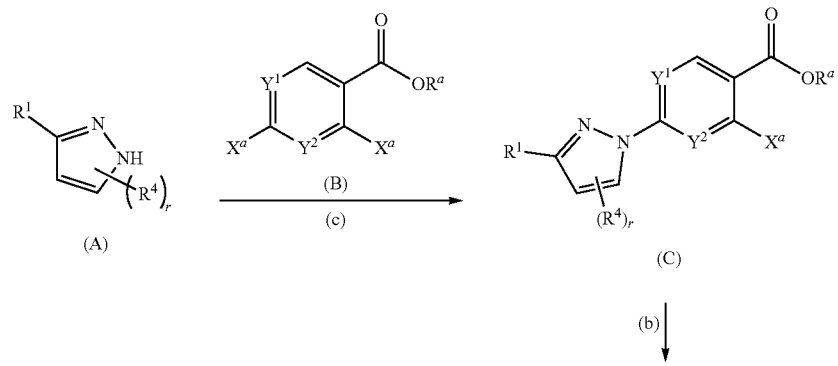

-continued

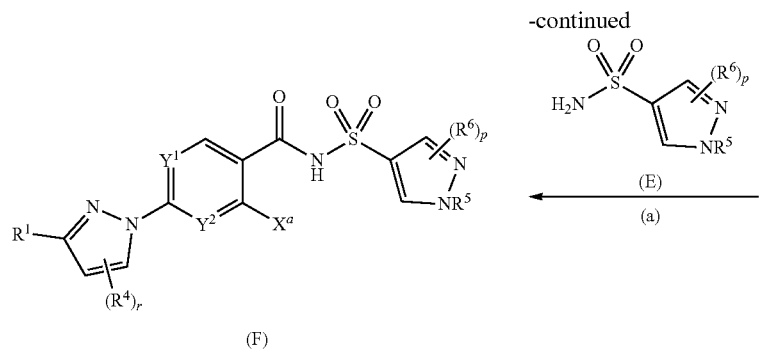

(F)

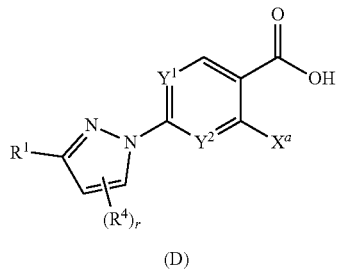

(D)

In some embodiments, disclosed herein is a method of preparing a compound of the following formula (Compound 1):

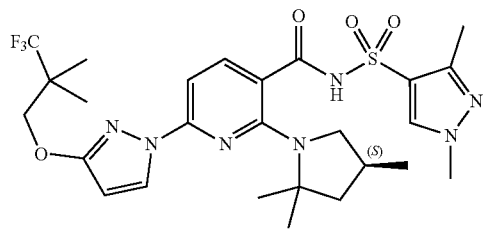

a pharmaceutically acceptable salt thereof, or a deuterated derivative of any of the foregoing. The method comprises reacting a compound of Formula (F-1) or a salt thereof with a compound of Formula (G-1) or a salt thereof, wherein $X^a$ is F or Cl, as shown in Scheme 3:

Scheme 3

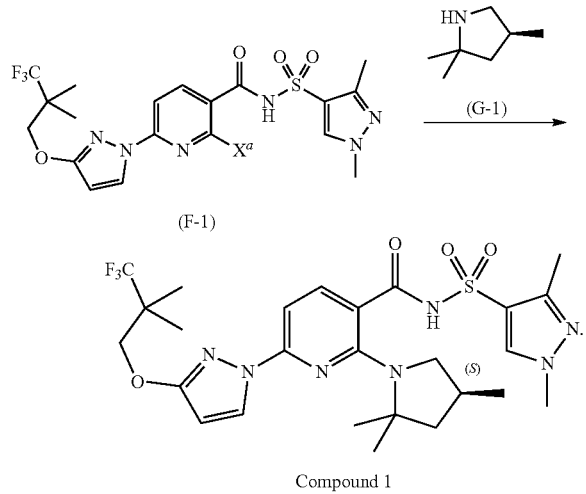

Compound 1

Any suitable conditions, such as those for a nucleophilic reaction of amine, known in the art can be used. In some embodiments, the reaction depicted in Scheme 3 is performed in the presence of a base, such as a metal carbonate (e.g., $Na_2CO_3$ or $K_2CO_3$).

In some embodiments, a salt of compound of Formula (G-1) is employed. In some embodiments, a HCl salt of a compound of Formula (G-1) is employed.

A compound of Formula (F-1) or a salt thereof and a compound of Formula (G-1) or a salt thereof can be prepared by any suitable method known in the art, for example, those in WO 2016/57572 and those in the exemplary syntheses described below in the Examples.

In some embodiments, as shown in Scheme 4, a compound of Formula (F-1) or a salt thereof, or a deuterated derivative of any of the foregoing is prepared by a method that comprises reacting a compound of Formula (D-1) or a salt thereof with a compound of Formula (E-1) or a salt thereof. In some embodiments, compounds of Formula (D-1) or salts thereof, or their deuterated derivatives are prepared by a method that comprises reacting a compound of Formula (A-1) or a salt thereof with a compound of Formula (B-1) or a salt thereof to generate a compound of formula (C-1) or a salt thereof; and hydrolyzing the —C(O)OR$^a$ of compound of Formula (C-1) or salt thereof to generate a compound of formula (D-1) or a salt thereof. Any suitable conditions known in the art can be used for steps (a-1), (b-1), and (c-1) of Scheme 4 below, such as those for a coupling reaction between carboxylic acid and sulfonamide or those for an acylation of sulfonamide for step (a-1), those for hydrolysis of ester for step (b-1), and those for a nucleophilic reaction of amine for step (c-1).

In some embodiments, step (a-1) of Scheme 4 below is performed in the presence of a base. In some embodiments, step (a-1) of Scheme 4 below is performed in the presence of a non-nucleophilic base. In some embodiments, in step (a-1), the reaction of a compound of Formula (D-1) or a salt thereof with a compound of Formula (E-1) or a salt thereof comprises reacting a compound of Formula (D-1) or a salt thereof with a coupling reagent, such as carbonyl diimidazole (CDI), and subsequently with a compound of Formula (E-1) or a salt thereof in the presence of a base, such as a non-nucleophilic base. In some embodiments, (i) a compound of Formula (D-1) or a salt thereof is reacted with CDI prior to the reaction with a compound of Formula (E-1) or a salt thereof, and then subsequently (ii) the reaction product of step (i) is reacted with a compound of Formula (E-1) or a salt thereof in the presence of a base, such as DBU (1,8-Diazabicyclo(5.4.0)undec-7-ene).

In some embodiments, step (b-1) of Scheme 4 below is performed in the presence of a base. In some embodiments, step (b-1) is performed in the presence of an aqueous base, such as aqueous hydroxide. In some embodiments, step (b-1) is performed in the presence of an aqueous metal hydroxide, such as aqueous NaOH. In some embodiments, step (b-1) of Scheme 4 below is performed in the presence of an acid. In some embodiments, step (b-1) is performed in the presence of an aqueous acid, such as an aqueous HCl.

In some embodiments, step (c-1) of Scheme 4 below is performed in the presence of a base. In some embodiments, step (c-1) is performed in the presence of a metal carbonate (e.g., $Na_2CO_3$ or $K_2CO_3$).

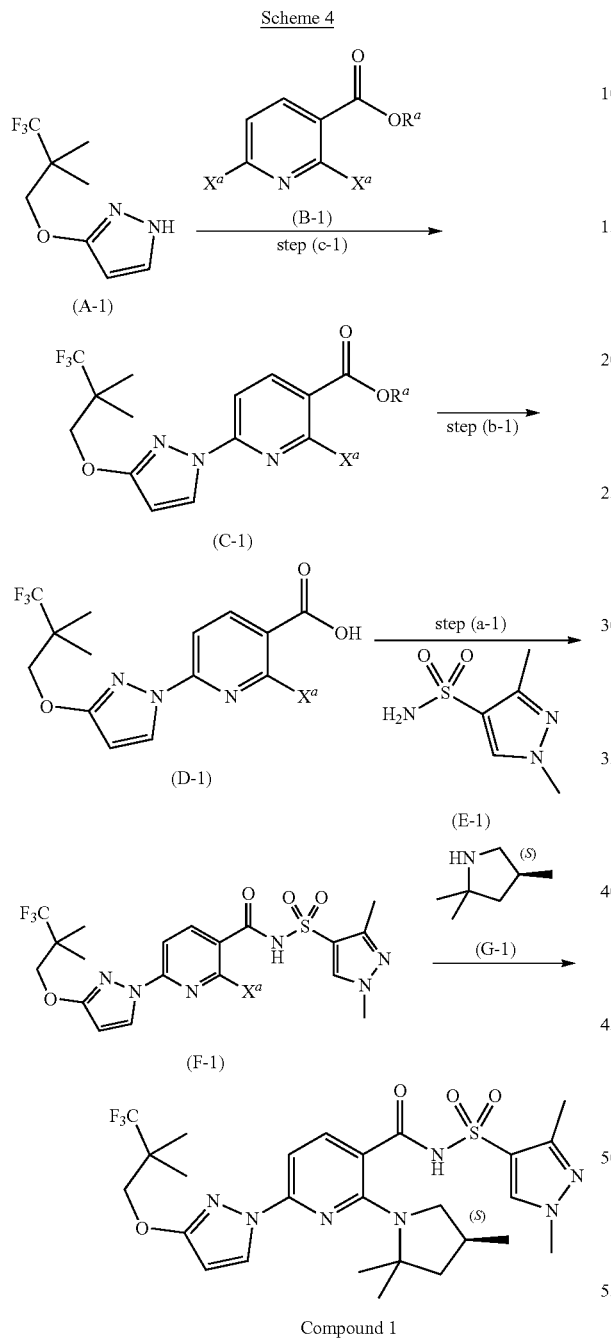

In Scheme 4, $R^a$ is chosen from $C_1$-$C_4$ alkyl groups; and each $X^a$ is independently F or Cl.

In some embodiments, methods of preparing a compound of Formulae (I) and (II), wherein X is NH or $N(C_1$-$C_4$ alkyl) or a pharmaceutically acceptable salt thereof, or a deuterated derivative of any of the foregoing, comprise reacting a compound of Formula (L) or a salt thereof with $NR*_3$ where R* is H or $C_1$-$C_4$ alkyl, as depicted in Schemes 5 and 6:

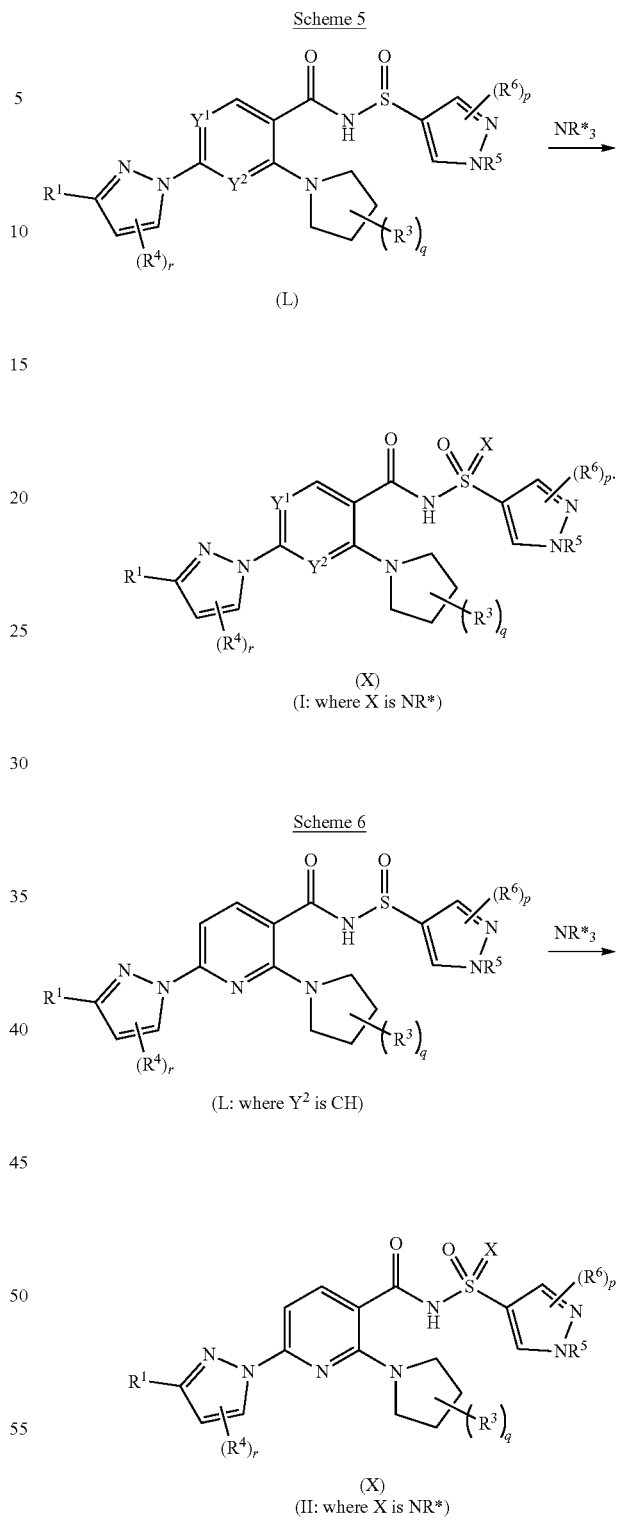

Any suitable conditions known in the art can be used for the sulfoxamination reaction, for example, for those for electrophilic additions by amines. In some embodiments, the sulfoxamination reaction is performed in the presence of a chlorinating or oxidizing agent, such as N-chlorosuccinimide (NCS).

In some embodiments, a compound of Formula (L) or a salt thereof is prepared by a method comprising oxidizing the sulfur unit of the

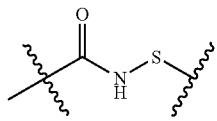

group of a compound of Formula (M) or salt thereof as shown in Scheme 7 below:

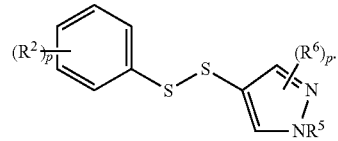

In some embodiments, a compound of Formula (P) or a salt thereof is prepared by amidating the —C(O)OH group of a compound of Formula (D) or salt thereof. Any suitable conditions known in the art can be used.

Scheme 7

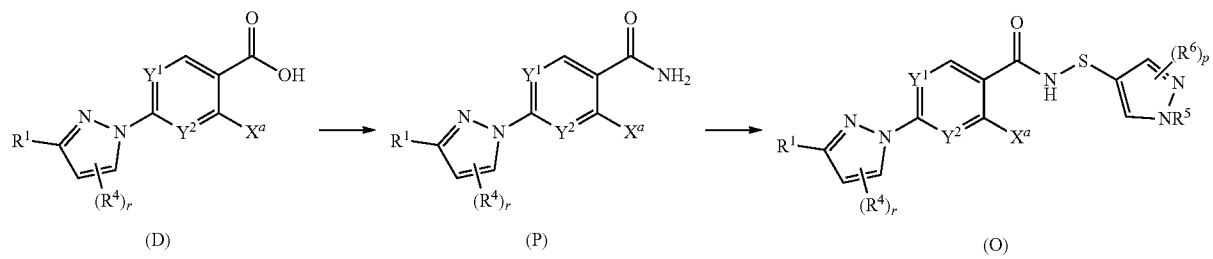

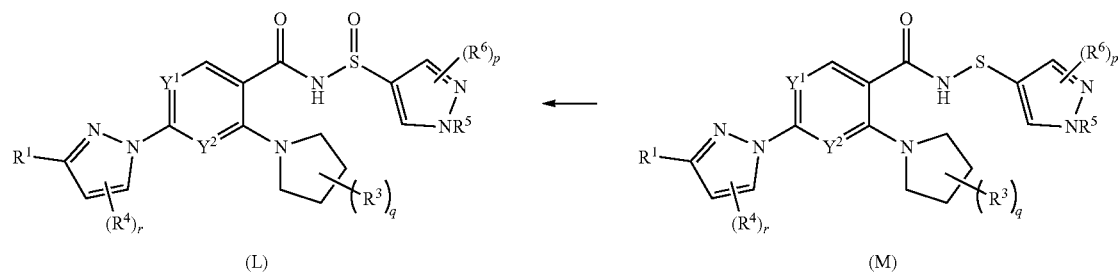

Any suitable conditions known in the art can be used for the oxidation reaction. In some embodiments, the oxidation is performed in the presence of a peroxycarboxylic acid, such as meta-Chloroperoxybenzoic acid (m-CPBA).

In some embodiments, a compound of Formula (M) or a salt thereof is prepared by a method comprising reacting a compound of Formula (O) with a compound of Formula (G) or a salt thereof. Any suitable conditions known in the art can be used.

In some embodiments, a compound of Formula (O) or a salt thereof is prepared by a method comprising reacting a compound of Formula (P) or salt thereof with a phenyl disulfide of Formula (Q):

Additional embodiments include:
1. A compound of Formula I:

(I)

a pharmaceutically acceptable salt thereof, or a deuterated derivative of any of the foregoing,
wherein:
one of $Y^1$ and $Y^2$ is N and the other is CH; X is chosen from O, NH, and N($C_1$-$C_4$ alkyl) groups;

$R^1$ is $-(C(R^2)_2)_k-O-(C(R^2)_2)_m R^7$, each $R^2$ is independently chosen from hydrogen; halogens; cyano; hydroxy; $C_1$-$C_2$ alkoxy groups; and $C_1$-$C_2$ alkyl groups optionally substituted with one or more substituents each independently chosen from halogens, hydroxy, and $C_{3-5}$ cycloalkyl groups optionally substituted with one or more substituents each independently chosen from $C_1$-$C_2$ alkyl groups, halogenated $C_1$-$C_2$ alkyl groups, and halogens;

each $R^3$ is independently chosen from $C_1$-$C_4$ alkyl groups optionally substituted with one or more hydroxy groups, or optionally two geminal $R^3$, together with the carbon atom to which they are attached, form a $C_{3-4}$ cycloalkyl;

each $R^4$ is independently chosen from halogens;

$R^5$ is chosen from hydrogen and $C_1$-$C_4$ alkyl groups;

each $R^6$ is independently chosen from halogens, cyano, hydroxy, hydroxymethyl, $C_1$-$C_2$ alkoxy groups, $C_1$-$C_2$ alkyl groups, and halogenated $C_1$-$C_2$ alkyl groups;

$R^7$ is chosen from hydrogen; halogens; cyano; $C_1$-$C_2$ alkyl groups optionally substituted with one or more substituents each independently chosen from halogens and hydroxy; and $C_3$-$C_{10}$ cycloalkyl groups optionally substituted with one or more substituents each independently chosen from $C_1$-$C_2$ alkyl groups, halogenated $C_1$-$C_2$ alkyl groups, and halogens;

k is 0 or 1;
r is 0 or 1;
m is 0, 1, 2, or 3;
p is 0, 1, or 2; and
q is 0, 1, 2, 3, 4, 5, 6, 7, or 8.

2. A compound of Formula II:

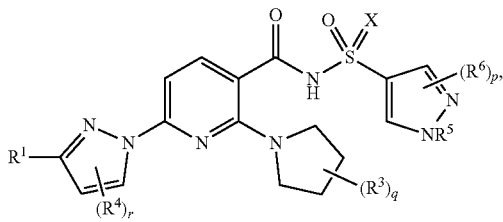

(II)

a pharmaceutically acceptable salt thereof, or a deuterated derivative of any of the foregoing, wherein:

X is chosen from O, NH, and N($C_1$-$C_4$ alkyl) groups;

$R^1$ is $-(C(R^2)_2)_k-O-(C(R^2)_2)_m R^7$, each $R^2$ is independently chosen from hydrogen; halogens; cyano; hydroxy; $C_1$-$C_2$ alkoxy groups; and $C_1$-$C_2$ alkyl groups optionally substituted with one or more substituents each independently chosen from halogens, hydroxy, and $C_{3-5}$ cycloalkyl groups optionally substituted with one or more substituents each independently chosen from $C_1$-$C_2$ alkyl groups, halogenated $C_1$-$C_2$ alkyl groups, and halogens;

each $R^3$ is independently chosen from $C_1$-$C_4$ alkyl groups optionally substituted with one or more hydroxy groups, or optionally two geminal $R^3$, together with the carbon atom to which they are attached, form a $C_{3-4}$ cycloalkyl;

each $R^4$ is independently chosen from halogens;

$R^5$ is chosen from hydrogen and $C_1$-$C_4$ alkyl groups;

each $R^6$ is independently chosen from halogens, cyano, hydroxy, hydroxymethyl, $C_1$-$C_2$ alkoxy groups, $C_1$-$C_2$ alkyl groups, and halogenated $C_1$-$C_2$ alkyl groups;

$R^7$ is chosen from hydrogen; halogens; cyano; $C_1$-$C_2$ alkyl groups optionally substituted with one or more substituents each independently chosen from halogens and hydroxy; and $C_3$-$C_{10}$ cycloalkyl groups optionally substituted with one or more substituents each independently chosen from $C_1$-$C_2$ alkyl groups, halogenated $C_1$-$C_2$ alkyl groups, and halogens;

k is 0 or 1;
r is 0 or 1;
m is 0, 1, 2, or 3;
p is 0, 1, or 2; and
q is 0, 1, 2, 3, 4, 5, 6, 7, or 8.

3. A compound of Formula III:

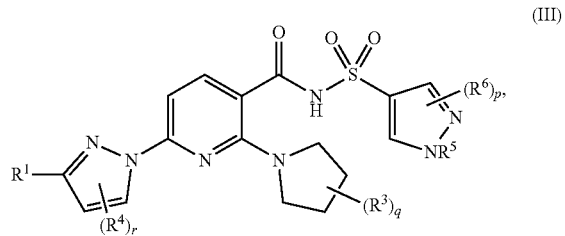

(III)

a pharmaceutically acceptable salt thereof, or a deuterated derivative of any of the foregoing, wherein:

$R^1$ is $-(C(R^2)_2)_k-O-(C(R^2)_2)_m R^7$, each $R^2$ is independently chosen from hydrogen; halogens; cyano; hydroxy; $C_1$-$C_2$ alkoxy groups; and $C_1$-$C_2$ alkyl groups optionally substituted with one or more substituents each independently chosen from halogens, hydroxy, and $C_{3-5}$ cycloalkyl groups optionally substituted with one or more substituents each independently chosen from $C_1$-$C_2$ alkyl groups, halogenated $C_1$-$C_2$ alkyl groups, and halogens;

each $R^3$ is independently chosen from $C_1$-$C_4$ alkyl groups optionally substituted with one or more hydroxy groups, or optionally two geminal $R^3$, together with the carbon atom to which they are attached, form a $C_{3-4}$ cycloalkyl;

each $R^4$ is independently chosen from halogens;

$R^5$ is chosen from hydrogen and $C_1$-$C_4$ alkyl groups;

each $R^6$ is independently chosen from halogens, cyano, hydroxy, hydroxymethyl, $C_1$-$C_2$ alkoxy groups, $C_1$-$C_2$ alkyl groups, and halogenated $C_1$-$C_2$ alkyl groups;

$R^7$ is chosen from hydrogen, halogens, cyano, $C_1$-$C_2$ alkyl groups optionally substituted with one or more substituents each independently chosen from halogens and hydroxy; and $C_3$-$C_{10}$ cycloalkyl groups optionally substituted with one or more substituents each independently chosen from $C_1$-$C_2$ alkyl groups, halogenated $C_1$-$C_2$ alkyl groups, and halogens;

k is 0 or 1;
r is 0 or 1;
m is 0, 1, 2, or 3;
p is 0, 1, or 2; and
q is 0, 1, 2, 3, 4, 5, 6, 7, or 8.

4. A compound according to any of embodiments 1-3, a pharmaceutically acceptable salt thereof, or a deuterated derivative of any of the foregoing, wherein:

each R² is independently chosen from hydrogen and C₁-C₂ alkyl groups;
R⁵ is chosen from hydrogen and C₁-C₂ alkyl groups; and
each R⁶ is independently chosen from C₁-C₂ alkyl groups.

5. A compound according to any of embodiments 1-3, a pharmaceutically acceptable salt thereof, or a deuterated derivative of any of the foregoing, wherein:
R¹ is —O—(CH₂)(C(R²)₂)$_{(m-1)}$R⁷,
R⁷ is independently chosen from C₁-C₂ alkyl groups optionally substituted with one or more substituents each independently chosen from halogens, hydroxy, and C₃-C₁₀ cycloalkyl groups optionally substituted with one or more substituents each independently chosen from C₁-C₂ alkyl groups, halogenated C₁-C₂ alkyl groups, and halogens, and
each R² is independently chosen from C₁-C₂ alkyl groups, OH, C₁-C₂ alkoxy groups, and halogens;
r is 0; and
q is 0, 1, 2, 3, or 4.

6. A compound according to embodiment 4 having Formula IV or V:

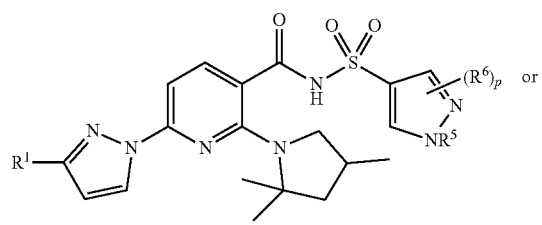

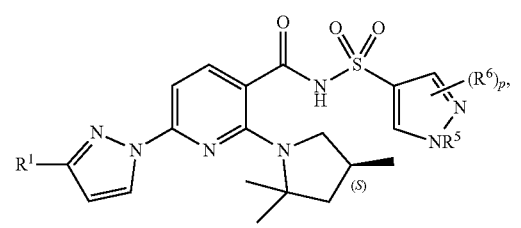

a pharmaceutically acceptable salt thereof, or a deuterated derivative of any of the foregoing,
wherein:
R¹ is —O—(CH₂)(C(R²)₂)$_{(m-1)}$R⁷,
each R² is independently chosen from C₁-C₂ alkyl groups, OH, C₁-C₂ alkoxy groups, and halogens;
R⁷ is chosen from C₁-C₂ alkyl groups optionally substituted with one or more substituents each independently chosen from halogens and C₃-C₁₀ cycloalkyl groups optionally substituted with one or more substituents each independently chosen from C₁-C₂ alkyl groups, halogenated C₁-C₂ alkyl groups, and halogens
R⁵ is chosen from hydrogen and C₁-C₂ alkyl groups;
each R⁶ is independently chosen from C₁-C₂ alkyl groups; and
p is 0, 1, or 2.

7. A compound according to embodiment 6, a pharmaceutically acceptable salt thereof, or a deuterated derivative of any of the foregoing, wherein p is 0 or 1.

8. A compound according to embodiment 6, a pharmaceutically acceptable salt thereof, or a deuterated derivative of any of the foregoing, wherein p is 1.

9. A compound according to any one of embodiments 1-8, a pharmaceutically acceptable salt thereof, or a deuterated derivative of any of the foregoing, wherein each R² is independently chosen from CH₃, OH, F, and OCH₃.

10. A compound according to embodiment 9, a pharmaceutically acceptable salt thereof, or a deuterated derivative of any of the foregoing, wherein p is 0 or 1.

11. A compound according to embodiment 10, a pharmaceutically acceptable salt thereof, or a deuterated derivative of any of the foregoing, wherein:
p is 1;
R⁵ is methyl; and
R⁶ is methyl.

12. A compound according to embodiment 6, a pharmaceutically acceptable salt thereof, or a deuterated derivative of any of the foregoing, wherein R⁷ is a cyclopropyl group.

13. A compound according to embodiment 6, a pharmaceutically acceptable salt thereof, or a deuterated derivative of any of the foregoing, wherein R⁷ is a cyclopropyl group substituted with a halogenated Ci alkyl group.

14. A compound according to embodiment 13, a pharmaceutically acceptable salt thereof, or a deuterated derivative of any of the foregoing, wherein R⁷ is a cyclopropyl group substituted with a CF₃ group.

15. A compound according to embodiment 6, a pharmaceutically acceptable salt thereof, or a deuterated derivative of any of the foregoing, wherein R⁷ is a cyclopropyl group substituted with one or more halogens.

15. A compound according to embodiment 6, a pharmaceutically acceptable salt thereof, or a deuterated derivative of any of the foregoing, wherein R⁷ is a cyclopropyl group substituted with one or more C₁ alkyl groups.

15. A compound according to embodiment 6, a pharmaceutically acceptable salt thereof, or a deuterated derivative of any of the foregoing, wherein R⁷ is a cyclopropyl group substituted with one or more halogens and one or more C₁ alkyl groups.

16. A compound according to embodiment 6, a pharmaceutically acceptable salt thereof, or a deuterated derivative of any of the foregoing, wherein R⁷ is a CF₃ group.

17. A compound according to embodiment 6, a pharmaceutically acceptable salt thereof, or a deuterated derivative of any of the foregoing, wherein R⁷ is chosen from C₄ cycloalkyl groups optionally substituted with one or more substituents each independently chosen from C₁-C₂ alkyl groups, halogenated C₁-C₂ alkyl groups, and halogens.

18. A compound according to embodiment 6, a pharmaceutically acceptable salt thereof, or a deuterated derivative of any of the foregoing, wherein R⁷ is chosen from C₅ cycloalkyl groups optionally substituted with one or more substituents each independently chosen from C₁-C₂ alkyl groups, halogenated C₁-C₂ alkyl groups, and halogens.

19. A compound according to embodiment 18, a pharmaceutically acceptable salt thereof, or a deuterated derivative of any of the foregoing, wherein said C₅ cycloalkyl groups are bicyclic.

20. A compound according to embodiment 6, a pharmaceutically acceptable salt thereof, or a deuterated derivative of any of the foregoing, wherein R⁷ is chosen from C₇ cycloalkyl groups optionally substituted with one or more substituents each independently chosen from C₁-C₂ alkyl groups, halogenated C₁-C₂ alkyl groups, and halogens.

21. A compound according to embodiment 20, a pharmaceutically acceptable salt thereof, or a deuterated derivative of any of the foregoing, wherein said C₇ cycloalkyl groups are bicyclic.

22. A compound according to embodiment 20, a pharmaceutically acceptable salt thereof, or a deuterated derivative of any of the foregoing, wherein said $C_7$ cycloalkyl groups are tricyclic.

23. A compound having a formula chosen from any one of the formulae depicted in FIG. 1, a pharmaceutically acceptable salt thereof, or a deuterated derivative of any of the foregoing.

24. A compound according to embodiment 1 having the following formula:

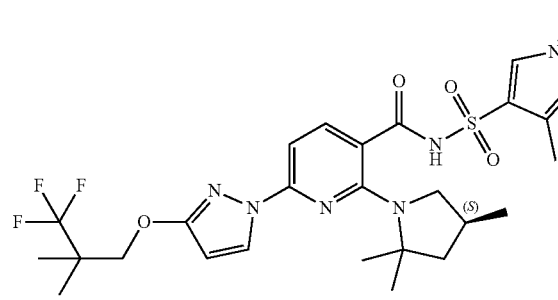

a pharmaceutically acceptable salt thereof, or a deuterated derivative of any of the foregoing 25. A compound according to embodiment 1 having the following formula:

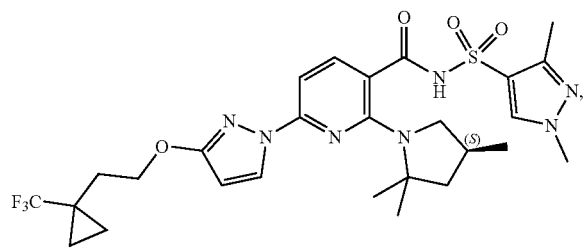

a pharmaceutically acceptable salt thereof, or a deuterated derivative of any of the foregoing.

26. A compound according to embodiment 1 having the following formula:

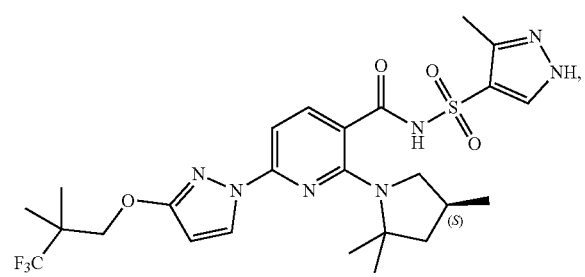

a pharmaceutically acceptable salt thereof, or a deuterated derivative of any of the foregoing.

27. A compound according to embodiment 1 having the following formula:

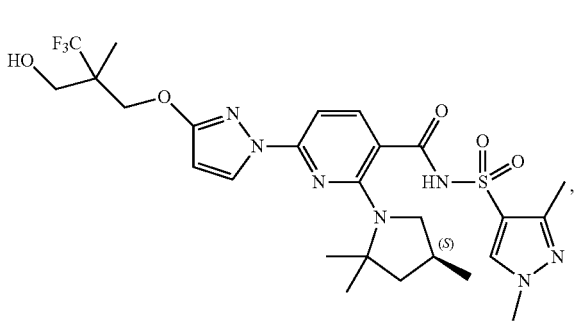

a pharmaceutically acceptable salt thereof, or a deuterated derivative of any of the foregoing.

28. A compound according to embodiment 1 having the following formula:

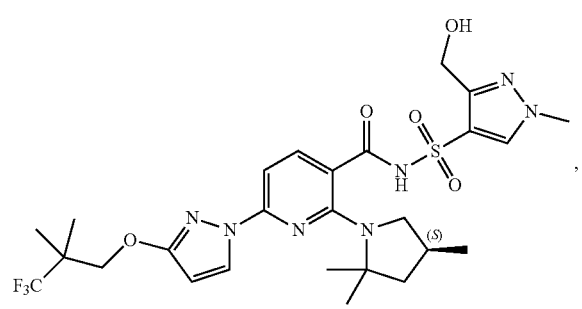

a pharmaceutically acceptable salt thereof, or a deuterated derivative of any of the foregoing.

29. A compound according to embodiment 1 having the following formula:

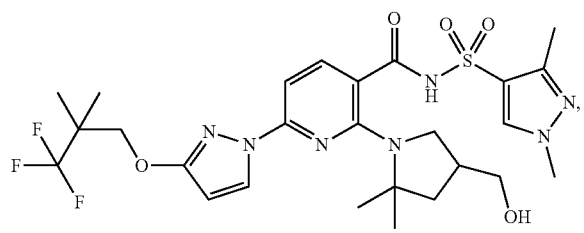 [SMILES: Cc1nn(C)cc1S(=O)(=O)NC(=O)c1ccc(-n2ccc(OCC(C)(C)C(F)(F)F)n2)nc1N1CC(CO)CC1(C)C]

a pharmaceutically acceptable salt thereof, or a deuterated derivative of any of the foregoing.

30. A compound according to embodiment 1 having the following formula:

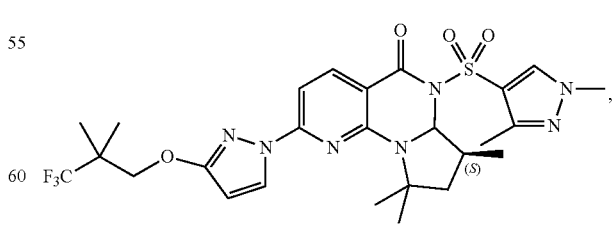

a pharmaceutically acceptable salt thereof, or a deuterated derivative of any of the foregoing.

31. A compound according to embodiment 1 having the following formula:

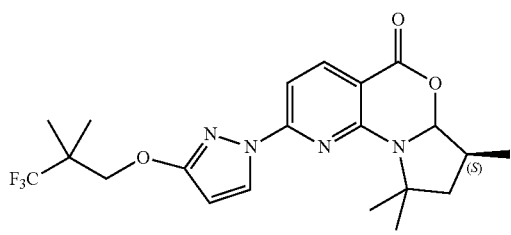

a pharmaceutically acceptable salt thereof, or a deuterated derivative of any of the foregoing.

32. A compound according to embodiment 1 having any one of the following formulae:

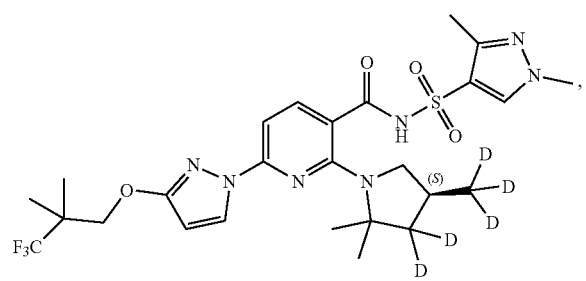

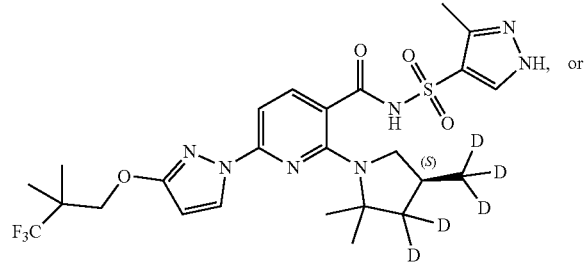

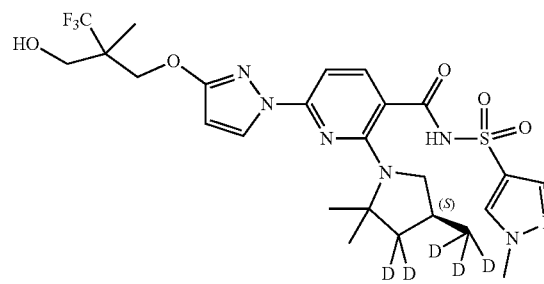

a pharmaceutically acceptable salt thereof, or a deuterated derivative of any of the foregoing.

33. A compound according to embodiment 1 having any one of the following formulae:

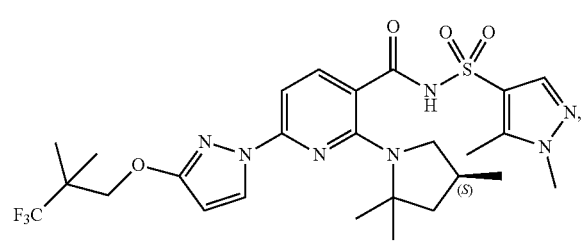

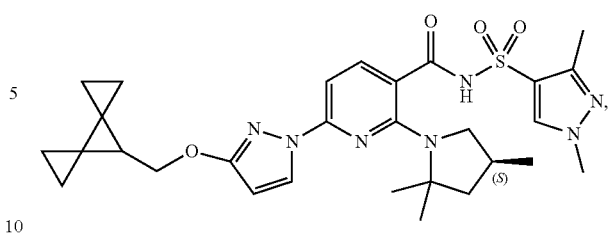

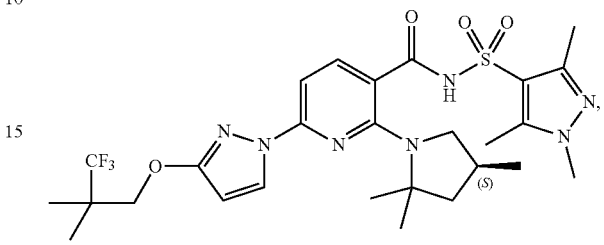

a pharmaceutically acceptable salt thereof, or a deuterated derivative of any of the foregoing.

34. A compound according to embodiment 1 having any one of the following formulae:

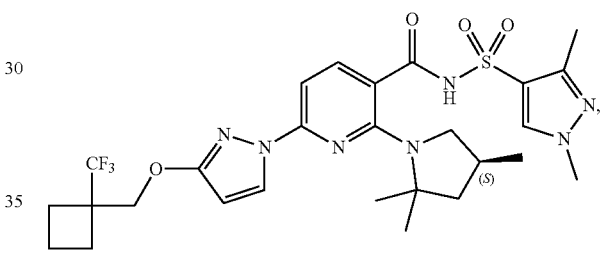

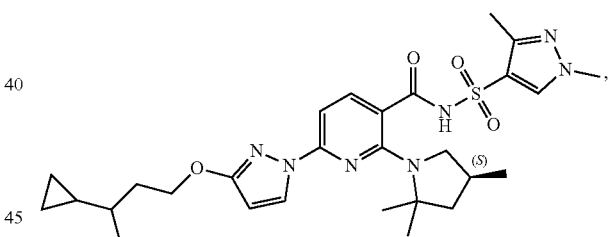

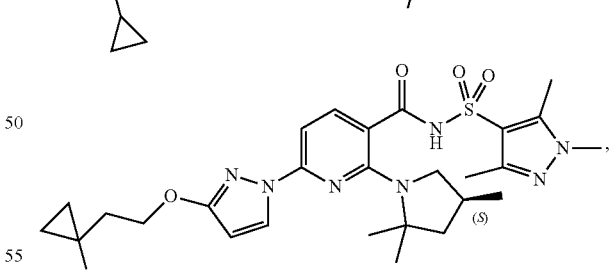

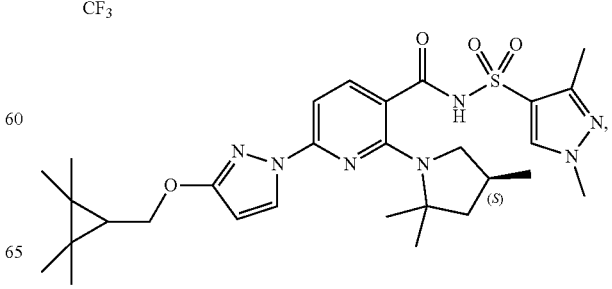

-continued

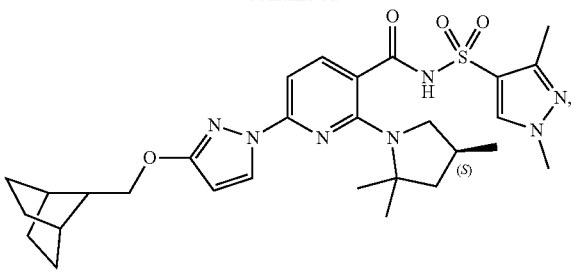

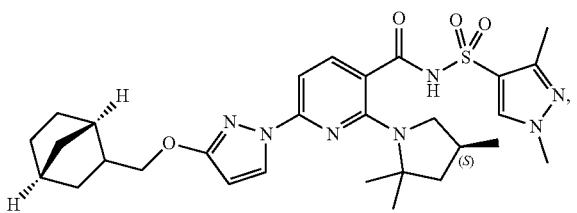

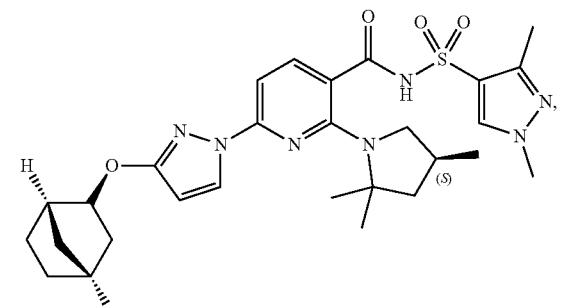

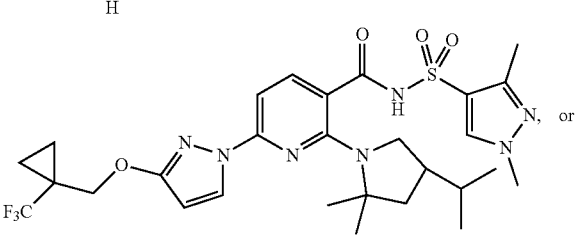

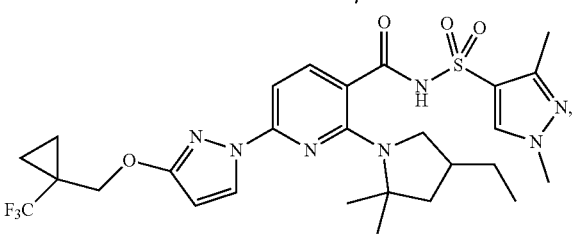

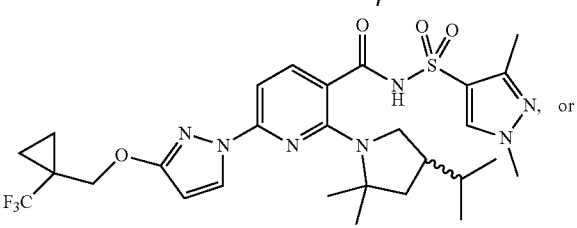

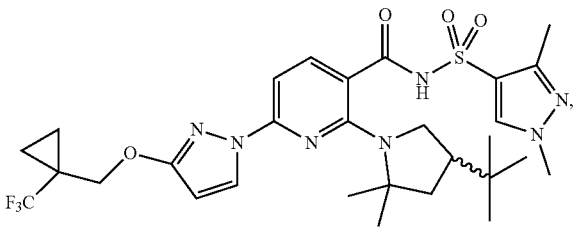

a pharmaceutically acceptable salt thereof, or a deuterated derivative of any of the foregoing.

35. A pharmaceutical composition comprising at least one compound chosen from compounds of any one of embodiments 1-34, a pharmaceutically acceptable salt thereof, or a deuterated derivative of any of the foregoing, and optionally one or more of:

(a) Compound II:

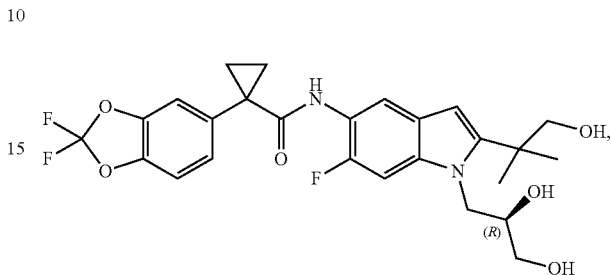

a pharmaceutically acceptable salt thereof, or a deuterated derivative of any of the foregoing;

(b) Compound III:

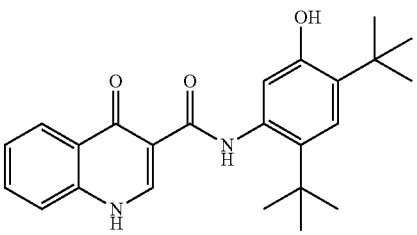

a pharmaceutically acceptable salt thereof, or a deuterated derivative of any of the foregoing; and (c) a pharmaceutically acceptable carrier.

36. A method of treating cystic fibrosis comprising administering to a patient in need thereof a compound of any one of embodiments 1-34, a pharmaceutically acceptable salt thereof, or a deuterated derivative of any of the foregoing; or a pharmaceutical composition according to embodiment 35.

37. A method of preparing a compound of Formula (X):

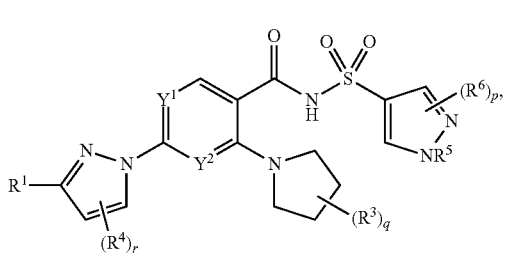

a pharmaceutically acceptable salt thereof, or a deuterated derivative of any of the foregoing, comprising reacting a compound of Formula (F) or a salt thereof with a compound of Formula (G) or a salt thereof to generate said compound of Formula (X) or a pharmaceutically acceptable salt thereof, or a deuterated derivative of any of the foregoing:

63

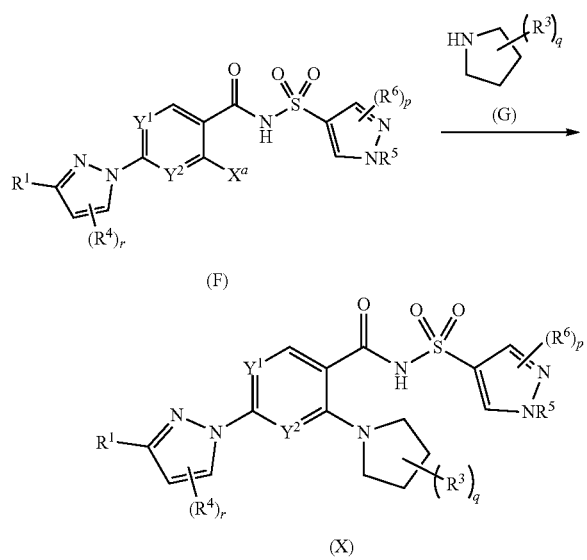

(F)

(X)

wherein in each of said formulae:
one of $Y^1$ and $Y^2$ is N and the other is CH;
$R^1$ is —$(C(R^2)_2)_k$—O—$(C(R^2)_2)_m R^7$,
each $R^2$ is independently chosen from hydrogen; halogens; cyano; hydroxy; $C_1$-$C_2$ alkoxy groups; and $C_1$-$C_2$ alkyl groups optionally substituted with one or more substituents each independently chosen from halogens, hydroxy, and $C_{3-5}$ cycloalkyl groups optionally substituted with one or more substituents each independently chosen from $C_1$-$C_2$ alkyl groups, halogenated $C_1$-$C_2$ alkyl groups, and halogens;
each $R^3$ is independently chosen from $C_1$-$C_4$ alkyl groups optionally substituted with one or more hydroxy groups, or optionally two geminal $R^3$, together with the carbon atom to which they are attached, form a $C_{3-4}$ cycloalkyl;
each $R^4$ is independently chosen from halogens;
$R^5$ is chosen from hydrogen and $C_1$-$C_4$ alkyl groups;
each $R^6$ is chosen from halogens, cyano, hydroxy, hydroxymethyl, $C_1$-$C_2$ alkoxy groups, $C_1$-$C_2$ alkyl groups, and halogenated $C_1$-$C_2$ alkyl groups;
$R^7$ is chosen from hydrogen, halogens, cyano, $C_1$-$C_2$ alkyl groups optionally substituted with one or more substituents each independently chosen from halogens and hydroxy, and $C_3$-$C_{10}$ cycloalkyl groups optionally substituted with one or more substituents each independently chosen from $C_1$-$C_2$ alkyl groups, halogenated $C_1$-$C_2$ alkyl groups, and halogens;
$X^a$ is F or Cl;
k is 0 or 1;
r is 0 or 1;
m is 0, 1, 2, or 3;
p is 0, 1, or 2; and
q is 0, 1, 2, 3, 4, 5, 6, 7, or 8.
38. The method of embodiment 37, wherein $Y^2$ is N; and each $Y^1$ is CH.
39. The method of embodiment 37 or 38, wherein said reacting a compound of Formula (F) or a salt thereof with a compound of Formula (G) or a salt thereof is performed in the presence of a base.
40. The method of any one of embodiments 37-39, wherein a salt of compound of Formula (G) is employed.

64

41. The method of embodiment 40, wherein said salt of compound of Formula (G) is a HCl salt of a compound of Formula (G).
42. A method of preparing a compound of Formula (F) or a salt thereof:

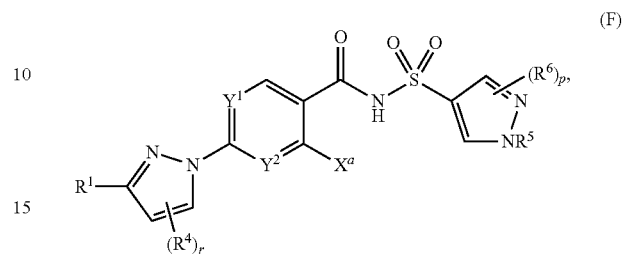

or a deuterated derivative of any of the foregoing, comprising reacting a compound of Formula (D) or salt thereof with a compound of Formula (E) or a salt thereof to generate a compound of Formula (F) or a salt thereof:

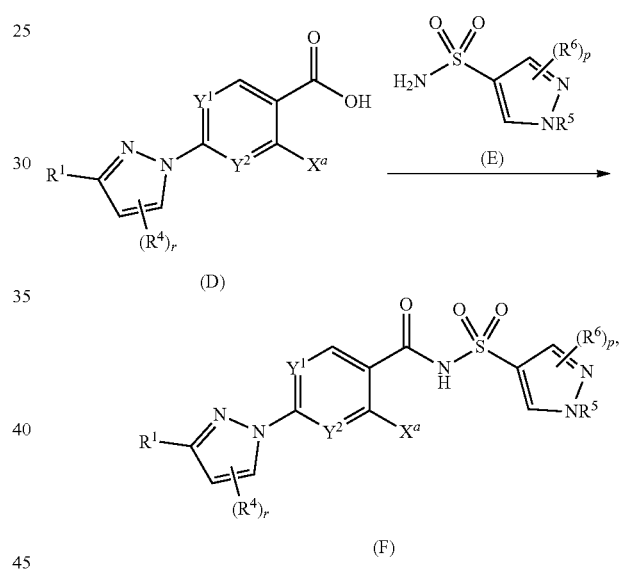

wherein in each of said formulae:
one of $Y^1$ and $Y^2$ is N and the other is CH;
$R^1$ is —$(C(R^2)_2)_k$—O—$(C(R^2)_2)_m R^7$,
each $R^2$ is independently chosen from hydrogen; halogens; cyano; hydroxy; $C_1$-$C_2$ alkoxy groups; and $C_1$-$C_2$ alkyl groups optionally substituted with one or more substituents each independently chosen from halogens, hydroxy, and $C_{3-5}$ cycloalkyl groups optionally substituted with one or more substituents each independently chosen from $C_1$-$C_2$ alkyl groups, halogenated $C_1$-$C_2$ alkyl groups, and halogens;
each $R^4$ is independently chosen from halogens;
each $R^5$ is independently chosen from hydrogen and $C_1$-$C_4$ alkyl groups;
each $R^6$ is chosen from halogens, cyano, hydroxy, hydroxymethyl, $C_1$-$C_2$ alkoxy groups, $C_1$-$C_2$ alkyl groups, and halogenated $C_1$-$C_2$ alkyl groups;
$R^7$ is chosen from hydrogen, halogens, cyano, $C_1$-$C_2$ alkyl groups optionally substituted with one or more substituents each independently chosen from halogens and hydroxy, and $C_3$-$C_{10}$ cycloalkyl groups optionally substituted with one or more substituents each independently chosen from $C_1$-$C_2$ alkyl groups, halogenated $C_1$-$C_2$ alkyl groups, and halogens;

$X^a$ is F or $C_1$;

k is 0 or 1;

r is 0 or 1;

m is 0, 1, 2, or 3; and p is 0, 1, or 2.

43. The method of embodiment 42, wherein $Y^2$ is N; and $Y^1$ is CH.

44. The method of embodiment 42 or 43, wherein said reacting a compound of Formula (D) or a salt thereof with a compound of Formula (E) or salt thereof is performed in the presence of a base.

45. The method of embodiment 42 or 43, wherein said reacting a compound of Formula (D) or salt thereof with a compound of Formula (E) or salt thereof comprises reacting a compound of Formula (D) with a coupling reagent and subsequently with a compound of Formula (E) in the presence of a base.

46. A method of preparing a compound of the following formula:

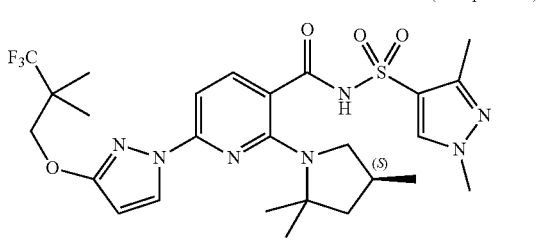

(Compound 1)

or a pharmaceutically acceptable salt thereof, or a deuterated derivative of any of the foregoing, comprising reacting a compound of Formula (F-1) or a salt thereof, wherein $X^a$ is F or Cl, with a compound of Formula (G-1) or a salt thereof to generate said compound or a pharmaceutically acceptable salt thereof, or a deuterated derivative of any of the foregoing:

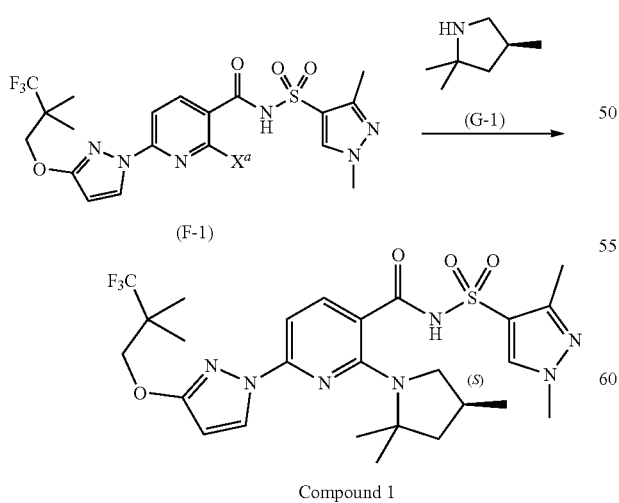

Compound 1 wherein $X^a$ in Formula (F-1) is F or Cl.

47. The method of embodiment 46, wherein said reacting a compound of Formula (F-1) or a salt thereof with a compound of Formula (G-1) or a salt thereof is performed in the presence of a base.

48. The method of embodiment 46 or 47, wherein a salt of compound of Formula (G-1) is employed.

49. The method of embodiment 48, wherein said salt of compound of Formula (G-1) is a HCl salt of a compound of Formula (G-1).

50. A method of preparing a compound of Formula (F-1) or a salt thereof:

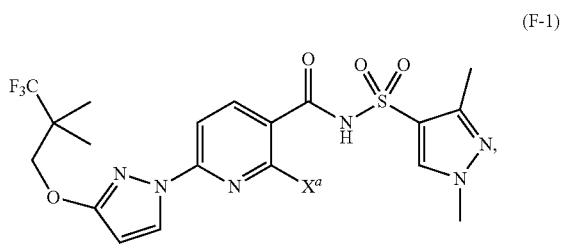

(F-1)

or a deuterated derivative of any of the foregoing, comprising reacting a compound of Formula (D-1) and a compound of Formula (E-1) to generate a compound of Formula (F-1) or a salt thereof:

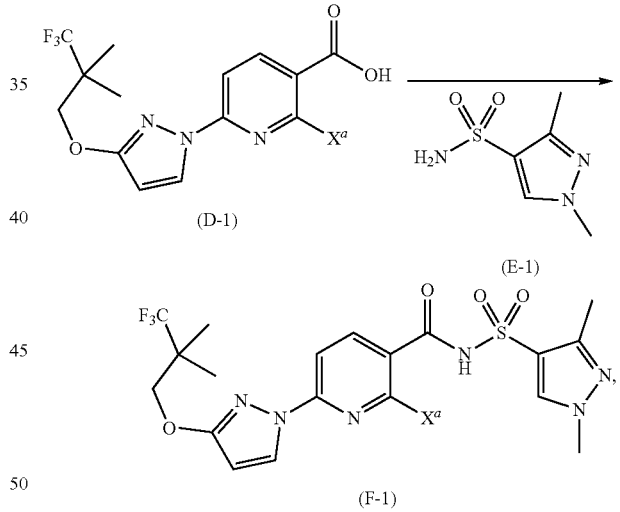

wherein in each said formulae, $X^a$ is F or $C_1$.

51. The method of embodiment 50, wherein said reacting a compound of Formula (D-1) or a salt thereof with a compound of Formula (E-1) or a salt thereof is performed in the presence of a base.

52. The method of embodiment 50, wherein said reacting a compound of Formula (D-1) or a salt thereof with a compound of Formula (E-1) or a salt thereof comprises reacting a compound of Formula (D-1) with a coupling reagent and subsequently with a compound of Formula (E-1) in the presence of a base.

53. A method of preparing a compound of Formula (D) or a salt thereof:

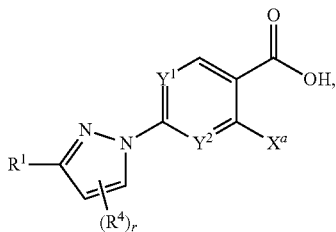

(D)

or a deuterated derivative of any of the foregoing, comprising:
(i) reacting a compound of Formula (A) or a salt thereof with a compound of Formula (B) or a salt thereof to generate a compound of Formula (C) or a salt thereof:

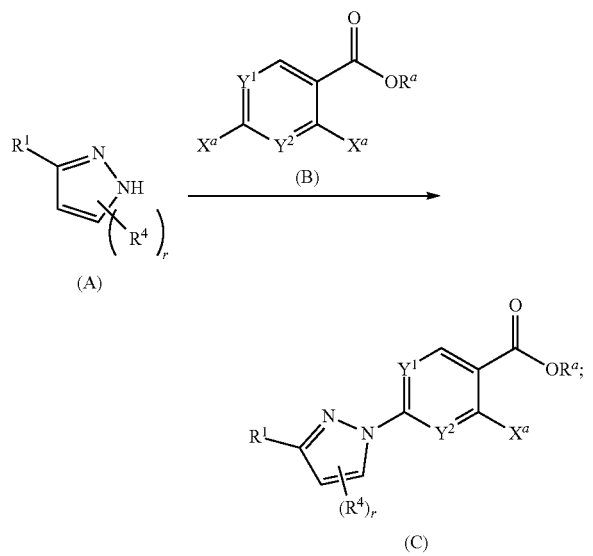

and
(ii) hydrolyzing the —C(O)OR$^a$ group of a compound of Formula (C) to generate a compound of Formula (D) or a salt thereof,
wherein in each said formulae:
one of Y$^1$ and Y$^2$ is N and the other is CH;
R$^1$ is —(C(R$^2$)$_2$)$_k$—O—(C(R$^2$)$_2$)$_m$R$^7$,
each R$^2$ is independently chosen from hydrogen; halogens; cyano; hydroxy; C$_1$-C$_2$ alkoxy groups; and C$_1$-C$_2$ alkyl groups optionally substituted with one or more substituents each independently chosen from halogens, hydroxy, and C$_{3-5}$ cycloalkyl groups optionally substituted with one or more substituents each independently chosen from C$_1$-C$_2$ alkyl groups, halogenated C$_1$-C$_2$ alkyl groups, and halogens;
each R$^4$ is independently chosen from halogens;
R$^7$ is chosen from hydrogen, halogens, cyano, C$_1$-C$_2$ alkyl groups optionally substituted with one or more substituents each independently chosen from halogens and hydroxy, and C$_3$-C$_{10}$ cycloalkyl groups optionally substituted with one or more substituents each independently chosen from C$_1$-C$_2$ alkyl groups, halogenated C$_1$-C$_2$ alkyl groups, and halogens;
X$^a$ is F or C$_1$;
k is 0 or 1;
r is 0 or 1; and
m is 0, 1, 2, or 3.

54. The method of embodiment 53, wherein Y$^2$ is N; and Y$^1$ is CH.
55. The method of embodiment 53 or 54, wherein the hydrolysis of the —C(O)OR$^a$ group is performed in the presence of a base or acid.
56. The method of any one of embodiments 53-55, wherein said reacting a compound of Formula (A) or a salt thereof with a compound of Formula (B) or salt thereof is performed in the presence of a base.
57. The method of any one of embodiments 53-56, wherein R$^a$ is ethyl or t-butyl.
58. A method of preparing a compound of Formula (D-1) or a salt thereof:

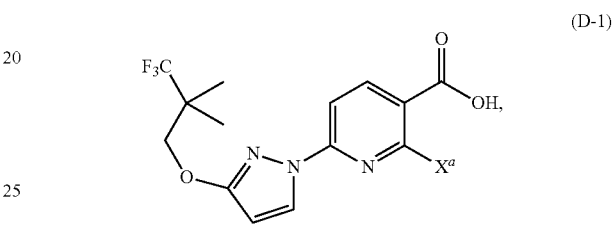

(D-1)

or a deuterated derivative of any of the foregoing, comprising:
(i) reacting a compound of Formula (A-1) or a salt thereof and a compound of Formula (B-1) or a salt thereof to generate a compound of Formula (C-1) or a salt thereof:

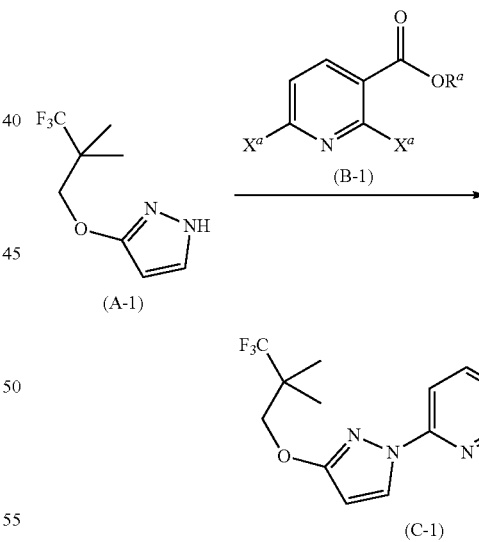

and
(ii) hydrolyzing the —C(O)OR$^a$ group of a compound of Formula (C-1) or a salt thereof to generate a compound of Formula (D-1) or a salt thereof,
wherein in each said formulae, each R$^a$ is independently chosen from C$_1$-C$_4$ alkyl; and each X$^a$ is independently F or C$_1$.
59. The method of embodiment 58, wherein the hydrolysis of the —C(O)OR$^a$ group is performed in the presence of a base or acid.

60. The method of 58 or 59, wherein said reacting a compound of Formula (A-1) or a salt thereof and a compound of Formula (B-1) or a salt thereof is performed in the presence of a base.

61. The method of any one of embodiments 58-60, wherein $R^a$ is ethyl or t-butyl.

62. A compound of Formula (F) or a salt thereof:

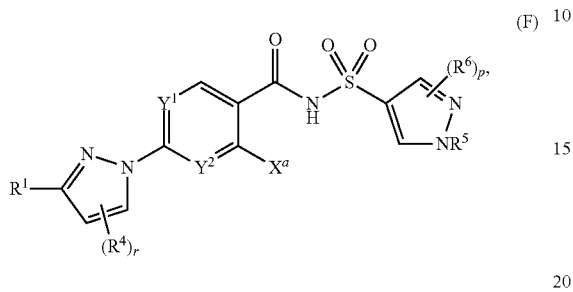

(F)

or a deuterated derivative of any of the foregoing, wherein in each of said formulae:

$R^1$ is $-(C(R^2)_2)_k-O-(C(R^2)_2)_m R^7$, each $R^2$ is independently chosen from hydrogen; halogens; cyano; hydroxy; $C_1$-$C_2$ alkoxy groups; and $C_1$-$C_2$ alkyl groups optionally substituted with one or more substituents each independently chosen from halogens, hydroxy, and $C_{3-5}$ cycloalkyl groups optionally substituted with one or more substituents each independently chosen from $C_1$-$C_2$ alkyl groups, halogenated $C_1$-$C_2$ alkyl groups, and halogens;

each $R^4$ is independently chosen from halogens;

$R^5$ is chosen from hydrogen and $C_1$-$C_4$ alkyl groups;

each $R^6$ is chosen from halogens, cyano, hydroxy, hydroxymethyl, $C_1$-$C_2$ alkoxy groups, $C_1$-$C_2$ alkyl groups, and halogenated $C_1$-$C_2$ alkyl groups;

$R^7$ is chosen from hydrogen, halogens, cyano, $C_1$-$C_2$ alkyl groups optionally substituted with one or more substituents each independently chosen from halogens and hydroxy, and $C_3$-$C_{10}$ cycloalkyl groups optionally substituted with one or more substituents each independently chosen from $C_1$-$C_2$ alkyl groups, halogenated $C_1$-$C_2$ alkyl groups, and halogens;

$X^a$ is F or Cl k is 0 or 1;

r is 0 or 1;

m is 0, 1, 2, or 3; and p is 0, 1, or 2.

63. A compound according to embodiment 62, a pharmaceutically acceptable salt thereof, or a deuterated derivative of any of the foregoing, wherein $Y^2$ is N; and each $Y^1$ is CH.

64. A compound of Formula (F-1) or a salt thereof:

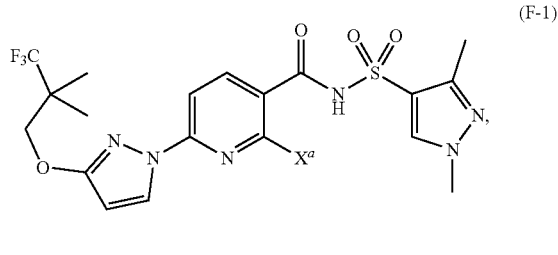

(F-1)

or a deuterated derivative of any of the foregoing, wherein $X^a$ is F or Cl.

65. A compound of Formula (C) or (D), or a salt thereof:

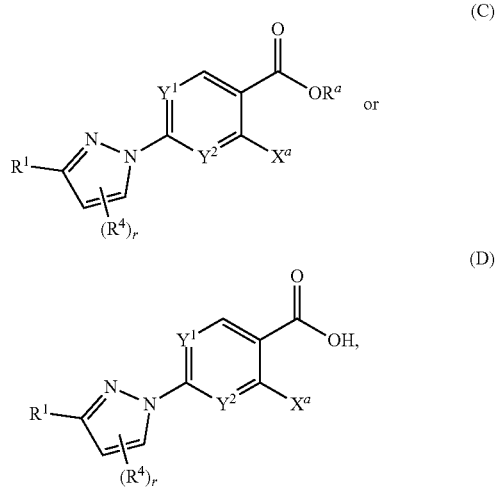

(C)

(D)

or a deuterated derivative of any of the foregoing, wherein in each said formulae:

one of $Y^1$ and $Y^2$ is independently N and the other is independently CH;

$R^1$ is $-(C(R^2)_2)_k-O-(C(R^2)_2)_m R^7$, each $R^2$ is independently chosen from hydrogen; halogens; cyano; hydroxy; $C_1$-$C_2$ alkoxy groups; and $C_1$-$C_2$ alkyl groups optionally substituted with one or more substituents each independently chosen from halogens, hydroxy, and $C_{3-5}$ cycloalkyl groups optionally substituted with one or more substituents each independently chosen from $C_1$-$C_2$ alkyl groups, halogenated $C_1$-$C_2$ alkyl groups, and halogens;

each $R^4$ is independently chosen from halogens;

$R^7$ is chosen from hydrogen, halogens, cyano, $C_1$-$C_2$ alkyl groups optionally substituted with one or more substituents each independently chosen from halogens and hydroxy, and $C_3$-$C_{10}$ cycloalkyl groups optionally substituted with one or more substituents each independently chosen from $C_1$-$C_2$ alkyl groups, halogenated $C_1$-$C_2$ alkyl groups, and halogens;

$R^a$ is $C_1$-$C_4$ alkyl;

$X^a$ is F or $C_1$;

k is 0 or 1;

r is 0 or 1; and m is 0, 1, 2, or 3.

66. A compound according to embodiment 65, a pharmaceutically acceptable salt thereof, or a deuterated derivative of any of the foregoing, wherein each $Y^2$ is independently N; and each $Y^1$ is independently CH.

67. A compound according to embodiment 65, a pharmaceutically acceptable salt thereof, or a deuterated derivative of any of the foregoing, wherein $R^a$ is ethyl or t-butyl.

68. A compound of Formula (C-1) or (D-1), or a salt thereof:

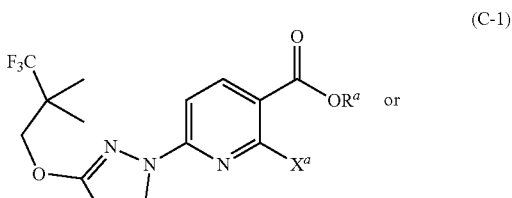

(C-1)

71

-continued

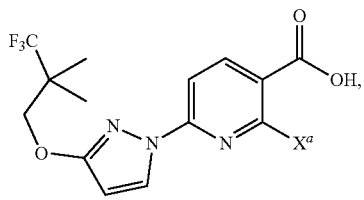
(D-1)

or a deuterated derivative of any of the foregoing, wherein $R^a$ is $C_1$-$C_4$ alkyl; and each $X^a$ is independently F or Cl.

69. A compound according to embodiment 68, a pharmaceutically acceptable salt thereof, or a deuterated derivative of any of the foregoing, wherein $R^a$ is ethyl or t-butyl.

70. A compound of Formula (A-1), (C-1) or (D-1), or a salt thereof:

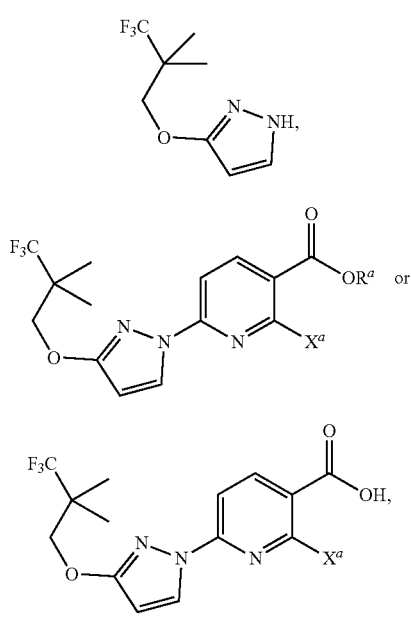

(A-1)

(C-1)

(D-1)

or a deuterated derivative of any of the foregoing, wherein $R^a$ is $C_1$-$C_4$ alkyl; and each $X^a$ is independently F or $C_1$.

71. Use of at least one compound chosen from compounds of any one of embodiments 1-34, a pharmaceutically acceptable salt thereof, or a deuterated derivative of any of the foregoing, and optionally one or more of:

(a) Compound II:

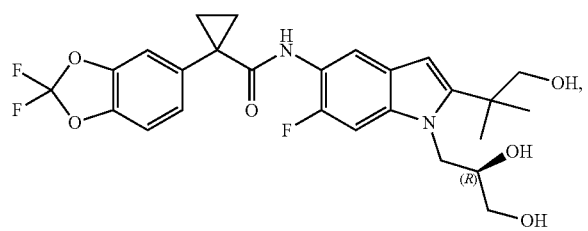

a pharmaceutically acceptable salt thereof, or a deuterated derivative of any of the foregoing; and

72

(b) Compound III:

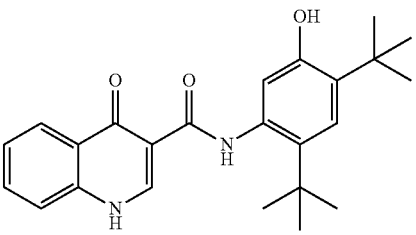

a pharmaceutically acceptable salt thereof, or a deuterated derivative of any of the foregoing, for treating cystic fibrosis.

72. Crystalline Form A of Compound 1:

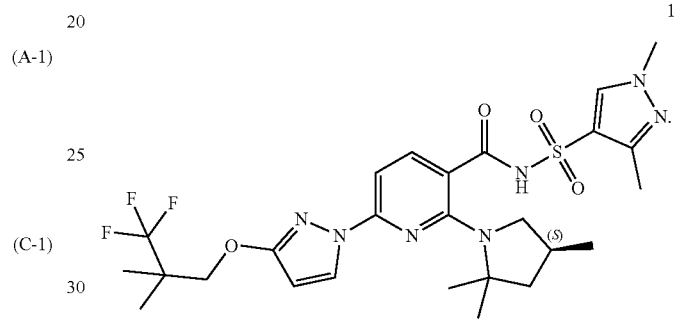

73. Crystalline Form A according to embodiment 72 in substantially pure form.

74. Crystalline Form A according to embodiment 72, characterized by an X-ray powder diffractogram having a signal at at least three two-theta values chosen from 6.6±0.2, 7.6±0.2, 9.6±0.2, 12.4±0.2, 13.1±0.2, 15.2±0.2, 16.4±0.2, 18.2±0.2, and 18.6±0.2.

75. Crystalline Form A according to embodiment 72, characterized by an X-ray powder diffractograph having a signal at at least three two-theta values chosen from 6.6±0.2, 9.6±0.2, 13.1±0.2, 15.2±0.2, 18.2±0.2, and 18.6±0.2.

76. Crystalline Form A according to embodiment 72, characterized by an X-ray powder diffractograph having a signal at three two-theta values of 6.6±0.2, 13.1±0.2, 18.2±0.2.

77. Crystalline Form A according to embodiment 72, characterized by an X-ray powder diffractograph having a signal at six two-theta values of 6.6±0.2, 9.6±0.2, 13.1±0.2, 15.2±0.2, 18.2±0.2, and 18.6±0.2.

78. Crystalline Form A of embodiment 72, characterized by an X-ray powder diffractogram substantially similar to that in FIG. 2.

79. Crystalline Form A of Compound 1 prepared by a process comprising desolvating at least one crystalline form of Compound 1 chosen from Crystalline Form M, Crystalline Form E, Crystalline Form P1, Crystalline Form P2, and Crystalline Form AA2.

80. Crystalline Form A of Compound 1 prepared by a process comprising desolvating at least one solvate chosen from methanol solvates, ethanol solvates, acetic acid solvates, toluene solvates, sulfolane solvates, 1-propanol solvates, 2-propanol solvates, propionic acid solvates, methyl tert-butyl ether solvates, and isobutyric acid solvates of Compound 1 (such as, for example, methanol solvates, ethanol solvates, acetic acid solvates, toluene solvates, sulfolane solvates, propionic acid solvates, methyl tert-butyl ether solvates, and isobutyric acid solvates of Compound 1, further such as, for example, methanol solvates, ethanol solvates, acetic acid solvates, toluene solvates, and sulfolane solvates of Compound 1, and further such as, for example, methanol solvates and ethanol solvates of Compound 1) followed by subjecting the resulting desolvate to vacuum drying at room temperature for 12 to 100 hours.

81. At least one solvate of Compound 1:

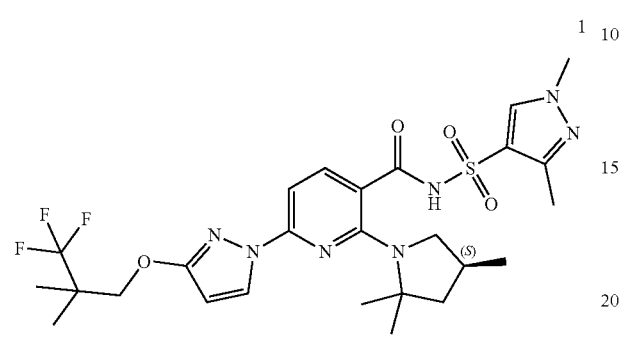

chosen from methanol solvates, ethanol solvates, 1-propanol solvates, 2-propanol solvates, acetic acid solvates, toluene solvates, sulfolane solvates, propionic acid solvates, methyl tert-butyl ether solvates, isobutyric acid solvates, anisole solvates, methylbutyl ketone solvates, and xylene solvates of Compound 1.

83. Crystalline Form M of Compound 1:

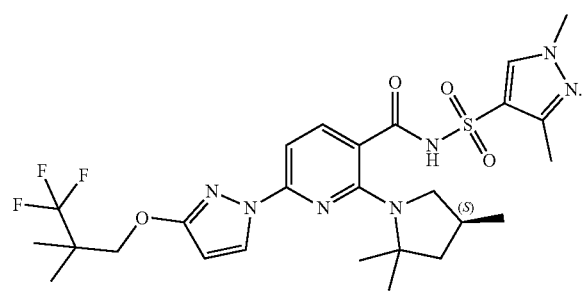

84. Crystalline Form M according to embodiment 83 in substantially pure form.
85. Crystalline Form M according to embodiment 83, characterized by an X-ray powder diffractogram having a signal at at least three two-theta values chosen from 7.0±0.2, 11.6±0.2, 13.1±0.2, 13.7±0.2, 15.2±0.2, 15.9±0.2, 16.4±0.2, 17.8±0.2, and 19.3±0.2.
86. Crystalline Form M according to embodiment 83, characterized by an X-ray powder diffractograph having a signal at at least three two-theta values chosen from 11.6±0.2, 13.1±0.2, 13.7±0.2, 15.2±0.2, 17.8±0.2, and 19.3±0.2.
87. Crystalline Form M according to embodiment 83, characterized by an X-ray powder diffractograph having a signal at three two-theta values of 11.6±0.2, 17.8±0.2, and 13.1±0.2.
88. Crystalline Form M according to embodiment 83, characterized by an X-ray powder diffractograph having a signal at six two-theta values of 11.6±0.2, 13.1±0.2, 13.7±0.2, 15.2±0.2, 17.8±0.2, and 19.3±0.2.
89. Crystalline Form M of embodiment 83, characterized by an X-ray powder diffractogram substantially similar to that in FIG. 13.

90. Crystalline Form E of Compound 1:

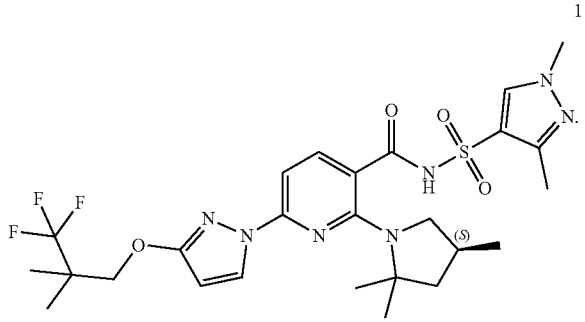

91. Crystalline Form E according to embodiment 90 in substantially pure form.
92. Crystalline Form E according to embodiment 90, characterized by an X-ray powder diffractogram having a signal at at least three two-theta values chosen from 7.0±0.2, 11.2±0.2, 12.8±0.2, 13.2±0.2, 14.1±0.2, 15.1±0.2, 16.1±0.2, 17.8±0.2, and 18.9±0.2.
93. Crystalline Form E according to embodiment 90, characterized by an X-ray powder diffractograph having a signal at at least three two-theta values chosen from 11.2±0.2, 12.8±0.2, 13.2±0.2, 15.1±0.2, 16.1±0.2, and 17.8±0.2.
94. Crystalline Form E according to embodiment 90, characterized by an X-ray powder diffractograph having a signal at three two-theta values of 12.8±0.2, 16.1±0.2, and 17.8±0.2.
95. Crystalline Form E according to embodiment 90, characterized by an X-ray powder diffractograph having a signal at six two-theta values of 11.2±0.2, 12.8±0.2, 13.2±0.2, 15.1±0.2, 16.1±0.2, and 17.8±0.2.
96. Crystalline Form E of embodiment 90, characterized by an X-ray powder diffractogram substantially similar to that in FIG. 14.
97. A method of preparing crystalline Form A of Compound 1:

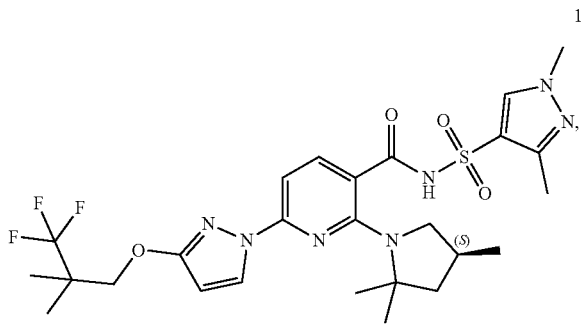

comprising stirring a solution or suspension of Compound 1 in a solvent system at a temperature in a range from 50° C. to 85° C.

98. A method of preparing crystalline Form A of Compound 1:

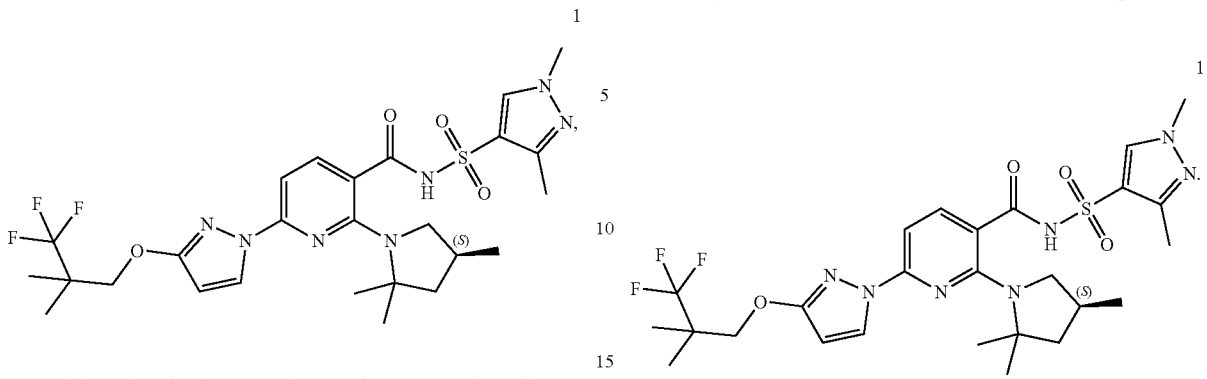

comprising desolvating a solvate of Compound 1 chosen from methanol solvates, ethanol solvates, 1-propanol solvates, 2-propanol solvates, acetic acid solvates, toluene solvates, sulfolane solvates, propionic acid solvates, methyl tert-butyl ether solvates, isobutyric acid solvates, anisole solvates, methylbutyl ketone solvates, and xylene solvates of Compound 1.

99. A crystalline Form X of a potassium salt of Compound 1:

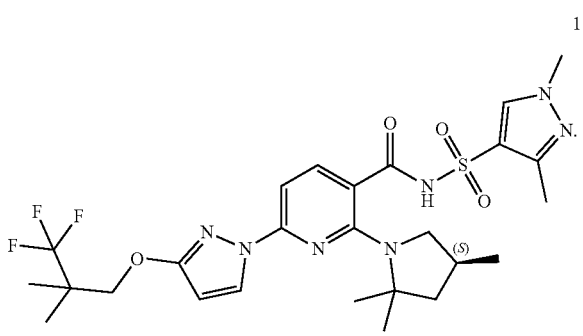

100. Crystalline Form X according to embodiment 99 in substantially pure form.

101. Crystalline Form X according to embodiment 99, characterized by an X-ray powder diffractogram having a signal at at least three two-theta values chosen from 4.9±0.2, 5.9±0.2, 8.1±0.2, 8.5±0.2, 10.3±0.2, 13.0±0.2, 13.9±0.2, 14.6±0.2, and 17.0±0.2.

102. Crystalline Form X according to embodiment 99, characterized by an X-ray powder diffractograph having a signal at at least three two-theta values chosen from 4.9±0.2, 5.9±0.2, 8.1±0.2, 13.0±0.2, 13.9±0.2, and 17.0±0.2.

103. Crystalline Form X according to embodiment 99, characterized by an X-ray powder diffractograph having a signal at three two-theta values of 4.9±0.2, 5.9±0.2, and 13.0±0.2.

104. Crystalline Form X according to embodiment 99, characterized by an X-ray powder diffractograph having a signal at six two-theta values of 4.9±0.2, 5.9±0.2, 8.1±0.2, 13.0±0.2, 13.9±0.2, and 17.0±0.2.

Figure 15:
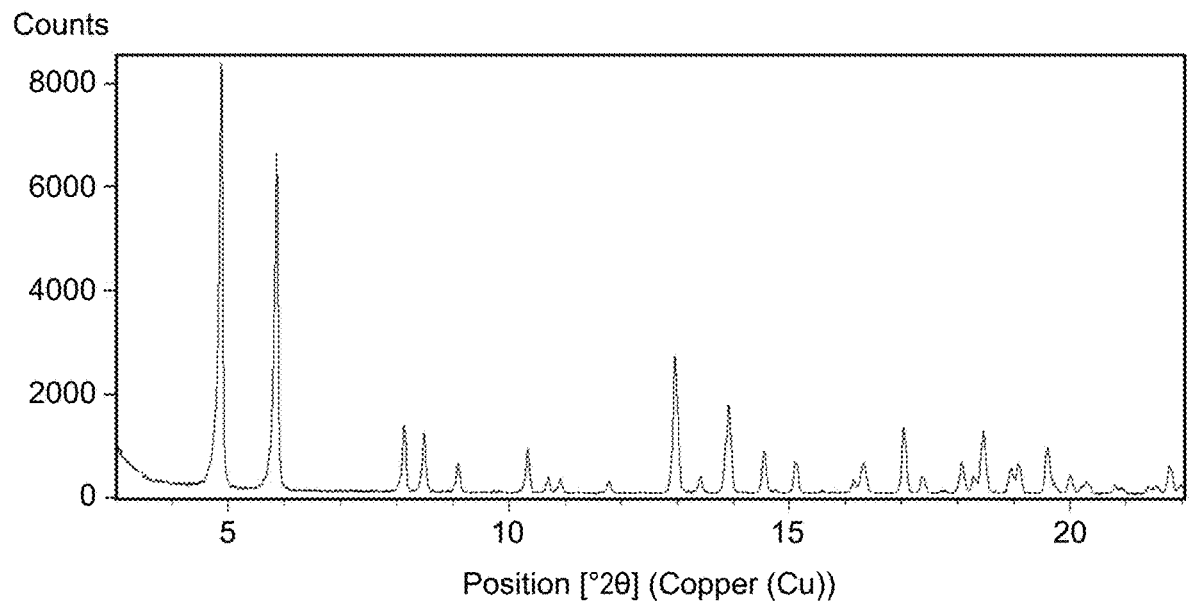
FIG. 15 shows an X-ray powder diffractogram of crystalline Form X of a potassium salt of Compound 1.

105. Crystalline Form X of embodiment 99, characterized by an X-ray powder diffractogram substantially similar to that in FIG. 15.

106. A crystalline Form Y of a sodium salt of Compound 1:

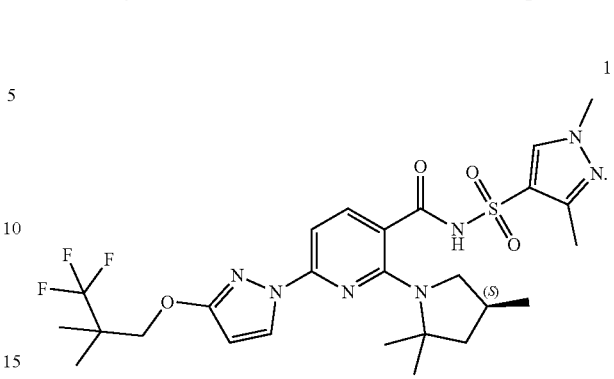

107. Crystalline Form Y according to embodiment 106 in substantially pure form.

108. Crystalline Form Y according to embodiment 106, characterized by an X-ray powder diffractogram having a signal at at least three two-theta values chosen from 3.5±0.2, 7.0+0.2, 11.7±0.2, 12.8±0.2, 13.2±0.2, 14.2±0.2, 15.4±0.2, 16.6±0.2, and 18.0±0.2.

109. Crystalline Form Y according to embodiment 106, characterized by an X-ray powder diffractograph having a signal at at least three two-theta values chosen from 3.5±0.2, 7.0±0.2, 11.7±0.2, 13.2±0.2, 14.2±0.2, and 18.0±0.2

110. Crystalline Form Y according to embodiment 106, characterized by an X-ray powder diffractograph having a signal at three two-theta values of 7.0±0.2, 11.7±0.2, and 13.2±0.2.

111. Crystalline Form Y according to embodiment 106, characterized by an X-ray powder diffractograph having a signal at six two-theta values of 3.5±0.2, 7.0±0.2, 11.7±0.2, 13.2+0.2, 14.2±0.2, and 18.0±0.2.

Figure 16:
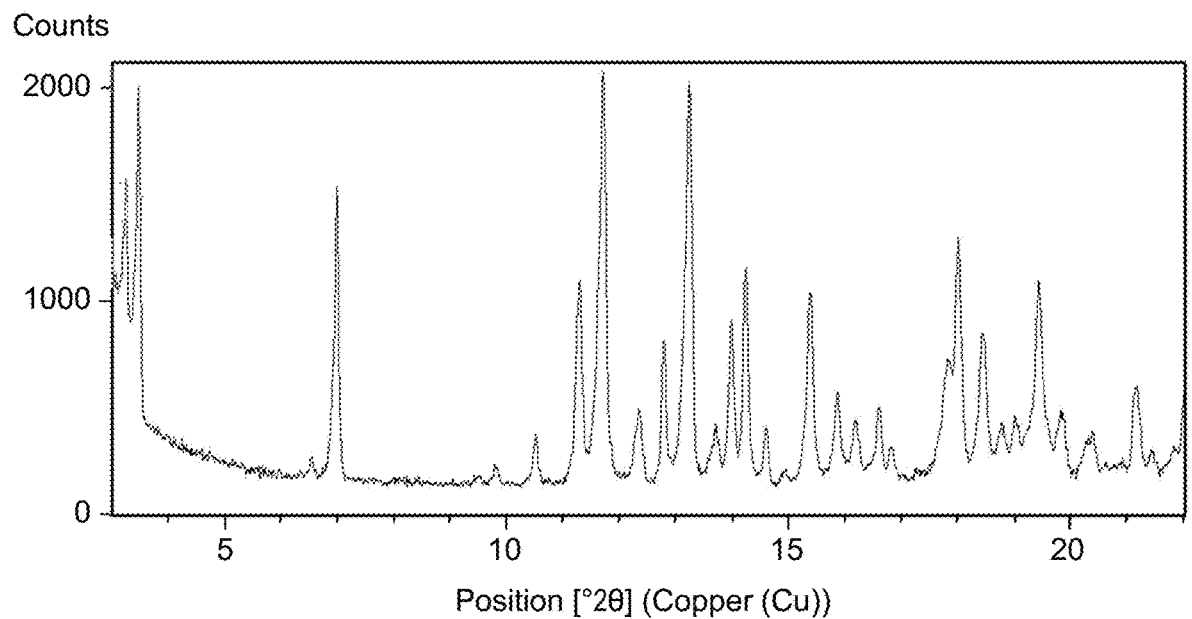
FIG. 16 shows an X-ray powder diffractogram of crystalline Form Y of a sodium salt of Compound 1.

112. Crystalline Form Y of embodiment 106, characterized by an X-ray powder diffractogram substantially similar to that in FIG. 16.

113. A solid dispersion comprising Compound 1 and a polymer.

114. The solid dispersion of embodiment 113, comprising 50 wt % of Compound 1 and 50 wt % of a polymer by the total weight of the solid dispersion or 80 wt % of Compound 1 and 20 wt % of a polymer by the total weight of the solid dispersion.

115. The solid dispersion of embodiment 113 or 114, wherein the polymer is a hypromellose acetate succinate, hydroxypropyl cellulose, hydroxypropyl methylcellulose, or polyvinylpyrrolidone.

116. A pharmaceutical formulation comprising at least one crystalline form according to any one of embodiments 72-96 and 99-112, and a pharmaceutically acceptable carrier.

117. A method of treating cystic fibrosis comprising administering to a patient in need thereof at least one crystalline form according to any one of embodiments 72-96, and 199-112.

118. A method of treating cystic fibrosis comprising administering to a patient in need thereof a solid dispersion according to any one of embodiments 113-115.

119. Crystalline Form P2 of Compound 1:

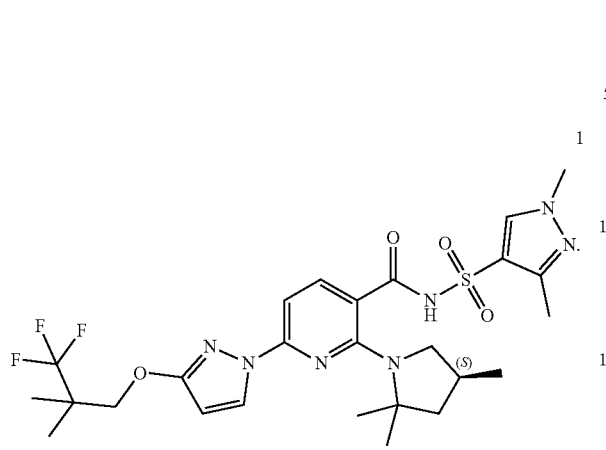

120. Crystalline Form P2 according to claim 119 in substantially pure form.

121. Crystalline Form P2 according to claim 119, characterized by an X-ray powder diffractogram having a signal at at least three two-theta values chosen from 10.2±0.2, 10.9±0.2, 12.6±0.2, 12.9±0.2, 15.0±0.2, 15.9±0.2, 16.2±0.2, 16.5±0.2, and 17.6±0.2.

122. Crystalline Form P2 according to claim 119, characterized by an X-ray powder diffractograph having a signal at at least three two-theta values chosen from 10.9±0.2, 12.6±0.2, 12.9±0.2, 15.0±0.2, 16.5±0.2, and 17.6±0.2.

123. Crystalline Form P2 according to claim 119, characterized by an X-ray powder diffractograph having a signal at three two-theta values of 10.9±0.2, 12.6±0.2, and 17.6±0.2.

124. Crystalline Form P2 according to claim 119, characterized by an X-ray powder diffractograph having a signal at six two-theta values of 10.9±0.2, 12.6±0.2, 12.9±0.2, 15.0±0.2, 16.5±0.2, and 17.6±0.2.

125. Crystalline Form P2 of claim 119, characterized by an X-ray powder diffractogram substantially similar to that in FIG. 17.

Other embodiments include:

A. Compound 1 of the formula

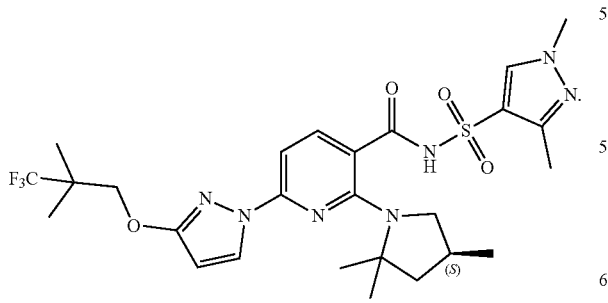

B. A pharmaceutically acceptable salt of Compound 1 of the formula

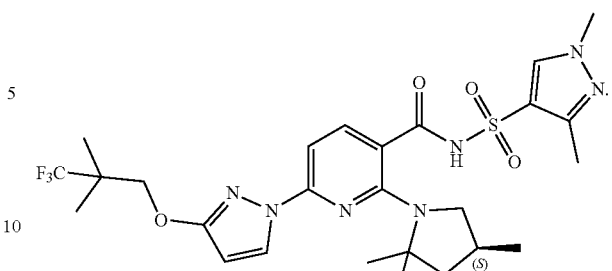

C. A pharmaceutical composition comprising:

(i) Compound 1 of the formula

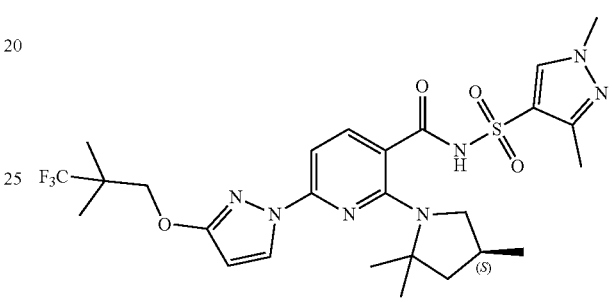

and (ii) a pharmaceutically acceptable carrier.

D. The pharmaceutical composition of embodiment C further comprising Compound II:

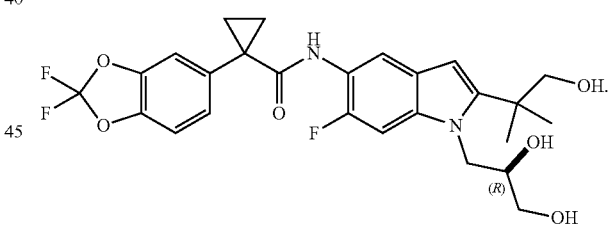

E. The pharmaceutical composition of embodiment C further comprising a pharmaceutically acceptable salt of Compound II:

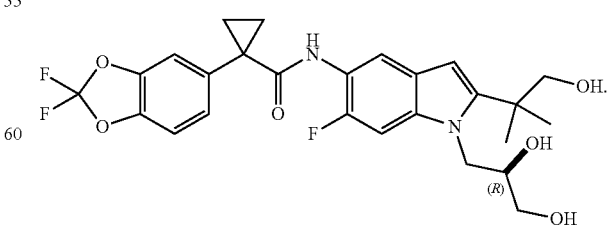

F. The pharmaceutical composition of embodiment C further comprising Compound III:

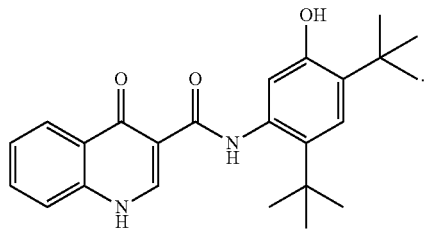 [SMILES: CC(C)(C)c1cc(C(C)(C)C)c(NC(=O)c2c[nH]c3ccccc3c2=O)cc1O]

G. The pharmaceutical composition of embodiment C further comprising a pharmaceutically acceptable salt of Compound III:

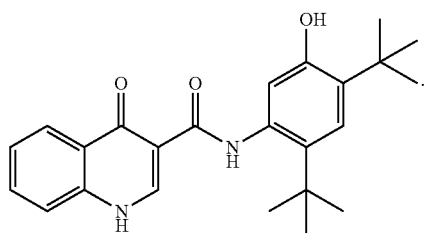 [SMILES: CC(C)(C)c1cc(C(C)(C)C)c(NC(=O)c2c[nH]c3ccccc3c2=O)cc1O]

H. The pharmaceutical composition of embodiment D further comprising Compound III:

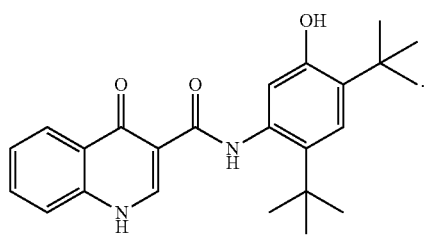 [SMILES: CC(C)(C)c1cc(C(C)(C)C)c(NC(=O)c2c[nH]c3ccccc3c2=O)cc1O]

I. The pharmaceutical composition of embodiment D further comprising a pharmaceutically acceptable salt of Compound III:

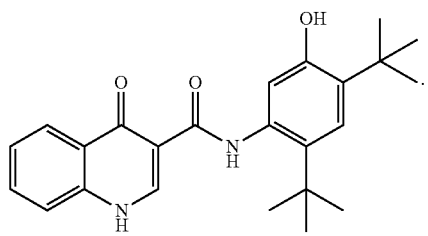 [SMILES: CC(C)(C)c1cc(C(C)(C)C)c(NC(=O)c2c[nH]c3ccccc3c2=O)cc1O]

J. The pharmaceutical composition of embodiment E further comprising Compound III:

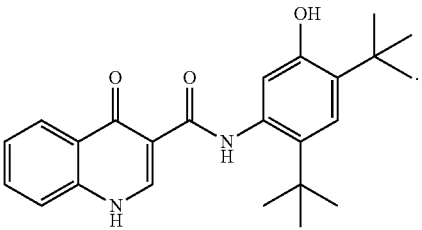 [SMILES: CC(C)(C)c1cc(C(C)(C)C)c(NC(=O)c2c[nH]c3ccccc3c2=O)cc1O]

K. The pharmaceutical composition of embodiment E further comprising a pharmaceutically acceptable salt of Compound III:

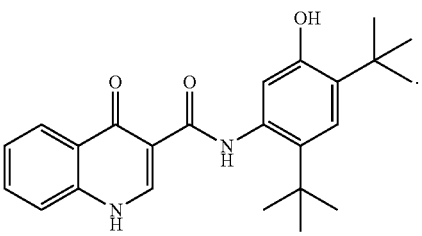 [SMILES: CC(C)(C)c1cc(C(C)(C)C)c(NC(=O)c2c[nH]c3ccccc3c2=O)cc1O]

L. A pharmaceutical composition comprising:
(A) a pharmaceutically acceptable salt of Compound 1 of the formula

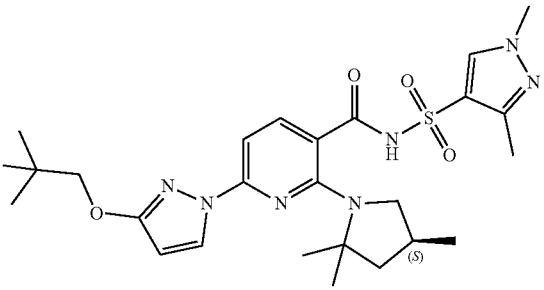

and
(B) a pharmaceutically acceptable carrier.

M. The pharmaceutical composition of embodiment L further comprising Compound II:

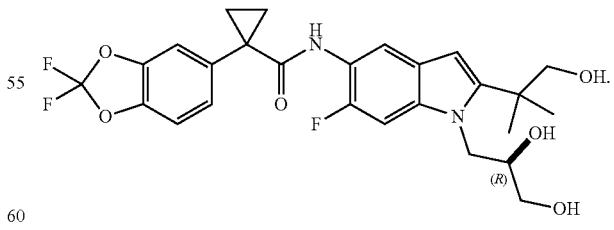

N. The pharmaceutical composition of embodiment L further comprising a pharmaceutically acceptable salt of Compound II:

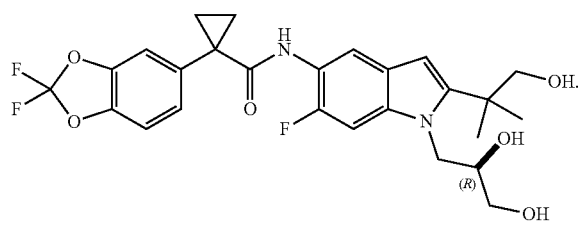

O. The pharmaceutical composition of embodiment L further comprising Compound III:

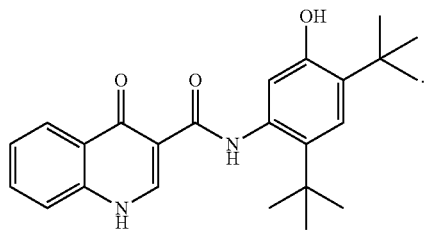 [SMILES: CC(C)(C)c1cc(C(C)(C)C)c(NC(=O)c2c[nH]c3ccccc3c2=O)cc1O]

P. The pharmaceutical composition of embodiment L further comprising a pharmaceutically acceptable salt of Compound III:

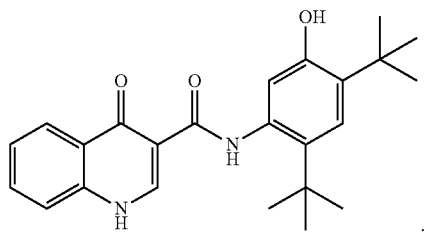 [SMILES: CC(C)(C)c1cc(C(C)(C)C)c(NC(=O)c2c[nH]c3ccccc3c2=O)cc1O]

Q. The pharmaceutical composition of embodiment M further comprising Compound III:

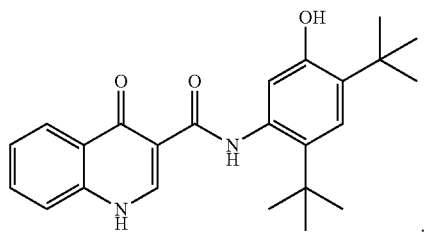 [SMILES: CC(C)(C)c1cc(C(C)(C)C)c(NC(=O)c2c[nH]c3ccccc3c2=O)cc1O]

R. The pharmaceutical composition of embodiment M further comprising a pharmaceutically acceptable salt of Compound III:

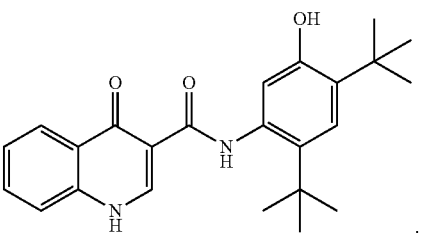 [SMILES: CC(C)(C)c1cc(C(C)(C)C)c(NC(=O)c2c[nH]c3ccccc3c2=O)cc1O]

S. The pharmaceutical composition of embodiment M further comprising Compound III:

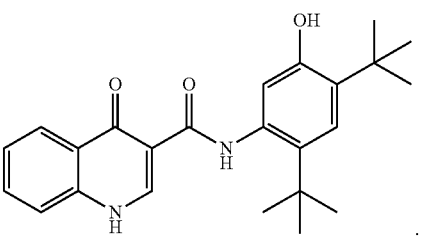 [SMILES: CC(C)(C)c1cc(C(C)(C)C)c(NC(=O)c2c[nH]c3ccccc3c2=O)cc1O]

T. The pharmaceutical composition of embodiment M further comprising a pharmaceutically acceptable salt of Compound III:

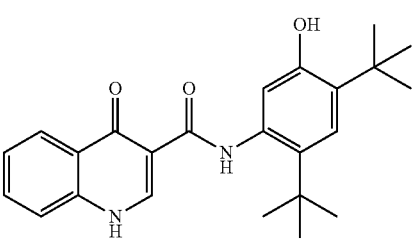

U. A method of treating cystic fibrosis comprising administering to a patient in need thereof Compound 1 of the formula

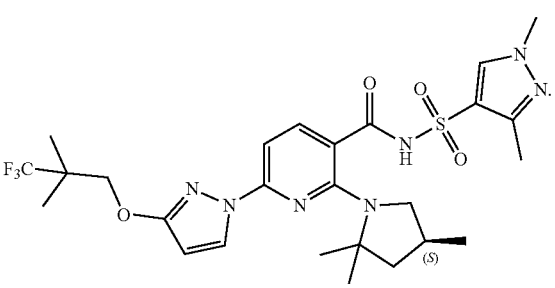

V. A method of treating cystic fibrosis comprising administering to a patient in need thereof a pharmaceutically acceptable salt of Compound 1 of the formula

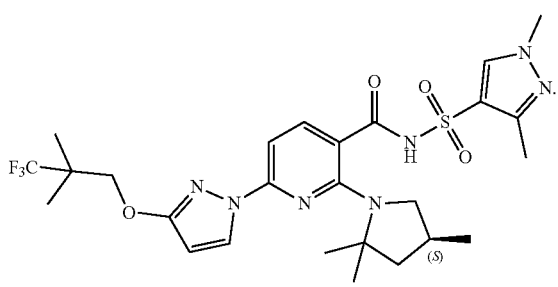

W. A method of treating cystic fibrosis comprising administering to a patient in need thereof a pharmaceutical composition comprising:
(A) Compound 1 of the formula

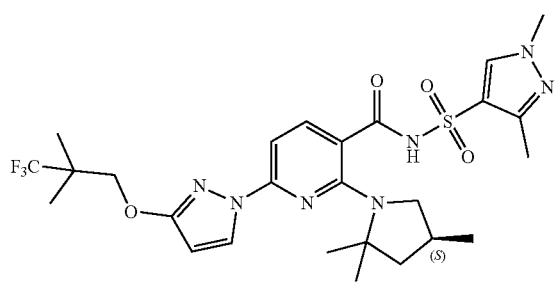

and
(B) a pharmaceutically acceptable carrier.

X. A method of treating cystic fibrosis comprising administering to a patient in need thereof a pharmaceutical composition comprising:
a pharmaceutically acceptable salt of Compound 1 of the formula

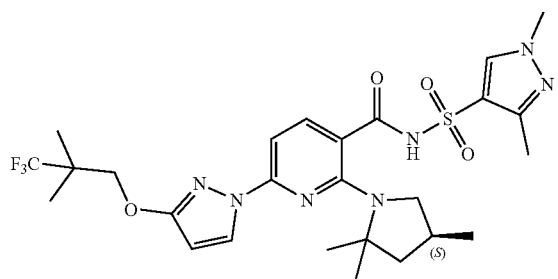

and
a pharmaceutically acceptable carrier.

GENERAL EXPERIMENTAL PROCEDURES

The definitions of certain abbreviations for the Examples below are summarized below:
Boc anhydride (Boc)$_2$O): di-tert-butyl dicarbonate
CDI: carbonyl diimidazole
DABCO: 1,4-diazabicyclo[2.2.2]octane
DBU: 1,8-diazabicyclo(5.4.0)undec-7-ene
DCM: dichloromethane
DIAD: diisopropyl azodicarboxylate
DIEA (DIPEA; N,N-diisopropylethylamine)
DMA: N,N-Dimethylacetamide
DMF: N,N-dimethylformamide
DMSO: dimethyl sulfoxide
Et$_2$O: diethyl ether
EtOH: ethanol
HATU: 1-[Bis(dimethylamino)methylene]-1H-1,2,3-triazolo[4,5-b]pyridinium 3-oxid hexafluorophosphate
IPA: isoproanol
MeOH: methanol
NMP: N-methyl-2-pyrrolidone
MTBE: methyl tert-butyl ether
TBS-Cl: tert-Butyldimethylsilyl chloride
TFA: trifluoroacetic acid
THF: tetrahydrofuran)
p-TsOH: p-Toluenesulfonic Acid
TPPO-DIAD complex: a complex of triphenylphosphine oxide with diisopropyl azodicarboxylate Reagents and starting materials were obtained by commercial sources unless otherwise stated and were used without purification. Proton and carbon NMR spectra were acquired on either of a Bruker Biospin DRX 400 MHz FTNMR spectrometer operating at a $^1$H and $^{13}$C resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters. Final purity of compounds was determined by reversed phase UPLC using an Acquity UPLC BEH Cis column (50×2.1 mm, 1.7 μm particle) made by Waters (pn: 186002350), and a dual gradient run from 1-99% mobile phase B over 3.0 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were reported as [M+H]$^+$ species obtained using a single quadrupole mass spectrometer equipped with an electrospray ionization (ESI) source capable of achieving a mass accuracy of 0.1 Da and a minimum resolution of 1000 (no units on resolution) across the detection range. Optical purity of methyl (2S)-2,4-dimethyl-4-nitro-pentanoate was determined using chiral gas chromatography (GC) analysis on an Agilent 7890A/MSD 5975C instrument, using a Restek Rt-βDEXcst (30m x 0.25 mm×0.25 um_df) column, with a 2.0 mL/min flow rate (H2 carrier gas), at an injection temperature of 220° C. and an oven temperature of 120° C., 15 minutes.

Powder X-Ray Diffraction

The powder x-ray diffraction measurements were performed using PANalytical's X-pert Pro diffractometer at room temperature with copper radiation (1.54060 Å). The incident beam optic was comprised of a variable divergence slit to ensure a constant illuminated length on the sample and on the diffracted beam side; a fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 s.

Figure 2:
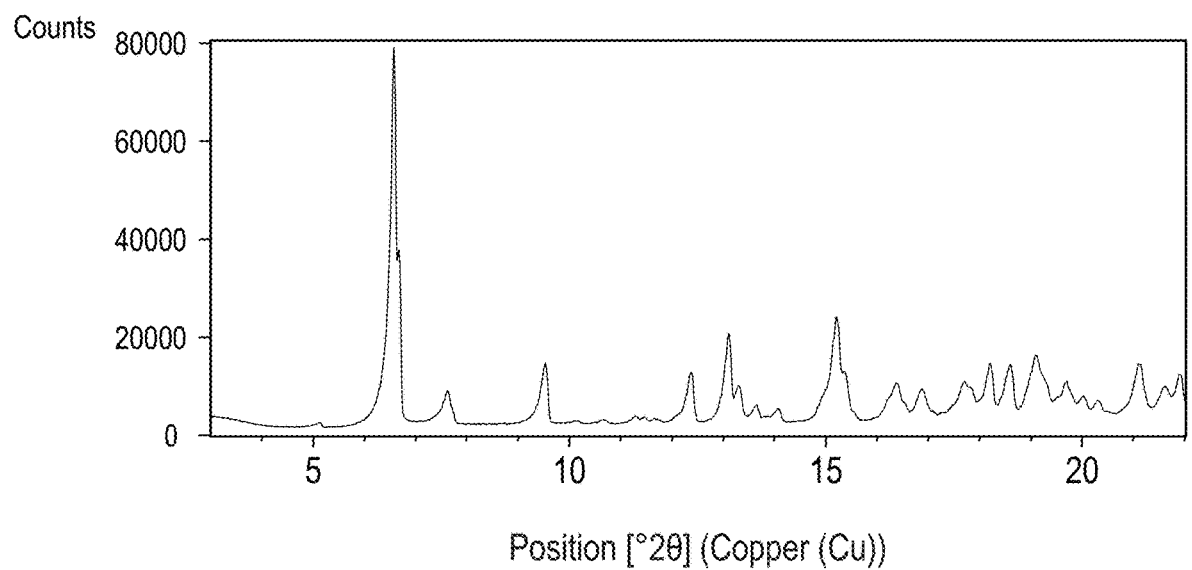
FIG. 2 is an XRPD of Form A of Compound 1.

FIG. 2 shows the XRPD spectrum of Form A of Compound 1. The single crystal structure of Form A has been elucidated. The crystal structure confirms the absolute configuration of the molecule, and the calculated XRPD patterns show good agreement with the experimental patterns. Form A of Compound 1 forms as an orthorhombic unit cell of $P2_12_12_1$, a=15.74 b=22.86 c=26.59 (angstroms), α=β=γ=90, Z=12 V=9575 Flack=0.08. One of ordinary skill in the art would recognize that there may be variation in these crystal parameters depending, for example, on the temperature, pressure, or instrument to instrument variability.

Figure 3:
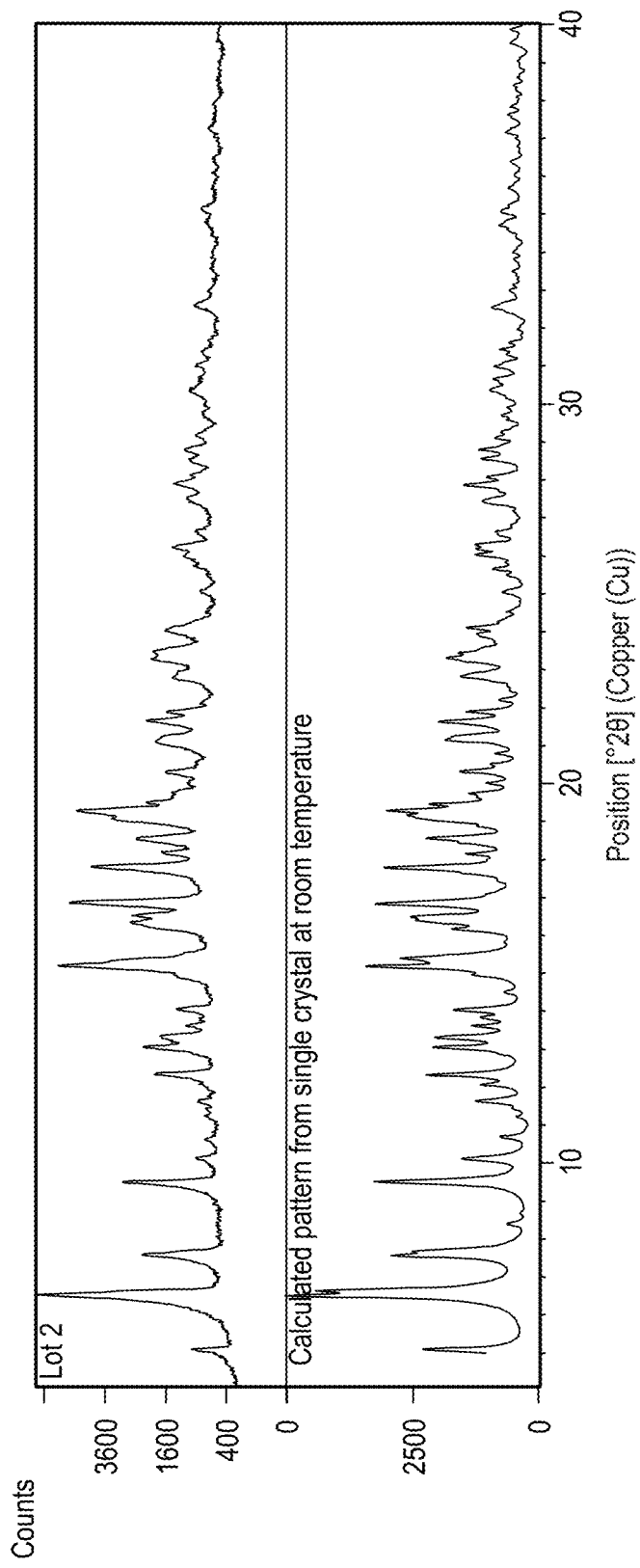
FIG. 3 is an experimental XRPD of Form A of Compound 1 (top) compared to a calculated XRD (bottom), which is calculated from the single crystal data.
Figure 4:
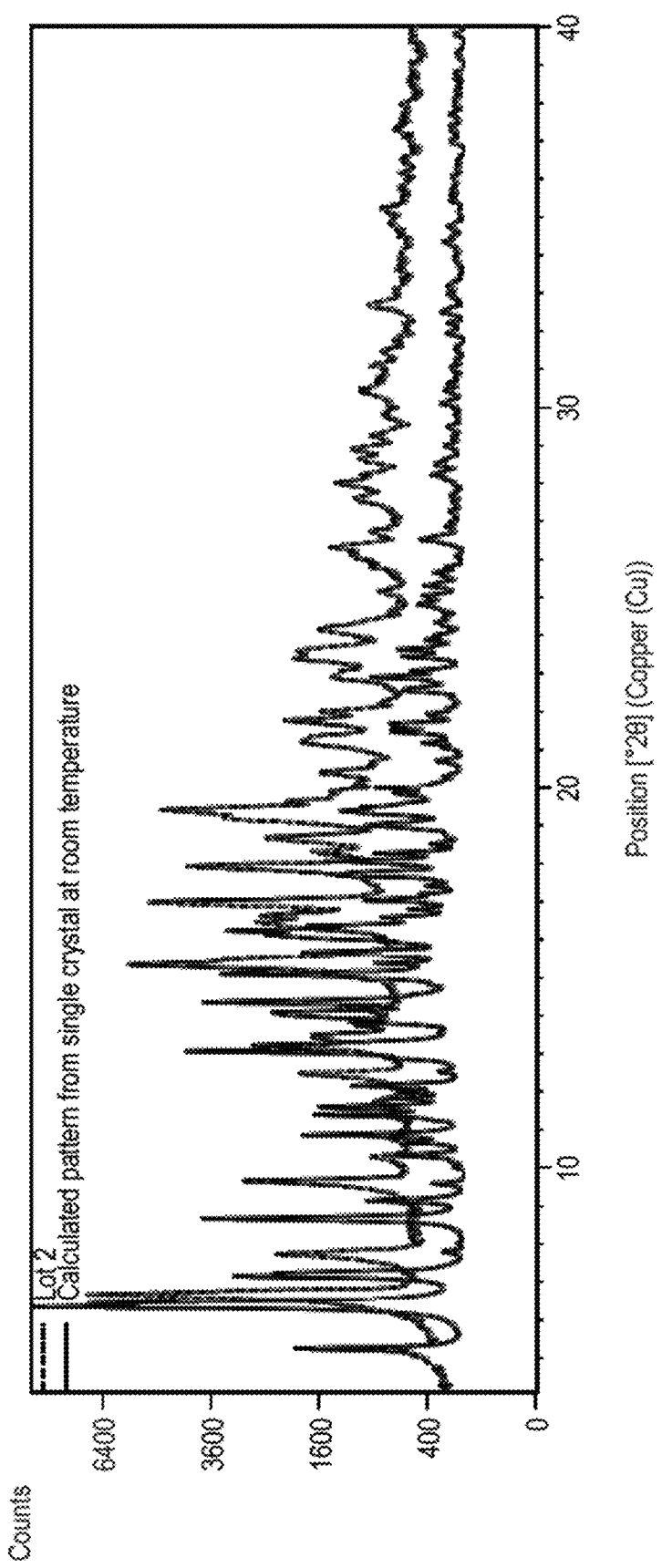
FIG. 4 is an overlay of the experimental and calculated XRPD of Form A of Compound 1 from FIG. 3.

FIG. 3 shows an experimental XRPD of Form A of Compound 1 (top) compared to a calculated XRD (bottom), which is calculated from the single crystal data. FIG. 3 shows an overlay of the experimental and calculated XRPD of Form A of Compound 1 from FIG. 3.

Figure 5:
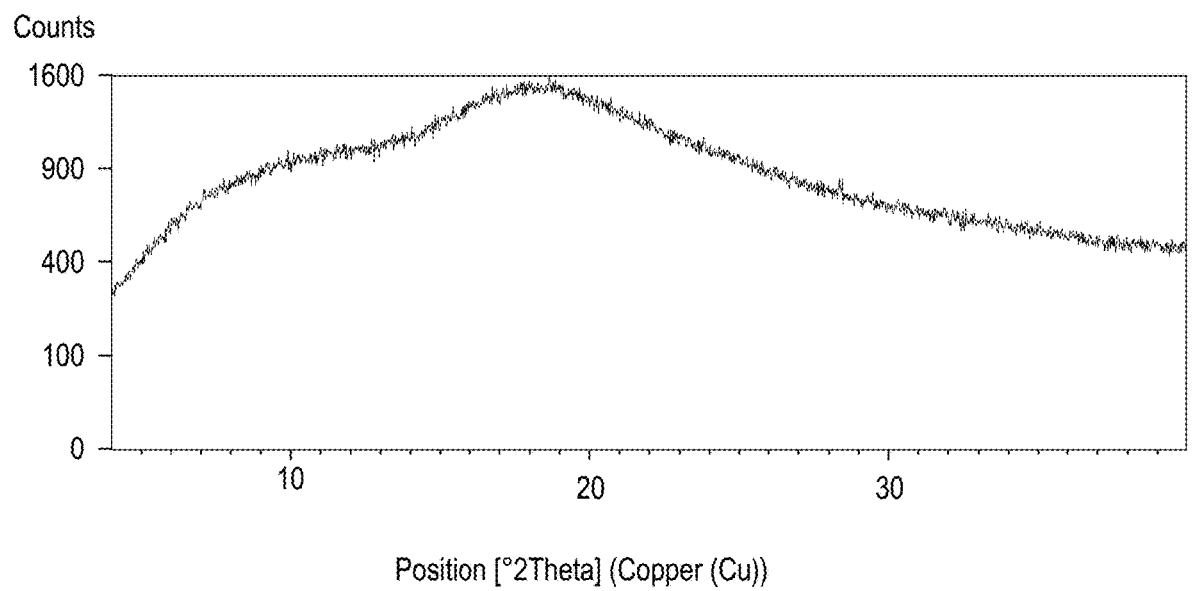
FIG. 5 is an XRPD of a spray dried dispersion (SDD) of 50 wt % Compound 1 with HPMCAS-HG.

FIG. 5 shows the XRPD spectrum of amorphous Compound 1 prepared by spray dried dispersion (SDD) of 50 wt % Compound 1 in HPMCAS-HG.

Modulated Differential Scanning Calorimetry (MDSC)

MDSC was used to determine the glass transition temperature of the amorphous material. MDSC was performed using TA Discovery DSC differential scanning calorimeter (TA Instruments, New Castle, Del.). The instrument was calibrated with indium. Samples of approximately 1-3 mg were weighed into hermetic pans that were crimped using lids with one hole. The MDSC sample was scanned from −20° C. to 200° C. at a heating rate of 2° C./min with +/−1° C. of modulation within 1 minute. Data was collected and analyzed by TA Instruments Trios Software (TA Instruments, New Castle, Del.).

Figure 6:
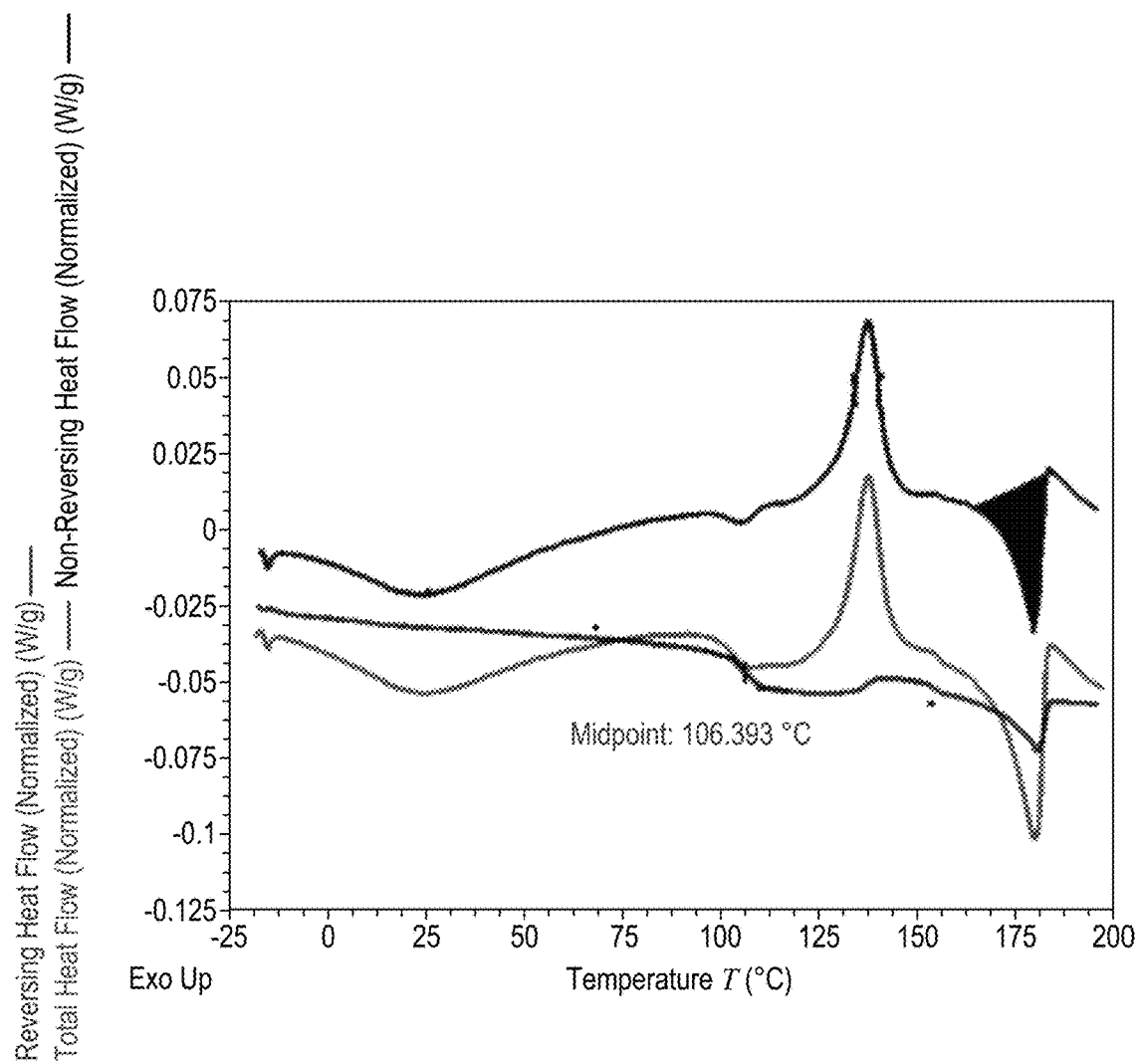
FIG. 6 is a MDSC spectrum of a SDD of 50 wt % Compound 1 with HPMCAS-HG.
Figure 8:
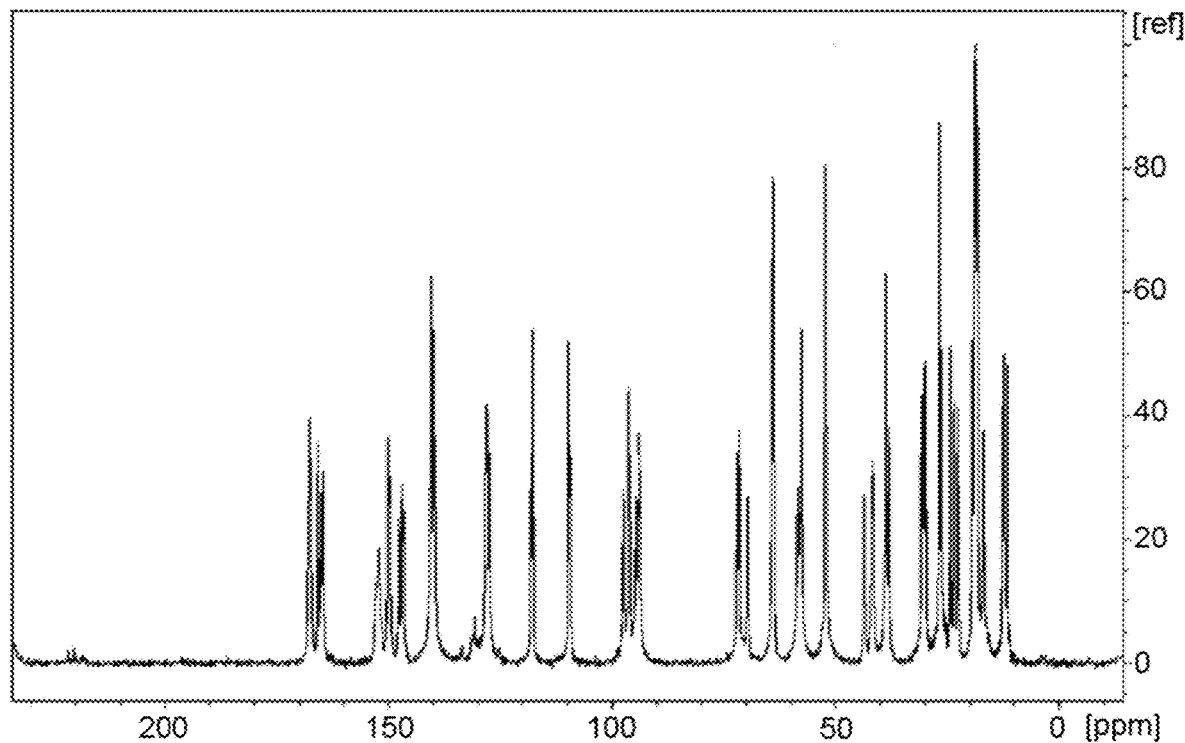
FIG. 8 is a solid state Carbon-13 NMR spectrum of Form A of Compound 1, with MAS spinning at 12.5 kHz, referenced against adamantane 29.5 ppm, at 275 K. The spectrum was taken on a Bruker 400 MHz WB SSNMR; BH085908; asset V019431 (console), V015741 (magnet).
Figure 9:
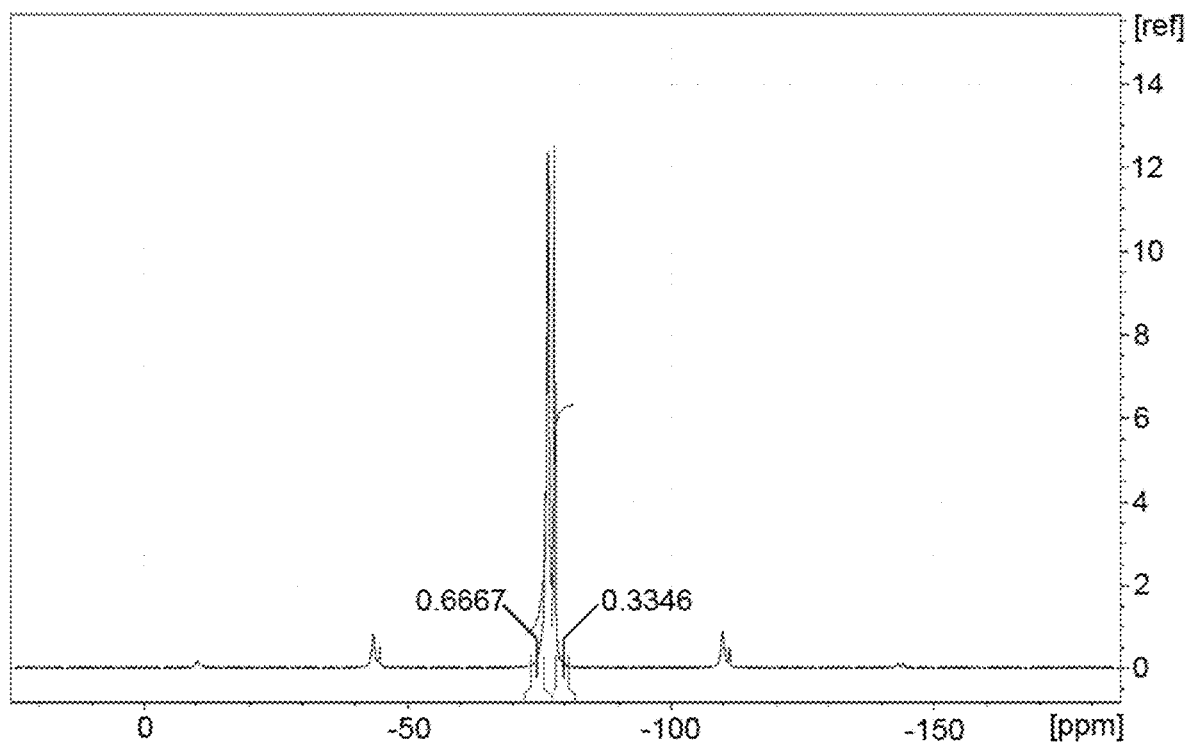
FIG. 9 is a solid state Fluorine-19 NMR spectrum of Form A of Compound 1, with MAS spinning at 12.5 kHz, referenced against adamantane 29.5 ppm, at 275 K. The spectrum was taken on a Bruker 400 MHz WB SSNMR; BH085908; asset V019431 (console), V015741 (magnet).
Figure 10:
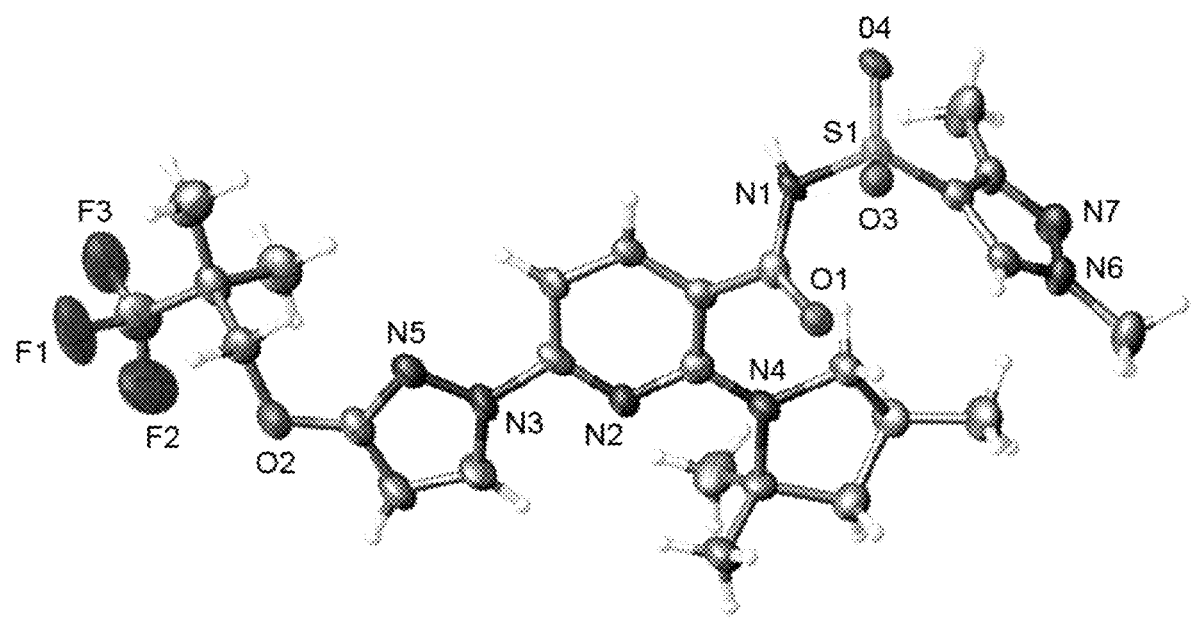
FIG. 10 shows a ball and stick plot of crystalline Form A of Compound 1.
Figure 11:
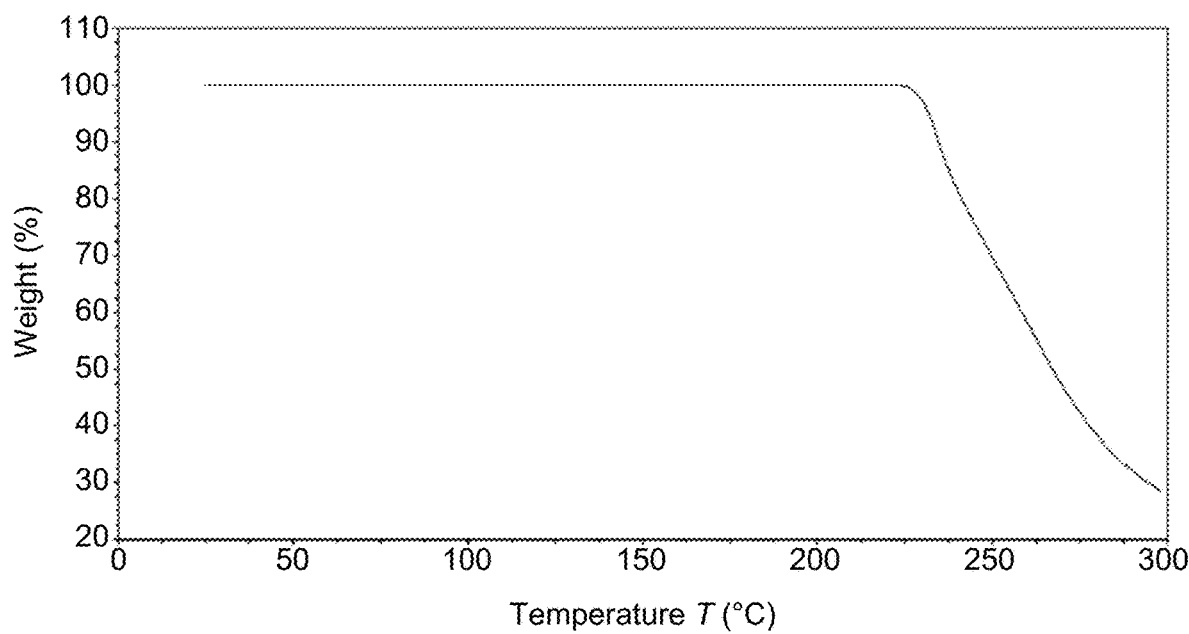
FIG. 11 shows a TGA plot of crystalline Form A of Compound 1.
Figure 12:
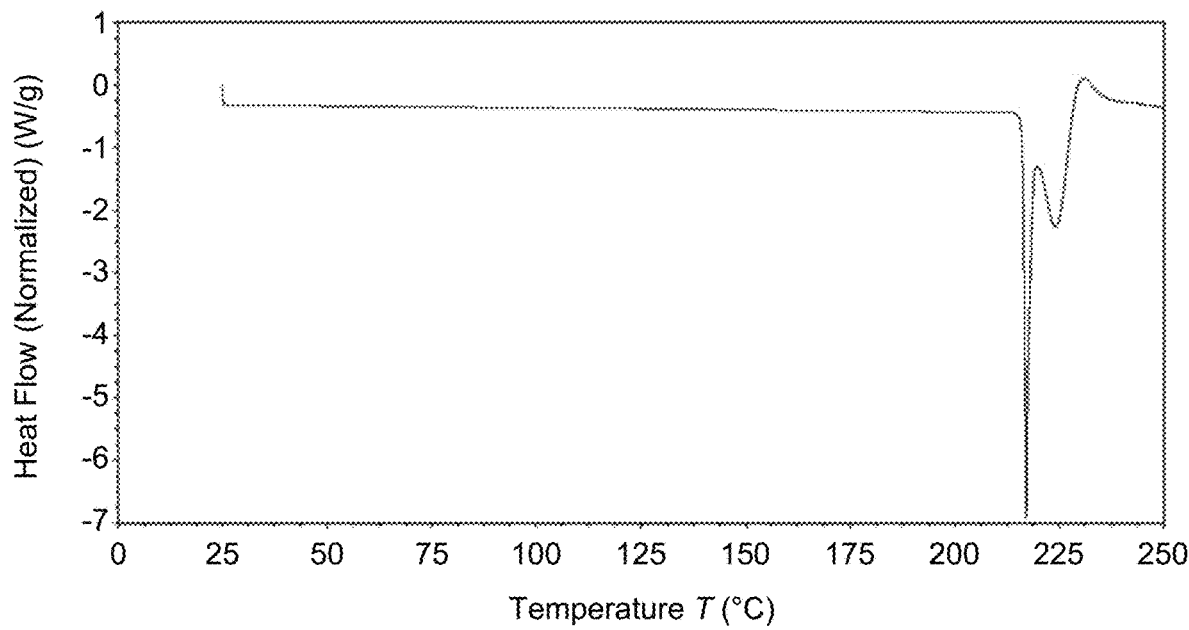
FIG. 12 shows a a dynamic vapor sorption (DVS) plot of crystalline Form A of Compound 1.

FIG. 6 shows a MDSC spectrum of a spray dried dispersion (SDD) of 50 wt % Compound 1 in HPMCAS-HG, and shows that the SDD has a midpoint temperature of about 106° C.

Single-Crystal Analysis

X-ray diffraction data were acquired at 100K or 298K on a Bruker diffractometer equipped with Mo $K_\alpha$ radiation (λ=0.71073 Å) or Cu $K_\alpha$ radiation (λ=1.5478) and an CCD detector. The structure was solved and refined using SHELX program (Sheldrick, G. M., Acta Cryst., (2008) A64, 112-122).

Thermogravimetric Analysis (TGA)

TGA was used to investigate the presence of residual solvents in the lots characterized, and identify the temperature at which decomposition of the sample occurs. TGA data were collected on a TA Discovery Thermogravimetric Analyzer or equivalent instrumentation. A sample with weight of approximately 1-5 mg was scanned from 25° C. to 350° C. at a heating rate of 10° C./min. Data were collected and analyzed by Trios software (TA Instruments, New Castle, Del.) or collected by Thermal Advantage Q Series™ software and analyzed by Universal Analysis software (TA Instruments, New Castle, Del.).

Differential Scanning Calorimetry (DSC)

DSC data were acquired using a TA Instruments Q2000 or equivalent instrumentation. A sample with a weight between 1 and 10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to a temperature of 200-350° C. When the run was completed, the data were analyzed using the DSC analysis program in the system software. The observed endo- and exotherms were integrated between baseline temperature points that were above and below the temperature range over which the endotherm was observed. The data reported were the onset of decomposition temperature, peak temperature and enthalpy.

SYNTHETIC EXAMPLES

Synthesis of Compound II: (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide

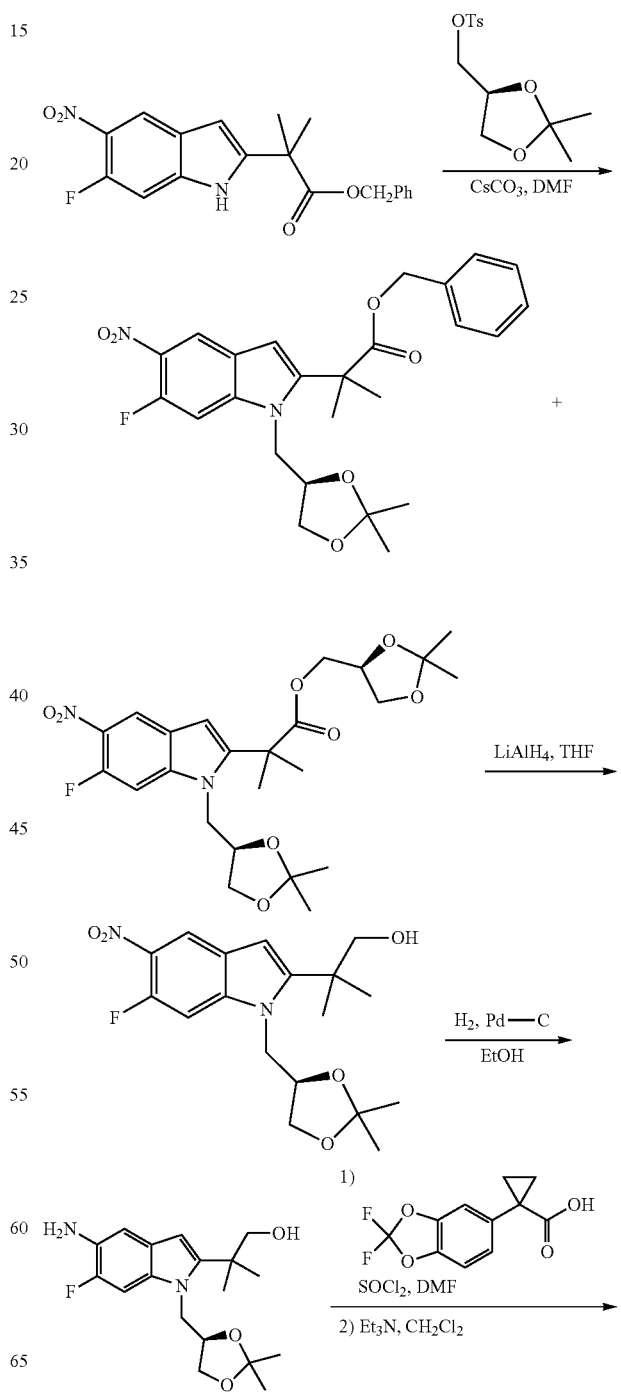

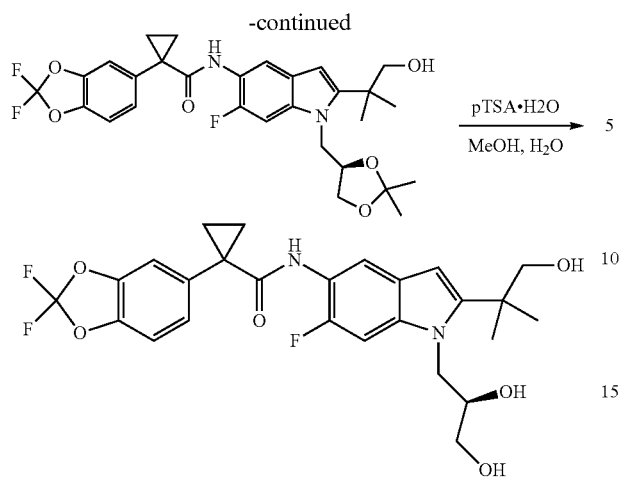

Step 1: (R)-Benzyl 2-(1-((2,2-dimethyl-1,3-dioxolan-4-yl)methyl)-6-fluoro-5-nitro-1H-indol-2-yl)-2-methylpropanoate and ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate Cesium carbonate (8.23 g, 25.3 mmol) was added to a mixture of benzyl 2-(6-fluoro-5-nitro-1H-indol-2-yl)-2-methylpropanoate (3.0 g, 8.4 mmol) and (S)-(2,2-dimethyl-1,3-dioxolan-4-yl)methyl 4-methylbenzenesulfonate (7.23 g, 25.3 mmol) in DMF (N,N-dimethylformamide) (17 mL). The reaction was stirred at 80° C. for 46 hours under a nitrogen atmosphere. The mixture was then partitioned between ethyl acetate and water. The aqueous layer was extracted with ethyl acetate. The combined ethyl acetate layers were washed with brine, dried over MgSO₄, filtered and concentrated. The crude product, a viscous brown oil which contains both of the products shown above, was taken directly to the next step without further purification. (R)-Benzyl 2-(1-((2,2-dimethyl-1,3-dioxolan-4-yl)methyl)-6-fluoro-5-nitro-1H-indol-2-yl)-2-methylpropanoate, ESI-MS m/z calc. 470.2, found 471.5 (M+1)⁺. Retention time 2.20 minutes. ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate, ESI-MS m/z calc. 494.5, found 495.7 (M+1)⁺. Retention time 2.01 minutes.

Step 2: (R)-2-(1-((2,2-dimethyl-1,3-dioxolan-4-yl)methyl)-6-fluoro-5-nitro-1H-indol-2-yl)-2-methylpropan-1-ol The crude reaction mixture obtained in step (A) was dissolved in THF (tetrahydrofuran) (42 mL) and cooled in an ice-water bath. LiAlH₄ (16.8 mL of 1 M solution, 16.8 mmol) was added drop-wise. After the addition was complete, the mixture was stirred for an additional 5 minutes. The reaction was quenched by adding water (1 mL), 15% NaOH solution (1 mL) and then water (3 mL). The mixture was filtered over Celite, and the solids were washed with THF and ethyl acetate. The filtrate was concentrated and purified by column chromatography (30-60% ethyl acetate-hexanes) to obtain (R)-2-(1-((2,2-dimethyl-1,3-dioxolan-4-yl)methyl)-6-fluoro-5-nitro-1H-indol-2-yl)-2-methylpropan-1-ol as a brown oil (2.68 g, 87% over 2 steps). ESI-MS m/z calc. 366.4, found 367.3 (M+1)⁺. Retention time 1.68 minutes. ¹H NMR (400 MHz, DMSO-d6) δ 8.34 (d, J=7.6 Hz, 1H), 7.65 (d, J=13.4 Hz, 1H), 6.57 (s, 1H), 4.94 (t, J=5.4 Hz, 1H), 4.64-4.60 (m, 1H), 4.52-4.42 (m, 2H), 4.16-4.14 (m, 1H), 3.76-3.74 (m, 1H), 3.63-3.53 (m, 2H), 1.42 (s, 3H), 1.38-1.36 (m, 6H) and 1.19 (s, 3H) ppm. (DMSO is dimethylsulfoxide).

Step 3: (R)-2-(5-amino-1-((2,2-dimethyl-1,3-dioxolan-4-yl)methyl)-6-fluoro-1H-indol-2-yl)-2-methylpropan-1-ol (R)-2-(1-((2,2-dimethyl-1,3-dioxolan-4-yl)methyl)-6-fluoro-5-nitro-1H-indol-2-yl)-2-methylpropan-1-ol (2.5 g, 6.82 mmol) was dissolved in ethanol (70 mL) and the reaction was flushed with N2. Then Pd—C (250 mg, 5% wt) was added. The reaction was flushed with nitrogen again and then stirred under H₂ (atm). After 2.5 hours only partial conversion to the product was observed by LCMS. The reaction was filtered through Celite and concentrated. The residue was re-subjected to the conditions above. After 2 hours LCMS indicated complete conversion to product. The reaction mixture was filtered through Celite. The filtrate was concentrated to yield the product (1.82 g, 79%). ESI-MS m/z calc. 336.2, found 337.5 (M+1)⁺. Retention time 0.86 minutes. ¹H NMR (400 MHz, DMSO-d6) δ 7.17 (d, J=12.6 Hz, 1H), 6.76 (d, J=9.0 Hz, 1H), 6.03 (s, 1H), 4.79-4.76 (m, 1H), 4.46 (s, 2H), 4.37-4.31 (m, 3H), 4.06 (dd, J=6.1, 8.3 Hz, 1H), 3.70-3.67 (m, 1H), 3.55-3.52 (m, 2H), 1.41 (s, 3H), 1.32 (s, 6H) and 1.21 (s, 3H) ppm.

Step 4: (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide DMF (3 drops) was added to a stirring mixture of 1-(2,2-difluorobenzo[d][1,3]dioxol-5-yl)cyclopropanecarboxylic acid (1.87 g, 7.7 mmol) and thionyl chloride (1.30 mL, 17.9 mmol). After 1 hour a clear solution had formed. The solution was concentrated under vacuum and then toluene (3 mL) was added and the mixture was concentrated again. The toluene step was repeated once more and the residue was placed on high vacuum for 10 minutes. The acid chloride was then dissolved in dichloromethane (10 mL) and added to a mixture of (R)-2-(5-amino-1-((2,2-dimethyl-1,3-dioxolan-4-yl)methyl)-6-fluoro-1H-indol-2-yl)-2-methylpropan-1-ol (1.8 g, 5.4 mmol) and triethylamine (2.24 mL, 16.1 mmol) in dichloromethane (45 mL). The reaction was stirred at room temperature for 1 hour. The reaction was washed with 1N HCl solution, saturated NaHCO₃ solution and brine, dried over MgSO₄ and concentrated to yield the product (3 g, 100%). ESI-MS m/z calc. 560.6, found 561.7 (M+1)⁺. Retention time 2.05 minutes. ¹H NMR (400 MHz, DMSO-d6) δ 8.31 (s, 1H), 7.53 (s, 1H), 7.42-7.40 (m, 2H), 7.34-7.30 (m, 3H), 6.24 (s, 1H), 4.51-4.48 (m, 1H), 4.39-4.34 (m, 2H), 4.08 (dd, J=6.0, 8.3 Hz, 1H), 3.69 (t, J=7.6 Hz, 1H), 3.58-3.51 (m, 2H), 1.48-1.45 (m, 2H), 1.39 (s, 3H), 1.34-1.33 (m, 6H), 1.18 (s, 3H) and 1.14-1.12 (m, 2H) ppm.

Step 5: (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide (3.0 g, 5.4 mmol) was dissolved in methanol (52 mL). Water (5.2 mL) was added followed by p-TsOH.H$_2$O (p-toluenesulfonic acid hydrate) (204 mg, 1.1 mmol). The reaction was heated at 80° C. for 45 minutes. The solution was concentrated and then partitioned between ethyl acetate and saturated NaHCO$_3$ solution. The ethyl acetate layer was dried over MgSO$_4$ and concentrated. The residue was purified by column chromatography (50-100% ethyl acetate-hexanes) to yield the product. (1.3 g, 47%, ee >98% by SFC). ESI-MS m/z calc. 520.5, found 521.7 (M+1)$^+$. Retention time 1.69 minutes. $^1$H NMR (400 MHz, DMSO-d6) δ 8.31 (s, 1H), 7.53 (s, 1H), 7.42-7.38 (m, 2H), 7.33-7.30 (m, 2H), 6.22 (s, 1H), 5.01 (d, J=5.2 Hz, 1H), 4.90 (t, J=5.5 Hz, 1H), 4.75 (t, J=5.8 Hz, 1H), 4.40 (dd, J=2.6, 15.1 Hz, 1H), 4.10 (dd, J=8.7, 15.1 Hz, 1H), 3.90 (s, 1H), 3.65-3.54 (m, 2H), 3.48-3.33 (m, 2H), 1.48-1.45 (m, 2H), 1.35 (s, 3H), 1.32 (s, 3H) and 1.14-1.11 (m, 2H) ppm.

Synthesis of Compound III: N-(2,4-di-tert-butyl-5-hydroxyphenyl)-4-oxo-1,4-dihydroquinoline-3-carboxamide Part A: Synthesis of 4-oxo-1,4-dihydroquinoline-3-carboxylic Acid

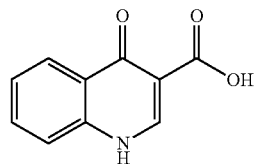 [SMILES: O=C(O)c1c[nH]c2ccccc2c1=O]

Step 1: 2-Phenylaminomethylene-malonic acid diethyl ester

A mixture of aniline (25.6 g, 0.275 mol) and diethyl 2-(ethoxymethylene)malonate (62.4 g, 0.288 mol) was heated at 140-150° C. for 2 h. The mixture was cooled to room temperature and dried under reduced pressure to afford 2-phenylaminomethylene-malonic acid diethyl ester as a solid, which was used in the next step without further purification. $^1$H NMR (DMSO-d6) δ 11.00 (d, 1H), 8.54 (d, J=13.6 Hz, 1H), 7.36-7.39 (m, 2H), 7.13-7.17 (m, 3H), 4.17-4.33 (m, 4H), 1.18-1.40 (m, 6H).

Step 2: 4-Hydroxyquinoline-3-carboxylic acid ethyl ester

A 1 L three-necked flask fitted with a mechanical stirrer was charged with 2-phenylaminomethylene-malonic acid diethyl ester (26.3 g, 0.100 mol), polyphosphoric acid (270 g) and phosphoryl chloride (750 g). The mixture was heated to 70° C. and stirred for 4 h. The mixture was cooled to room temperature and filtered. The residue was treated with aqueous Na$_2$CO$_3$ solution, filtered, washed with water and dried. 4-Hydroxyquinoline-3-carboxylic acid ethyl ester was obtained as a pale brown solid (15.2 g, 70%). The crude product was used in next step without further purification.

Step 3: 4-Oxo-1,4-dihydroquinoline-3-carboxylic acid

4-Hydroxyquinoline-3-carboxylic acid ethyl ester (15 g, 69 mmol) was suspended in sodium hydroxide solution (2N, 150 mL) and stirred for 2 h at reflux. After cooling, the mixture was filtered, and the filtrate was acidified to pH 4 with 2N HCl. The resulting precipitate was collected via filtration, washed with water and dried under vacuum to give 4-oxo-1,4-dihydroquinoline-3-carboxylic acid as a pale white solid (10.5 g, 92%). $^1$H NMR (DMSO-d6) δ 15.34 (s, 1H), 13.42 (s, 1H), 8.89 (s, 1H), 8.28 (d, J=8.0 Hz, 1H), 7.88 (m, 1H), 7.81 (d, J=8.4 Hz, 1H), 7.60 (m, 1H).

Part B: Synthesis of N-(2,4-di-tert-butyl-5-hydroxyphenyl)-4-oxo-1,4-dihydroquinoline-3-carboxamide

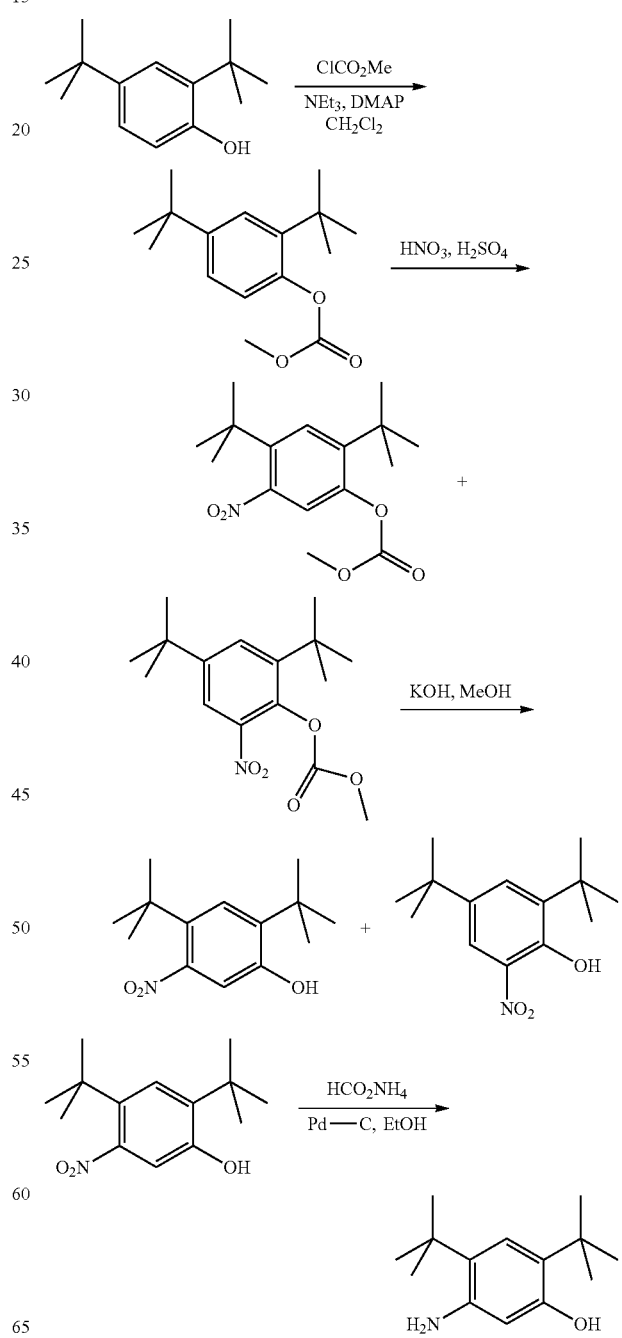

Step 1: Carbonic acid 2,4-di-tert-butyl-phenyl ester methyl ester

Methyl chloroformate (58 mL, 750 mmol) was added dropwise to a solution of 2,4-di-tert-butyl-phenol (103.2 g, 500 mmol), Et₃N (139 mL, 1000 mmol) and DMAP (3.05 g, 25 mmol) in dichloromethane (400 mL) cooled in an ice-water bath to 0° C. The mixture was allowed to warm to room temperature while stirring overnight, then filtered through silica gel (approx. 1 L) using 10% ethyl acetate—hexanes (~4 L) as the eluent. The combined filtrates were concentrated to yield carbonic acid 2,4-di-tert-butyl-phenyl ester methyl ester as a yellow oil (132 g, quant.). $^1$H NMR (400 MHz, DMSO-d6) δ 7.35 (d, J=2.4 Hz, 1H), 7.29 (dd, J=8.5, 2.4 Hz, 1H), 7.06 (d, J=8.4 Hz, 1H), 3.85 (s, 3H), 1.30 (s, 9H), 1.29 (s, 9H).

Step 2: Carbonic acid 2,4-di-tert-butyl-5-nitro-phenyl ester methyl ester and Carbonic acid 2,4-di-tert-butyl-6-nitro-phenyl ester methyl ester To a stirring mixture of carbonic acid 2,4-di-Cert-butyl-phenyl ester methyl ester (4.76 g, 180 mmol) in conc. sulfuric acid (2 mL), cooled in an ice-water bath, was added a cooled mixture of sulfuric acid (2 mL) and nitric acid (2 mL). The addition was done slowly so that the reaction temperature did not exceed 50° C. The reaction was allowed to stir for 2 h while warming to room temperature. The reaction mixture was then added to ice-water and extracted into diethyl ether. The ether layer was dried (MgSO₄), concentrated and purified by column chromatography (0-10% ethyl acetate-hexanes) to yield a mixture of carbonic acid 2,4-di-tert-butyl-5-nitro-phenyl ester methyl ester and carbonic acid 2,4-di-tert-butyl-6-nitro-phenyl ester methyl ester as a pale yellow solid (4.28 g), which was used directly in the next step.

Step 3: 2,4-Di-tert-butyl-5-nitro-phenol and 2,4-Di-tert-butyl-6-nitro-phenol The mixture of carbonic acid 2,4-di-tert-butyl-5-nitro-phenyl ester methyl ester and carbonic acid 2,4-di-tert-butyl-6-nitro-phenyl ester methyl ester (4.2 g, 14.0 mmol) was dissolved in MeOH (65 mL) before KOH (2.0 g, 36 mmol) was added. The mixture was stirred at room temperature for 2 h. The reaction mixture was then made acidic (pH 2-3) by adding conc. HCl and partitioned between water and diethyl ether. The ether layer was dried (MgSO₄), concentrated and purified by column chromatography (0-5% ethyl acetate—hexanes) to provide 2,4-di-tert-butyl-5-nitro-phenol (1.31 g, 29% over 2 steps) and 2,4-di-tert-butyl-6-nitro-phenol. 2,4-Di-tert-butyl-5-nitro-phenol: $^1$H NMR (400 MHz, DMSO-d₆) δ 10.14 (s, 1H, OH), 7.34 (s, 1H), 6.83 (s, 1H), 1.36 (s, 9H), 1.30 (s, 9H). 2,4-Di-tert-butyl-6-nitro-phenol: $^1$H NMR (400 MHz, CDCl₃) δ 11.48 (s, 1H), 7.98 (d, J=2.5 Hz, 1H), 7.66 (d, J=2.4 Hz, 1H), 1.47 (s, 9H), 1.34 (s, 9H).

Step 4: 5-Amino-2,4-di-tert-butyl-phenol

To a refluxing solution of 2,4-di-tert-butyl-5-nitro-phenol (1.86 g, 7.40 mmol) and ammonium formate (1.86 g) in ethanol (75 mL) was added Pd-5% wt. on activated carbon (900 mg). The reaction mixture was stirred at reflux for 2 h, cooled to room temperature and filtered through Celite. The Celite was washed with methanol and the combined filtrates were concentrated to yield 5-amino-2,4-di-tert-butyl-phenol as a grey solid (1.66 g, quant.). $^1$H NMR (400 MHz, DMSO-d6) δ 8.64 (s, 1H, OH), 6.84 (s, 1H), 6.08 (s, 1H), 4.39 (s, 2H, NH₂), 1.27 (m, 18H); HPLC ret. time 2.72 min, 10-99% CH₃CN, 5 min run; ESI-MS 222.4 m/z [M+H]⁺.

Step 5: N-(5-hydroxy-2,4-di-tert-butyl-phenyl)-4-oxo-1H-quinoline-3-carboxamide

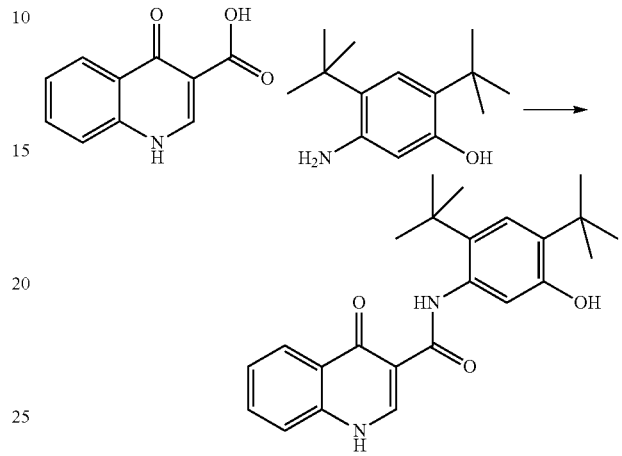

To a suspension of 4-oxo-1,4-dihydroquinolin-3-carboxylic acid (35.5 g, 188 mmol) and HBTU (85.7 g, 226 mmol) in DMF (280 mL) was added Et₃N (63.0 mL, 451 mmol) at ambient temperature. The mixture became homogeneous and was allowed to stir for 10 min before 5-amino-2,4-di-tert-butyl-phenol (50.0 g, 226 mmol) was added in small portions. The mixture was allowed to stir overnight at ambient temperature. The mixture became heterogeneous over the course of the reaction. After all of the acid was consumed (LC-MS analysis, MH+ 190, 1.71 min), the solvent was removed in vacuo. EtOH (ethyl alcohol) was added to the orange solid material to produce a slurry. The mixture was stirred on a rotovap (bath temperature 65° C.) for 15 min without placing the system under vacuum. The mixture was filtered and the captured solid was washed with hexanes to provide a white solid that was the EtOH crystalate. Et₂O (diethyl ether) was added to the solid obtained above until a slurry was formed. The mixture was stirred on a rotovapor (bath temperature 25° C.) for 15 min without placing the system under vacuum. The mixture was filtered and the solid captured. This procedure was performed a total of five times. The solid obtained after the fifth precipitation was placed under vacuum overnight to provide N-(5-hydroxy-2,4-di-tert-butyl-phenyl)-4-oxo-1H-quinoline-3-carboxamide (38 g, 52%). HPLC ret. time 3.45 min, 10-99% CH₃CN, 5 min run; $^1$H NMR (400 MHz, DMSO-d₆) δ 12.88 (s, 1H), 11.83 (s, 1H), 9.20 (s, 1H), 8.87 (s, 1H), 8.33 (dd, J=8.2, 1.0 Hz, 1H), 7.83-7.79 (m, 1H), 7.76 (d, J=7.7 Hz, 1H), 7.54-7.50 (m, 1H), 7.17 (s, 1H), 7.10 (s, 1H), 1.38 (s, 9H), 1.37 (s, 9H); ESI-MS m/z calc'd 392.21; found 393.3 [M+H]⁺.

Synthesis of Compound IV: 3-(6-(1-(2,2-difluorobenzo[d][1,3]dioxol-5-yl) cyclopropanecarboxamido)-3-methylpyridin-2-yl)benzoic acid Compound IV may be prepared by coupling an acid chloride moiety with an amine moiety according to Schemes IV-A through IV-D.

Scheme IV-A. Synthesis of the acid chloride moiety.

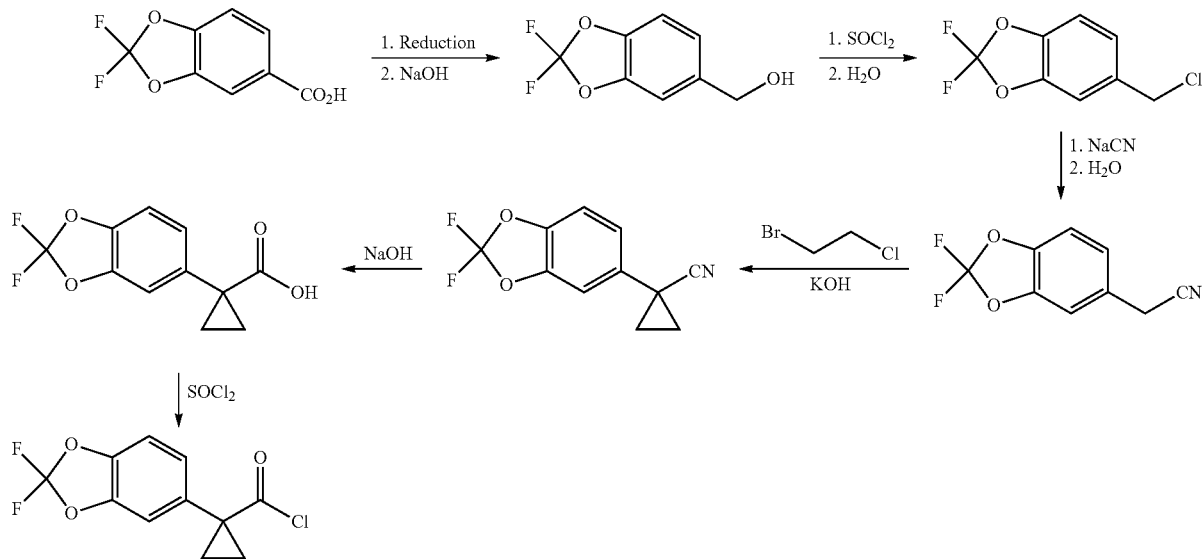

Scheme IV-A depicts the preparation of 1-(2,2-difluorobenzo[d][1,3]dioxol-5-yl)cyclopropanecarbonyl chloride, which is used in Scheme IV-C to make the amide linkage of Compound IV.

The starting material, 2,2-difluorobenzo[d][1,3]dioxole-5-carboxylic acid, is commercially available from Saltigo (an affiliate of the Lanxess Corporation). Reduction of the carboxylc acid moiety in 2,2-difluorobenzo[d][1,3]dioxole-5-carboxylic acid to the primary alcohol, followed by conversion to the corresponding chloride using thionyl chloride ($SOCl_2$), provides 5-(chloromethyl)-2,2-difluorobenzo[d][1,3]dioxole, which is subsequently converted to 2-(2,2-difluorobenzo[d][1,3]dioxol-5-yl)acetonitrile using sodium cyanide. Treatment of 2-(2,2-difluorobenzo[d][1,3]dioxol-5-yl)acetonitrile with base and 1-bromo-2-chloroethane provides 1-(2,2-difluorobenzo[d][1,3]dioxol-5-yl)cyclopropanecarbonitrile. The nitrile moiety in 1-(2,2-difluorobenzo[d][1,3]dioxol-5-yl)cyclopropanecarbonitrile is converted to a carboxylic acid using base to give 1-(2,2-difluorobenzo[d][1,3]dioxol-5-yl)cyclopropanecarboxylic acid, which is converted to the desired acid chloride using thionyl chloride.

Scheme IV-B. Alternative synthesis of the acid chloride moiety.

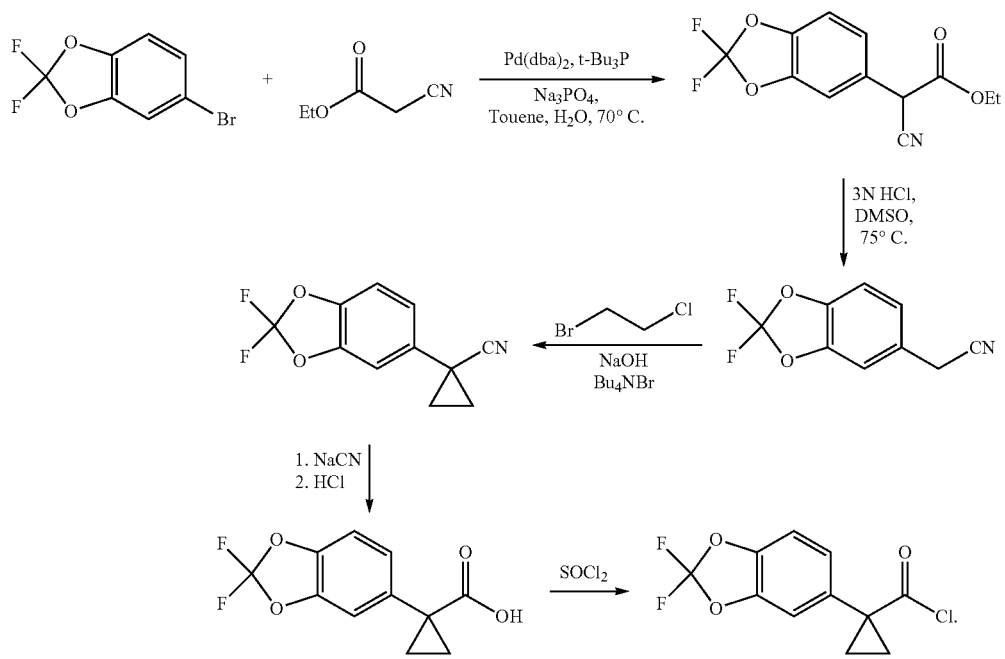

Scheme IV-B depicts an alternative synthesis of the requisite acid chloride. 5-bromomethyl-2,2-difluoro-1,3-benzodioxole is coupled with ethyl cyanoacetate in the presence of a palladium catalyst to form the corresponding alpha cyano ethyl ester. Saponification of the ester moiety to the carboxylic acid gives the cyanoethyl Compound IV. Alkylation of the cyanoethyl compound with 1-bromo-2-chloro ethane in the presence of base gives the cyanocyclopropyl compound. Treatment of the cyanocyclopropyl compound with base gives the carboxylate salt, which is converted to the carboxylic acid by treatment with acid. Conversion of the carboxylic acid to the acid chloride is then accomplished using a chlorinating agent such as thionyl chloride or the like.

Scheme IV-C. Synthesis of the amine moiety.

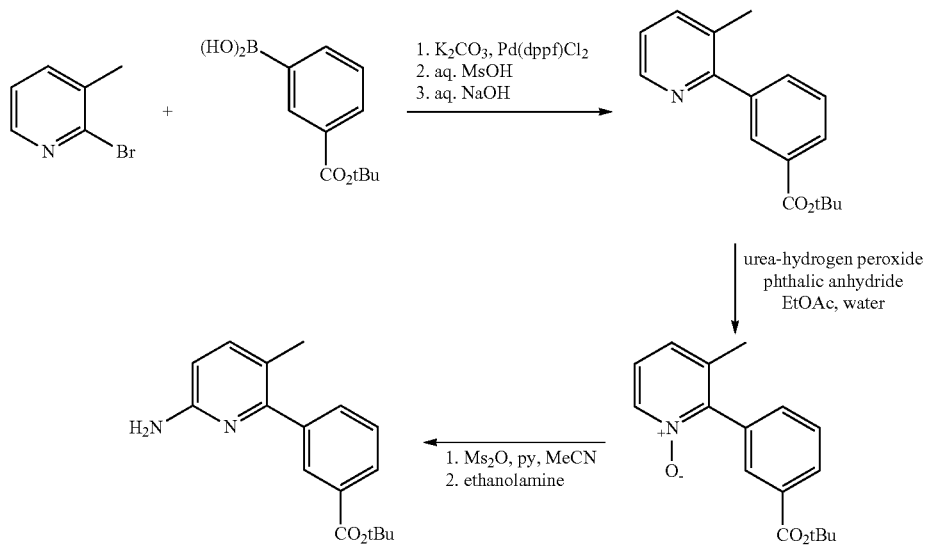

Scheme IV-C depicts the preparation of the requisite tert-butyl 3-(6-amino-3-methylpyridin-2-yl)benzoate, which is coupled with 1-(2,2-difluorobenzo[d][1,3]dioxol-5-yl)cyclopropanecarbonyl chloride in Scheme IV-C to give Compound IV. Palladium-catalyzed coupling of 2-bromo-3-methylpyridine with 3-(tert-butoxycarbonyl)phenylboronic acid gives tert-butyl 3-(3-methylpyridin-2-yl)benzoate, which is subsequently converted to the desired compound.

Scheme IV-D. Formation of an acid salt of 3-(6-(1-(2,2-difluorobenzo[d][1,3]dioxol-5-yl)cyclopropanecarboxamido)-3-methylpyridin-2-yl)benzoic acid.

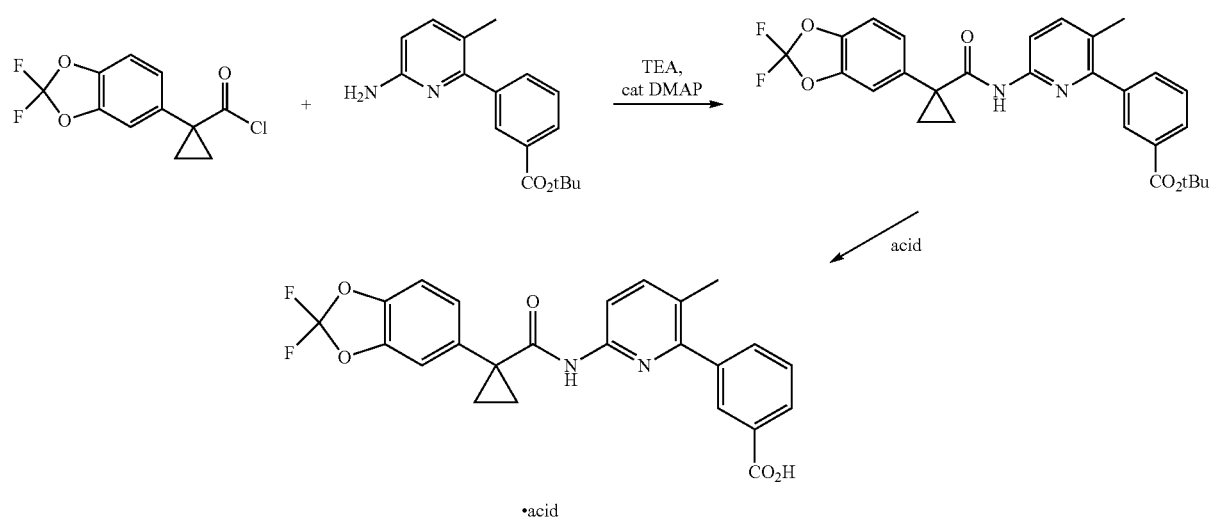

Scheme IV-D depicts the coupling of 1-(2,2-difluorobenzo[d][1,3]dioxol-5-yl)cyclopropanecarbonyl chloride with tert-butyl 3-(6-amino-3-methylpyridin-2-yl)benzoate using triethyl amine and 4-dimethylaminopyridine to initially provide the tert-butyl ester of Compound IV.

SYNTHESES OF COMPOUNDS

Synthesis of Compound 1

Part A: Synthesis of (4S)-2,2,4-trimethylpyrrolidine hydrochloride

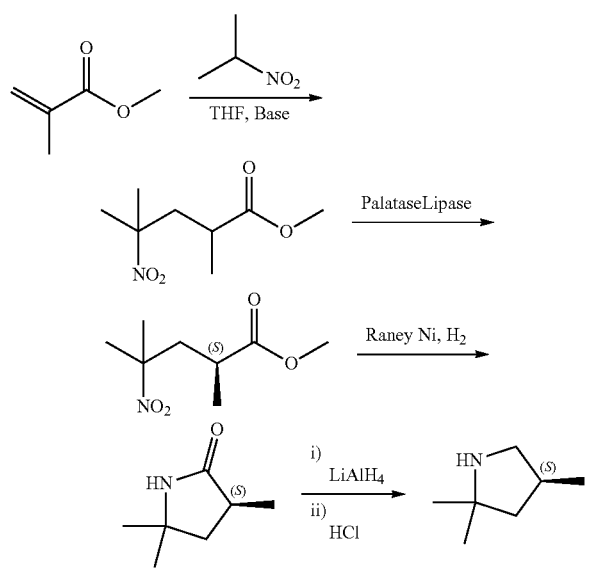

Step 1: methyl-2,4-dimethyl-4-nitro-pentanoate

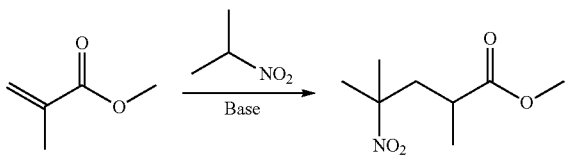

Tetrahydrofuran (THF, 4.5 L) was added to a 20 L glass reactor and stirred under N2 at room temperature. 2-Nitropropane (1.5 kg, 16.83 mol) and 1,8-diazabicyclo[5.4.0]undec-7-ene (DBU) (1.282 kg, 8.42 mol) were then charged to the reactor, and the jacket temperature was increased to 50° C. Once the reactor contents were close to 50° C., methyl methacrylate (1.854 kg, 18.52 mol) was added slowly over 100 minutes. The reaction temperature was maintained at or close to 50° C. for 21 hours. The reaction mixture was concentrated in vacuo then transferred back to the reactor and diluted with methyl tert-butyl ether (MTBE) (14 L). 2 M HCl (7.5 L) was added, and this mixture was stirred for 5 minutes then allowed to settle. Two clear layers were visible—a lower yellow aqueous phase and an upper green organic phase. The aqueous layer was removed, and the organic layer was stirred again with 2 M HCl (3 L). After separation, the HCl washes were recombined and stirred with MTBE (3 L) for 5 minutes. The aqueous layer was removed, and all of the organic layers were combined in the reactor and stirred with water (3 L) for 5 minutes. After separation, the organic layers were concentrated in vacuo to afford a cloudy green oil. Crude product was treated with MgSO$_4$ and filtered to afford methyl-2,4-dimethyl-4-nitropentanoate as a clear green oil (3.16 kg, 99% yield).

$^1$H NMR (400 MHz, Chloroform-d) δ 3.68 (s, 3H), 2.56-2.35 (m, 2H), 2.11-2.00 (m, 1H), 1.57 (s, 3H), 1.55 (s, 3H), 1.19 (d, J=6.8 Hz, 3H).

Step 2: Synthesis of methyl (2S)-2,4-dimethyl-4-nitropentanoate

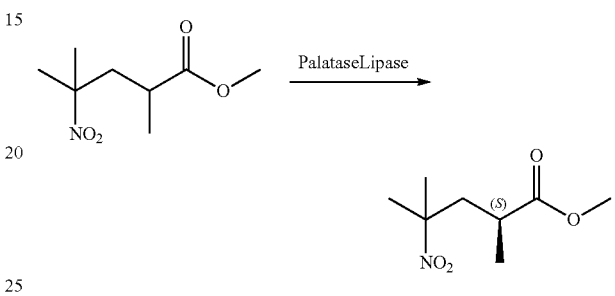

A reactor was charged with purified water (2090 L; 10 vol) and then potassium phosphate monobasic (27 kg, 198.4 moles; 13 g/L for water charge). The pH of the reactor contents was adjusted to pH 6.5 (±0.2) with 20% (w/v) potassium carbonate solution. The reactor was charged with racemic methyl-2,4-dimethyl-4-nitro-pentanoate (209 kg; 1104.6 moles), and Palatase 20000 L lipase (13 L, 15.8 kg; 0.06 vol).

The reaction mixture was adjusted to 32±2° C. and stirred for 15-21 hours, and pH 6.5 was maintained using a pH stat with the automatic addition of 20% potassium carbonate solution. When the racemic starting material was converted to >98% ee of the S-enantiomer, as determined by chiral GC, external heating was switched off. The reactor was then charged with MTBE (35 L; 5 vol), and the aqueous layer was extracted with MTBE (3 times, 400-1000 L). The combined organic extracts were washed with aqueous Na$_2$CO$_3$ (4 times, 522 L, 18% w/w 2.5 vol), water (523 L; 2.5 vol), and 10% aqueous NaCl (314 L, 1.5 vol). The organic layer was concentrated in vacuo to afford methyl (2S)-2,4-dimethyl-4-nitro-pentanoate as a mobile yellow oil (>98% ee, 94.4 kg; 45% yield).

Step 3: Synthesis of (3S)-3,5,5-trimethylpyrrolidin-2-one

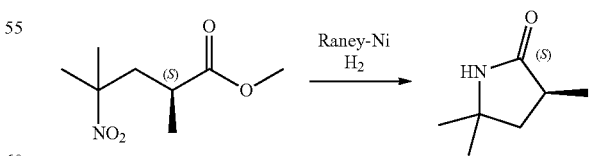

A 20 L reactor was purged with N2. The vessel was charged sequentially with DI water-rinsed, damp Raney® Ni (2800 grade, 250 g), methyl (2S)-2,4-dimethyl-4-nitro-pentanoate (1741 g, 9.2 mol), and ethanol (13.9 L, 8 vol). The reaction was stirred at 900 rpm, and the reactor was flushed with H$_2$ and maintained at ~2.5 bar. The reaction mixture was then warmed to 60° C. for 5 hours. The reaction mixture was cooled and filtered to remove Raney nickel, and the solid cake was rinsed with ethanol (3.5 L, 2 vol). The ethanolic solution of the product was combined with a second equal sized batch and concentrated in vacuo to reduce to a minimum volume of ethanol (~1.5 volumes). Heptane (2.5 L) was added, and the suspension was concentrated again to ~1.5 volumes. This was repeated 3 times; the resulting suspension was cooled to 0-5° C., filtered under suction, and washed with heptane (2.5 L). The product was dried under vacuum for 20 minutes then transferred to drying trays and dried in a vacuum oven at 40° C. overnight to afford (3S)-3,5,5-trimethylpyrrolidin-2-one as a white crystalline solid (2.042 kg, 16.1 mol, 87%). $^1$H NMR (400 MHz, Chloroform-d) δ 6.39 (s, 1H), 2.62 (ddq, J=9.9, 8.6, 7.1 Hz, 1H), 2.17 (dd, J=12.4, 8.6 Hz, 1H), 1.56 (dd, J=12.5, 9.9 Hz, 1H), 1.31 (s, 3H), 1.25 (s, 3H), 1.20 (d, J=7.1 Hz, 3H).

Step 4: Synthesis of (4S)-2,2,4-trimethylpyrrolidine hydrochloride

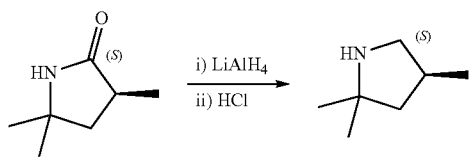

A glass lined 120 L reactor was charged with lithium aluminum hydride pellets (2.5 kg, 66 mol) and dry THF (60 L) and warmed to 30° C. The resulting suspension was charged with (S)-3,5,5-trimethylpyrrolidin-2-one (7.0 kg, 54 mol) in THF (25 L) over 2 hours while maintaining the reaction temperature at 30 to 40° C. After complete addition, the reaction temperature was increased to 60-63° C. and maintained overnight. The reaction mixture was cooled to 22° C., then cautiously quenched with the addition of ethyl acetate (EtOAc) (1.0 L, 10 moles), followed by a mixture of THF (3.4 L) and water (2.5 kg, 2.0 eq), and then a mixture of water (1.75 kg) with 50% aqueous sodium hydroxide (750 g, 2 equiv water with 1.4 equiv sodium hydroxide relative to aluminum), followed by 7.5 L water. After the addition was complete, the reaction mixture was cooled to room temperature, and the solid was removed by filtration and washed with THF (3×25 L). The filtrate and washings were combined and treated with 5.0 L (58 moles) of aqueous 37% HCl (1.05 equiv.) while maintaining the temperature below 30° C. The resultant solution was concentrated by vacuum distillation to a slurry. Isopropanol (8 L) was added and the solution was concentrated to near dryness by vacuum distillation. Isopropanol (4 L) was added, and the product was slurried by warming to about 50° C. MTBE (6 L) was added, and the slurry was cooled to 2-5° C. The product was collected by filtration and rinsed with 12 L MTBE and dried in a vacuum oven (55° C./300 torr/N2 bleed) to afford (4S)-2,2,4-trimethylpyrrolidine.HCl as a white, crystalline solid (6.21 kg, 75% yield). $^1$H NMR (400 MHz, DMSO-d6) δ 9.34 (br d, 2H), 3.33 (dd, J=11.4, 8.4 Hz, 1H), 2.75 (dd, J=11.4, 8.6 Hz, 1H), 2.50-2.39 (m, 1H), 1.97 (dd, J=12.7, 7.7 Hz, 1H), 1.42 (s, 3H), 1.38 (dd, J=12.8, 10.1 Hz, 1H), 1.31 (s, 3H), 1.05 (d, J=6.6 Hz, 3H).

Part B: Preparation of N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound 1)

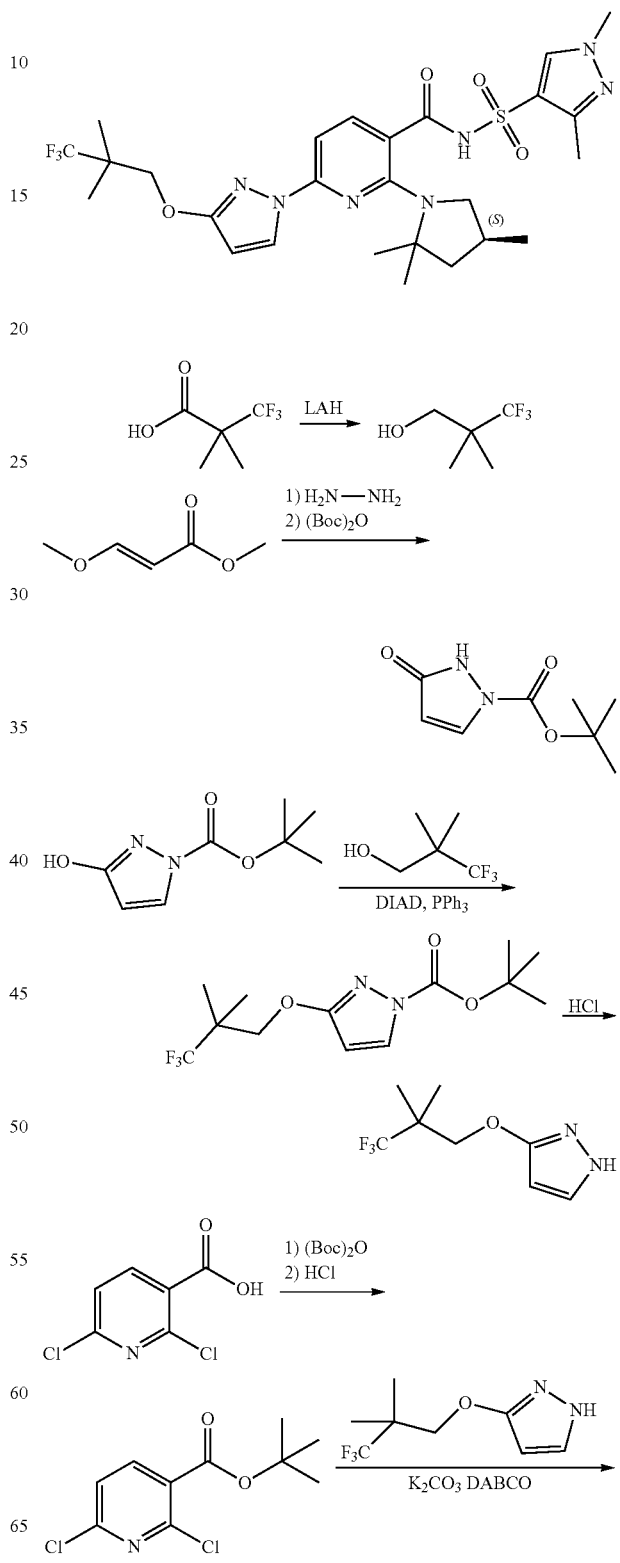

-continued

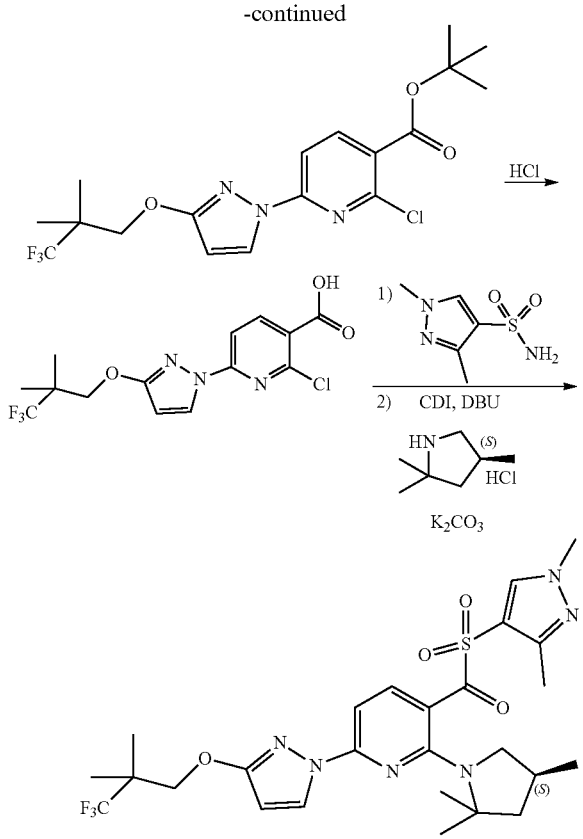

Preparation of Starting Materials 3,3,3-Trifluoro-2,2-dimethyl-propan-1-ol

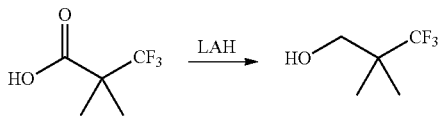

A 1 L 3 neck round bottom flask was fitted with a mechanical stirrer, a cooling bath, an addition funnel, and a J-Kem temperature probe. The vessel was charged with lithium aluminum hydride (LAH) pellets (6.3 g, 0.1665 mol) under a nitrogen atmosphere. The vessel was then charged with tetrahydrofuran (200 mL) under a nitrogen atmosphere. The mixture was allowed to stir at room temperature for 0.5 hours to allow the pellets to dissolve. The cooling bath was then charged with crushed ice in water and the reaction temperature was lowered to 0° C. The addition funnel was charged with a solution of 3,3,3-trifluoro-2,2-dimethyl-propanoic acid (20 g, 0.1281 mol) in tetrahydrofuran (60 mL) and the clear pale yellow solution was added drop wise over 1 hour. After the addition was complete the mixture was allowed to slowly warm to room temperature and stirring was continued for 24 hours. The suspension was cooled to 0° C. with a crushed ice-water in the cooling bath and then quenched by the very slow and drop wise addition of water (6.3 ml), followed by sodium hydroxide solution (15 weight %; 6.3 mL) and then finally with water (18.9 mL). The reaction temperature of the resulting white suspension was recorded at 5° C. The suspension was stirred at ~5° C. for 30 minutes and then filtered through a 20 mm layer of Celite. The filter cake was washed with tetrahydrofuran (2×100 mL). The filtrate was dried over sodium sulfate (150 g) and then filtered. The filtrate was concentrated under reduced pressure to provide a clear colorless oil (15 g) containing a mixture of the product 3,3,3-trifluoro-2,2-dimethyl-propan-1-ol in THF (73% weight of product ~10.95 g, and 27 wt. % THF as determined by 1H-NMR). The distillate from the rotary evaporation was distilled at atmospheric pressure using a 30 cm Vigreux column to provide 8.75 g of a residue containing 60% weight of THF and 40% weight of product (~3.5 g). The estimated total amount of product is 14.45 g (79% yield). 1H NMR (400 MHz, DMSO-d6) δ 4.99 (t, J=5.7 Hz, 1H), 3.38 (dd, J=5.8, 0.9 Hz, 2H), 1.04 (d, J=0.9 Hz, 6H).

tert-Butyl 3-oxo-2,3-dihydro-1H-pyrazole-1-carboxylate

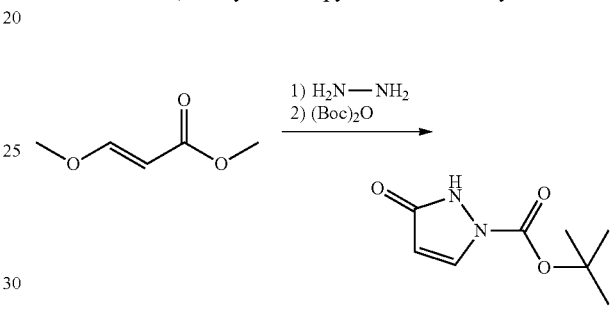

A 50 L Syrris controlled reactor was started and jacket set to 20° C., stirring at 150 rpm, reflux condenser (10° C.) and nitrogen purge. MeOH (2.860 L) and methyl (E)-3-methoxyprop-2-enoate (2.643 kg, 22.76 mol) were added and the reactor was capped. The reaction was heated to an internal temperature of 40° C. and the system was set to hold jacket temp at 40° C. Hydrazine hydrate (1300 g of 55% w/w, 22.31 mol) was added portion wise via addition funnel over 30 min. The reaction was heated to 60° C. for 1 h. The reaction mixture was cooled to 20° C. and triethylamine (2.483 kg, 3.420 L, 24.54 mol) was added portion wise (exothermic), maintaining reaction temp <30° C. A solution of Boc anhydride (di-tert-butyl dicarbonate) (4.967 kg, 5.228 L, 22.76 mol) in MeOH (2.860 L) was added portion wise maintaining temperature <45° C. The reaction mixture was stirred at 20° C. for 16 h. The reaction solution was partially concentrated to remove MeOH, resulting in a clear light amber oil. The resulting oil was transferred to the 50 L reactor, stirred and added water (7.150 L) and heptane (7.150 L). The additions caused a small amount of the product to precipitate. The aqueous layer was drained into a clean container and the interface and heptane layer were filtered to separate the solid (product). The aqueous layer was transferred back to the reactor, and the collected solid was placed back into the reactor and mixed with the aqueous layer. A dropping funnel was added to the reactor and loaded with acetic acid (1.474 kg, 1.396 L, 24.54 mol), then began dropwise addition of acid. The jacket was set to 0° C. to absorb the quench exotherm. After addition (pH=5), the reaction mixture was stirred for 1 h. The solid was collected by filtration and washed with water (7.150 L), and washed a second time with water (3.575 L) and pulled dry. The crystalline solid was scooped out of the filter into a 20 L rotovap bulb and heptane (7.150 L) was added. The mixture was slurried at 45° C. for 30 mins, and then distilled off 1-2 volumes of solvent. The slurry in the rotovap flask was filtered and the solids washed with heptane (3.575 L) and pulled dry. The solid was further dried in vacuo (50° C., 15 mbar) to give tert-butyl 5-oxo-1H-pyrazole-2-carboxylate (2921 g, 71%) as coarse, crystalline solid. $^1$H NMR (400 MHz, DMSO-d6) δ 10.95 (s, 1H), 7.98 (d, J=2.9 Hz, 1H), 5.90 (d, J=2.9 Hz, 1H), 1.54 (s, 9H).

Step A: tert-Butyl 3-(3,3,3-trifluoro-2,2-dimethyl-propoxy)pyrazole-1-carboxylate

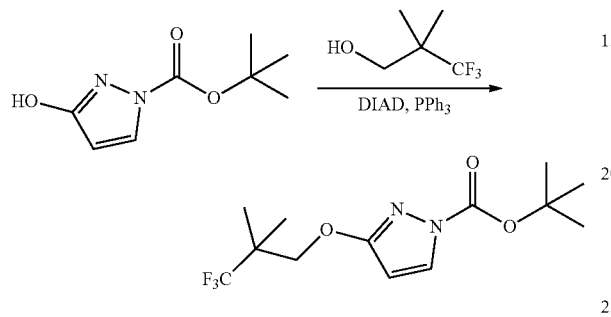

A mixture of 3,3,3-trifluoro-2,2-dimethyl-propan-1-ol (10 g, 70.36 mmol) and tert-butyl 3-hydroxypyrazole-1-carboxylate (12.96 g, 70.36 mmol) in toluene (130 mL) was treated with triphenyl phosphine (20.30 g, 77.40 mmol) followed by isopropyl N-isopropoxycarbonyliminocarbamate (14.99 mL, 77.40 mmol) and the mixture was stirred at 110° C. for 16 hours. The yellow solution was concentrated under reduced pressure, diluted with heptane (100 mL) and the precipitated triphenylphosphine oxide was removed by filtration and washed with heptane/toluene 4:1 (100 mL). The yellow filtrate was evaporated and the residue purified by silica gel chromatography with a linear gradient of ethyl acetate in hexane (0-40%) to give tert-butyl 3-(3,3,3-trifluoro-2,2-dimethyl-propoxy)pyrazole-1-carboxylate (12.3 g, 57%) as an off white solid. ESI-MS m/z calc. 308.13477, found 309.0 (M+1)$^+$; Retention time: 1.84 minutes. $^1$H NMR (400 MHz, DMSO-d6) δ 8.10 (d, J=3.0 Hz, 1H), 6.15 (d, J=3.0 Hz, 1H), 4.18 (s, 2H), 1.55 (s, 9H), 1.21 (s, 6H).

Step B: 3-(3,3,3-trifluoro-2,2-dimethyl-propoxy)-1H-pyrazole

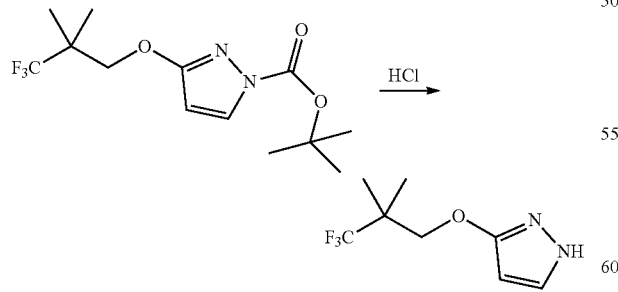

tert-Butyl 3-(3,3,3-trifluoro-2,2-dimethyl-propoxy)pyrazole-1-carboxylate (13.5 g, 43.79 mmol) was treated with 4 M hydrogen chloride in dioxane (54.75 mL, 219.0 mmol) and the mixture was stirred at 45° C. for 1 hour. The reaction mixture was evaporated to dryness and the residue was extracted with 1 M aqueous NaOH (100 ml) and methyl tert-butyl ether (100 ml), washed with brine (50 ml) and extracted with methyl tert-butyl ether (50 ml). The combined organic phases were dried, filtered and evaporated to give 3-(3,3,3-trifluoro-2,2-dimethyl-propoxy)-1H-pyrazole (9.0 g, 96%) as an off white waxy solid. ESI-MS m/z calc. 208.08235, found 209.0 (M+1)$^+$; Retention time: 1.22 minutes. $^1$H NMR (400 MHz, DMSO-d6) δ 11.91 (s, 1H), 7.52 (d, J=2.2 Hz, 1H), 5.69 (t, J=2.3 Hz, 1H), 4.06 (s, 2H), 1.19 (s, 6H).

Step C: tert-Butyl 2,6-dichloropyridine-3-carboxylate

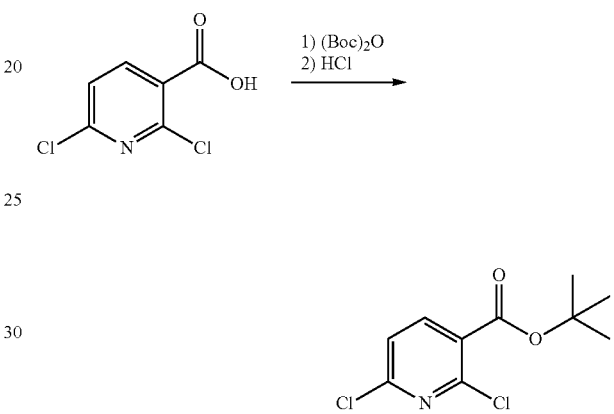

A solution of 2,6-dichloropyridine-3-carboxylic acid (10 g, 52.08 mmol) in THF (210 mL) was treated successively with di-tert-butyl dicarbonate (17 g, 77.89 mmol) and 4-(dimethylamino)pyridine (3.2 g, 26.19 mmol) and left to stir overnight at room temperature. At this point, HCl 1N (400 mL) was added and the mixture was stirred vigorously for about 10 minutes. The product was extracted with ethyl acetate (2×300 mL) and the combined organics layers were washed with water (300 mL) and brine (150 mL) and dried over sodium sulfate and concentrated under reduced pressure to give 12.94 g (96% yield) of tert-butyl 2,6-dichloro-pyridine-3-carboxylate as a colorless oil. ESI-MS m/z calc. 247.01668, found 248.1 (M+1)$^+$; Retention time: 2.27 minutes. NMR (300 MHz, CDCl$_3$) ppm 1.60 (s, 9H), 7.30 (d, J=7.9 Hz, 1H), 8.05 (d, J=8.2 Hz, 1H).

Step D: tert-Butyl 2-chloro-6-[3-(3,3,3-trifluoro-2,2-dimethyl-propoxy)pyrazol-1-yl]pyridine-3-carboxylate

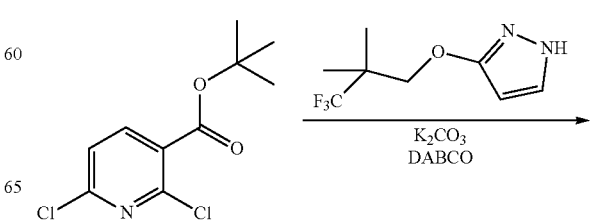

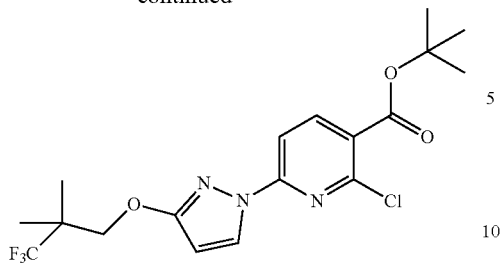

To a solution of tert-butyl 2,6-dichloropyridine-3-carboxylate (10.4 g, 41.9 mmol) and 3-(3,3,3-trifluoro-2,2-dimethyl-propoxy)-1H-pyrazole (9.0 g, 41.93 mmol) in DMF (110 mL) were added potassium carbonate (7.53 g, 54.5 mmol) and 1,4-diazabicyclo[2.2.2]octane (706 mg, 6.29 mmol) and he mixture was stirred at room temperature for 16 hours. The cream suspension was cooled in a cold water bath and cold water (130 mL) was slowly added. The thick suspension was stirred at room temperature for 1 hour, filtered and washed with plenty of water to give tert-butyl 2-chloro-6-[3-(3,3,3-trifluoro-2,2-dimethyl-propoxy)pyrazol-1-yl]pyridine-3-carboxylate (17.6 g, 99%) as an off white solid. ESI-MS m/z calc. 419.12234, found 420.0 (M+1)⁺; Retention time: 2.36 minutes. ¹H NMR (400 MHz, DMSO-d6) δ 8.44 (d, J=2.9 Hz, 1H), 8.31 (d, J=8.4 Hz, 1H), 7.76 (d, J=8.4 Hz, 1H), 6.26 (d, J=2.9 Hz, 1H), 4.27 (s, 2H), 1.57 (s, 9H), 1.24 (s, 6H).

Step E: 2-chloro-6-[3-(3,3,3-trifluoro-2,2-dimethyl-propoxy)pyrazol-1-yl]pyridine-3-carboxylic acid

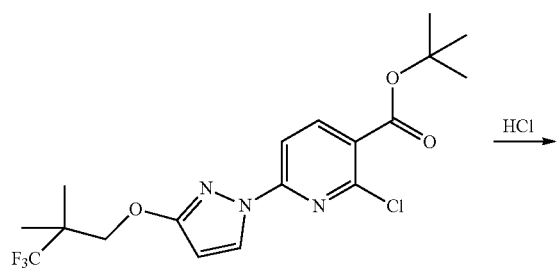

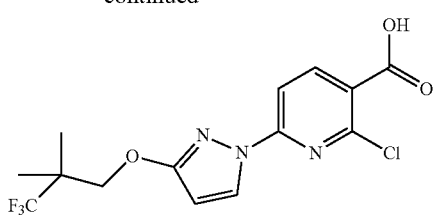

tert-butyl 2-chloro-6-[3-(3,3,3-trifluoro-2,2-dimethyl-propoxy)pyrazol-1-yl]pyridine-3-carboxylate (17.6 g, 40.25 mmol) was suspended in isopropanol (85 mL) treated with hydrochloric acid (34 mL of 6 M, 201 mmol) and heated to reflux for 3 hours (went almost complete into solution at reflux and started to precipitate again). The suspension was diluted with water (51 mL) at reflux and left to cool to room temperature under stirring for 2.5 h. The solid was collected by filtration, washed with isopropanol/water 1:1 (50 mL), plenty of water and dried in a drying cabinet under vacuum at 45-50° C. with a nitrogen bleed overnight to give 2-chloro-6-[3-(3,3,3-trifluoro-2,2-dimethyl-propoxy)pyrazol-1-yl]pyridine-3-carboxylic acid (13.7 g, 91%) as an off white solid. ESI-MS m/z calc. 363.05975, found 364.0 (M+1)⁺; Retention time: 1.79 minutes. ¹H NMR (400 MHz, DMSO-d6) δ 13.61 (s, 1H), 8.44 (d, J=2.9 Hz, 1H), 8.39 (d, J=8.4 Hz, 1H), 7.77 (d, J=8.4 Hz, 1H), 6.25 (d, J=2.9 Hz, 1H), 4.28 (s, 2H), 1.24 (s, 6H).

Step F: 2-Chloro-N-(1,3-dimethylpyrazol-4-yl)sulfonyl-6-[3-(3,3,3-trifluoro-2,2-dimethyl-propoxy)pyrazol-1-yl]pyridine-3-carboxamide

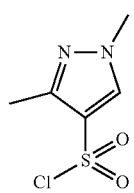

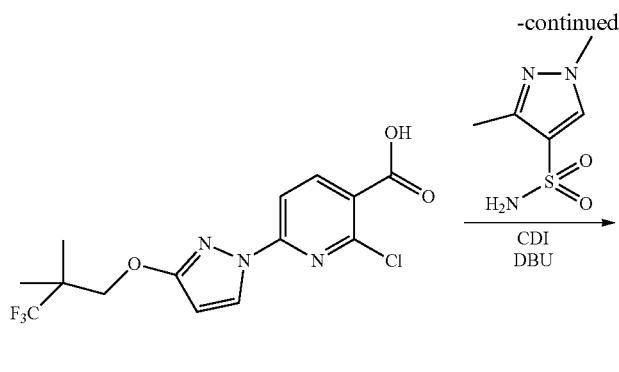
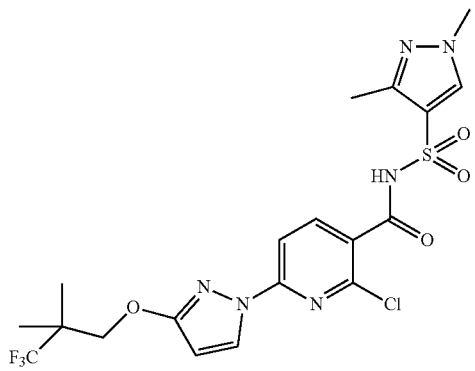

2-Chloro-6-[3-(3,3,3-trifluoro-2,2-dimethyl-propoxy)pyrazol-1-yl]pyridine-3-carboxylic acid (100 mg, 0.2667 mmol) and CDI (512 mg, 3.158 mmol) were combined in THF (582.0 μL) and the mixture was stirred at room temperature. Meanwhile, 1,3-dimethylpyrazole-4-sulfonyl chloride (62 mg, 0.3185 mmol) was combined with ammonia (in methanol) in a separate vial, instantly forming a white solid. After stirring for an additional 20 min, the volatiles were removed by evaporation, and 1 mL of dichloromethane was added to the solid residue, and was also evaporated. DBU (100 μL, 0.6687 mmol) was then added and the mixture stirred at 60° C. for 5 minutes, followed by addition of THF (1 mL) which was subsequently evaporated. The contents of the vial containing the CDI activated carboxylic acid in THF were then added to the vial containing the newly formed sulfonamide and DBU, and the reaction mixture was stirred for 4 hours at room temperature. The reaction mixture was diluted with 10 mL of ethyl acetate, and washed with 10 mL solution of citric acid (1 M). The aqueous layer was extracted with ethyl acetate (2×10 mL) and the combined organics were washed with brine, dried over sodium sulfate, and concentrated to give the product as white solid (137 mg, 99%) that was used in the next step without further purification. ESI-MS m/z calc. 520.09076, found 521.1 (M+1)$^+$; Retention time: 0.68 minutes.

Step G: N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide

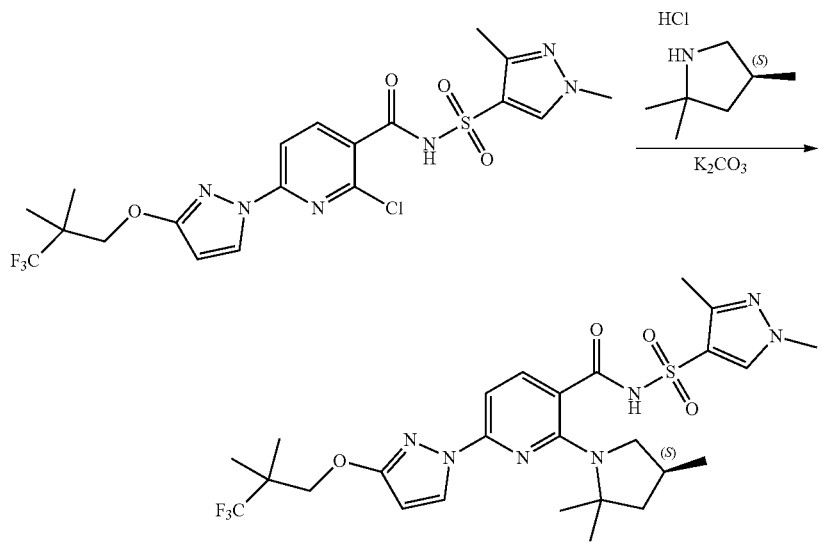

2-Chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (137 mg, 0.2630 mmol), (4S)-2,2,4-trimethylpyrrolidine (Hydrochloride salt) (118 mg, 0.7884 mmol), and potassium carbonate (219 mg, 1.585 mmol) were combined in DMSO (685.0 μL) and the mixture was heated at 130° C. for 16 hours. The reaction was cooled to room temperature, and 1 mL of water was added. After stirring for 15 minutes, the contents of the vial were allowed to settle, and the liquid portion was removed via pipet and the remaining solids were dissolved with 20 mL of ethyl acetate and were washed with 1 M citric acid (15 mL). The layers were separated and the aqueous layer was extracted two additional times with 15 mL of ethyl acetate. The organics were combined, washed with brine, dried over sodium sulfate and concentrated. The resulting solid was further purified by silica gel chromatography eluting with a gradient of methanol in dichloromethane (0-10%) to give N-(1,3- dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (72 mg, 41%) as a white solid. ESI-MS m/z calc. 597.2345, found 598.3 (M+1)⁺; Retention time: 2.1 minutes. ¹H NMR (400 MHz, DMSO) δ 12.36 (s, 1H), 8.37 (s, 1H), 8.22 (d, J=2.8 Hz, 1H), 7.74 (d, J=8.2 Hz, 1H), 6.93 (d, J=8.2 Hz, 1H), 6.17 (d, J=2.8 Hz, 1H), 4.23 (s, 2H), 3.81 (s, 3H), 2.56 (d, J=10.4 Hz, 1H), 2.41 (t, J=8.7 Hz, 1H), 2.32 (s, 3H), 2.18 (dd, J=12.4, 6.1 Hz, 1H), 1.87 (dd, J=11.7, 5.5 Hz, 1H), 1.55 (d, J=11.2 Hz, 6H), 1.42 (t, J=12.0 Hz, 1H), 1.23 (s, 6H), 0.81 (d, J=6.2 Hz, 3H).

Alternative Steps F and G

Alternative Step F: 2-chloro-N-((1,3-dimethyl-1H-pyrazol-4-yl)sulfonyl)-6-(3-(3,3,3-trifluoro-2,2-dimethylpropoxy)-1H-pyrazol-1-y)nicotinamide

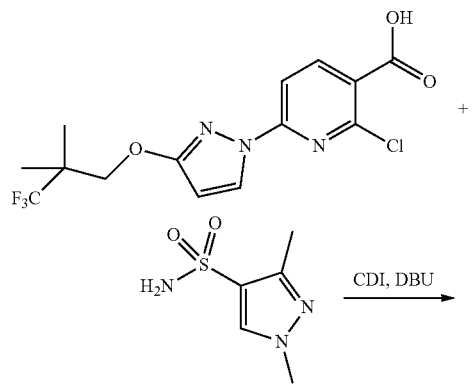

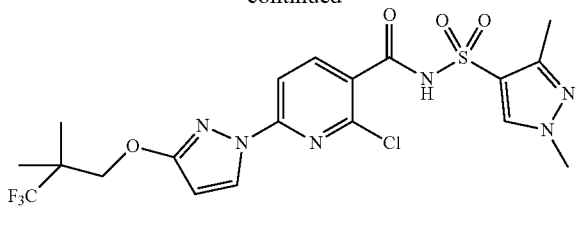

To a suspension of 2-chloro-6-[3-(3,3,3-trifluoro-2,2-dimethyl-propoxy)pyrazol-1-yl]pyridine-3-carboxylic acid (20.0 g, 53.89 mmol) in THF (78.40 mL) was added solid carbonyldiimidazole (approximately 10.49 g, 64.67 mmol) portion wise and the resulting solution was stirred at room temperature (slight exotherm from 18-21° C. was observed). After 1 h, solid 1,3-dimethylpyrazole-4-sulfonamide (approximately 11.33 g, 64.67 mmol) was added, followed by DBU (approximately 9.845 g, 9.671 mL, 64.67 mmol) in two equal portions over 1 min (exotherm from 19 to 35° C.). The reaction mixture was stirred at room temperature for 16 h. The reaction mixture was diluted with ethyl acetate (118 mL) and then HCl (approximately 107.8 mL of 2 M, 215.6 mmol). The phases were separated and the aqueous phase was extracted with ethyl aceate (78 mL). The combined organics were washed with water (39.2 mL), then brine (40 mL), dried over sodium sulfate and concentrated. The resulting foam was crystallized from a 1:1 isopropanol:heptane mixture (80 mL) to afford 2-chloro-N-((1,3-dimethyl-1H-pyrazol-4-yl)sulfonyl)-6-(3-(3,3,3-trifluoro-2,2-dimethyl-propoxy)-1H-pyrazol-1-yl)nicotinamide (26.1 g, 93%) as a white solid. ESI-MS m/z calc. 520.0, found 520.9 (M+1)⁺; Retention time: 1.83 minutes.

Alternative Step G: N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide

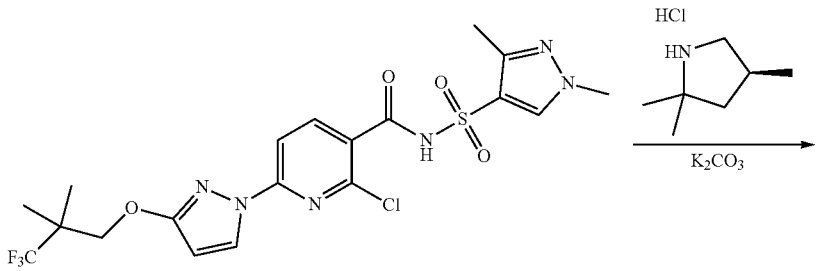

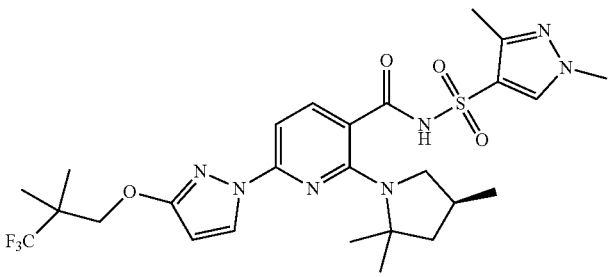

2-chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (20.0 g, 38.39 mmol), (4S)-2,2,4-trimethylpyrrolidine (Hydrochloride salt) (approximately 14.36 g, 95.98 mmol), and K2CO3 (approximately 26.54 g, 192.0 mmol) were combined in DMSO (80.00 mL) and 1,2-diethoxyethane (20.00 mL) in a 500-mL flask with reflux condenser. The reaction mixture was heated at 120° C. for 16 h then cooled to room temperature. The reaction was diluted with DCM (200.0 mL) and HCl (approximately 172.8 mL of 2 M, 345.5 mmol); aqueous pH ~1. The phases were separated, and the aqueous phase was extracted with DCM (100.0 mL). The organic phases were combined, washed with water (100.0 mL) (3×), and dried (Na2SO4) to afford an amber solution. The solution was filtered through a DCM-packed silica gel bed (80 g; 4 g/g) and washed with 20% EtOAc/DCM (5×200 mL). The combined filtrate/washes were concentrated to afford 22.2 g of an off-white powder. The powder was slurried in MTBE (140 mL) for 30 min. The solid was collected by filtration (paper/sintered-glass) to afford 24 g after air-drying. The solid was transferred to a drying dish and vacuum-dried (40° C./200 torr/N2 bleed) overnight to afford 20.70 g (90%) of a white powder. ESI-MS m/z calc. 597.2345, found 598.0 (M+1)+; Retention time: 2.18 minutes.

$^1$H NMR (400 MHz, Chloroform-d) δ 13.85 (s, 1H), 8.30 (d, J=8.6 Hz, 1H), 8.23 (d, J=2.8 Hz, 1H), 8.08 (s, 1H), 7.55 (d, J=8.5 Hz, 1H), 5.98 (d, J=2.8 Hz, 1H), 4.24 (s, 2H), 3.86 (s, 3H), 3.44 (dd, J=10.3, 8.4 Hz, 1H), 3.09 (dd, J=10.3, 7.8 Hz, 1H), 2.67-2.52 (m, 1H), 2.47 (s, 3H), 2.12 (dd, J=12.3, 7.8 Hz, 1H), 1.70 (dd, J=12.4, 9.6 Hz, 1H), 1.37 (s, 3H), 1.33 (s, 3H), 1.27 (s, 6H), 1.20 (d, 3H).

Alternative Synthesis of 3-(3,3,3-trifluoro-2,2-dimethyl-propoxy)-1H-Pyrazole

Step 1: Preparation of 3,3,3-trifluoro-2,2-dimethylpropan-1-ol

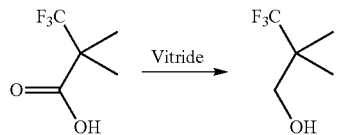

A reactor was loaded with toluene (300 mL) and 3,3,3-trifluoro-2,2-dimethylpropanoic acid (30 g, 192.2 mmol), capped, purged under nitrogen. The reaction was set to control the internal temperature to 40° C. A solution of Vitride (65% in toluene. approximately 119.6 g of 65% w/w, 115.4 mL of 65% w/w, 384.4 mmol) was set up for addition via syringe, and addition was begun at 40° C., with the target addition temperature between 40 and 50° C. The reaction was stirred at 40° C. for 90 min. The reaction was cooled to 10° C. then the remaining Vitride was quenched with slow addition of water (6 mL). A solution of 15% aq NaOH (30 mL) was added in portions, and solids precipitated half way through the base addition. Water (60.00 mL) was added. The mixture was warmed to 30° C. and held for at least 15 mins. The mixture was then cooled to 20° C. The aqueous layer was removed. The organic layer was washed with water (60 mL×3), and then washed with brine (60 mL). The washed organic layer was dried under Na2SO4, followed with MgSO4. The mix was filtered through Celite, and the cake washed with toluene (60.00 mL) and pulled dry. The product 3,3,3-trifluoro-2,2-dimethyl-propan-1-ol (22.5 g, 82%) was obtained as clear colorless solution.

Step 2: Preparation of 1-(tert-butyl) 4-ethyl 3-(3,3,3-trifluoro-2,2-dimethylpropoxy)-1H-pyrazole-1,4-dicarboxylate

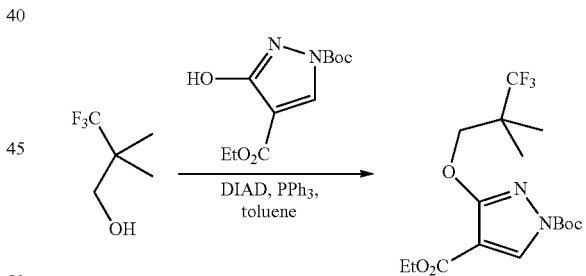

A reactor was charged with 3,3,3-trifluoro-2,2-dimethyl-propan-1-ol (17.48 g, 123.0 mmol) solution in toluene (250 g), 1-(tert-butyl) 4-ethyl 3-hydroxy-1H-pyrazole-1,4-dicarboxylate (30.0 g, 117.1 mmol), and PPh3 (35.33 g, 134.7 mmol). The reaction was heated to 40° C. DIAD (26.09 mL, 134.7 mmol) was weighed and placed into a syringe and added over 10 minutes while maintaining an internal temperature ranging between 40 and 50° C. The reaction was then heated to 100° C. over 30 minutes. After holding at 100° C. for 30 minutes, the reaction was complete, and the mixture was cooled to 70° C. over 15 minutes. Heptane (180.0 mL) was added, and the jacket was cooled to 15° C. over 1 hour. (TPPO began crystallizing at ~35° C.). The mixture stirring at 15° C. was filtered (fast), the cake was washed with a pre-mixed solution of toluene (60 mL) and heptane (60 mL) and then pulled dry. The clear solution was

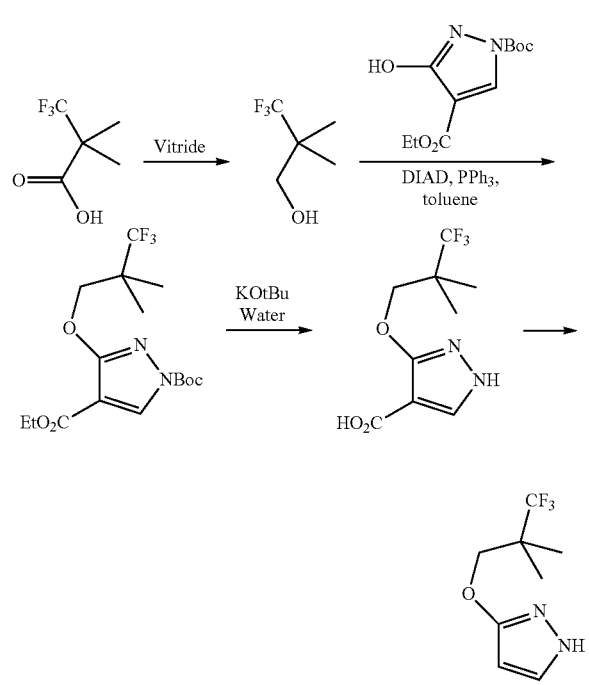

concentrated to a waxy solid (45° C., vacuum, rotovap). Crude 1-(tert-butyl) 4-ethyl 3-(3,3,3-trifluoro-2,2-dimethyl-propoxy)-1H-pyrazole-1,4-dicarboxylate (53.49 g) was obtained as a waxy solid, (~120% of theoretical mass recovered).

Step 3: Preparation of 3-(3,3,3-trifluoro-2,2-dimethylpropoxy)-1H-pyrazole-4-carboxylic acid

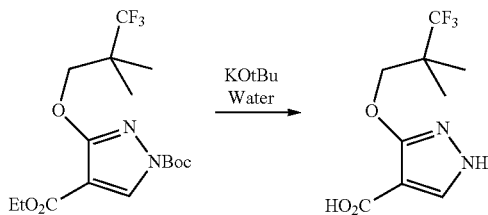 [SMILES: CCOC(=O)c1cn(C(=O)OC(C)(C)C)nc1OCC(C)(C)C(F)(F)F ; "KOtBuWater" ; CC(C)(COc1n[nH]cc1C(=O)O)C(F)(F)F]

A solution of 1-(tert-butyl) 4-ethyl 3-(3,3,3-trifluoro-2,2-dimethylpropoxy)-1H-pyrazole-1,4-dicarboxylate (50.0 g, 131 mmol) in 2-methyltetrahydrofuran (500 mL) was prepared in a reactor and stirred at 40° C. Portions of KOt-Bu (80.85 g, 720.5 mmol) were then added over 30 minutes. Addition was exothermic. After 20 53.49 g UPLC-MS showed complete removal of the Boc group, so water (3.53 g, 3.53 mL, 196 mmol) was added drop-wise addition via syringe over 20 min to keep the reaction temperature between 40-50° C. The mixture was then stirred for 17 hours to complete the reaction. The mixture was then cooled to 20° C. and water (400 mL) was added. The stirring was stopped and the layers were separated. The desired product in the aqueous layer was returned to the reactor and the organic layer was discarded. The aqueous layer was washed with 2-Me-THF (200 mL). Isopropanol (50. mL) was added followed by dropwise addition of aqueous HCl (131 mL of 6.0 M, 786.0 mmol) to adjust the pH to <3 while maintaining the temperature below 30° C. The resulting solid was then isolated by filtration and the filter cake washer with water (100 mL) then pulled dry until a sticky cake was obtained. The solids were then dried under vacuum at 55° C. to afford 3-(3,3,3-trifluoro-2,2-dimethylpropoxy)-1H-pyrazole-4-carboxylic acid (23.25 g) as an off-white fine solid.

Step 4: Preparation of 3-(3,3,3-trifluoro-2,2-dimethyl-propoxy)-1H-pyrazole 3-(3,3,3-trifluoro-2,2-dimethylpropoxy)-1H-pyrazole-4-carboxylic acid (1.0 equiv) was added to a reactor followed by DMF (6.0 vol, 2.6 wt equiv). The mixture was stirred at 18-22° C. DBU (0.2 equiv.) was charged to the reaction mixture at a rate of approximately 45 mL/min. The reaction temperature was then raised to 98-102° C. over 45 minutes. The reaction mixture was stirred at 98-102° C. for no less than 10 h. The reaction mixture was then cooled to −2° C. to 2° C. over approximately 1 hour and was used without isolation to make ethyl 2-chloro-6-(3-(3,3,3-trifluoro-2,2-dimethylpropoxy)-1H-pyrazol-1-yl)nicotinate.

Alternate procedure for the preparation of 2-chloro-6-[3-(3,3,3-trifluoro-2,2-dimethyl-propoxy)pyrazol-1-yl]pyridine-3-carboxylic acid

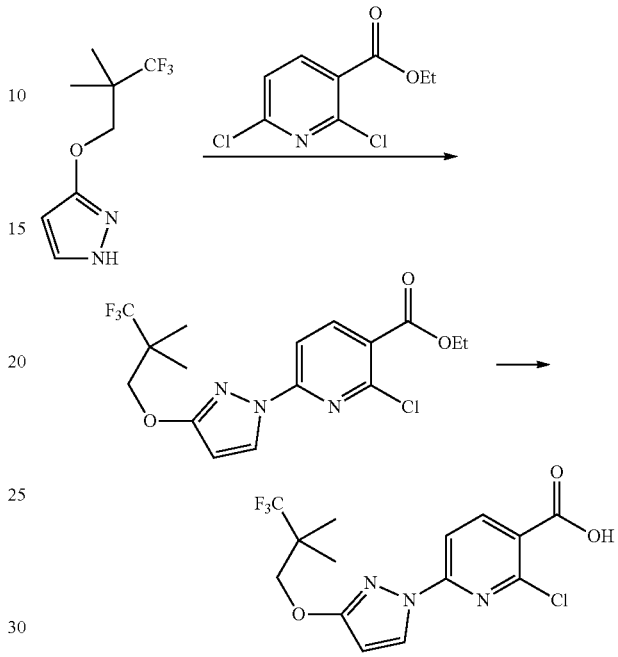

Step 1. Ethyl 2-chloro-6-(3-(3,3,3-trifluoro-2,2-dimethylpropoxy)-1H-pyrazol-1-yl)nicotinate

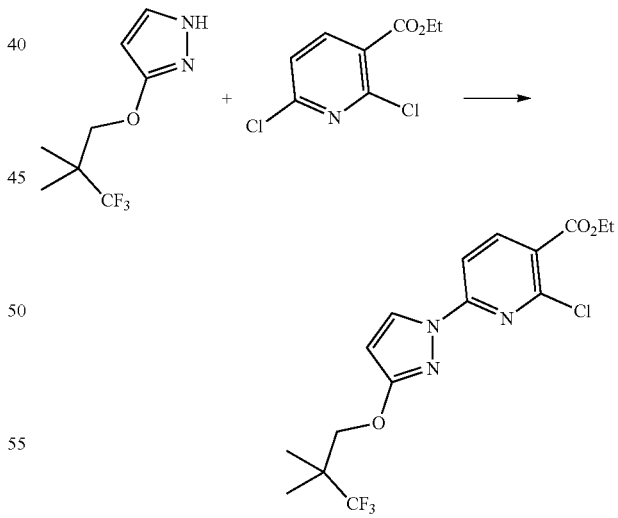

A solution of ethyl 2,6-dichloronicotinate (256 g, 1.16 mol) and 3-(3,3,3-trifluoro-2,2-dimethyl-propoxy)-1H-pyrazole (242 g, 1.16 mol) in DMF (1.53 L) was treated with potassium carbonate (209 g, 1.51 mol) and DABCO (19.6 g, 174 mmol). The resultant suspension was stirred allowed to exotherm from 14 to 25° C. and then maintained at 20-25° C. with external cooling for 3 days. The suspension was cooled to below 10° C. when water (2.0 L) was added in a thin stream while maintaining the temperature below 25° C. After the addition was complete, the suspension was stirred for an additional 1 h. The solid was collected by filtration (sintered-glass/polypad) and the filter-cake was washed with water (2×500-mL) and dried with suction for 2 h to afford water-damp ethyl 2-chloro-6-(3-(3,3,3-trifluoro-2,2-dimethylpropoxy)-1H-pyrazol-1-yl)nicotinate (512 g; 113% yield) as white powder which was used without further steps in the subsequent reaction.

Step 2. 2-chloro-6-(3-(3,3,3-trifluoro-2,2-dimethylpropoxy)-1h-pyrazol-1-yl)nicotinic acid

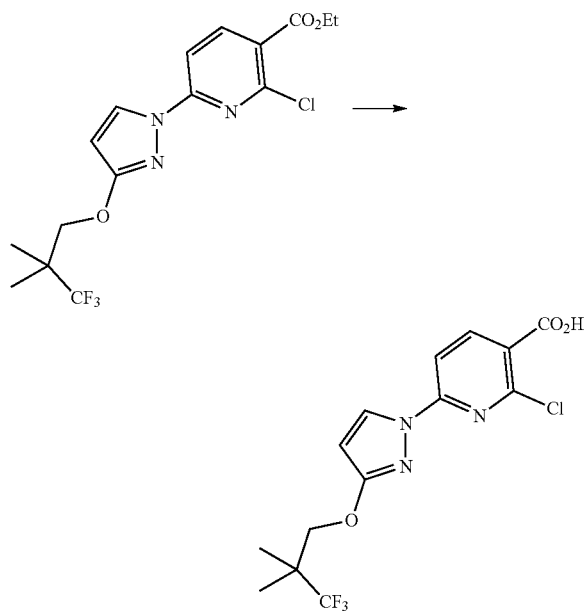

The water-damp ethyl 2-chloro-6-(3-(3,3,3-trifluoro-2,2-dimethylpropoxy)-1H-pyrazol-1-yl)nicotinate (455 g, 1.16 mol; assumed 100% yield from previous step) in EtOH (1.14 L) and THF (455 mL) was stirred at ambient temperature (17° C.) when 1 M NaOH (1.16 L, 1.16 mol) was added. The reaction mixture exothermed to 30° C. and was further warmed at 40° C. for 2 h. The solution was quenched with 1 M HCl (1.39 L, 1.39 mol) which resulted in an immediate precipitation which became thicker as the acid was added. The creamy suspension was allowed to cool to room temperature and was stirred overnight. The solid was collected by filtration (sintered-glass/poly pad). The filter-cake was washed with water (2×500-mL). The filter-cake was dried by suction for 1 h but remained wet. The damp solid was transferred to a 10-L Buchi flask for further drying (50° C./20 torr), but was not effective. Further effort to dry by chasing with i-PrOH was also ineffective. Successful drying was accomplished after the damp solid was backfilled with i-PrOAc (3 L), the suspension was heated at 60° C. (homogenization), and re-concentrated to dryness (50° C./20 torr) to afford dry 2-chloro-6-(3-(3,3,3-trifluoro-2,2-dimethylpropoxy)-1h-pyrazol-1-yl)nicotinic acid (408 g; 97% yield for two steps) as a fine, white powder. The product was further dried in a vacuum oven (50° C./10 torr/N2 bleed) for 2 h but marginal weight loss was observed. 1H NMR (400 MHz, DMSO-d6) δ 13.64 (s, 1H), 8.49-8.36 (m, 2H), 7.77 (d, J=8.4 Hz, 1H), 6.26 (d, J=2.8 Hz, 1H), 4.28 (s, 2H), 1.24 (s, 6H). 19F NMR (376 MHz, DMSO-d6) δ −75.2. KF analysis: 0.04% water.

2. Preparation of Form a of Compound 1

The crystalline Form A of Compound 1 was obtained as a result of the following synthesis. Combined 2-chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (108 g, 207.3 mmol), (4S)-2,2,4-trimethylpyrrolidine (Hydrochloride salt) (77.55 g, 518.2 mmol), was combined with $K_2CO_3$ (143.2 g, 1.036 mol) in DMSO (432.0 mL) and 1,2-diethoxyethane (108.0 mL) in a 1-L RB flask with a reflux condenser. The resulting suspension was heated at 120° C. and was stirred at temperature overnight. Then the reaction was diluted with DCM (1.080 L) and HCl (933.0 mL of 2 M, 1.866 mol) was slowly added. The liquid phases were separated, and the aqueous phase was extracted with DCM (540.0 mL). The organic phases were combined, washed with water (540.0 mL) (3×), then dried with ($Na_2SO_4$) to afford an amber solution. Silica gel (25 g) was added and then the drying agent/silica gel was filtered off. The filter-bed was washed with DCM (3×50-mL). The organic phases were combined and concentrated (40° C./40 torr) to afford crude N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (198.6 g, 160% theory) as an off-white solid. The solid was diluted with MTBE (750 mL), warmed at 60° C. (external temperature), and mixed to a homogenous suspension. The suspension was cooled to 30° C. with stirring and the solid was collected by filtration, air-dried, and vacuum-dried to afford Compound 1 (111.1 g; 90%) as a fine, white powder.

The crystalline Form A of Compound 1 was also obtained through the following procedure. A suspension of Compound 1 (150.0 g, 228.1 mmol) in iPrOH (480 mL) and water (120 mL) was heated at 82° C. to obtain a solution. The solution was cooled with a J-Kern controller at a cooling rate of 10° C./h. Once the temperature reached 74° C., the solution was seeded with a sample of Compound 1 in crystalline Form A. Crystallization occurred immediately. The suspension was cooled to 20° C. The solid was collected by filtration, washed with i-PrOH (2×75 mL), air-dried with suction, and vacuum-dried (55° C./300 torr/$N_2$ bleed) to afford Compound 1, Form A (103.3 g) as a white powder. The sample was cooled to ~5° C., let stir for 1 h, and then the solid was collected by filtration (sintered glass/paper). the filter-cake was washed with i-PrOH (75 mL) (2×), air-dried with suction, air-dried in a drying dish (120.6 g mostly dried), vacuum-dried (55° C./300 torr/N2 bleed) for 4 h, and then RT overnight. Overnight drying afforded 118.3 g (87% yield) of a white powder.

Preparation of Crystalline Form M of Compound 1 (Methanol Solvate of Compound 1)

Compound 1 (free acid neutral form) (800 mg) was added to 9.2 g methanol and a clear solution formed. An additional 701.2 mg of Compound 1 was added, and a suspension formed. The temperature was raised to 45° C., at which point a clear solution formed. The solution was slowly cooled, and solids precipitated.

Figure 13:
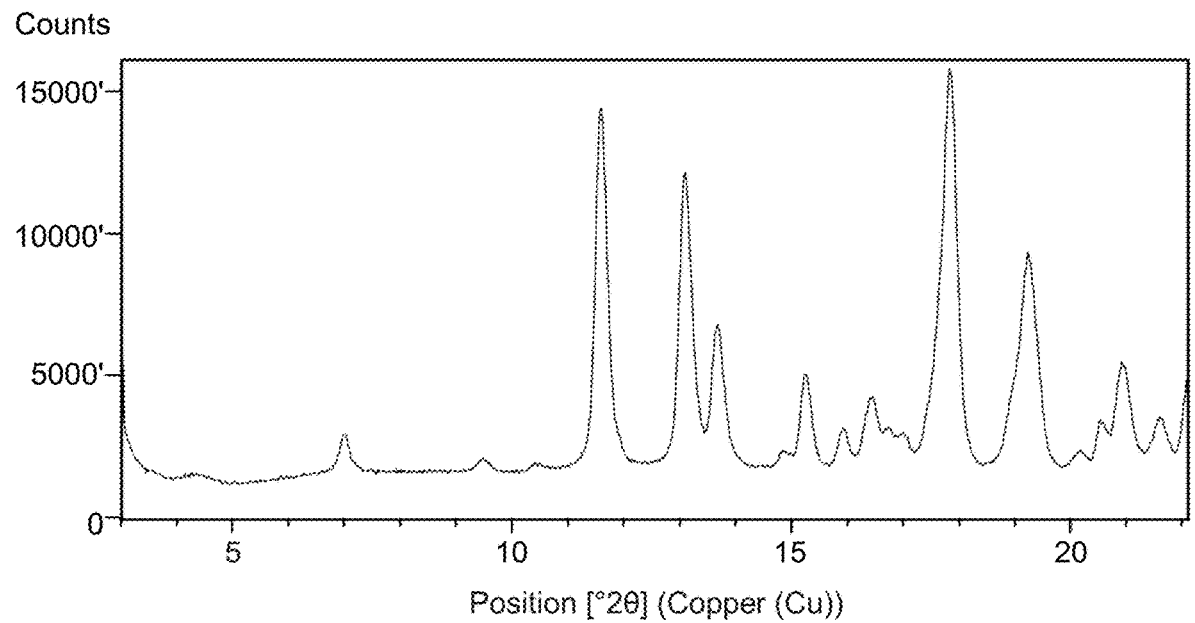
FIG. 13 shows an X-ray powder diffractogram of crystalline Form M of Compound 1.

The XRPD data of crystalline Form M of Compound 1 are summarized below. X-ray powder diffractogram of crystalline Form M of Compound 1 is shown in FIG. 13.

TABLE

XRPD data for crystalline Form M of Compound 1

| Pos. [°2 Th.] | D spacings |
|---|---|
| 6.99 | 12.64 |
| 11.61 | 7.60 |
| 13.08 | 6.76 |
| 13.66 | 6.48 |
| 15.24 | 5.81 |
| 15.91 | 5.56 |
| 16.44 | 5.39 |
| 17.82 | 4.97 |
| 19.25 | 4.61 |

Preparation of Crystalline Form E of Compound 1 (Ethanol Solvate of Compound 1)

Compound 1 (free acid neutral form) (800 mg) was added to 9.2 g ethanol and heated to 80° C. A clear solution formed. The solution was slowly cooled, and solids precipitated.

Figure 14:
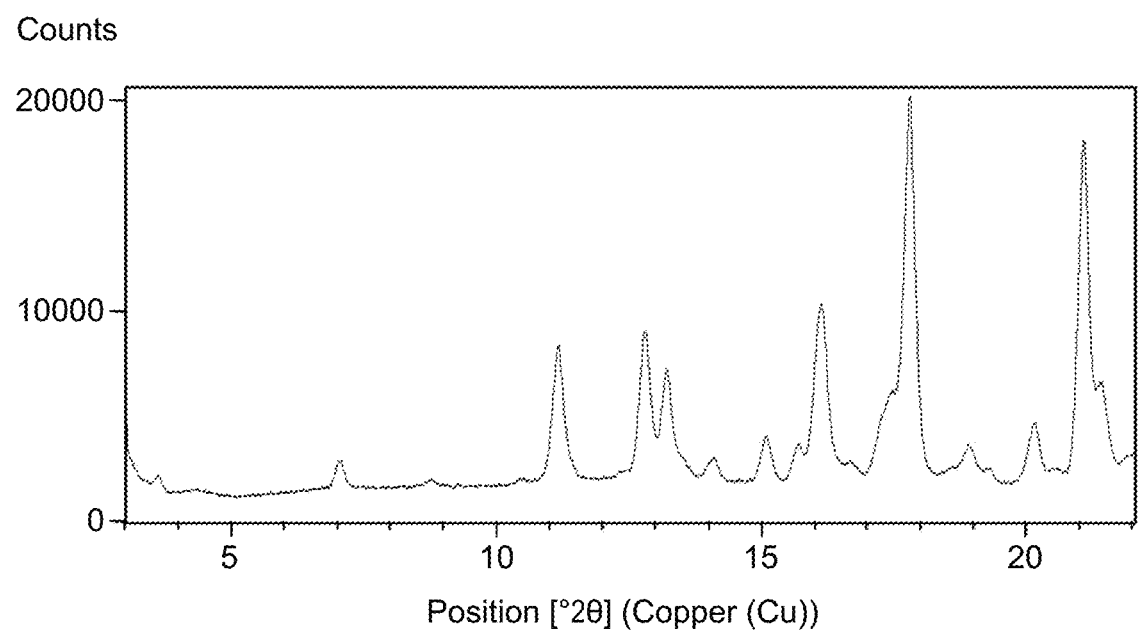
FIG. 14 shows an X-ray powder diffractogram of crystalline Form E of Compound 1.

The XRPD data of crystalline Form E of Compound 1 are summarized below. X-ray powder diffractogram of crystalline Form E of Compound 1 is shown in FIG. 14.

TABLE

XRPD data for crystalline Form E of Compound 1

| Pos. [°2 Th.] | D spacings |
|---|---|
| 7.03 | 12.56 |
| 11.16 | 7.92 |
| 12.79 | 6.91 |
| 13.21 | 6.70 |
| 15.08 | 5.87 |
| 16.12 | 5.49 |
| 14.08 | 6.28 |
| 17.79 | 4.98 |
| 18.92 | 4.69 |

Preparation of Crystalline Form P2 of Compound 1 (Isopropanol Solvate of Compound 1)

A 200 mg/mL solution of Compound 1 in 2-propanol was heated to 75° C., and all solids dissolved. The solution was cooled to 50° C., and precipitation occurred. The mixture was kept at 50° C. for several hours, then cooled to room temperature and aged for several hours.

Figure 17:
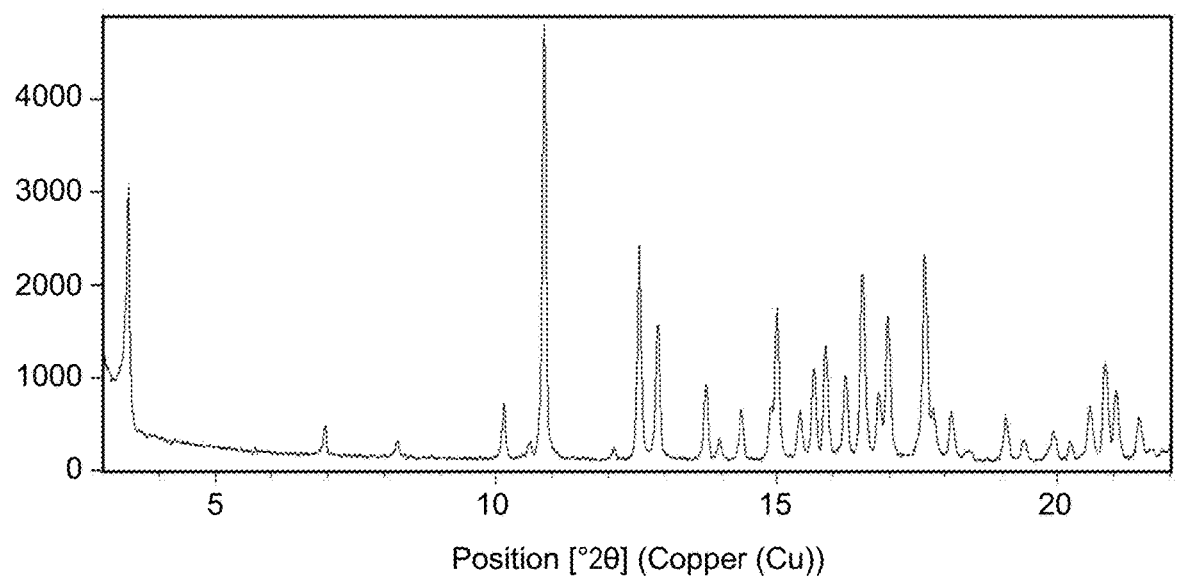
FIG. 17 shows an X-ray powder diffractogram of crystalline Form P2 of Compound 1.

The XRPD data of crystalline Form P2 of Compound 1 are summarized below. X-ray powder diffractogram of crystalline Form P2 of Compound 1 is shown in FIG. 17.

TABLE

XRPD data for crystalline Form P2 of Compound 1

| Pos. [°2 Th.] | D spacings |
|---|---|
| 10.15 | 8.71 |
| 10.86 | 8.14 |
| 12.55 | 7.05 |
| 12.88 | 6.87 |
| 15.01 | 5.90 |
| 15.87 | 5.58 |
| 16.22 | 5.46 |
| 16.52 | 5.36 |
| 17.63 | 5.03 |

Preparation of Various Solvates of Compound 1

Various solvates of Compound 1 were prepared by stirring amorphous Compound 1 in the relevant dry solvent as shown in the following Table 8 for three weeks at room temperature for sulfolane, propionic acid, MTBE, isobutyric acid, anisole, methylbutyl ketone, acetic acid and xylene solvates, or at 40° C. for toluene solvates. Solid forms observed after vacumm drying the resulting solvates in vacuum at room temperature are also summarized in the table. As used herein, "Crystalline Form PA" refers to the crystalline form of Compound 1 prepared from propionic acid as discussed herein, "Crystalline Form AN" refers to the crystalline form of Compound 1 prepared from anisole as discussed herein, "Crystalline Form MK" refers to the crystalline form of Compound 1 prepared from methylbutyl ketone as discussed herein, and "Crystalline Form AA1" refers to a crystalline form of Compound 1 prepared from acetic acid as discussed herein.

TABLE 8

| Solvent | Concentration (mg/mL) | Form after desolvation |
|---|---|---|
| Toluene | 74 | Form A |
| Sulfolane | 249 | Form A |
| Propionic acid | 420 | Form A |
| MTBE | 123 | Form A |
| Isobutyric acid | 213 | Form A |
| Anisole | 194 | Not Determined |
| Methylbutyl ketone | 465 | Not Determined |
| Acetic acid | 267 | Form A |
| Xylene | 126 | Largely Amorphous |

Synthesis of N-(1,3-dimethylpyrazol-4-yl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (Compound 15)

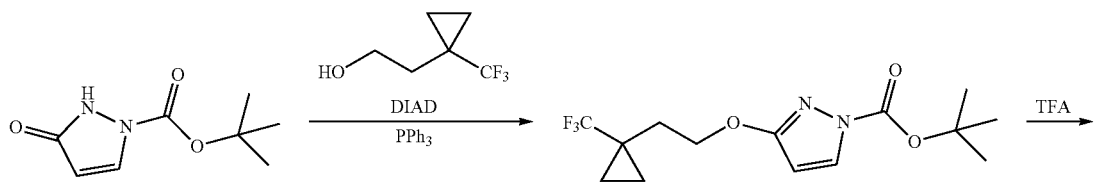

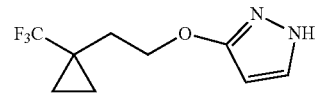

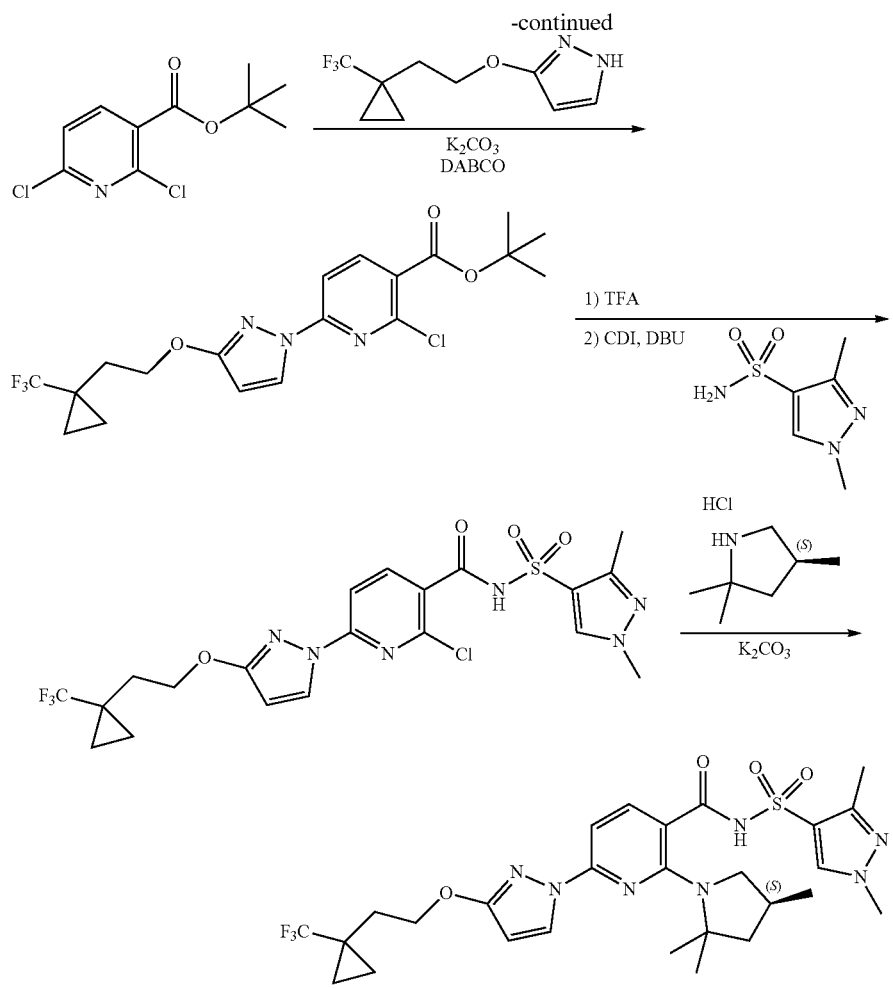

Synthesis of Starting Materials

Synthesis of tert-butyl 2,6-dichloropyridine-3-carboxylate

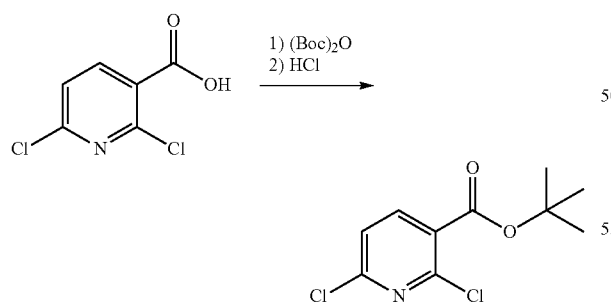

A solution of 2,6-dichloropyridine-3-carboxylic acid (10 g, 52.08 mmol) in THF (210 mL) was treated successively with di-tert-butyl dicarbonate (17 g, 77.89 mmol) and 4-(dimethylamino)pyridine (3.2 g, 26.19 mmol) and stirred overnight at room temperature. At this point, HCl 1N (400 mL) was added, and the mixture was stirred vigorously for about 10 minutes. The product was extracted with ethyl acetate (2×300 mL), and the combined organic layers were washed with water (300 mL) and brine (150 mL) and dried over sodium sulfate and concentrated under reduced pressure to give 12.94 g (96% yield) of tert-butyl 2,6-dichloropyridine-3-carboxylate as a colorless oil. ESI-MS m/z calc. 247.02, found 248.1 (M+1)$^+$; Retention time: 2.27 minutes. $^1$H NMR (300 MHz, CDCl$_3$) ppm 1.60 (s, 9H), 7.30 (d, J=7.9 Hz, 1H), 8.05 (d, J=8.2 Hz, 1H).

Synthesis of tert-butyl 3-oxo-2,3-dihydro-1H-pyrazole-1-carboxylate

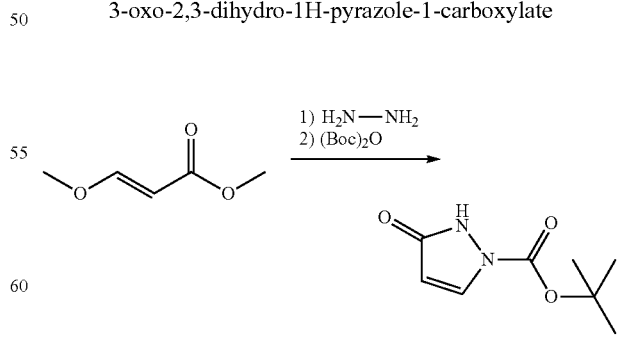

A 50 L reactor was started, and the jacket was set to 20° C., with stirring at 150 rpm, reflux condenser (10° C.) and nitrogen purge. MeOH (2.860 L) and methyl (E)-3-methoxyprop-2-enoate (2.643 kg, 22.76 mol) were added, and the reactor was capped. The reaction was heated to an internal temperature of 40° C., and the system was set to hold jacket temperature at 40° C. Hydrazine hydrate (1300 g of 55% w/w, 22.31 mol) was added portion wise via addition funnel over 30 min. The reaction was heated to 60° C. for 1 h. The reaction mixture was cooled to 20° C. and triethyamine (2.483 kg, 3.420 L, 24.54 mol) was added portion-wise, maintaining reaction temperature <30° C. A solution of Boc anhydride (di-tert-butyl dicarbonate) (4.967 kg, 5.228 L, 22.76 mol) in MeOH (2.860 L) was added portion-wise maintaining temperature <45° C. The reaction mixture was stirred at 20° C. for 16 h. The reaction solution was partially concentrated to remove MeOH, resulting in a clear, light amber oil. The resulting oil was transferred to the 50 L reactor, stirred and water (7.150 L) and heptane (7.150 L) were added. The additions caused a small amount of the product to precipitate. The aqueous layer was drained into a clean container, and the interface and heptane layer were filtered to separate the solid (product). The aqueous layer was transferred back to the reactor, and the collected solid was placed back into the reactor and mixed with the aqueous layer. A dropping funnel was added to the reactor and loaded with acetic acid (1.474 kg, 1.396 L, 24.54 mol) and added dropwise. The jacket was set to 0° C. to absorb the quench exotherm. After the addition was complete (pH=5), the reaction mixture was stirred for 1 h. The solid was collected by filtration and washed with water (7.150 L), and washed a second time with water (3.575 L). The crystalline solid was transferred into a 20 L rotovap bulb, and heptane (7.150 L) was added. The mixture was slurried at 45° C. for 30 mins, and 1-2 volumes of solvent were distilled off. The slurry in the rotovap flask was filtered, and the solids were washed with heptane (3.575 L). The solid was further dried in vacuo (50° C., 15 mbar) to give tert-butyl 5-oxo-1H-pyrazole-2-carboxylate (2921 g, 71%) as a coarse, crystalline solid. $^1$H NMR (400 MHz, DMSO-d6) δ 10.95 (s, 1H), 7.98 (d, J=2.9 Hz, 1H), 5.90 (d, J=2.9 Hz, 1H), 1.54 (s, 9H).

Synthesis of 1,3-dimethyl-1H-pyrazole-4-sulfonamide

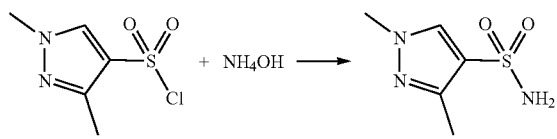

Ammonium hydroxide (approximately 186.5 mL of 28% w/v, 1.490 mol) was cooled at 0-5° C. in a jacketed reaction vessel. A solution of 1,3-dimethylpyrazole-4-sulfonyl chloride (29.0 g, 149.0 mmol) in DCM (116.0 mL) was added while maintaining the reaction temperature between 0 to 5° C. The two phases were separated, and the organic phase was washed with water (100 mL). The aqueous phases were combined and concentrated to remove most of the residual ammonia. The aqueous phase was extracted twice with ethyl acetate (200 mL and 100 mL). The organic phases were combined, dried over sodium sulfate and concentrated to afford 14.1 g of a white solid. The aqueous phase was acidified with citric acid (approximately 28.63 g, 17.20 mL, 149.0 mmol) (pH~2). The acidic aqueous was extracted twice with ethyl acetate (200 mL and 100 mL). The combined organic phases were dried over sodium sulfate, and concentrated to afford another 7.8 g of a white solid. The solids were combined and recrystallized from hot (78° C.) ethyl acetate (50 mL) to afford 16.1 g of 1,3-dimethyl-1H-pyrazole-4-sulfonamide as a white, crystalline solid.

$^1$H NMR (400 MHz, DMSO) δ 8.01 (s, 1H), 7.16 (s, 2H), 3.77 (s, 3H), 2.77 (s, 3H).

Synthesis of 2-[1-(trifluoromethyl)cyclopropyl]ethanol

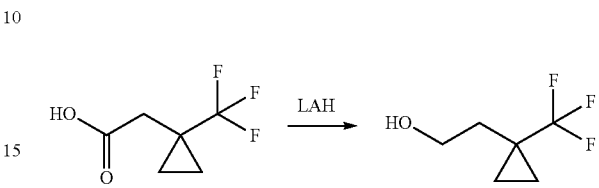

To a solution of lithium aluminum hydride (293 mg, 7.732 mmol) in THF (10.00 mL) in an ice-bath, 2-[1-(trifluoromethyl)cyclopropyl]acetic acid (1.002 g, 5.948 mmol) in THF (3.0 mL) was added dropwise over a period of 30 minutes keeping the reaction temperature below 20° C. The mixture was allowed to gradually warm to ambient temperature and was stirred for 18 h. The mixture was cooled with an ice-bath and sequentially quenched with water (294 mg, 295 µL, 16.36 mmol), NaOH (297 µL of 6 M, 1.784 mmol), and then water (884.0 µl, 49.07 mmol) to afford a granular solid in the mixture. The solid was filtered off using Celite, and the precipitate was washed with ether. The filtrate was further dried with MgSO$_4$ and filtered and concentrated in vacuo to afford the product with residual THF and ether. The mixture was taken directly into the next step without further purification.

Step 1: tert-Butyl 3-[2-[1-(trifluoromethyl)cyclopropyl]ethoxy]pyrazole-1-carboxylate

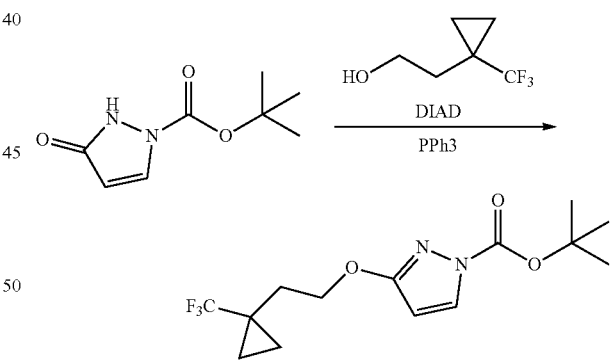

tert-Butyl 5-oxo-1H-pyrazole-2-carboxylate (1.043 g, 5.660 mmol), 2-[1-(trifluoromethyl)cyclopropyl]ethanol (916 mg, 5.943 mmol), and triphenyl phosphine (1.637 g, 6.243 mmol) were combined in THF (10.48 mL), and the reaction was cooled in an ice-bath. Diisopropyl azodicarboxylate (1.288 g, 1.254 mL, 6.368 mmol) was added dropwise to the reaction mixture, and the reaction was allowed to warm to room temperature for 16 hours. The mixture was evaporated, and the resulting material was partitioned between ethyl acetate (30 mL) and 1 N sodium hydroxide (30 mL). The organic layer was separated, washed with brine (30 mL), dried over sodium sulfate, and concentrated. The crude material was purified by silica gel chromatography eluting with a gradient of ethyl acetate in hexanes (0-30%) to give tert-butyl 3-[2-[1-(trifluoromethyl)cyclopropyl]ethoxy]pyrazole-1-carboxylate (1.03 g, 57%). ESI-MS m/z calc. 320.13, found 321.1 (M+1)+; Retention time: 0.72 minutes.

Step 2: 3-[2-[1-(Trifluoromethyl)cyclopropyl]ethoxy]-1H-pyrazole

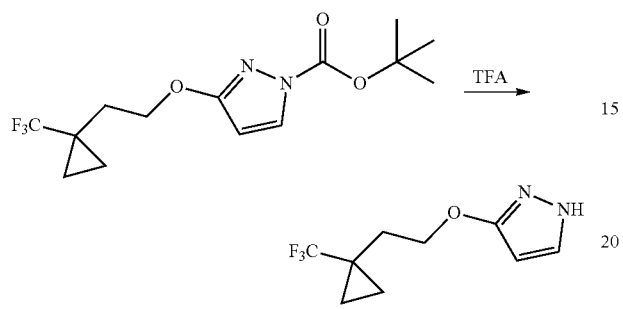

tert-Butyl-3-[2-[1-(trifluoromethyl)cyclopropyl]ethoxy]pyrazole-1-carboxylate (1.03 g, 3.216 mmol) was dissolved in dichloromethane (10.30 mL) with trifluoroacetic acid (2.478 mL, 32.16 mmol), and the reaction was stirred at room temperature for 2 hours. The reaction was evaporated, and the resulting oil was partitioned between ethyl acetate (10 mL) and a saturated sodium bicarbonate solution. The organic layer was separated, washed with brine, dried over sodium sulfate, and evaporated to give 3-[2-[1-(trifluoromethyl)cyclopropyl]ethoxy]-1H-pyrazole (612 mg, 86%). ESI-MS m/z calc. 220.08, found 221.0 (M+1)+; Retention time: 0.5 minutes. 1H NMR (400 MHz, DMSO-d6) δ 11.86 (s, 1H), 7.50 (t, J=2.1 Hz, 1H), 5.63 (t, J=2.3 Hz, 1H), 4.14 (t, J=7.1 Hz, 2H), 2.01 (t, J=7.1 Hz, 2H), 0.96-0.88 (m, 2H), 0.88-0.81 (m, 2H).

Step 3: tert-Butyl 2-chloro-6-[3-[2-[1-(trifluoromethyl)cyclopropyl]ethoxy]pyrazol-1-yl]pyridine-3-carboxylate

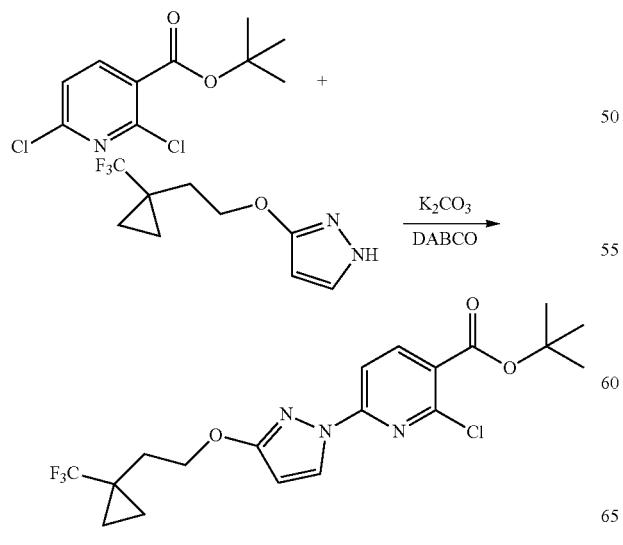

tert-Butyl 2,6-dichloropyridine-3-carboxylate (687 mg, 2.770 mmol), 3-[2-[1-(trifluoromethyl)cyclopropyl]ethoxy]-1H-pyrazole (610 mg, 2.770 mmol), and freshly ground potassium carbonate (459 mg, 3.324 mmol) were combined in anhydrous DMSO (13.75 mL). 1,4-diazabicyclo[2.2.2]octane (DABCO (1,4-diazabicyclo[2.2.2]octane), 62 mg, 0.5540 mmol) was added, and the mixture was stirred at room temperature under nitrogen for 16 hours. The reaction mixture was diluted with water (20 mL) and stirred for 15 minutes. The resulting solid was collected and washed with water. The solid was dissolved in dichloromethane and dried over magnesium sulfate. The mixture was filtered and concentrated to give tert-butyl 2-chloro-6-[3-[2-[1-(trifluoromethyl)cyclopropyl]ethoxy]pyrazol-1-yl]pyridine-3-carboxylate (1.01 g, 84%). ESI-MS m/z calc. 431.12, found 432.1 (M+1)+; Retention time: 0.88 minutes.

Step 4: 2-Chloro-6-[3-[2-[1-(trifluoromethyl)cyclopropyl]ethoxy]pyrazol-1-yl]pyridine-3-carboxylic acid

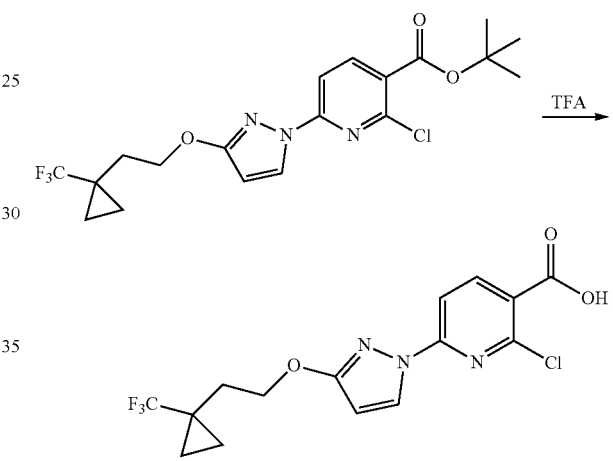

tert-Butyl 2-chloro-6-[3-[2-[1-(trifluoromethyl)cyclopropyl]ethoxy]pyrazol-1-yl]pyridine-3-carboxylate (1.01 g, 2.339 mmol) and trifluoroacetic acid (1.8 mL, 23.39 mmol) were combined in dichloromethane (10 mL) and heated at 40° C. for 3 h. The reaction was concentrated. Hexanes were added, and the mixture was concentrated again to give 2-chloro-6-[3-[2-[1-(trifluoromethyl)cyclopropyl]ethoxy]pyrazol-1-yl]pyridine-3-carboxylic acid (873 mg, 99%) ESI-MS m/z calc. 375.06, found 376.1 (M+1)4; Retention time: 0.69 minutes.

Step 5: 2-Chloro-N-(1,3-dimethylpyrazol-4-yl)sulfonyl-6-[3-[2-[1-(trifluoromethyl)cyclopropyl]ethoxy]pyrazol-1-yl]pyridine-3-carboxamide

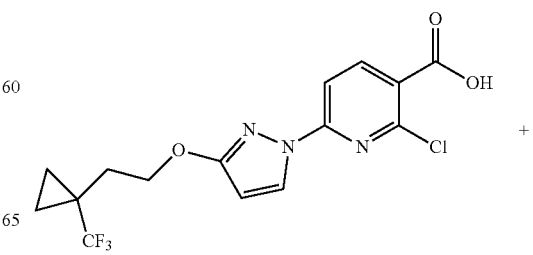

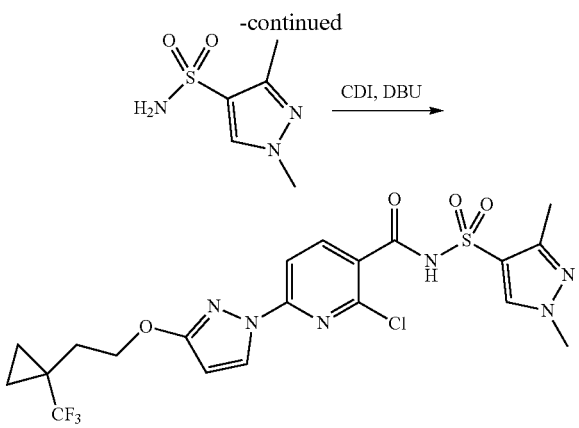

2-Chloro-6-[3-[2-[1-(trifluoromethyl)cyclopropyl]ethoxy]pyrazol-1-yl]pyridine-3-carboxylic acid (6 g, 15.97 mmol) in THF (60.00 mL) was treated with CDI (approximately 3.107 g, 19.16 mmol), and the cloudy solution was stirred at room temperature for 1 h. Then 1,3-dimethylpyrazole-4-sulfonamide (approximately 3.110 g, 17.57 mmol), followed by DBU (approximately 2.917 g, 2.865 mL, 19.16 mmol) was added, and the reaction was stirred at room temperature for 12 hours. The mixture was treated with cold citric acid (approximately 83.84 mL of 1 M, 83.84 mmol) to give an emulsion. Most of the THF was removed under reduced pressure and extracted with ethyl acetate (100 ml), washed with 0.5 M citric acid (80 ml) and brine (80 ml) and the aqueous phases were back extracted once with ethyl acetate (80 ml). The combined organic phases were dried, filtered and evaporated. The crude was purified by chromatography over silica gel with a linear gradient of dichloromethane to 2% methanol. Product fractions were evaporated to give 2-chloro-N-(1,3-dimethylpyrazol-4-yl)sulfonyl-6-[3-[2-[1-(trifluoromethyl)cyclopropyl]ethoxy]pyrazol-1-yl]pyridine-3-carboxamide (4.64 g, 53%). ESI-MS m/z calc. 532.09076, found 533.0 (M+1)+; Retention time: 1.83 minutes.

$^1$H NMR (400 MHz, DMSO-d6) δ 12.73 (s, 1H), 8.41 (d, J=2.5 Hz, 2H), 8.10 (d, J=8.3 Hz, 1H), 7.69 (d, J=8.3 Hz, 1H), 6.19 (d, J=2.9 Hz, 1H), 4.34 (t, J=7.1 Hz, 2H), 3.84 (s, 3H), 2.35 (s, 3H), 2.09 (t, J=7.1 Hz, 2H), 1.01-0.82 (m, 4H).

Step 6: N-(1,3-Dimethylpyrazol-4-yl)sulfonyl-6-[3-[2-[1-(trifluoromethyl)cyclopropyl]ethoxy]pyrazol-1-yl]-2-[(4S)-2,2,4-trimethylpyrrollidin-1-yl]pyridine-3-carboxamide

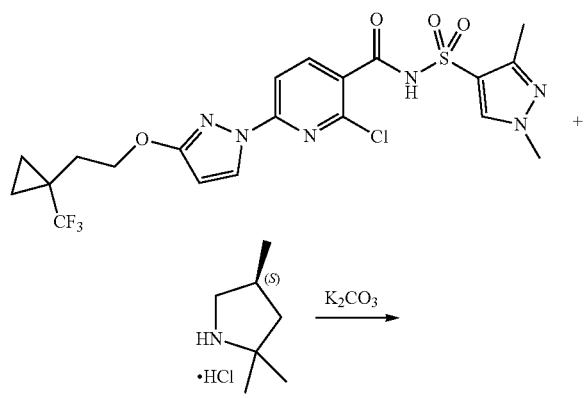

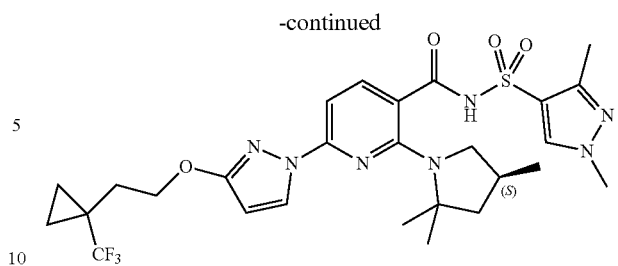

2-Chloro-N-(1,3-dimethylpyrazol-4-yl)sulfonyl-6-[3-[2-[1-(trifluoromethyl)cyclopropyl]ethoxy]pyrazol-1-yl]pyridine-3-carboxamide (5.9 g, 10.74 mmol) was dissolved in NMP (28.62 mL) and 1,2-diethoxyethane (5.723 mL), treated with potassium carbonate (approximately 7.422 g, 53.70 mmol) and (4S)-2,2,4-trimethylpyrrolidine (Hydrochloride salt) (approximately 3.537 g, 23.63 mmol), cycled 3 times with vacuum/nitrogen and heated to 130° C. (oil bath at 135° C.) under stirring and nitrogen for 20 hours. The reaction suspension was cooled, diluted with water (34.34 mL) and carefully added to a strongly stirred solution of acetic acid (approximately 9.674 g, 9.161 mL, 161.1 mmol) in water (137.4 mL). The suspension was stirred at room temperature for one hour, filtered and washed with plenty of water. The still water wet crude was dissolved in warm ethanol (~100 ml, brown cloudy solution), cleared with charcoal over Celite (only slightly lighter) and the hot clear solution was treated with water (~25 ml) till cloudy. The hot cloudy solution was left to cool to room temperature under stirring for 2 hours to give a thick suspension. The solid was collected by filtration, washed with cold ethanol/water 1:1 and plenty of water. The solid was dried under vacuum in a drying cabinet at 45° C. with a nitrogen bleed over the weekend to give N-(1,3-dimethylpyrazol-4-yl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (4.27 g, 65%). ESI-MS m/z calc. 609.2345, found 610.0 (M+1)+; Retention time: 3.07 minutes.

$^1$H NMR (400 MHz, DMSO-d6) δ 12.35 (s, 1H), 8.38 (s, 1H), 8.20 (d, J=2.8 Hz, 1H), 7.74 (d, J=8.3 Hz, 1H), 6.91 (d, J=8.2 Hz, 1H), 6.11 (d, J=2.7 Hz, 1H), 4.31 (t, J=7.0 Hz, 2H), 3.81 (s, 3H), 2.55 (t, J=10.5 Hz, 1H), 2.41 (dd, J=10.1, 7.1 Hz, 1H), 2.33 (s, 3H), 2.18 (dp, J=17.8, 6.2 Hz, 1H), 2.07 (t, J=7.1 Hz, 2H), 1.87 (dd, J=11.9, 5.6 Hz, 1H), 1.55 (d, J=11.1 Hz, 6H), 1.42 (t, J=12.2 Hz, 1H), 0.99-0.86 (m, 4H), 0.82 (d, J=6.3 Hz, 3H).

Synthesis of N-(1,5-dimethylpyrazol-4-yl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide Step 1: 1,5-dimethylpyrazole-4-sulfonamide (Compound 14)

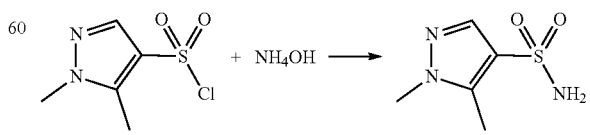

1,5-Dimethylpyrazole-4-sulfonyl chloride (9 g, 46.24 mmol) was suspended in cold ammonium hydroxide (54 mL of 30% w/w), and THF (27.00 mL) was added as a co-solvent, and the cloudy emulsion was stirred at room temperature for 2 hours. The mixture was concentrated under reduced pressure (remove THF and ammonia) to give a nice suspension. The solid was collected by filtration, washed with ice water and dried to give 1,5-dimethylpyrazole-4-sulfonamide (7.35 g, 90%) as an off white solid. ESI-MS m/z calc. 175.04155, found 176.0 (M+1)+; Retention time: 2.8 minutes.

$^1$H NMR (400 MHz, DMSO-d6) δ 7.58 (s, 1H), 7.18 (s, 2H), 3.75 (s, 3H), 2.41 (s, 3H).

Step 2: 2-Chloro-N-(1,5-dimethylpyrazol-4-yl)sulfonyl-6-[3-[2-[1-(trifluoromethyl)cyclopropyl]ethoxy]pyrazol-1-yl]pyridine-3-carboxamide

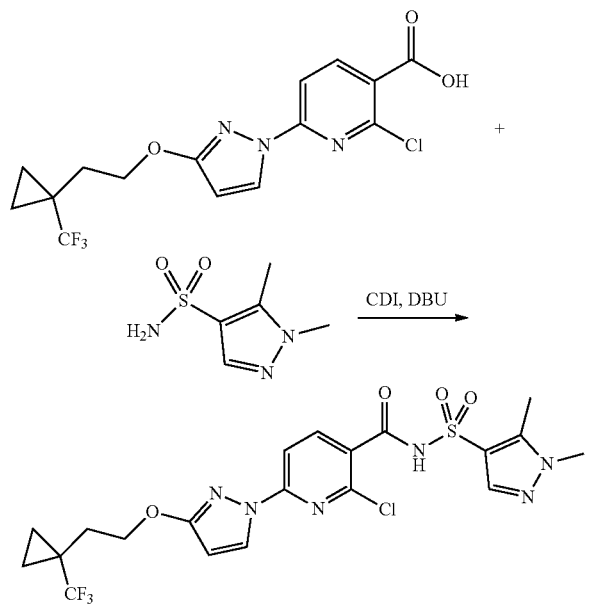

2-Chloro-6-[3-[2-[1-(trifluoromethyl)cyclopropyl]ethoxy]pyrazol-1-yl]pyridine-3-carboxylic acid (6 g, 15.97 mmol) in THF (60.00 mL) was treated with CDI (approximately 3.107 g, 19.16 mmol), and the cloudy solution was stirred at room temperature for 1 hour. Then 1,5-dimethylpyrazole-4-sulfonamide (approximately 3.110 g, 17.57 mmol), followed by DBU (approximately 2.917 g, 2.865 mL, 19.16 mmol) was added, and the formed thick suspension was stirred at room temperature for 4 hours. The suspension was treated with cold citric acid (approximately 83.84 mL of 1 M, 83.84 mmol), and most of the THF was removed under reduced pressure, and the solid collected by filtration, washed with plenty of water and sucked dry. The crude (8 g) was crystallized from ethanol (150 ml for solution at reflux) to give 2-chloro-N-(1,5-dimethylpyrazol-4-yl)sulfonyl-6-[3-[2-[1-(trifluoromethyl)cyclopropyl]ethoxy]pyrazol-1-yl]pyridine-3-carboxamide (6.9 g, 80%) as an off white solid. ESI-MS m/z calc. 532.09076, found 533.0 (M+1)+; Retention time: 0.53 minutes.

$^1$H NMR (400 MHz, DMSO-d6) δ 12.73 (s, 1H), 8.41 (d, J=2.8 Hz, 1H), 8.09 (d, J=8.3 Hz, 1H), 7.84 (s, 1H), 7.69 (d, J=8.3 Hz, 1H), 6.19 (d, J=2.9 Hz, 1H), 4.34 (t, J=7.1 Hz, 2H), 3.82 (s, 3H), 2.52 (s, 3H), 2.08 (t, J=7.1 Hz, 2H), 1.02-0.84 (m, 4H).

Step 3: N-(1,5-Dimethylpyrazol-4-yl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide

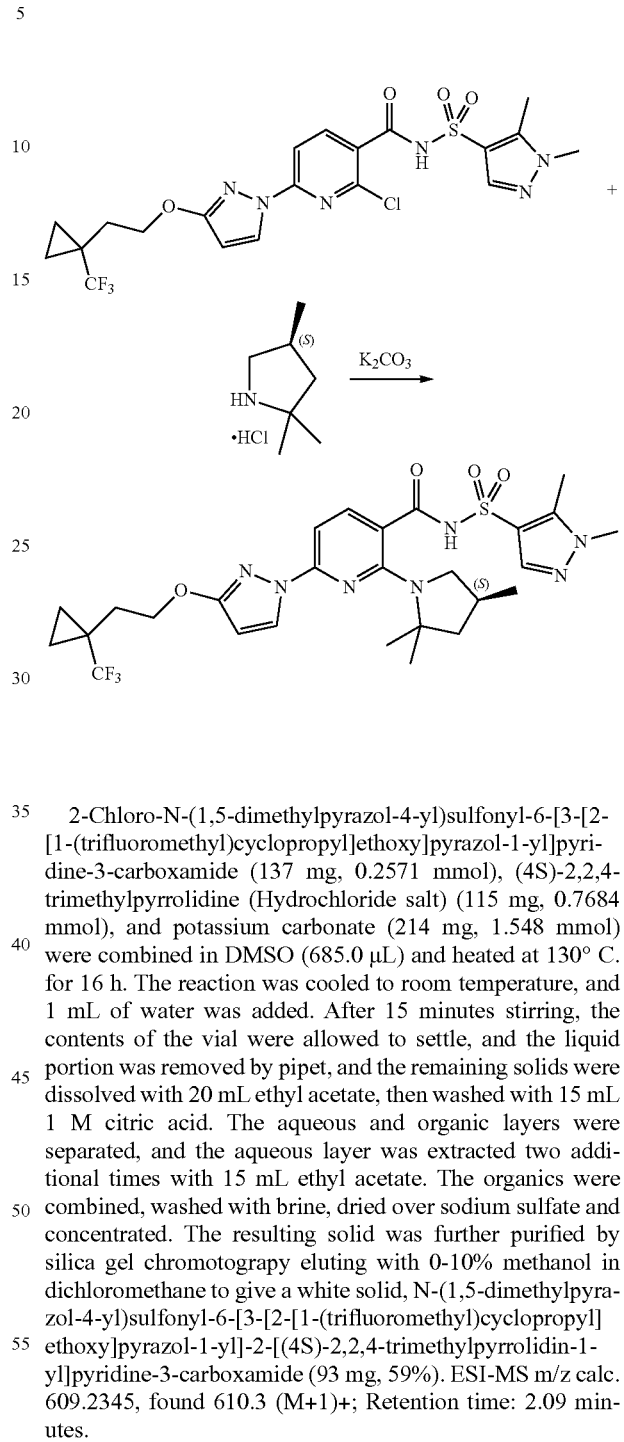

2-Chloro-N-(1,5-dimethylpyrazol-4-yl)sulfonyl-6-[3-[2-[1-(trifluoromethyl)cyclopropyl]ethoxy]pyrazol-1-yl]pyridine-3-carboxamide (137 mg, 0.2571 mmol), (4S)-2,2,4-trimethylpyrrolidine (Hydrochloride salt) (115 mg, 0.7684 mmol), and potassium carbonate (214 mg, 1.548 mmol) were combined in DMSO (685.0 µL) and heated at 130° C. for 16 h. The reaction was cooled to room temperature, and 1 mL of water was added. After 15 minutes stirring, the contents of the vial were allowed to settle, and the liquid portion was removed by pipet, and the remaining solids were dissolved with 20 mL ethyl acetate, then washed with 15 mL 1 M citric acid. The aqueous and organic layers were separated, and the aqueous layer was extracted two additional times with 15 mL ethyl acetate. The organics were combined, washed with brine, dried over sodium sulfate and concentrated. The resulting solid was further purified by silica gel chromotograpy eluting with 0-10% methanol in dichloromethane to give a white solid, N-(1,5-dimethylpyrazol-4-yl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (93 mg, 59%). ESI-MS m/z calc. 609.2345, found 610.3 (M+1)+; Retention time: 2.09 minutes.

$^1$H NMR (400 MHz, DMSO) δ 12.31 (s, 1H), 8.20 (d, J=2.8 Hz, 1H), 7.78 (s, 1H), 7.73 (d, J=8.2 Hz, 1H), 6.90 (d, J=8.2 Hz, 1H), 6.11 (d, J=2.7 Hz, 1H), 4.31 (t, J=7.0 Hz, 2H), 3.78 (s, 3H), 2.58 (d, J=10.4 Hz, 1H), 2.53 (s, 3H), 2.41 (dd, J=10.3, 7.0 Hz, 1H), 2.17 (dq, J=11.9, 6.0 Hz, 1H), 2.07 (t, J=7.1 Hz, 2H), 1.91-1.82 (m, 1H), 1.57 (s, 3H), 1.53 (s, 3H), 1.43 (t, J=12.1 Hz, 1H), 0.96 (td, J=5.0, 4.5, 3.2 Hz, 2H), 0.93-0.85 (m, 2H), 0.80 (d, J=6.2 Hz, 3H).

Synthesis of 6-[3-[2-[1-(trifluoromethyl)cyclopropyl]ethoxy]pyrazol-1-yl]-N-(1,3,5-trimethylpyrazol-4-yl)sulfonyl-2-[(4S)-2,2,4-trimethylpyrrolidin-1-yl]pyridine-3-carboxamide (Compound 18)

Step 1: 2-Chloro-6-[3-[2-[1-(trifluoromethyl)cyclopropyl]ethoxy]pyrazol-1-yl]-N-(1,3,5-trimethylpyrazol-4-yl)sulfonyl-pyridine-3-carboxamide

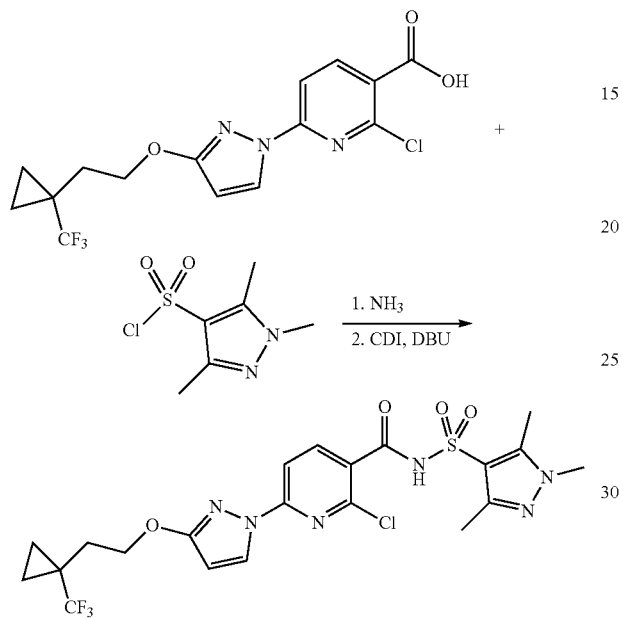

2-Chloro-6-[3-[2-[1-(trifluoromethyl)cyclopropyl]ethoxy]pyrazol-1-yl]pyridine-3-carboxylic acid (100 mg, 0.2661 mmol) and CDI (approximately 51.38 mg, 0.3169 mmol) were combined in THF (600.0 µL) and stirred at room temperature for 2 hours. Meanwhile, 1,3,5-trimethylpyrazole-4-sulfonyl chloride (approximately 55.53 mg, 0.2661 mmol) was combined with ammonia (approximately 250.0 µL of 7 M, 1.750 mmol) (in methanol) in a seperate vial, instantly forming a white solid. After stirring for an additional 20 min, the volatiles were removed by evaporation, and 1 mL of dichloromethane was added to the solid residue, and also evaporated. DBU (approximately 54.41 mg, 53.45 µL, 0.3574 mmol) was added and stirred at 60° C. for 5 minutes, (to facilitate the removal of ammonia from any residual ammonium chloride) followed by 1 mL THF, which was subsequently evaporated. The contents of the vial containing the CDI activated carboxylic acid in THF were then added to the vial containing the newly formed sulfonamide and DBU, and the reaction mixture was stirred for 4 h at room temperature. The reaction mixture was diluted with 10 mL ethyl acetate, and washed with 10 mL 1 M citric acid. The aqueous layer was extracted with ethyl acetate (2×10 mL), and the combined organics were washed with brine, dried over sodium sulfate, and concentrated to give a white solid. This material was used in the next step without further purification. 2-Chloro-6-[3-[2-[1-(trifluoromethyl)cyclopropyl]ethoxy]pyrazol-1-yl]-N-(1,3,5-trimethylpyrazol-4-yl)sulfonyl-pyridine-3-carboxamide (139 mg, 96%). ESI-MS m/z calc. 546.1064, found 547.1 (M+1)+; Retention time: 0.7 minutes.

Step 2: 6-[3-[2-[1-(Trifluoromethyl)cyclopropyl]ethoxy]pyrazol-1-yl]-N-(1,3,5-trimethylpyrazol-4-yl)sulfonyl-2-[(4S)-2,2,4-trimethylpyrrolidin-1-yl]pyridine-3-carboxamide

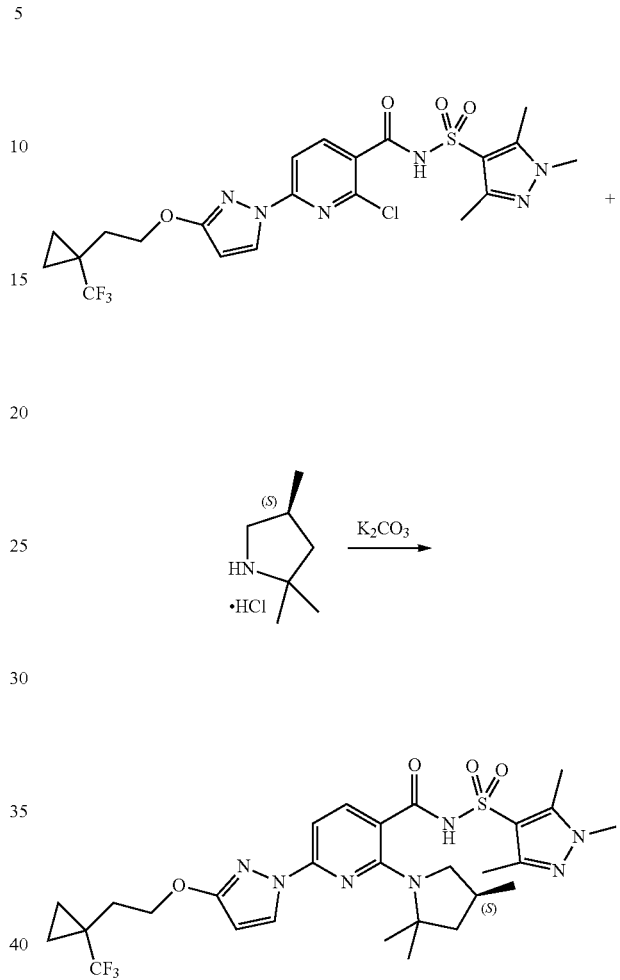

2-Chloro-6-[3-[2-[1-(trifluoromethyl)cyclopropyl]ethoxy]pyrazol-1-yl]-N-(1,3,5-trimethylpyrazol-4-yl)sulfonyl-pyridine-3-carboxamide (139 mg, 0.2541 mmol), (4S)-2,2,4-trimethylpyrrolidine (Hydrochloride salt) (114 mg, 0.7617 mmol), and potassium carbonate (211 mg, 1.527 mmol) were combined in DMSO (508.2 µL) and heated at 130° C. for 16 h. The reaction was cooled to room temperature, and 1 mL of water was added. After 15 minutes stirring, the contents of the vial were allowed to settle, the liquid portion was removed by pipet, and the remaining solids were dissolved with 20 mL ethyl acetate, then washed with 15 mL 1 M citric acid. The aqueous and organic layers were separated, and the aqueous layer was extracted two additional times with 15 mL ethyl acetate. The organics were combined, washed with brine, dried over sodium sulfate and concentrated. The resulting solid was further purified by silica gel chromotograpy eluting with 0-10% methanol in dichloromethane to give a white solid, 6-[3-[2-[1-(trifluoromethyl)cyclopropyl]ethoxy]pyrazol-1-yl]-N-(1,3,5-trimethylpyrazol-4-yl)sulfonyl-2-[(4S)-2,2,4-trimethylpyrrolidin-1-yl]pyridine-3-carboxamide (80 mg, 50%) ESI-MS m/z calc. 623.2502, found 624.3 (M+1)+; Retention time: 2.16 minutes.

131

Synthesis of N-[1-methyl-3-(trifluoromethyl)pyrazol-4-yl]sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (Compound 55)

Step 1:
1-Methyl-3-(trifluoromethyl)pyrazole-4-sulfonamide

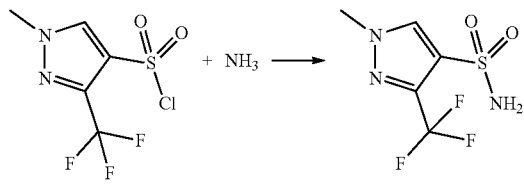

1-Methyl-3-(trifluoromethyl)pyrazole-4-sulfonyl chloride (250 mg, 1.006 mmol) was dissolved in THF (2 mL), and ammonia in methanol (750 µL of 7 M, 5.2 mmol) was added. The reaction was stirred at room temperature for 3 h. The reaction mixture was evaporated to dryness, and the residue was suspended in ethyl acetate and heated for 20 min at 65° C. The mixture was filtered hot (to remove ammonium chloride formed in the reaction), and the solids were discarded. The mother liquor was evaporated to give 1-methyl-3-(trifluoromethyl)pyrazole-4-sulfonamide (186 mg, 81%) ESI-MS m/z calc. 229.01328, found 230.0 (M+1)+; Retention time: 0.28 minutes.

Step 2: 2-Chloro-N-[1-methyl-3-(trifluoromethyl)pyrazol-4-yl]sulfonyl-6-[3-[2-[1-(trifluoromethyl)cyclopropyl]ethoxy]pyrazol-1-yl]pyridine-3-carboxamide

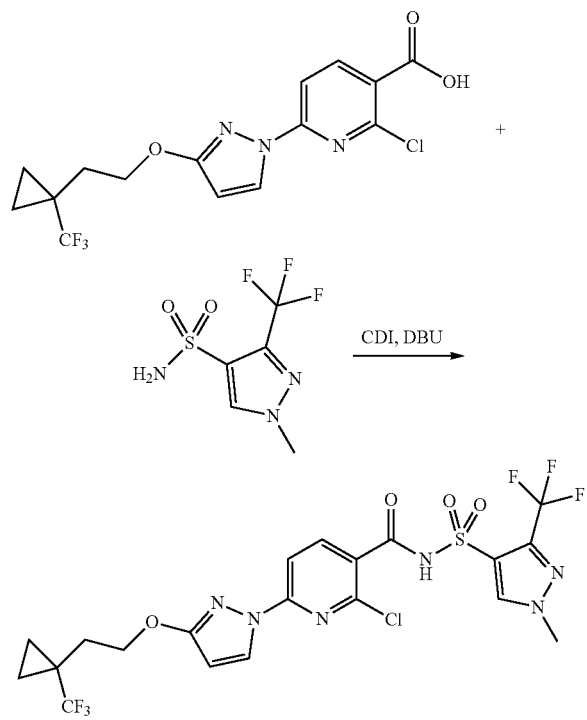

2-Chloro-6-[3-[2-[1-(trifluoromethyl)cyclopropyl]ethoxy]pyrazol-1-yl]pyridine-3-carboxylic acid (51 mg, 0.14 mmol) and CDI (37 mg, 0.23 mmol) were combined in THF (1 mL) and stirred for 1 h at room temperature. 1-Methyl-3-(trifluoromethyl)pyrazole-4-sulfonamide (34 mg, 0.15 mmol) and DBU (64 µL, 0.4280 mmol) were added, and the reaction was stirred for an additional 16 h. The reaction mixture was partitioned between ethyl acetate and a 1 M citric acid solution. The organics were separated, washed with brine, dried over sodium sulfate, and evaporated. The crude material was used directly in the next step. 2-Chloro-N-[1-methyl-3-(trifluoromethyl)pyrazol-4-yl]sulfonyl-6-[3-[2-[1-(trifluoromethyl)cyclopropyl]ethoxy]pyrazol-1-yl]pyridine-3-carboxamide (82 mg, 100%) ESI-MS m/z calc. 586.0625, found 587.2 (M+1)+; Retention time: 0.73 minutes.

Step 3: N-[1-Methyl-3-(trifluoromethyl)pyrazol-4-yl]sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide

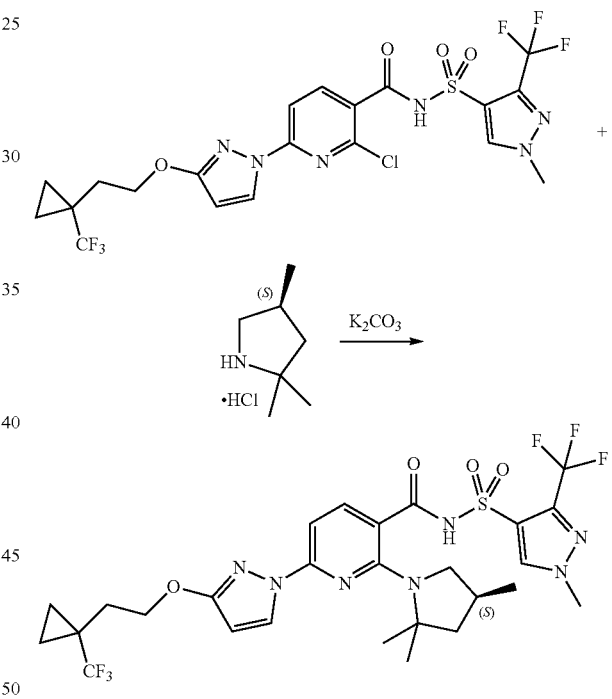

2-Chloro-N-[1-methyl-3-(trifluoromethyl)pyrazol-4-yl]sulfonyl-6-[3-[2-[1-(trifluoromethyl)cyclopropyl]ethoxy]pyrazol-1-yl]pyridine-3-carboxamide (82 mg, 0.14 mmol), (4S)-2,2,4-trimethylpyrrolidine (Hydrochloride salt) (64 mg, 0.43 mmol), and potassium carbonate (100 mg, 0.724 mmol) were combined in DMSO (1 mL) and heated at 130° C. for 16 h. The reaction mixture was diluted with water (3 mL) resulting in a gum. The water was decanted and discarded. The residue was partitioned between ethyl acetate and a 1 M citric acid solution. The organics were separated, washed with brine, dried over sodium sulfate, and evaporated. The crude material was purified by silica gel chromatography eluting with 0-10% methanol in dichloromethane to give N-[1-methyl-3-(trifluoromethyl)pyrazol-4-yl]sulfonyl-6-[3-[2-[1-(trifluoromethyl)cyclopropyl]-ethoxy]pyrazol-1-yl]-2-[(4S)-2,2,4-trimethylpyrrolidin-1-yl]pyridine-3- carboxamide (29.6 mg, 32%). ESI-MS m/z calc. 663.20624, found 664.4 (M+1)+; Retention time: 2.16 minutes.

¹H NMR (400 MHz, DMSO-d6) δ 12.87 (s, 1H), 8.79 (s, 1H), 8.20 (d, J=2.8 Hz, 1H), 7.74 (d, J=8.2 Hz, 1H), 6.91 (d, J=8.3 Hz, 1H), 6.11 (d, J=2.8 Hz, 1H), 4.31 (t, J=7.1 Hz, 2H), 3.99 (s, 3H), 2.56 (d, J=10.5 Hz, 1H), 2.45 (dd, J=3.9, 2.0 Hz, 1H), 2.29-2.12 (m, 1H), 2.07 (t, J=7.1 Hz, 2H), 1.88 (dd, J=12.0, 5.7 Hz, 1H), 1.56 (s, 3H), 1.54 (s, 3H), 1.42 (t, J=12.1 Hz, 1H), 0.99-0.92 (m, 2H), 0.90 (d, J=10.7 Hz, 2H), 0.80 (d, J=6.2 Hz, 3H).

Synthesis of N-(1,3-dimethylpyrazol-4-yl)sulfonyl-6-[3-[[1-(trifluoromethyl)cyclobutyl]methoxy]pyrazol-1-yl]-2-[(4S)-2,2,4-trimethylpyrrolidin-1-yl]pyridine-3-carboxamide (Compound 19)

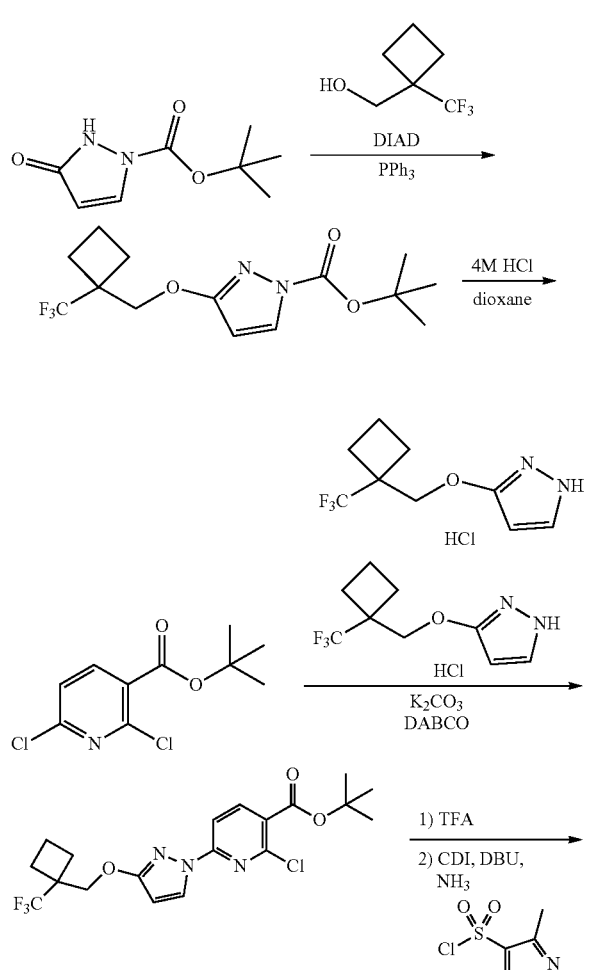

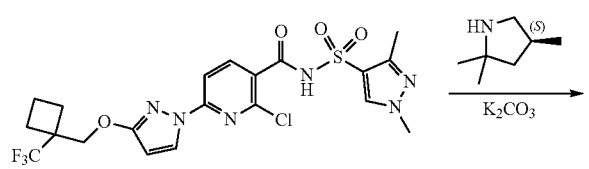

Synthesis of (1-trifluoromethyl-cyclobutyl)-methanol

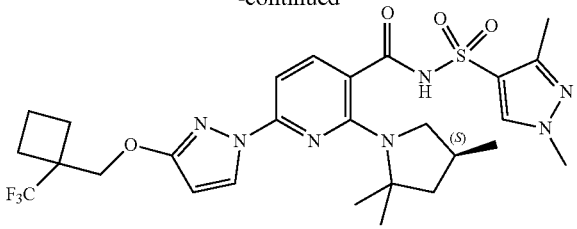

1-Trifluoromethyl-cyclobutanecarboxylic acid (5.0 g, 30. mmol) was dissolved in diethyl ether (60 mL) and cooled to 0° C. Lithium aluminum hydride (38.66 mL, 1 M in diethyl ether) was added dropwise, and the solution was allowed to warm to room temperature overnight. The reaction solution was cooled to 0° C. with stirring, and sodium sulfate decahydrate was added, which resulted in gradual evolution of gas. Portionwise addition was continued until no more bubbling was observed at room temperature. The reaction solution was then filtered over a bed of Celite, washing with diethyl ether. The filtrate was concentrated under reduced pressure to give 5.44 g of a mixture containing the desired product and some diethyl ether residue (36% by NMR integration). This afforded 1-trifluoromethyl-cyclobutyl-methanol (3.46 g, 78%) as a colorless oil. ¹H NMR (250 MHz, CDCl3) δ (ppm): 3.82 (s, 2H), 2.39-2.14 (m, 2H), 2.10-1.85 (m, 4H).

Step 1: 3-(1-Trifluoromethyl-cyclobutylmethoxy)-pyrazole-1-carboxylic acid tert-butyl ester

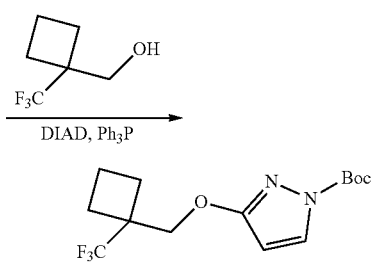

1-Trifluoromethyl-cyclobutyl-methanol (1.50 g, 9.73 mmol) and 3-oxo-2,3-dihydro-pyrazole-1-carboxylic acid tert-butyl ester (1.63 g, 8.85 mmol) were dissolved in anhydrous tetrahydrofuran (32 mL). The solution was degassed by sonication and flushed with nitrogen gas. Triphenylphosphine (2.55 g, 9.73 mmol) was added, and diisopropyl azodicarboxylate (1.92 mL, 9.73 mmol) was then added dropwise. Upon completion of addition, the reaction was heated to 50° C. for 16 hours. After cooling to room temperature, the reaction was diluted with ethyl acetate (100 mL) and washed with 1 M sodium hydroxide solution (2×100 mL), then brine (125 mL). The organics were dried over sodium sulfate, filtered, and concentrated under reduced pressure. The crude yellow oil was purified by flash chromatography using a 0-10% ethyl acetate in hexanes gradient method to afford 3-(1-trifluoromethyl-cyclobutyl-methoxy)-pyrazole-1-carboxylic acid tert-butyl ester (2.48 g, 87%) as an off-white solid. ESI-MS m/z calc. 320.31, found 321.1 (M+1)$^+$. Retention time: 3.74 minutes.

Step 2: 3-(1-Trifluoromethyl-cyclobutylmethoxy)-1H-pyrazole hydrochloride salt

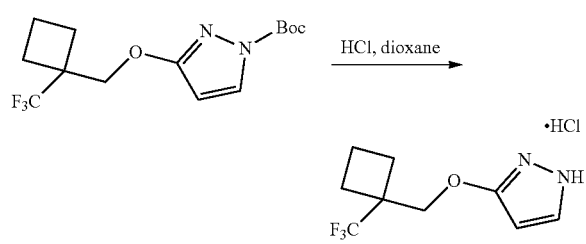

3-(1-Trifluoromethyl-cyclobutylmethoxy)-pyrazole-1-carboxylic acid tert-butyl ester (2.48 g, 7.74 mmol) was dissolved in 4 M hydrogen chloride in dioxane (77 mL). The solution was stirred overnight at room temperature, followed by removal of the volatiles under reduced pressure to afford the hydrochloride salt of 3-(1-trifluoromethyl-cyclobutyl-methoxy)-1H-pyrazole (1.95 g, 98%) as a white powder. ESI-MS m/z calc. 220.20, found 221.2 (M+1)$^+$. Retention time: 2.67 minutes.

Step 3: 2-Chloro-6-[3-(1-trifluoromethyl-cyclobutyl-methoxy)-pyrazole-1-yl]-nicotinic acid tert-butyl ester

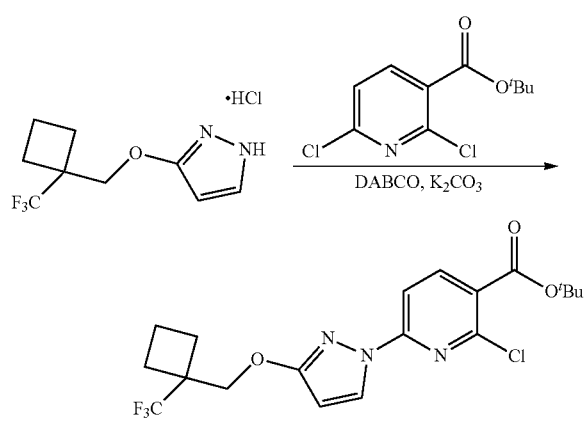

3-(1-Trifluoromethyl-cyclobutylmethoxy)-1H-pyrazole hydrochloride salt (1.95 g, 7.61 mmol) and 2,6-dichloro-nicotinic acid tert-butyl ester (1.89 g, 7.62 mmol) were dissolved in dimethylformamide (15 mL), and potassium carbonate (4.21 g, 30.5 mmol) was added followed by 1,4-diazabicyclo[2.2.2]octane (0.43 g, 3.8 mmol). The reaction was stirred at room temperature overnight, then water (150 mL) was added and the aqueous layer was extracted with 4:1 ethyl acetate:hexanes (100 mL). The organic phase was washed with brine (70 mL), dried over sodium sulfate, and concentrated under reduced pressure. The crude oil was purified by silica gel chromatography using a 0-10% ethyl acetate in hexanes gradient method to afford 2-chloro-6-[3-(1-trifluoromethyl-cyclobutylmethoxy)-pyrazole-1-yl]-nicotinic acid tert-butyl ester (1.94 g, 66%) as a white solid. ESI-MS m/z calc. 431.85, found 432.2 (M+1)$^+$. Retention time: 4.61 minutes.

Step 4: 2-Chloro-6-[3-(1-trifluoromethyl-cyclobutyl-methoxy)-pyrazole-1-yl]-nicotinic acid

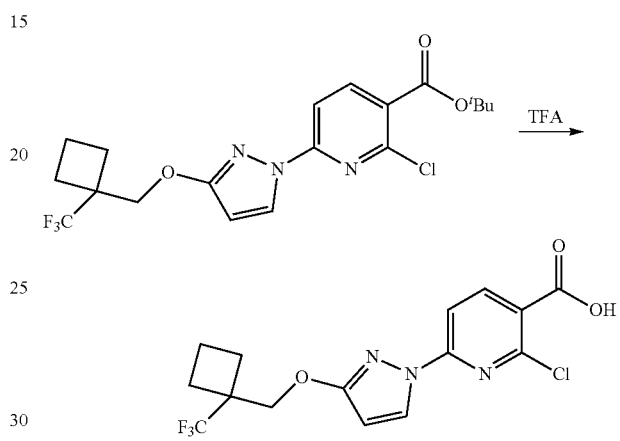

2-Chloro-6-[3-(1-trifluoromethyl-cyclobutylmethoxy)-pyrazole-1-yl]-nicotinic acid tert-butyl ester (1.9 g, 4.40 mmol) was dissolved in dichloromethane (20 mL), and trifluoroacetic acid (5.0 mL) was added. The reaction solution was stirred at room temperature overnight, after which the volatiles were removed under reduced pressure to afford 2-chloro-6-[3-(1-trifluoromethyl-cyclobutylmethoxy)-pyrazole-1-yl]-nicotinic acid (1.61 g, 97%) as a white solid. ESI-MS m/z calc. 375.74, found 376.2 (M+1)$^+$. Retention time: 3.57 minutes.

Step 5: 2-Chloro-N-(1,3-dimethylpyrazol-4-yl)sulfonyl-6-[3-[[1-(trifluoromethyl)cyclobutyl]methoxy]pyrazol-1-yl]pyridine-3-carboxamide

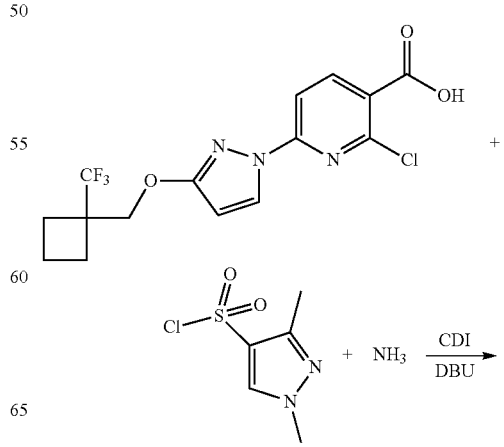

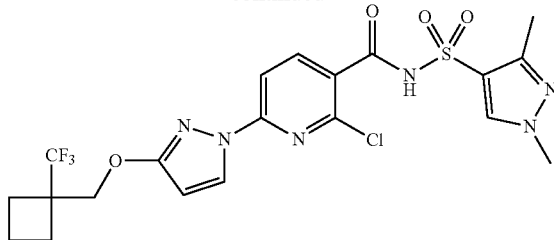

2-Chloro-6-[3-[[1-(trifluoromethyl)cyclobutyl]methoxy]pyrazol-1-yl]pyridine-3-carboxylic acid (100 mg, 0.2661 mmol) and CDI (51 mg, 0.3145 mmol) were combined in THF (600.0 μL) and stirred at room temperature for 2 hours in a vial (vial 1). Meanwhile, 1,3-dimethylpyrazole-4-sulfonyl chloride (62 mg, 0.3185 mmol) was combined with ammonia (approximately 250.0 μL of 7 M, 1.750 mmol) (in methanol) in a separate vial (vial 2). After stirring for an additional 20 min, the volatiles were removed from vial 2 by evaporation, and 1 mL of dichloromethane was added to the solid residue, and was also evaporated. DBU (60 μL, 0.4012 mmol) was then added to vial 2 and stirred at 60° C. for 5 minutes (to facilitate the removal of ammonia from any residual ammonium chloride). Upon cooling to room temperature, 1 mL THF was added and then evaporated under reduced pressure. The contents of vial 1 were then added to vial 2 by syringe, and the reaction mixture was stirred for 4 h at room temperature. The reaction mixture was diluted with 10 mL ethyl acetate and washed with 10 mL 1 M citric acid. The aqueous layer was extracted 2×10 mL ethyl acetate, and the combined organics were washed with brine, dried over sodium sulfate, and concentrated to give a a white solid. This material was used in the next step without further purification. 2-chloro-N-(1,3-dimethylpyrazol-4-yl)sulfonyl-6-[3-[[1-(trifluoromethyl)cyclobutyl]methoxy]pyrazol-1-yl]pyridine-3-carboxamide (132 mg, 93%) ESI-MS m/z calc. 532.09076, found 533.1 (M+1)+; Retention time: 0.7 minutes.

Step 6: N-(1,3-Dimethylpyrazol-4-yl)sulfonyl-6-[3-[[1-(trifluoromethyl)cyclobutyl]methoxy]pyrazol-1-yl]-2-[(4S)-2,2,4-trimethylpyrrolidin-1-yl]pyridine-3-carboxamide

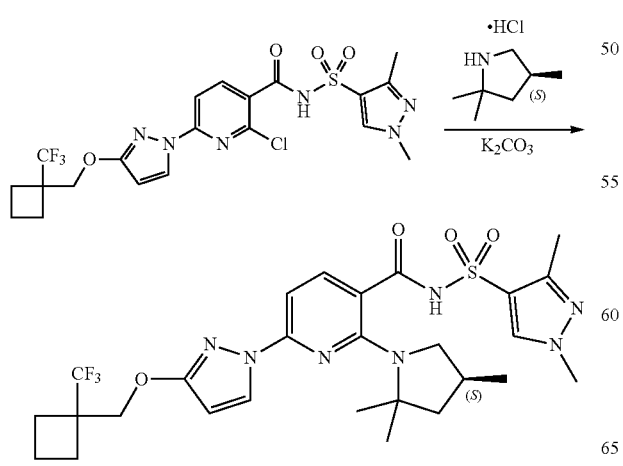

2-Chloro-N-(1,3-dimethylpyrazol-4-yl)sulfonyl-6-[3-[[1-(trifluoromethyl)cyclobutyl]methoxy]pyrazol-1-yl]pyridine-3-carboxamide (132 mg, 0.2477 mmol), (4S)-2,2,4-trimethylpyrrolidine (hydrochloride salt) (111 mg, 0.7417 mmol), and potassium carbonate (206 mg, 1.491 mmol) were combined in DMSO (500 μL) and heated at 130° C. for 16 h. The reaction was cooled to room temperature, and 1 mL of water was added. After 15 minutes stirring the liquid portion was removed by pipet, and the remaining solids were dissolved with 20 mL ethyl acetate then washed with 15 mL 1 M citric acid. The aqueous and organic layers were separated, and the aqueous layer was extracted two additional times with 15 mL ethyl acetate. The organics were combined, washed with brine, dried over sodium sulfate, and concentrated. The resulting solid was further purified by silica gel chromatography eluting with 0-10% methanol in dichloromethane to give a white solid, N-(1,3-dimethylpyrazol-4-yl)sulfonyl-6-[3-[[1-(trifluoromethyl)cyclobutyl]methoxy]pyrazol-1-yl]-2-[(4S)-2,2,4-trimethylpyrrolidin-1-yl]pyridine-3-carboxamide (93 mg, 62%) ESI-MS m/z calc. 609.2345, found 610.3 (M+1)+; Retention time: 2.14 minutes.

$^1$H NMR (400 MHz, DMSO) δ 12.36 (s, 1H), 8.37 (s, 1H), 8.22 (d, J=2.8 Hz, 1H), 7.75 (d, J=8.2 Hz, 1H), 6.95 (d, J=8.2 Hz, 1H), 6.18 (d, J=2.7 Hz, 1H), 4.48 (s, 2H), 3.81 (s, 3H), 2.56 (d, J=10.4 Hz, 1H), 2.41 (dd, J=10.2, 7.0 Hz, 1H), 2.32 (s, 3H), 2.31-2.26 (m, 2H), 2.20-2.07 (m, 4H), 2.01-1.92 (m, 1H), 1.88 (dt, J=11.8, 6.5 Hz, 1H), 1.55 (d, J=11.3 Hz, 6H), 1.42 (t, J=12.2 Hz, 1H), 0.81 (d, J=6.2 Hz, 3H).

Synthesis of N-(1,3-Dimethylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (Compound 10)

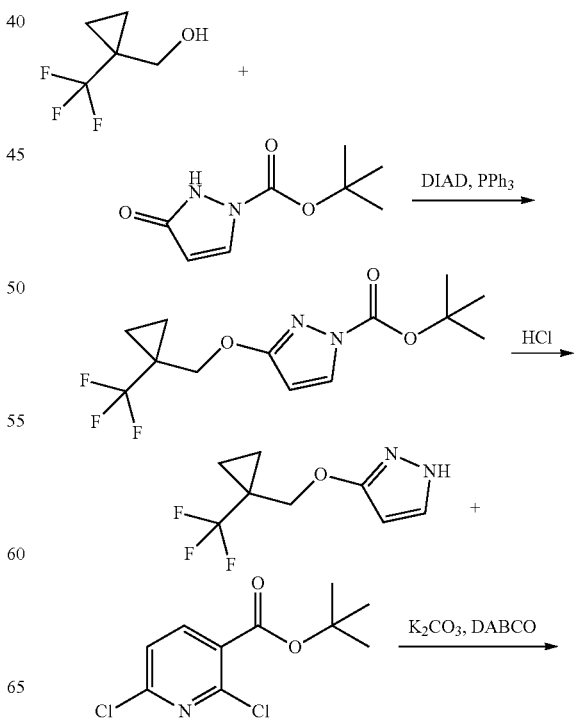

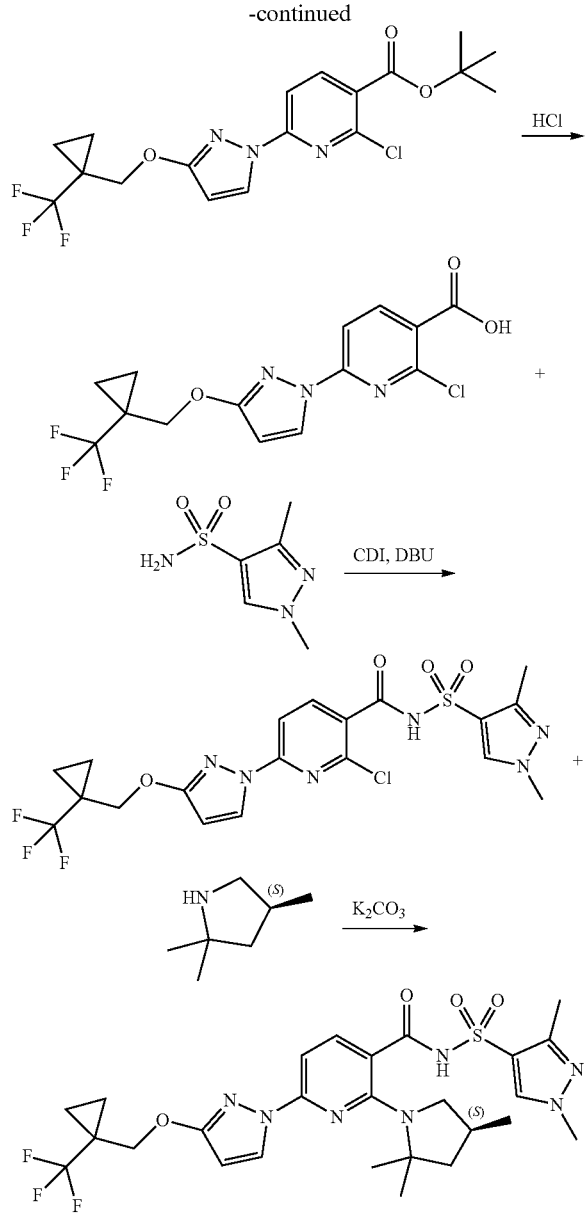

Step A: (1-(Trifluoromethyl)cyclopropyl)methanol

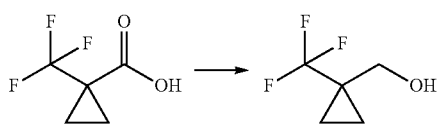 [SMILES: O=C(O)C1(C(F)(F)F)CC1 ; OCC1(C(F)(F)F)CC1]

Lithium aluminum hydride (approximately 78.45 g, 2.067 mol) (pellets) were added to the flask, THF (2.450 L) was added to the addition funnel, and the system was cycled 3 times with vacuum/nitrogen. The solvent was quickly added to the LAH pellets, stirred at room temperature for 0.5 h (pellets start to fall apart to give a grey suspension), and cooled in an ice bath. A solution of 1-(trifluoromethyl) cyclopropanecarboxylic acid (245 g, 1.590 mol) in THF (735.0 mL) was slowly added via an addition funnel over 0.5-1 h, keeping the internal temperature below 30° C. The grey suspension was stirred in the melting ice bath for 14 hours. The grey suspension was quenched under ice cooling by slow addition of water (approximately 75.92 g, 75.92 mL, 4.214 mol), followed by NaOH (approximately 76.32 mL of 6 M, 457.9 mmol) and water (approximately 75.92 g, 75.92 mL, 4.214 mol). The grey suspension was stirred at ~50° C. till the solid became colorless (~0.5 h), treated with magnesium sulfate (20 g), filtered over Celite, and the aluminium salts were washed with three portions of hot THF. The filtrate was dried again over magnesium sulfate, filtered, and concentrated by evaporation at 55° C. and 450 mbar to give [1-(trifluoromethyl)cyclopropyl]methanol as a 62 wt % solution (NMR) in THF (327 g, 91%).

1H NMR (400 MHz, DMSO-d6) δ 4.94 (t, J=6.0 Hz, 1H), 3.56 (d, J=6.0 Hz, 2H), 0.91-0.74 (m, 4H)

Step 1: tert-Butyl 3-[[1-(trifluoromethyl)cyclopropyl]methoxy]pyrazole-1-carboxylate

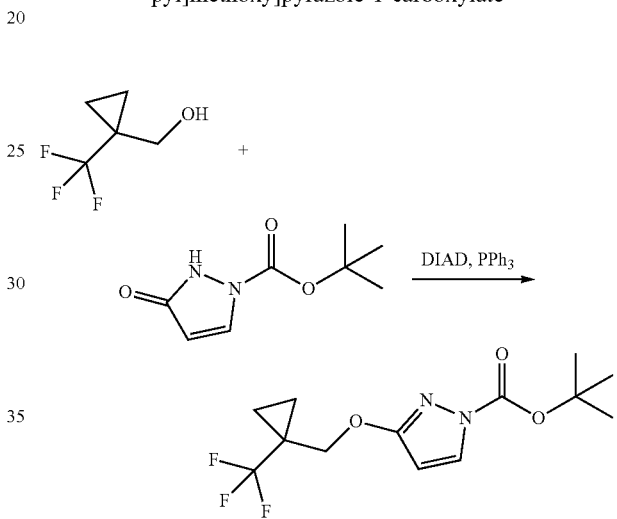

A 5000 mL 3-neck round bottom flask was fitted with a mechanical stirrer, a heating mantle, a J-Kem temperature probe/controller, an addition funnel, a water cooled reflux condenser, and a nitrogen inlet/outlet. The vessel was charged under a nitrogen atmosphere with tert-butyl 5-oxo-1H-pyrazole-2-carboxylate (70 g, 0.3800 mol) and tetrahydrofuran (840 mL, 12 mL/g) which provided a clear pale yellow solution. Stirring was commenced, and the pot temperature was recorded at 19° C. The vessel was then charged with [1-(trifluoromethyl)cyclopropyl]methanol (58.56 g, 0.4180 mol) added neat in one portion followed by triphenylphosphine (109.6 g, 0.4180 mol) added as a solid in one portion. The resulting clear pale yellow solution was then treated with diisopropyl azodicarboxylate (clear reddish-orange liquid) (82.3 mL, 0.4180 mol) added neat dropwise over 1 hour which resulted in a gradual exotherm to 40° C. and a clear light amber solution. The reaction mixture was then heated to a pot temperature of 50° C., and the condition was maintained for 2 hours, when analysis by LC/MS indicated complete consumption of the starting material. The clear amber reaction mixture was concentrated under reduced pressure, and the resulting clear dark amber oil was suspended in toluene (560 mL) and stirred at room temperature for 1 hour, during which time a solid (triphenylphosphine oxide MW=278.28) precipitated. The thick slurry was filtered through a glass frit Buchner funnel, and the filter cake was displacement washed with toluene (150 mL) and then pulled for 30 minutes. The clear amber filtrate was concentrated under reduced pressure to provide a clear amber oil. The material was purified by silica gel column flash chromatography (solid load on Celite 1.5 kg RediSep column) eluting with a gradient of 100% hexane to 20% EtOAc in hexane collecting 450 mL fractions. The product elutes around 5% EtOAc in hexane. The desired fractions were combined and concentrated under reduced pressure to provide a clear pale yellow oil as the desired product tert-butyl 3-[[1-(trifluoromethyl)cyclopropyl]methoxy]pyrazole-1-carboxylate (81 g, 0.264 mol, 70%). ¹H NMR (400 MHz, DMSO-d6) δ 8.10 (d, J=2.9 Hz, 1H), 6.14 (d, J=3.0 Hz, 1H), 4.31 (s, 2H), 1.55 (s, 9H), 1.07 (dp, J=4.9, 1.3 Hz, 4H). ESI-MS m/z calc. 306.11914, found 259.0 (M-48)+; Retention time: 1.76 minutes.

Step 2: 3-[[1-(Trifluoromethyl)cyclopropyl]methoxy]-1H-pyrazole

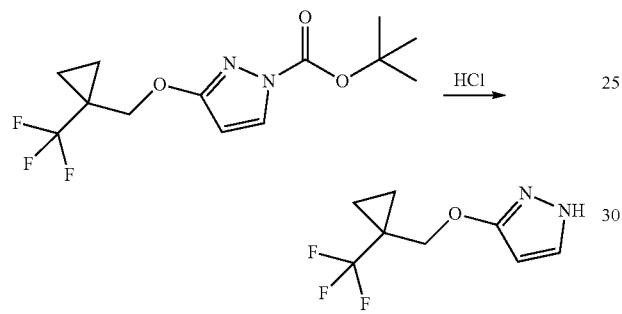

A 5000 mL 3-neck round bottom flask was fitted with a mechanical stirrer, a heating mantle, a J-Kem temperature probe, a water cooled reflux condenser, an addition funnel, and a nitrogen inlet/outlet. The vessel was charged under a nitrogen atmosphere with tert-butyl 3-[[1-(trifluoromethyl)cyclopropyl]methoxy]pyrazole-1-carboxylate (80 g, 0.2612 mol), dichloromethane (320 mL, 4 mL/g) and methyl alcohol (320 mL, 4 mL/g) which provided a clear pale yellow solution. Stirring was commenced, and the pot temperature was recorded at 19° C. The addition funnel was charged with 4 M HCl in 1,4-dioxane (195.9 mL, 0.7836 mol) which was subsequently added dropwise over 1 hour which resulted in a gradual exotherm to 30° C. The resulting clear pale yellow solution was heated to a pot temperature of 45° C., and the condition was maintained for 1 hour, when analysis by LC/MS indicated reaction completion. The reaction mixture was allowed to cool to room temperature and then concentrated under reduced pressure. The remaining residue was dissolved in tert-butyl methyl ether (640 mL) and then transferred to a separatory funnel and partitioned with 2 M sodium hydroxide solution (391.8 mL, 0.7836 mol). The organic layer was removed, and the residual aqueous was extracted with tert-butyl methyl ether (2×200 mL). The combined organic was washed with saturated sodium chloride solution (500 mL), dried over sodium sulfate (300 g), and then filtered through a glass frit Buchner funnel. The clear pale yellow filtrate was concentrated under reduced pressure to provide a clear light yellow oil which solidified upon standing to provide a white solid (49.5 g, 0.240 mol, 92%) as the desired product 3-[[1-(trifluoromethyl)cyclopropyl]methoxy]-1H-pyrazole. NMR (400 MHz, DMSO-d6) δ 11.90 (s, 1H), 7.51 (d, J=2.4 Hz, 1H), 5.67 (d, J=2.4 Hz, 1H), 4.19 (s, 2H), 1.09-0.97 (m, 4H). ESI-MS m/z calc. 206.0667, found 207.0 (M+1)+; Retention time: 1.07 minutes.

Step 3: tert-Butyl 2-chloro-6-[3-[[1-(trifluoromethyl)cyclopropyl]meth-oxy]pyrazol-1-yl]pyridine-3-carboxylate

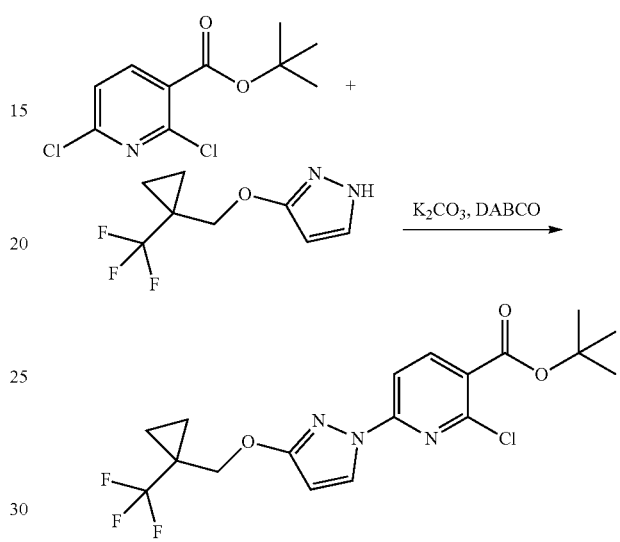

A 5000 mL 3-neck round bottom flask was fitted with a mechanical stirrer, a cooling bath used as secondary containment, a J-Kem temperature probe, a water cooled reflux condenser, an addition funnel, and a nitrogen inlet/outlet. The vessel was charged under a nitrogen atmosphere with 3-[[1-(trifluoromethyl)cyclopropyl]methoxy]-1H-pyrazole (45 g, 0.2183 mol) and N,N-dimethylformamide (540 ml, 12 mL/g) which provided a clear pale yellow solution. Stirring was commenced, and the pot temperature was recorded at 17° C. The vessel was then charged with tert-butyl 2,6-dichloropyridine-3-carboxylate (54.16 g, 0.2183 mol) added as a solid in one portion. The resulting clear pale yellow solution was then treated with potassium carbonate (39.22 g, 0.2838 mol) added as a solid in one portion followed by 1,4-diazabicyclo[2.2.2]octane (3.67 g, 0.03274 mol) added as a solid in one portion. The resulting pale yellow suspension was allowed to stir at room temperature for 24 hours. The reaction mixture was cooled to 10° C. with a crushed ice/water cooling bath. The addition funnel was charged with water (540 mL) added dropwise over 45 minutes which resulted in a thick suspension and an exotherm to 15° C. The resulting suspension was continued to stir at 15° C. for 30 minutes and then filtered through a glass frit Buchner funnel. The filter cake was displacement washed with water (2×500 ml) and then pulled in the Buchner for 2 hours. The material was then allowed to air dry overnight to provide (73 g, 0.175 mol, 80%) of a white granular solid as tert-butyl 2-chloro-6-[3-[[1-(trifluoromethyl)cyclopropyl]methoxy]pyrazol-1-yl]pyridine-3-carboxylate. ESI-MS m/z calc. 361.0441, found 361.9 (M+1)+; Retention time: 2.27 minutes.

Step 4: 2-Chloro-6-[3-[[1-(trifluoromethyl)cyclopropyl]methoxy]pyrazol-1-yl]pyridine-3-carboxylic acid

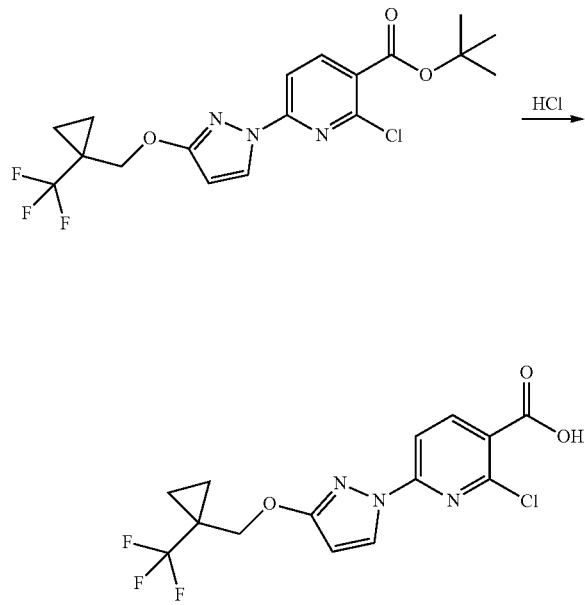

A 1000 mL 3-neck round bottom flask was fitted with a mechanical stirrer, a heating mantle, a J-Kem temperature probe/controller, an addition funnel, a water cooled reflux condenser, and a nitrogen inlet/outlet. The vessel was charged under a nitrogen atmosphere with tert-butyl 2-chloro-6-[3-[[1-(trifluoromethyl)cyclopropyl]methoxy]pyrazol-1-yl]pyridine-3-carboxylate (70 g, 0.1675 mol) and 2-propanol (350 mL) which provided an off-white suspension. Stirring was commenced, and the pot temperature was recorded at 19° C. The addition funnel was charged with aqueous 6 M HCl (139.6 mL, 0.8375 mol) which was added dropwise over 10 minutes which resulted in an exotherm to 30° C. The resulting suspension was then heated to reflux (pot temperature ~82° C.). Upon heating the suspension turns to a clear pale yellow solution (pot temperature ~75° C. at this point). After stirring at reflux for ~30 minutes a solid began to precipitate. The suspension was continued to stir at reflux for an additional 30 minutes at which point water (210 mL) was added dropwise over 15 minutes. The heat was then removed, and the suspension was continued to stir and allowed to slowly cool to room temperature. The material was collected by vacuum filtration in a glass frit Buchner funnel and the filter cake was displacement washed with 1:1 water/2-propanol (100 mL) followed by water (2×100 mL) and then pulled in the Buchner for 30 minutes. The material was further dried in a vacuum oven at 45° C. for 24 hours to provide 2-chloro-6-[3-[[1-(trifluoromethyl)cyclopropyl]methoxy]pyrazol-1-yl]pyridine-3-carboxylic acid (56 g, 0.155 mol, 92%) as a white solid. $^1$H NMR (400 MHz, DMSO-$d_6$) δ 13.64 (s, 1H), 8.44 (d, J=2.9 Hz, 1H), 8.41 (d, J=8.4 Hz, 1H), 7.74 (d, J=8.4 Hz, 1H), 6.24 (d, J=2.9 Hz, 1H), 4.41 (s, 2H), 1.16-1.07 (m, 4H). ESI-MS m/z calc. 361.0441, found 361.9 (M+1)+; Retention time: 3.23 minutes.

Step 5: 2-Chloro-N-(1,3-dimethylpyrazol-4-yl)sulfonyl-6-[3-[[1-(trifluoromethyl)cyclopropyl]methoxy]pyrazol-1-yl]pyridine-3-carboxamide

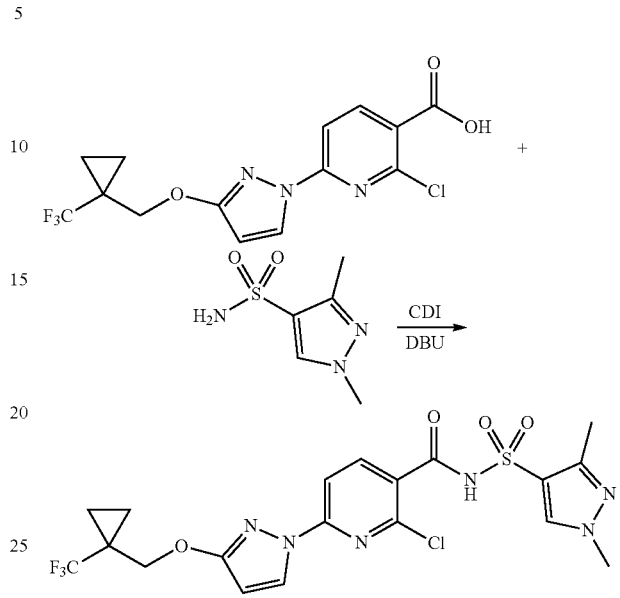

To a solution of 2-chloro-6-[3-[[1-(trifluoromethyl)cyclopropyl]methoxy]pyrazol-1-yl]pyridine-3-carboxylic acid (1.05 g, 2.903 mmol) in THF (20.0 mL) was added carbonyl diimidazole (670.8 mg, 4.137 mmol). The solution was stirred at room temperature for 1 hour. Then, 1,3-dimethylpyrazole-4-sulfonamide (580.5 mg, 3.313 mmol) and DBU (670.0 µL, 4.480 mmol) were added. The mixture was stirred at room temperature for 3 hours. The reaction mixture was quenched with saturated ammonium chloride solution and extracted with ethyl acetate. The combined extracts were washed with brine, dried over sodium sulfate, and evaporated to afford 2-chloro-N-(1,3-dimethylpyrazol-4-yl)sulfonyl-6-[3-[[1-(trifluoromethyl)cyclopropyl]methoxy]pyrazol-1-yl]pyridine-3-carboxamide (1.4 g, 93%) as sticky white solid, which was used as-is in the next reaction. ESI-MS m/z calc. 518.0751, found 519.4 (M+1)+; Retention time: 0.66 minutes.

Step 6: N-(1,3-Dimethylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

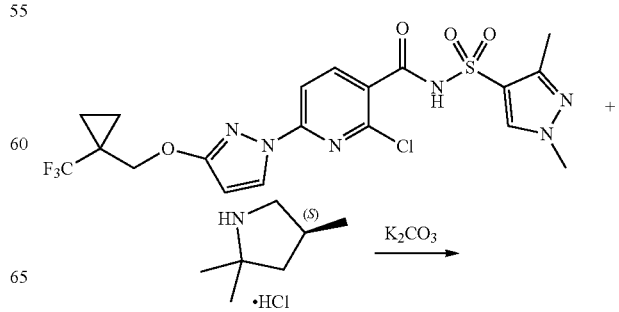

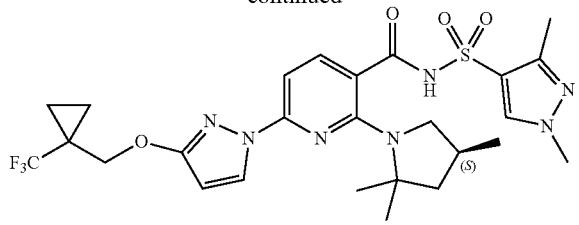

2-Chloro-N-(1,3-dimethylpyrazol-4-yl)sulfonyl-6-[3-[[1-(trifluoromethyl)cyclopropyl]methoxy]pyrazol-1-yl]pyridine-3-carboxamide (190 mg, 0.3662 mmol) was dissolved in DMSO (1 mL), and (4S)-2,2,4-trimethylpyrrolidine (approximately 124.4 mg, 1.099 mmol) was added followed by finely ground potassium carbonate (approximately 303.6 mg, 2.197 mmol). The reaction mixture was allowed to stir at 130° C. overnight. The reaction mixture was diluted with EtOAc (50 mL) and washed with aqueous 1 M citric acid (1×50 mL) and brine (1×50 mL). The organic layer was dried over sodium sulfate, filtered, and concentrated under reduced pressure. The product was isolated by silica gel column chromatography: 12 gram silica gel column, 0-5% MeOH/DCM gradient. N-(1,3-Dimethylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide was obtained (49.5 mg, 0.08310 mmol, 22.70%). ESI-MS m/z calc. 595.2189, found 596.5 (M+1)+; Retention time: 2.06 minutes.

$^1$H NMR (400 MHz, DMSO-$d_6$) δ 12.32 (s, 1H), 8.35 (s, 1H), 8.21 (d, J=2.8 Hz, 1H), 7.73 (d, J=8.2 Hz, 1H), 6.91 (d, J=8.2 Hz, 1H), 6.14 (d, J=2.8 Hz, 1H), 4.42-4.30 (m, 2H), 3.80 (s, 3H), 2.56 (t, J=10.4 Hz, 1H), 2.44 (t, J=8.6 Hz, 1H), 2.32 (s, 3H), 2.18 (dq, J=12.0, 5.9 Hz, 1H), 1.87 (dd, J=11.9, 5.6 Hz, 1H), 1.56 (s, 3H), 1.53 (s, 3H), 1.42 (t, J=12.2 Hz, 1H), 1.12-1.05 (m, 4H), 0.82 (d, J=6.3 Hz, 3H).

Synthesis of two enantiomers of 2-(4-tert-butyl-2,2-dimethyl-pyrrolidin-1-yl)-N-(1,3-dimethylpyrazol-4-yl)sulfonyl-6-[3-[[1-(trifluoromethyl)cyclopropyl]methoxy]pyrazol-1-yl]pyridine-3-carboxamide

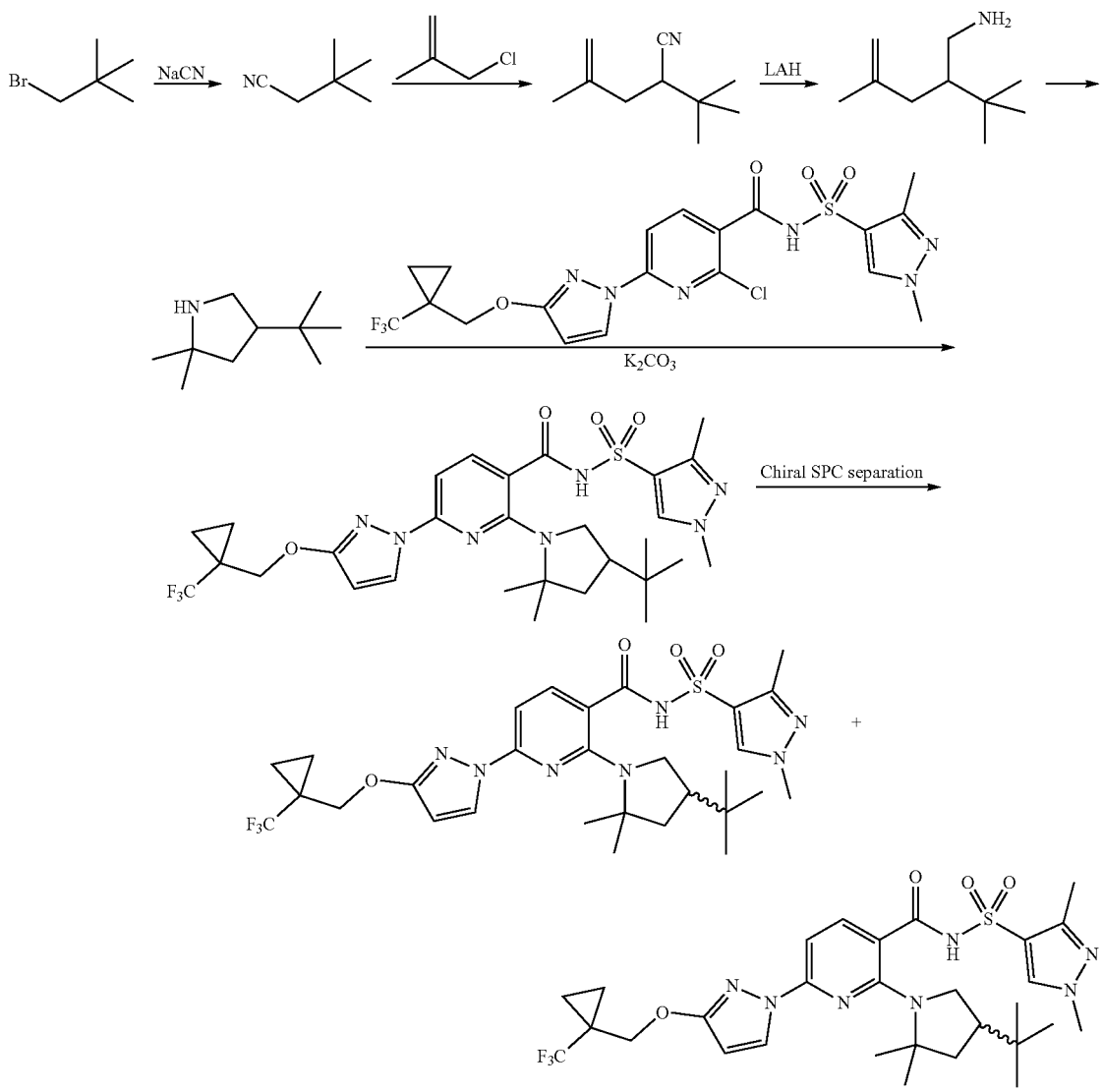

Step 1: 3,3-Dimethylbutanenitrile

Sodium cyanide (9.20 g, 187.7 mmol) was added to a solution of 1-bromo-2,2-dimethylpropane (15.74 g, 104.2 mmol) in DMSO (100 mL), and the reaction mixture was stirred at 90° C. overnight. Once cooled to room temperature the reaction mixture was poured into water (900 mL) and extracted using diethyl ether (3×300 mL). The organic layers were combined, washed with 3 N HCl (300 mL), water (300 mL), and brine (300 mL), dried over magnesium sulfate, filtered, and concentrated under reduced pressure to afford 3,3-dimethylbutanenitrile (11.78 g containing 50% of diethyl ether, 58% yield) as a clear liquid.

$^1$H NMR (300 MHz, CDCl3) ppm 1.09 (s, 9H), 2.22 (s, 2H).

Step 2: 2-tert-Butyl-4-methyl-pent-4-enenitrile

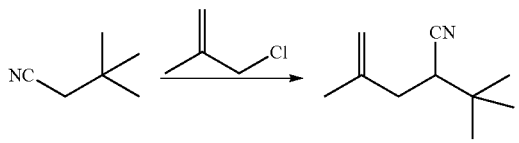

n-Butyllithium (27.2 mL of 2.5 M, 68.00 mmol) was added to a solution of diisopropylamine (8.7 mL, 62.07 mmol) in dry THF (100 mL) at −78° C., and the mixture was stirred at this temperature for 15 minutes, warmed at 0° C. for 15 minutes, then cooled back to −78° C. After that, 3,3-dimethylbutanenitrile (6.0 g, 61.75 mmol) was added, and the reaction mixture was stirred at −78° C. for 1 hour. 3-Chloro-2-methyl-prop-1-ene (12.1 mL, 123.6 mmol) was added, and the reaction mixture was slowly warmed to room temperature and stirred at room temperature overnight. The reaction mixture was diluted with DCM (200 mL) and washed with water (3×100 mL). Organic layer was dried over magnesium sulfate and concentrated under reduced pressure to afford 2-tert-butyl-4-methyl-pent-4-enenitrile (10.69 g, 87% purity (13% of THF), 99% yield) as yellow oil.

$^1$H NMR (300 MHz, CDCl3) ppm 1.08 (s, 9H), 1.78 (s, 3H), 2.17-2.28 (m, 2H), 2.46 (dd, J=11.3, 4.8 Hz, 1H), 4.91 (d, J=9.4 Hz, 2H).

Step 3: 2-tert-Butyl-4-methyl-pent-4-en-1-amine

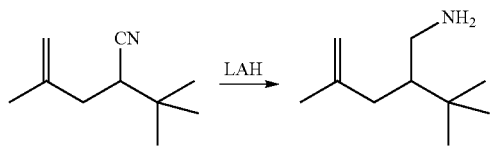

Lithium aluminium hydride (9.33 g, 245.8 mmol) was suspended in dry diethyl ether (250 mL) at 0° C. 2-tert-Butyl-4-methyl-pent-4-enenitrile (9.30 g, 61.49 mmol) was added, and the reaction mixture was stirred at room temperature overnight under nitrogen. The reaction mixture was cooled to 0° C. and quenched with water (10 mL), 2 N NaOH (10 mL), and water (30 mL). The mixture was stirred at room temperature for 30 minutes, then magnesium sulfate was added, and stirring was continued for 30 more minutes. The reaction was filtered over Celite, washed with diethyl ether, and concentrated under reduced pressure to afford 2-tert-butyl-4-methyl-pent-4-en-1-amine (10.70 g, contains 29% mol of solvent, 79% yield) as yellowish liquid.

$^1$H NMR (300 MHz, CDCl3) ppm 0.91 (s, 9H), 1.22-1.45 (m, 3H), 1.76 (s, 3H), 1.87-1.98 (m, 1H), 2.20 (d, J=14.1 Hz, 1H), 2.56 (dd, J=13.1, 6.0 Hz, 1H), 2.83 (dd, J=13.1, 3.7 Hz, 1H), 4.73-4.82 (m, 2H).

Step 4: 4-tert-Butyl-2,2-dimethyl-pyrrolidine

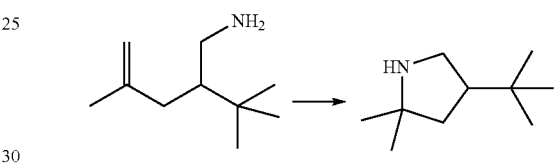

Bis(1,5-cyclooctadiene)rhodium(I) tetrafluoroborate (262 mg, 0.64 mmol) and DavePhos (305 mg, 0.77 mmol) were added to a solution of 2-tert-butyl-4-methyl-pent-4-en-1-amine (2.00 g, 12.88 mmol) in dioxane (12 mL) in a sealed tube, and the reaction mixture was bubbled with nitrogen for 5 minutes. The tube was sealed and heated at 120° C. for 48 hours. Once cooled to room temperature, 4 M HCl in dioxane (6.0 mL) was added, and the reaction mixture was concentrated under reduced pressure. The residue was diluted with 1 N HCl (20 mL) and washed using diethyl ether (3×20 mL). The aqueous layer was basified to pH 8-9 with 2 N NaOH, and the resulting solution was extracted with diethyl ether (3×20 mL). Organic layers were combined, dried over sodium sulfate, and concentrated under reduced pressure to afford 4-tert-butyl-2,2-dimethyl-pyrrolidine (1.18 g, 59% yield) as brown liquid.

$^1$H NMR (300 MHz, CDCl3) ppm 0.85 (s, 9H), 1.14 (s, 3H), 1.19 (s, 3H), 1.24-1.32 (m, 1H), 1.50-1.63 (m, 2H), 2.00-2.12 (m, 1H), 2.73 (dd, J=11.3, 8.7 Hz, 1H), 2.97 (dd, J=11.4, 8.2 Hz, 1H).

Step 5: 2-(4-tert-Butyl-2,2-dimethyl-pyrrodlidin-1-yl)-N-(1,3-dimethylpyrazol-4-yl)sulfonyl-6-[3-[[1-(trifluoromethyl)cyclopropyl]methoxy]pyrazol-1-yl]pyridine-3-carboxamide (Compound 40)

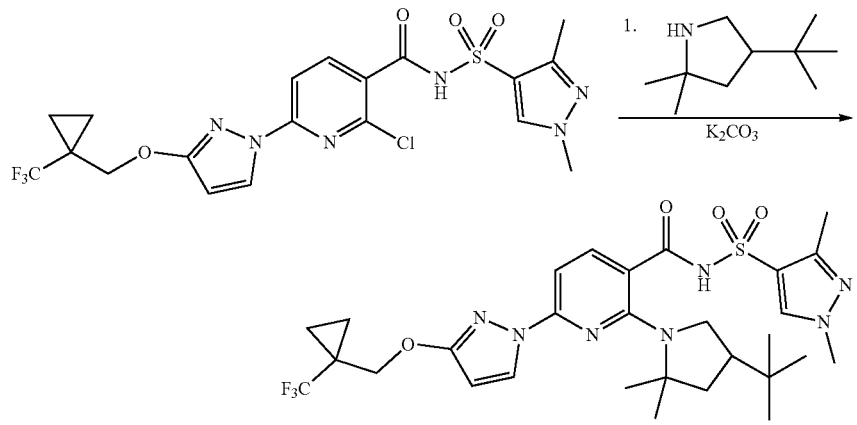

To a solution of 2-chloro-N-(1,3-dimethylpyrazol-4-yl)sulfonyl-6-[3-[[1-(trifluoromethyl)cyclopropyl]methoxy]pyrazol-1-yl]pyridine-3-carboxamide (300.6 mg, 0.5793 mmol) and 4-tert-butyl-2,2-dimethyl-pyrrolidine (272.8 mg, 1.757 mmol) in anhydrous DMSO (6.012 mL) was added cesium fluoride (441.2 mg, 2.904 mmol). The reaction mixture was stirred at 130° C. for 16 h in an oil bath. The reaction mixture was filtered and purified by a reverse phase HPLC-MS utilizing a gradient of 50-99% acetonitrile in 5 mM HCl to afford racemic 2-(4-tert-butyl-2,2-dimethyl-pyrrolidin-1-yl)-N-(1,3-dimethylpyrazol-4-yl)sulfonyl-6-[3-[[1-(trifluoromethyl)cyclopropyl]methoxy]pyrazol-1-yl]pyridine-3-carboxamide (78 mg, 20%) as a white solid. ESI-MS m/z calc. 637.2658, found 638.6 (M+1)+; Retention time: 2.32 minutes.

$^1$H NMR (400 MHz, Chloroform-d) δ 8.37-8.31 (m, 1H), 8.24 (d, J=2.8 Hz, 1H), 8.07 (s, 1H), 7.54 (d, J=8.2 Hz, 1H), 5.99 (d, J=2.8 Hz, 1H), 4.39 (s, 2H), 3.86 (s, 3H), 3.35 (dt, J=19.1, 9.8 Hz, 2H), 2.46 (s, 3H), 2.44-2.37 (m, 1H), 1.94-1.86 (m, 2H), 1.36 (s, 3H), 1.32 (s, 3H), 1.20-1.12 (m, 2H), 0.99-0.94 (m, 2H), 0.97 (s, 9H).

Step 6: Two enantiomers of 2-(4-tert-butyl-2,2-dimethyl-pyrrolidin-1-yl)-N-(1,3-dimethylpyrazol-4-yl)sulfonyl-6-[3-[[1-(trifluoromethyl)cyclopropyl]methoxy]pyrazol-1-yl]pyridine-3-carboxamide

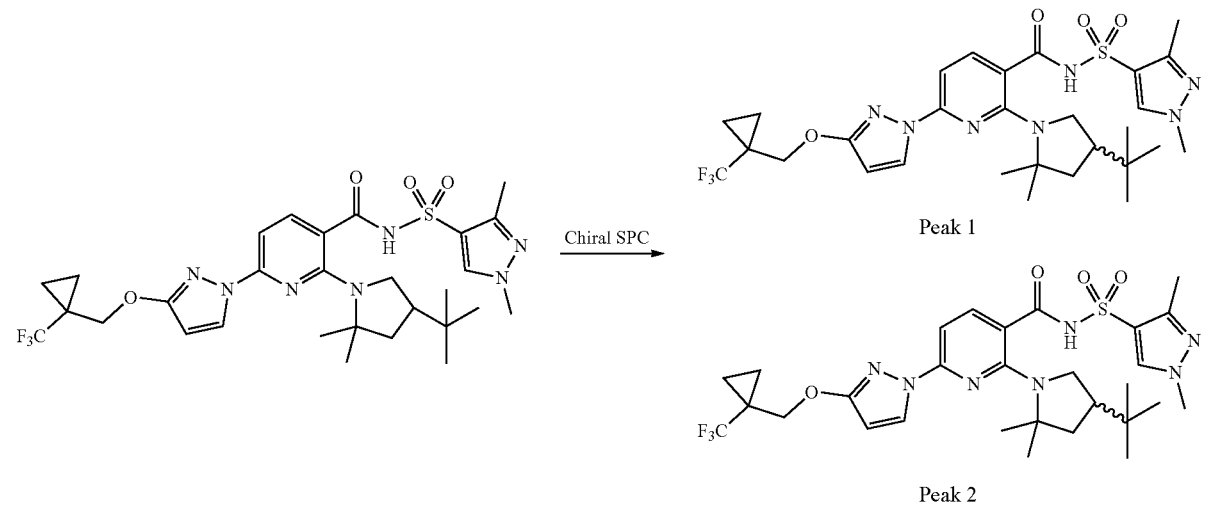 [SMILES: Cc1nn(C)cc1S(=O)(=O)NC(=O)c1ccc(-n2ccc(OCC3(C(F)(F)F)CC3)n2)nc1N1CC(C(C)(C)C)CC1(C)C ; Cc1nn(C)cc1S(=O)(=O)NC(=O)c1ccc(-n2ccc(OCC3(C(F)(F)F)CC3)n2)nc1N1CC(C(C)(C)C)CC1(C)C ; Cc1nn(C)cc1S(=O)(=O)NC(=O)c1ccc(-n2ccc(OCC3(C(F)(F)F)CC3)n2)nc1N1CC(C(C)(C)C)CC1(C)C]

Peak 1

Peak 2

Racemic 2-(4-tert-butyl-2,2-dimethyl-pyrrolidin-1-yl)-N-(1,3-dimethylpyrazol-4-yl)sulfonyl-6-[3-[[1-(trifluoromethyl)cyclopropyl]methoxy]pyrazol-1-yl]pyridine-3-carboxamide (78 mg, 0.122 mmol) was purified by chiral SFC using a ChiralPak AD-3 column (250×10 mm, 5 μm), eluting with 15% methanol, 85% CO$_2$, at a pressure of 100 bar, and flow rate of 10 mL/min.

Peak 1: Pure enantiomer 1 of 2-(4-tert-butyl-2,2-dimethyl-pyrrolidin-1-yl)-N-(1,3-dimethylpyrazol-4-yl)sulfonyl-6-[3-[[1-(trifluoromethyl)cyclopropyl]methoxy]pyrazol-1-yl]pyridine-3-carboxamide (24.9 mg, 7%) with 100% purity and 98% ee (Compound 53). ESI-MS m/z calc. 637.2658, found 638.6 (M+1)+; Retention time: 1.19 minutes.

¹H NMR (400 MHz, Chloroform-d) δ 13.68 (s, 1H), 8.32 (d, J=8.2 Hz, 1H), 8.23 (d, J=2.8 Hz, 1H), 8.06 (s, 1H), 7.53 (d, J=7.9 Hz, 1H), 5.98 (d, J=2.7 Hz, 1H), 4.39 (s, 2H), 3.86 (s, 3H), 3.35 (t, J=11.1 Hz, 2H), 2.46 (s, 3H), 2.39 (t, J=9.1 Hz, 1H), 1.96-1.84 (m, 2H), 1.36 (s, 3H), 1.33 (s, 3H), 1.17-1.12 (m, 2H), 0.98-0.90 (m, 2H), 0.96 (s, 9H).

Peak 2: Pure enantiomer 2 of 2-(4-tert-butyl-2,2-dimethyl-pyrrolidin-1-yl)-N-(1,3-dimethylpyrazol-4-yl)sulfonyl-6-[3-[[1-(trifluoromethyl)cyclopropyl]methoxy]pyrazol-1-yl]pyridine-3-carboxamide (25.0 mg) with 100% purity and 98% ee (Compound 54). ESI-MS m/z calc. 637.2658, found 638.6 (M+1)+; Retention time: 1.18 minutes.

¹H NMR (400 MHz, Chloroform-d) δ 13.69 (s, 1H), 8.32 (d, J=8.6 Hz, 1H), 8.24 (d, J=2.8 Hz, 1H), 8.07 (s, 1H), 7.53 (d, J=8.5 Hz, 1H), 5.99 (d, J=2.8 Hz, 1H), 4.40 (s, 2H), 3.86 (s, 3H), 3.43-3.27 (m, 2H), 2.46 (s, 3H), 2.44-2.32 (m, 1H), 1.94-1.87 (m, 2H), 1.36 (s, 3H), 1.33 (s, 3H), 1.18-1.13 (m, 2H), 0.99-0.94 (m, 2H), 0.97 (s, 9H).

Synthesis of two enantiomers of N-(1,3-dimethylpyrazol-4-yl)sulfonyl-2-(4-isopropyl-2,2-dimethyl-pyrrolidin-1-yl)-6-[3-[[1-(trifluoromethyl)cyclopropyl]methoxy]pyrazol-1-yl]pyridine-3-carboxamide

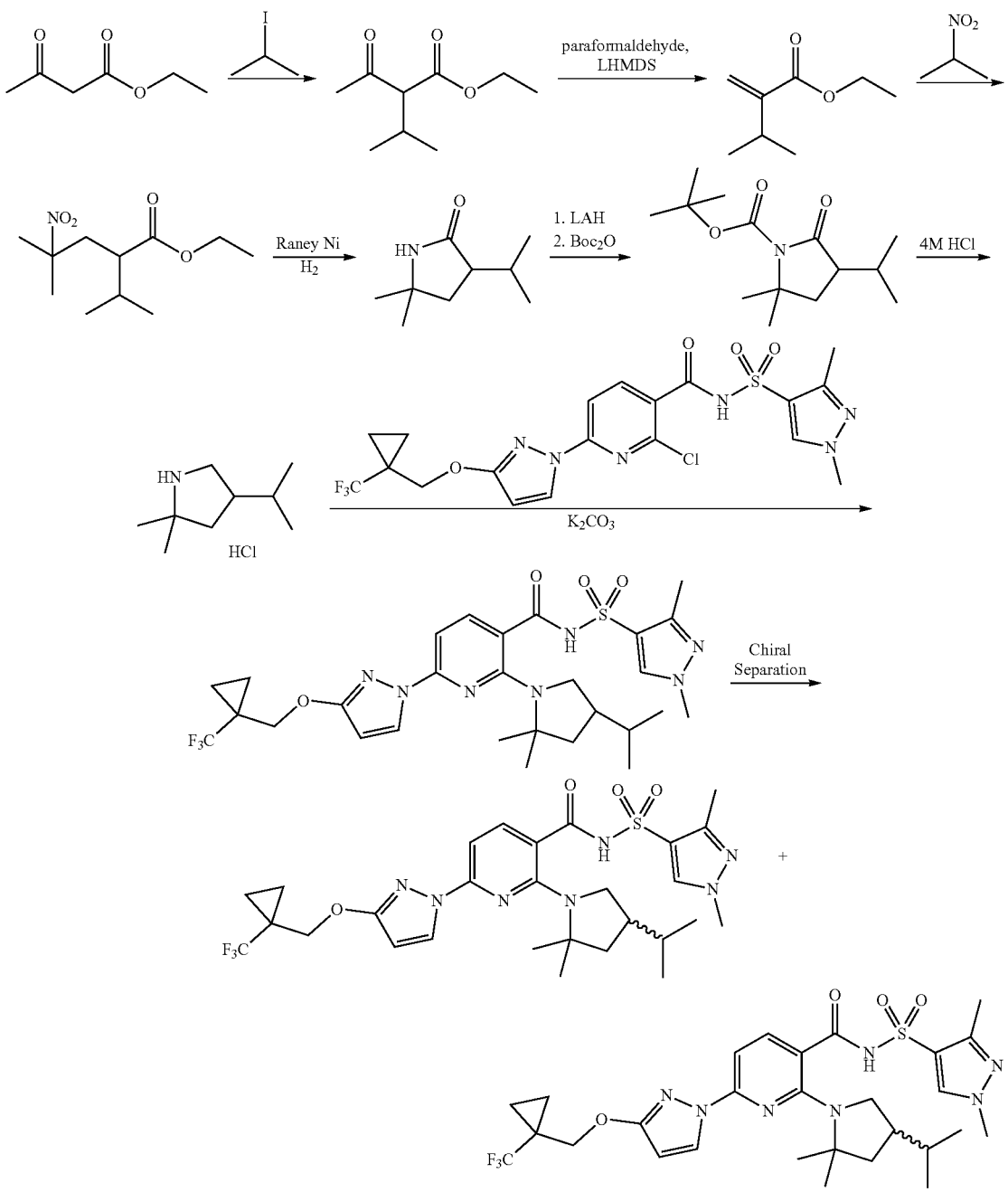

Step 1: 2-Isopropyl-3-oxo-butyric acid ethyl ester

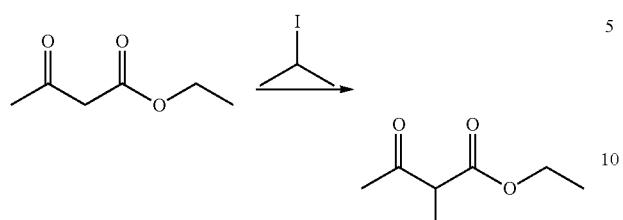

To potassium tert-butoxide (61.7 g, 550 mmol) in tetrahydrofuran (1 L) in an ice bath was added dropwise ethyl acetoacetate (64 mL, 500 mmol). To this solution was added 2-iodopropane (55 mL, 750 mmol). After heating overnight at 70° C., the reaction was cooled, and 2-iodopropane (18 mL, 250 mmol) was added, and the reaction was heated an additional 24 hours at 70° C. Water (250 mL) and saturated aqueous sodium bicarbonate (250 mL) were added to the reaction, and it was extracted with diethyl ether (3×250 mL). The crude was concentrated under vacuum and purified by silica gel column chromatography using 0-7% hexanes-ethyl acetate to give 2-isopropyl-3-oxo-butyric acid ethyl ester (55.11 g, 64%) as a yellow oil. ESI-MS m/z calc. 172.2, found 173.0 (M1). Retention time: 2.99 minutes.

$^1$H NMR (250 MHz, CDCl3) (ppm): 0.87-1.07 (m, 6H) 1.27 (t, J=7.14 Hz, 3H) 2.23 (s, 3H) 2.32-2.52 (m, 1H) 3.18 (d, J=9.45 Hz, 1H) 4.19 (q, J=7.07 Hz, 2H).

Step 2: 3-Methyl-2-methylene-butyric acid ethyl ester

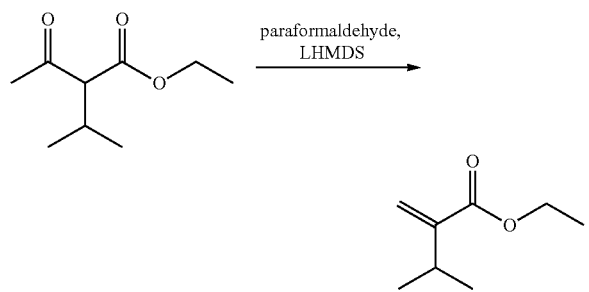

A solution of 2-isopropyl-3-oxo-butyric acid ethyl ester (53.77 g, 312.2 mmol) in tetrahydrofuran (1.07 L) was cooled to −78° C. 1.0 M Lithium bis(trimethylsilyl)amide solution in tetrahydrofuran (343.0 mL, 343.0 mmol) was added dropwise, and the dry ice bath was removed for 30 minutes. The reaction was recooled to −78° C., and paraformaldehyde (43 g, 1.4 mol) was added in one portion. After 30 minutes the dry ice bath was removed and allowed to warm to room temperature overnight. The reaction was then filtered through Celite. The filtrate was concentrated in vacuum, and the crude material was purified by distillation, collecting fraction boils 72-75° C. at 67 torr to give 3-methyl-2-methylene-butyric acid ethyl ester (19.63 g, 40%) as a clear oil.

$^1$H NMR (250 MHz, CDCl3) (ppm): 1.09 (d, J=6.92 Hz, 6H) 1.31 (t, J=7.14 Hz, 3H) 2.75-2.90 (m, 1H) 4.22 (d, J=7.14 Hz, 2H) 5.51 (d, J=1.21 Hz, 1H) 6.12 (s, 1H).

Step 3: 2-Isopropyl-4-methyl-4-nitro-pentanoic acid ethyl ester

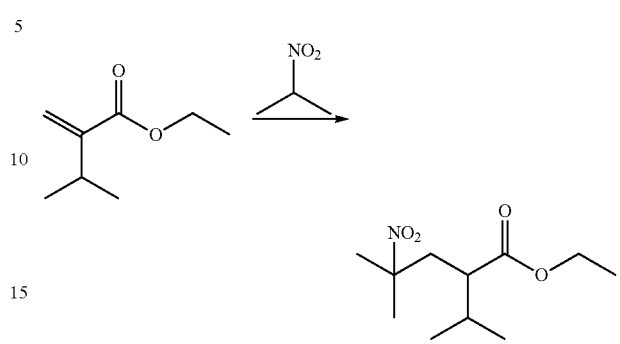

3-Methyl-2-methylene-butyric acid ethyl ester (15.6 g, 109.7 mmol) and 2-nitropropane (2.2 mL, 24.2 mmol) were added to acetonitrile (250 mL). 1,8-Diazabicyclo[5.4.0]undec-7-ene (3.6 mL, 24.2 mmol) was added dropwise, and the reaction mixture was stirred for 16 hours at room temperature. The acetonitrile was removed under vacuum, and 1 M hydrochloric acid (200 mL) was added to the residue. The product was extracted with diethyl ether (3×150 mL) and concentrated. The crude residue was purified by silica gel column chromatography using 0-15% hexanes-diethyl ether to give 2-isopropyl-4-methyl-4-nitro-pentanoic acid ethyl ester (13.4 g, 53%) as a colorless oil.

$^1$H NMR (250 MHz, CDCl3) (ppm): 0.83-0.97 (m, 6H) 1.18-1.35 (m, 3H) 1.54 (d, J=17.03 Hz, 6H) 1.86 (d, J=13.21, 1H) 2.06-2.22 (m, 2H) 2.25-2.45 (m, 1H) 4.07-4.21 (m, 2H).

Step 4: 3-Isopropyl-5,5-dimethyl-pyrrolidin-2-one

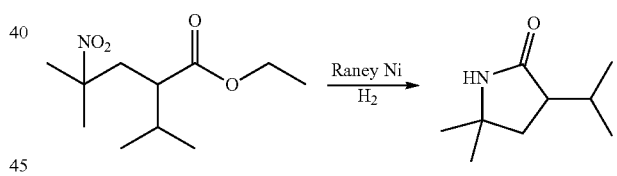

To a solution of 2-isopropyl-4-methyl-4-nitro-pentanoic acid ethyl ester (14.6 g, 63.2 mmol) in ethanol (100 mL) was added Raney nickel (~2 g, 34.0 mmol), and the reaction was heated under hydrogen atmosphere at 60° C. and 120 PSI for 24 hours. Further Raney nickel (~1 g, 17.0 mmol) was then added, and the reaction was heated at 60° C. and 120 PSI overnight for 24 hours. The reaction was filtered through Celite, and the mother liquor was concentrated to give a mixture of 4-amino-2-isopropyl-4-methyl-pentanoic acid and 3-isopropyl-5,5-dimethyl-pyrrolidin-2-one. The mixture was dissolved in toluene (125 mL) and heated at 110° C. for 16 hours. The solvent was removed, and the residue was purified by silica gel column chromatography using 0-10% dichloromethane-methanol to give 3-isopropyl-5,5-dimethyl-pyrrolidin-2-one (6.18 g, 63%) as a tan solid. ESI-MS m/z calc. 155.0, found 155.3 [M+1]. Retention time: 2.14 minutes.

$^1$H NMR (250 MHz, CDCl3) (ppm): 0.87 (d, J=6.81 Hz, 3H) 0.97 (d, J=6.92 Hz, 3H) 1.27 (d, J=10.66 Hz, 6H) 1.64-1.76 (m, 1H) 1.84-1.96 (m, 1H) 2.13-2.30 (m, 1H) 2.57 (ddd, J=10.57, 8.98, 4.61 Hz, 1H) 5.59 (br. s., 1H).

Step 5: 4-Isopropyl-2,2-dimethyl-pyrrolidine-1-carboxylic acid tert-butyl ester

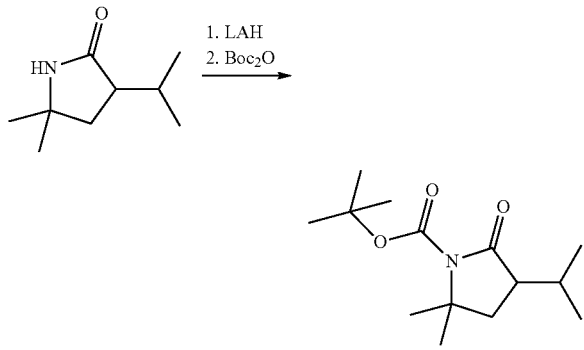

To a suspension of lithium aluminum hydride (1.00 g, 26.28 mmol) in tetrahydrofuran (15 mL) at room temperature was added dropwise a solution of (3-isopropyl-5,5-dimethyl-pyrrolidin-2-one (1.02 g, 6.57 mmol) in tetrahydrofuran (7 mL), and the reaction was heated at 60° C. for 3 days. The reaction was then cooled in an ice bath, and 2-methyltetrahydrofuran (20 mL) was added followed by aqueous Rochelle's salt (50 mL). The reaction was then extracted with 2-methyltetrahydrofuran (4×50 mL), dried over sodium sulfate, and concentrated to afford crude 4-isopropyl-2,2-dimethyl-pyrrolidine. The crude material was dissolved in dichloromethane (26 mL) and treated with di-tert-butyl dicarbonate (1.72 g, 7.88 mmol) and N,N-diisopropylethylamine (1.4 mL, 7.88 mmol) at 0° C. and allowed to warm over 48 hours. The reaction was then poured into 5% aqueous sodium bicarbonate (40 mL) and extracted with dichloromethane (2×50 mL). The organic layer was dried over sodium sulfate and purified by silica gel column chromatography using 0-30% hexanes-diethyl ether to give 4-isopropyl-2,2-dimethyl-pyrrolidine-1-carboxylic acid tert-butyl ester (1.23 g, 76%) as a yellow oil. ESI-MS m/z calc. 241.0, found 242.0 [M+1]. Retention time: 4.01 minutes.

Step 6: 4-Isopropyl-2,2-dimethyl-pyrrolidine hydrochloride

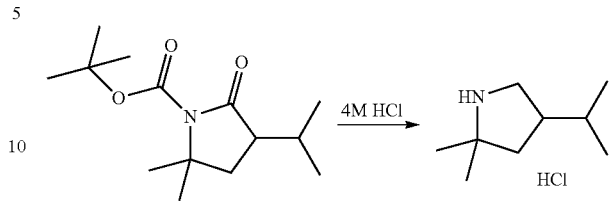

To 4-isopropyl-2,2-dimethyl-pyrrolidine-1-carboxylic acid tert-butyl ester (1.23 g, 5.1 mmol) was added dichloromethane (15 mL) followed by 4 M hydrochloric acid in 1,4-dioxane (5 mL, 20.0 mmol). The reaction was stirred overnight at room temperature and concentrated down. The residue was sonicated with hexanes (30 mL) and filtered to give 4-isopropyl-2,2-dimethyl-pyrrolidine hydrochloride (669 mg, 74%) as a white crystalline solid. ESI-MS m/z calc. 141.0, found 140.6 [M+1]. Retention time: 1.53 minutes.

$^1$H NMR (250 MHz, CDCl3) (ppm): 0.87 (dd, J=6.43, 3.46 Hz, 6H) 1.30 (s, 3H) 1.40 (s, 3H) 1.42-1.59 (m, 2H) 1.91 (dd, J=12.69, 7.53 Hz, 1H) 1.99-2.21 (m, 1H) 2.88 (t, J=9.72 Hz, 1H).

Step 7: N-(1,3-dimethylpyrazol-4-yl)sulfonyl-2-(4-isopropyl-2,2-dimethyl-pyrrolidin-1-yl)-6-[3-[[1-(trifluoromethyl)cyclopropyl]methoxy]pyrazol-1-yl]pyridine-3-carboxamide (Compound 41)

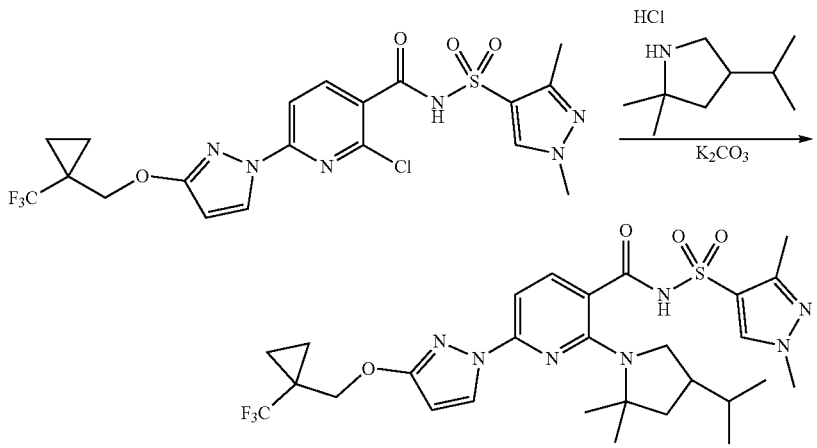

To a solution of 2-chloro-N-(1,3-dimethylpyrazol-4-yl)sulfonyl-6-[3-[[1-(trifluoromethyl)cyclopropyl]methoxy]pyrazol-1-yl]pyridine-3-carboxamide (300 mg, 0.5781 mmol) and 4-isopropyl-2,2-dimethyl-pyrrolidine (250.0 mg, 1.770 mmol) in anhydrous DMSO (5.0 mL) was added cesium fluoride (450.0 mg, 2.962 mmol). The reaction mixture was stirred at 130° C. for 16 h in an oil bath. The reaction mixture was poured on crushed ice. The resultant brown solid was collected by filtration and dried. The crude material was purified by silica gel column chromatography using 10-100% EtOAc-hexanes to afford racemic N-(1,3-dimethylpyrazol-4-yl)sulfonyl-2-(4-isopropyl-2,2-dimethyl-pyrrolidin-1-yl)-6-[3-[[1-(trifluoromethyl)cyclopropyl]methoxy]pyrazol-1-yl]pyridine-3-carboxamide (90 mg, 25%) as white amorphous solid. ESI-MS m/z calc. 623.2502, found 624.5 (M+1)+; Retention time: 2.25 minutes.

$^1$H NMR (400 MHz, Chloroform-d) δ 8.32 (d, J=8.5 Hz, 1H), 8.22 (d, J=2.8 Hz, 1H), 8.06 (s, 1H), 7.54 (d, J=8.5 Hz, 1H), 5.99 (d, J=2.8 Hz, 1H), 4.39 (s, 2H), 3.86 (s, 3H), 3.46 (dd, J=10.3, 8.5 Hz, 1H), 3.25 (dd, J=10.4, 7.9 Hz, 1H), 2.46 (s, 3H), 2.16 (d, J=9.6 Hz, 1H), 2.11-2.03 (m, 1H), 1.78 (dd, J=12.0, 10.1 Hz, 1H), 1.67 (dt, J=9.5, 6.6 Hz, 1H), 1.39 (s, 3H), 1.31 (s, 3H), 1.20-1.11 (m, 2H), 0.98 (d, J=6.6 Hz, 3H), 0.96-0.94 (m, 2H), 0.92 (d, J=6.6 Hz, 3H).

Step 8: Two enantiomers of N-(1,3-dimethylpyrazol-4-yl)sulfonyl-2-(4-isopropyl-2,2-dimethyl-pyrrolidin-1-yl)-6-[3-[[1-(trifluoromethyl)cyclopropyl]methoxy]pyrazol-1-yl]pyridine-3-carboxamide Peak 2: Pure enantiomer 2 N-(1,3-dimethylpyrazol-4-yl)sulfonyl-2-(4-isopropyl-2,2-dimethyl-pyrrolidin-1-yl)-6-[3-[[1-(trifluoromethyl)cyclopropyl]methoxy]pyrazol-1-yl]pyridine-3-carboxamide (34.2 mg, 19%); (>98% ee) (Compound 47). ESI-MS m/z calc. 623.2502, found 624.5 (M+1)+; Retention time: 2.25 minutes.

$^1$H NMR (400 MHz, Chloroform-d) δ 13.75 (s, 1H), 8.23 (d, J=8.5 Hz, 1H), 8.20 (d, J=2.8 Hz, 1H), 8.07 (s, 1H), 7.45 (d, J=8.5 Hz, 1H), 5.96 (d, J=2.8 Hz, 1H), 4.39 (m, 2H), 3.84 (s, 3H), 3.40 (dd, J=10.3, 8.3 Hz, 1H), 3.24 (dd, J=10.4, 8.0 Hz, 1H), 2.45 (s, 3H), 2.18-2.01 (m, 2H), 1.75 (dd, J=11.9, 10.2 Hz, 1H), 1.64 (dp, J=9.1, 6.6 Hz, 1H), 1.38 (s, 3H), 1.32 (s, 3H), 1.18-1.12 (m, 2H), 0.97 (d, J=6.6 Hz, 3H), 0.96-0.92 (m, 2H), 0.90 (d, J=6.5 Hz, 3H).

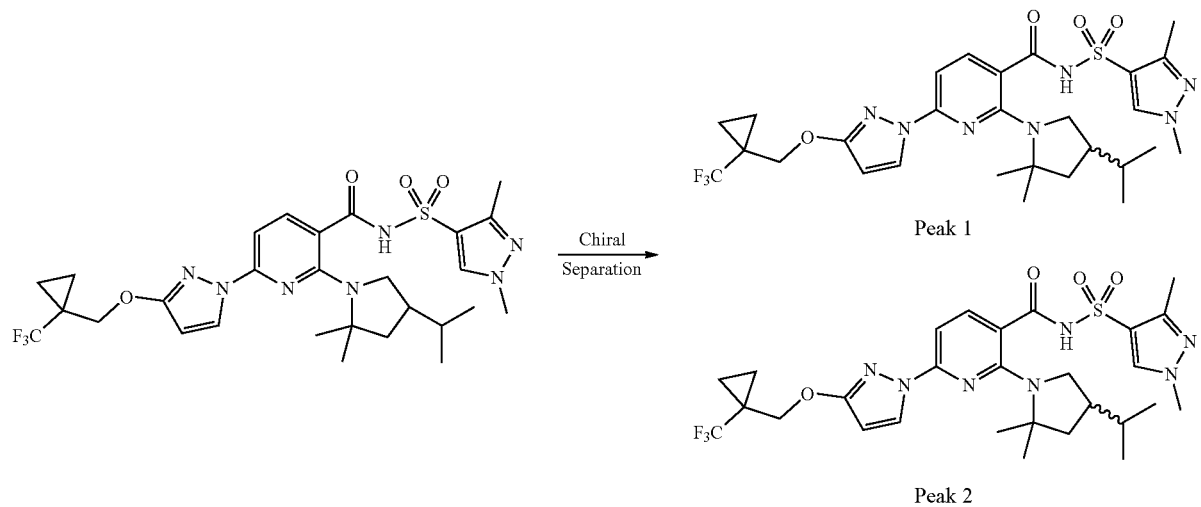 [SMILES: Cc1nn(C)cc1S(=O)(=O)NC(=O)c1ccc(-n2ccc(OCC3(C(F)(F)F)CC3)n2)nc1N1CC(C(C)C)CC1(C)C ; Cc1nn(C)cc1S(=O)(=O)NC(=O)c1ccc(-n2ccc(OCC3(C(F)(F)F)CC3)n2)nc1N1CC(C(C)C)CC1(C)C ; Cc1nn(C)cc1S(=O)(=O)NC(=O)c1ccc(-n2ccc(OCC3(C(F)(F)F)CC3)n2)nc1N1CC(C(C)C)CC1(C)C]

Racemic N-(1,3-dimethylpyrazol-4-yl)sulfonyl-2-(4-isopropyl-2,2-dimethyl-pyrrolidin-1-yl)-6-[3-[[1-(trifluoromethyl)cyclopropyl]methoxy]pyrazol-1-yl]pyridine-3-carboxamide (90 mg, 0.144 mmol) was purified by chiral SFC using a ChiralPak AD-3 column (250×10 mm, 5 μm), eluting with 15% methanol, 85% CO$_2$, at a pressure of 100 bar, and flow rate of 10 mL/min.

Peak 1: Pure enantiomer 1 of N-(1,3-dimethylpyrazol-4-yl)sulfonyl-2-(4-isopropyl-2,2-dimethyl-pyrrolidin-1-yl)-6-[3-[[1-(trifluoromethyl)cyclopropyl]methoxy]pyrazol-1-yl]pyridine-3-carboxamide (33.8 mg, 19%); (>98% ee) (Compound 46). ESI-MS m/z calc. 623.2502, found 624.5 (M+1)+; Retention time: 2.25 minutes.

$^1$H NMR (400 MHz, Chloroform-d) δ 13.91 (s, 1H), 8.30 (d, J=8.5 Hz, 1H), 8.22 (d, J=2.8 Hz, 1H), 8.07 (s, 1H), 7.52 (d, J=8.5 Hz, 1H), 5.98 (d, J=2.8 Hz, 1H), 4.39 (d, J=1.7 Hz, 2H), 3.85 (s, 3H), 3.49-3.40 (m, 1H), 3.25 (dd, J=10.4, 7.9 Hz, 1H), 2.46 (s, 3H), 2.16 (dt, J=17.4, 8.7 Hz, 1H), 2.06 (dd, J=12.0, 7.6 Hz, 1H), 1.77 (dd, J=12.0, 10.1 Hz, 1H), 1.71-1.57 (m, 1H), 1.39 (s, 3H), 1.31 (s, 3H), 1.19-1.12 (m, 2H), 0.98 (d, J=6.6 Hz, 3H), 0.96-0.94 (m, 2H), 0.92 (d, J=6.5 Hz, 3H).

Synthesis of N-(1,3-dimethylpyrazol-4-yl)sulfonyl-2-(7-methyl-5-azaspiro[3.4]octan-5-yl)-6-[3-[[1-(trifluoromethyl)cyclopropyl]methoxy]pyrazol-1-yl]pyridine-3-carboxamide (Compound 43)

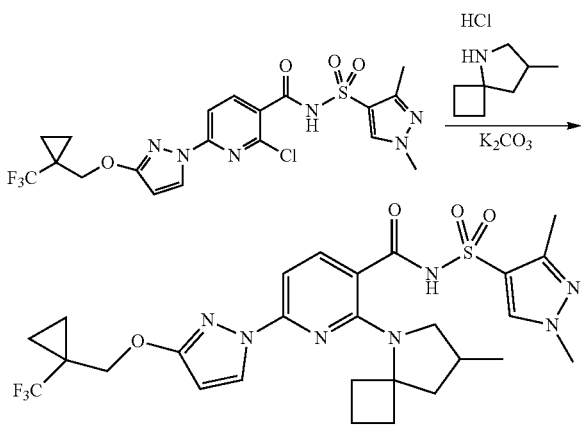

To a solution of 2-chloro-N-(1,3-dimethylpyrazol-4-yl)sulfonyl-6-[3-[[1-(trifluoromethyl)cyclopropyl]methoxy]pyrazol-1-yl]pyridine-3-carboxamide (50.0 mg, 0.09636 mmol) and 7-methyl-5-azaspiro[3.4]octane (hydrochloride salt) (50.0 mg, 0.3093 mmol) in anhydrous DMSO (1.000 mL) was added cesium fluoride (75.0 mg, 0.4937 mmol). The reaction mixture was stirred at 130° C. for 16 h in an oil bath. The reaction mixture was filtered and purified using a reverse phase HPLC-MS method with a dual gradient run from 50-99% acetonitrile in 5 mM HCl to afford N-(1,3-dimethylpyrazol-4-yl)sulfonyl-2-(7-methyl-5-azaspiro[3.4]octan-5-yl)-6-[3-[[1-(trifluoromethyl)cyclopropyl]methoxy]pyrazol-1-yl]pyridine-3-carboxamide (8.6 mg, 15%). ESI-MS m/z calc. 607.2189, found 608.5 (M+1)+; Retention time: 2.18 minutes.

¹H NMR (400 MHz, Chloroform-d) δ 8.45 (d, J=8.5 Hz, 1H), 8.27 (d, J=2.8 Hz, 1H), 8.06 (s, 1H), 7.63 (d, J=8.5 Hz, 1H), 5.99 (d, J=2.8 Hz, 1H), 4.40 (s, 2H), 3.86 (s, 3H), 3.63-3.54 (m, 1H), 2.97 (dd, J=10.0, 6.7 Hz, 1H), 2.54 (q, J=6.5, 5.2 Hz, 2H), 2.46 (s, 3H), 2.25-2.15 (m, 2H), 2.10 (t, J=10.3 Hz, 1H), 2.03-1.95 (m, 1H), 1.91 (dd, J=10.1, 5.5 Hz, 2H), 1.74-1.60 (m, 1H), 1.55-1.41 (m, 1H), 1.22 (d, J=6.3 Hz, 3H), 1.19-1.12 (m, 2H), 1.02-0.90 (m, 2H).

Synthesis of N-(1,3-dimethylpyrazol-4-yl)sulfonyl-2-(6-methyl-4-azaspiro[2.4]heptan-4-yl)-6-[3-[[1-(trifluoromethyl)cyclopropyl]methoxy]pyrazol-1-yl]pyridine-3-carboxamide (Compound 44)

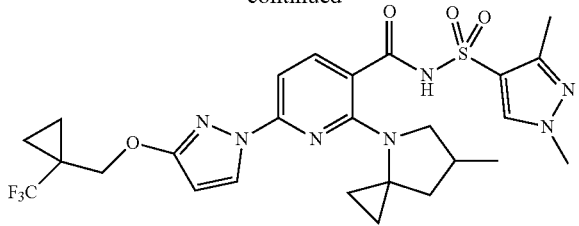

To a solution of 2-chloro-N-(1,3-dimethylpyrazol-4-yl)sulfonyl-6-[3-[[1-(trifluoromethyl)cyclopropyl]methoxy]pyrazol-1-yl]pyridine-3-carboxamide (50.0 mg, 0.09636 mmol) and 6-methyl-4-azaspiro[2.4]heptane (hydrochloride salt) (45.0 mg, 0.3048 mmol) in anhydrous DMSO (1 mL) was added cesium fluoride (75.0 mg, 0.4937 mmol). The reaction mixture was stirred at 130° C. overnight in an oil bath. The reaction mixture was filtered and purified using a reverse phase HPLC-MS method with a dual gradient run from 50-99% acetonitrile in 5 mM HCl to afford N-(1,3-dimethylpyrazol-4-yl)sulfonyl-2-(6-methyl-4-azaspiro[2.4]heptan-4-yl)-6-[3-[[1-(trifluoromethyl)cyclopropyl]methoxy]pyrazol-1-yl]pyridine-3-carboxamide (42.8 mg, 75%). ESI-MS m/z calc. 593.2032, found 594.6 (M+1)+; Retention time: 2.17 minutes.

¹H NMR (400 MHz, Chloroform-d) δ 8.40 (d, J=8.6 Hz, 1H), 8.29 (d, J=2.8 Hz, 1H), 8.06 (s, 1H), 7.59 (d, J=8.5 Hz, 1H), 6.00 (d, J=2.8 Hz, 1H), 4.39 (s, 2H), 3.86 (s, 3H), 3.64 (dd, J=10.5, 7.9 Hz, 1H), 3.14 (dd, J=10.5, 7.1 Hz, 1H), 2.75-2.59 (m, 1H), 2.46 (s, 3H), 2.33 (dd, J=12.2, 8.8 Hz, 1H), 1.77 (dd, J=12.3, 6.4 Hz, 1H), 1.22 (d, J=6.8 Hz, 3H), 1.18-1.12 (m, 2H), 0.95 (tt, J=5.6, 2.8 Hz, 2H), 0.72-0.54 (m, 4H).

Synthesis of N-(1,3-dimethylpyrazol-4-yl)sulfonyl-2-(4-ethyl-2,2-dimethyl-pyrrolidin-1-yl)-6-[3-[[1-(trifluoromethyl)cyclopropyl]methoxy]pyrazol-1-yl]pyridine-3-carboxamide (Compound 49)

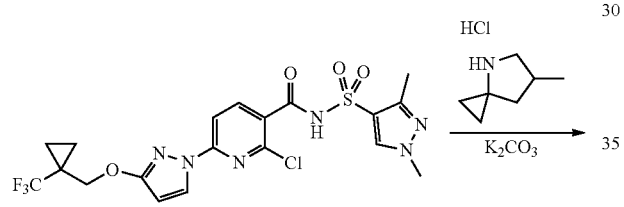

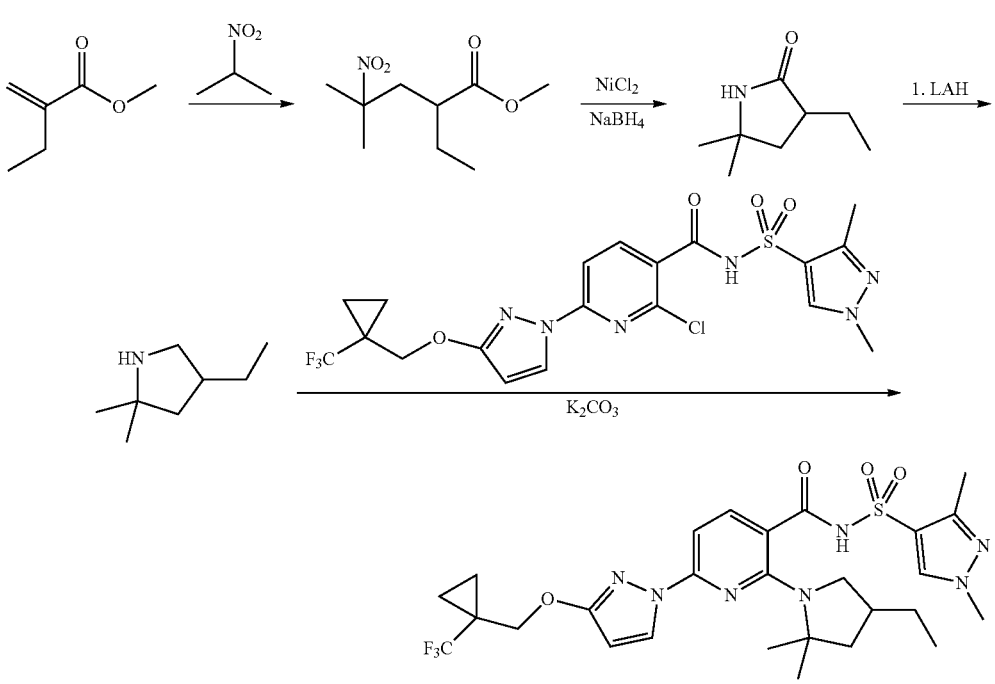

Step 1: Methyl 2-ethyl-4-methyl-4-nitro-pentanoate

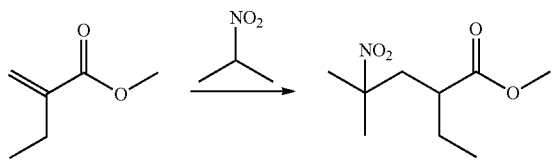

2-Nitropropane (1.20 mL, 13.36 mmol) was dissolved in dioxane (10.0 mL). An aqueous solution of benzyl(trimethyl)ammonium hydroxide (110.0 µL of 40% w/v, 0.2631 mmol) was added. The reaction mixture was stirred at 70° C. during the dropwise addition of methyl 2-methylenebutanoate (2.5 g, 21.90 mmol) over 20 minutes. The reaction mixture was then allowed to stir at 100° C. for 4.5 hours. The reaction was quenched with the addition of aqueous HCl (50.0 mL of 1 M, 50.00 mmol). The mixture was diluted with diethyl ether (75 mL) and washed with water (3×75 mL) and brine (1×75 mL). The organic layer was dried over sodium sulfate, filtered and concentrated under reduced pressure to give a yellow liquid. The crude product was purified by silica gel column chromatography using a gradient of 5% to 25% EtOAc-hexanes to afford methyl 2-ethyl-4-methyl-4-nitro-pentanoate (1.6 g, 34%) as a colorless oil.

$^1$H NMR (400 MHz, Chloroform-d) δ 3.68 (s, 3H), 2.44-2.36 (m, 1H), 2.30 (tdd, J=9.8, 6.9, 1.9 Hz, 1H), 2.10 (dd, J=14.6, 2.0 Hz, 1H), 1.69-1.45 (m, 2H), 1.58 (s, 3H), 1.53 (s, 3H), 0.89 (t, J=7.5 Hz, 3H).

Step 2: 3-Ethyl-5,5-dimethyl-pyrrolidin-2-one

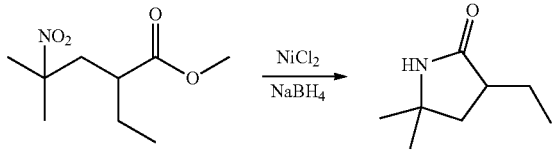

A solution of methyl 2-ethyl-4-methyl-4-nitro-pentanoate (1.56 g, 7.676 mmol) and dichloronickel hexahydrate (366.4 mg, 1.541 mmol) in 1:4 water (5 mL) and MeOH (20.0 mL) was cooled to 0° C. To this solution, sodium borohydride (730.8 mg, 19.32 mmol) was added slowly portions wise. After the addition was completed, the reaction mixture was allowed to warm up to room temperature and stir at room temperature for 2 h. The reaction mixture was cooled again, and a solution of aqueous potassium carbonate (1 M, 25 mL) was added. The color changed from black to gray to green. The mixture was allowed to age for 3 h, then Celite was added. The solid was removed by filtration through a Celite-packed filter pad and washed with MeOH (3×100 mL). The combined filtrate and washings were concentrated to remove most of the MeOH. Solid sodium chloride was added to the aqueous concentrate and extracted with diethyl ether. The combined organic extracts were washed with brine, dried over magnesium sulfate, and concentrated. The resultant residue was purified by silica gel column chromatography using 10% EtOAc-hexanes to 100% EtOAc to afford 3-ethyl-5,5-dimethyl-pyrrolidin-2-one (608 mg, 14%) as colorless oil with about 59% purity. ESI-MS m/z calc. 141.11537, found 142.2 (M+1)+; Retention time: 0.38 minutes.

Step 3: 4-Ethyl-2,2-dimethyl-pyrrolidine

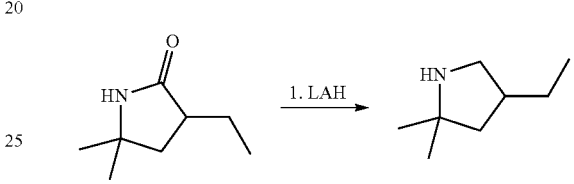

To a solution of 3-ethyl-5,5-dimethyl-pyrrolidin-2-one (302.6 mg, 2.143 mmol) in dry THF (3 mL) was added a lithium aluminum hydride (3.5 mL of 2 M, 7.000 mmol) solution at 0° C. under nitrogen atmosphere slowly dropwise. The mixture was allowed to warm up to ambient temperature and stirred for 1 h, then heated at 60° C. for 14 h. The mixture was cooled in an ice-bath and sequentially quenched with water (150.0 µL, 8.326 mmol) (slowly), followed by NaOH (150.0 µL of 6 M, 0.9000 mmol), then water (500 µL, 27.75 mmol) affording a granular solid in the mixture. The solid was filtered off using Celite, and the precipitate was washed with ether. The filtrate was further dried with magnesium sulfate, filtered, and concentrated without vacuum on rota-vap to afford 4-ethyl-2,2-dimethyl-pyrrolidine (130.9 mg, 24%). The mixture was taken directly into the next step (E33068-152).

Step 4: N-(1,3-Dimethylpyrazol-4-yl)sulfonyl-2-(4-ethyl-2,2-dimethyl-pyrrolidin-1-yl)-6-[3-[[1-(trifluoromethyl)cyclopropyl]methoxy]pyrazol-1-yl]pyridine-3-carboxamide

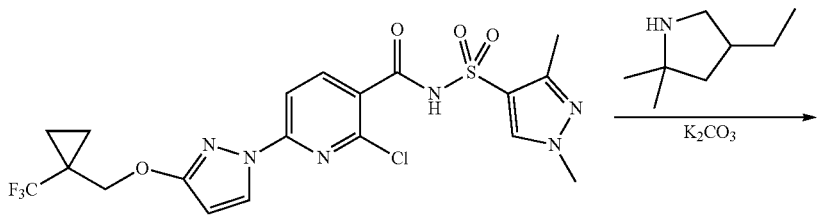

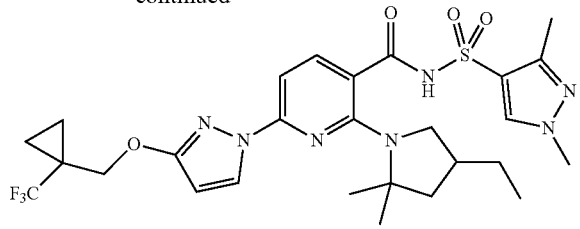

To a solution of 2-chloro-N-(1,3-dimethylpyrazol-4-yl)sulfonyl-6-[3-[[1-(trifluoromethyl)cyclopropyl]methoxy]pyrazol-1-yl]pyridine-3-carboxamide (175.4 mg, 0.3380 mmol) and 4-ethyl-2,2-dimethyl-pyrrolidine (130.9 mg, 1.029 mmol) in anhydrous DMSO (2 mL) was added cesium fluoride (267.2 mg, 1.759 mmol). The reaction mixture was stirred at 130° C. for 16 h in an oil bath. The reaction mixture was filtered and purified using a reverse phase HPLC-MS method with a dual gradient run from 50-99% acetonitrile in 5 mM HCl to afford N-(1,3-dimethylpyrazol-4-yl)sulfonyl-2-(4-ethyl-2,2-dimethyl-pyrrolidin-1-yl)-6-[3-[[1-(trifluoromethyl)cyclopropyl]methoxy]pyrazol-1-yl]pyridine-3-carboxamide (4.5 mg, 2%). ESI-MS m/z calc. 609.2345, found 610.59 (M+1)+; Retention time: 2.17 minutes.

$^1$H NMR (400 MHz, Chloroform-d) δ 8.35 (d, J=8.5 Hz, 1H), 8.23 (d, J=2.8 Hz, 1H), 8.06 (s, 1H), 7.56 (d, J=8.5 Hz, 1H), 5.99 (d, J=2.8 Hz, 1H), 4.39 (s, 2H), 3.86 (s, 3H), 3.56-3.48 (m, 1H), 3.15 (dd, J=10.4, 7.5 Hz, 1H), 2.47 (s, 3H), 2.39 (dt, J=16.9, 8.3 Hz, 1H), 2.13 (dd, J=12.3, 7.9 Hz, 1H), 1.72 (dd, J=12.4, 9.5 Hz, 1H), 1.59 (p, J=7.3 Hz, 2H), 1.36 (s, 3H), 1.30 (s, 3H), 1.18-1.13 (m, 2H), 0.99-0.94 (m, 5H).

Synthesis of N-(1,3-dimethylpyrazol-4-yl)sulfonyl-6-[3-[[1-(trifluoromethyl)cyclopropyl]methoxy]pyrazol-1-yl]-2-(2,2,4-trimethylpyrrolidin-1-yl)pyridine-3-carboxamide (Compound 42)

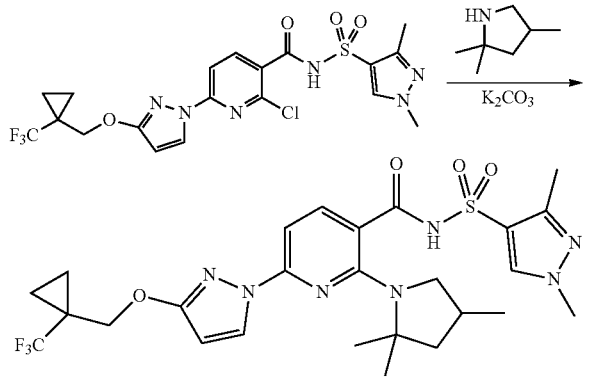

To a solution of 2-chloro-N-(1,3-dimethylpyrazol-4-yl)sulfonyl-6-[3-[[1-(trifluoromethyl)cyclopropyl]methoxy]pyrazol-1-yl]pyridine-3-carboxamide (50.0 mg, 0.09636 mmol) and 2,2,5-trimethylpyrrolidine (35.0 mg, 0.3092 mmol) in anhydrous DMSO (1.000 mL) was added cesium fluoride (75.0 mg, 0.4937 mmol). The reaction mixture was stirred at 130° C. for 16 h in an oil bath. The reaction mixture was filtered and purified using a reverse phase HPLC-MS method with a dual gradient run from 50-99% acetonitrile in 5 mM HCl to afford N-(1,3-dimethylpyrazol-4-yl)sulfonyl-6-[3-[[1-(trifluoromethyl)cyclopropyl]methoxy]pyrazol-1-yl]-2-(2,2,4-trimethylpyrrolidin-1-yl)pyridine-3-carboxamide (5.8 mg, 10%). ESI-MS m/z calc. 595.2189, found 596.6 (M+1)+; Retention time: 1.91 minutes.

$^1$H NMR (400 MHz, Chloroform-d) δ 8.57 (d, J=8.2 Hz, 1H), 8.24 (d, J=2.7 Hz, 1H), 8.07 (s, 1H), 7.73 (d, J=8.0 Hz, 1H), 6.00 (d, J=2.4 Hz, 1H), 4.40 (s, 2H), 4.26-4.18 (m, 1H), 3.87 (s, 3H), 2.48 (s, 3H), 2.39-2.36 (m, 1H), 2.23-2.12 (m, 1H), 1.99-1.94 (m, 1H), 1.89-1.80 (m, 1H), 1.30 (s, 3H), 1.20 (d, J=5.9 Hz, 3H), 1.18-1.14 (m, 2H), 1.10 (s, 3H), 0.99-0.93 (m, 2H).

Synthesis of N-(1,5-dimethylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (Compound 9)

Step 1: 2-Chloro-N-(1,5-dimethylpyrazol-4-yl)sulfonyl-6-[3-[[1-(trifluoromethyl)cyclopropyl]methoxy]pyrazol-1-yl]pyridine-3-carboxamide

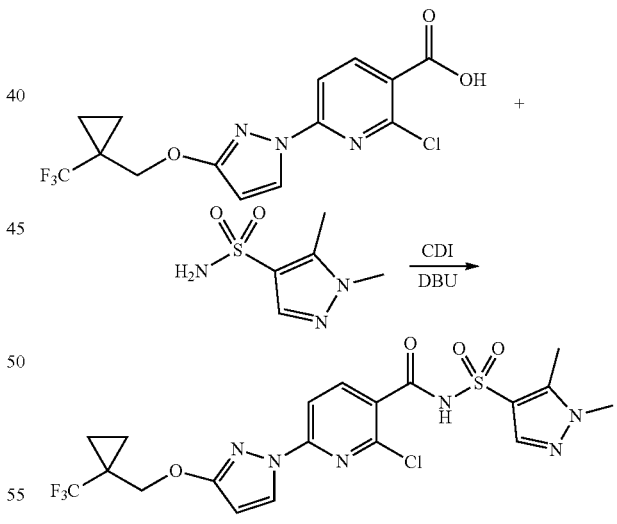

2-Chloro-6-[3-[[1-(trifluoromethyl)cyclopropyl]methoxy]pyrazol-1-yl]pyridine-3-carboxylic acid (200 mg, 0.5529 mmol) was dissolved in THF (2 mL), and CDI (approximately 107.6 mg, 0.6635 mmol) was added. After stirring at room temperature for 1.5 hours, 1,5-dimethylpyrazole-4-sulfonamide (approximately 125.9 mg, 0.7188 mmol) was added followed by DBU (approximately 101.0 mg, 99.21 μL, 0.6635 mmol). The reaction mixture was allowed to stir overnight at room temperature. The reaction mixture was diluted with EtOAc (50 mL) and washed with aqueous 1 M citric acid (1×50 mL) and brine (1×50 mL). The organic layer was dried over sodium sulfate, filtered and concentrated under reduced pressure to give 2-chloro-N-(1,5-dimethylpyrazol-4-yl)sulfonyl-6-[3-[[1-(trifluoromethyl)cyclopropyl]methoxy]pyrazol-1-yl]pyridine-3-carboxamide (332 mg) ESI-MS m/z calc. 518.08, found 519.0 (M+1)⁺; Retention time: 0.65 minutes.

Step 2: N-(1,5-Dimethylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

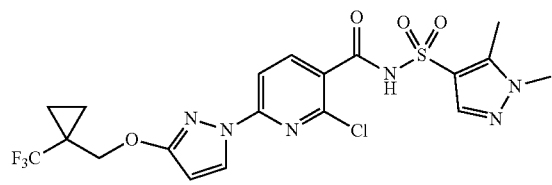

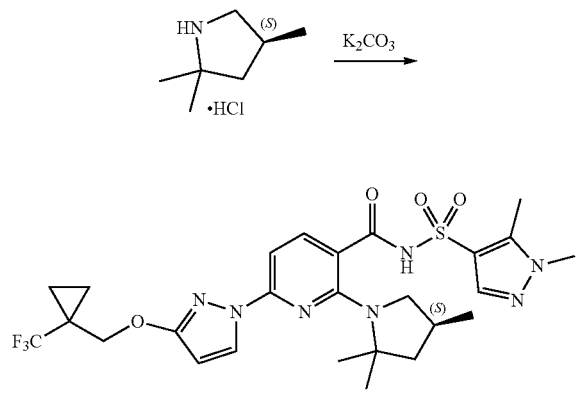

2-Chloro-N-(1,5-dimethylpyrazol-4-yl)sulfonyl-6-[3-[[1-(trifluoromethyl)cyclopropyl]methoxy]pyrazol-1-yl]pyridine-3-carboxamide (286.8 mg, 0.5528 mmol) was dissolved in DMSO (2 mL). (4S)-2,2,4-Trimethylpyrrolidine (hydrochloride salt) (approximately 248.1 mg, 1.658 mmol) was added followed by finely ground potassium carbonate (approximately 458.4 mg, 3.317 mmol). The reaction mixture was allowed to stir at 130° C. overnight. After cooling to room temperature, EtOAc (50 mL) was added. The mixture was washed with 1 N HCl (1×50 mL) and brine (1×50 mL). The organic layer was dried over sodium sulfate, filtered and concentrated under reduced pressure to give N-(1,5-dimethylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (72.7 mg) ESI-MS m/z calc. 595.22, found 596.4 (M+1)+; Retention time: 2.07 minutes.

¹H NMR (400 MHz, DMSO-d₆) δ 12.28 (s, 1H), 8.21 (d, J=2.7 Hz, 1H), 7.78 (s, 1H), 7.73 (d, J=8.2 Hz, 1H), 6.91 (d, J=8.2 Hz, 1H), 6.14 (d, J=2.7 Hz, 1H), 4.43-4.31 (m, 2H), 3.78 (s, 3H), 2.57 (t, J=10.4 Hz, 1H), 2.53 (s, 3H), 2.43 (dd, J=10.2, 7.1 Hz, 1H), 2.25-2.10 (m, 1H), 1.87 (dd, J=11.9, 5.6 Hz, 1H), 1.57 (s, 3H), 1.53 (s, 3H), 1.44 (t, J=12.1 Hz, 1H), 1.09 (dt, J=6.7, 2.0 Hz, 4H), 0.81 (d, J=6.2 Hz, 3H).

Synthesis of N-(1H-pyrazol-4-ylsulfonyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide (Compound 5)

Step 1: 2-Chloro-N-(1H-pyrazol-4-ylsulfonyl)-6-[3-[[1-(trifluoromethyl)cyclopropyl]methoxy]pyrazol-1-yl]pyridine-3-carboxamide 2-Chloro-6-[3-[[1-(trifluoromethyl)cyclopropyl]methoxy]pyrazol-1-yl]pyridine-3-carboxylic acid (200 mg, 0.5529 mmol) and CDI (approximately 107.6 mg, 0.6635 mmol) were combined in THF (1.200 mL) and stirred at room temperature for 2 hours. 1H-Pyrazole-4-sulfonamide (approximately 105.8 mg, 0.7188 mmol) was added followed by DBU (approximately 101.0 mg, 99.21 μl, 0.6635 mmol), and the reaction was stirred for an additional 16 h at room temperature. The reaction mixture was further washed with 1 M citric acid and water, and extracted with 3×20 mL ethyl acetate. The combined organics were washed with brine, dried over sodium sulfate, concentrated, then purified by silica gel chromatography using a gradient of 0-10% methanol in dichloromethane to give a white solid. 2-chloro-N-(1H-pyrazol-4-ylsulfonyl)-6-[3-[[1-(trifluoromethyl)cyclopropyl]methoxy]pyrazol-1-yl]pyridine-3-carboxamide (190 mg, 70%) ESI-MS m/z calc. 490.0438, found 491.1 (M+1)+; Retention time: 0.61 minutes.

Step 2: N-(1H-Pyrazol-4-ylsulfonyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide

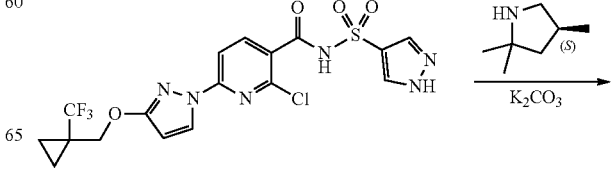

167
-continued

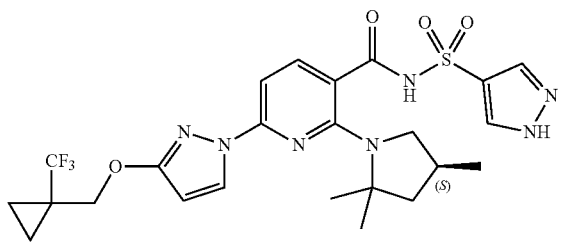

2-Chloro-N-(1H-pyrazol-4-ylsulfonyl)-6-[3-[[1-(trifluoromethyl)cyclopropyl]methoxy]pyrazol-1-yl]pyridine-3-carboxamide (115 mg, 0.2343 mmol), (4S)-2,2,4-trimethylpyrrolidine (hydrochloride salt) (105 mg, 0.7016 mmol), and potassium carbonate (194 mg, 1.404 mmol) were combined in DMSO (575.0 µL) and heated at 130° C. for 16 h. The reaction was cooled to room temperature, and diluted with 15 mL water, 15 mL 1 M citric acid, and 30 mL ethyl acetate. The aqueous and organic layers were separated, and the aqueous layer was extracted two additional times with 30 mL ethyl acetate. The organics were combined, washed with brine, dried over sodium sulfate and concentrated. The resulting solid was purified by silica gel chromatography eluting with a gradient of 0-10% methanol in dichloromethane to give a white solid: N-(1H-pyrazol-4-ylsulfonyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide (100 mg, 75%) ESI-MS m/z calc. 567.18756, found 568.2 (M+1)+; Retention time: 1.84 minutes.

$^1$H NMR (400 MHz, DMSO) δ 13.71 (s, 1H), 12.30 (s, 1H), 8.49 (s, 1H), 8.21 (d, J=2.8 Hz, 1H), 7.94 (s, 1H), 7.73 (d, J=8.3 Hz, 1H), 6.90 (d, J=8.2 Hz, 1H), 6.14 (d, J=2.8 Hz, 1H), 4.47-4.26 (m, 2H), 2.60 (t, J=10.4 Hz, 1H), 2.43 (t, J=8.4 Hz, 1H), 2.15 (dd, J=12.5, 6.6 Hz, 1H), 1.88 (dt, J=11.6, 6.3 Hz, 1H), 1.55 (d, J=17.6 Hz, 6H), 1.42 (t, J=12.4 Hz, 1H), 1.14-1.05 (m, 4H), 0.79 (d, J=6.3 Hz, 3H).

Synthesis of N-(1-methylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (Compound 6)

Step 1: 2-Chloro-N-(1-methylpyrazol-4-yl)sulfonyl-6-[3-[[1-(trifluoromethyl)cyclopropyl]methoxy]pyrazol-1-yl]pyridine-3-carboxamide

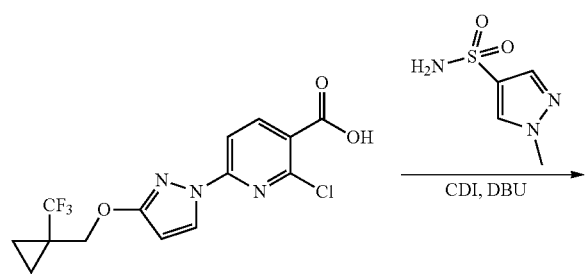

168
-continued

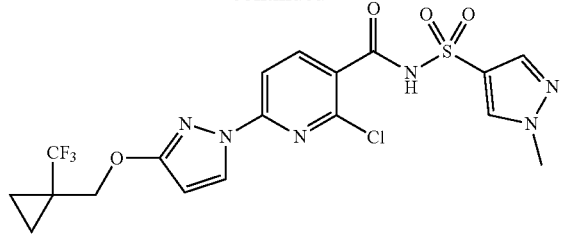

2-Chloro-6-[3-[[1-(trifluoromethyl)cyclopropyl]methoxy]pyrazol-1-yl]pyridine-3-carboxylic acid (200 mg, 0.5529 mmol) and CDI (approximately 107.6 mg, 0.6635 mmol) were combined in THF (1.200 mL) and stirred at room temperature for 2 hours. 1-Methylpyrazole-4-sulfonamide (approximately 115.9 mg, 0.7188 mmol) was added followed by DBU (approximately 101.0 mg, 99.21 µL, 0.6635 mmol), and the reaction was stirred for an additional 16 h at room temperature. The reaction mixture was diluted with 1 M citric acid and water, and extracted 3×20 mL ethyl acetate. The combined organics were washed with brine, then dried over sodium sulfate, concentrated, and purified by silica gel chromatography eluting with a 0-10% methanol/dichloromethane gradient to give a white solid. 2-chloro-N-(1-methylpyrazol-4-yl)sulfonyl-6-[3-[[1-(trifluoromethyl)cyclopropyl]methoxy]pyrazol-1-yl]pyridine-3-carboxamide (227 mg, 81%) ESI-MS m/z calc. 504.05945, found 505.1 (M+1)+; Retention time: 0.64 minutes.

Step 2: N-(1-Methylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

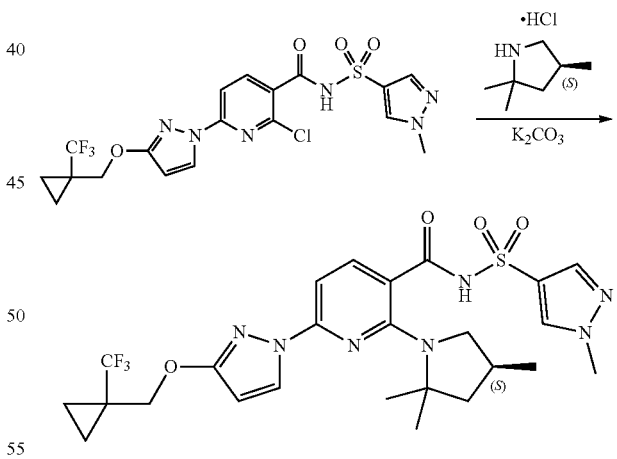

2-Chloro-N-(1-methylpyrazol-4-yl)sulfonyl-6-[3-[[1-(trifluoromethyl)cyclopropyl]methoxy]pyrazol-1-yl]pyridine-3-carboxamide (115 mg, 0.2278 mmol), (4S)-2,2,4-trimethylpyrrolidine (hydrochloride salt) (102 mg, 0.6815 mmol), and potassium carbonate (189 mg, 1.368 mmol) were combined in DMSO (575.0) 1 L) and heated at 130° C. for 16 h. The reaction was cooled to room temperature and diluted with 15 mL water, 15 mL 1 M citric acid, and 30 mL ethyl acetate. The aqueous and organic layers were separated, and the aqueous layer was extracted two additional times with 30 mL ethyl acetate. The organics were combined, washed with brine, dried over sodium sulfate and concentrated. The resulting solid was further purified by silica gel chromatography eluting with a gradient of 0-10% methanol in dichloromethane to give N-(1-methylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (88 mg, 66%) ESI-MS m/z calc. 581.2032, found 582.3 (M+1)+; Retention time: 1.95 minutes.

$^1$H NMR (400 MHz, DMSO) δ 12.35 (s, 1H), 8.51 (s, 1H), 8.21 (d, J=2.8 Hz, 1H), 7.88 (s, 1H), 7.73 (d, J=8.2 Hz, 1H), 6.90 (d, J=8.3 Hz, 1H), 6.15 (d, J=2.8 Hz, 1H), 4.43-4.31 (m, 2H), 3.90 (s, 3H), 2.64 (t, J=10.4 Hz, 1H), 2.48-2.40 (m, 1H), 2.17 (dp, J=18.4, 6.3 Hz, 1H), 1.88 (dd, J=11.8, 5.6 Hz, 1H), 1.55 (d, J=17.0 Hz, 6H), 1.44 (t, J=12.1 Hz, 1H), 1.14-1.04 (m, 4H), 0.80 (d, J=6.2 Hz, 3H).

Synthesis of N-(1-ethylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (Compound 7)

Step 1: 2-Chloro-N-(1-ethylpyrazol-4-yl)sulfonyl-6-[3-[[1-(trifluoromethyl)cyclopropyl]methoxy]pyrazol-1-yl]pyridine-3-carboxamide

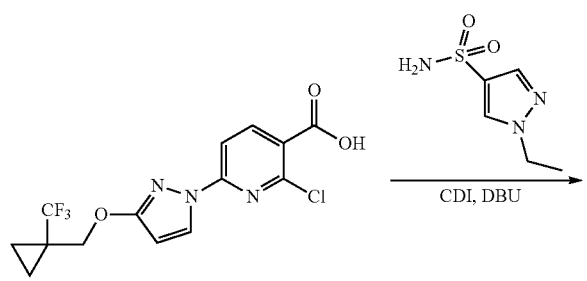

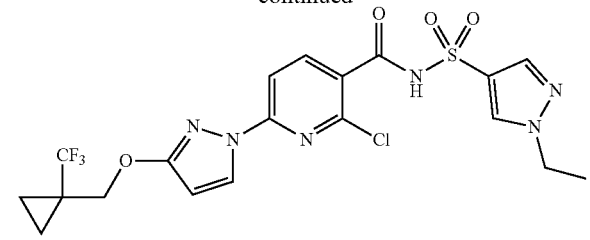

2-Chloro-6-[3-[[1-(trifluoromethyl)cyclopropyl]methoxy]pyrazol-1-yl]pyridine-3-carboxylic acid (200 mg, 0.5529 mmol) and CDI (approximately 107.6 mg, 0.6635 mmol) were combined in THF (1.200 mL) and stirred at room temperature for 2 hours. 1-Ethylpyrazole-4-sulfonamide (approximately 125.9 mg, 0.7188 mmol) was added followed by DBU (approximately 101.0 mg, 99.21 µL, 0.6635 mmol), and the reaction was stirred for an additional 6 h at room temperature. A 1 M citric acid solution (1 mL) was added and the reaction was stirred for 20 min. The reaction mixture was diluted with 1 M citric acid and water, and extracted 3×20 mL ethyl acetate. The combined organics were washed with brine, dried over sodium sulfate, concentrated, then purified by silica gel chromatography using a gradient of 0-10% methanol in dichloromethane to give a white solid. 2-chloro-N-(1-ethylpyrazol-4-yl)sulfonyl-6-[3-[[1-(trifluoromethyl)cyclopropyl]methoxy]pyrazol-1-yl]pyridine-3-carboxamide (250 mg, 87%) ESI-MS m/z calc. 518.0751, found 519.0 (M+1)+; Retention time: 0.67 minutes.

Step 2: N-(1-Ethylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

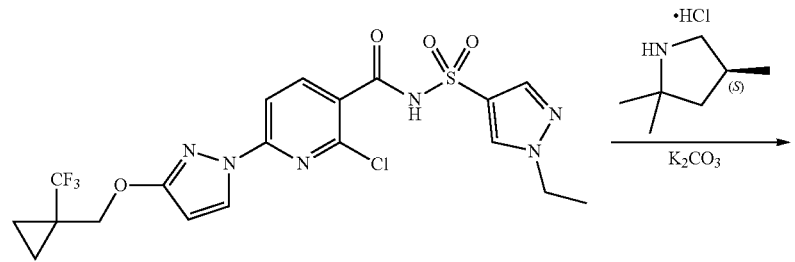

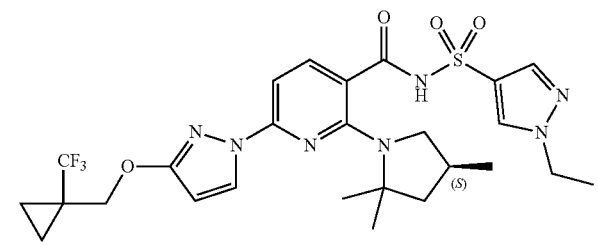

2-Chloro-N-(1-ethylpyrazol-4-yl)sulfonyl-6-[3-[[1-(trifluoromethyl)cyclopropyl]methoxy]pyrazol-1-yl]pyridine-3-carboxamide (115 mg, 0.2216 mmol), (4S)-2,2,4-trimethylpyrrolidine (hydrochloride salt) (100 mg, 0.6682 mmol), and potassium carbonate (184 mg, 1.331 mmol) were combined in DMSO (570 μL) and heated at 130° C. for 16 h. The reaction was cooled to room temperature, and diluted with 15 mL water, 15 mL 1 M citric acid, and 30 mL ethyl acetate. The aqueous and organic layers were separated, and the aqueous layer was extracted two additional times with 30 mL ethyl acetate. The organics were combined, washed with brine, dried over sodium sulfate and concentrated. The resulting material was purified by silica gel chromatography eluting with 0-10% methanol in dichloromethane to give a white solid. N-(1-ethylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (110 mg, 83%) ESI-MS m/z calc. 595.2189, found 596.2 (M+1)+; Retention time: 2.03 minutes.

$^1$H NMR (400 MHz, DMSO) δ 12.34 (s, 1H), 8.53 (d, J=0.8 Hz, 1H), 8.21 (d, J=2.8 Hz, 1H), 7.91 (d, J=0.7 Hz, 1H), 7.74 (d, J=8.2 Hz, 1H), 6.90 (d, J=8.2 Hz, 1H), 6.15 (d, J=2.7 Hz, 1H), 4.48-4.31 (m, 2H), 4.20 (qd, J=7.3, 5.0 Hz, 2H), 2.66 (t, J=10.4 Hz, 1H), 2.47 (s, 1H), 2.17 (dp, J=18.3, 6.4 Hz, 1H), 1.92-1.83 (m, 1H), 1.55 (d, J=17.5 Hz, 6H), 1.45 (d, J=12.0 Hz, 1H), 1.39 (t, J=7.2 Hz, 3H), 1.09 (dt, J=5.2, 1.6 Hz, 4H), 0.80 (d, J=6.3 Hz, 3H).

Synthesis of N-(1-tert-butylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (Compound 8)

Step 1: N-(1-tert-Butylpyrazol-4-yl)sulfonyl-2-chloro-6-[3-[[1-(trifluoromethyl)cyclopropyl]methoxy]pyrazol-1-yl]pyridine-3-carboxamide

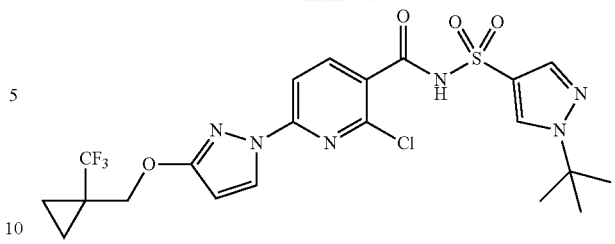

2-Chloro-6-[3-[[1-(trifluoromethyl)cyclopropyl]methoxy]pyrazol-1-yl]pyridine-3-carboxylic acid (200 mg, 0.5529 mmol) and CDI (approximately 107.6 mg, 0.6635 mmol) were combined in THF (1.200 mL) and stirred at room temperature for 2 hours. 1-tert-Butylpyrazole-4-sulfonamide (approximately 146.1 mg, 0.7188 mmol) was added followed by DBU (approximately 101.0 mg, 99.21 μL, 0.6635 mmol), and the reaction was stirred for an additional 6 h at room temperature. A 1 M citric acid solution (1 mL) was added, and the reaction was stirred for 20 min. The reaction was diluted with 1 M citric acid and water, and extracted 3×20 mL ethyl acetate. The combined organics were washed with brine, dried over sodium sulfate, concentrated, and purified by silica gel chromatography using a gradient of 0-10% methanol in dichloromethane to give a white solid. N-(1-tert-butylpyrazol-4-yl)sulfonyl-2-chloro-6-[3-[[1-(trifluoromethyl)cyclopropyl]methoxy]pyrazol-1-yl]pyridine-3-carboxamide (190 mg, 63%) ESI-MS m/z calc. 546.1064, found 547.1 (M+1)+; Retention time: 0.73 minutes.

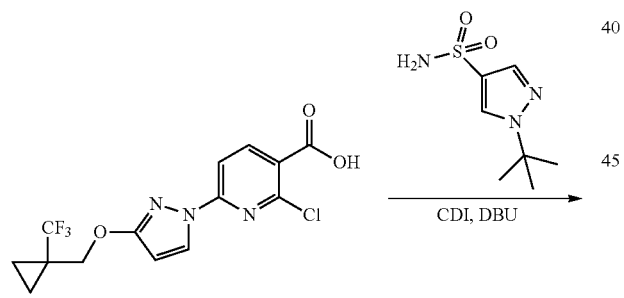

Step 2: N-(1-tert-Butylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

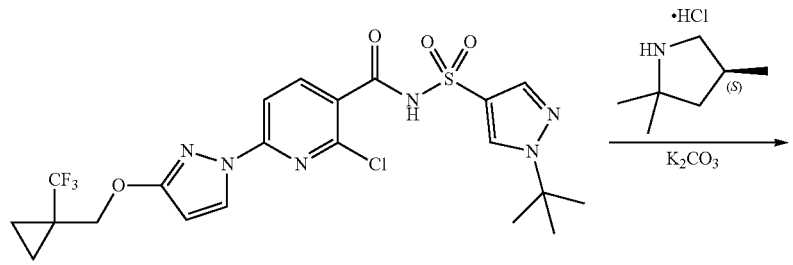

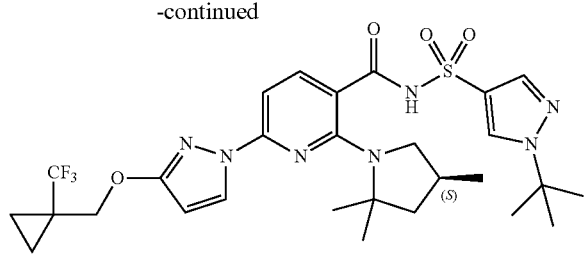

N-(1-tert-Butylpyrazol-4-yl)sulfonyl-2-chloro-6-[3-[[1-(trifluoromethyl)cyclopropyl]methoxy]pyrazol-1-yl]pyridine-3-carboxamide (125 mg, 0.2285 mmol), (4S)-2,2,4-trimethylpyrrolidine (hydrochloride salt) (103 mg, 0.6882 mmol), and potassium carbonate (190 mg, 1.375 mmol) were combined in DMSO (600 μL) and heated at 130° C. for 16 h. The reaction was cooled to room temperature, and diluted with 15 mL water, 15 mL 1 M citric acid, and 30 mL ethyl acetate. The aqueous and organic layers were separated, and the aqueous layer was extracted two additional times with 30 mL ethyl acetate. The organics were combined, washed with brine, dried over sodium sulfate and concentrated. The resulting solid was further purified by silica gel chromotograpy eluting with 0-10% methanol in dichloromethane to give a white solid. N-(1-tert-butylpyrazol-4-yl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (122 mg, 86%) ESI-MS m/z calc. 623.2502, found 624.3 (M+1)+; Retention time: 2.19 minutes.

$^1$H NMR (400 MHz, DMSO) δ 12.33 (s, 1H), 8.46 (s, 1H), 8.21 (d, J=2.7 Hz, 1H), 7.95 (s, 1H), 7.75 (d, J=8.1 Hz, 1H), 6.91 (d, J=8.0 Hz, 1H), 6.15 (d, J=2.7 Hz, 1H), 4.45-4.27 (m, 2H), 2.73 (t, J=10.3 Hz, 1H), 2.58 (dd, J=9.9, 7.1 Hz, 1H), 2.21 (dt, J=11.3, 5.9 Hz, 1H), 1.89 (dd, J=11.9, 5.5 Hz, 1H), 1.62-1.52 (m, 15H), 1.45 (t, J=12.0 Hz, 1H), 1.13-1.06 (m, 4H), 0.83 (d, J=6.5 Hz, 3H).

Synthesis of 6-[3-[[1-(trifluoromethyl)cyclopropyl]methoxy]pyrazol-1-yl]-N-(1,3,5-trimethylpyrazol-4-yl)sulfonyl-2-[(4S)-2,2,4-trimethylpyrrolidin-1-yl]pyridine-3-carboxamide (Compound 16)

Step 1: 2-Chloro-6-[3-[[1-(trifluoromethyl)cyclopropyl]methoxy]pyrazol-1-yl]-N-(1,3,5-trimethylpyrazol-4-yl)sulfonyl-pyridine-3-carboxamide

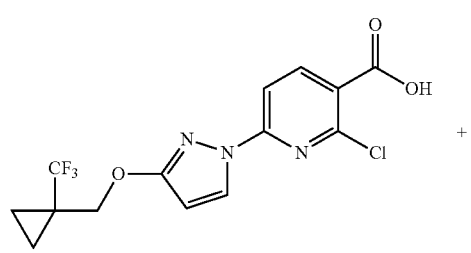

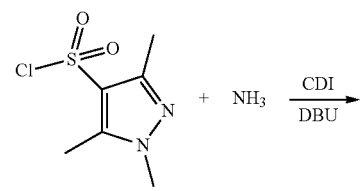

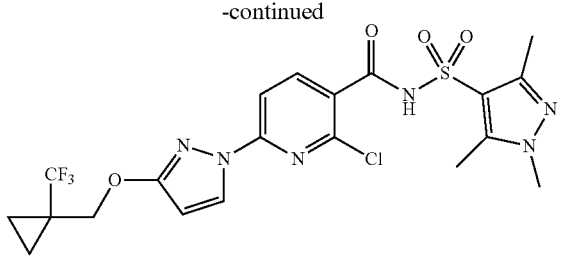

2-Chloro-6-[3-[[1-(trifluoromethyl)cyclopropyl]methoxy]pyrazol-1-yl]pyridine-3-carboxylic acid (100 mg, 0.2682 mmol) and CDI (52 mg, 0.3207 mmol) were combined in THF (582.0 μL) and stirred at room temperature for 2 hours in a vial (vial 1). Meanwhile, 1,3,5-trimethylpyrazole-4-sulfonyl chloride (56 mg, 0.2684 mmol) was combined with ammonia (250 μL of 7 M, 1.750 mmol) (in methanol) in a separate vial (vial 2). After stirring for an additional 20 min, the volatiles were removed from vial 2 by evaporation, and 1 mL of dichloromethane was added to the solid residue, and was also evaporated. DBU (54 μL, 0.3611 mmol) was then added to vial 2 and stirred at 60° C. for 5 minutes (to facilitate the removal of ammonia from any residual ammonium chloride). Upon cooling to room temperature, 1 mL THF was added and then evaporated under reduced pressure. The contents of vial 1 were then added to vial 2 by syringe, and the reaction mixture was stirred for 4 h at room temperature. The reaction mixture was diluted with 10 mL ethyl acetate, and washed with 10 mL 1 M citric acid. The aqueous layer was extracted 2×10 mL ethyl acetate, and the combined organics were washed with brine, dried over sodium sulfate, and concentrated to give a white solid. This material was used in the next step without further purification. 2-chloro-6-[3-[[1-(trifluoromethyl)cyclopropyl]methoxy]pyrazol-1-yl]-N-(1,3,5-trimethylpyrazol-4-yl)sulfonyl-pyridine-3-carboxamide (140 mg, 98%) ESI-MS m/z calc. 532.09076, found 533.1 (M+1)+; Retention time: 0.67 minutes.

Step 2: 6-[3-[[1-(Ttrifluoromethyl)cyclopropyl]methoxy]pyrazol-1-yl]-N-(1,3,5-trimethylpyrazol-4-yl)sulfonyl-2-[(4S)-2,2,4-trimethylpyrrolidin-1-yl]pyridine-3-carboxamide

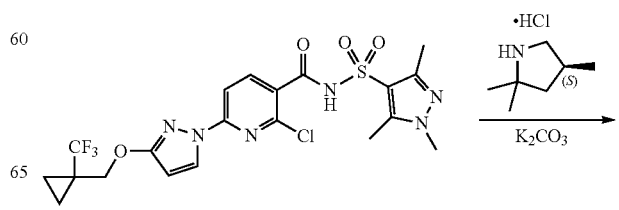

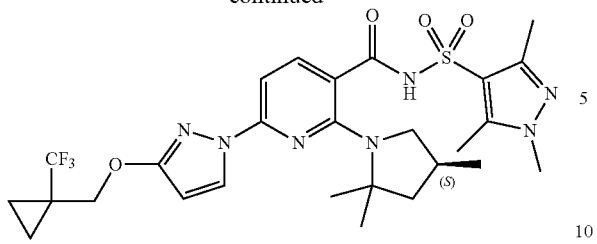

2-Chloro-6-[3-[[1-(trifluoromethyl)cyclopropyl]methoxy]pyrazol-1-yl]-N-(1,3,5-trimethylpyrazol-4-yl)sulfonyl-pyridine-3-carboxamide (140 mg, 0.2627 mmol), (4S)-2,2,4-trimethylpyrrolidine (hydrochloride salt) (118 mg, 0.7884 mmol), and potassium carbonate (219 mg, 1.585 mmol) were combined in DMSO (700.0 µL) and heated at 130° C. for 16 h. The reaction was cooled to room temperature, and 1 mL of water was added. After 15 minutes stirring, the contents of the vial were allowed to settle, the liquid portion was removed by pipet, and the remaining solids were dissolved with 20 mL ethyl acetate, then washed with 15 mL 1 M citric acid. The aqueous and organic layers were separated, and the aqueous layer was extracted two additional times with 15 mL ethyl acetate. The organics were combined, washed with brine, dried over sodium sulfate, and concentrated. The resulting solid was further purified by silica gel chromatography eluting with 0-10% methanol in dichloromethane to give a white solid. 6-[3-[[1-(trifluoromethyl)cyclopropyl]methoxy]pyrazol-1-yl]-N-(1,3,5-trimethylpyrazol-4-yl)sulfonyl-2-[(4S)-2,2,4-trimethylpyrrolidin-1-yl]pyridine-3-carboxamide (77 mg, 48%) ESI-MS m/z calc. 609.2345, found 610.3 (M+1)+; Retention time: 2.07 minutes.

Synthesis of N-(1,5-dimethylpyrazol-4-yl)sulfonyl-6-[3-[(2,2,3,3-tetramethylcyclopropyl)methoxy]pyrazol-1-yl]-2-[(4S)-2,2,4-trimethylpyrrolidin-1-yl]pyridine-3-carboxamide (Compound 21)

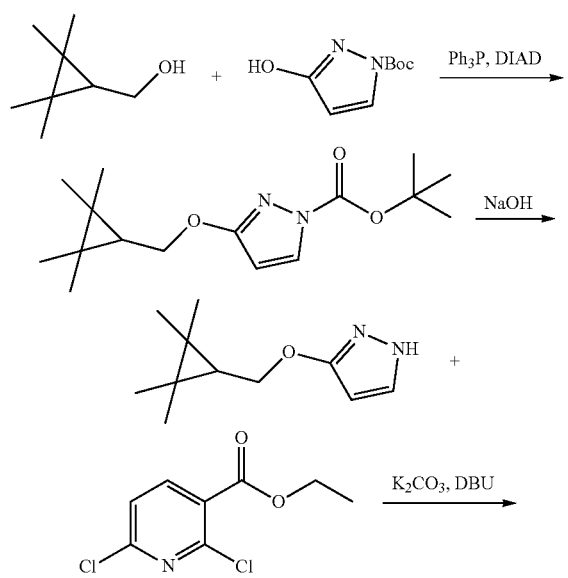

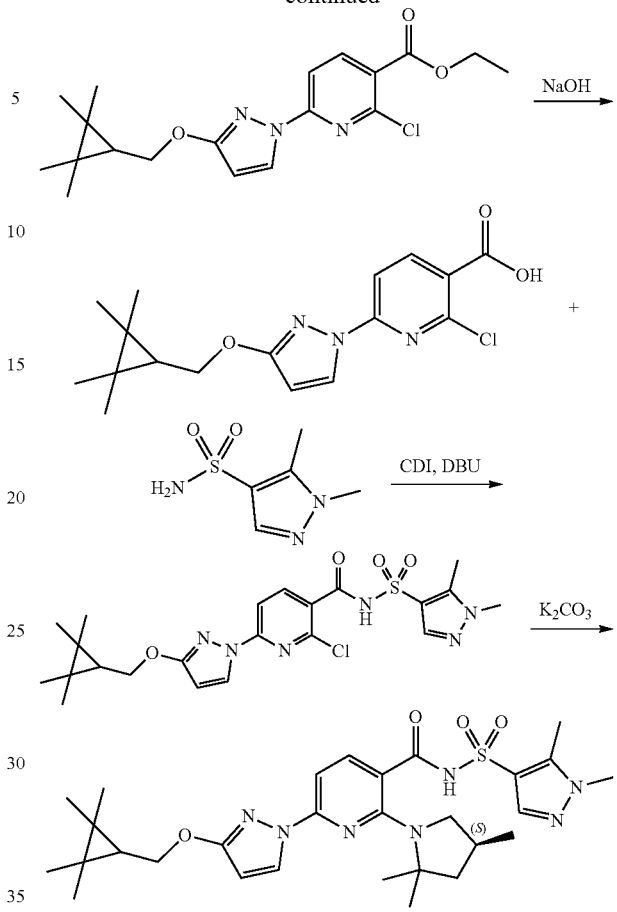

Step 1: tert-Butyl 3-[(2,2,3,3-tetramethylcyclopropyl)methoxy]pyrazole-1-carboxylate

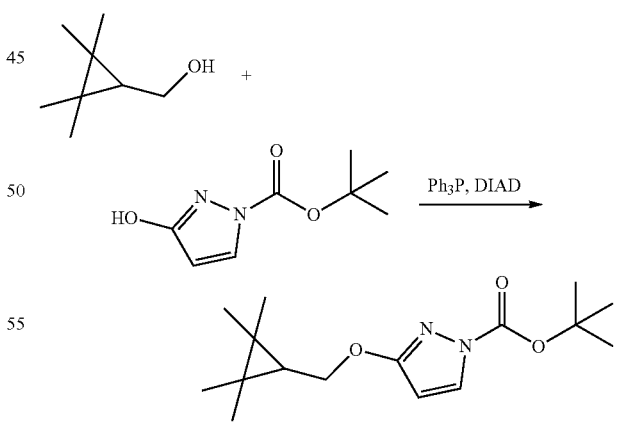

To a degassed solution of triphenyl phosphine (approximately 51.28 g, 195.5 mmol) in toluene (360.0 mL) under nitrogen gas at 0° C. was added DIAD (diisopropylazodicarboxylate) (approximately 39.53 g, 37.86 mL, 195.5 mmol) dropwise. The mixture was stirred at 0° C. for 30 min affording a white slurry. To the mixture was added a solution of (2,2,3,3-tetramethylcyclopropyl)methanol (approximately 29.84 g of 70% w/w, 162.9 mmol) and tert-butyl 3-hydroxypyrazole-1-carboxylate (30 g, 162.9 mmol) in toluene (600.0 mL) dropwise at ~5° C. over 2 hours. The mixture was allowed to warm to ambient temperature and stirred for 18 hours. The mixture was heated to 75° C. for a total of 6 hours and then allowed to cool to ambient temperature. The slurry was diluted with heptane (900.0 mL) and stirred at ambient temperature for 3 hours. The slurry was filtered over Celite, and the precipitate washed 3× with 100 mL of heptane. The filtrate was concentrated in vacuo affording a thick yellow oil. The crude product chromatographed on a 750 gram silica gel column loading with dichloromethane and eluting with a 0-20% EtOAc/hexanes gradient. Collected fractions containing product were concentrated in vacuo affording an off-white solid. tert-butyl 3-[(2,2,3,3-tetramethylcyclopropyl)methoxy]pyrazole-1-carboxylate (30.1 g, 63%) was obtained. $^1$H NMR (400 MHz, Chloroform-d) δ 7.82 (d, J=3.0 Hz, 1H), 5.88 (d, J=2.9 Hz, 1H), 4.30 (d, J=7.7 Hz, 2H), 1.61 (s, 9H), 1.12 (s, 6H), 1.04 (s, 6H), 0.70 (t, J=7.8 Hz, 1H). ESI-MS m/z calc. 294.19434, found 295.0 (M+1)+; Retention time: 2.19 minutes.

Step 2: 3-[(2,2,3,3-Tetramethylcyclopropyl)methoxy]-1H-pyrazole

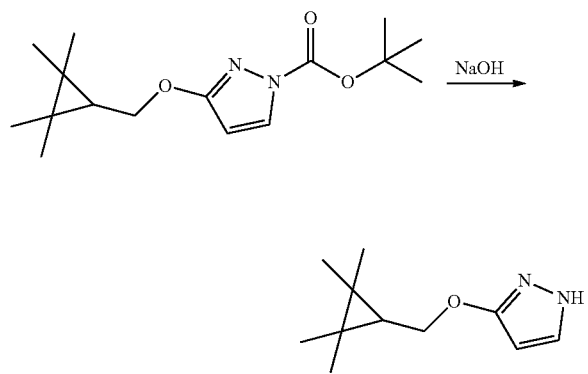

To a solution of tert-butyl 3-[(2,2,3,3-tetramethylcyclopropyl)methoxy]pyrazole-1-carboxylate (127 g, 431.4 mmol) in THF (317.5 mL) and ethyl alcohol (635.0 mL) was slowly added sodium hydroxide (approximately 431.4 mL of 2 M, 862.8 mmol) and stirred at room temperature overnight. Most of the solvent was removed under reduced pressure. The aqueous residue was diluted with water (400 mL) and extracted with methyl t-butyl ether (762.0 mL). The organic phase was washed twice with brine (2×300 mL), and the aqueous phases were back extracted once with methyl t-butyl ether (250 mL). The combined organic phases were dried, filtered and evaporated to give 3-[(2,2,3,3-tetramethylcyclopropyl)methoxy]-1H-pyrazole (75 g, 89%) as a viscous oil. $^1$H NMR (400 MHz, DMSO-$d_6$) δ 11.78 (s, 1H), 7.48 (t, J=2.1 Hz, 1H), 5.65 (s, 1H), 4.05 (d, J=7.7 Hz, 2H), 1.08 (s, 6H), 1.00 (s, 6H), 0.67 (t, J=7.7 Hz, 1H). ESI-MS m/z calc. 194.1419, found 195.0 (M+1)+; Retention time: 1.43 minutes.

Step 3: Ethyl 2-chloro-6-[3-[(2,2,3,3-tetramethylcyclopropyl)methoxy]pyrazol-1-yl]pyridine-3-carboxylate

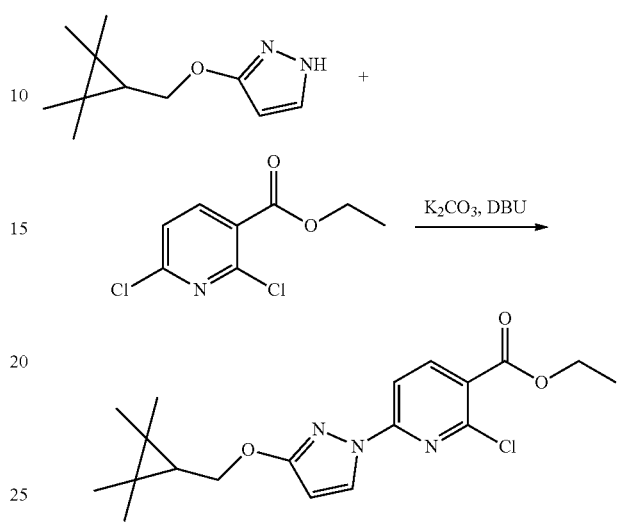

To ethyl 2,6-dichloropyridine-3-carboxylate (16.8 g, 76.35 mmol) and 3-[(2,2,3,3-tetramethylcyclopropyl)methoxy]-1H-pyrazole (approximately 14.83 g, 76.35 mmol) in DMF (201.6 mL) was added potassium carbonate (approximately 13.72 g, 99.26 mmol) followed by DABCO (approximately 1.284 g, 11.45 mmol). The slurry was stirred at ambient temperature for 16 hours. The cream fine suspension was slowly diluted with water (201.6 mL), and the resulting thick slurry was stirred at ambient temperature for 30 minutes with an overhead stirrer. The precipitate was collected using a medium frit and washed 3 times with 25 mL of water. The solid was air dried for 30 minutes, and then dried in vacuo using an EtOAc azeotrope. Ethyl 2-chloro-6-[3-[(2,2,3,3-tetramethylcyclopropyl)methoxy]pyrazol-1-yl]pyridine-3-carboxylate (28.8 g, 100%) was obtained as an off-white solid. ESI-MS m/z calc. 377.1506, found 378.37 (M+1)+; Retention time: 2.47 minutes.

$^1$H NMR (400 MHz, DMSO-$d_6$) δ 8.43 (dd, J=2.9, 0.9 Hz, 1H), 8.39 (dd, J=8.5, 0.9 Hz, 1H), 7.76 (dd, J=8.5, 0.9 Hz, 1H), 6.24 (dd, J=2.9, 0.9 Hz, 1H), 4.34 (td, J=7.5, 6.6 Hz, 2H), 4.28 (d, J=7.8 Hz, 2H), 1.34 (td, J=7.1, 0.9 Hz, 3H), 1.11 (s, 6H), 1.05 (s, 6H), 0.75 (t, J=7.8 Hz, 1H).

Step 4: 2-Chloro-6-[3-[(2,2,3,3-tetramethylcyclopropyl)methoxy]pyrazol-1-yl]pyridine-3-carboxylic acid

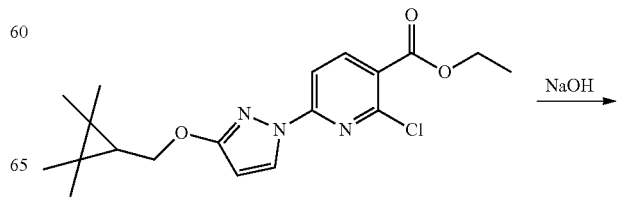

-continued

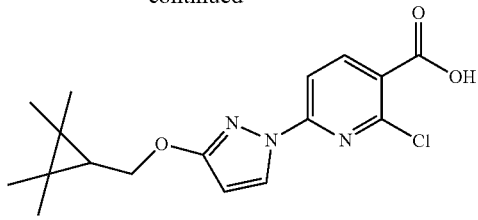

Ethyl 2-chloro-6-[3-[(2,2,3,3-tetramethylcyclopropyl)methoxy]pyrazol-1-yl]pyridine-3-carboxylate (146 g, 386.4 mmol) in THF (730.0 mL) and EtOH (292.0 mL) was treated with NaOH (approximately 772.8 mL of 1 M, 772.8 mmol), and the solution was stirred at room temperature for 5 hours. Most of the solvent was removed under reduced pressure, and the solution was acidified by addition of citric acid (approximately 148.5 g, 89.19 mL, 772.8 mmol) under ice cooling. The formed thick suspension (pH 2-3) was stirred in the ice bath for 1 hour, filtered, washed with plenty of water and dried in a drying cabinet under vacuum at 45° C. with a nitrogen bleed for two days to give 2-chloro-6-[3-[(2,2,3,3-tetramethylcyclopropyl)methoxy]pyrazol-1-yl]pyridine-3-carboxylic acid (128.2 g, 90%) as an off white solid. ESI-MS m/z calc. 349.11932, found 350.0 (M+1)+; Retention time: 2.11 minutes. $^1$H NMR (400 MHz, DMSO-d6) δ 13.64 (s, 1H), 8.69-8.22 (m, 2H), 7.73 (d, J=8.4 Hz, 1H), 6.22 (d, J=2.9 Hz, 1H), 4.28 (d, J=7.8 Hz, 2H), 1.08 (d, J=24.9 Hz, 12H), 0.75 (t, J=7.8 Hz, 1H).

Step 5: 2-Chloro-N-(1,5-dimethylpyrazol-4-yl)sulfonyl-6-[3-[(2,2,3,3-tetramethylcyclopropyl)methoxy]pyrazol-1-yl]pyridine-3-carboxamide

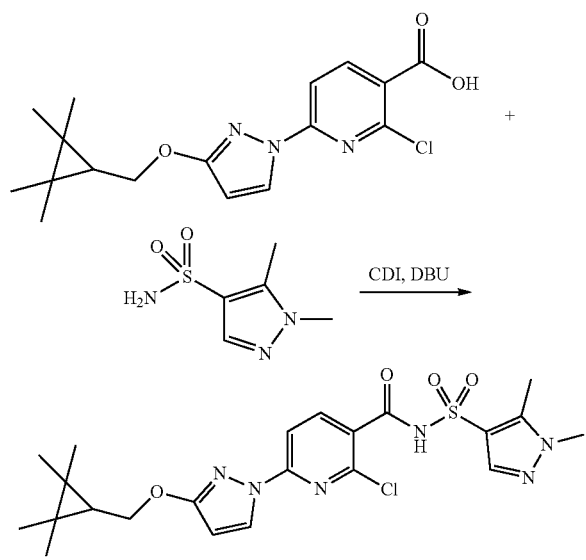

2-Chloro-6-[3-[(2,2,3,3-tetramethylcyclopropyl)methoxy]pyrazol-1-yl]pyridine-3-carboxylic acid (4 g, 11.43 mmol) in THF (40.00 mL) was treated with CDI (approximately 2.225 g, 13.72 mmol), and the cloudy solution was stirred at room temperature for 1 hour. Then 1,5-dimethylpyrazole-4-sulfonamide (approximately 2.225 g, 12.57 mmol), followed by DBU (approximately 2.089 g, 2.052 mL, 13.72 mmol) was added, and the formed thick suspension was stirred at room temperature for 4.5 hours. The suspension was treated with cold citric acid (approximately 60.01 mL of 1 M, 60.01 mmol) (pH~2) to give an emulsion, which started to precipitate some solid. Most of the THF was removed under reduced pressure, and the solid collected by filtration, washed with plenty of water, and dried. The crude solid was absorbed on silica gel and purified by chromatography over silica gel (220 g) with a linear gradient of dichloromethane to 10% methanol in dichloromethane. Product fractions were evaporated and dried to give 2-chloro-N-(1,5-dimethylpyrazol-4-yl)sulfonyl-6-[3-[(2,2,3,3-tetramethylcyclopropyl)methoxy]pyrazol-1-yl]pyridine-3-carboxamide (5 g, 86%). ESI-MS m/z calc. 506.1503, found 507.0 (M+1)+; Retention time: 2.9 minutes.

$^1$H NMR (400 MHz, DMSO-d6) δ 8.39 (d, J=2.9 Hz, 1H), 8.07 (d, J=8.3 Hz, 1H), 7.84 (s, 1H), 7.70 (d, J=8.3 Hz, 1H), 6.21 (d, J=2.9 Hz, 1H), 4.27 (d, J=7.8 Hz, 2H), 3.82 (s, 3H), 2.52 (s, 3H), 1.10 (s, 6H), 1.04 (s, 6H), 0.74 (t, J=7.8 Hz, 1H).

Step 6: N-(1,5-Dimethylpyrazol-4-yl)sulfonyl-6-[3-[(2,2,3,3-tetramethylcyclopropyl)methoxy]pyrazol-1-yl]-2-[(4S)-2,2,4-trimethylpyrrolidin-1-yl]pyridine-3-carboxamide

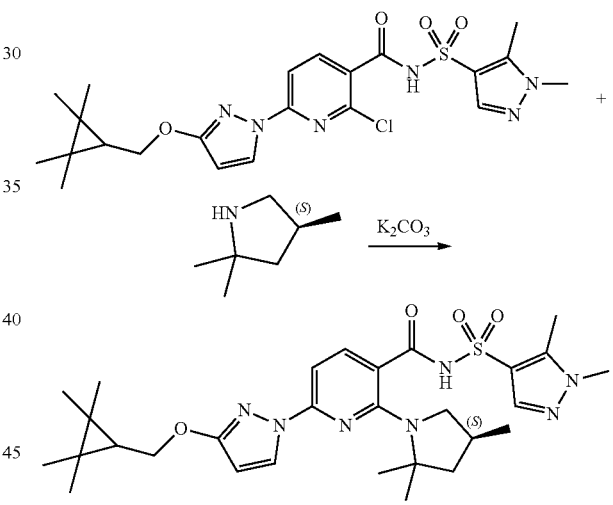

2-Chloro-N-(1,5-dimethylpyrazol-4-yl)sulfonyl-6-[3-[(2,2,3,3-tetramethylcyclopropyl)methoxy]pyrazol-1-yl]pyridine-3-carboxamide (4.9 g, 9.665 mmol) in NMP (24.50 mL) and 1,2-diethoxyethane (4.900 mL) was treated with potassium carbonate (approximately 6.678 g, 48.32 mmol) followed by careful addition of (4S)-2,2,4-trimethylpyrrolidine (hydrochloride salt) (approximately 3.182 g, 21.26 mmol). The suspension was cycled 3 times vacuum/nitrogen and heated at 130° C. (oilbath) under nitrogen for 16 hours. Then another portion of (4S)-2,2,4-trimethylpyrrolidine (hydrochloride salt) (1 g, 6.682 mmol) was added, and the suspension was heated at 130° C. (oilbath) under nitrogen for another 3 hours. The warm suspension was slowly added to a vigorously stirred solution of acetic acid (approximately 8.708 g, 8.246 mL, 145.0 mmol) in water (147.0 mL) (off gasing, foaming), stirred at room temperature for 1 h, filtered and washed with plenty of water. The solid was dissolved in dichloromethane, dried over magnesium sulfate, filtered and evaporated. The crude product was purified by chromatography over silica gel (220 g, solid load) with a linear gradient of DCM to 5% methanol in dichloromethane. Product fractions were evaporated to give 4.9 g of a yellow foam. The compound was dissolved in DMSO (12 ml) and methanol (12 mL) and water (8 mL) was added slowly resulting in crystallization. Heated again and diluted with more methanol (~30 ml) and the thick hot suspension was left stirring at room temperature for 1 h. The solid was collected by filtration, washed with cold methanol/water 4:1, plenty of cold water and dried under vacuum in a drying cabinet at 45° C. with a nitrogen bleed over the weekend to give N-(1,5-dimethylpyrazol-4-yl)sulfonyl-6-[3-[(2,2,3,3-tetramethylcyclopropyl)methoxy]pyrazol-1-yl]-2-[(4S)-2,2,4-trimethylpyrrolidin-1-yl]pyridine-3-carboxamide (3.12 g, 55%) as an off white solid. ESI-MS m/z calc. 583.29407, found 584.0 (M+1)+; Retention time: 3.39 minutes.

¹H NMR (400 MHz, DMSO-d6) δ 12.32 (s, 1H), 8.19 (d, J=2.8 Hz, 1H), 7.78 (s, 1H), 7.73 (d, J=8.2 Hz, 1H), 6.90 (d, J=8.2 Hz, 1H), 6.13 (d, J=2.8 Hz, 1H), 4.23 (d, J=7.8 Hz, 2H), 3.78 (s, 3H), 2.53 (s, 4H), 2.40 (dd, J=10.2, 7.1 Hz, 1H), 2.18 (tt, J=12.4, 6.6 Hz, 1H), 1.87 (dd, J=11.9, 5.6 Hz, 1H), 1.55 (d, J=15.2 Hz, 6H), 1.43 (t, J=12.1 Hz, 1H), 1.10 (s, 6H), 1.04 (s, 6H), 0.80 (d, J=6.2 Hz, 3H), 0.73 (t, J=7.8 Hz, 1H).

Synthesis of N-(1,3-dimethylpyrazol-4-yl)sulfonyl-6-[3-[(2,2,3,3-tetramethylcyclopropyl)methoxy]pyrazol-1-yl]-2-[(4S)-2,2,4-trimethylpyrrolidin-1-yl]pyridine-3-carboxamide (Compound 20)

Step 1: 2-Chloro-N-(1,3-dimethylpyrazol-4-yl)sulfonyl-6-[3-[(2,2,3,3-tetramethylcyclopropyl)methoxy]pyrazol-1-yl]pyridine-3-carboxamide

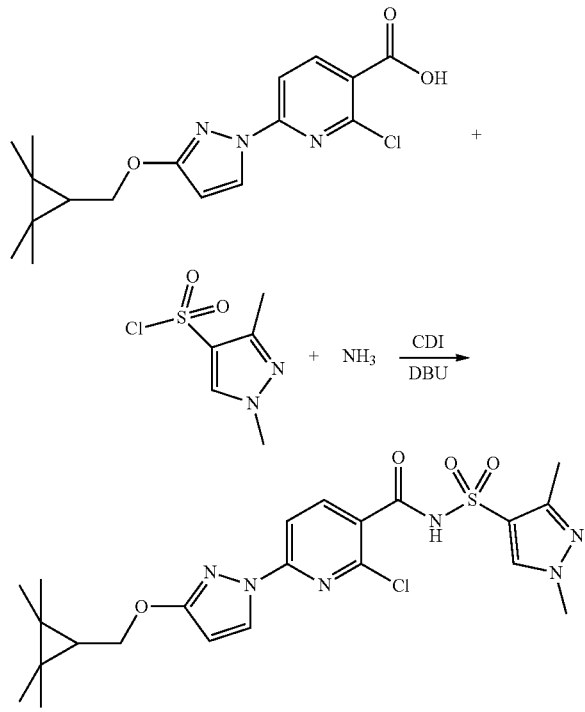

2-Chloro-6-[3-[(2,2,3,3-tetramethylcyclopropyl)methoxy]pyrazol-1-yl]pyridine-3-carboxylic acid (100 mg, 0.2773 mmol) and CDI (54 mg, 0.3330 mmol) were combined in THF (500 µL) and stirred at room temperature for 2 hours in a vial (vial 1). Meanwhile, 1,3-dimethylpyrazole-4-sulfonyl chloride (64 mg, 0.3288 mmol) was combined with ammonia (260 µL of 7 M, 1.820 mmol) (in methanol) in a separate vial (vial 2). After stirring for an additional 20 min, the volatiles were removed from vial 2 by evaporation, and 1 mL of dichloromethane was added to the solid residue, and was also evaporated. DBU (100 µL, 0.6687 mmol) was then added to vial 2 and stirred at 60° C. for 5 minutes (to facilitate the removal of ammonia from any residual ammonium chloride). Upon cooling to room temperature, 1 mL THF was added and then evaporated under reduced pressure. The contents of vial 1 were then added to vial 2 by syringe, and the reaction mixture was stirred for 4 h at room temperature. The reaction mixture was diluted with 10 mL ethyl acetate, and washed with 10 mL 1 M citric acid. The aqueous layer was extracted 2×10 mL ethyl acetate, and the combined organics were washed with brine, dried over sodium sulfate, and concentrated to give a white solid. This material was used in the next step without further purification. 2-chloro-N-(1,3-dimethylpyrazol-4-yl)sulfonyl-6-[3-[(2,2,3,3-tetramethylcyclopropyl)methoxy]pyrazol-1-yl]pyridine-3-carboxamide (133 mg, 95%) ESI-MS m/z calc. 506.1503, found 507.2 (M+1)+; Retention time: 0.75 minutes.

Step 2: N-(1,3-Dimethylpyrazol-4-yl)sulfonyl-6-[3-[(2,2,3,3-tetramethylcyclopropyl)methoxy]pyrazol-1-yl]-2-[(4S)-2,2,4-trimethylpyrrolidin-1-yl]pyridine-3-carboxamide

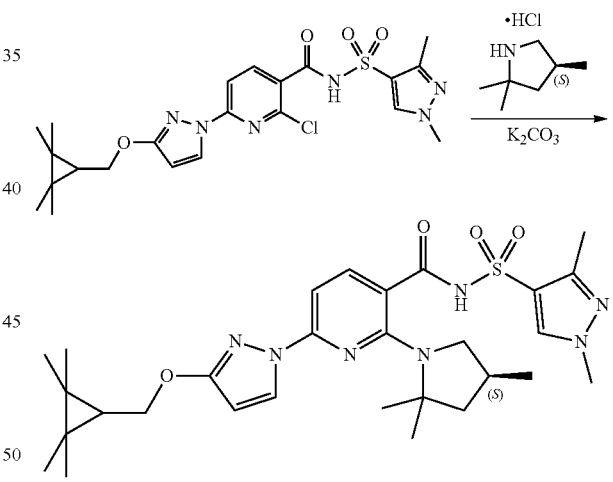

2-Chloro-N-(1,3-dimethylpyrazol-4-yl)sulfonyl-6-[3-[(2,2,3,3-tetramethylcyclopropyl)methoxy]pyrazol-1-yl]pyridine-3-carboxamide (131 mg, 0.2584 mmol), (4S)-2,2,4-trimethylpyrrolidine (hydrochloride salt) (approximately 116.0 mg, 0.7752 mmol), and potassium carbonate (approximately 214.8 mg, 1.554 mmol) were combined in DMSO (444.6 µL) and heated at 130° C. for 16 h. The reaction was cooled to room temperature, and 1 mL of water was added. After 15 minutes stirring, the contents of the vial were allowed to settle, the liquid portion was removed by pipet, and the remaining solids were dissolved with 20 mL ethyl acetate, then washed with 15 mL 1 M citric acid. The aqueous and organic layers were separated, and the aqueous layer was extracted two additional times with 15 mL ethyl acetate. The organics were combined, washed with brine, dried over sodium sulfate and concentrated. The resulting solid was purified by silica gel chromatography eluting with 0-10% methanol in dichloromethane to give a white solid. The resulting material was further purified by a second round of silica gel chromatography with a gradient of 0-100% ethyl acetate in dichloromethane, to give a white solid. N-(1,3-dimethylpyrazol-4-yl)sulfonyl-6-[3-[(2,2,3,3-tetramethylcyclopropyl)methoxy]pyrazol-1-yl]-2-[(4S)-2,2,4-trimethylpyrrolidin-1-yl]pyridine-3-carboxamide (31 mg, 21%) ESI-MS m/z calc. 583.29407, found 584.4 (M+1)+; Retention time: 2.29 minutes.

$^1$H NMR (400 MHz, DMSO) δ 12.35 (s, 1H), 8.37 (s, 1H), 8.19 (d, J=2.7 Hz, 1H), 7.73 (d, J=8.2 Hz, 1H), 6.91 (d, J=8.2 Hz, 1H), 6.13 (d, J=2.7 Hz, 1H), 4.24 (d, J=7.7 Hz, 2H), 3.80 (s, 3H), 2.56 (d, J=10.5 Hz, 1H), 2.42 (q, J=9.1 Hz, 1H), 2.32 (s, 3H), 2.19 (dt, J=11.9, 6.1 Hz, 1H), 1.87 (dd, J=11.8, 5.5 Hz, 1H), 1.55 (d, J=11.0 Hz, 6H), 1.42 (t, J=12.1 Hz, 1H), 1.10 (s, 6H), 1.04 (d, J=0.9 Hz, 6H), 0.81 (d, J=6.2 Hz, 3H), 0.73 (t, J=7.7 Hz, 1H).

Synthesis of N-(1,3-dimethylpyrazol-4-yl)sulfonyl-6-[3-[2-(trifluoromethyl)cyclopropoxy]pyrazol-1-yl]-2-[(4S)-2,2,4-trimethylpyrrolidin-1-yl]pyridine-3-carboxamide (mixture of cis isomers) (Compound 34)

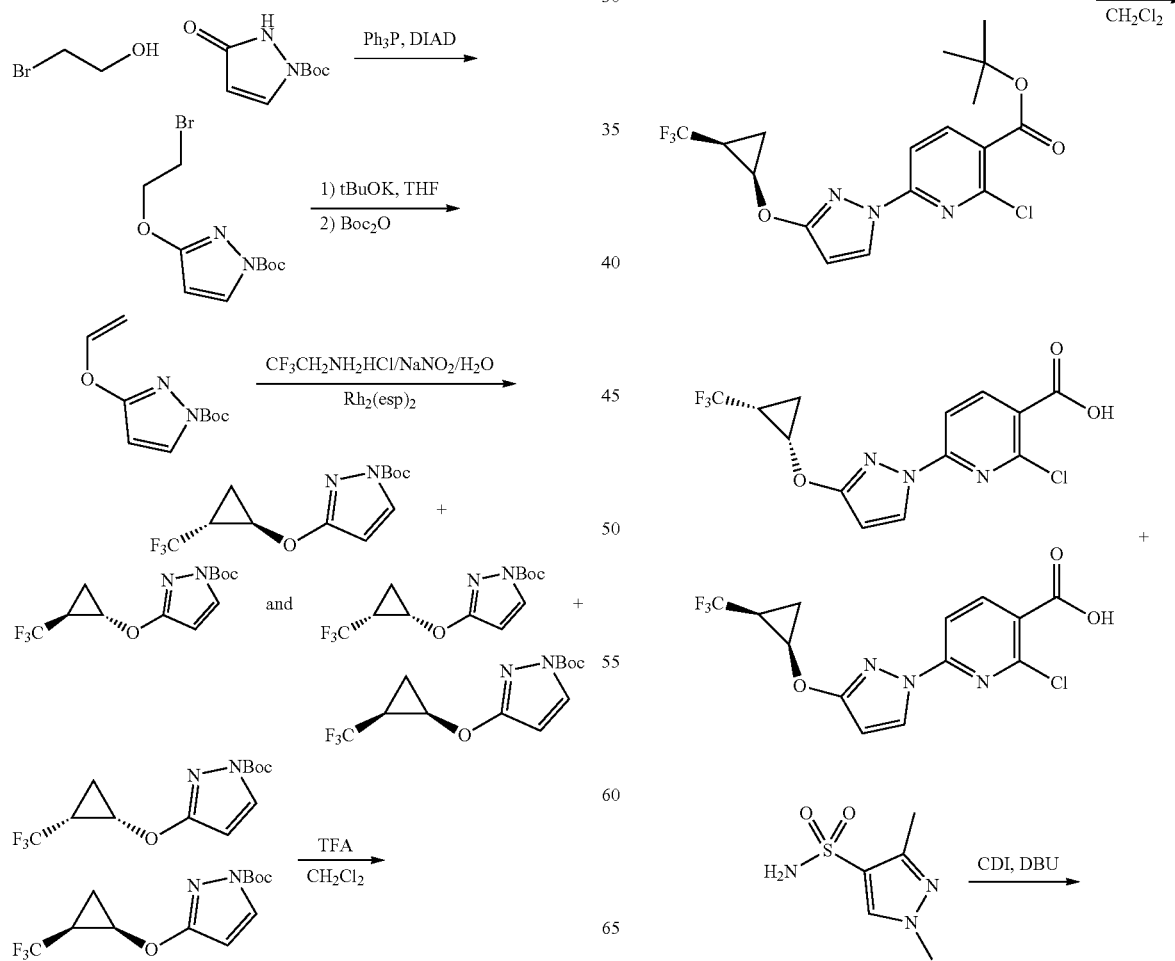

185

-continued

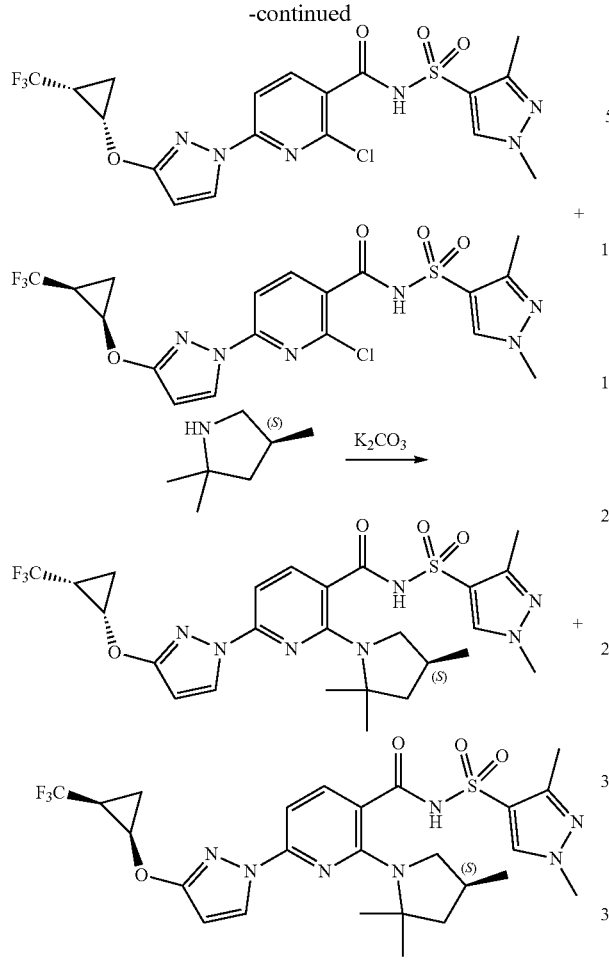

Step 1: tert-Butyl
3-(2-bromoethoxy)-1H-pyrazole-1-carboxylate

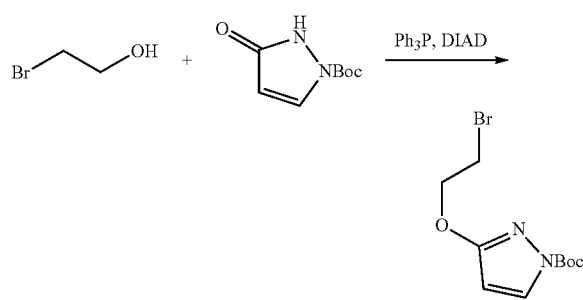

To the solution of 2-bromoethanol (1.69 g, 13.53 mmol), tert-butyl-2,3-dihydro-3-oxopyrazole-1-carboxylate (2.08 g, 11.28 mmol) and triphenylphosphine (3.55 g, 13.53 mmol) in anhydrous tetrahydrofuran (45 mL) at 0° C., diisopropyl azodicarboxylate (2.74 g, 13.53 mmol) was added dropwise. After the addition was complete, the reaction solution was stirred at 0° C. for 1 hour, then warmed up to room temperature and stirred for additional 2 hours. Ether (400 mL) was added. The organic solution was washed with saturated sodium carbonate aqueous solution (80 mL), brine (50 mL), then dried over magnesium sulfate, filtered and

186 concentrated under reduced pressure. The residue obtained was purified by silica gel chromatography using hexanes-ethyl acetate gradient method (0 to 15% ethyl acetate) to afford tert-butyl 3-(2-bromoethoxy)-1H-pyrazole-1-carboxylate (2.56 g, 78%) as white solid.

$^1$H NMR (250 MHz, CDCl$_3$) δ (ppm): 7.85 (d, J=3.0 Hz, 1H), 5.92 (d, J=3.0 Hz, 1H), 4.63 (t, J=6.0 Hz, 2H), 3.68 (t, J=6.0 Hz, 2H), 1.64 (s, 9H). ESI-MS m/z calc. 292.0 found 292.9 (M+1)$^+$. Retention time: 4.91 minutes.

Step 2: tert-Butyl
3-(vinyloxy)-1H-pyrazole-1-carboxylate

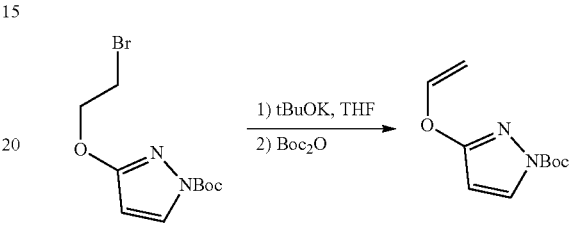

To the solution of tert-butyl 3-(2-bromoethoxy)-1H-pyrazole-1-carboxylate (2.52 g, 8.66 mmol) in anhydrous tetrahydrofuran (90 mL) was added potassium tert-butoxide (1.46 g, 13.0 mmol). The resulting solution was stirred for 2 hours, then di-tert-butyl dicarbonate (5.67 g, 26.0 mmol) was added, and the reaction was stirred for another 1 hour. Diethyl ether (400 mL) was added. Organic layers were washed with water (50 mL), brine (2×50 mL), dried over dried over magnesium sulfate, filtered and concentrated under reduced pressure. The residue obtained was purified by silica gel chromatography using hexanes-ethyl acetate gradient method (0 to 10% ethyl acetate) to afford tert-butyl 3-(vinyloxy)-1H-pyrazole-1-carboxylate (1.10 g, 60%) as colorless oil.

$^1$H NMR (250 MHz, CDCl$_3$) δ (ppm): 7.89 (d, J=3.0 Hz, 1H), 7.24 (dd, J=6, 13.5 Hz, 1H), 5.95 (d, J=3.0 Hz, 1H), 4.88 (dd, J=1.8, 13.5 Hz, 1H), 4.50 (dd, J=1.8, 6.0 Hz, 1H), 1.62 (s, 9H). ESI-MS m/z calc. 210.1 found 211.0 (M+1)$^+$. Retention time: 4.74 minutes.

Step 3: tert-Butyl 3-((cis)-2-(trifluoromethyl)cyclo-propoxy)-1H-pyrazole-1-carboxylate and tert-butyl 3-((trans)-2-(trifluoromethyl)cyclopropoxy)-1H-pyrazole-1-carboxylate

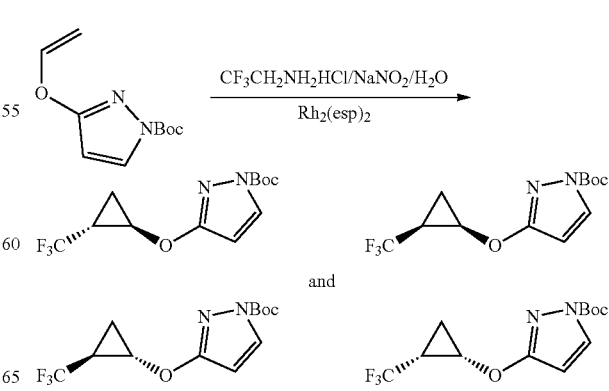

tert-Butyl 3-(vinyloxy)-1H-pyrazole-1-carboxylate (1.10 g, 5.23 mmol) in pear-shape flask (100 mL) was added water (20 mL) and bubbled with argon for 5 minutes, then sodium acetate (85.8 mg, 1.05 mmol) was added followed by 2,2,2-trifluoroethylamine hydrochloride (3.57 g, 26.17 mmol) and concentrated sulfuric acid (51.3 mg, 0.523 mmol). The solution was bubbled with argon for another 5 minutes before bis[rhodium(α,α,α',α'-tetramethyl-1,3-benzenedipropionic acid)] (397 mg, 0.523 mmol) was added. The reaction solution was kept under argon with balloon while aqueous solution of sodium nitrite (2.17 g, 31.4 mmol) in water (12.8 mL) was added by syringe pump within 10 hours. After the addition was complete, the resulting solution was stirred for an additional 6 hours. Diethyl ether (300 mL) was added and the organic layer was separated. Then organic layer was washed with brine (30 mL), dried over magnesium sulfate, filtered and concentrated under reduced pressure. The residue obtained was purified by silica gel chromatography using hexanes-dichloromethane gradient method (0 to 100% dichloromethane). The residue obtained was subjected to silica gel chromatography again (hexanes and ethyl acetate, 0 to 10% ethyl acetate gradient) to afford the cis and trans isomers.

tert-butyl 3-((trans)-2-(trifluoromethyl)cyclopropoxy)-1H-pyrazole-1-carboxylate: (366 mg, 24%). ESI-MS m/z calc. 292.1 found 293.1 (M+1)$^+$. Retention time: 5.22 minutes.

$^1$H NMR (250 MHz, CDCl$_3$) δ (ppm): 7.84 (d, J=2.8 Hz, 1H), 5.91 (d, J=2.8 Hz, 1H), 4.49 (m, 1H), 1.75 (m, 1H), 1.62 (s, 9H), 1.56-1.25 (m, 2H). tert-butyl 3-(1,2-cis-2-tert-butyl 3-((cis)-2-(trifluoromethyl)cyclopropoxy)-1H-pyrazole-1-carboxylate: (314 mg, 21%). ESI-MS m/z calc. 292.1 found 293.1 (M+1)$^+$. Retention time: 5.48 minutes.

$^1$H NMR (250 MHz, CDCl$_3$) δ (ppm): 7.90 (d, J=2.8 Hz, 1H), 5.92 (d, J=2.8 Hz, 1H), 4.49 (m, 1H), 1.94 (m, 1H), 1.62 (s, 9H), 1.30 (m, 2H).

Step 4: 3-((cis)-2-(Trifluoromethyl)cyclopropoxy)-1H-pyrazole

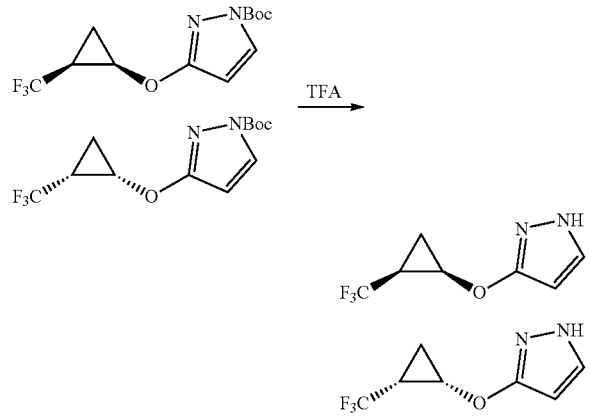

Trifluoroacetic acid (2.76 g, 24.3 mmol) was added to the solution of tert-butyl 3-((cis)-2-(trifluoromethyl)cyclopropoxy)-1H-pyrazole-1-carboxylate (708 mg, 2.43 mmol) in anhydrous dichloromethane (24 mL). The resulting solution was stirred at room temperature for 16 hours. 1,2-Dichloroethane (10 mL) was added to the reaction solution. All the solvents were removed under reduced pressure. The residue obtained was dissolved in ethyl ether (150 mL), washed with saturated sodium bicarbonate aqueous solution (30 mL). The organic solution was dried over magnesium sulfate, filtered and concentrated under the reduced pressure to afford crude 3-((cis)-2-(trifluoromethyl)cyclopropoxy)-1H-pyrazole (461 mg, 99%) as yellow-brown oil. The crude product was used directly in next step without any further purification. ESI-MS m/z calc. 192.1 found 193.0 (M+1)$^+$. Retention time: 3.26 minutes.

Step 5: tert-Butyl 2-chloro-6-(3-((cis)-2-(trifluoromethyl)cyclopropoxy)-1H-pyrazol-1-yl)nicotinate

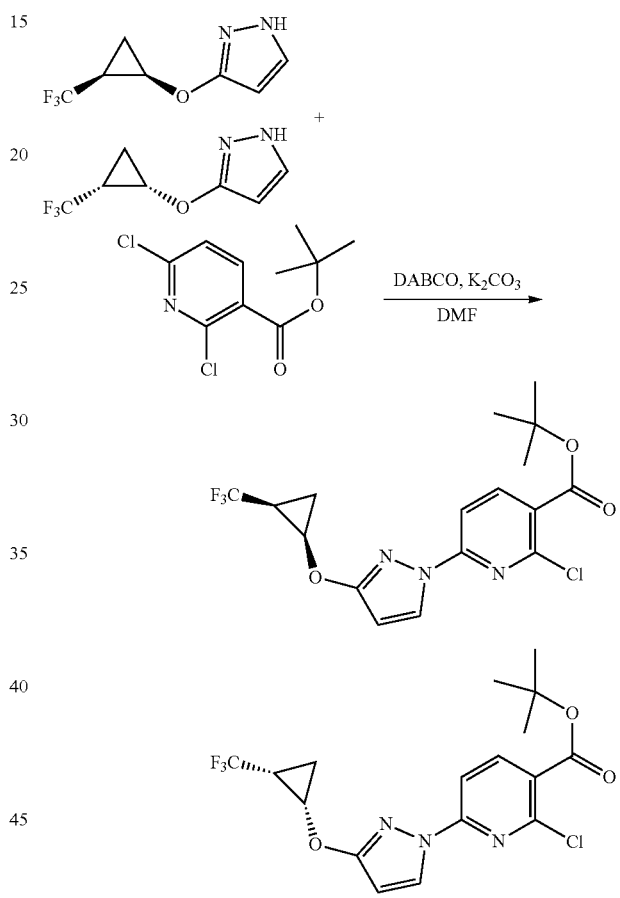

To the solution of crude 3-((cis)-2-(trifluoromethyl)cyclopropoxy)-1H-pyrazole (461 mg, 2.43 mmol) in dimethylformamide (8 mL) was added tert-butyl 2,6-dichloropyridine-3-carboxylate (659 mg, 2.67 mmol), potassium carbonate (669 mg, 4.85 mmol) and 1,4-diazabicyclo[2.2.2]octane (55 mg, 0.49 mmol). The reaction was stirred at room temperature for 48 hours. The reaction solution was diluted with ether (200 mL), washed with water (4×20 mL) and brine (20 mL). The organic layer was dried over magnesium sulfate, filtered and concentrated under reduced pressure. The residue obtained was purified by silica gel chromatography using hexanes—dichloromethane gradient method (0 to 100% dichloromethane) to afford tert-butyl 2-chloro-6-(3-((cis)-2-(trifluoromethyl)cyclopropoxy)-1H-pyrazol-1-yl)nicotinate (731 mg, 68%) as a white solid.

$^1$H NMR (250 MHz, CDCl$_3$) δ (ppm): 8.39 (d, J=2.8 Hz, 1H), 8.22 (d, J=8.5 Hz, 1H), 7.74 (d, J=8.5 Hz, 1H), 6.01 (d, J=2.8 Hz, 1H), 4.33 (m, 1H), 1.93 (m, 1H), 1.62 (s, 9H), 1.45-1.26 (m, 2H). ESI-MS m/z calc. 403.1 found 404.1 (M+1)+. Retention time: 7.29 minutes.

Step 6: 2-Chloro-6-(3-((cis)-2-(trifluoromethyl)cyclopropoxy)-1H-pyrazol-1-yl)nicotinic acid

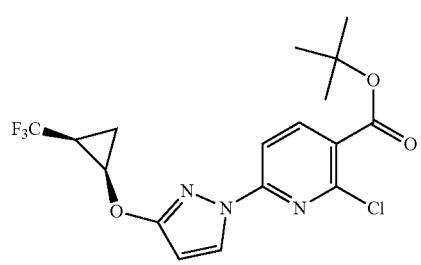

TFA →

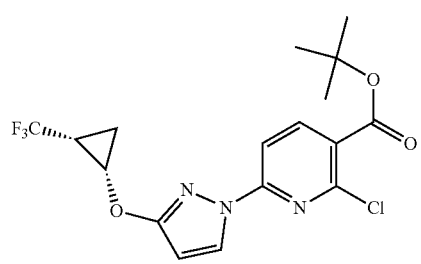

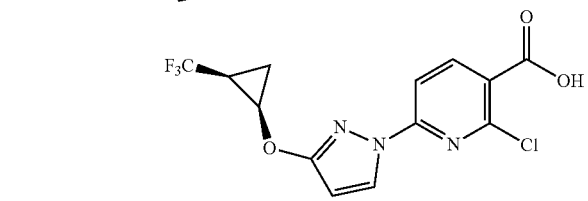

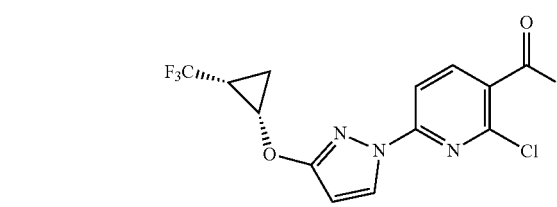

Trifluoroacetic acid (2.03 g, 17.8 mmol) was added to the solution of tert-butyl 2-chloro-6-(3-((cis)-2-(trifluoromethyl)cyclopropoxy)-1H-pyrazol-1-yl)nicotinate (718 mg, 1.78 mmol) in anhydrous dichloromethane (18 mL). The resulting solution was stirred at room temperature for 16 hours. 1,2-Dichloroethane (10 mL) was added to the reaction solution. All the solvents were removed under the reduced pressure. The crude solid obtained was added 10% ethyl ether in hexanes (25 mL) and sonicated for 30 minutes, filtered, washed with 10% ethyl ether in hexanes (10 ml), hexances (10 mL) and dried under high vacuum to afford 2-chloro-6-(3-((cis)-2-(trifluoromethyl)cyclopropoxy)-1H-pyrazol-1-yl)nicotinic acid (517 mg, 84%) as a white solid. $^1$H NMR (500 MHz, DMSO) δ (ppm): 13.6 (bs, 1H), 8.47 (d, J=3.0 Hz, 1H), 8.42 (d, J=8.8 Hz, 1H), 7.72 (d, J=8.8 Hz, 1H), 6.27 (d, J=3.0 Hz, 1H), 4.46 (m, 1H), 2.40 (m, 1H), 1.47 (m, 1H), 1.32 (m, 1H). ESI-MS m/z calc. 347.0 found 347.9 (M+1)+. Retention time: 5.20 minutes.

Step 7: 2-Chloro-N-((1,3-dimethyl-1H-pyrazol-4-yl)sulfonyl)-6-(3-((cis)-2-(trifluoromethyl)cyclopropoxy)-1H-pyrazol-1-yl)nicotinamide

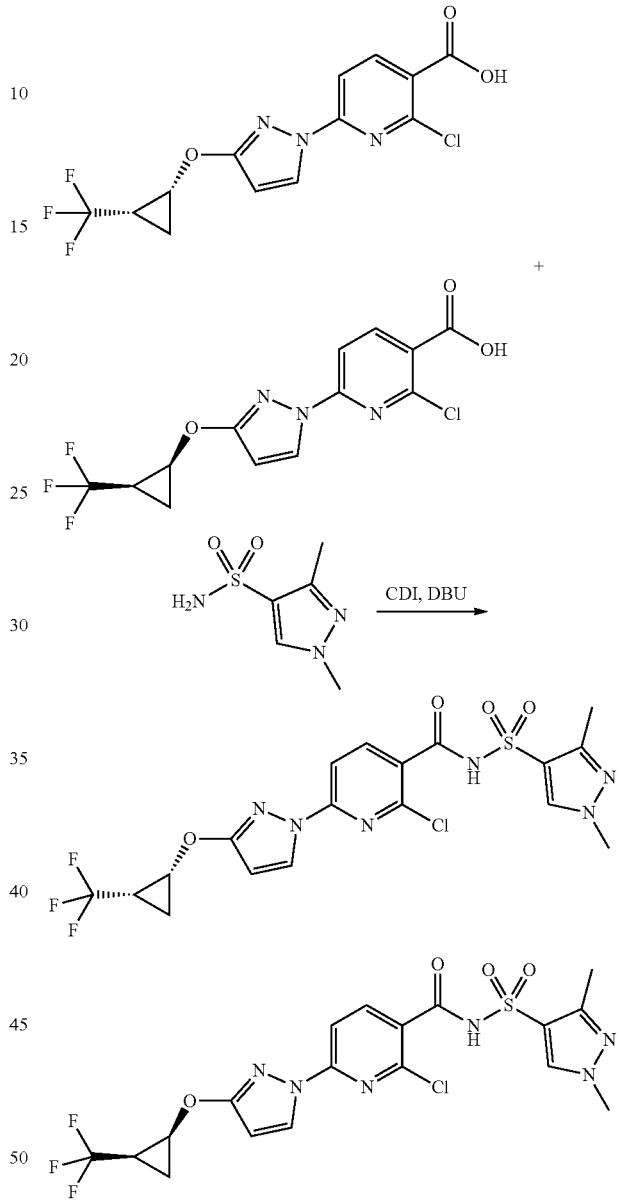

2-Chloro-6-(3-((cis)-2-(trifluoromethyl)cyclopropoxy)-1H-pyrazol-1-yl)nicotinic acid (125 mg, 0.3595 mmol) was dissolved in THF (1 mL). Di(imidazol-1-yl)methanone (approximately 69.95 mg, 0.4314 mmol) was added. The reaction mixture was allowed to stir at room temperature for 1 hour. 1,3-Dimethylpyrazole-4-sulfonamide (approximately 75.59 mg, 0.4314 mmol) was added followed by DBU (approximately 65.67 mg, 64.51 μL, 0.4314 mmol). The final reaction mixture was allowed to stir overnight at room temperature. Volatiles were removed by evaporation. It was taken up in EtOAc (50 mL) and washed with aqueous 1 M citric acid solution (2×50 mL) and brine (1×50 mL). The organic layer was dried over sodium sulfate, filtered, and concentrated under reduced pressure to give 2-chloro-N-((1, 3-dimethyl-1H-pyrazol-4-yl)sulfonyl)-6-(3-((cis)-2-(trifluoromethyl)cyclopropoxy)-1H-pyrazol-1-yl)nicotinamide (210 mg). ESI-MS m/z calc. 504.05945, found 505.0 (M+1)+; Retention time: 0.61 minutes.

Step 8: N-(1,3-Dimethylpyrazol-4-yl)sulfonyl-6-[3-[2-(trifluoromethyl)cyclopropoxy]pyrazol-1-yl]-2-[(4S)-2,2,4-trimethylpyrrolidin-1-yl]pyridine-3-carboxamide (mixture of cis isomers)

2-Chloro-N-((1,3-dimethyl-1H-pyrazol-4-yl)sulfonyl)-6-(3-((cis)-2-(trifluoromethyl)cyclopropoxy)-1H-pyrazol-1-yl)nicotinamide (181.5 mg, 0.3595 mmol) was dissolved in DMSO (1 mL). (4S)-2,2,4-trimethylpyrrolidine (hydrochloride salt) (approximately 161.3 mg, 1.078 mmol) was added followed by potassium carbonate (approximately 298.1 mg, 2.157 mmol). The reaction mixture was allowed to stir at 130° C. overnight. After cooling to room temperature, the reaction mixture was diluted with EtOAc (50 mL) and washed with aqueous citric acid (1 M, 2×50 mL) and brine (1×50 mL). The organic layer was dried over sodium sulfate, filtered and concentrated under reduced pressure. The product was isolated by silica gel column chromatography on a 12 gram silica gel column eluting with a 0-10% EtOAc/hexane gradient to give N-(1,3-dimethylpyrazol-4-yl)sulfonyl-6-[3-[2-(trifluoromethyl)cyclopropoxy]pyrazol-1-yl]-2-[(4S)-2,2,4-trimethylpyrrolidin-1-yl]pyridine-3-carboxamide (mixture of cis isomers) (128.4 mg) ESI-MS m/z calc. 581.2032, found 582.3 (M+1)+; Retention time: 1.93 minutes.

Synthesis of N-(1,3-dimethylpyrazol-4-yl)sulfonyl-6-[3-[2-(trifluoromethyl)cyclopropoxy]pyrazol-1-yl]-2-[(4S)-2,2,4-trimethylpyrrolidin-1-yl]pyridine-3-carboxamide (mixture of trans isomers)
(Compound 35)

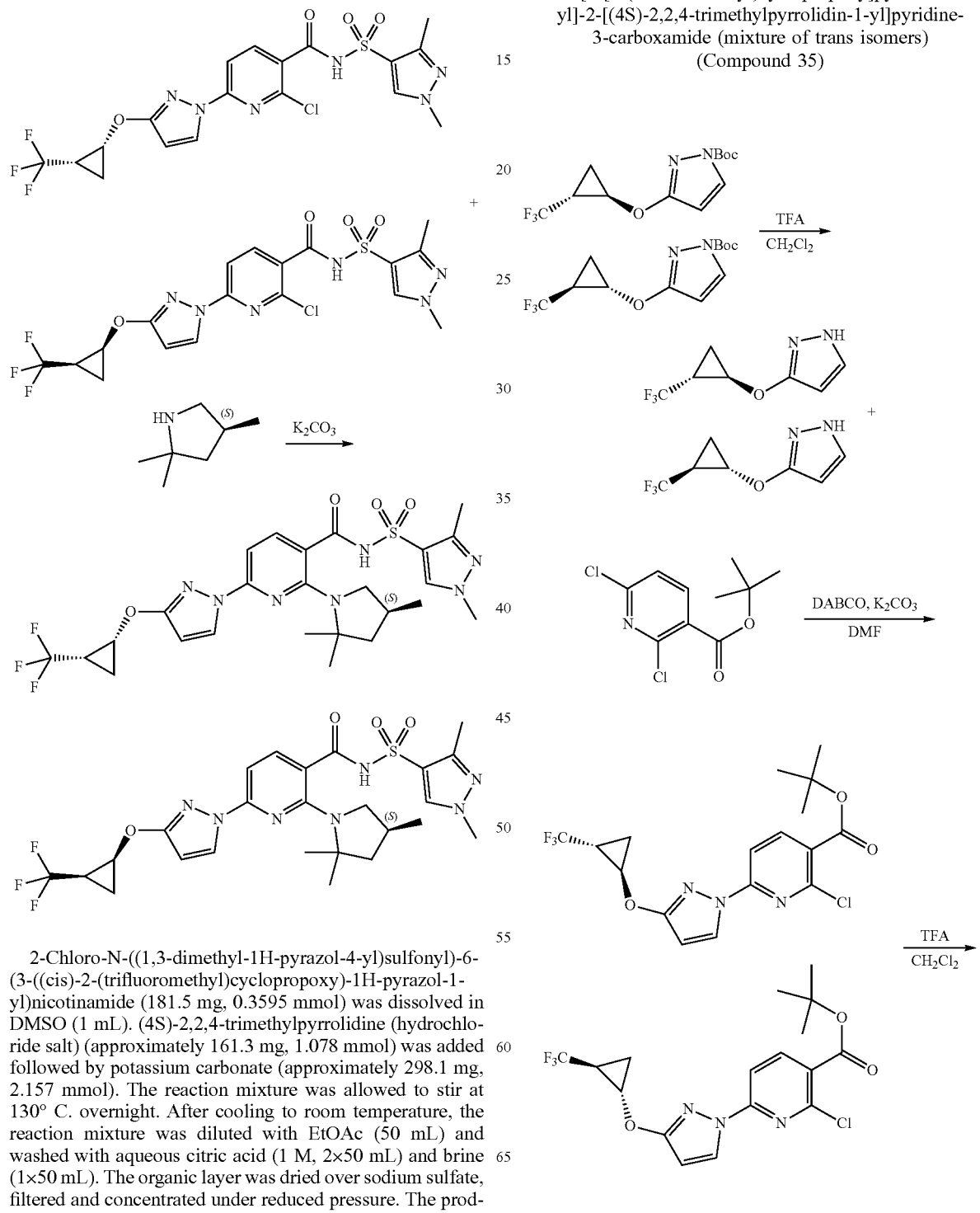

-continued

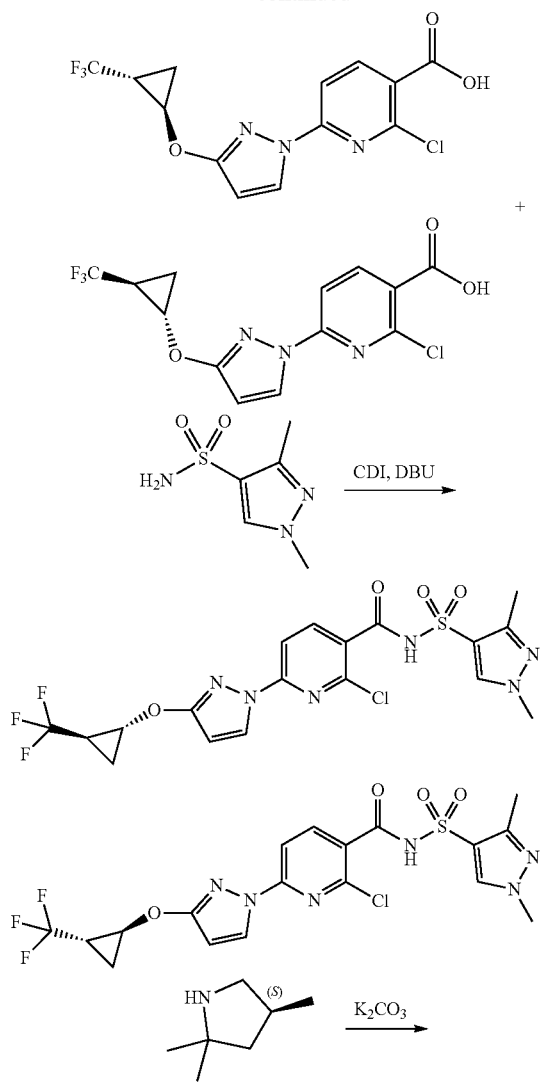

Step 1: 3-((trans)-2-(Trifluoromethyl)cyclopropoxy)-1H-pyrazole

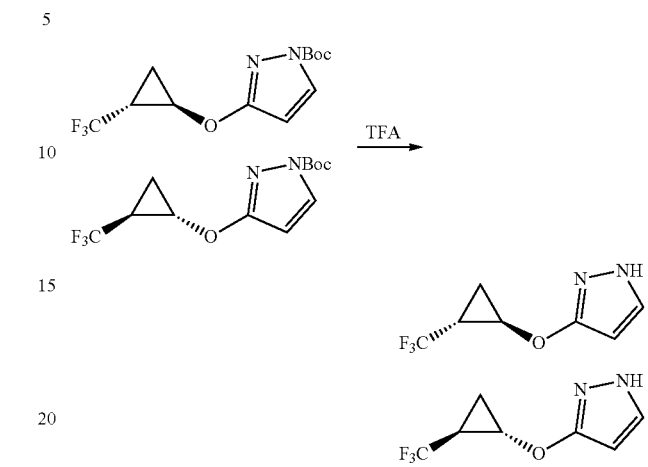

Trifluoroacetic acid (3.15 g, 27.64 mmol) was added to the solution of tert-butyl 3-((trans)-2-(trifluoromethyl)cyclopropoxy)-1H-pyrazole-1-carboxylate (807 mg, 2.76 mmol) in anhydrous dichloromethane (28 mL). The resulting solution was stirred at room temperature for 16 hours. 1,2-Dichloroethane (15 mL) was added to the reaction solution. All the solvents were removed under the reduced pressure. The residue obtained was dissolved in ethyl ether (200 mL), washed with saturated sodium bicarbonate aqueous solution (30 mL). The organic solution was dried over magnesium sulfate, filtered and concentrated under reduced pressure to afford crude 3-((trans)-2-(trifluoromethyl)cyclopropoxy)-1H-pyrazole (525 mg, 99%) as yellow-brown oil. The crude product was used directly in next step without any further purification. ESI-MS m/z calc. 192.1 found 193.0 (M+1)$^+$. Retention time: 2.97 minutes.

Step 2: tert-Butyl 2-chloro-6-(3-((trans)-2-(trifluoromethyl)cyclopropoxy)-1H-pyrazol-1-yl)nicotinate

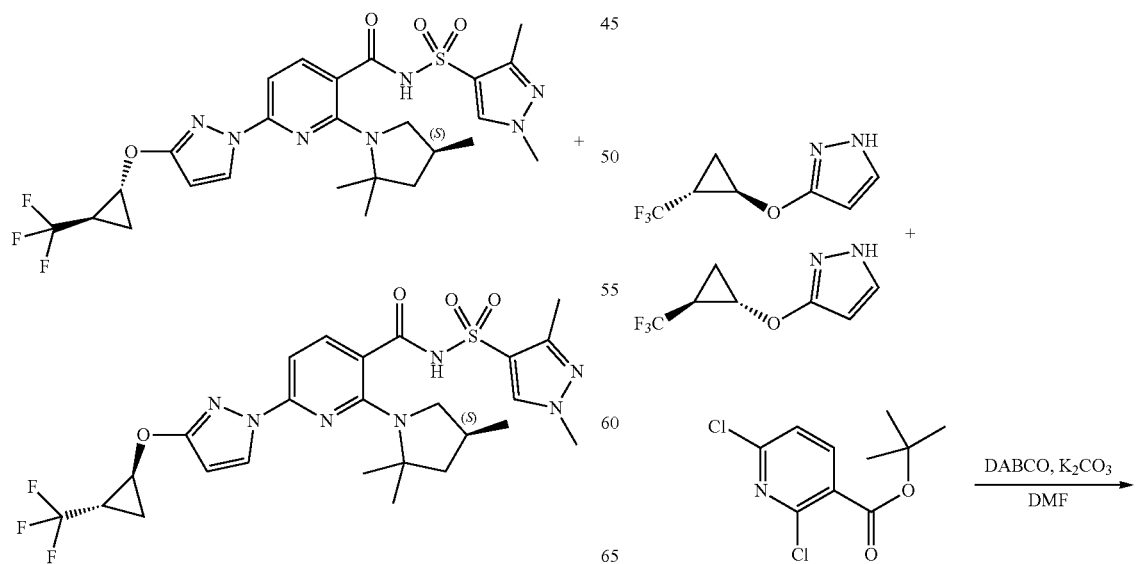

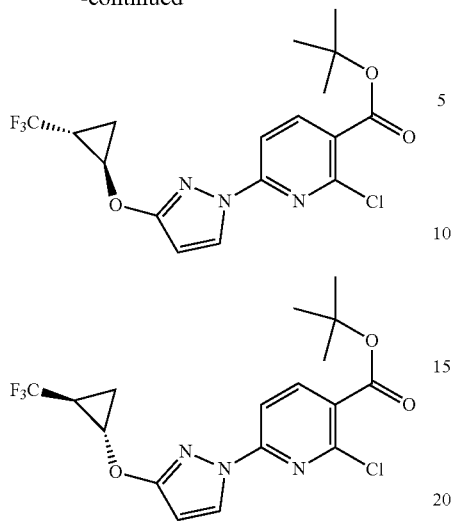

To the solution of crude 3-((trans)-2-(trifluoromethyl) cyclopropoxy)-1H-pyrazole (525 mg, 2.76 mmoL) in dimethylformamide (9.2 mL) was added tert-butyl 2,6-dichloropyridine-3-carboxylate (751 mg, 3.04 mmol), potassium carbonate (763 mg, 5.53 mmol) and 1,4-diazabicyclo[2.2.2]octane (62 mg, 0.55 mmol). The reaction was stirred at room temperature for 48 hours. The reaction solution was diluted with ether (250 mL), washed with water (4×20 mL) and brine (20 mL). The organic layer was dried over magnesium sulfate, filtered and concentrated under reduced pressure. The residue obtained was purified by silica gel chromatography using hexanes—dichloromethane gradient method (0 to 100% dichloromethane) to afford tert-butyl 2-chloro-6-(3-((trans)-2-(trifluoromethyl)cyclopropoxy)-1H-pyrazol-1-yl)nicotinate (314 mg, 21%) as a colorless oil. ESI-MS m/z calc. 403.1 found 404.1 (M+1)⁺. Retention time: 6.92 minutes. $^1$H NMR (250 MHz, CDCl$_3$) δ (ppm): 8.38 (d, J=3.0 Hz, 1H), 8.20 (d, J=8.5 Hz, 1H), 7.73 (d, J=8.5 Hz, 1H), 6.03 (d, J=3.0 Hz, 1H), 4.39 (m, 1H), 1.77 (m, 1H), 1.62 (s, 9H), 1.44 (m, 1H), 1.31 (m, 1H).

Step 3: 2-Chloro-6-(3-((trans)-2-(trifluoromethyl) cyclopropoxy)-1H-pyrazol-1-yl)nicotinic acid

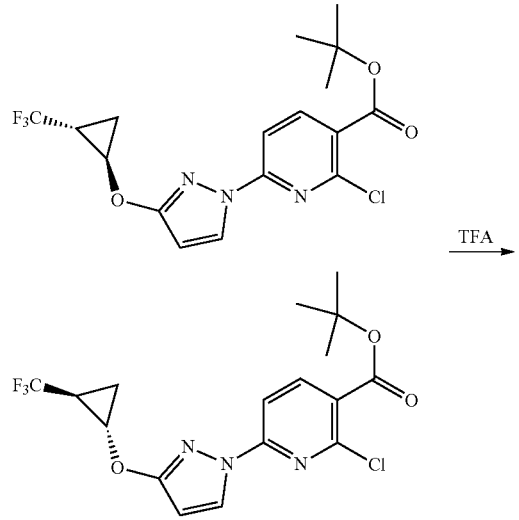

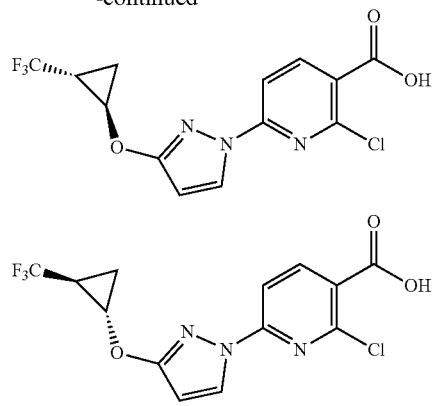

Trifluoroacetic acid (2.39 g, 21.0 mmol) was added to the solution of tert-butyl 2-chloro-6-(3-((trans)-2-(trifluoromethyl)cyclopropoxy)-1H-pyrazol-1-yl)nicotinate (847 mg, 2.10 mmol) in anhydrous dichloromethane (21 mL). The resulting solution was stirred at room temperature for 20 hours. 1,2-Dichloroethane (15 mL) was added to the reaction mixture. All the solvents were removed under reduced pressure. Crude solid obtained was added 10% ethyl ether in hexanes (30 mL) and sonicated for 30 minutes, filtered, washed with 10% ethyl ether in hexanes (10 mL), hexances (10 mL) and dried under high vacuum to afford 2-chloro-6-(3-((trans)-2-(trifluoromethyl)cyclopropoxy)-1H-pyrazol-1-yl)nicotinic acid (600 mg, 82%) as a white solid. ESI-MS m/z calc. 347.0 found 347.9 (M+1)⁺. Retention time: 4.91 minutes. $^1$H NMR (500 MHz, DMSO) δ (ppm): 8.46 (d, J=2.8 Hz, 1H), 8.41 (d, J=8.3 Hz, 1H), 7.74 (d, J=8.3 Hz, 1H), 6.30 (d, J=2.8 Hz, 1H), 4.46 (m, 1H), 2.15 (m, 1H), 1.40 (m, 1H), 1.34 (m, 1H).

Step 4: 2-Chloro-N-((1,3-dimethyl-1H-pyrazol-4-yl) sulfonyl)-6-(3-((trans)-2-(trifluoromethyl)cyclopropoxy)-1H-pyrazol-1-yl)nicotinamide

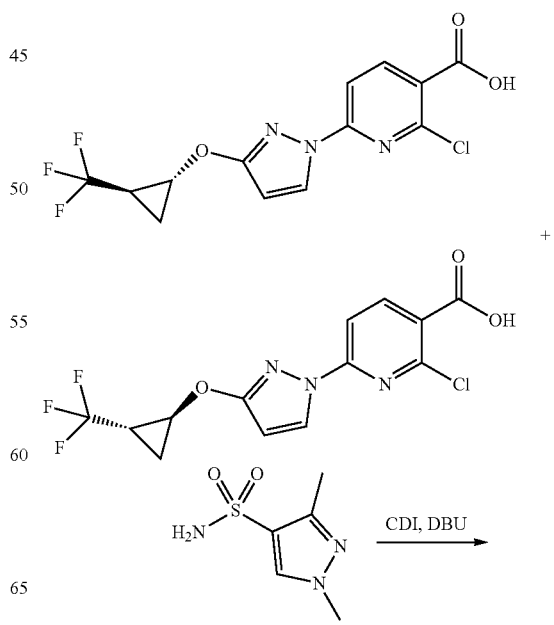

-continued

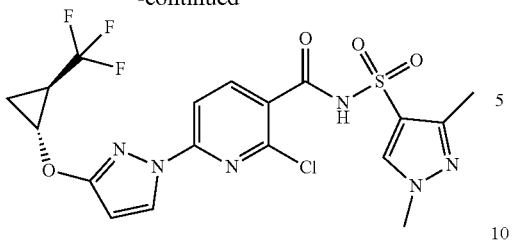

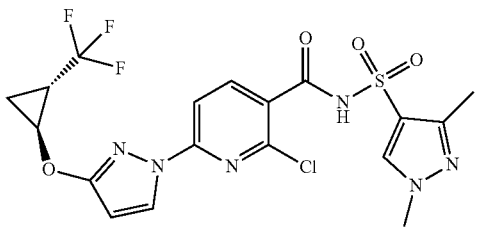

2-Chloro-6-(3-((trans)-2-(trifluoromethyl)cyclopropoxy)-1H-pyrazol-1-yl)nicotinic acid (125 mg, 0.3595 mmol) was dissolved in THF (1 mL). Di(imidazol-1-yl)methanone (approximately 69.95 mg, 0.4314 mmol) was added. The reaction mixture was allowed to stir at room temperature for 1 hour. 1,3-Dimethylpyrazole-4-sulfonamide (approximately 75.59 mg, 0.4314 mmol) was added followed by DBU (approximately 65.67 mg, 64.51 µL, 0.4314 mmol). The final reaction mixture was allowed to stir overnight at room temperature. Volatiles were removed by evaporation. It was taken up in EtOAc (50 mL) and washed with aqueous 1 M citric acid solution (2×50 mL) and brine (1×50 mL). The organic layer was dried over sodium sulfate, filtered and concentrated under reduced pressure to give 2-chloro-N-((1,3-dimethyl-1H-pyrazol-4-yl)sulfonyl)-6-(3-((trans)-2-(trifluoromethyl)cyclopropoxy)-1H-pyrazol-1-yl)nicotinamide (203 mg). ESI-MS m/z calc. 504.05945, found 505.0 (M+1)+; Retention time: 0.59 minutes.

Step 5: N-(1,3-Dimethylpyrazol-4-yl)sulfonyl-6-[3-[2-(trifluoromethyl)cyclopropoxy]pyrazol-1-yl]-2-[(4S)-2,2,4-trimethylpyrrolidin-1-yl]pyridine-3-carboxamide (mixture of trans isomers)

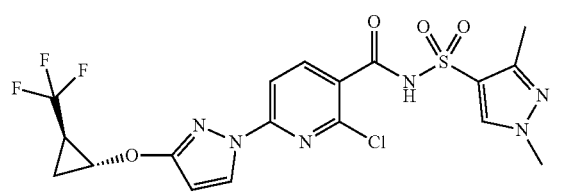

+

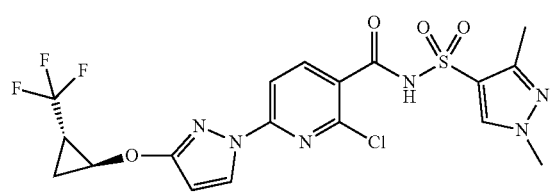

-continued

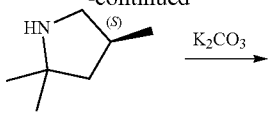

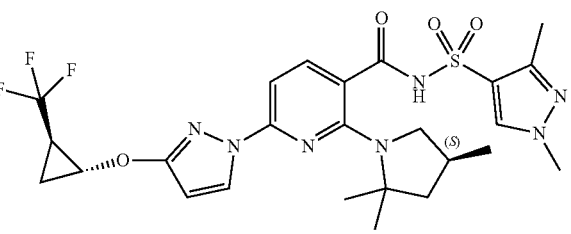

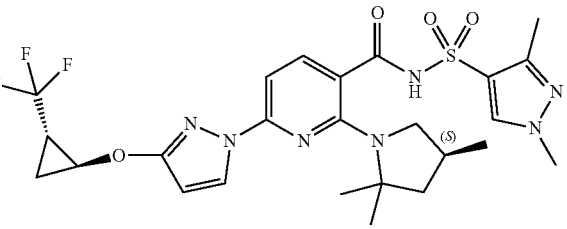

2-Chloro-N-((1,3-dimethyl-1H-pyrazol-4-yl)sulfonyl)-6-(3-((trans)-2-(trifluoromethyl)cyclopropoxy)-1H-pyrazol-1-yl)nicotinamide (181.5 mg, 0.3595 mmol) was dissolved in DMSO (1 mL). (4S)-2,2,4-trimethylpyrrolidine (hydrochloride salt) (approximately 161.3 mg, 1.078 mmol) was added followed by potassium carbonate (approximately 298.1 mg, 2.157 mmol). The reaction mixture was allowed to stir at 130° C. overnight. After cooling to room temperature, the reaction mixture was diluted with EtOAc (50 mL) and washed with aqueous citric acid (1 M, 2×50 mL) and brine (1×50 mL). The organic layer was dried over sodium sulfate, filtered, and concentrated under reduced pressure. The product was isolated by silica gel column chromatography on a 12 gram silica gel column eluting with a 0-10% EtOAc/hexane gradient to give N-(1,3-dimethylpyrazol-4-yl)sulfonyl-6-[3-[2-(trifluoromethyl)cyclopropoxy]pyrazol-1-yl]-2-[(4S)-2,2,4-trimethylpyrrolidin-1-yl]pyridine-3-carboxamide (mixture of trans isomers) (114.9 mg). ESI-MS m/z calc. 581.2032, found 582.4 (M+1)+; Retention time: 1.86 minutes.

Synthesis of (S)—N-((1,5-dimethyl-1H-pyrazol-4-yl)sulfonyl)-6-(3-(((1-(trifluoromethyl)cyclopropyl)methoxy)methyl)-1H-pyrazol-1-yl)-2-(2,2,4-trimethylpyrrolidin-1-yl)nicotinamide (Compound 25)
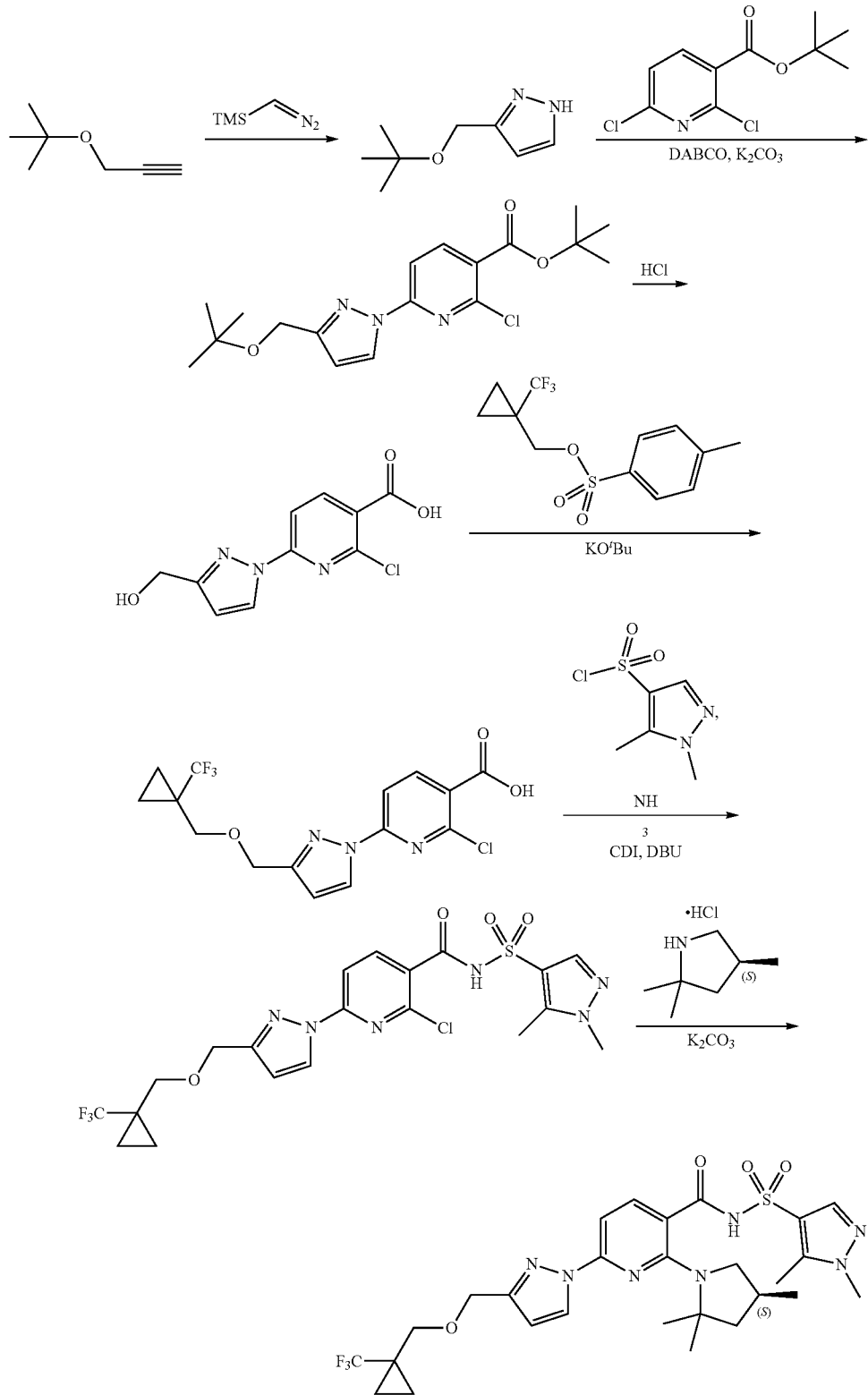

Step 1: 3-(tert-Butoxymethyl)-1H-pyrazole

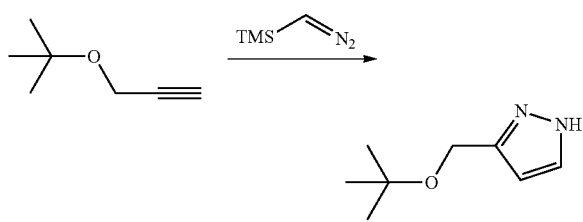

tert-Butylpropargyl alcohol (2.5 g, 22.2 mmol) was mixed with trimethylsilyl diazomethane (2.0 M in hexane, 11.1 mL, 22.2 mmol) and stirred in a sealed tube at 115° C. for 18 hours. The mixture was cooled to 40° C. and quenched with methanol (5 mL) and concentrated. Column chromatography (silica; heptanes/EtOAc 2:1 to 1:1) afforded 3-(tert-butoxymethyl)-1H-pyrazole as colorless oil (1.5 g, 44%). $^1$H NMR (CDCl3, 300 MHz): δ 1.26 (s, 9H); 4.53 (s, 2H); 6.22 (s, 1H); 7.48 (s, 1H).

Step 2: tert-Butyl 6-[3-(tert-butoxymethyl)pyrazol-1-yl]-2-chloro-pyridine-3-carboxylate

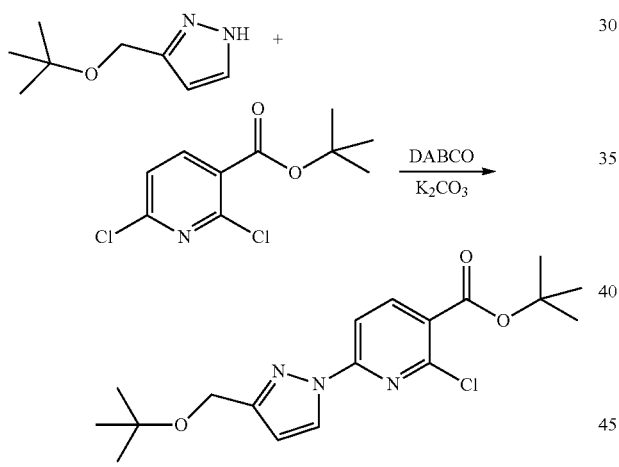

A 100 mL round bottom flask was charged under nitrogen with 3-(tert-butoxymethyl)-1H-pyrazole (1.241 g, 8.047 mmol), tert-butyl 2,6-dichloropyridine-3-carboxylate (2.0 g, 8.061 mmol), potassium carbonate (1.448 g, 10.48 mmol) (freshly ground in a mortar) and anhydrous DMF (12.41 mL). DABCO (163 mg, 1.453 mmol) was added, and the mixture was stirred at room temperature under nitrogen for 16 hours. The reaction mixture was diluted with ethyl acetate (50 mL) and water and brine (50 mL), and the two phases were separated. The aqueous phase was further extracted with ethyl acetate (2×30 mL). The combined extracts were washed with brine, dried over sodium sulfate, and the solvent removed under reduced pressure. The material was subjected to flash chromatography on silica gel using a gradient of ethyl acetate (0 to 10%) in hexanes. The pure fractions were combined and the solvents removed under reduced pressure to provide tert-butyl 6-[3-(tert-butoxymethyl)pyrazol-1-yl]-2-chloro-pyridine-3-carboxylate (1.956 g, 66%) as a colorless oil, which solidified to a white solid overnight on high vac. ESI-MS m/z calc. 365.1506, found 366.2 (M+1)$^+$; Retention time: 0.82 minutes.

Step 3: 2-Chloro-6-[3-(hydroxymethyl)pyrazol-1-yl]pyridine-3-carboxylic acid

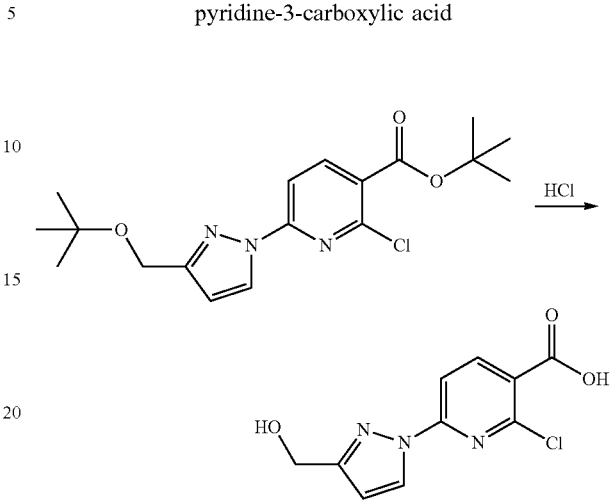

tert-Butyl 6-[3-(tert-butoxymethyl)pyrazol-1-yl]-2-chloro-pyridine-3-carboxylate (538 mg, 1.471 mmol) was dissolved in HCl in dioxane (8.0 mL of 4 M, 32.00 mmol) and heated at 60° C. for 2 hours. The reaction mixture was then cooled to room temperature and concentrated to dryness, giving a white powder. 2-chloro-6-[3-(hydroxymethyl)pyrazol-1-yl]pyridine-3-carboxylic acid (370 mg, 99%) ESI-MS m/z calc. 253.02542, found 254.1 (M+1)$^+$; Retention time: 0.33 minutes.

Step 4: 2-Chloro-6-(3-(((1-(trifluoromethyl)cyclopropyl)methoxy)methyl)-1H-pyrazol-1-yl)nicotinic acid

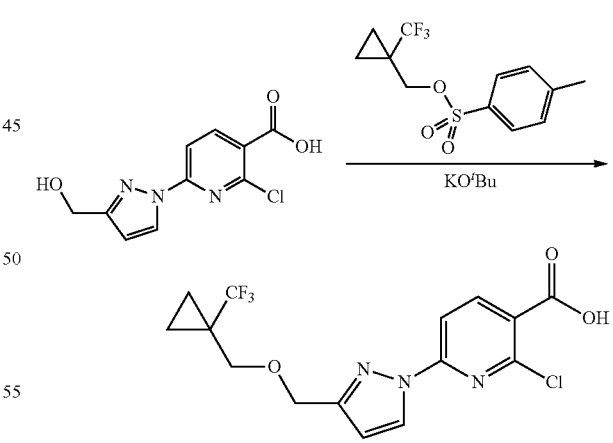

[1-(Trifluoromethyl)cyclopropyl]methyl 4-methylbenzenesulfonate (1.3 g, 4.417 mmol), and 2-chloro-6-[3-(hydroxymethyl)pyrazol-1-yl]pyridine-3-carboxylic acid (370 mg, 1.459 mmol), were combined in anhydrous DMSO (9.250 mL). tert-Butoxypotassium (660 mg, 5.882 mmol) was added, and the reaction mixture was stirred at room temperature. After 30 minutes the reaction mixture was poured into 1 M citric acid (15 mL) and extracted 3×15 mL ethyl acetate. The combined organics were washed with brine, dried over sodium sulfate and concentrated. The resulting material was purified by chromatography on silica gel using a 0-10% methanol in dichloromethane gradient. The fractions containing product were collected and concentrated to give a white solid. 2-chloro-6-(3-(((1-(trifluoromethyl)cyclopropyl)methoxy)methyl)-1H-pyrazol-1-yl)nicotinic acid (292 mg, 53%) ESI-MS m/z calc. 375.05975, found 376.1 (M+1)+; Retention time: 0.62 minutes.

Step 5: 2-Chloro-N-((1,5-dimethyl-1H-pyrazol-4-yl)sulfonyl)-6-(3-(((1-(trifluoromethyl)cyclopropyl)methoxy)methyl)-1H-pyrazol-1-yl)nicotinamide

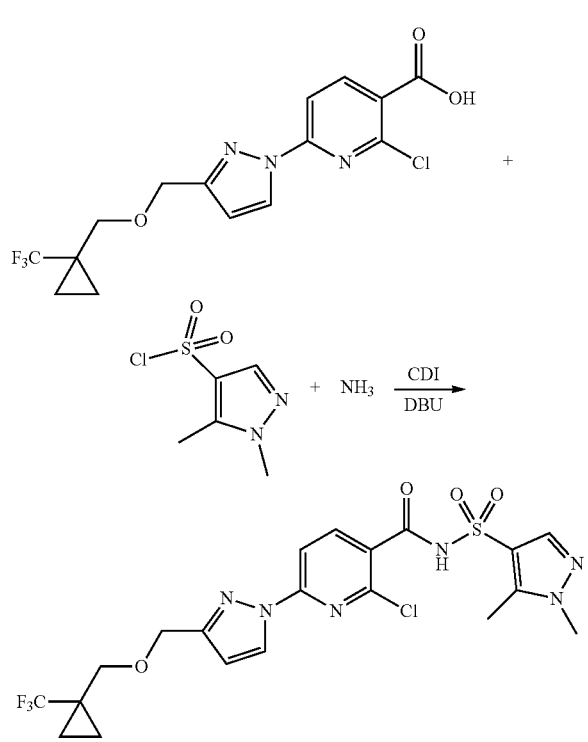

2-Chloro-6-(3-(((1-(trifluoromethyl)cyclopropyl)methoxy)methyl)-1H-pyrazol-1-yl)nicotinic acid (50 mg, 0.1331 mmol) and CDI (26 mg, 0.1603 mmol) were combined in THF (300.0 µL) and stirred at room temperature for 2 hours in a vial (vial 1). Meanwhile, 1,5-dimethylpyrazole-4-sulfonyl chloride (31 mg, 0.1593 mmol) was combined with ammonia (125 µL of 7 M, 0.8750 mmol) in a separate vial (vial 2). After stirring for an additional 20 min, the volatiles were removed from vial 2 by evaporation, and 1 mL of dichloromethane was added to the solid residue, and was also evaporated. DBU (60 µL, 0.4012 mmol) was then added to vial 2 and stirred at 60° C. for 5 minutes (to facilitate the removal of ammonia from any residual ammonium chloride). Upon cooling to room temperature, 1 mL THF was added and then evaporated under reduced pressure. The contents of vial 1 were then added to vial 2 by syringe, and the reaction mixture was stirred for 4 h at room temperature. The reaction mixture was diluted with 10 mL ethyl acetate, and washed with 10 mL 1 M citric acid. The aqueous layer was extracted 2×10 mL ethyl acetate, and the combined organics were washed with brine, dried over sodium sulfate, and concentrated to give a a white solid. This material was used in the next step without further purification. 2-chloro-N-((1,5-dimethyl-1H-pyrazol-4-yl)sulfonyl)-6-(3-(((1-(trifluoromethyl)cyclopropyl)methoxy)methyl)-1H-pyrazol-1-yl)nicotinamide (65 mg, 50%) ESI-MS m/z calc. 532.09076, found 533.2 (M+1)+; Retention time: 1.34 minutes.

Step 6: (S)—N-((1,5-Dimethyl-1H-pyrazol-4-yl)sulfonyl)-6-(3-(((1-(trifluoromethyl)cyclopropyl)methoxy)methyl)-1H-pyrazol-1-yl)-2-(2,2,4-trimethylpyrrolidin-1-yl)nicotinamide

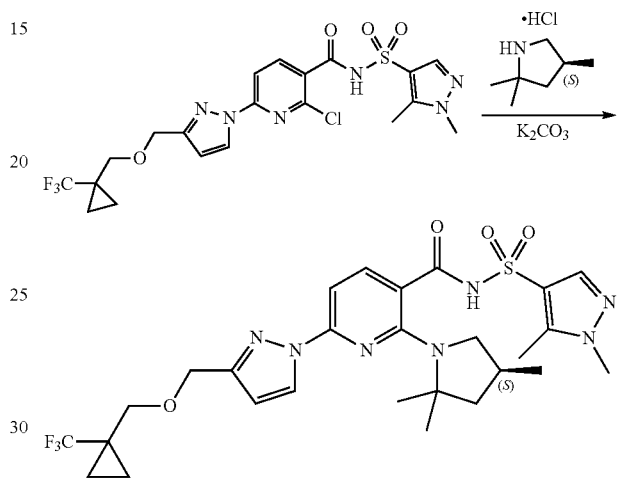

2-Chloro-N-((1,5-dimethyl-1H-pyrazol-4-yl)sulfonyl)-6-(3-(((1-(trifluoromethyl)cyclopropyl)methoxy)methyl)-1H-pyrazol-1-yl)nicotinamide (67 mg, 0.1257 mmol), (4S)-2,2,4-trimethylpyrrolidine (hydrochloride salt) (94 mg, 0.6281 mmol), and potassium carbonate (174 mg, 1.259 mmol) were combined in DMSO (335.0 µL) and heated at 130° C. for 16 h. The reaction was cooled to room temperature, and 1 mL of water was added. After 15 minutes stirring, the contents of the vial were allowed to settle, the liquid portion was removed by pipet, and the remaining solids were dissolved with 20 mL ethyl acetate, then washed with 15 mL 1 M citric acid. The aqueous and organic layers were separated, and the aqueous layer was extracted two additional times with 15 mL ethyl acetate. The organics were combined, washed with brine, dried over sodium sulfate and concentrated. The resulting solid was further purified by silica gel chromatography eluting with 0-10% methanol in dichloromethane to give a white solid. (S)—N-((1,5-dimethyl-1H-pyrazol-4-yl)sulfonyl)-6-(3-(((1-(trifluoromethyl)cyclopropyl)methoxy)methyl)-1H-pyrazol-1-yl)-2-(2,2,4-trimethylpyrrolidin-1-yl)nicotinamide (17 mg, 22%). ESI-MS m/z calc. 609.2345, found 610.3 (M+1)+; Retention time: 1.96 minutes.

$^1$H NMR (400 MHz, DMSO) δ 12.36 (s, 1H), 8.34 (d, J=2.6 Hz, 1H), 7.85-7.71 (m, 2H), 7.05 (d, J=8.1 Hz, 1H), 6.56 (d, J=2.6 Hz, 1H), 4.55 (s, 2H), 3.78 (s, 3H), 3.59 (s, 2H), 2.58 (t, J=10.4 Hz, 1H), 2.53 (s, 3H), 2.45 (t, J=8.4 Hz, 1H), 2.19 (dt, J=12.2, 6.6 Hz, 1H), 1.94-1.84 (m, 1H), 1.56 (d, J=15.0 Hz, 6H), 1.45 (t, J=12.2 Hz, 1H), 1.00-0.96 (m, 2H), 0.86 (tq, J=4.4, 3.1, 2.4 Hz, 2H), 0.81 (d, J=6.2 Hz, 3H).

Synthesis of N-(1,3-dimethylpyrazol-4-yl)sulfonyl-6-[3-[(1S,2S,4R)-norbornan-2-yl]oxypyrazol-1-yl]-2-[(4S)-2,2,4-trimethylpyrrolidin-1-yl]pyridine-3-carboxamide (Compound 51)

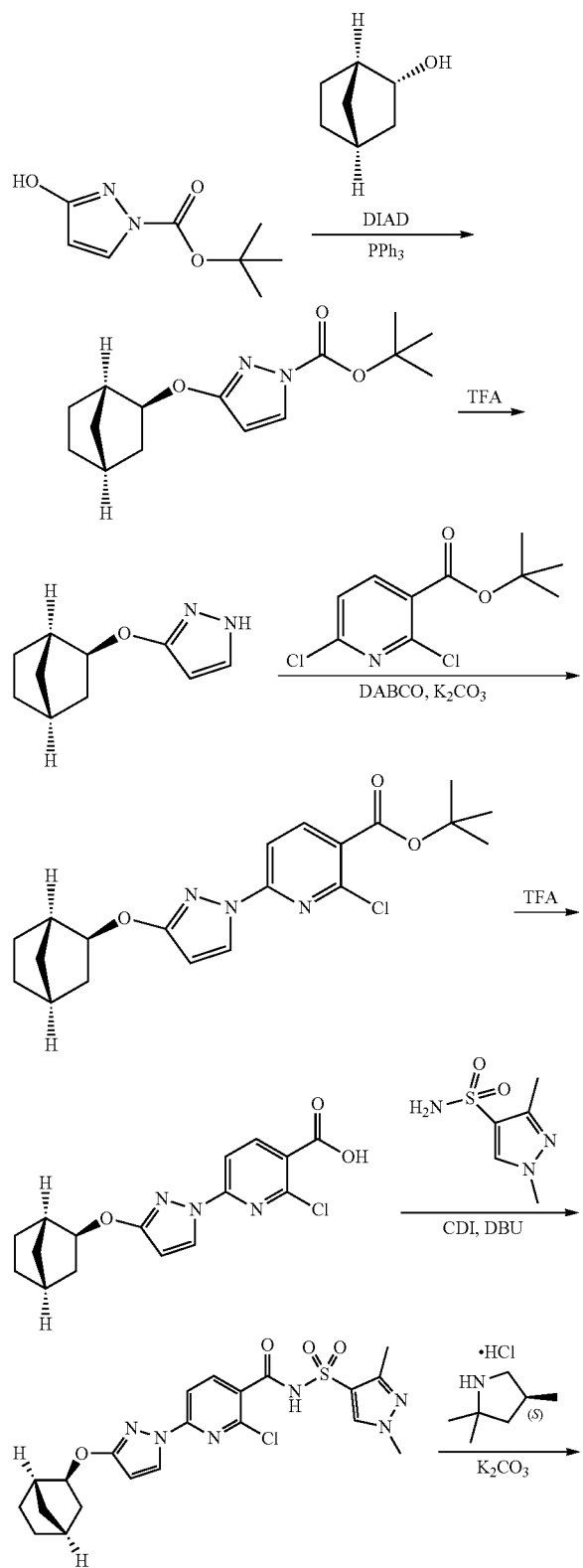

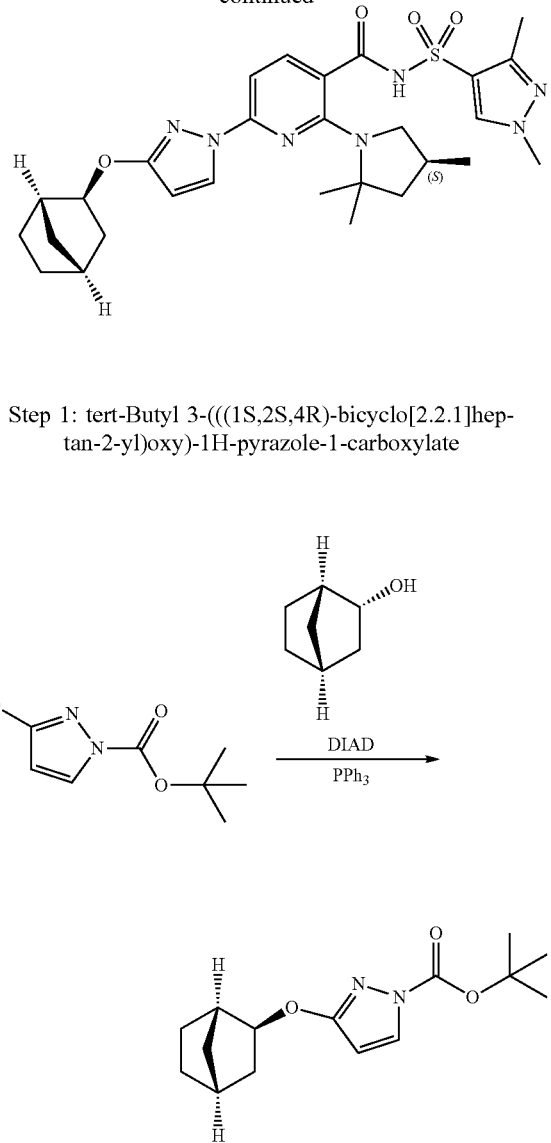

Step 1: tert-Butyl 3-(((1S,2S,4R)-bicyclo[2.2.1]heptan-2-yl)oxy)-1H-pyrazole-1-carboxylate tert-Butyl 3-hydroxypyrazole-1-carboxylate (1.632 g, 8.860 mmol), (+)-endo-2-norborneol (1 g, 8.915 mmol), and triphenyl phosphine (2.57 g, 9.798 mmol) were combined in THF (21.98 mL), and the reaction was cooled in an ice bath. To the mixture was added DIAD (2 mL, 10.16 mmol) dropwise, and the reaction was allowed to warm to room temperature and stir for 16 h. The mixture was evaporated, and the resulting material was partitioned between ethyl acetate (30 mL) and 1 N sodium hydroxide (30 mL). The organics were separated, washed with brine (30 mL), dried over sodium sulfate and evaporated. The crude material was purified by silica gel chromatography eluting with 0-30% ethyl acetate in hexanes to give tert-butyl 3-(((1S,2S,4R)-bicyclo[2.2.1]heptan-2-yl)oxy)-1H-pyrazole-1-carboxylate (2.08 g, 84%) ESI-MS m/z calc. 278.16306, found 279.3 (M+1)+; Retention time: 0.72 minutes.

$^1$H NMR (400 MHz, DMSO) δ 8.05 (d, J=3.0 Hz, 1H), 6.07 (d, J=3.0 Hz, 1H), 4.47 (d, J=6.8 Hz, 1H), 2.43-2.36 (m, 1H), 2.32-2.22 (m, 1H), 1.75 (td, J=6.7, 2.4 Hz, 1H), 1.54 (s, 9H), 1.53-1.49 (m, 2H), 1.42 (ddt, J=14.8, 7.8, 4.4 Hz, 2H), 1.18-1.07 (m, 3H).

Step 2: 3-[(1S,2S,4R)-Norbornan-2-yl]oxy-1H-pyrazole

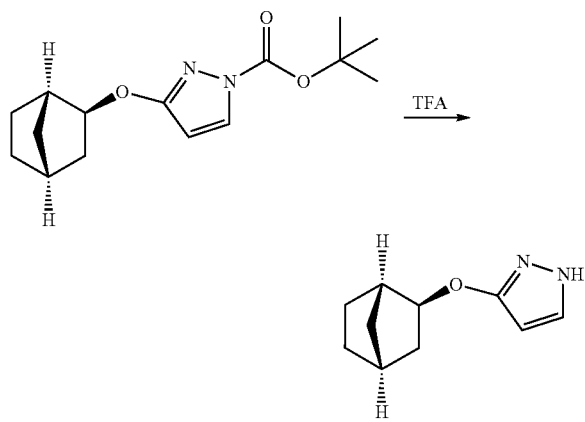

tert-Butyl 3-[(1S,2S,4R)-norbornan-2-yl]oxypyrazole-1-carboxylate (2.08 g, 7.473 mmol) was dissolved in dichloromethane (20.80 mL) with trifluoroacetic acid (5.8 mL, 75.28 mmol), and the reaction was stirred at room temperature for 1 h. The reaction was evaporated under reduced pressure, and the resulting oil was partitioned between ethyl acetate (50 mL) and a saturated sodium bicarbonate solution (30 mL). The organics were separated, washed with brine, dried over sodium sulfate and concentrated under vacuum to give an oil, 3-[(1S,2S,4R)-norbornan-2-yl]oxy-1H-pyrazole (1.29 g, 97%) ESI-MS m/z calc. 178.11061, found 179.2 (M+1)+; Retention time: 0.45 minutes.

Step 3: tert-Butyl 2-chloro-6-[3-[(1S,2S,4R)-norbornan-2-yl]oxypyrazol-1-yl]pyridine-3-carboxylate

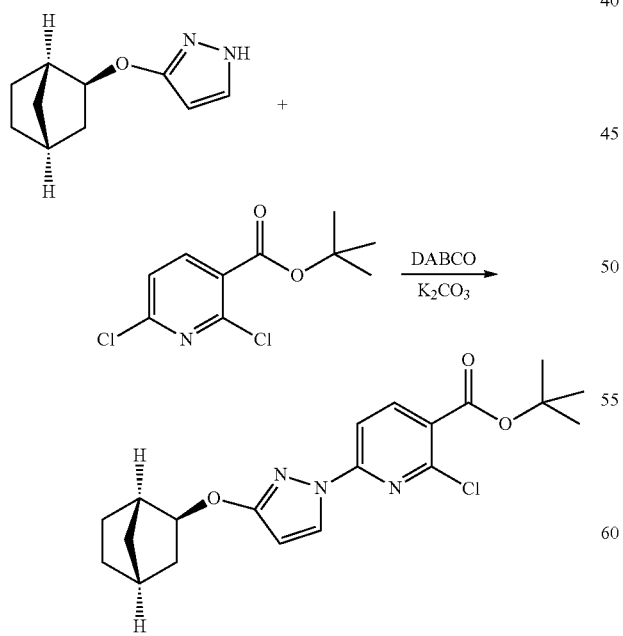

A 100 mL round bottom flask was charged under nitrogen with tert-butyl 2,6-dichloropyridine-3-carboxylate (1.796 g, 7.239 mmol), 3-[(1S,2S,4R)-norbornan-2-yl]oxy-1H-pyrazole (1.29 g, 7.238 mmol), and potassium carbonate (1.310 g, 9.479 mmol) (freshly ground in a mortar) and anhydrous DMF (12 mL). DABCO (146 mg, 1.302 mmol) was added, and the mixture was stirred at room temperature under nitrogen for 8 hours. The reaction mixture was diluted with ethyl acetate (50 mL), water and brine (50 mL), and the two phases were separated. The aqueous phase was further extracted with ethyl acetate (2×50 mL). The combined extracts were dried over sodium sulfate and the solvent removed under reduced pressure. The material was subjected to flash chromatography on silica gel using a gradient of ethyl acetate (0 to 20%) in hexanes. The pure fractions were combined and the solvents removed under reduced pressure to provide tert-butyl 2-chloro-6-[3-[(1S,2S,4R)-norbornan-2-yl]oxypyrazol-1-yl]pyridine-3-carboxylate (1.814 g, 64%) ESI-MS m/z calc. 389.1506, found 390.3 (M+1)+; Retention time: 0.92 minutes.

$^1$H NMR (400 MHz, DMSO) δ 8.40 (d, J=2.9 Hz, 1H), 8.32 (d, J=8.4 Hz, 1H), 7.72 (d, J=8.4 Hz, 1H), 6.18 (d, J=2.9 Hz, 1H), 4.53 (d, J=6.6 Hz, 1H), 1.88-1.78 (m, 1H), 2.45 (d, J=4.6 Hz, 1H), 2.29 (t, J=4.3 Hz, 1H), 1.56 (s, 9H), 1.55-1.39 (m, 4H), 1.22-1.08 (m, 3H).

Step 4: 2-Chloro-6-[3-[(1S,2S,4R)-norbornan-2-yl]oxypyrazol-1-yl]pyridine-3-carboxylic acid

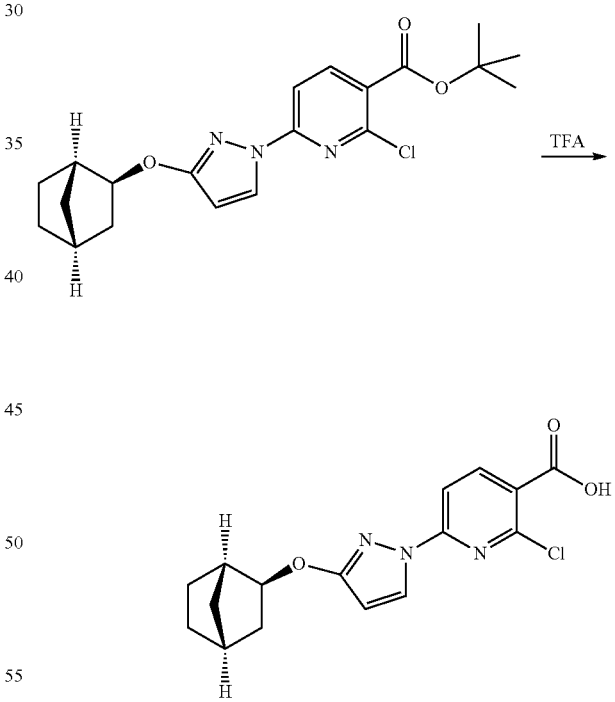

tert-Butyl 2-chloro-6-[3-[(1S,2S,4R)-norbornan-2-yl]oxypyrazol-1-yl]pyridine-3-carboxylate (1.814 g, 4.653 mmol) and TFA (5 mL, 64.90 mmol) were combined in dichloromethane (18.14 mL) and heated at 40° C. for 2 h. The reaction was evaporated. Hexanes were added and the mixture evaporated again to give a white solid which was used in the next step without further purification. 2-chloro-6-[3-[(1S,2S,4R)-norboman-2-yl]oxypyrazol-1-yl]pyridine-3-carboxylic acid (1.47 g, 79%) ESI-MS m/z calc. 333.088, found 334.2 (M+1)$^+$; Retention time: 0.71 minutes.

Step 5: 2-Chloro-N-(1,3-dimethylpyrazol-4-yl)sulfonyl-6-[3-[(1S,2S,4R)-norbornan-2-yl]oxypyrazol-1-yl]pyridine-3-carboxamide

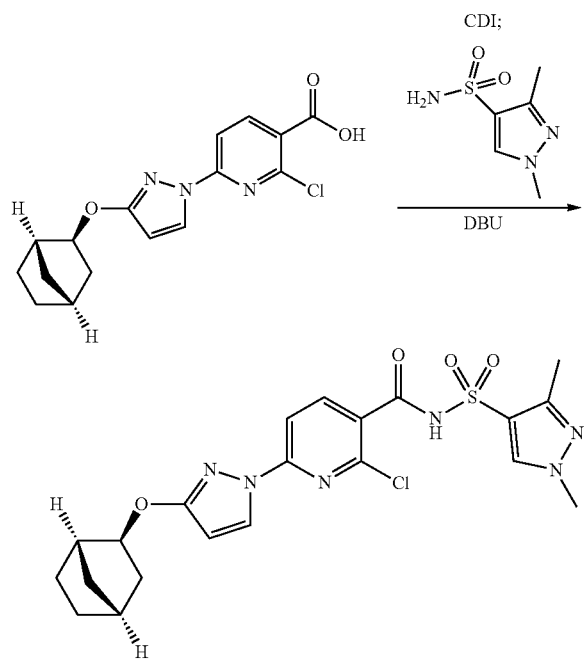

2-Chloro-6-[3-[(1S,2S,4R)-norboman-2-yl]oxypyrazol-1-yl]pyridine-3-carboxylic acid (100 mg, 0.2487 mmol) and CDI (approximately 52.42 mg, 0.3233 mmol) were combined in THF (approximately 415.4 µL) and stirred for 2 hours at room temperature. 1,3-Dimethylpyrazole-4-sulfonamide (58 mg, 0.3310 mmol) and DBU (approximately 48.35 µL, 0.3233 mmol) were then added, and the reaction was stirred an additional 2 hours at room temperature. The reaction mixture was then poured into 20 mL 1 M citric acid and extracted with 3×20 mL ethyl acetate. The combined organics were washed with water, then brine, dried over sodium sulfate, and concentrated to give crude (substantial impurities but used in the next step without further purification) 2-chloro-N-(1,3-dimethylpyrazol-4-yl)sulfonyl-6-[3-[(1S,2S,4R)-norbornan-2-yl]oxypyrazol-1-yl]pyridine-3-carboxamide ESI-MS m/z calc. 490.12, found 491.3 (M+1)+; Retention time: 0.75 minutes.

Step 6: N-(1,3-Dimethylpyrazol-4-yl)sulfonyl-6-[3-[(1S,2S,4R)-norbornan-2-yl]oxypyrazol-1-yl]-2-[(4S)-2,2,4-trimethylpyrrolidin-1-yl]pyridine-3-carboxamide

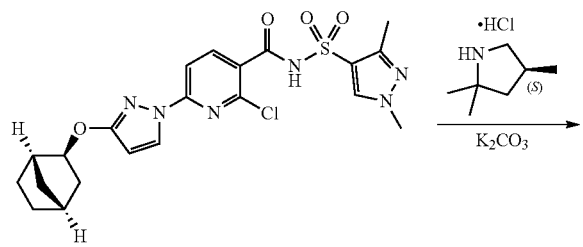

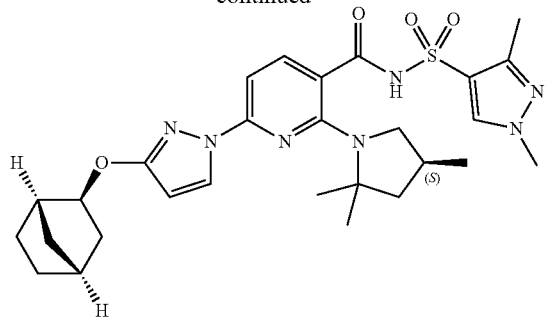

Crude 2-chloro-N-(1,3-dimethylpyrazol-4-yl)sulfonyl-6-[3-[(1S,2S,4R)-norbornan-2-yl]oxypyrazol-1-yl]pyridine-3-carboxamide (125 mg, 0.2546 mmol), (4S)-2,2,4-trimethylpyrrolidine (hydrochloride salt) (approximately 114.3 mg, 0.7638 mmol), and potassium carbonate (approximately 211.2 mg, 1.528 mmol) were combined in DMSO (approximately 0.4243 mL) in a screwcap vial and heated to 130° C. for 16 hours. The reaction mixture was then cooled to room temperature, and 3 mL of water was added, resulting in the formation of a precipitate. After 30 minutes, the liquid portion was removed by syringe and discarded, and the remaining solids were dissolved in 15 mL ethyl acetate. The organics were washed with 15 mL 1 M citric acid, and the aqueous layer was extracted an additional time with 15 mL ethyl acetate. The combined organics were washed with brine, dried over sodium sulfate and concentrated. The crude material was purified by column chromatography on silica gel using a gradient of 0-10% methanol in dichloromethane. The pure fractions were combined and concentrated to give N-(1,3-dimethylpyrazol-4-yl)sulfonyl-6-[3-[(1 S,2S,4R)-norbornan-2-yl]oxypyrazol-1-yl]-2-[(4S)-2,2,4-trimethylpyrrolidin-1-yl]pyridine-3-carboxamide (37 mg, 25%) ESI-MS m/z calc. 567.26, found 568.3 (M+1)+; Retention time: 2.23 minutes.

$^1$H NMR (400 MHz, DMSO) δ 12.35 (s, 1H), 8.37 (s, 1H), 8.18 (d, J=2.8 Hz, 1H), 7.73 (d, J=8.2 Hz, 1H), 6.89 (d, J=8.2 Hz, 1H), 6.08 (d, J=2.7 Hz, 1H), 4.49 (d, J=6.7 Hz, 1H), 3.81 (s, 3H), 2.56 (d, J=10.4 Hz, 1H), 2.42 (dd, J=13.7, 6.6 Hz, 2H), 2.32 (s, 3H), 2.29 (d, J=4.4 Hz, 1H), 2.19 (tt, J=12.1, 6.4 Hz, 1H), 1.91-1.78 (m, 2H), 1.59-1.38 (m, 11H), 1.20-1.11 (m, 3H), 0.81 (d, J=6.2 Hz, 3H).

Synthesis N-(1,3-dimethylpyrazol-4-yl)sulfonyl-6-[3-[[(1S,4R)-norbornan-2-yl]methoxy]pyrazol-1-yl]-2-[(4S)-2,2,4-trimethylpyrrolidin-1-yl]pyridine-3-carboxamide (Compound 50)

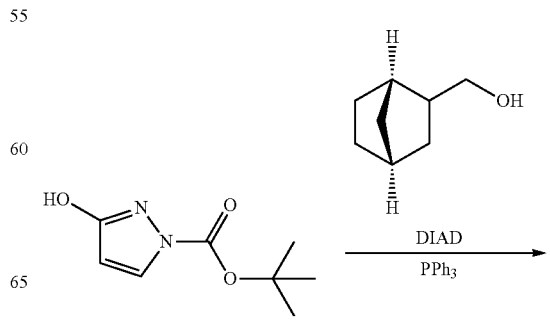

211
-continued

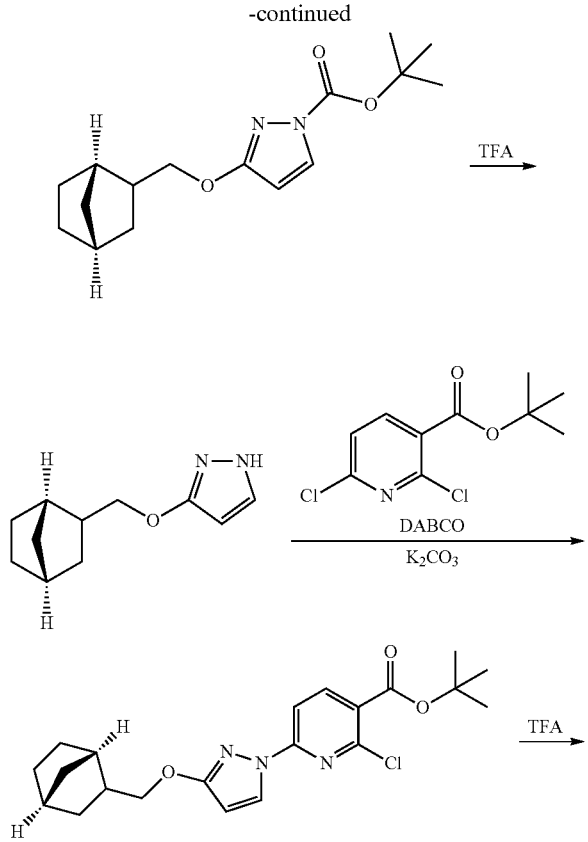

212

Step 1: tert-Butyl 3-[[(1S,4R)-norbornan-2-yl]methoxy]pyrazole-1-carboxylate

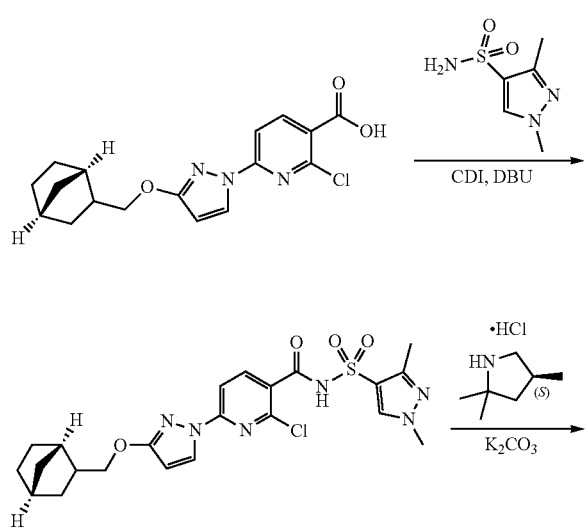

tert-Butyl 3-hydroxypyrazole-1-carboxylate (1.327 g, 7.204 mmol), [(1S,4R)-norbornan-2-yl]methanol (1 g, 7.924 mmol) (mixture of endo and exo), and triphenyl phosphine (2.09 g, 7.968 mmol) were combined in THF (17.87 mL), and the reaction was cooled in an ice bath. To the mixture was added DIAD (1.627 mL, 8.263 mmol) dropwise and the reaction was allowed to warm to room temperature and stirred for 72 h. The mixture was evaporated, and the resulting material was partitioned between ethyl acetate (50 mL) and 1 N sodium hydroxide (50 mL). The organics were separated, washed with brine, dried over sodium sulfate and evaporated. The crude material was purified by silica gel chromatography eluting with 0-30% ethyl acetate in hexanes to give tert-butyl 3-[[(1S,4R)-norbornan-2-yl]methoxy]pyrazole-1-carboxylate (1.698 g, 81%) ESI-MS m/z calc. 292.17868, found 293.3 (M+1)$^+$; Retention time: 0.77 minutes. (2 diastereomers-mix of endo and exo substituted norbornane).

$^1$H NMR (400 MHz, DMSO) δ 8.06 (d, J=2.9 Hz, 1H), 6.10 (dd, J=2.9, 1.0 Hz, 1H), 4.23-3.81 (m, 2H), 2.29-2.15 (m, 2H), 1.69 (dq, J=12.1, 4.2 Hz, 1H), 1.54 (d, J=1.4 Hz, 9H), 1.51-1.03 (m, 7H), 0.75 (dd, J=5.0, 2.4 Hz, 1H).

Step 2: 3-[[(1S,4R)-Norbornan-2-yl]methoxy]-1H-pyrazole

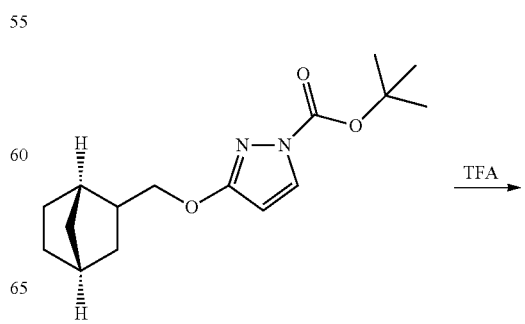

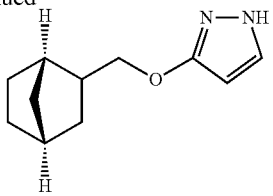

tert-Butyl 3-[[(1S,4R)-norbornan-2-yl]methoxy]pyrazole-1-carboxylate (1.698 g, 5.808 mmol) was dissolved in dichloromethane (16.98 mL) with trifluoroacetic acid (approximately 6.622 g, 4.474 mL, 58.08 mmol), and the reaction was stirred at room temperature for 2 h. The reaction was evaporated, and the resulting oil was partitioned between ethyl acetate (50 mL) and a saturated sodium bicarbonate solution (30 mL). The organics were separated, washed with brine, dried over sodium sulfate and concentrated under vacuum to give an oil, 3-[[(1S,4R)-norbornan-2-yl]methoxy]-1H-pyrazole (1.11 g, 99%) ESI-MS m/z calc. 192.12627, found 193.2 (M+1)+; Retention time: 0.52 minutes.

Step 3: tert-Butyl 2-chloro-6-[3-[[(1S,4R)-norbornan-2-yl]methoxy]pyrazol-1-yl]pyridine-3-carboxylate

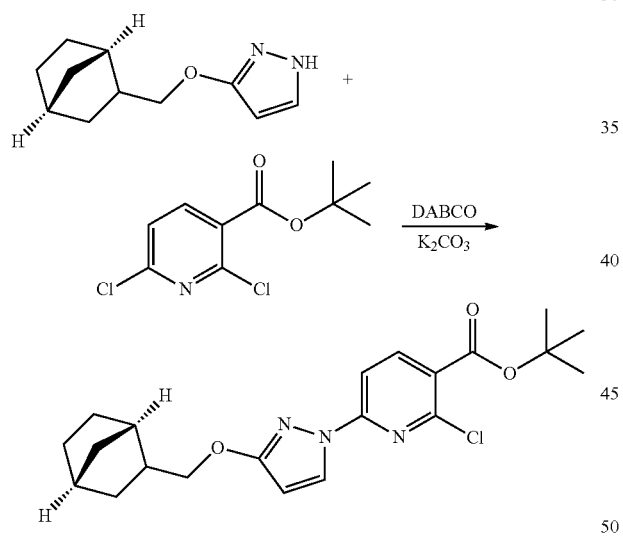

A round bottom flask was charged under nitrogen with 3-[[(1S,4R)-norbornan-2-yl]methoxy]-1H-pyrazole (1.11 g, 5.774 mmol) (mix of two diastereomers), tert-butyl 2,6-dichloropyridine-3-carboxylate (1.433 g, 5.776 mmol), potassium carbonate (1.05 g, 7.597 mmol) (freshly ground in a mortar) and anhydrous DMF (10 mL). DABCO (117 mg, 1.043 mmol) was added, and the mixture was stirred at room temperature under nitrogen for 16 hours. The reaction mixture was diluted with ethyl acetate (50 mL) and water (50 mL), and the two phases were separated. The aqueous phase was further extracted with ethyl acetate (2×30 mL). The combined extracts were washed with brine, dried over sodium sulfate and the solvent removed under reduced pressure. The material was subjected to flash chromatography on silica gel using a gradient of ethyl acetate (0 to 20%) in hexanes. The pure fractions were combined and the solvents removed under reduced pressure to provide tert-butyl 2-chloro-6-[3-[[(1S,4R)-norbornan-2-yl]methoxy]pyrazol-1-yl]pyridine-3-carboxylate (1.88 g, 81%) ESI-MS m/z calc. 403.16626, found 404.3 (M+1)+; Retention time: 0.94 minutes.

Step 4: 2-Chloro-6-[3-[[(1S,4R)-norbornan-2-yl]methoxy]pyrazol-1-yl]pyridine-3-carboxylic acid

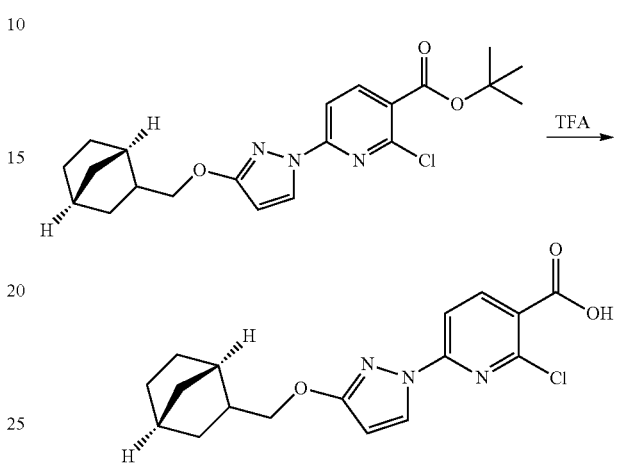

tert-Butyl 2-chloro-6-[3-[[(1S,4R)-norbornan-2-yl]methoxy]pyrazol-1-yl]pyridine-3-carboxylate (1.88 g, 4.655 mmol) and TFA (5 mL, 64.90 mmol) were combined in dichloromethane (18.80 mL) and heated at 40° C. for 2 h. The reaction was evaporated. Hexanes were added and the mixture evaporated again to give a white solid 2-chloro-6-[3-[[(1S,4R)-norbornan-2-yl]methoxy]pyrazol-1-yl]pyridine-3-carboxylic acid (1.58 g, 98%) ESI-MS m/z calc. 347.10367, found 348.2 (M+1)+; Retention time: 0.75 minutes.

Step 5: 2-Chloro-N-(1,3-dimethylpyrazol-4-yl)sulfonyl-6-[3-[[(1S,4R)-norbornan-2-yl]methoxy]pyrazol-1-yl]pyridine-3-carboxamide

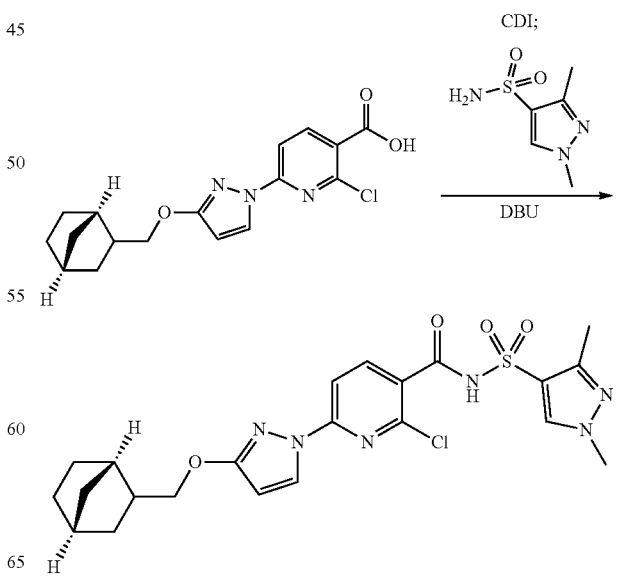

2-Chloro-6-[3-[[(1S,4R)-norbornan-2-yl]methoxy]pyrazol-1-yl]pyridine-3-carboxylic acid (100 mg, 0.2875 mmol) and CDI (60.59 mg, 0.3737 mmol) were stirred in THF (0.5 mL) at room temperature for 2 hours. 1,3-Dimethylpyrazole-4-sulfonamide (56 mg, 0.3196 mmol) was then added, followed by DBU (55.88 µL, 0.3737 mmol), and the reaction was stirred an additional 4 hours at room temperature. The reaction mixture was then diluted with 25 mL ethyl acetate and poured into 25 mL 1 M citric acid, and the layers were separated. The aqueous layer was extracted with an additional 25 mL ethyl acetate, and the combined organics were washed with water then brine, dried over sodium sulfate, and concentrated. The product was used in the next step without further purification, 2-chloro-N-(1,3-dimethylpyrazol-4-yl)sulfonyl-6-[3-[[(1S,4R)-norbornan-2-yl]methoxy]pyrazol-1-yl]pyridine-3-carboxamide (138 mg, 95%) (mixture of exo and endo norbornane stereoisomers) ESI-MS m/z calc. 504.13, found 505.3 (M+1)+; Retention time: 0.78 minutes.

Step 6: N-(1,3-Dimethylpyrazol-4-yl)sulfonyl-6-[3-[[(1S,4R)-norbornan-2-yl]methoxy]pyrazol-1-yl]-2-[(4S)-2,2,4-trimethylpyrrolidin-1-yl]pyridine-3-carboxamide

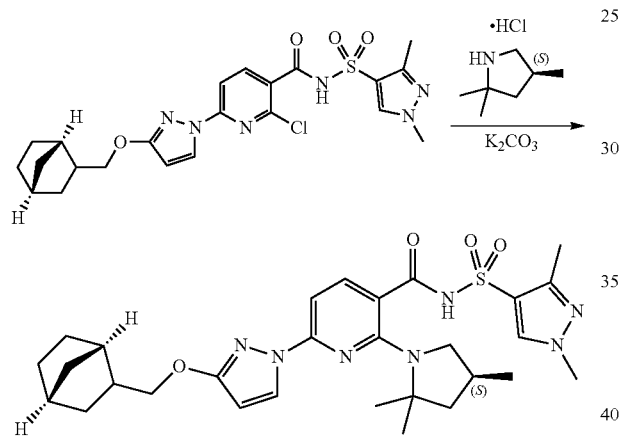

2-Chloro-N-(1,3-dimethylpyrazol-4-yl)sulfonyl-6-[3-[[(1S,4R)-norbornan-2-yl]methoxy]pyrazol-1-yl]pyridine-3-carboxamide (138 mg, 0.2733 mmol), (4S)-2,2,4-trimethylpyrrolidine (hydrochloride salt) (122.7 mg, 0.8199 mmol), and potassium carbonate (226.7 mg, 1.640 mmol) were combined in DMSO (0.4555 mL) in a screwcap vial and heated to 130° C. for 16 hours. The reaction mixture was then cooled to room temperature, and 3 mL of water was added, resulting in the formation of a precipitate. After 30 minutes, the liquid portion was removed by syringe and discarded, and the remaining solids were dissolved in 15 mL ethyl acetate and washed with 15 mL 1 M citric acid. The aqueous layer was extracted an additional time with 15 mL ethyl acetate. The combined organics were washed with brine, dried over sodium sulfate and concentrated. The crude material was purified by column chromatography on silica gel using a gradient of 0-10% methanol in dichloromethane. The pure fractions were combined and concentrated to give N-(1,3-dimethylpyrazol-4-yl)sulfonyl-6-[3-[[(1S,4R)-norbornan-2-yl]methoxy]pyrazol-1-yl]-2-[(4S)-2,2,4-trimethylpyrrolidin-1-yl]pyridine-3-carboxamide (101 mg, 63%) (mixture of exo and endo norbornane stereoisomers) ESI-MS m/z calc. 581.28, found 582.4 (M+1)+; Retention time: 2.32 minutes.

Synthesis of 6-[3-(2,2-dicyclopropylethoxy)pyrazol-1-yl]-N-(1,3-dimethylpyrazol-4-yl)sulfonyl-2-[(4S)-2,2,4-trimethylpyrrolidin-1-yl]pyridine-3-carboxamide (Compound 32)

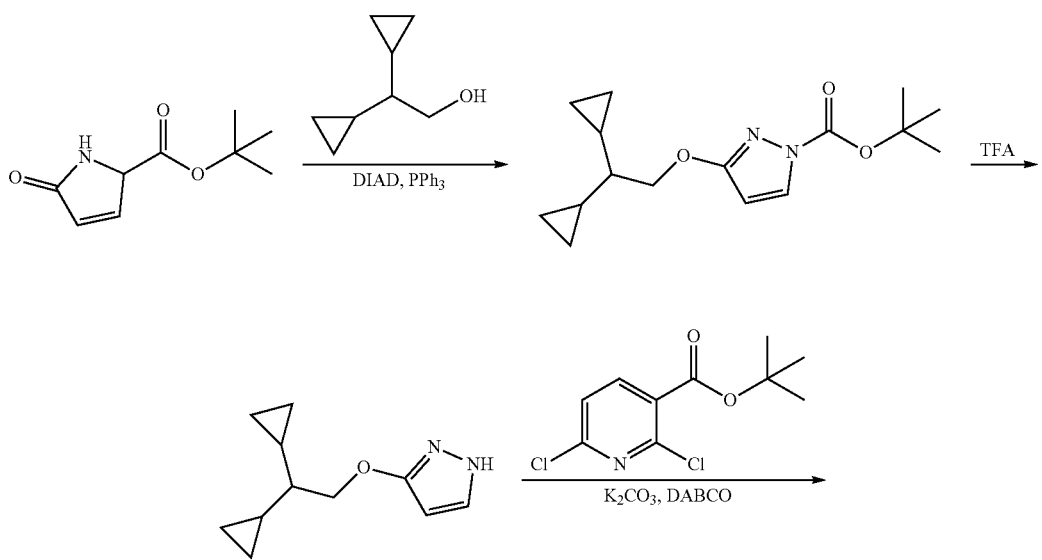

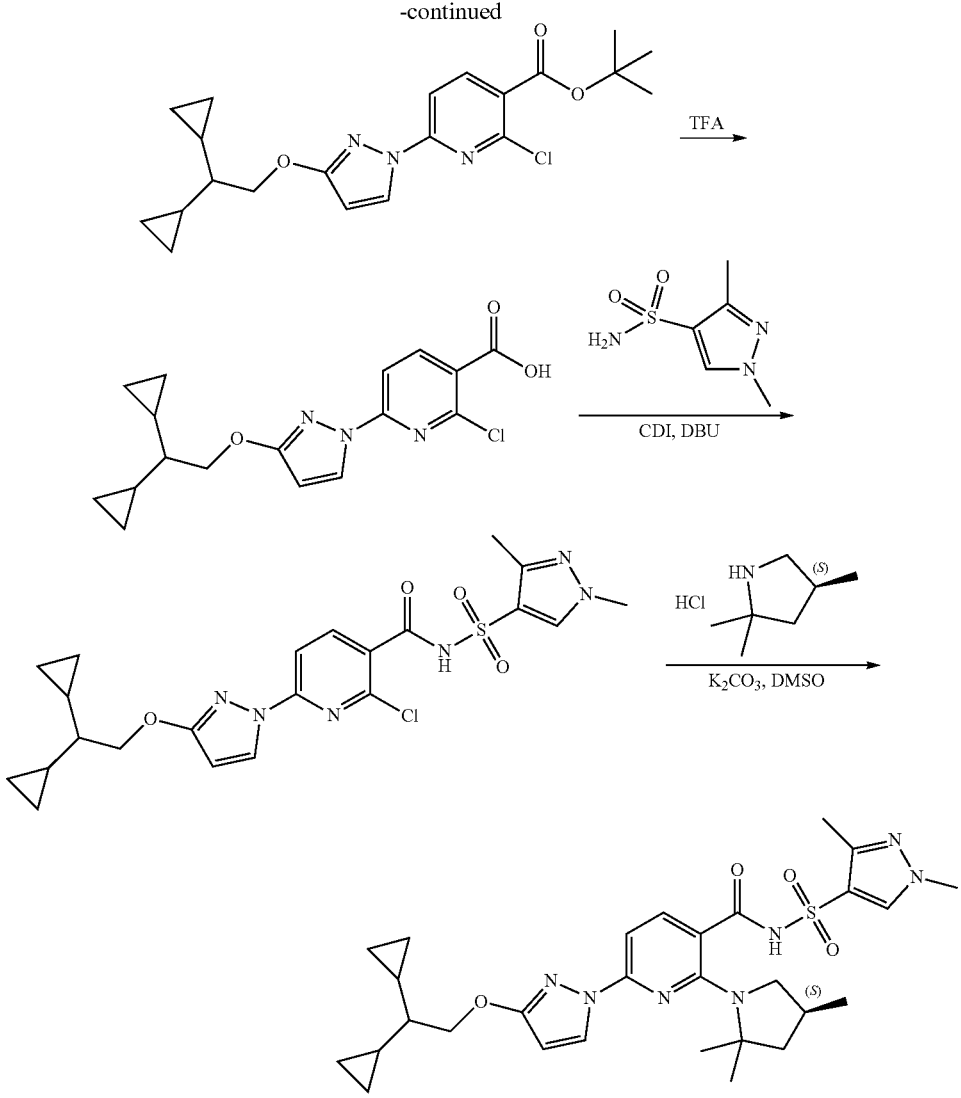

Step 1: tert-Butyl 3-(2,2-dicyclopropylethoxy)pyrazole-1-carboxylate

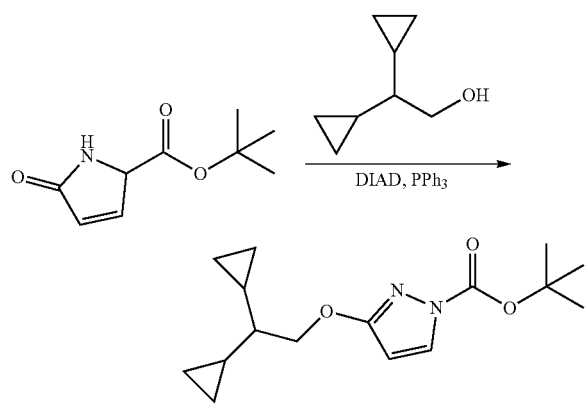

A solution of 2,2-dicyclopropylethanol (500 mg, 3.962 mmol), tert-butyl 3-hydroxypyrazole-1-carboxylate (730 mg, 3.963 mmol), and triphenylphosphane (1.1 g, 4.194 mmol) in dry THF (20.0 mL) was cooled in an ice bath, and DIAD (800.0 μL, 4.063 mmol) was slowly added under nitrogen atmosphere. The reaction was allowed to slowly warm to room temperature and was stirred for 16 h. The reaction mixture was diluted with ethyl acetate, washed with saturated aqueous sodium bicarbonate, brine, dried over sodium sulfate, and concentrated. The residue was purified by silica gel chromatography with 100% hexanes to 50% ethyl acetate in hexanes to afford tert-butyl 3-(2,2-dicyclopropylethoxy)pyrazole-1-carboxylate (783 mg, 68%) as colorless oil. ESI-MS m/z calc. 292.17868, found 293.3 (M+1)$^+$; Retention time: 1.98 minutes. $^1$H NMR (400 MHz, Chloroform-d) δ 7.62 (d, J=3.0 Hz, 1H), 5.67 (s, 1H), 4.13 (d, J=5.3 Hz, 2H), 1.44 (s, 9H), 0.58 (qt, J=8.2, 5.0 Hz, 2H), 0.36 (tt, J=8.9, 5.6 Hz, 1H), 0.32-0.12 (m, 4H) 0.10-0.08 (m, 4H).

Step 2: 3-(2,2-Dicyclopropylethoxy)-1H-pyrazole

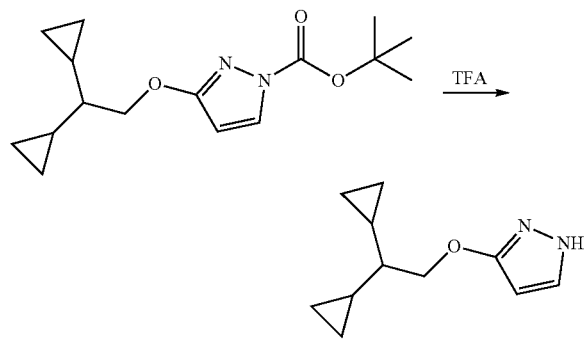

A solution of tert-butyl 3-(2,2-dicyclopropylethoxy) pyrazole-1-carboxylate (750 mg, 2.565 mmol) and trifluoroacetic acid (1.0 mL, 12.98 mmol) in dichloromethane (4 mL) was stirred for 2.5 hours. The volatiles were removed under reduced pressure, and the residue was basified with saturated aqueous sodium bicarbonate and extracted with ethyl acetate. The combined extracts were dried over sodium sulfate and evaporated to give 3-(2,2-dicyclopropylethoxy)-1H-pyrazole as colorless oil which was used as it is without further purification for next reaction. ESI-MS m/z calc. 192.12627, found 193.3 (M+1)$^+$; Retention time: 1.32 minutes.

Step 3: tert-Butyl 2-chloro-6-[3-(2, 2-dicyclopropylethoxy) pyrazol-1-yl]pyridine-3-carboxylate

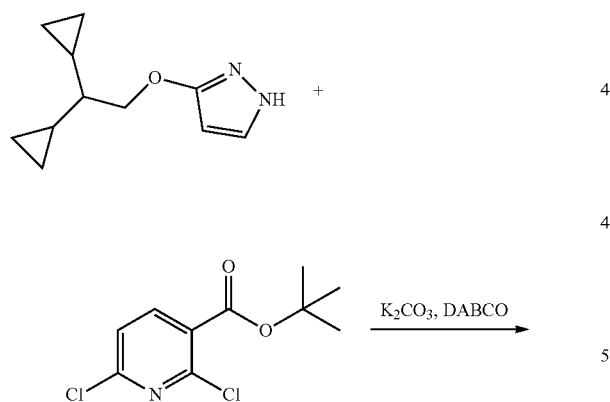

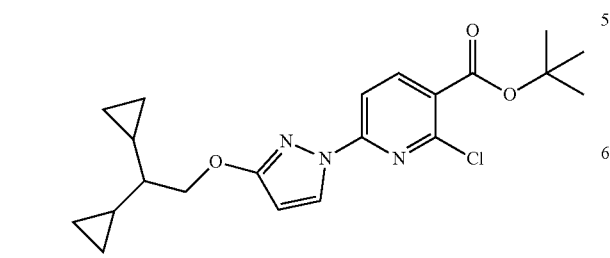

A mixture of 3-(2,2-dicyclopropylethoxy)-1H-pyrazole (493.0 mg, 2.564 mmol), tert-butyl 2,6-dichloropyridine-3-carboxylate (682.0 mg, 2.749 mmol), potassium carbonate (430.0 mg, 3.111 mmol), and 1,4-diazabicyclo[2.2.2]octane (60 mg, 0.5349 mmol) in DMSO (20.0 mL) was stirred at room temperature for 15 hours. The reaction was diluted with water and extracted with ethyl acetate. The combined extracts were washed with brine and dried over sodium sulfate and evaporated. The residue was purified by silica gel column chromatography with 100% hexanes to 20% ethyl acetate in hexanes to afford tert-butyl 2-chloro-6-[3-(2,2-dicyclopropylethoxy)pyrazol-1-yl]pyridine-3-carboxylate (680 mg, 66%) as colorless oil. ESI-MS M/z calc. 403.16626, found 404.4 (M+1)$^+$; Retention time: 2.49 minutes.

$^1$H NMR (400 MHz, Chloroform-d) δ 8.35 (d, J=2.8 Hz, 1H), 8.18 (d, J=8.4 Hz, 1H), 7.70 (d, J=8.5 Hz, 1H), 5.98 (d, J=2.9 Hz, 1H), 4.32 (d, J=5.6 Hz, 2H), 1.61 (s, 9H), 0.92-0.75 (m, 2H), 0.70-0.56 (m, 1H), 0.54-0.36 (m, 4H), 0.32-0.13 (m, 4H).

Step 4: 2-Chloro-6-[3-(2, 2-dicyclopropylethoxy) pyrazol-1-yl]pyridine-3-carboxylic acid

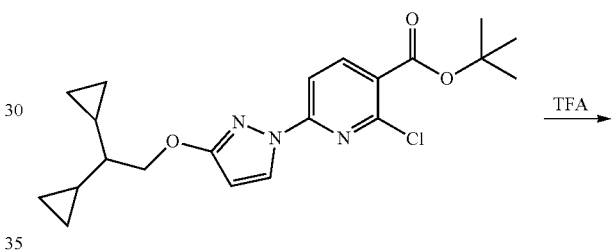

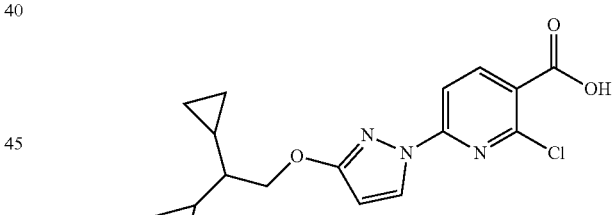

A solution of tert-butyl2-chloro-6-[3-(2,2-dicyclopropylethoxy)pyrazol-1-yl]pyridine-3-carboxylate (675 mg, 1.671 mmol) in trifluoroacetic acid (1.5 mL, 19.47 mmol) and dichloromethane (4.5 mL) was stirred for 4 hours at room temperature. The solvent was evaporated, and twice the residue was taken up in THF and concentrated under vacuum to afford 2-chloro-6-[3-(2, 2-dicyclopropylethoxy) pyrazol-1-yl]pyridine-3-carboxylic acid (580 mg, 100%). ESI-MS m/z calc. 347.10367, found 348.3 (M+1)$^+$; Retention time: 1.95 minutes.

Step 5: 2-Chloro-6-[3-(2,2-dicyclopropylethoxy)pyrazol-1-yl]-N-(1,3-dimethylpyrazol-4-yl)sulfonyl-pyridine-3-carboxamide and evaporated to afford 2-chloro-6-[3-(2,2-dicyclopropylethoxy)pyrazol-1-yl]-N-(1,3-dimethylpyrazol-4-yl)sulfonyl-pyridine-3-carboxamide which was used as is for the next reaction. ESI-MS m/z calc. 504.13464, found 505.5 (M+1)+; Retention time: 0.73 minutes.

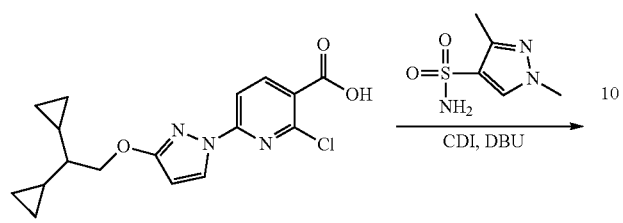

Step 6: 6-[3-(2,2-Dicyclopropylethoxy)pyrazol-1-yl]-N-(1,3-dimethylpyrazol-4-yl)sulfonyl-2-[(4S)-2,2,4-trimethylpyrrolidin-1-yl]pyridine-3-carboxamide

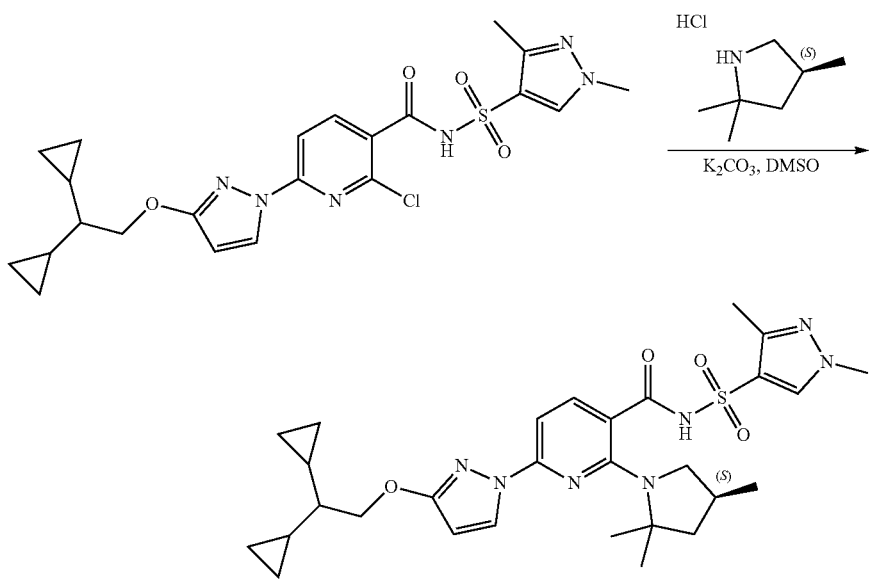

-continued

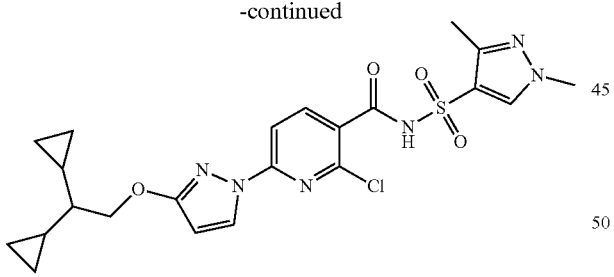

A solution of 2-chloro-6-[3-(2,2-dicyclopropylethoxy)pyrazol-1-yl]pyridine-3-carboxylic acid (100 mg, 0.2875 mmol) and carbonyl diimidazole (60 mg, 0.3700 mmol) in THF (2 mL) was stirred for 45 minutes. Then 1,3-dimethylpyrazole-4-sulfonamide (60.0 mg, 0.3424 mmol) and 2,3,4,6,7,8,9,10-octahydropyrimido[1,2-a]azepine (60 µL, 0.4012 mmol) were added, and the reaction mixture was stirred for additional 2 hr at room temperature. The reaction mixture was quenched with saturated ammonium chloride solution and extracted with ethyl acetate. The combined extracts were washed with brine, dried over sodium sulfate A mixture of 2-chloro-6-[3-(2,2-dicyclopropylethoxy)pyrazol-1-yl]-N-(1,3-dimethylpyrazol-4-yl)sulfonyl-pyridine-3-carboxamide (140.0 mg, 0.2772 mmol), (4S)-2,2,4-trimethylpyrrolidine (hydrochloride salt) (125.0 mg, 0.8352 mmol), and potassium carbonate (230.0 mg, 1.664 mmol) in DMSO (2.0 mL) was stirred at 130° C. for 15 hours. The reaction mixture was filtered and purified using a reverse phase HPLC-MS method with a dual gradient run from 50-99% acetonitrile in 5 mM HCl to afford 6-[3-(2,2-dicyclopropylethoxy)pyrazol-1-yl]-N-(1,3-dimethylpyrazol-4-yl)sulfonyl-2-[(4S)-2,2,4-trimethylpyrrolidin-1-yl]pyridine-3-carboxamide (50.1 mg, 31%). ESI-MS m/z calc. 581.27844, found 582.5 (M+1)+; Retention time: 2.2 minutes.

$^1$H NMR (400 MHz, Chloroform-d) δ 8.32 (d, J=8.5 Hz, 1H), 8.22 (d, J=2.8 Hz, 1H), 8.07 (s, 1H), 7.58 (d, J=8.5 Hz, 1H), 5.96 (d, J=2.8 Hz, 1H), 4.32 (d, J=5.7 Hz, 2H), 3.86 (s, 3H), 3.48 (dd, J=10.3, 8.4 Hz, 1H), 3.09 (dd, J=10.4, 7.7 Hz, 1H), 2.62 (dt, J=15.7, 7.8 Hz, 1H), 2.46 (s, 3H), 2.13 (dd, J=12.3, 7.9 Hz, 1H), 1.70 (dd, J=12.4, 9.5 Hz, 1H), 1.36 (s, 3H), 1.31 (s, 3H), 1.21 (d, J=6.7 Hz, 3H), 0.90-0.76 (m, 2H), 0.67-0.57 (m, 1H), 0.53-0.38 (m, 4H), 0.31-0.11 (m, 4H).

6-[3-(2,2-dicyclopropylethoxy)pyrazol-1-yl]-N-(1,5-dimethylpyrazol-4-yl)sulfonyl-2-[(4S)-2,2,4-trimethylpyrrolidin-1-yl]pyridine-3-carboxamide (Compound 33)

Step 1: 2-Chloro-6-[3-(2,2-dicyclopropylethoxy)pyrazol-1-yl]-N-(1,5-dimethylpyrazol-4-yl)sulfonyl-pyridine-3-carboxamide

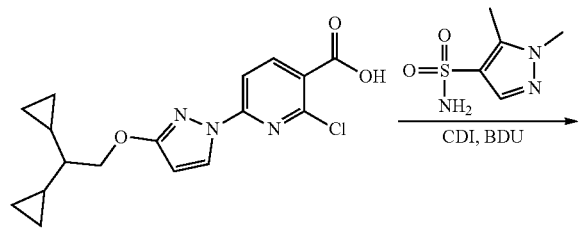

A solution of 2-chloro-6-[3-(2,2-dicyclopropylethoxy)pyrazol-1-yl]pyridine-3-carboxylic acid (50 mg, 0.1438 mmol) and carbonyl diimidazole (30 mg, 0.1850 mmol) in THF (2 mL) was stirred for 45 minutes. Then, 1,5-dimethylpyrazole-4-sulfonamide (30 mg, 0.1712 mmol) and 2,3,4,6,7,8,9,10-octahydropyrimido[1,2-a]azepine (30 μL, 0.2006 mmol) were added, and the reaction mixture was stirred for an additional 2 hr at room temperature. The reaction mixture was quenched with saturated ammonium chloride solution and extracted with ethyl acetate. The combined extracts were washed with brine, dried over sodium sulfate and evaporated to give 2-chloro-6-[3-(2,2-dicyclopropylethoxy)pyrazol-1-yl]-N-(1,5-dimethylpyrazol-4-yl)sulfonyl-pyridine-3-carboxamide which was used as is for the next reaction. ESI-MS m/z calc. 504.13464, found 505.5 (M+1)+; Retention time: 0.74 minutes.

Step 2: 6-[3-(2,2-Dicyclopropylethoxy)pyrazol-1-yl]-N-(1,5-dimethylpyrazol-4-yl)sulfonyl-2-[(4S)-2,2,4-trimethylpyrrolidin-1-yl]pyridine-3-carboxamide

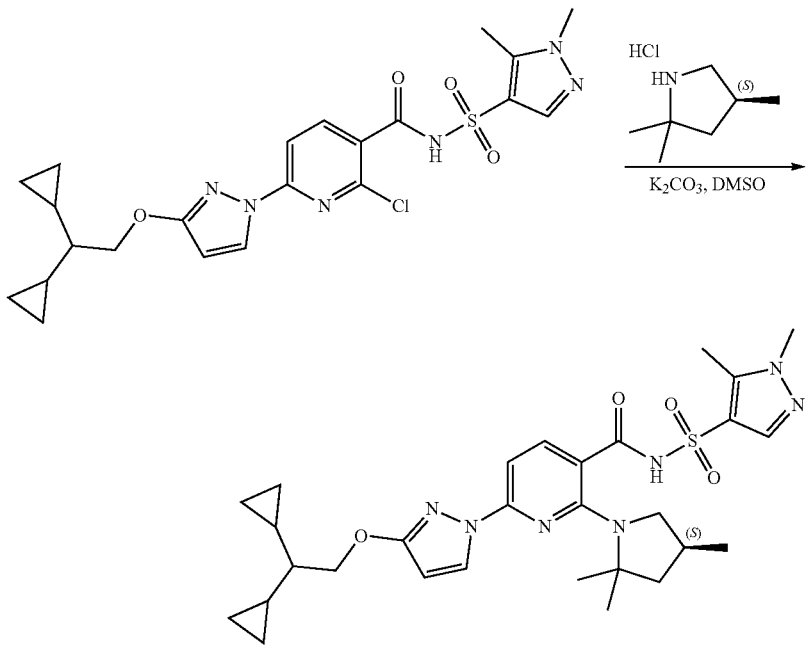

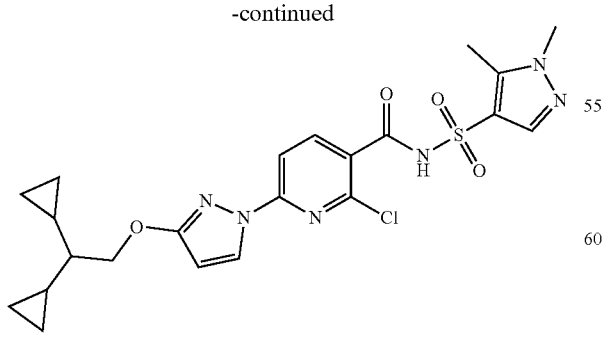

A mixture of 2-chloro-6-[3-(2,2-dicyclopropylethoxy)pyrazol-1-yl]-N-(1,5-dimethylpyrazol-4-yl)sulfonyl-pyridine-3-carboxamide (72.0 mg, 0.1426 mmol), (4S)-2,2,4-trimethylpyrrolidine (hydrochloride salt) (72.0 mg, 0.4811 mmol), and potassium carbonate (120.0 mg, 0.8683 mmol) in DMSO (2.0 μL) was stirred at 130° C. for 15 hours. The reaction mixture was filtered and purified using a reverse phase HPLC-MS method with a dual gradient run from 50-99% acetonitrile in 5 mM HCl to afford 6-[3-(2,2-dicyclopropylethoxy)pyrazol-1-yl]-N-(1,5-dimethylpyrazol-4-yl)sulfonyl-2-[(4S)-2,2,4-trimethylpyrrolidin-1-yl]pyridine-3-carboxamide (33.6 mg, 41%). ESI-MS m/z calc. 581.27844, found 582.5 (M+1)+; Retention time: 2.2 minutes.

$^1$H NMR (400 MHz, Chloroform-d) δ 8.32 (d, J=8.5 Hz, 1H), 8.22 (d, J=2.8 Hz, 1H), 8.07 (s, 1H), 7.58 (d, J=8.5 Hz, 1H), 5.96 (d, J=2.8 Hz, 1H), 4.32 (d, J=5.7 Hz, 2H), 3.86 (s, 3H), 3.48 (dd, J=10.3, 8.4 Hz, 1H), 3.09 (dd, J=10.4, 7.7 Hz, 1H), 2.62 (dt, J=15.7, 7.8 Hz, 1H), 2.46 (s, 3H), 2.13 (dd, J=12.3, 7.9 Hz, 1H), 1.70 (dd, J=12.4, 9.5 Hz, 1H), 1.36 (s, 3H), 1.31 (s, 3H), 1.21 (d, J=6.7 Hz, 3H), 0.90-0.76 (m, 2H), 0.67-0.57 (m, 1H), 0.53-0.38 (m, 4H), 0.31-0.11 (m, 4H).
Synthesis of 6-[3-(3,3-dicyclopropylpropoxy)pyrazol-1-yl]-N-(1,3-dimethylpyrazol-4-yl)sulfonyl-2-[(4S)-2,2,4-trimethylpyrrolidin-1-yl]pyridine-3-carboxamide (Compound 38)
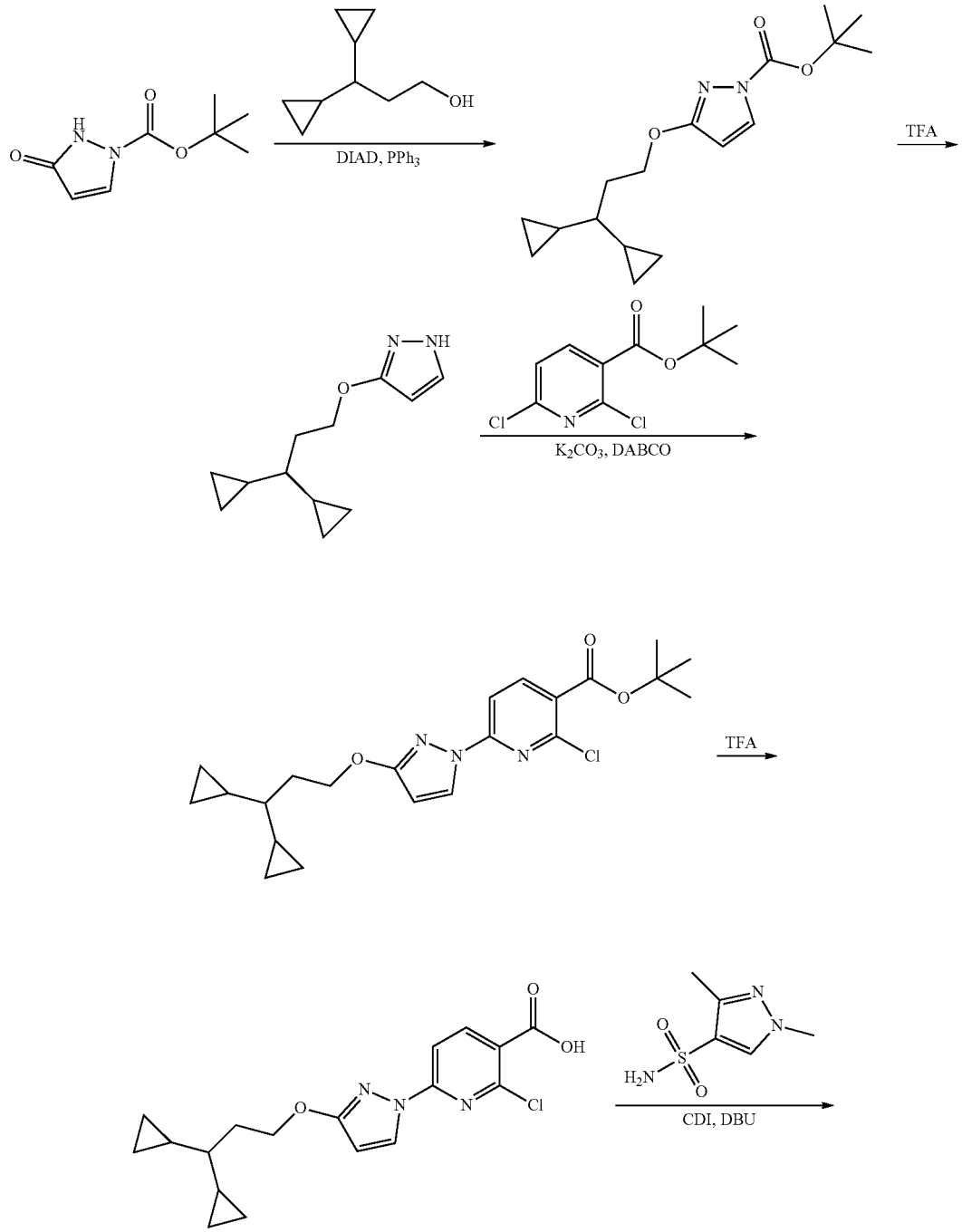

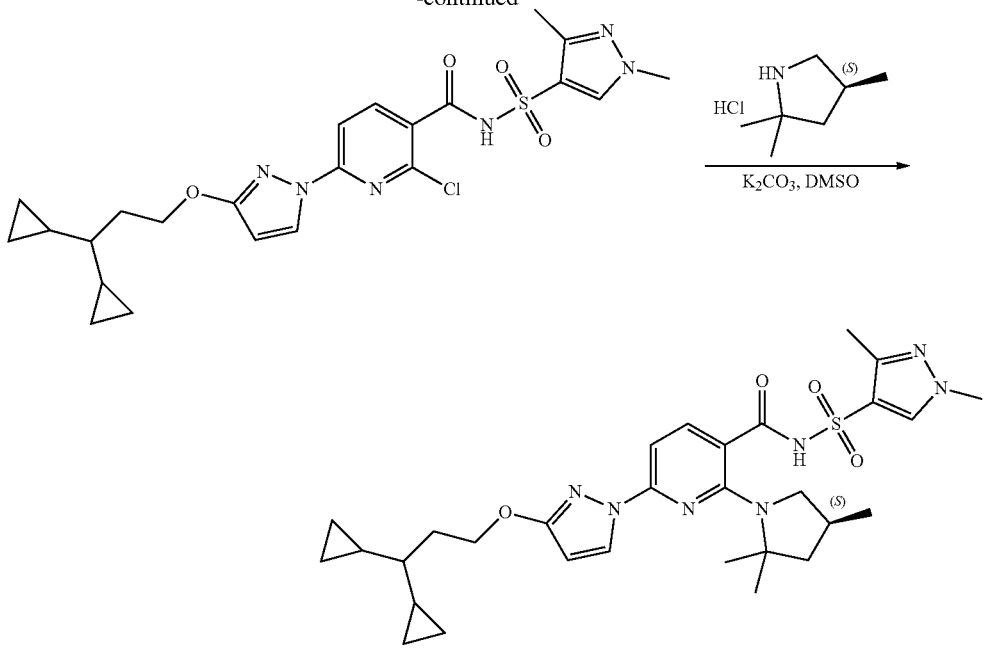

3,3-Dicyclopropylpropan-1-ol

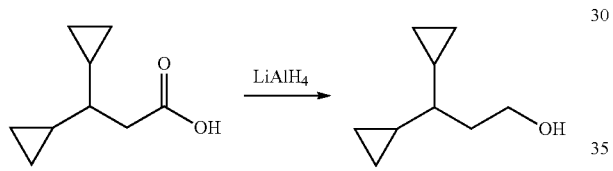

To a solution of 3, 3-dicyclopropylpropanoic acid (200 mg, 1.297 mmol) in dry THF (2.000 mL) was added lithium aluminum hydride (845.0 μL of 2 M, 1.690 mmol) in an ice/water bath under nitrogen atmosphere slowly drop wise. The mixture was allowed to gradually warm to room temperature and stirred for 16 hours. The flask was again cooled in an ice-bath and sequentially quenched with water (70.0 μL, 3.886 mmol) (slowly), followed by NaOH (70.0 μL of 6 M, 0.4200 mmol), then water (200 μL, 11.10 mmol) affording a white granular solid in the mixture. To this mixture anhydrous magnesium sulfate was added and stirred for 10 minutes. The resultant white heterogeneous mixture was filtered through Celite, and the precipitate was washed with ether. The filtrate was concentrated to afford 3, 3-dicyclopropylpropan-1-ol (140 mg, 77%). ESI-MS m/z calc. 140.12012, found 141.2 (M+1)$^+$; Retention time: 0.5 minutes.

Step 1: tert-Butyl 3-(3,3-dicyclopropylpropoxy)pyrazole-1-carboxylate

A solution of 3, 3-dicyclopropylpropan-1-ol (140.0 mg, 0.9984 mmol), tert-butyl 3-hydroxypyrazole-1-carboxylate (185.0 mg, 1.004 mmol), and triphenylphosphane (278 mg, 1.060 mmol) in dry THF (7.0 mL) was cooled in an ice bath, and DIAD (200.04, 1.016 mmol) was slowly added under a nitrogen atmosphere. The reaction was allowed to slowly warm to room temperature and was stirred for 16 hours. The reaction mixture was diluted with ethyl acetate, washed with saturated aqueous sodium bicarbonate solution, brine, dried over sodium sulfate, and evaporated under vacuum. The residue was purified by silica gel chromatography using 100% hexanes to 50% ethyl acetate in hexanes to afford tert-butyl 3-(3,3-dicyclopropylpropoxy)pyrazole-1-carboxylate (255 mg, 83%) as colorless oil. ESI-MS m/z calc. 306.19434, found 307.4 (M+1)$^+$; Retention time: 0.81 minutes.

Step 2: 3-(3, 3-Dicyclopropylpropoxy)-1H-pyrazole

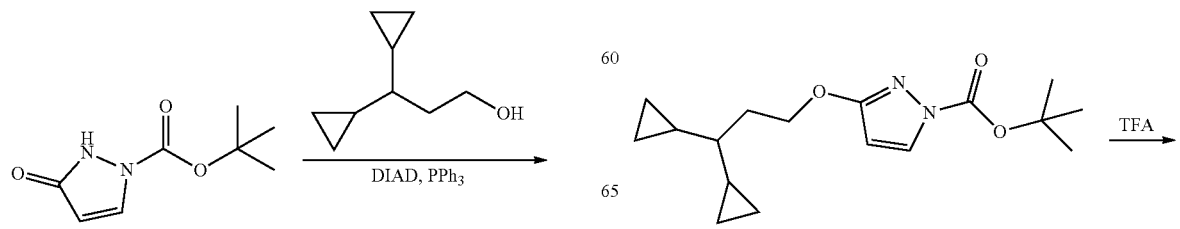

-continued

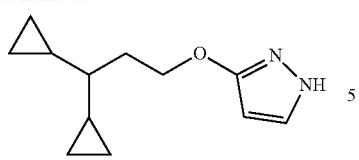

A solution of tert-butyl 3-(3,3-dicyclopropylpropoxy) pyrazole-1-carboxylate (255 mg, 0.8322 mmol) and trifluoroacetic acid (325.0 μL, 4.218 mmol) in dichloromethane (1 mL) was stirred for 2.5 hours. The volatiles were removed under vacuum to afford 3-(3, 3-dicyclopropylpropoxy)-1H-pyrazole (trifluoroacetate salt) as colorless oil which was used as it is without further purification for next reaction. ESI-MS m/z calc. 206.1419, found 207.2 (M+1)$^+$; Retention time: 0.59 minutes.

Step 3: tert-Butyl 2-chloro-6-[3-(3, 3-dicyclopropyl-propoxy) pyrazol-1-yl] pyridine-3-carboxylate

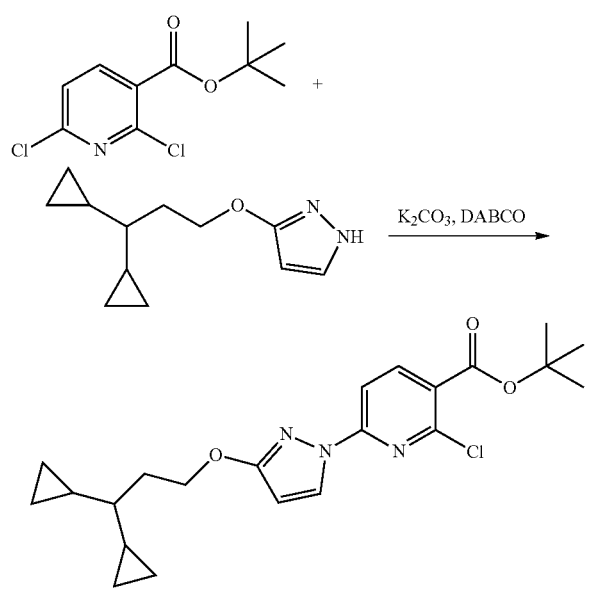

A mixture of tert-butyl 2,6-dichloropyridine-3-carboxylate (220.0 mg, 0.8867 mmol), 3-(3,3-dicyclopropylpropoxy)-1H-pyrazole (266.0 mg, 0.8305 mmol), potassium carbonate (230 mg, 1.664 mmol) and 1,4-diazabicyclo [2.2.2]octane (20 mg, 0.1783 mmol) in DMSO (10 mL) was stirred at room temperature for 15 hours. The reaction was diluted with water and extracted with ethyl acetate. The combined organic extracts were washed with brine, dried over sodium sulfate and evaporated. The residue was purified by silica gel column chromatography using 100% hexanes to 20% ethyl acetate in hexanes to afford tert-butyl 2-chloro-6-[3-(3,3-dicyclopropylpropoxy)pyrazol-1-yl] pyridine-3-carboxylate (245 mg, 71%) as colorless oil. ESI-MS m/z calc. 417.18192, found 418.4 (M+1)$^+$; Retention time: 1.28 minutes.

Step 4: 2-Chloro-6-[3-(3, 3-dicyclopropylpropoxy) pyrazol-1-yl] pyridine-3-carboxylic acid

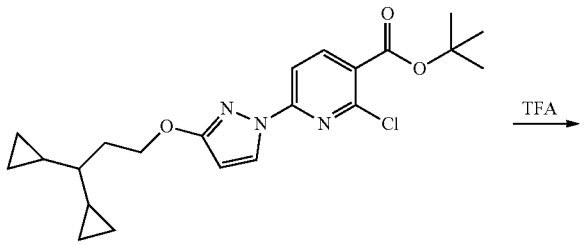

A solution of tert-butyl 2-chloro-6-[3-(3, 3-dicyclopropylpropoxy) pyrazol-1-yl]pyridine-3-carboxylate (245.0 mg, 0.5862 mmol) in trifluoroacetic acid (500.0 μL, 6.490 mmol) and dichloromethane (1.5 mL) was stirred for 4 hours at room temperature. The solvent was evaporated, and twice the residue was taken up in THF and concentrated under vacuum to afford 2-chloro-6-[3-(3,3-dicyclopropylpropoxy) pyrazol-1-yl]pyridine-3-carboxylic acid (204 mg, 96%) as white solid which was used as it is for the next reaction. ESI-MS m/z calc. 361.11932, found 362.3 (M+1)$^+$; Retention time: 0.8 minutes.

$^1$H NMR (400 MHz, Methanol-d4) δ 8.47-8.32 (m, 2H), 7.73 (d, J=8.5 Hz, 1H), 6.03 (d, J=2.9 Hz, 1H), 4.45 (t, J=6.7 Hz, 2H), 1.98 (q, J=7.0 Hz, 2H), 0.75-0.64 (m, 2H), 0.50-0.39 (m, 4H), 0.35-0.26 (m, 1H), 0.26-0.19 (m, 2H), 0.15-0.06 (m, 2H).

Step 5: 2-Chloro-6-[3-(3,3-dicyclopropylpropoxy) pyrazol-1-yl]-N-(1,3-dimethylpyrazol-4-yl)sulfonyl-pyridine-3-carboxamide

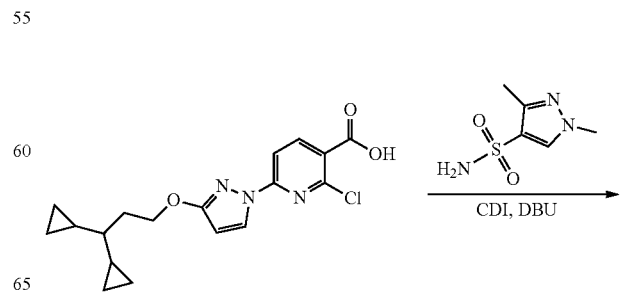

-continued

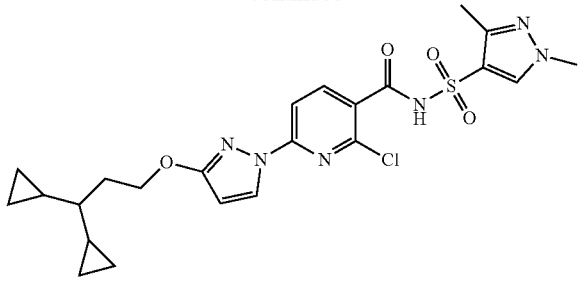

A solution of 2-chloro-6-[3-(3,3-dicyclopropylpropoxy)pyrazol-1-yl]pyridine-3-carboxylic acid (50 mg, 0.1382 mmol) and carbonyl diimidazole (30.0 mg, 0.1850 mmol) in THF (1.000 mL) was stirred for 45 minutes. Then 1,3-dimethylpyrazole-4-sulfonamide (30.0 mg, 0.1712 mmol) and 2,3,4,6,7,8,9,10-octahydropyrimido[1,2-a]azepine (30.0 μL, 0.2006 mmol) were added, and the reaction mixture was stirred for additional 2 hr at room temperature. The reaction mixture was quenched with saturated ammonium chloride solution and extracted with ethyl acetate. The combined extracts were washed with brine, dried over sodium sulfate and evaporated to afford 2-chloro-6-[3-(3,3-dicyclopropylpropoxy)pyrazol-1-yl]-N-(1,3-dimethylpyrazol-4-yl)sulfonyl-pyridine-3-carboxamide (70 mg, 98%) which was used as is for the next reaction. ESI-MS m/z calc. 518.1503, found 519.5 (M+1)+; Retention time: 0.78 minutes.

Step 6: 6-[3-(3,3-Dicyclopropylpropoxy)pyrazol-1-yl]-N-(1,3-dimethylpyrazol-4-yl)sulfonyl-2-[(4S)-2,2,4-trimethylpyrrolidin-1-yl]pyridine-3-carboxamide A mixture of 2-chloro-6-[3-(3,3-dicyclopropylpropoxy)pyrazol-1-yl]-N-(1,3-dimethylpyrazol-4-yl)sulfonyl-pyridine-3-carboxamide (70.0 mg, 0.1349 mmol), (4S)-2,2,4-trimethylpyrrolidine (hydrochloride salt) (70.08 mg, 0.4683 mmol), and potassium carbonate (112.0 mg, 0.8104 mmol) in DMSO (1 mL) was stirred at 130° C. for 15 hours. The reaction mixture was filtered and purified using a reverse phase HPLC-MS method with a dual gradient run from 50-99% acetonitrile in 5 mM HCl to afford 6-[3-(3,3-dicyclopropylpropoxy)pyrazol-1-yl]-N-(1,3-dimethylpyrazol-4-yl)sulfonyl-2-[(4S)-2,2,4-trimethylpyrrolidin-1-yl]pyridine-3-carboxamide (34.7 mg, 43%). ESI-MS m/z calc. 595.29407, found 596.6 (M+1)+; Retention time: 2.42 minutes.

¹H NMR (400 MHz, Chloroform-d) δ 8.34 (d, J=8.5 Hz, 1H), 8.22 (d, J=2.8 Hz, 1H), 8.07 (s, 1H), 7.60 (d, J=8.6 Hz, 1H), 5.94 (d, J=2.7 Hz, 1H), 4.43 (t, J=6.8 Hz, 2H), 3.86 (s, 3H), 3.49 (dd, J=10.2, 8.5 Hz, 1H), 3.09 (dd, J=10.3, 7.6 Hz, 1H), 2.62 (q, J=7.7 Hz, 1H), 2.47 (s, 3H), 2.13 (dd, J=12.3, 7.9 Hz, 1H), 1.97 (q, J=6.8 Hz, 2H), 1.71 (dd, J=12.4, 9.5 Hz, 1H), 1.36 (s, 3H), 1.31 (s, 3H), 1.21 (d, J=6.7 Hz, 3H), 0.73-0.60 (m, 2H), 0.48-0.38 (m, 4H), 0.39-0.27 (m, 1H), 0.23-0.16 (m, 2H), 0.16-0.07 (m, 2H).

Synthesis of 6-[3-(Cyclopropoxy)pyrazol-1-yl]-N-(1-methylpyrazol-4-yl)sulfonyl-2-[(4S)-2,2,4-trimethylpyrrolidin-1-yl]pyridine-3-carboxamide (Compound 22)

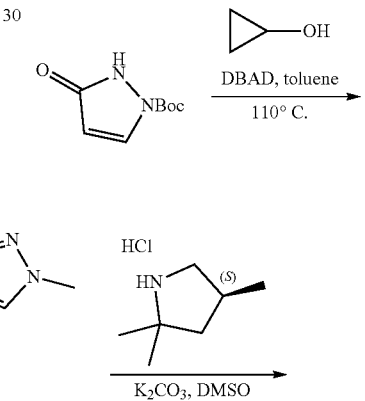

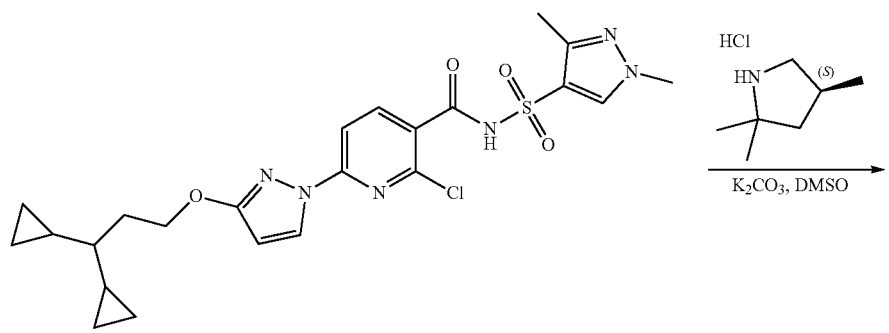

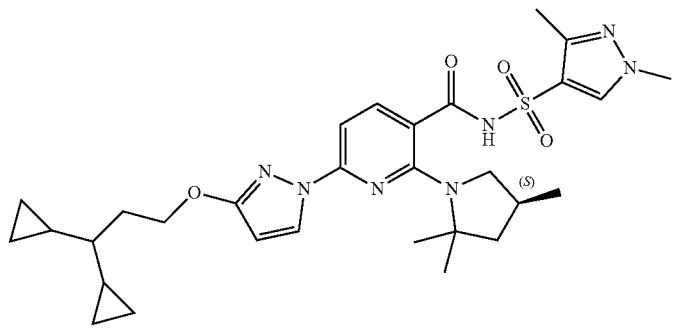

233
-continued

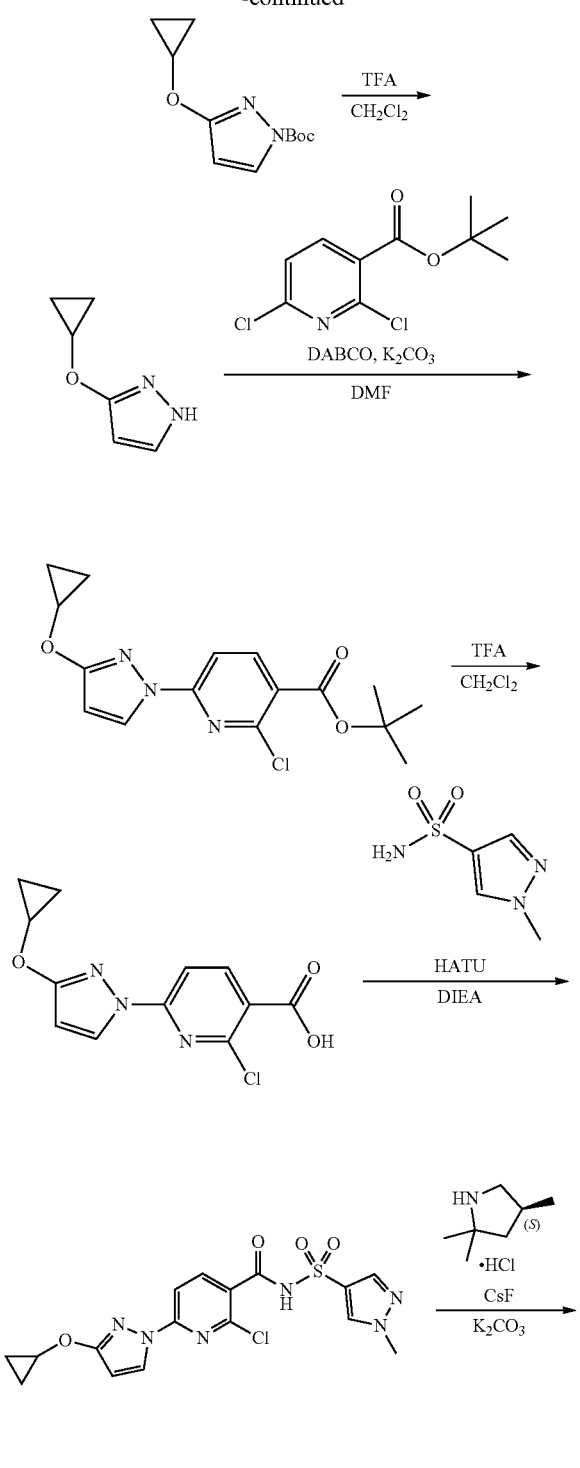

234

Step 1: tert-Butyl 3-cyclopropoxy-1H-pyrazole-1-carboxylate

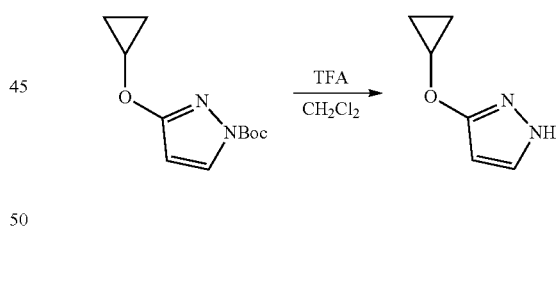

To a solution of cyclopropanol (30.8 mg, 0.531 mmol), tert-butyl 2,3-dihydro-3-oxopyrazole-1-carboxylate (97.7 mg, 0.531 mmol) and triphenylphosphine (139.3 mg, 0.531 mmol) in anhydrous toluene (2 mL) was added di-tert-butyl azodicarboxylate (122.2 mg, 0.531 mmol). The solution was purged with argon for 1 minute, and stirred at ambient temperature for 30 minutes. Then the reaction solution was heated at 110° C. for additional 5 hours before it was cooled to ambient temperature. The solution was diluted with ether (50 mL), washed with NaOH aqueous solution, brine, dried over sodium sulfate, filtered and concentrated under the reduced pressure. Residue obtained was purified by silica gel chromatography (hexane and ethyl acetate, 0 to 10% ethyl acetate gradient) to afford tert-butyl 3-cyclopropoxy-1H-pyrazole-1-carboxylate (52 mg, 46%) as a white solid. ESI-MS m/z calc. 224.116, found 225.0 (M+1)$^+$; Retention time: 4.38 minutes. $^1$H NMR (250 MHz, CDCl$_3$) δ (ppm) 7.86 (d, J=2.8 Hz, 1H), 5.93 (d, J=2.8 Hz, 1H), 4.20-4.15 (m, 1H), 1.61 (s, 9H), 0.85-0.72 (m, 4H).

Step 2: 3-Cyclopropoxy-1H-pyrazole

To a solution of tert-butyl 3-cyclopropoxy-1H-pyrazole-1-carboxylate (131 mg, 0.584 mmol) in dichloromethane (6 mL) was added TFA (667 mg, 0.38 mL, 5.84 mmol). The resulting solution was stirred at ambient temperature for 3 hours. All solvents were removed under the reduced pressure. The residue obtained was dissolved in ether (100 mL), washed with saturated sodium bicarbonate aqueous solution, dried over magnesium sulfate, filtered and concentrated under the reduced pressure to afford 3-cyclopropoxy-1H-pyrazole as a pale yellow oil. Crude product obtained was directly used in next step.

Step 3: tert-Butyl 2-chloro-6-(3-cyclopropoxy-1H-pyrazole-1-yl)pyridine-3-carboxylate

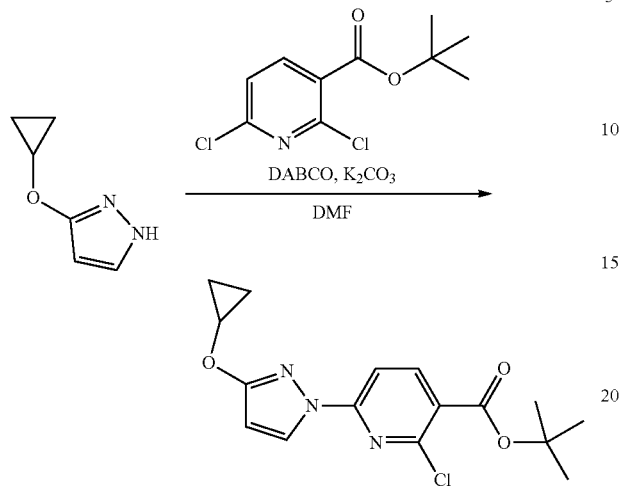

Crude 3-cyclopropoxy-1H-pyrazole (73 mg, 0.584 mmol), tert-butyl 2,6-dichloro pyridine-3-carboxylate (159 mg, 0.643 mmol), K₂CO₃ (162 mg, 1.17 mmol) and DABCO (13 mg, 0.117 mmol) were dissolved in anhydrous DMF (1.5 mL). The reaction solution was stirred at ambient temperature for 16 hours. The reaction solution was diluted with ether (100 mL), washed with water (3×25 mL) and brine (25 mL). Organic layers were separated, dried over magnesium sulfate, filtered and concentrated under the reduced pressure. Residue obtained was purified by silica gel chromatography (hexane and dichloromethane, 0 to 100% dichloromethane gradient) to afford tert-butyl 2-chloro-6-(3-cyclopropoxy-1H-pyrazole-1-yl)pyridine-3-carboxylate (153 mg, 78%) as a sticky oil. ESI-MS m/z calc. 335.104, found 336.1 (M+1)⁺; Retention time: 6.84 minutes.

Step 4: 2-Chloro-6-(3-cyclopropoxy-1H-pyrazole-1-yl)pyridine-3-carboxylic acid

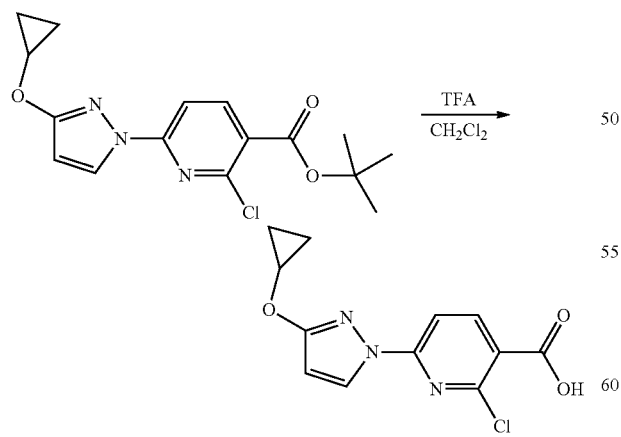

To a solution of tert-butyl 2-chloro-6-(3-cyclopropoxy-1H-pyrazole-1-yl)pyridine-3-carboxylate (153 mg, 0.456 mmol) in dichloromethane (2.2 mL) was added TFA (519 mg, 0.35 mL, 4.56 mmol). The resulting solution was stirred at ambient temperature for 48 hours. Then 1,2-dichloroethane (2 mL) was added, and all solvents were removed under the reduced pressure. The white solid obtained was suspended in the mixture of hexane and ether (10 mL, hexane/ether, 19/1), sonicated, filtered, washed with hexane (10 mL) and dried to afford 2-chloro-6-(3-cyclopropoxy-1H-pyrazole-1-yl)pyridine-3-carboxylic acid (122 mg, 97%) as a white solid. ESI-MS m/z calc. 279.041, found 279.9 (M+1)⁺; Retention time: 4.43 minutes.

¹H NMR (500 MHz, DMSO-d₆) δ (ppm) 13.6 (s, 1H), 8.43 (d, J=3.0 Hz, 1H), 8.39 (d, J=8.5 Hz, 1H), 7.72 (d, J=8.5 Hz, 1H), 6.28 (d, J=3.0 Hz, 1H), 4.16-4.13 (m, 1H), 0.79-0.71 (m, 4H).

Step 5: 2-Chloro-6-[3-(cyclopropoxy)pyrazol-1-yl]-N-(1-methylpyrazol-4-yl)sulfonyl-pyridine-3-carboxamide

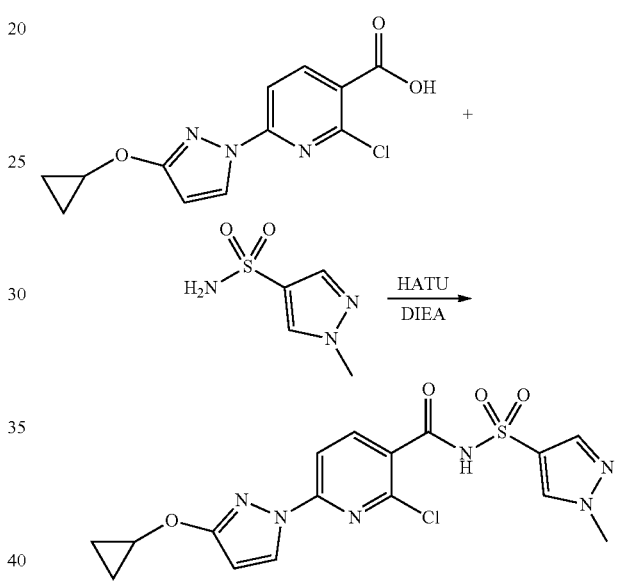

2-Chloro-6-[3-(cyclopropoxy)pyrazol-1-yl]pyridine-3-carboxylic acid (25 mg, 0.08939 mmol) in DMF (0.5 mL), 1-methylpyrazole-4-sulfonamide (24 mg, 0.1489 mmol), HATU (70 mg, 0.1841 mmol), and DIEA (32 µL, 0.1837 mmol) were combined and stirred at room temperature for 16 hours. The reaction mixture was filtered and purified on reverse phase HPLC (Waters, HCl, 25-75% ACN-H₂O) to give 2-chloro-6-[3-(cyclopropoxy)pyrazol-1-yl]-N-(1-methylpyrazol-4-yl)sulfonyl-pyridine-3-carboxamide (25 mg). Used directly in next step.

Step 6: 6-[3-(Cyclopropoxy)pyrazol-1-yl]-N-(1-methylpyrazol-4-yl)sulfonyl-2-[(4S)-2,2,4-trimethylpyrrolidin-1-yl]pyridine-3-carboxamide

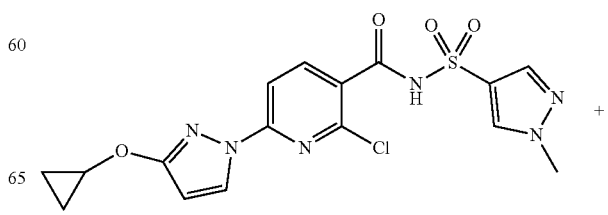

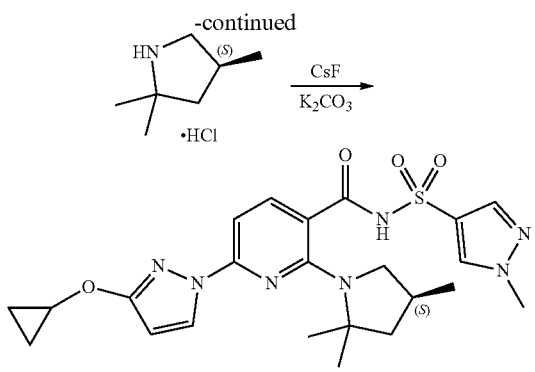

A mixture of 2-chloro-6-[3-(cyclopropoxy)pyrazol-1-yl]-N-(1-methylpyrazol-4-yl)sulfonyl-pyridine-3-carboxamide (25 mg), (4S)-2,2,4-trimethylpyrrolidine (hydrochloride salt) (20 mg, 0.1336 mmol), cesium fluoride (30 mg, 0.1975 mmol), potassium carbonate (60 mg, 0.4341 mmol) in DMSO (0.5 mL) was stirred at 140° C. for 16 hours. The reaction was filtered and purified on reverse phase HPLC (Waters, HCl, 25-75% ACN-H$_2$O) to give 6-[3-(cyclopropoxy)pyrazol-1-yl]-N-(1-methylpyrazol-4-yl)sulfonyl-2-[(4S)-2,2,4-trimethylpyrrolidin-1-yl]pyridine-3-carboxamide (8.3 mg, 18%). ESI-MS m/z calc. 499.20016, found 500.0 (M+1)+; Retention time: 1.69 minutes.

$^1$H NMR (400 MHz, DMSO) δ 12.39 (s, 1H), 8.52 (s, 1H), 8.22 (d, J=2.1 Hz, 1H), 7.89 (s, 1H), 7.74 (d, J=8.2 Hz, 1H), 6.90 (d, J=8.7 Hz, 1H), 6.21 (d, J=2.0 Hz, 1H), 4.10 (s, 1H), 3.90 (s, 3H), 2.63 (s, 1H), 2.44 (s, 1H), 2.18 (s, 1H), 1.92-1.85 (m, 1H), 1.55 (d, J=17.1 Hz, 6H), 1.44 (t, J=12.2 Hz, 1H), 0.80 (d, J=6.2 Hz, 3H), 0.73 (s, 4H).

Synthesis of N-(1,5-dimethylpyrazol-4-yl)sulfonyl-6-[3-(spiro[2.2]pentan-2-ylmethoxy)pyrazol-1-yl]-2-[(4S)-2,2,4-trimethylpyrrolidin-1-yl]pyridine-3-carboxamide (Compound 26)

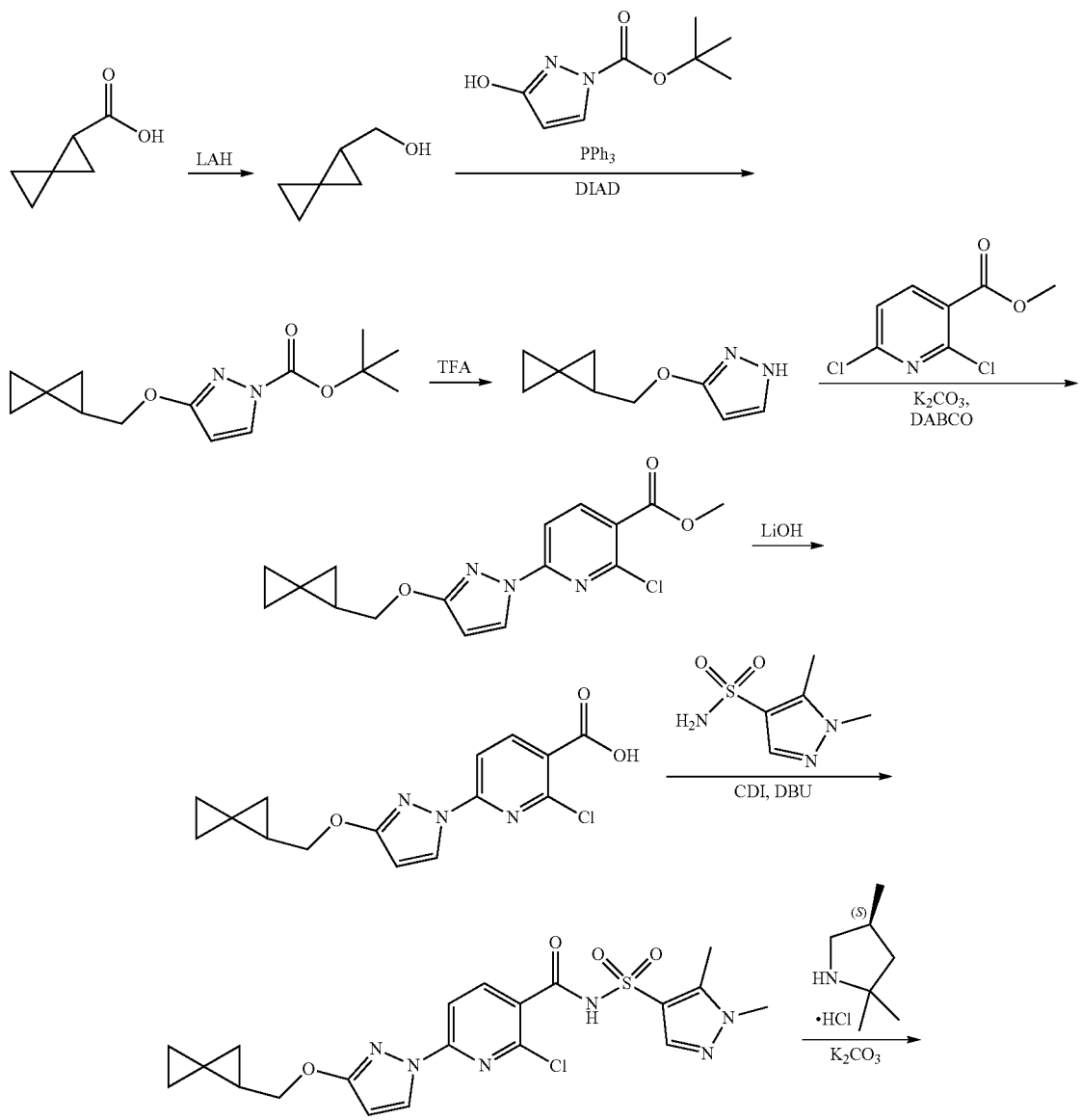

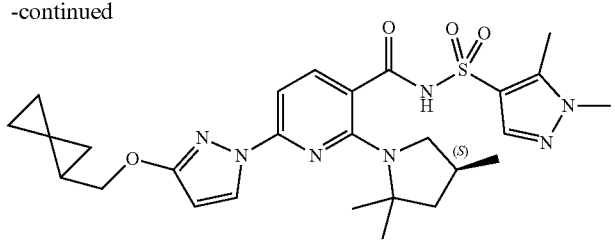

Step 1: spiro[2.2]Pent-1-yl-methanol

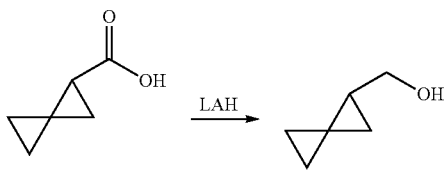 [SMILES: O=C(O)C1CC12CC2 ; "LAH" ; OCC1CC12CC2]

To a suspension of lithium aluminum hydride (888 mg, 23.4 mmol) in tetrahydrofuran (30 mL) was added spiro[2.2]pentane-1-carboxylic acid (1.75 g, 15.6 mmol) in tetrahydrofuran (5 mL) dropwise over 5 minutes. The reaction was heated to 50° C. for 16 hours. The reaction was diluted with diethyl ether (20 mL) and quenched with solid sodium sulfate decahydrate. The mixture was diluted with diethyl ether (100 mL), filtered through celite pad and concentrated to give spiro[2.2]pent-1-yl-methanol (793 mg, 52%) as an oil. ESI-MS m/z calc. 98.15 found 98.8 (M+1)$^+$. Retention time: 2.54 minutes.

$^1$H NMR (250 MHz, CDCl3) ppm 0.58-0.89 (m, 4H) 0.91-1.09 (m, 1H) 1.20-1.37 (m, 1H) 1.43 (m, 1H) 3.60 (dd, J=11.98, 6.37 Hz, 2H)

Step 2: 3-(spiro[2.2]Pent-1-ylmethoxy)-pyrazole-1-carboxylic acid tert-butyl ester

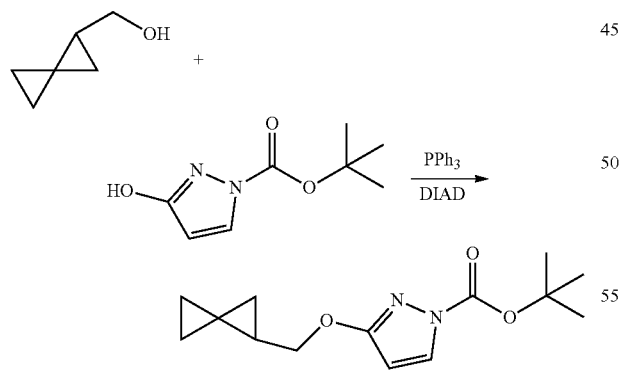

To a solution of crude spiro[2.2]pent-1-yl-methanol (966 mg, 9.8 mmol) in tetrahydrofuran (40 mL) was added triphenyl phosphine (2.58 g, 9.8 mmol), 3-hydroxy-pyrazole-1-carboxylic acid tert-butyl ester (1.64 g, 8.9 mmol). The reaction mixture was cooled in an ice bath followed by the addition of diisopropyl azodicarboxylate (1.9 mL, 9.8 mmol). The ice bath was removed and the reaction was stirred for 2 hours. The solvent was removed in vacuum and the crude mixture was purified by silica gel column chromatography using 10-20% hexanes-diethyl ether to give 3-(spiro[2.2]pent-1-ylmethoxy)-pyrazole-1-carboxylic acid tert-butyl ester (1.20 g, 44%) as a clear oil. ESI-MS m/z calc. 264.33 found 265.1 (M+1)+. Retention time: 3.36 minutes.

Step 3: 3-(spiro[2.2]Pent-1-ylmethoxy)-1H-pyrazole

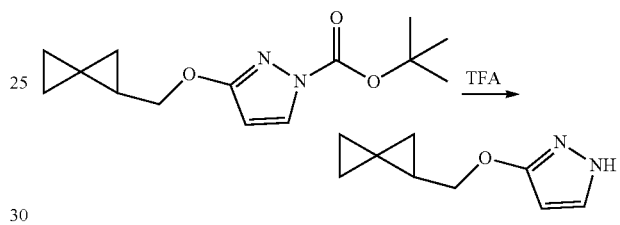

To 3-(spiro[2.2]pent-1-ylmethoxy)-pyrazole-1-carboxylic acid tert-butyl ester (1.2 g, 4.54 mmol) was added dichloromethane (30 mL) and trifluoroacetic acid (3.4 mL, 45 mmol). The reaction mixture was stirred for 2 hours at room temperature and concentrated to dryness in vacuum. The residue was azeotroped twice with 1,2-dichloroethane (15 mL) to give crude 3-(spiro[2.2]pent-1-ylmethoxy)-1H-pyrazole (1.87 g, 51%) as a yellow oil. ESI-MS m/z calc. 164.09 found 164.6 (M+1)+. Retention time: 2.11 minutes.

Step 4: 2-Chloro-6-[3-(spiro[2.2]pent-1-ylmethoxy)pyrazol-1-yl]-nicotinic acid methyl ester

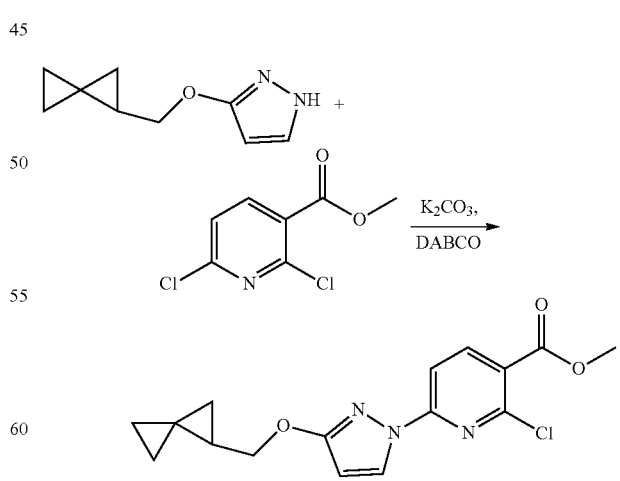

To crude 3-(spiro[2.2]pent-1-ylmethoxy)-1H-pyrazole (1.87 g, assumed 4.54 mmol) was added methyl 2,6-dichloronicotinate (935 mg, 4.54 mmol), 1,4-diazabicyclo[2.2.2]octane (102 mg, 0.91 mmol), dimethylformamide (8 mL)

and potassium carbonate (1.9 g, 13.6 mmol). The reaction was stirred for 48 hours at room temperature, diluted with diethyl ether (75 mL) and washed with water containing a small amount of brine (3×50 mL) and brine (50 mL). This organic layer was dried over sodium sulfate and concentrated in vacuum. The crude reaction mixture was purified by silica gel column chromatography using 0-15% hexanes:diethyl ether to afford 2-chloro-6-[3-(spiro[2.2]pent-1-ylmethoxy) pyrazol-1-yl]-nicotinic acid methyl ester (1.02 g, 67%) as an off-white solid. ESI-MS m/z calc. 333.09 found 333.9 (M+1)+. Retention time: 3.85 minutes.

Step 5: 2-Chloro-6-[3-(spiro[2.2]pent-1-ylmethoxy)-pyrazol-1-yl]-nicotinic acid

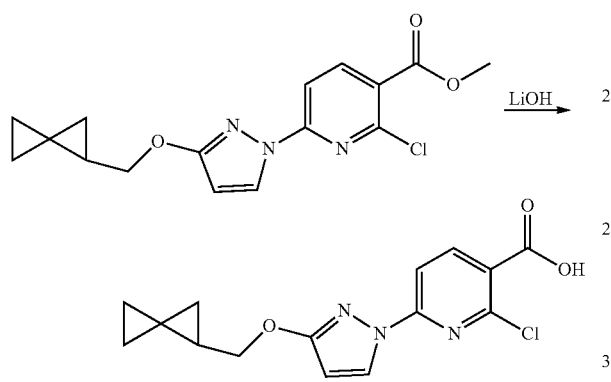

To 2-Chloro-6-[3-(spiro[2.2]pent-1-ylmethoxy) pyrazol-1-yl]-nicotinic acid methyl ester (990 mg, 2.97 mmol) was added water (6 mL), methanol (6 mL) and tetrahydrofuran (6 mL) followed by lithium hydroxide (285 mg, 11.88 mmol). The reaction was stirred for 1 hour and 1M hydrochloric acid (12 mL) was added. Formed white solid was filtered off, washed with water and hexanes to give 2-chloro-6-[3-(spiro[2.2]pent-1-ylmethoxy)-pyrazol-1-yl]-nicotinic acid (927 mg, 98%) as a white solid. ESI-MS m/z calc. 319.07 found 320.0 (M+1)+. Retention time: 3.25 minutes.

$^1$H NMR (250 MHz, CDCl3) ppm: 0.76-0.88 (m, 5H), 1.11-1.13 (m, 1H), 1.60-1.75 (m, 1H), 4.22 (dd, J=7.0, 3.3, Hz, 2H) 6.00 (d, J=2.5 Hz, 1H), 7.76 (d, J=8.5 Hz, 1H), 8.38 (d, J=2.5 Hz, 1H), 8.43 (d, J=8.5 Hz, 1H).

Step 6: 2-chloro-N-(1,5-dimethylpyrazol-4-yl)sulfonyl-6-[3-(spiro[2.2]pentan-2-ylmethoxy)pyrazol-1-yl]pyridine-3-carboxamide

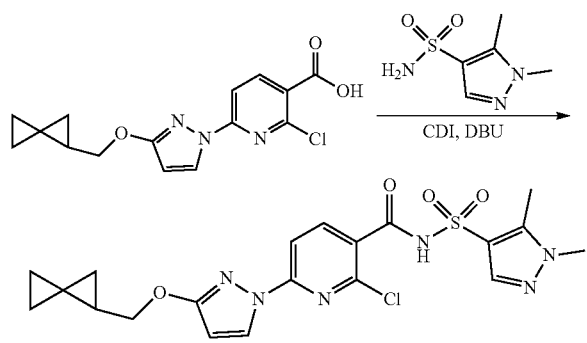

2-chloro-6-[3-(spiro[2.2]pentan-2-ylmethoxy)pyrazol-1-yl]pyridine-3-carboxylic acid (approximately 50 mg, 0.16 mmol) and carbonyl diimidazole (approximately 38 mg, 0.23 mmol) were combined in THF (1.5 mL) and stirred for 1 h. At this point, 1,5-dimethylpyrazole-4-sulfonamide (approximately 28 mg, 0.16 mmol) was added followed by DBU (approximately 70 µL, 0.47 mmol) and the reaction was stirred for an additional 3 h at room temperature. The reaction was diluted with ethyl acetate and washed with a 1M citric acid solution, followed by brine. The organics were separated, dried over sodium sulfate, and evaporated. The crude material was used without further purification. 2-chloro-N-(1,5-dimethylpyrazol-4-yl)sulfonyl-6-[3-(spiro[2.2]pentan-2-ylmethoxy)pyrazol-1-yl]pyridine-3-carboxamide (75 mg, 98%) ESI-MS m/z calc. 476.10336, found 477.2 (M+1)$^+$; Retention time: 0.67 minutes.

Step 7: N-(1,5-dimethylpyrazol-4-yl)sulfonyl-6-[3-(spiro[2.2]pentan-2-ylmethoxy)pyrazol-1-yl]-2-[(4S)-2,2,4-trimethylpyrrolidin-1-yl]pyridine-3-carboxamide

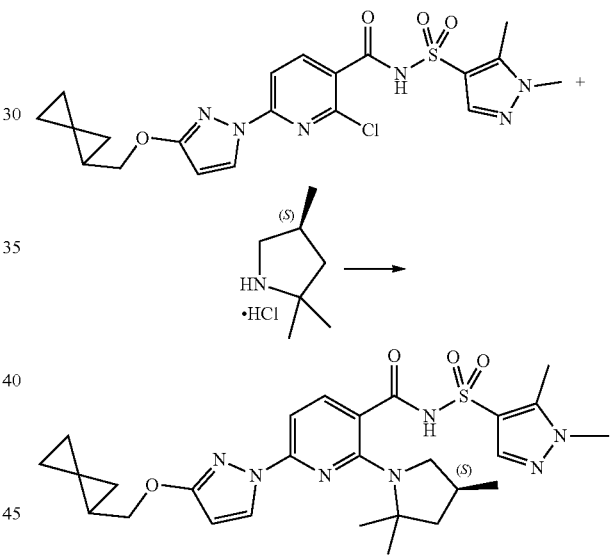

2-chloro-N-(1,5-dimethylpyrazol-4-yl)sulfonyl-6-[3-(spiro[2.2]pentan-2-ylmethoxy)pyrazol-1-yl]pyridine-3-carboxamide (75 mg, 0.16 mmol), (4S)-2,2,4-trimethylpyrrolidine (Hydrochloride salt) (approximately 70.63 mg, 0.4719 mmol), and potassium carbonate (approximately 108.7 mg, 0.7865 mmol) were combined in DMSO (1 mL) and heated at 130° C. for 16 h. The reaction was diluted with water (3 mL) and stirred for 20 min. A solid formed and the aqueous liquid was decanted. The solid was dissolved in ethyl acetate and washed with a 1M citric acid solution, then brine. The organics were dried over sodium sulfate and evaporated. The crude material was purified by silica gel chromatography eluting with 0-10% methanol in dichloromethane to give N-(1,5-dimethylpyrazol-4-yl)sulfonyl-6-[3-(spiro[2.2]pentan-2-ylmethoxy)pyrazol-1-yl]-2-[(4S)-2,2,4-trimethylpyrrolidin-1-yl]pyridine-3-carboxamide (35 mg, 40.19%). ESI-MS m/z calc. 553.24713, found 554.3 (M+1)$^+$; Retention time: 2.07 minutes.

Synthesis of N-(1,5-Dimethylpyrazol-4-yl)sulfonyl-6-[3-[(3-fluoro-1-bicyclo[1.1.1]pentanyl)methoxy]pyrazol-1-yl]-2-[(4S)-2,2,4-trimethylpyrrolidin-1-yl]pyridine-3-carboxamide (Compound 27)

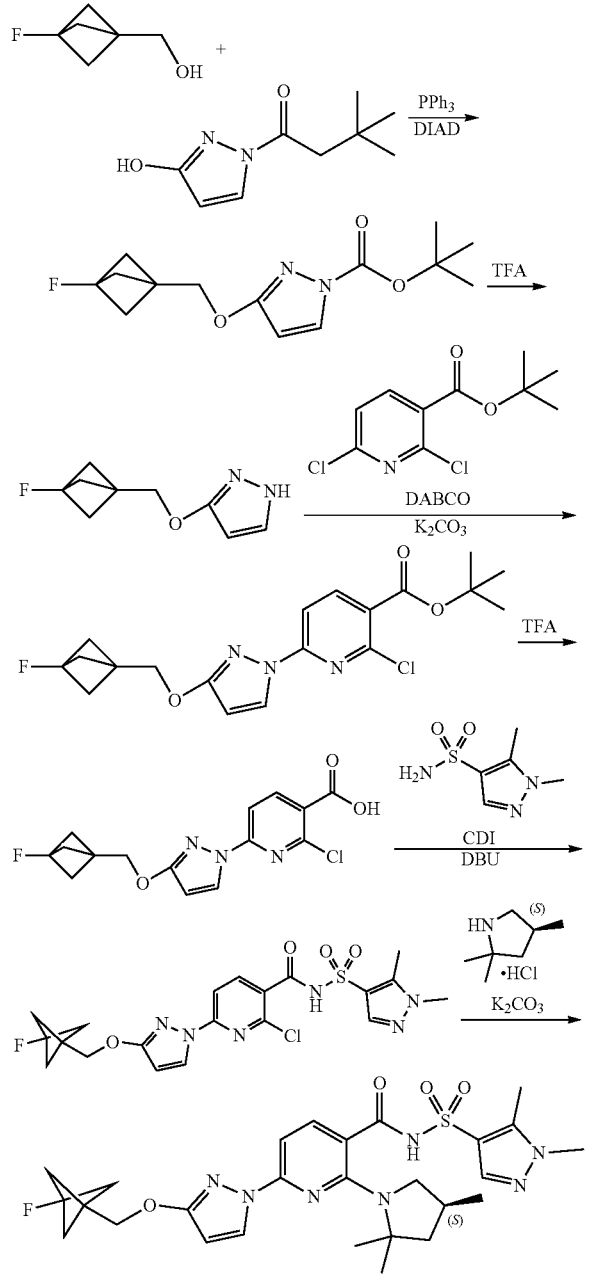

Step 1: tert-Butyl 3-[(3-fluoro-1-bicyclo[1.1.1]pentanyl)methoxy]pyrazole-1-carboxylate

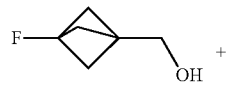

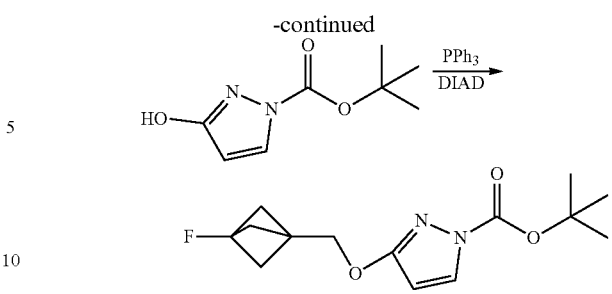

A solution of (3-fluoro-1-bicyclo[1.1.1]pentanyl)methanol (0.27 g, 2.3 mmol), tert-butyl 3-hydroxypyrazole-1-carboxylate (0.46 g, 2.5 mmol), and triphenyl phosphine (0.67 g, 2.6 mmol) in THF (12 mL) was cooled in an ice bath, and isopropyl N-isopropoxycarbonyliminocarbamate (0.50 mL, 2.6 mmol) was slowly added. The reaction was allowed to slowly warm to room temperature and was stirred for three days. It was diluted with ethyl acetate, washed with saturated aqueous sodium bicarbonate, dried over sodium sulfate, and evaporated under vacuum. The residue was purified by silica gel chromatography with 0-40% ethyl acetate in hexanes to give tert-butyl 3-[(3-fluoro-1-bicyclo[1.1.1]pentanyl)methoxy]pyrazole-1-carboxylate (0.43 g, 66%) ESI-MS m/z calc. 282.13797, found 283.3 (M+1)$^+$; Retention time: 0.65 minutes.

Step 2: 3-[(3-Fluoro-1-bicyclo[1.1.1]pentanyl)methoxy]-1H-pyrazole

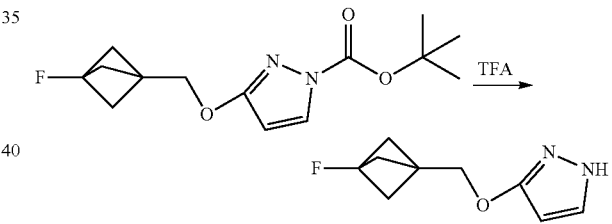

A solution of tert-butyl 3-[(3-fluoro-1-bicyclo[1.1.1]pentanyl)methoxy]pyrazole-1-carboxylate (0.43 g, 1.523 mmol) and trifluoroacetic acid (587 µL, 7.62 mmol) in dichloromethane (4 mL) was stirred for 5 hours. The volatiles were removed under vacuum, and the residue was basified with saturated aqueous sodium bicarbonate and extracted with ethyl acetate. The combined extracts were dried over sodium sulfate and evaporated to give 3-[(3-fluoro-1-bicyclo[1.1.1]pentanyl)methoxy]-1H-pyrazole (0.28 g, 100%) ESI-MS m/z calc. 182.08554, found 183.1 (M+1); Retention time: 0.39 minutes.

Step 3: tert-Butyl 2-chloro-6-[3-[(3-fluoro-1-bicyclo[1.1.1]pentanyl)methoxy]pyrazol-1-yl]pyridine-3-carboxylate

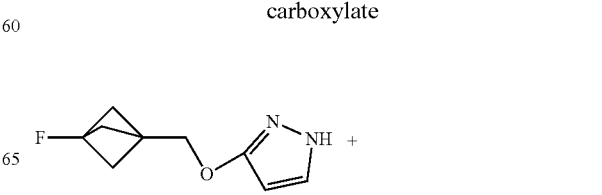

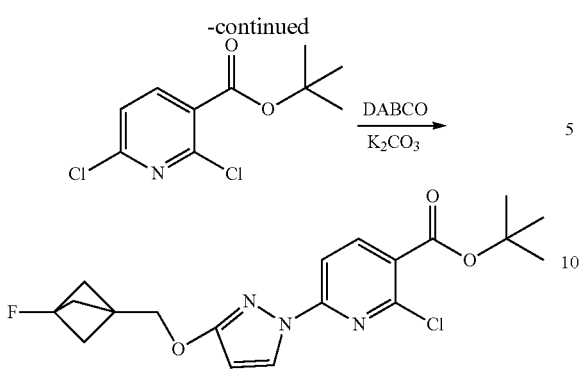

A mixture of 3-[(3-fluoro-1-bicyclo[1.1.1]pentanyl)methoxy]-1H-pyrazole (0.28 g, 1.5 mmol), tert-butyl 2,6-dichloropyridine-3-carboxylate (0.38 g, 1.5 mmol), potassium carbonate (0.26 g, 1.9 mmol), and 1,4-diazabicyclo[2.2.2]octane (34 mg, 0.30 mmol) in DMSO (7.5 mL) was stirred at room temperature for 16 h. The reaction was diluted with water and extracted with ethyl acetate. The combined extracts were washed with brine and water, dried over sodium sulfate, and evaporated. The residue was purified by silica gel chromatography with 0-5% methanol in dichloromethane to give tert-butyl 2-chloro-6-[3-[(3-fluoro-1-bicyclo[1.1.1]pentanyl)methoxy]pyrazol-1-yl]pyridine-3-carboxylate (0.50 g, 85%) ESI-MS m/z calc. 393.12555, found 394.2 (M+1); Retention time: 0.86 minutes.

Step 4: 2-Chloro-6-[3-[(3-fluoro-1-bicyclo[1.1.1]pentanyl)methoxy]pyrazol-1-yl]pyridine-3-carboxylic acid

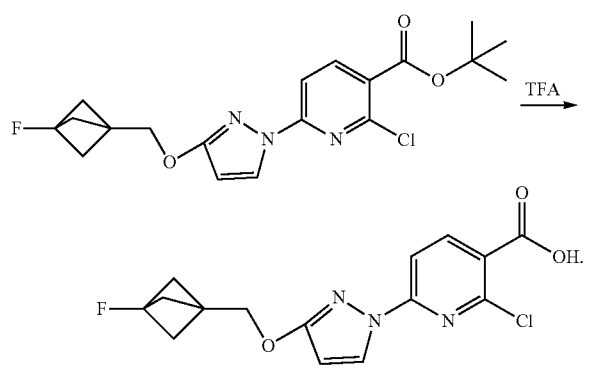

A solution of tert-butyl 2-chloro-6-[3-[(3-fluoro-1-bicyclo[1.1.1]pentanyl)methoxy]pyrazol-1-yl]pyridine-3-carboxylate (0.50 g, 1.270 mmol) and trifluoroacetic acid (978 µL, 12.7 mmol) in dichloromethane (6 mL) was stirred for 15 hours. The solvent was evaporated, and the residue was taken up in acetonitrile. The solvent was evaporated to give 2-chloro-6-[3-[(3-fluoro-1-bicyclo[1.1.1]pentanyl)methoxy]pyrazol-1-yl]pyridine-3-carboxylic acid (0.43 g, 100%) ESI-MS m/z calc. 337.06296, found 338.1 (M+1)$^+$; Retention time: 0.63 minutes.

$^1$H NMR (400 MHz, Chloroform-d) δ 8.43 (d, J=8.5 Hz, 1H), 8.39 (d, J=2.9 Hz, 1H), 7.73 (d, J=8.5 Hz, 1H), 6.00 (d, J=2.8 Hz, 1H), 4.51 (s, 2H), 2.13 (d, J=2.6 Hz, 6H).

Step 5: 2-Chloro-N-(1,5-dimethylpyrazol-4-yl)sulfonyl-6-[3-[(3-fluoro-1-bicyclo[1.1.1]pentanyl)methoxy]pyrazol-1-yl]pyridine-3-carboxamide

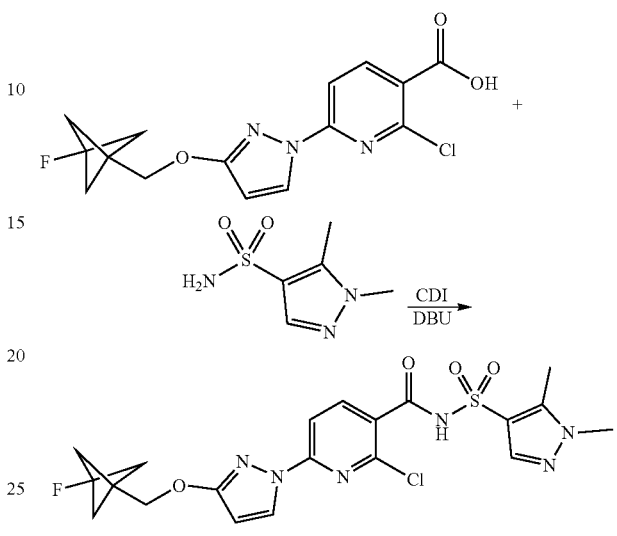

A solution of 2-chloro-6-[3-[(3-fluoro-1-bicyclo[1.1.1]pentanyl)methoxy]pyrazol-1-yl]pyridine-3-carboxylic acid (0.10 g, 0.30 mmol) and carbonyl diimidazole (approximately 58 mg, 0.36 mmol) in THF (1.5 mL) was stirred for 30 minutes, and 1,5-dimethylpyrazole-4-sulfonamide (approximately 68 mg, 0.39 mmol) and 2,3,4,6,7,8,9,10-octahydropyrimido[1,2-a]azepine (approximately 55 mg, 54 µL, 0.36 mmol) were added. After 16 hours the reaction was diluted with 1 M aqueous citric acid and extracted with ethyl acetate. The combined extracts were washed with brine, dried over sodium sulfate and evaporated to give 2-chloro-N-(1,5-dimethylpyrazol-4-yl)sulfonyl-6-[3-[(3-fluoro-1-bicyclo[1.1.1]pentanyl)methoxy]pyrazol-1-yl]pyridine-3-carboxamide (0.18 g). The material was taken on to the next step as-is.

Step 6: N-(1,5-Dimethylpyrazol-4-yl)sulfonyl-6-[3-[(3-fluoro-1-bicyclo[1.1.1]pentanyl)methoxy]pyrazol-1-yl]-2-[(4S)-2,2,4-trimethylpyrrolidin-1-yl]pyridine-3-carboxamide

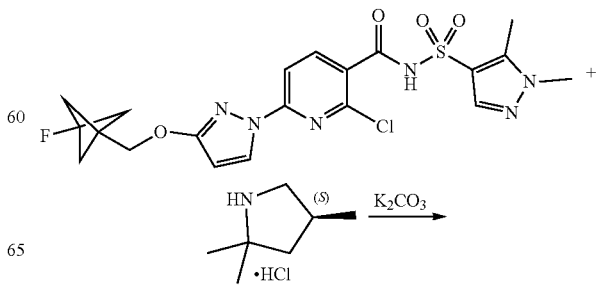

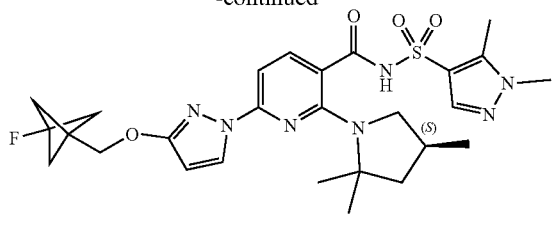
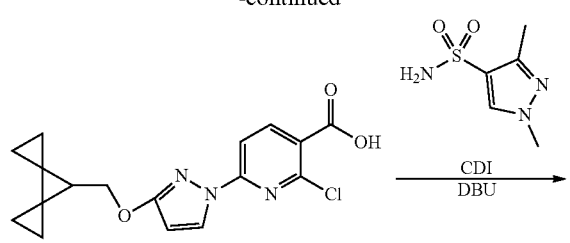

A mixture of crude 2-chloro-N-(1,5-dimethylpyrazol-4-yl)sulfonyl-6-[3-[(3-fluoro-1-bicyclo[1.1.1]pentanyl)methoxy]pyrazol-1-yl]pyridine-3-carboxamide (0.15 g, 0.3031 mmol), (4S)-2,2,4-trimethylpyrrolidine (hydrochloride salt) (approximately 136.1 mg, 0.9093 mmol), and potassium carbonate (approximately 251.4 mg, 1.819 mmol) in DMSO (1.515 mL) was stirred at 130° C. for 15 hours. The reaction was filtered and purified by reverse-phase HPLC-MS (30%-99% acetonitrile/water (5 mM HCl)) to give N-(1,5-dimethylpyrazol-4-yl)sulfonyl-6-[3-[(3-fluoro-1-bicyclo[1.1.1]pentanyl)methoxy]pyrazol-1-yl]-2-[(4S)-2,2,4-trimethylpyrrolidin-1-yl]pyridine-3-carboxamide (51 mg, 29%) as a colorless solid. ESI-MS m/z calc. 571.23773, found 572.4 (M+1)+; Retention time: 2.01 minutes.

$^1$H NMR (400 MHz, DMSO-d6) δ 8.20 (d, J=2.7 Hz, 1H), 7.78 (s, 1H), 7.72 (d, J=8.2 Hz, 1H), 6.90 (d, J=8.2 Hz, 1H), 6.14 (d, J=2.8 Hz, 1H), 4.47 (s, 2H), 3.78 (s, 3H), 2.60-2.54 (m, 1H), 2.53 (s, 3H), 2.46-2.37 (m, 1H), 2.25-2.12 (m, 1H), 2.08 (d, J=2.8 Hz, 6H), 1.87 (dd, J=11.8, 5.5 Hz, 1H), 1.55 (d, J=15.0 Hz, 6H), 1.43 (t, J=12.1 Hz, 1H), 0.80 (d, J=6.3 Hz, 3H).

Synthesis of (S)—N-((1,3-Dimethyl-1H-pyrazol-4-yl)sulfonyl)-6-(3-(dispiro[2.0.2.1]heptan-7-yl-methoxy)-1H-pyrazol-1-yl)-2-(2,2,4-trimethylpyrrolidin-1-yl)nicotinamide (Compound 28)

Step 1: tert-butyl 3-(dispiro[2.0.2.1]heptan-7-yl-methoxy)-1H-pyrazole-1-carboxylate

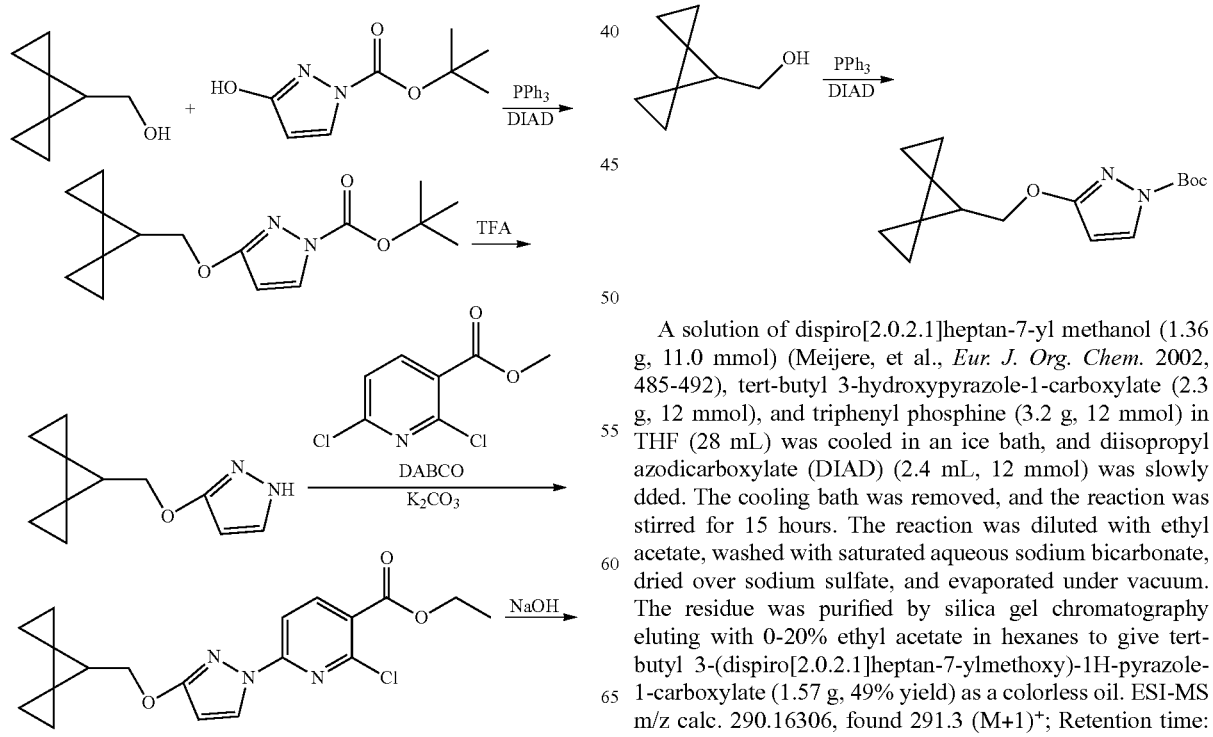

A solution of dispiro[2.0.2.1]heptan-7-yl methanol (1.36 g, 11.0 mmol) (Meijere, et al., *Eur. J. Org. Chem.* 2002, 485-492), tert-butyl 3-hydroxypyrazole-1-carboxylate (2.3 g, 12 mmol), and triphenyl phosphine (3.2 g, 12 mmol) in THF (28 mL) was cooled in an ice bath, and diisopropyl azodicarboxylate (DIAD) (2.4 mL, 12 mmol) was slowly dded. The cooling bath was removed, and the reaction was stirred for 15 hours. The reaction was diluted with ethyl acetate, washed with saturated aqueous sodium bicarbonate, dried over sodium sulfate, and evaporated under vacuum. The residue was purified by silica gel chromatography eluting with 0-20% ethyl acetate in hexanes to give tert-butyl 3-(dispiro[2.0.2.1]heptan-7-ylmethoxy)-1H-pyrazole-1-carboxylate (1.57 g, 49% yield) as a colorless oil. ESI-MS m/z calc. 290.16306, found 291.3 (M+1)$^+$; Retention time: 0.76 minutes.

Step 2: 3-(Dispiro[2.0.2.1]heptan-7-ylmethoxy)-1H-pyrazole

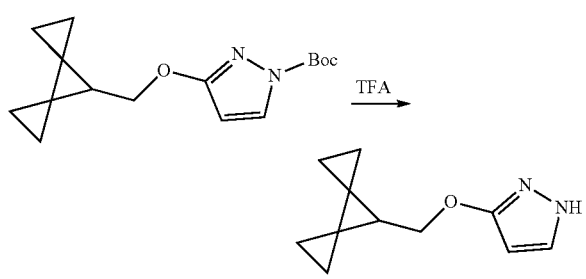

A solution of tert-butyl 3-(dispiro[2.0.2.1]heptan-7-ylmethoxy)-1H-pyrazole-1-carboxylate (1.57 g, 5.41 mmol) and trifluoroacetic acid (2.2 mL, 29 mmol) in dichloromethane (20 mL) was stirred for three hours. The volatiles were removed under vacuum, and the residue was basified with saturated aqueous sodium bicarbonate and extracted with ethyl acetate. The combined extracts were dried over sodium sulfate and evaporated to give 3-(dispiro[2.0.2.1]heptan-7-ylmethoxy)-1H-pyrazole (0.94 g, 91% yield) as pale yellow oil. ESI-MS m/z calc. 190.11061, found 191.1 (M+1)+; Retention time: 0.52 minutes.

Step 3: Ethyl 2-chloro-6-(3-(dispiro[2.0.2.1]heptan-7-ylmethoxy)-1H-pyrazol-1-yl)nicotinate

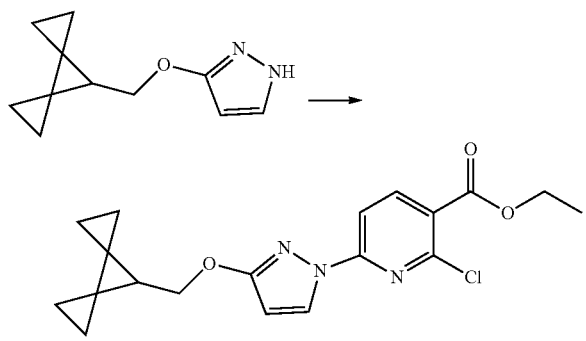

A mixture of 3-(dispiro[2.0.2.1]heptan-7-ylmethoxy)-1H-pyrazole (0.94 g, 4.9 mmol), ethyl 2,6-dichloropyridine-3-carboxylate (1.15 g, 5.23 mmol), potassium carbonate (0.83 g, 6.0 mmol), and 1,4-diazabicyclo[2.2.2]octane (0.12 g, 1.1 mmol) in DMSO (16 mL) was stirred for 24 hours. The reaction was diluted with water and extracted with ethyl acetate. The combined extracts were washed with brine and water, dried over sodium sulfate, and evaporated under vacuum. The residue was purified by silica gel column chromatography eluting with 0-20% ethyl acetate in hexanes to give ethyl 2-chloro-6-(3-(dispiro[2.0.2.1]heptan-7-ylmethoxy)-1H-pyrazol-1-yl)nicotinate (1.39 g, 75% yield) as a colorless solid. ESI-MS m/z calc. 373.11932, found 374.2 (M+1)+; Retention time: 0.87 minutes.
¹H NMR (400 MHz, Chloroform-d) δ 8.36 (d, J=2.8 Hz, 1H), 8.27 (d, J=8.5 Hz, 1H), 7.72 (d, J=8.5 Hz, 1H), 5.96 (d, J=2.9 Hz, 1H), 4.41 (q, J=7.1 Hz, 2H), 4.30 (d, J=7.0 Hz, 2H), 1.94 (t, J=7.0 Hz, 1H), 1.42 (t, J=7.1 Hz, 3H), 1.02-0.89 (m, 4H), 0.75-0.65 (m, 2H), 0.65-0.53 (m, 2H)

Step 4: 2-Chloro-6-[3-(dispiro[2.0.2.1]heptan-7-ylmethoxy)pyrazol-1-yl]pyridine-3-carboxylic acid

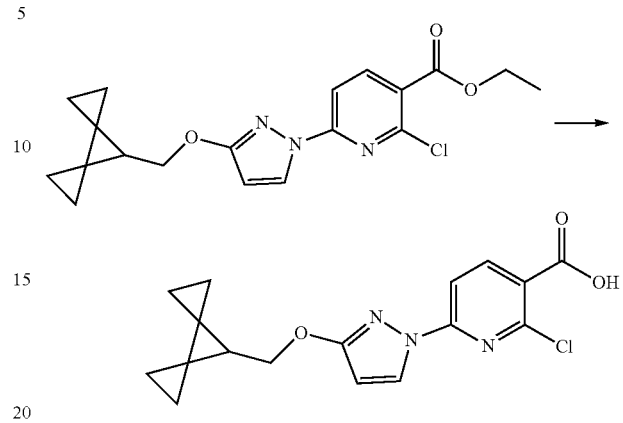

A solution of ethyl 2-chloro-6-(3-(dispiro[2.0.2.1]heptan-7-ylmethoxy)-1H-pyrazol-1-yl)nicotinate (1.39 g, 3.72 mmol) and sodium hydroxide (7.5 mL of 1 M solution, 7.5 mmol) in THF (6 mL) and ethanol (3 mL) was stirred for 90 minutes. The volatiles were removed under vacuum, and water was added. The reaction was cooled in an ice bath, and hydrochloric acid (7.5 mL of 1 M solution, 7.5 mmol) was slowly added. The reaction was diluted with water and extracted with ethyl acetate. The combined extracts were washed with brine, dried over sodium sulfate, and evaporated to give 2-chloro-6-[3-(dispiro[2.0.2.1]heptan-7-ylmethoxy)pyrazol-1-yl]pyridine-3-carboxylic acid (1.16 g, 82% yield) as a colorless solid. ESI-MS m/z calc. 345.088, found 346.1 (M+1)+; Retention time: 0.73 minutes. ¹H NMR (400 MHz, DMSO-d₆) δ 8.41 (d, J=2.9 Hz, 1H), 8.38 (d, J=8.4 Hz, 1H), 7.73 (d, J=8.4 Hz, 1H), 6.19 (d, J=2.8 Hz, 1H), 4.27 (d, J=7.0 Hz, 2H), 1.93 (t, J=7.0 Hz, 1H), 0.97-0.79 (m, 4H), 0.76-0.66 (m, 2H), 0.65-0.56 (m, 2H)

Step 5: 2-Chloro-N-((1,3-dimethyl-1H-pyrazol-4-yl)sulfonyl)-6-(3-(dispiro[2.0.2.1]heptan-7-ylmethoxy)-1H-pyrazol-1-yl)nicotinamide

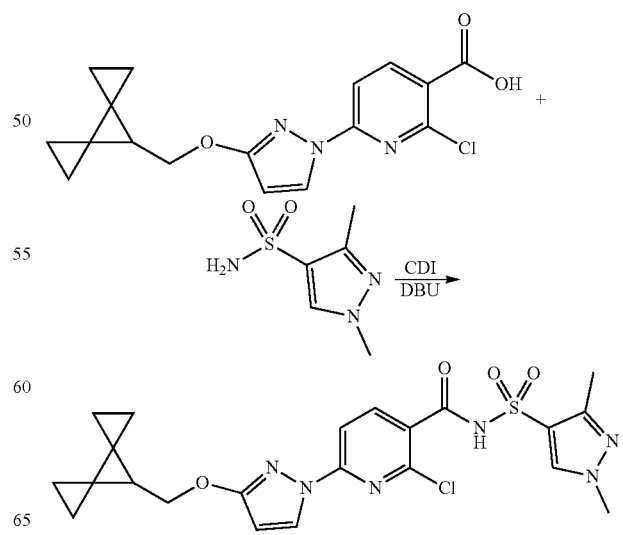

To 2-chloro-6-(3-(dispiro[2.0.2.1]heptan-7-ylmethoxy)-1H-pyrazol-1-yl)nicotinic acid (19.0 g, 54.95 mmol) in THF (250 mL) was slowly added CDI (11.1 g, 68.5 mmol). The mixture was stirred at ambient temperature for two hours. Added additional CDI (1.0 g, 6.167 mmol) and stirred for one hour. To the activated ester was added 1,3-dimethylpyrazole-4-sulfonamide (12.0 g, 68.5 mmol) portionwise followed by DBU (12.3 mL, 82.2 mmol), and the mixture was stirred at ambient temperature for one hour. To the reaction mixture was slowly added citric acid (61 g, 320 mmol) in water (500 mL). The mixture was diluted with EtOAc (1.0 L), and the aqueous phase was further acidified to ~pH 1 with 1 M hydrochloric acid. The organic phase was separated, washed with 300 mL of brine, dried over magnesium sulfate, filtered over Celite, and concentrated in vacuo. The product was crystalized using 80 mL EtOH and warming. To the solution was added 50 mL of water to the cloud point. The solution was warmed until homogenous and allowed to stand at ambient temperature for 16 hours, affording an off-white solid. To the mixture was added 200 mL of 50% aqueous EtOH, and the slurry was filtered. The solid was washed twice with 200 mL of 50% aqueous EtOH, air dried for three hours, then dried in vacuo at 45° C. for 24 hours, affording an off-white solid, 2-chloro-N-((1,3-dimethyl-1H-pyrazol-4-yl)sulfonyl)-6-(3-(dispiro[2.0.2.1]heptan-7-ylmethoxy)-1H-pyrazol-1-yl)nicotinamide (25.49 g, 92%). ESI-MS m/z calc. 502.119, found 503.0 (M+1)+; Retention time: 1.95 minutes.

¹H NMR (400 MHz, DMSO-d6) δ 12.73 (s, 1H), 8.41 (s, 1H), 8.39 (d, J=2.9 Hz, 1H), 8.08 (d, J=8.3 Hz, 1H), 7.69 (d, J=8.3 Hz, 1H), 6.18 (d, J=2.9 Hz, 1H), 4.26 (d, J=7.1 Hz, 2H), 3.84 (s, 3H), 2.35 (s, 3H), 1.92 (t, J=7.2 Hz, 1H), 0.95-0.84 (m, 4H), 0.76-0.65 (m, 2H), 0.65-0.54 (m, 2H).

Step 6: (S)—N-((1,3-Dimethyl-1H-pyrazol-4-yl)sulfonyl)-6-(3-(dispiro[2.0.2.1]heptan-7-ylmethoxy)-1H-pyrazol-1-yl)-2-(2,2,4-trimethylpyrrolidin-1-yl)nicotinamide

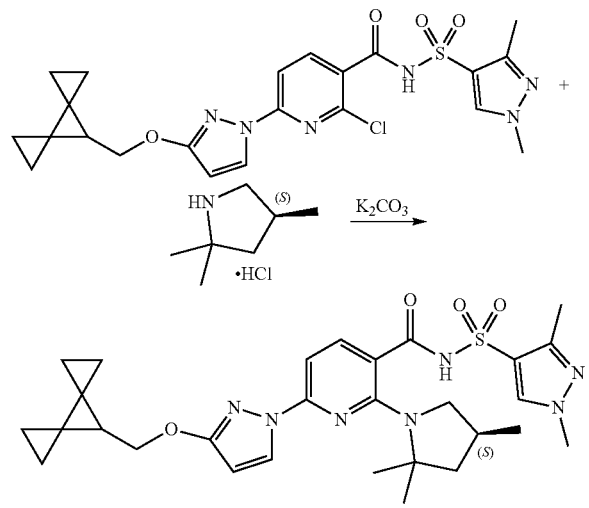

To a solution of 2-chloro-N-((1,3-dimethyl-1H-pyrazol-4-yl)sulfonyl)-6-(3-(dispiro[2.0.2.1]heptan-7-ylmethoxy)-1H-pyrazol-1-yl)nicotinamide (2.0 g, 3.976 mmol) and (4S)-2,2,4-trimethylpyrrolidine (hydrochloride salt) (2.0 g, 13 mmol) in NMP (10 mL) was added potassium carbonate (2.9 g, 21 mmol). The slurry was heated at 130° C. for 20 hours. The reaction was cooled to ambient temperature and added slowly to a rapidly stirred solution of HCl (7 mL of 6 M, 42.00 mmol) in ice water (100 mL) affording an off-white slurry. The precipitate was collected and washed three times with 10 mL of water. The solid was air dried for one hour. The solid was dissolved in 50 mL of EtOAc, and the water was removed. The solvent was removed in vacuo, the oil dissolved in acetonitrile, and the crude product was chromatographed on a 415 g ISCO reverse-phase column eluting with 5-100% acetonitrile/water. Product fractions were collected and concentrated in vacuo affording an off-white foam, (S)—N-((1,3-Dimethyl-1H-pyrazol-4-yl)sulfonyl)-6-(3-(dispiro[2.0.2.1]heptan-7-ylmethoxy)-1H-pyrazol-1-yl)-2-(2,2,4-trimethylpyrrolidin-1-yl)nicotinamide (1.8 g, 75%). ESI-MS m/z calc. 579.26276, found 580.1 (M+1)+; Retention time: 3.26 minutes.

¹H NMR (400 MHz, DMSO-d6) δ 12.35 (s, 1H), 8.37 (s, 1H), 8.18 (d, J=2.7 Hz, 1H), 7.73 (d, J=8.2 Hz, 1H), 6.90 (d, J=8.2 Hz, 1H), 6.10 (d, J=2.8 Hz, 1H), 4.23 (d, J=7.0 Hz, 2H), 3.81 (s, 3H), 2.56 (d, J=10.5 Hz, 1H), 2.41 (t, J=8.6 Hz, 1H), 2.32 (s, 3H), 2.18 (dq, J=11.6, 6.1 Hz, 1H), 1.95-1.82 (m, 2H), 1.54 (d, J=11.1 Hz, 6H), 1.42 (t, J=12.2 Hz, 1H), 0.94-0.84 (m, 4H), 0.81 (d, J=6.2 Hz, 3H), 0.75-0.66 (m, 2H), 0.63-0.56 (m, 2H).

Synthesis of (S)—N-((3-methyl-1H-pyrazol-4-yl)sulfonyl)-6-(3-(3,3,3-trifluoro-2,2-dimethyl-propoxy)-1H-pyrazol-1-yl)-2-(2,2,4-trimethylpyrrolidin-1-yl)nicotinamide (Compound 31)

Step 1: 2-chloro-N-[(3-methyl-1H-pyrazol-4-yl)sulfonyl]-6-[3-(3,3,3-trifluoro-2,2-dimethyl-propoxy)pyrazol-1-yl]pyridine-3-carboxamide

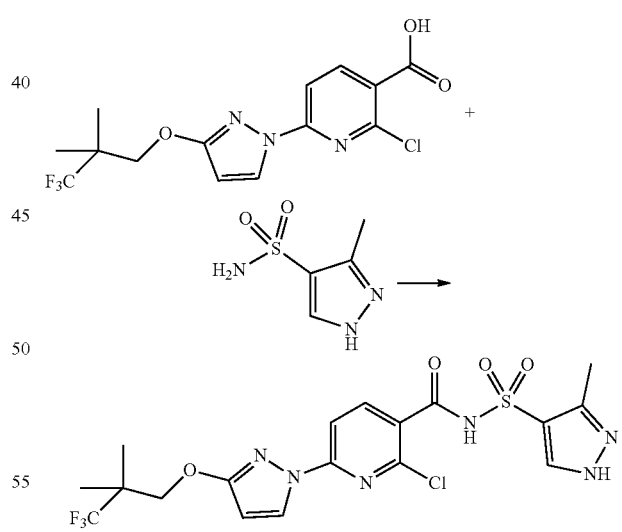

2-chloro-6-[3-(3,3,3-trifluoro-2,2-dimethyl-propoxy)pyrazol-1-yl]pyridine-3-carboxylic acid (75 mg, 0.2000 mmol) and carbonyl diimidazole (approximately 42.16 mg, 0.2600 mmol) were combined in THF (1.5 mL) and stirred for 2 h. At this point, 5-methyl-1H-pyrazole-4-sulfonamide (approximately 32.24 mg, 0.2000 mmol) was added followed by DBU (approximately 101.4 mg, 99.61 µL, 0.6658 mmol) and the reaction was stirred for an additional 2 h at room temperature. The reaction was diluted with ethyl acetate and washed with a 1M citric acid solution, followed by brine. The organics were separated, dried over sodium sulfate, and evaporated. The crude material was purified by silica gel chromatography eluting with 0-10% methanol in dichloromethane to give 2-chloro-N-[(3-methyl-1H-pyrazol-4-yl)sulfonyl]-6-[3-(3,3,3-trifluoro-2,2-dimethylpropoxy)pyrazol-1-yl]pyridine-3-carboxamide (70 mg, 69%) ESI-MS m/z calc. 506.07507, found 507.1 (M+1)+; Retention time: 0.67 minutes.

Step 2: (S)—N-((3-methyl-1H-pyrazol-4-yl)sulfonyl)-6-(3-(3,3,3-trifluoro-2,2-dimethylpropoxy)-1H-pyrazol-1-yl)-2-(2,2,4-trimethylpyrrolidin-1-yl)nicotinamide

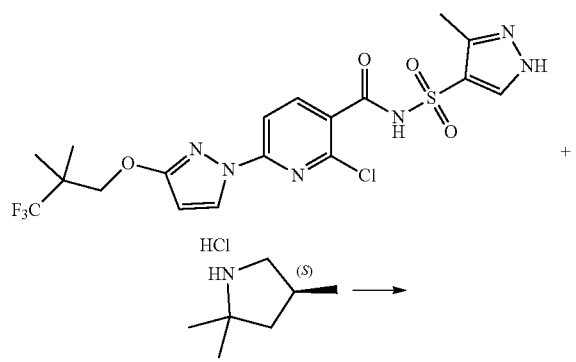

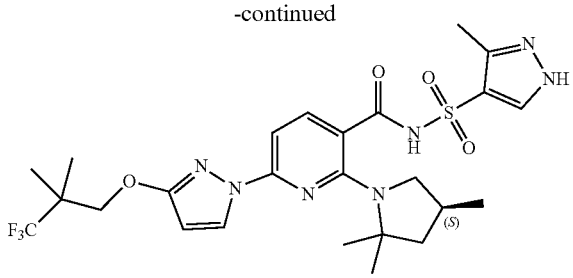

2-chloro-N-[(3-methyl-1H-pyrazol-4-yl)sulfonyl]-6-[3-(3,3,3-trifluoro-2,2-dimethyl-propoxy)pyrazol-1-yl]pyridine-3-carboxamide (70 mg, 0.1381 mmol), (4S)-2,2,4-trimethylpyrrolidine (Hydrochloride salt) (approximately 62.00 mg, 0.4143 mmol), and potassium carbonate (approximately 95.43 mg, 0.6905 mmol) were combined in DMSO (1 mL) and heated at 130° C. for 16 h. The reaction was partitioned between ethyl acetate and a 1M citric acid solution. The organics were separated, washed with brine, dried over sodium sulfate and evaporated. The crude material was purified by silica gel chromatography eluting with 0-10% methanol in dichloromethane to give N-[(3-methyl-1H-pyrazol-4-yl)sulfonyl]-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (18 mg, 23%). ESI-MS m/z calc. 583.2189, found 584.3 (M+1)+; Retention time: 2.07 minutes.

Synthesis of (S)—N-((1,3-dimethyl-1H-pyrazol-4-yl)sulfonyl)-2-(2,2-dimethyl-4-(methyl-d3)pyrrolidin-1-yl-3,3-d2)-6-(3-(3,3,3-trifluoro-2,2-dimethylpropoxy)-1H-pyrazol-1-yl)nicotinamide (Compound 29)

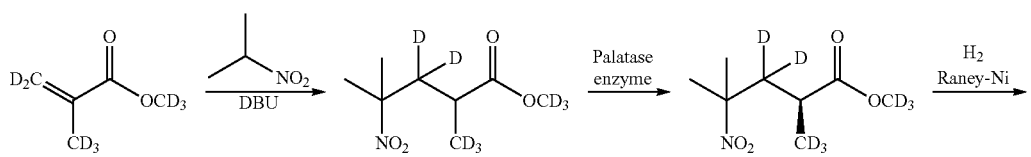

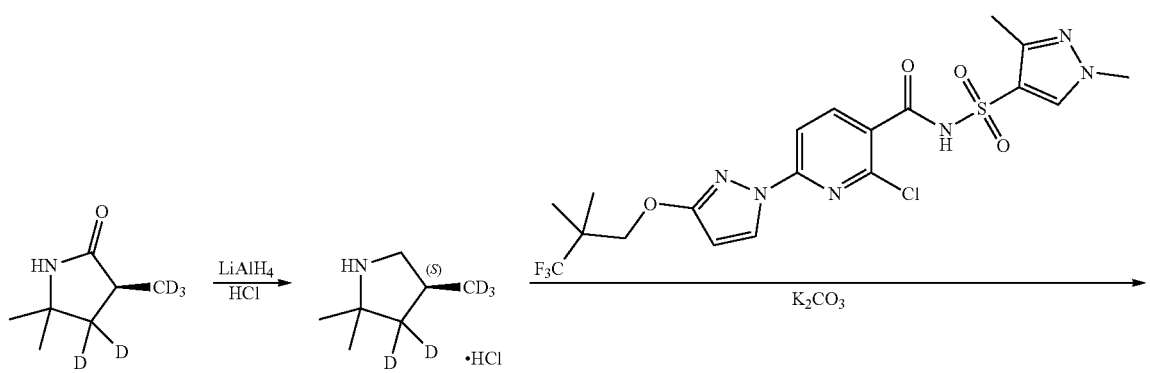

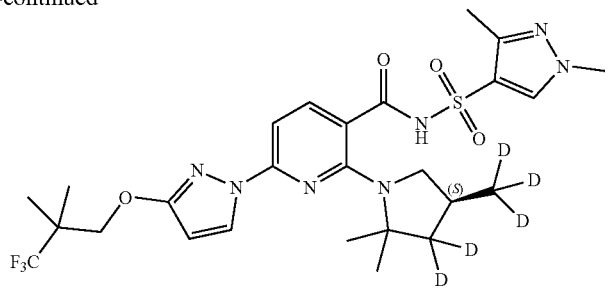

Step 1: Methyl-d₃ 4-methyl-2-(methyl-d₃)-4-nitropentanoate-3,3-d₂

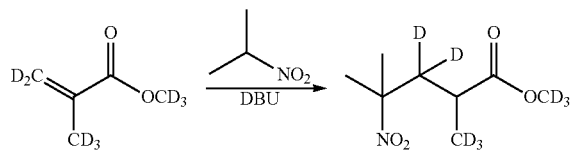

A 500-mL, three-neck round bottom flask equipped with a magnetic stir bar, a nitrogen line and a J-Kem thermocouple with heating mantle was charged with 2-nitropropane (34.3 g, 385 mmol), d₈-methyl methacrylate (50.0 g, 460 mmol), and was stirred at ambient temperature when 1,8-diazabicyclo[5.4.0]undec-7-ene (DBU, 1.47 g, 9.62 mmol) was added in one portion. The reaction solution exothermed from 20 to ~40° C. and was allowed to stir without heating or cooling for 16 h. The reaction was only partially completed (HPLC) so the solution was warmed at 80° C. for 4 h. The reaction mixture is diluted with MTBE (170 mL), washed with 1 M HCl (15 mL), dried over magnesium sulfate, filtered and concentrated (29" Hg at 60° C.) to remove solvent and any residual starting materials to afford product as light yellow oil (75 g, 99%). It was used to the next step without further purification by distillation.

Step 2: Methyl-d₃ (S)-4-methyl-2-(methyl-d₃)-4-nitropentanoate-3,3-d2

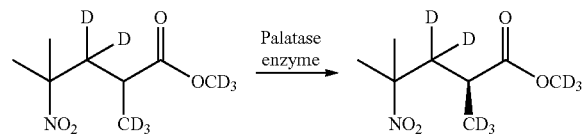

A 5-L, three-neck round bottom flask equipped an overhead mechanical stirrer, a nitrogen line and a J-Kem thermocouple with heating mantle was charged with methyl-d₃ 4-methyl-2-(methyl-d₃)-4-nitropentanoate-3,3-d2 (75 g, 380 mmol) and 2000 mL of pH 7.5 Na-phosphate buffer @ 0.8 M. To this was added lipase from *Rhizomucor miehei* (sigma L4277, palatase from Novozymes) (0.5 vol) and stirred at 30° C. for 25 h. Chiral HPLC (ADH 4.6×250 mm, 5 μm, 1.0 mL/min, 98% Heptane/2% IPA) shows 99.8/0.2 ratio of enantiomers. The reaction mixture was extracted twice with MTBE (1 L each time). The organic included any emulsion formed during the extractions. The combined organics were washed two times with an aqueous solution of sodium bicarbonate (5 vol), brine (5 vol), dried over sodium sulfate and concentrated under vacuum to afford the desired product methyl-d3 (5)-4-methyl-2-(methyl-d3)-4-nitropentanoate-3,3-d2 as pale yellow oil (32.5 g, 43% yield).

Step 3: (S)-5,5-Dimethyl-3-(methyl-d3)pyrrolidin-2-one-4,4-d₂

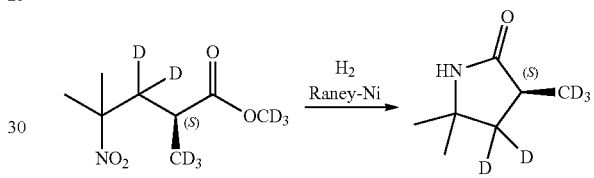

A high-pressure vessel (Parr shaker bottle, 500 mL) was purged with and maintained under N2. The vessel was charged sequentially with deionized water rinsed (3 times) damp Raney®2800 Ni (6.1 g), methyl-d3 (S)-4-methyl-2-(methyl-d3)-4-nitropentanoate-3,3-d2 (32.5 g, 165 mmol), and ethanol (290 mL). The vessel was sealed and evacuated/backfilled with N2 (3 times). With no stirring, the vessel was then evacuated and backfilled with H₂ (30 psi). The Parr bottle was shaken while heating the contents to 60° C., and the H2 pressure was maintained at 30 psi for 8 hours. The vessel was evacuated/backfilled with N₂ (3 times) and the contents were removed by vacuum filtration (Celite pad; N2 blanket). The flask/filter-pad was washed with ethanol (3×50 mL). After the final wash, the solvent-wet filter-cake was transferred to another receiver and covered with water for disposal. Note: At no time should the catalyst be fully dried (keep damp throughout the filtration process). The filtrate and washes were combined and concentrated (40° C./40 torr) to afford (S)-5,5-dimethyl-3-(methyl-d3)pyrrolidin-2-one-4,4-d2 as white solid (20 g, 92%).

Step 4: (4S)-3,3-Dideuterio-2,2-dimethyl-4-(trideuteriomethyl)pyrrolidine Hydrochloride

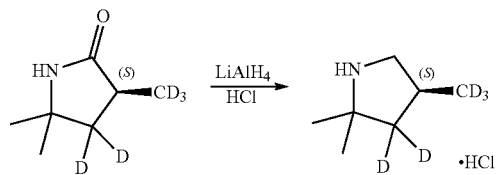

A 1-L, three-neck round bottom flask equipped an overhead mechanical stirrer, a nitrogen line and a J-Kem thermocouple was charged with lithium aluminum hydride pellets (7.6 g, 202 mmol) in THF (80 mL, 4 vol) warmed from 20-36° C. (heat of mixing). A solution of (S)-5,5-dimethyl-3-(methyl-d3)pyrrolidin-2-one-4,4-$d_2$ (20. g, 150 mmol) in THF (120 mL, 6 vol) was added to the suspension over 30 minutes while allowing the reaction temperature to rise to ~60° C. The reaction temperature was increased to near reflux (~68° C.) and maintained there for 16 h. The reaction mixture was cooled to below 40° C. and diluted with 200 mL (10 vol) of MTBE. The mixture was quenched slowly with drop-wise addition of a saturated aqueous solution of sodium sulfate (1 vol) over 2 h. Note: Vigorous degassing ($H_2$) was observed, the mixture becomes thick then thins, and the dark gray mixture turns white. After the addition was completed, the reaction mixture was cooled to room temperature. The solid was removed by filtration (Celite pad) and washed with ethyl acetate (4 vol). With external cooling and a N2 blanket, the filtrate and washings were combined and treated with drop-wise addition of anhydrous 4 M HCl in dioxane (38 mL, 152 mmol) while maintaining the temperature below 20° C. After the addition was completed (20 minutes), the resultant suspension was concentrated under vacuum at 45° C. The suspension was backfilled with heptanes (4 vol) twice during concentration. The suspension was cooled to below 30° C. when the solid was collected by filtration under a $N_2$ blanket. The solid was dried under $N_2$ suction and further dried under high vacuum at 45° C. to afford (4S)-3,3-dideuterio-2,2-dimethyl-4-(trideuteriomethyl)pyrrolidine hydrochloride (17.5 g, 75%). The product is quite hygroscopic so it was manipulated under nitrogen.

Step 5: (S)—N-((1,3-dimethyl-1H-pyrazol-4-yl)sulfonyl)-2-(2,2-dimethyl-4-(methyl-d3)pyrrolidin-1-yl-3,3-d2)-6-(3-(3,3,3-trifluoro-2,2-dimethyl-propoxy)-1H-pyrazol-1-yl)nicotinamide

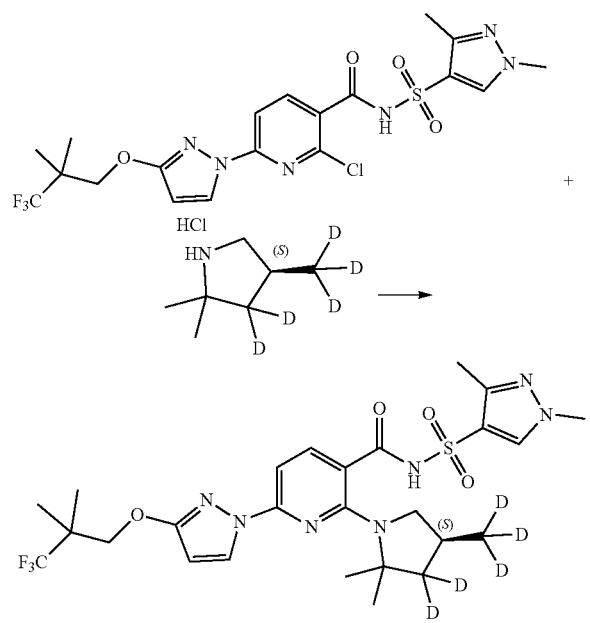

2-chloro-N-((1,3-dimethyl-1H-pyrazol-4-yl)sulfonyl)-6-(3-(3,3,3-trifluoro-2,2-dimethylpropoxy)-1H-pyrazol-1-yl)nicotinamide (2 g, 3.839 mmol) was dissolved in DMSO (10 mL) and 1,2-diethoxyethane (2.000 mL). Potassium carbonate (approximately 2.654 g, 19.20 mmol) and (4S)-3,3-dideuterio-2,2-dimethyl-4-(trideuteriomethyl)pyrrolidine (Hydrochloride salt) (approximately 1.485 g, 9.598 mmol) were added and the resulting slurry was heated at 130° C. for 28 h. The reaction mixture was cooled and poured into rapidly stirred ice water (60.00 mL) and acetic acid (approximately 3.458 g, 3.275 mL, 57.58 mmol). After stirring for 20 min the solids were filtered off and washed with water. The resulting solid was dissolved in ethyl acetate and washed with water, then brine. The organics were dried over sodium sulfate and concentrated. The resulting material was heated in heptanes and the resulting solid was collected and dried to give (5)-N-((1,3-dimethyl-1H-pyrazol-4-yl)sulfonyl)-2-(2,2-dimethyl-4-(methyl-d3)pyrrolidin-1-yl-3,3-d2)-6-(3-(3,3,3-trifluoro-2,2-dimethylpropoxy)-1H-pyrazol-1-yl)nicotinamide (0.8 g, 35%). ESI-MS m/z calc. 602.27, found 603.1 (M+1)$^+$; Retention time: 1.82 minutes.

Synthesis of N-(1,5-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound 13)

Step 1: 2-chloro-N-(1,5-dimethylpyrazol-4-yl)sulfonyl-6-[3-(3,3,3-trifluoro-2,2-dimethyl-propoxy)pyrazol-1-yl]pyridine-3-carboxamide

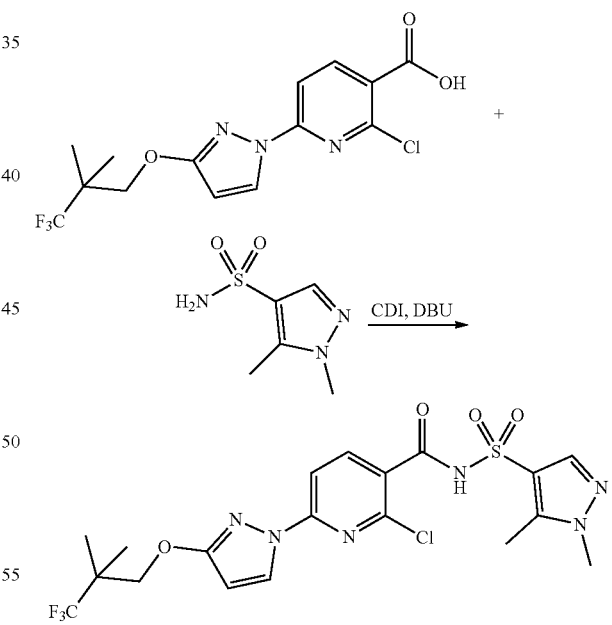

2-chloro-6-[3-(3,3,3-trifluoro-2,2-dimethyl-propoxy)pyrazol-1-yl]pyridine-3-carboxylic acid (100 mg, 0.2749 mmol) and carbonyldiimidazole (53 mg, 0.3269 mmol) were combined in THF (600.0 μL) and stirred at room temperature for 2 hours. 1,5-dimethylpyrazole-4-sulfonamide (53 mg, 0.3025 mmol) was added followed by DBU (55 μl, 0.3678 mmol) and the reaction was stirred for an additional 16 h at room temperature. The reaction mixture was diluted with 10 mL of 1 M citric acid, and extracted with ethyl acetate (3×10 mL). The combined organics were washed with brine, dried over sodium sulfate, and concentrated to give a white solid, which was used in the next step without further purification. 2-chloro-N-(1,5-dimethylpyrazol-4-yl)sulfonyl-6-[3-(3,3,3-trifluoro-2,2-dimethyl-propoxy)pyrazol-1-yl]pyridine-3-carboxamide (140 mg, 98%) ESI-MS m/z calc. 520.09076, found 521.1 (M+1)+; Retention time: 0.68 minutes.

Step 2: N-(1,5-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide

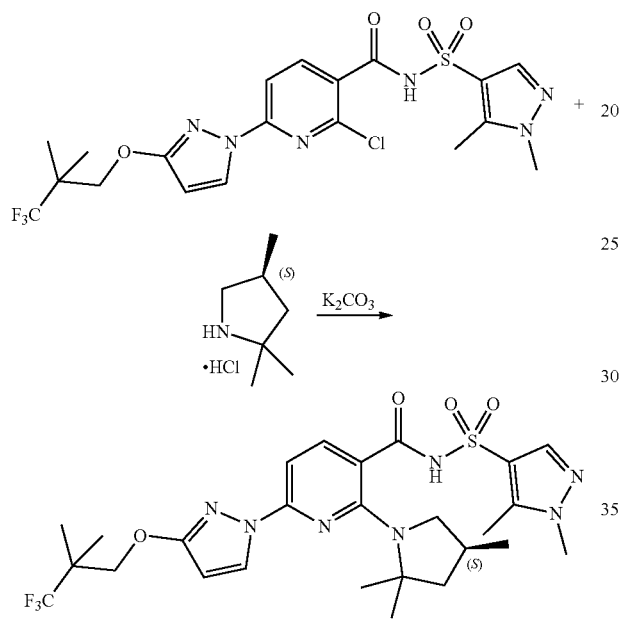

2-chloro-N-(1,5-dimethylpyrazol-4-yl)sulfonyl-6-[3-(3,3,3-trifluoro-2,2-dimethyl-propoxy)pyrazol-1-yl]pyridine-3-carboxamide (140 mg, 0.2688 mmol), (4S)-2,2,4-trimethylpyrrolidine (Hydrochloride salt) (120 mg, 0.8018 mmol), and potassium carbonate (224 mg, 1.621 mmol) were combined in DMSO (700.0 µL) and heated at 130° C. for 16 h. The reaction was cooled to room temperature, and 1 mL of water was added. After 15 minutes stirring, the contents of the vial were allowed to settle, and the liquid portion was removed by pipet. The remaining solids were dissolved with 20 mL of ethyl acetate, then washed with 15 mL of 1M citric acid. The aqueous and organic layers were separated, and the aqueous layer was extracted two additional times with 15 mL ethyl acetate. The organics were combined, washed with brine, dried over sodium sulfate and concentrated. The resulting solid was further purified by silica gel chromatography eluting with 0-10% methanol in dichloromethane to give a white solid. N-(1,5-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (96 mg, 60%) ESI-MS m/z calc. 597.2345, found 598.3 (M+1)+; Retention time: 2.1 minutes.

$^1$H NMR (400 MHz, DMSO) δ 12.32 (s, 1H), 8.22 (d, J=2.8 Hz, 1H), 7.78 (s, 1H), 7.73 (d, J=8.2 Hz, 1H), 6.93 (d, J=8.2 Hz, 1H), 6.17 (d, J=2.7 Hz, 1H), 4.23 (s, 2H), 3.78 (s, 3H), 2.57 (d, J=10.4 Hz, 1H), 2.53 (s, 3H), 2.41 (dd, J=10.3, 7.1 Hz, 1H), 2.17 (dq, J=12.1, 6.0 Hz, 1H), 1.87 (dd, J=11.8, 5.5 Hz, 1H), 1.57 (s, 3H), 1.53 (s, 3H), 1.43 (t, J=12.2 Hz, 1H), 1.23 (s, 6H), 0.80 (d, J=6.2 Hz, 3H).

Synthesis of N-(1,3-dimethylpyrazol-4-yl)sulfonyl-2-[4-(hydroxymethyl)-2,2-dimethyl-pyrrolidin-1-yl]-6-[3-(3,3,3-trifluoro-2,2-dimethyl-propoxy)pyrazol-1-yl]pyridine-3-carboxamide (Compound 30)

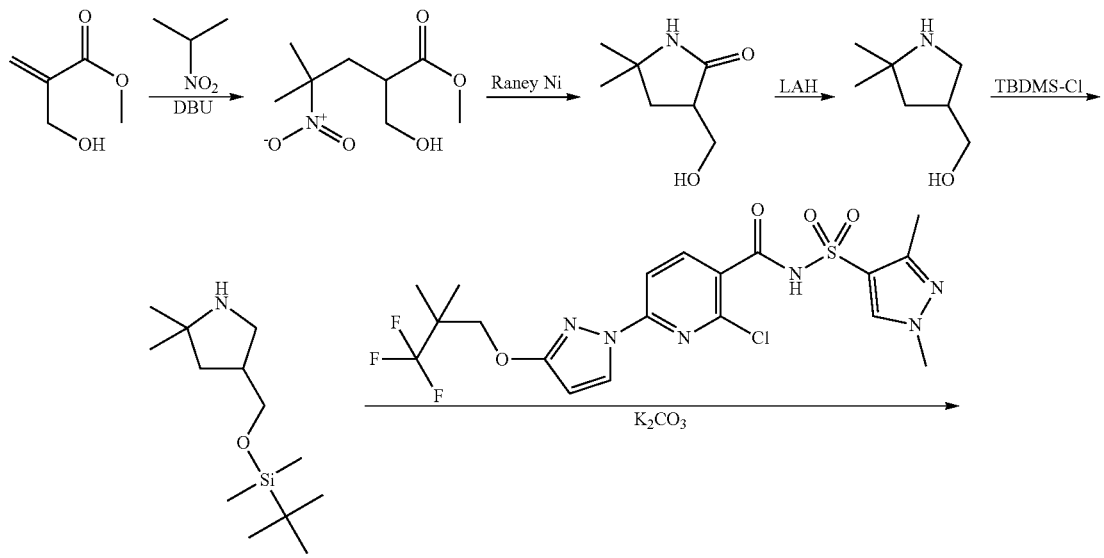

-continued

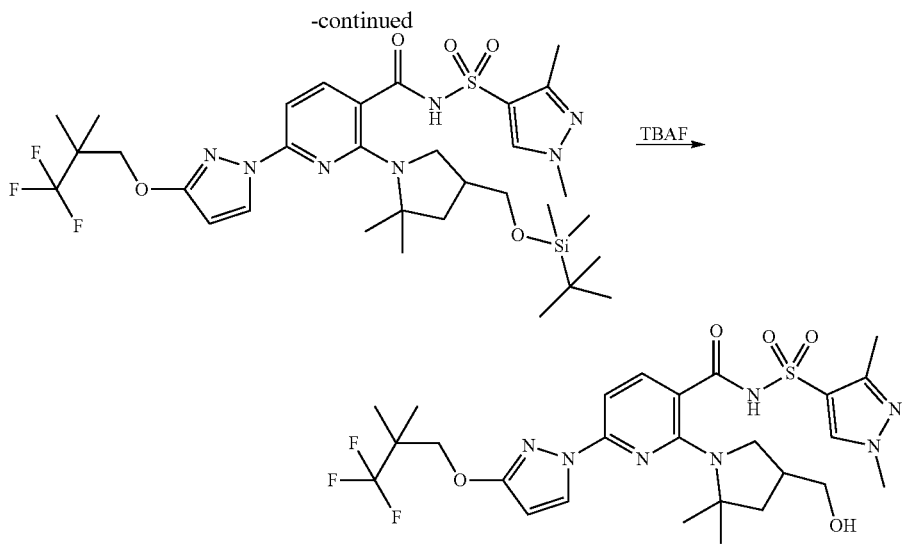

Step 1:
2-Hydroxymethyl-4-methyl-4-nitro-pentanoic acid methyl ester

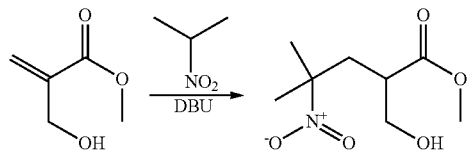

1,8-Diazabicyclo[5.4.0]undec-7-ene (3.6 mL, 24 mmol) was added to 2-nitropropane (26.5 mL, 292 mmol). This mixture was heated to 65° C. and the heat was turned off and methyl 2-(hydroxymethyl)acrylate (25 mL, 243 mmol) was added dropwise. The heat was then turned back on at 80° C. After heating for 1 h the heat was turned off and the reaction was stirred at room temperature overnight before heating at 80° C. for another 2h. The reaction was diluted with ethyl acetate (250 mL) and washed with 1M hydrogen chloride (2×125 mL), aqueous bicarbonate (125 mL) and brine (125 mL). The reaction product mixture was chromatographed on a 330 g column of silica gel in 0-60% hexanes:ether eluting at 55-60% to give 2-hydroxymethyl-4-methyl-4-nitro-pentanoic acid methyl ester (29.68 g, 60%) as a light green oil. ESI-MS m/z calc. 205.21, found 206.1 (M+1)$^+$. Retention time: 1.67 minutes.

Step 2:
3-Hydroxymethyl-5,5-dimethyl-pyrrolidin-2-one

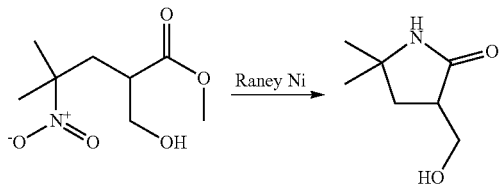

2-hydroxymethyl-4-methyl-4-nitro-pentanoic acid methyl ester (4.45 g, 21.7 mmol) was added to absolute ethanol (60 mL) followed by Raney Nickel (1.7 g, ~15% wt). The reaction was heated at 60° C. under 2 bar of H2 overnight. More Raney Nickel (1.0 g, ~50% wt) was added and the reaction heated at 60° C. under 5 bar H2 for 3.5 h. At this point, more 2-hydroxymethyl-4-methyl-4-nitro-pentanoic acid methyl ester (3.95 g, 19.3 mmol) was added and the reaction heated for 72 h refilling H2 to maintain 5 bar. The reaction was filtered through celite and washed with methanol. The crude reaction was chromatographed on silica gel and eluted with 0-10% dichloromethane:methanol at 10%, resulting 3-hydroxymethyl-5,5-dimethyl-pyrrolidin-2-one (3.69 g, 63%) as a white solid. $^1$H NMR (250 MHz, CDCl$_3$) δ ppm 1.31 (d, J=9.01 Hz, 6H) 1.72 (dd, J=12.52, 10.33 Hz, 1H) 2.04 (dd, J=12.58, 8.84 Hz, 1H) 2.73-2.91 (m, 1H) 3.31 (d, J=4.72 Hz, 1H) 3.64-3.95 (m, 2H) 5.93 (br. s., 1H)

Step 3: (5,5-Dimethyl-pyrrolidin-3-yl)-methanol

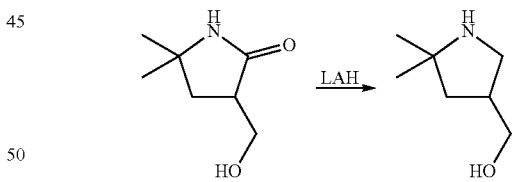

Lithium aluminum hydride (3.90 g, 103.00 mmol) was suspended in tetrahydrofuran (60 mL). 3-hydroxymethyl-5,5-dimethyl-pyrrolidin-2-one (3.69 g, 25.77 mmol) in tetrahydrofuran (30 mL) was then added dropwise and the reaction was heated at 65° C. for 40h. The reaction was diluted with 2-methyl-tetrahydrofuran (125 mL) and then cooled in an ice bath before saturated aqueous Rochelle Salt (200 mL) was added dropwise. The organic layer was extracted with 2-methyl-tetrahydrofuran (2×200 mL) and dried over sodium sulfate to give crude (5,5-dimethyl-pyrrolidin-3-yl)-methanol (3.47 g, 104%). $^1$H NMR (250 MHz, CDCl$_3$ δ ppm 1.06-1.24 (m, 6H) 1.29 (dd, J=12.58, 7.20 Hz, 2H) 1.43 (s, 1H) 1.68-1.89 (bs, 1H) 2.31-2.52 (m, 1H) 2.83 (dd, J=11.10, 5.49 Hz, 1H) 3.05-3.26 (m, 1H) 3.48-3.71 (m, 1H)

Step 4: 4-(tert-Butyl-dimethyl-silanyloxymethyl)-2,2-dimethyl-pyrrolidine

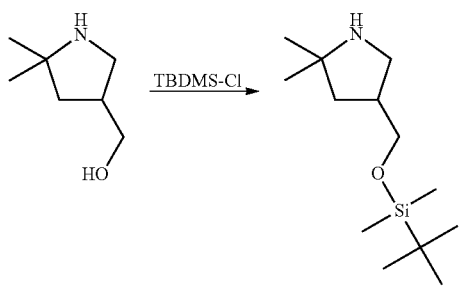

To (5,5-dimethyl-pyrrolidin-3-yl)-methanol (3.08 g, 23.8 mmol), tert-butyldimethylsilyl chloride (4.31 g, 28.6 mmol) in acetonitrile (24 mL) was added 1,8-Diazabicyclo[5.4.0]undec-7-ene (5.3 mL, 35.7 mmol). The reaction was stirred for 3.5 h. The reaction was diluted with chloroform (250 mL) and washed with water (125 mL) and brine (125 mL) then dried over sodium sulfate. The crude was chromatographed on silica gel and eluted with dichloromethane/methanol, eluting at 15-35% methanol to give 4-(tert-butyl-dimethyl-silanyloxymethyl)-2,2-dimethyl-pyrrolidine (3.88 g, 67%) as a yellow oil after two columns. ESI-MS m/z calc. 243.47, found 244.2 (M+1)+ Retention time: 2.52 minutes. $^1$H NMR (250 MHz, CDCl$_3$) δ ppm −0.05-0.11 (m, 6H) 0.89 (s, 9H) 1.19 (d, J=18.02 Hz, 6H) 1.25-1.32 (m, 1H) 1.74 (dd, J=12.63, 8.79 Hz, 1H) 1.92 (br. s., 1H) 2.32-2.50 (m, 1H) 2.81 (dd, J=11.54, 6.37 Hz, 1H) 3.11 (dd, J=11.48, 7.97 Hz, 1H) 3.45-3.61 (m, 2H).

Step 5. 2-[4-[[tert-butyl(dimethyl)silyl]oxymethyl]-2,2-dimethyl-pyrrolidin-1-yl]-N-(1,3-dimethylpyrazol-4-yl)sulfonyl-6-[3-(3,3,3-trifluoro-2,2-dimethyl-propoxy)pyrazol-1-yl]pyridine-3-carboxamide 2-chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (30 mg, 0.05759 mmol), tert-butyl-[(5,5-dimethylpyrrolidin-3-yl)methoxy]-dimethyl-silane (approximately 42.07 mg, 0.1728 mmol), and K$_2$CO$_3$ (approximately 39.80 mg, 0.2880 mmol) were combined in DMSO (600.0 μL) and heated at 130° C. for 16 h. The reaction was partitioned between a 1M citric acid solution and ethyl acetate and the organics were separated. The organics were washed with brine, dried over sodium sulfate and evaporated. The crude material was purified by silica gel chromatography eluting with 0-10% methanol in dichloromethane to give 2-[4-[[tert-butyl(dimethyl)silyl]oxymethyl]-2,2-dimethyl-pyrrolidin-1-yl]-N-(1,3-dimethylpyrazol-4-yl)sulfonyl-6-[3-(3,3,3-trifluoro-2,2-dimethyl-propoxy)pyrazol-1-yl]pyridine-3-carboxamide (19 mg, 45%). ESI-MS m/z calc. 727.3159, found 728.4 (M+1)+; Retention time: 0.94 minutes.

Step 6. N-(1,3-dimethylpyrazol-4-yl)sulfonyl-2-[4-(hydroxymethyl)-2,2-dimethyl-pyrrolidin-1-yl]-6-[3-(3,3,3-trifluoro-2,2-dimethyl-propoxy)pyrazol-1-yl]pyridine-3-carboxamide

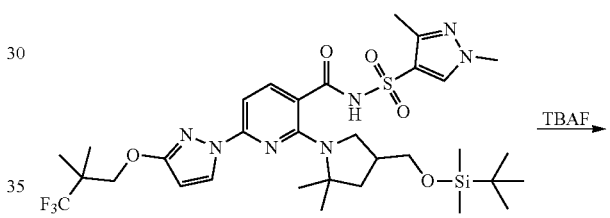

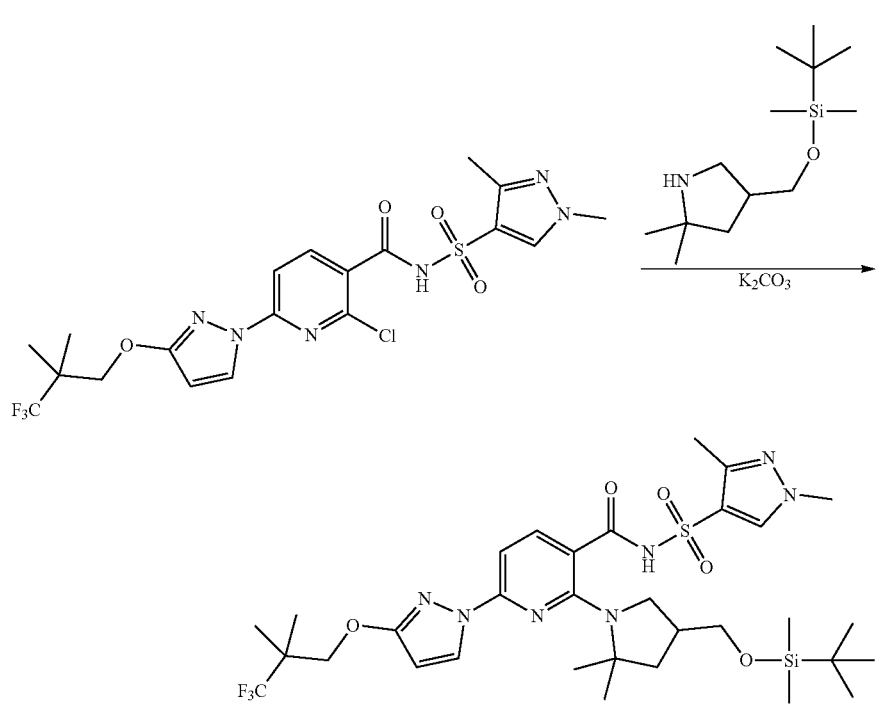

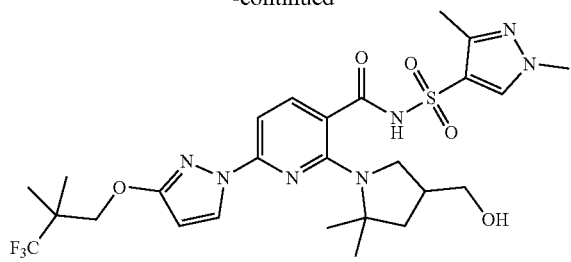

2-[4-[[tert-butyl(dimethyl)silyl]oxymethyl]-2,2-dimethyl-pyrrolidin-1-yl]-N-(1,3-dimethylpyrazol-4-yl)sulfonyl-6-[3-(3,3,3-trifluoro-2,2-dimethyl-propoxy)pyrazol-1-yl]pyridine-3-carboxamide (19 mg) was dissolved in THF (1 mL) and cooled in an ice bath. TBAF (approximately 288.0 µL of 1 M, 0.2880 mmol) was added and the reaction was allowed to warm to room temperature. The reaction mixture was stirred for 1 h and then partitioned between ethyl acetate and 1M citric acid solution. The organics were washed with brine, dried over sodium sulfate and evaporated. The crude material was purified by silica gel chromatography eluting with 0-10% methanol in dichloromethane to give N-(1,3-dimethylpyrazol-4-yl)sulfonyl-2-[4-(hydroxymethyl)-2,2-dimethyl-pyrrolidin-1-yl]-6-[3-(3,3,3-trifluoro-2,2-dimethyl-propoxy)pyrazol-1-yl]pyridine-3-carboxamide (8.7 mg, 54%). ESI-MS m/z calc. 613.22943, found 614.3 (M+1)+; Retention time: 1.81 minutes.

Synthesis of N-[3-(hydroxymethyl)-1-methyl-pyrazol-4-yl]sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound 39)

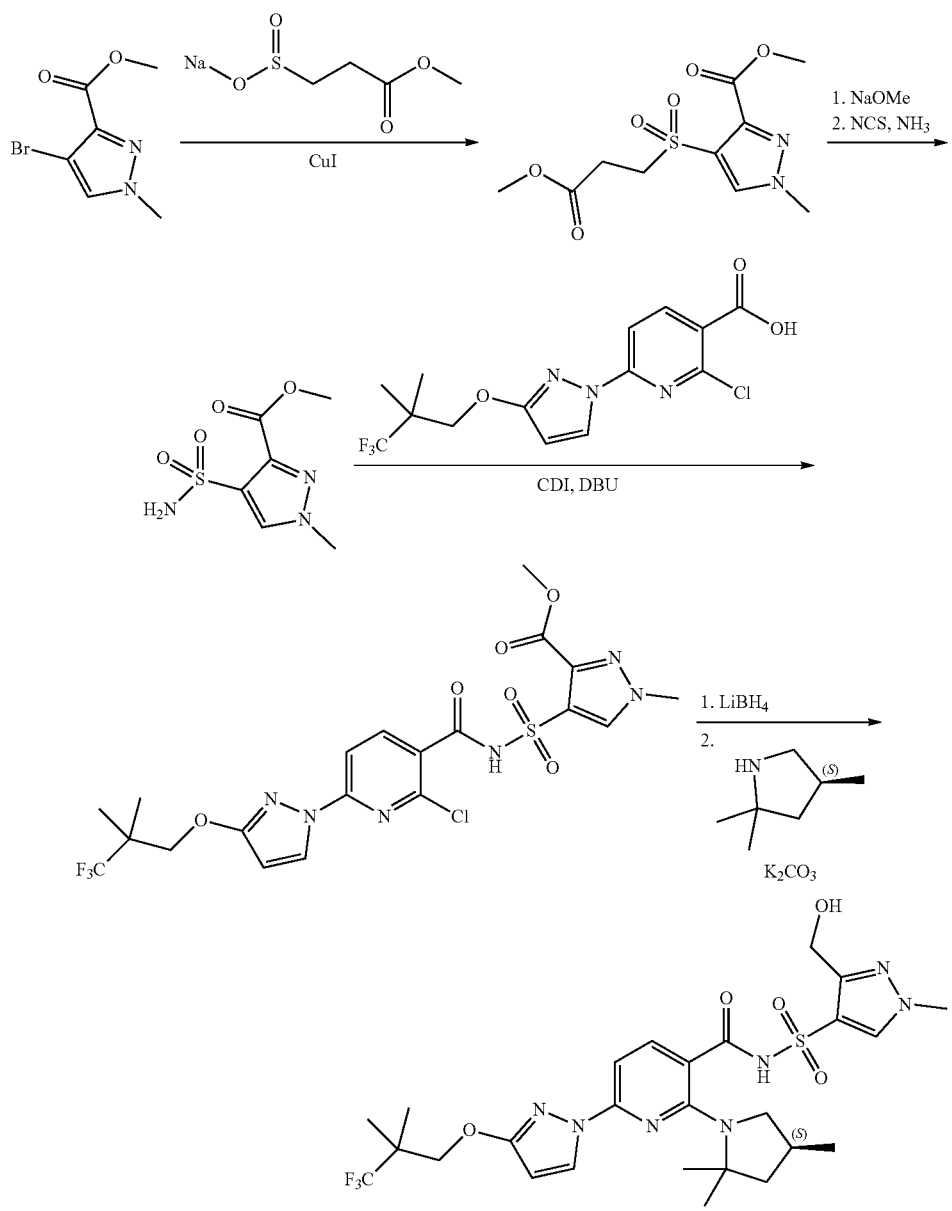

Step 1: methyl 4-(3-methoxy-3-oxo-propyl)sulfonyl-1-methyl-pyrazole-3-carboxylate

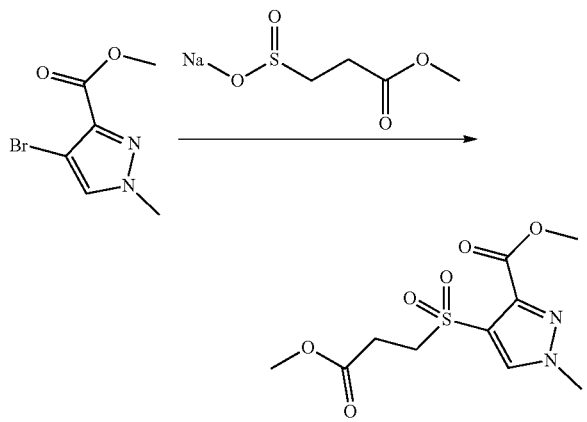

methyl 4-bromo-1-methyl-pyrazole-3-carboxylate (508 mg, 2.319 mmol), (3-methoxy-3-oxo-propyl)sulfinyloxysodium (810 mg, 4.651 mmol), and copper(1+) (Iodide Ion (1)) (1.31 g, 6.878 mmol) were combined in degassed DMSO (3.048 mL). Nitrogen was bubbled through the reaction for another 5 min and then it was sealed and heated to 80° C. The reaction was heated for 48 h then cooled to room temperature. The reaction was diluted with ethyl acetate (25 mL) and NH₄Cl (10 mL). A thick precipitate formed which was filtered and discarded. The layers were separated and the organics were washed with a saturated NH₄Cl (30 mL) solution, a satd NaHCO₃ solution (30 mL), and brine (30 mL). The organics were dried over sodium sulfate and evaporated. The crude material was purified by silica gel chromatography eluting with 0-100% ethyl acetate in hexanes to give methyl 4-(3-methoxy-3-oxo-propyl)sulfonyl-1-methyl-pyrazole-3-carboxylate (297 mg, 44%) ESI-MS m/z calc. 290.05725, found 291.1 (M+1)+; Retention time: 0.32 minutes.

Step 2: methyl 1-methyl-4-sulfamoyl-pyrazole-3-carboxylate

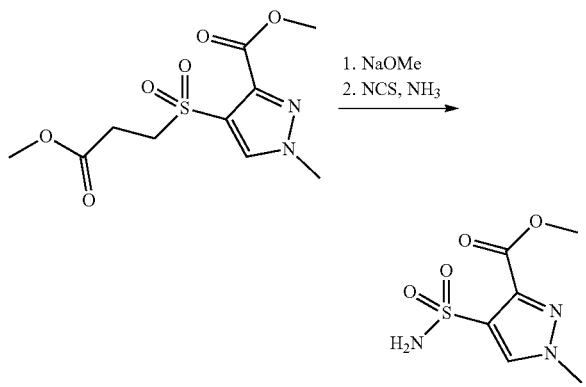

Step 1 methyl 4-(3-methoxy-3-oxo-propyl)sulfonyl-1-methyl-pyrazole-3-carboxylate (297 mg, 1.023 mmol) was dissolved in THF (4 mL) and 25% NaOMe in methanol (220 μL of 25% w/v, 1.018 mmol) was added. The reaction was stirred for 5 min and evaporated. Hexane was added and the mixture evaporated again.

Step 2

The product from step 1 was dissolved in dichloromethane (4 mL) and N-chlorosuccinimide (138 mg, 1.033 mmol) was added. The reaction was stirred for 30 min. The reaction mixture was added slowly to an ice bath cooled solution of ammonia in methanol (1.5 mL of 7 M, 10.50 mmol) and it was stirred for another 30 min. The reaction mixture was partitioned between ethyl acetate and water. The organics were separated, washed with brine, dried over sodium sulfate and evaporated. The crude product was used in the next step without further purification. methyl 1-methyl-4-sulfamoyl-pyrazole-3-carboxylate (110 mg, 49%) ESI-MS m/z calc. 219.03137, found 220.1 (M+1)+; Retention time: 0.2 minutes.

Step 3: methyl 4-[[2-chloro-6-[3-(3,3,3-trifluoro-2,2-dimethyl-propoxy)pyrazol-1-yl]pyridine-3-carbonyl]sulfamoyl]-1-methyl-pyrazole-3-carboxylate

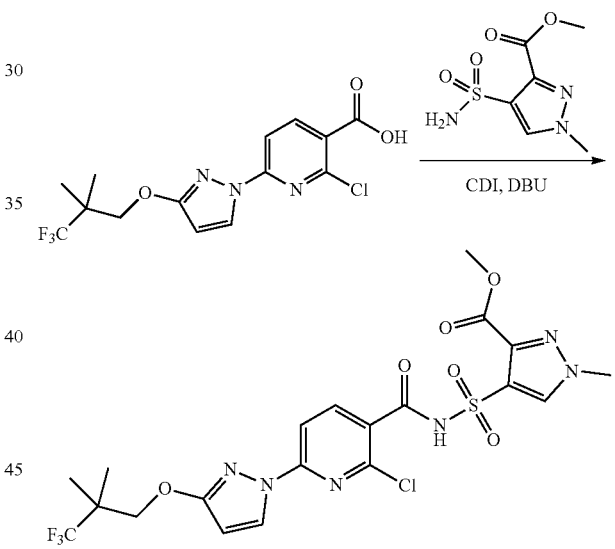

2-chloro-6-[3-(3,3,3-trifluoro-2,2-dimethyl-propoxy) pyrazol-1-yl]pyridine-3-carboxylic acid (approximately 186.2 mg, 0.5018 mmol) and carbonyl diimidazole (approximately 81.37 mg, 0.5018 mmol) were combined in THF (2 mL) and stirred at room temperature for 3 h. To the reaction mixture was added methyl 1-methyl-4-sulfamoyl-pyrazole-3-carboxylate (110 mg, 0.5018 mmol) and DBU (approximately 76.39 mg, 75.04 μL, 0.5018 mmol) and the reaction was stirred an additional 16 h. The reaction mixture was partitioned between ethyl acetate and a 1M citric acid solution. The organics were separated, washed with brine, dried over sodium sulfate and evaporated. The crude product was taken on to the next step without further purification. methyl 4-[[2-chloro-6-[3-(3,3,3-trifluoro-2,2-dimethyl-propoxy)pyrazol-1-yl]pyridine-3-carbonyl]sulfamoyl]-1-methyl-pyrazole-3-carboxylate (178 mg, 63%) ESI-MS m/z calc. 564.08057, found 565.1 (M+1)+; Retention time: 0.67 minutes.

Step 4. N-[3-(hydroxymethyl)-1-methyl-pyrazol-4-yl]sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide

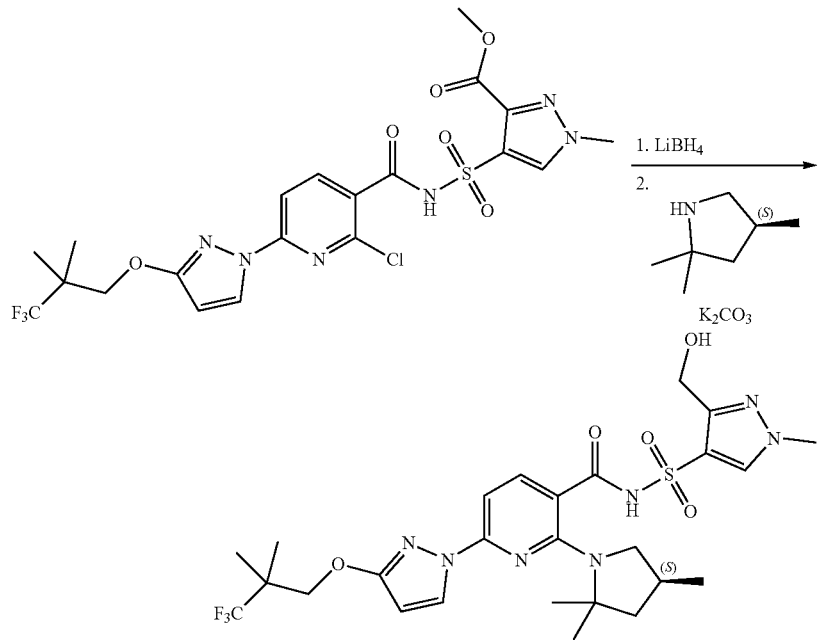

Step 1 methyl 4-[[2-chloro-6-[3-(3,3,3-trifluoro-2,2-dimethyl-propoxy)pyrazol-1-yl]pyridine-3-carbonyl]sulfamoyl]-1-methyl-pyrazole-3-carboxylate (145 mg, 0.2567 mmol) was dissolved in lithium borohydride (2.0 M in THF) (approximately 1.283 mL of 2 M, 2.567 mmol) and stirred for 4 h. The reaction mixture was quenched with methanol, then partitioned between ethyl acetate and a 1M citric acid solution. The organics were separated, washed with brine, dried over sodium sulfate and evaporated.

Step 2

Resulting alcohol from step 1 was dissolved in NMP (0.5 mL) with (4S)-2,2,4-trimethylpyrrolidine (Hydrochloride salt) (approximately 76.84 mg, 0.5134 mmol) and potassium carbonate (approximately 106.4 mg, 0.7701 mmol) and the reaction was heated at 130° C. for 16 h. The reaction mixture was partitioned between ethyl acetate and a 1M citric acid solution. The organics were separated, washed with brine, dried over sodium sulfate and evaporated. The crude reaction mixture was purified by silica gel chromatography eluting with 0-10% methanol in dichloromethane. The product contained NMP so the product was further purified by LC/MS utilizing a gradient of 10-99% acetonitrile in 5 mM aq HCl. The desired fraction was extracted with ethyl acetate. The organics were separated, washed with brine, dried over sodium sulfate and evaporated to give N-[3-(hydroxymethyl)-1-methyl-pyrazol-4-yl]sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (8 mg, 5%) ESI-MS m/z calc. 613.22943, found 614.5 (M+1)+; Retention time: 1.96 minutes.

$^1$H NMR (400 MHz, DMSO-d6) δ 12.25 (s, 1H), 8.42 (s, 1H), 8.22 (d, J=2.8 Hz, 1H), 7.78 (d, J=8.2 Hz, 1H), 6.91 (d, J=8.2 Hz, 1H), 6.17 (d, J=2.8 Hz, 1H), 4.98 (s, 1H), 4.60 (q, J=13.0 Hz, 2H), 4.23 (s, 2H), 3.85 (s, 3H), 2.56 (t, J=10.5 Hz, 1H), 2.16 (s, 1H), 1.91-1.84 (m, 1H), 1.56 (s, 3H), 1.53 (s, 3H), 1.42 (t, J=12.1 Hz, 1H), 1.23 (s, 6H), 0.83 (d, J=6.3 Hz, 3H).

Synthesis of (7S)-7,9,9-trimethyl-2-(3-(3,3,3-trifluoro-2,2-dimethylpropoxy)-1H-pyrazol-1-yl)-6a,7,8,9-tetrahydro-5H-pyrido[2,3-d]pyrrolo[2,1-b][1,3]oxazin-5-one (Compound 57)

Step 1: 6-[3-(3,3,3-Trifluoro-2,2-dimethyl-propoxy)pyrazol-1-yl]-2-[(4S)-2,2,4-trimethylpyrrolidin-1-yl]pyridine-3-carboxylic acid

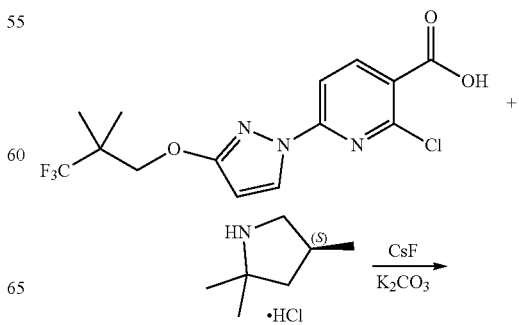

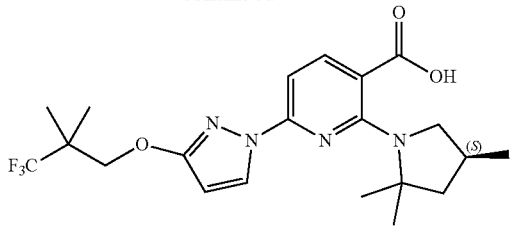

2-Chloro-6-[3-(3,3,3-trifluoro-2,2-dimethyl-propoxy) pyrazol-1-yl]pyridine-3-carboxylic acid (200 mg, 0.5389 mmol) and cesium fluoride (approximately 81.86 mg, 0.5389 mmol) were combined in DMSO (2 mL). (4S)-2,2,4-trimethylpyrrolidine (hydrochloride salt) (approximately 242.0 mg, 1.617 mmol) was added followed by finely ground potassium carbonate (approximately 223.5 mg, 1.617 mmol). The reaction mixture was capped and allowed to stir overnight at 150° C. The reaction mixture was diluted with EtOAc (50 mL) and washed with aqueous citric acid (1 M, 2×50 mL) and brine (1×50 mL). The organic layer was dried over sodium sulfate, filtered and concentrated under reduced pressure. The product was isolated by silica gel column chromatography eluting with a 0-5% MeOH/DCM gradient over 40 minutes on a 12 gram silica gel column. Pure fractions were combined and concentrated to provide 6-[3-(3,3,3-trifluoro-2,2-dimethyl-propoxy)pyrazol-1-yl]-2-[(4S)-2,2,4-trimethylpyrrolidin-1-yl]pyridine-3-carboxylic acid (154 mg, 65%) as a white foaming solid. ESI-MS m/z calc. 440.20352, found 441.6 (M+1)+; Retention time: 1.87 minutes.

Step 2: (7S)-7,9,9-trimethyl-2-(3-(3,3,3-trifluoro-2,2-dimethylpropoxy)-1H-pyrazol-1-yl)-6a,7,8,9-tetrahydro-5H-pyrido[2,3-d]pyrrolo[2,1-b][1,3]oxazin-5-one

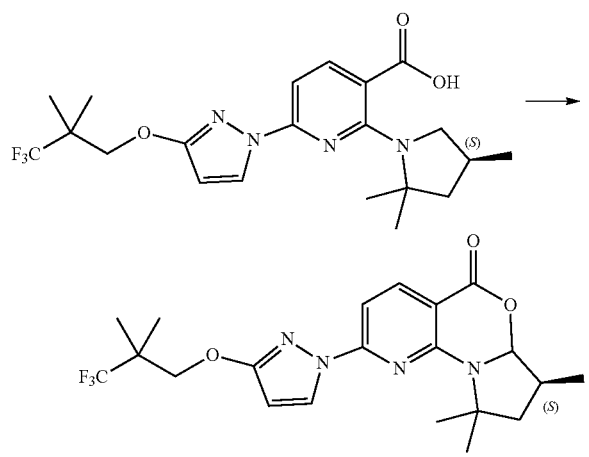

6-[3-(3,3,3-Trifluoro-2,2-dimethyl-propoxy)pyrazol-1-yl]-2-[(4S)-2,2,4-trimethylpyrrolidin-1-yl]pyridine-3-carboxylic acid (50 mg, 0.1135 mmol), water (20 μL, 1.110 mmol), sodium acetate (19 mg, 0.2316 mmol) and [Ir[dF(CF₃)ppy]₂(dtbpy)]PF₆ (5 mg, 0.004457 mmol) were dissolved in DMA (872 mL). The reaction mixture was placed under a 23 W compact fluorescent light source for five hours. The light source emitted enough heat to warm the reaction mixture to ~40° C. The crude mixture was purified by silica gel chromatography eluting with 0-100% EtOAc/hexane gradient to give (7S)-7,9,9-trimethyl-2-(3-(3,3,3-trifluoro-2,2-dimethylpropoxy)-1H-pyrazol-1-yl)-6a,7,8,9-tetrahydro-5H-pyrido[2,3-d]pyrrolo[2,1-b][1,3]oxazin-5-one (24.6 mg, 50%). ESI-MS m/z calc. 438.18787, found 439.6 (M+1)+; Retention time: 2.27 minutes.

Synthesis of N-(1,3-Dimethylpyrazol-4-yl)sulfonyl-6-[3-(3,3,3-trifluoro-2,2-dimethyl-propoxy)pyrazol-1-yl]-2-[(4R)-2,2,4-trimethylpyrrolidin-1-yl]pyridine-3-carboxamide (Compound 37)

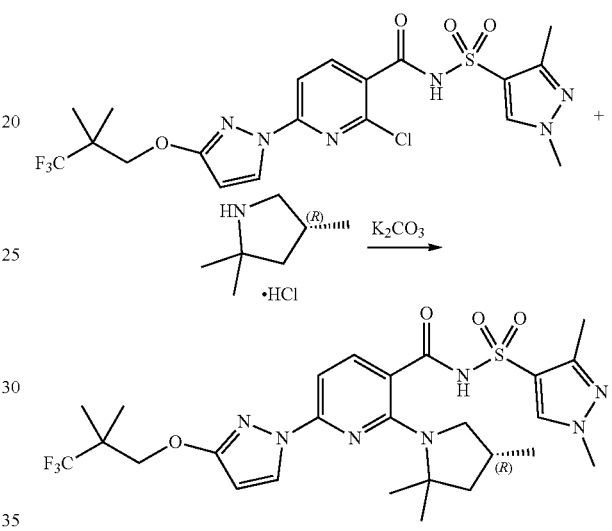

To a mixture of 2-chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (2 g, 3.839 mmol) and (4R)-2,2,4-trimethylpyrrolidine (hydrochloride salt) (approximately 1.322 g, 8.830 mmol) in N-methylpyrrolidinone (10.00 mL) and 1,2-diethoxyethane (2.000 mL) was added potassium carbonate (approximately 2.654 g, 19.20 mmol). The slurry was heated at 130° C. for 40 hours. The reaction suspension was cooled to ambient temperature and added slowly to a rapidly stirred solution of HCl (approximately 8.958 mL of 6 M, 53.75 mmol) in ice water (100.0 mL) affording an off-white slurry. The precipitate was collected and washed three times with 10 mL of water. The solid was air dried for one hour. The crude solid was dissolved in hot isopropyl alcohol (30.00 mL) and allowed to stand for two hours. The solid was collected, and the off-white solid was washed three times with 2 mL of cold isopropyl alcohol. The solid was air dried for one hour and then dried in vacuo at 45° C. for 18 hours to give N-(1,3-dimethylpyrazol-4-yl)sulfonyl-6-[3-(3,3,3-trifluoro-2,2-dimethyl-propoxy)pyrazol-1-yl]-2-[(4R)-2,2,4-trimethylpyrrolidin-1-yl]pyridine-3-carboxamide (1.4 g, 61%). ESI-MS m/z calc. 597.2345, found 598.1 (M+1)+; Retention time: 3.1 minutes.

¹H NMR (400 MHz, DMSO-d6) δ 12.36 (s, 1H), 8.38 (s, 1H), 8.22 (d, J=2.8 Hz, 1H), 7.75 (d, J=8.2 Hz, 1H), 6.93 (d, J=8.2 Hz, 1H), 6.17 (d, J=2.8 Hz, 1H), 4.23 (s, 2H), 3.81 (s, 3H), 2.55 (d, J=10.5 Hz, 1H), 2.41 (t, J=8.6 Hz, 1H), 2.32 (s, 3H), 2.19 (dt, J=12.0, 6.2 Hz, 1H), 1.87 (dd, J=11.9, 5.6 Hz, 1H), 1.56 (s, 3H), 1.53 (s, 3H), 1.42 (t, J=12.1 Hz, 1H), 1.23 (s, 6H), 0.81 (d, J=6.2 Hz, 3H).

Synthesis of 6-[3-(3,3,3-trifluoro-2,2-dimethyl-propoxy)pyrazol-1-yl]-N-(1,3,5-trimethylpyrazol-4-yl)sulfonyl-2-[(4S)-2,2,4-trimethylpyrrolidin-1-yl]pyridine-3-carboxamide (Compound 17)

Step 1: 2-chloro-6-[3-(3,3,3-trifluoro-2,2-dimethyl-propoxy)pyrazol-1-yl]-N-(1,3,5-trimethylpyrazol-4-yl)sulfonyl-pyridine-3-carboxamide

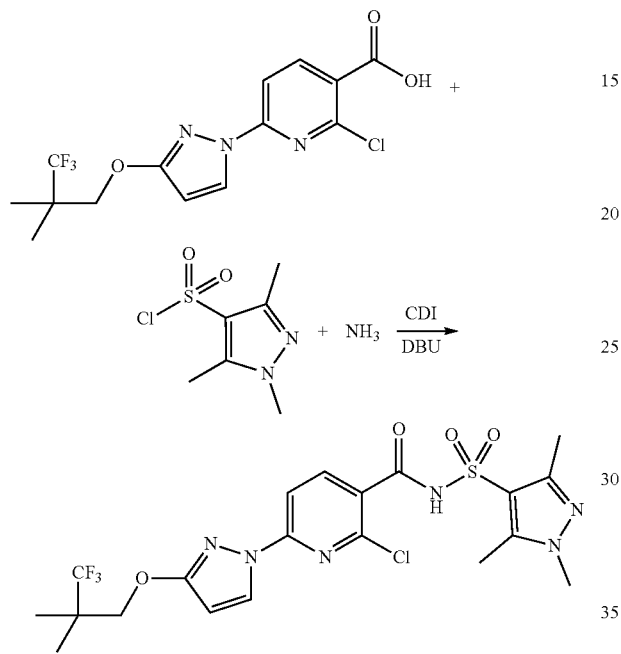

2-chloro-6-[3-(3,3,3-trifluoro-2,2-dimethyl-propoxy)pyrazol-1-yl]pyridine-3-carboxylic acid (100 mg, 0.2749 mmol) and CDI (53 mg, 0.3269 mmol) were combined in THF (600.0 µL) and stirred at room temperature for 2 hours in a vial (vial 1). Meanwhile, 1,3,5-trimethylpyrazole-4-sulfonyl chloride (69 mg, 0.3307 mmol) was combined with ammonia (250 µL of 7 M, 1.750 mmol) (in methanol) in a seperate vial (vial 2). After stirring for an additional 20 min, the volatiles were removed from vial 2 by evaporation, and 1 mL of dichloromethane was added to the solid residue, and was also evaporated. DBU (60 µL, 0.4012 mmol) was then added to vial 2 and stirred at 60° C. for 5 minutes (to facilitate the removal of ammonia from any residual ammonium chloride). Upon cooling to room temperature, 1 mL THF was added and then evaporated under reduced pressure. The contents of vial 1 were then added to vial 2 by syringe, and the reaction mixture was stirred for 4 h at room temperature. The reaction mixture was diluted with 10 mL ethyl acetate, and washed with 10 mL 1M citric acid. The aqueous layer was extracted 2×10 mL ethyl acetate, and the combined organics were washed with brine, dried over sodium sulfate, and concentrated to give a a white solid. This material was used in the next step without further purification. 2-chloro-6-[3-(3,3,3-trifluoro-2,2-dimethyl-propoxy)pyrazol-1-yl]-N-(1,3,5-trimethylpyrazol-4-yl)sulfonyl-pyridine-3-carboxamide (142 mg, 97%) ESI-MS m/z calc. 534.1064, found 535.1 (M+1)+; Retention time: 0.7 minutes.

Step 2: 6-[3-(3,3,3-trifluoro-2,2-dimethyl-propoxy)pyrazol-1-yl]-N-(1,3,5-trimethylpyrazol-4-yl)sulfonyl-2-[(4S)-2,2,4-trimethylpyrrolidin-1-yl]pyridine-3-carboxamide

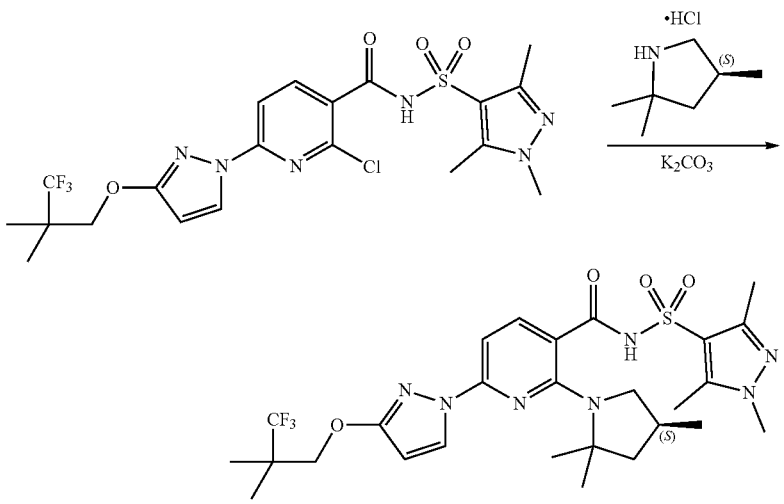

2-chloro-6-[3-(3,3,3-trifluoro-2,2-dimethyl-propoxy)pyrazol-1-yl]-N-(1,3,5-trimethylpyrazol-4-yl)sulfonyl-pyridine-3-carboxamide (142 mg, 0.2655 mmol), (4S)-2,2,4-trimethylpyrrolidine (hydrochloride salt) (119 mg, 0.7951 mmol), and potassium carbonate (221 mg, 1.599 mmol) were combined in DMSO (531.0 µL) and heated at 130° C.

for 16 h. The reaction was cooled to room temperature, and 1 mL of water was added. After 15 minutes stirring, the contents of the vial were allowed to settle, the liquid portion was removed by pipet and the remaining solids were dissolved with 20 mL ethyl acetate then washed with 15 mL 1M citric acid. The aqueous and organic layers were separated, and the aqueous layer was extracted two additional times with 15 mL ethyl acetate. The organics were combined, washed with brine, dried over sodium sulfate and concentrated. The resulting solid was further purified by silica gel chromotograpy eluting with 0-10% methanol in dichloromethane to give a white solid. 6-[3-(3,3,3-trifluoro-2,2-dimethyl-propoxy)pyrazol-1-yl]-N-(1,3,5-trimethylpyrazol-4-yl)sulfonyl-2-[(4S)-2,2,4-trimethylpyrrolidin-1-yl] pyridine-3-carboxamide (84 mg, 52%) ESI-MS m/z calc. 611.2502, found 612.2 (M+1)+; Retention time: 2.16 minutes.

(S)-2-(2,2-dimethyl-4-(methyl-d3)pyrrolidin-1-yl-3, 3-d2)-N-((3-methyl-1H-pyrazol-4-yl)sulfonyl)-6-(3-(3,3,3-trifluoro-2,2-dimethylpropoxy)-1H-pyrazol-1-yl)nicotinamide (Compound 3)

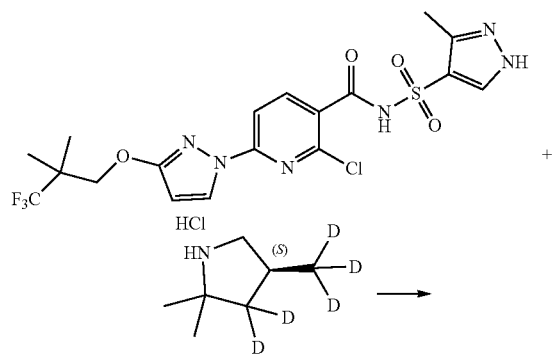

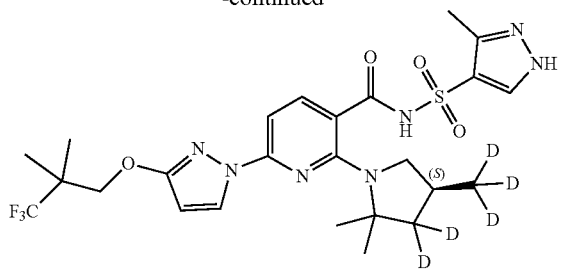

2-Chloro-N-[(3-methyl-1H-pyrazol-4-yl)sulfonyl]-6-[3-(3,3,3-trifluoro-2,2-dimethyl-propoxy)pyrazol-1-yl]pyridine-3-carboxamide (5.34 g, 10.5 mmol), potassium carbonate (7.27 g, 52.6 mmol) and (4S)-3,3-dideuterio-2,2-dimethyl-4-(trideuteriomethyl)pyrrolidine (Hydrochloride salt) (4.88 g, 31.6 mmol) were combined in DMSO (45 mL) and heated at 130° C. for 16 h. The reaction was portioned between ethyl acetate (30 vol) and a 1M citric acid solution (pH 4-5). The organics were separated, and washed with brine, dried over sodium sulfate and evaporated. The crude material was purified by silica gel chromatography eluting with 0-40% ethyl acetate in heptane followed by trituration with MTBE/dichloromethane (2:1). The solid obtained was transferred to a 100 mL round bottom flask and dried for 4 days at room temperature to give (S)-2-(2,2-dimethyl-4-(methyl-d3)pyrrolidin-1-yl-3,3-d2)-N-((3-methyl-1H-pyrazol-4-yl)sulfonyl)-6-(3-(3,3,3-trifluoro-2,2-dimethyl-propoxy)-1H-pyrazol-1-yl)nicotinamide (2.6 g, 42%). ESI-MS m/z calc. 588.66, found 589.2 (M+1)+; Retention time: 20.2 minutes (35 min run).

Synthesis of N-(1,3-dimethylpyrazol-4-yl)sulfonyl-6-[3-(3,3,3-trifluoropropoxy)pyrazol-1-yl]-2-[(4S)-2, 2,4-trimethylpyrrolidin-1-yl]pyridine-3-carboxamide (Compound 11)

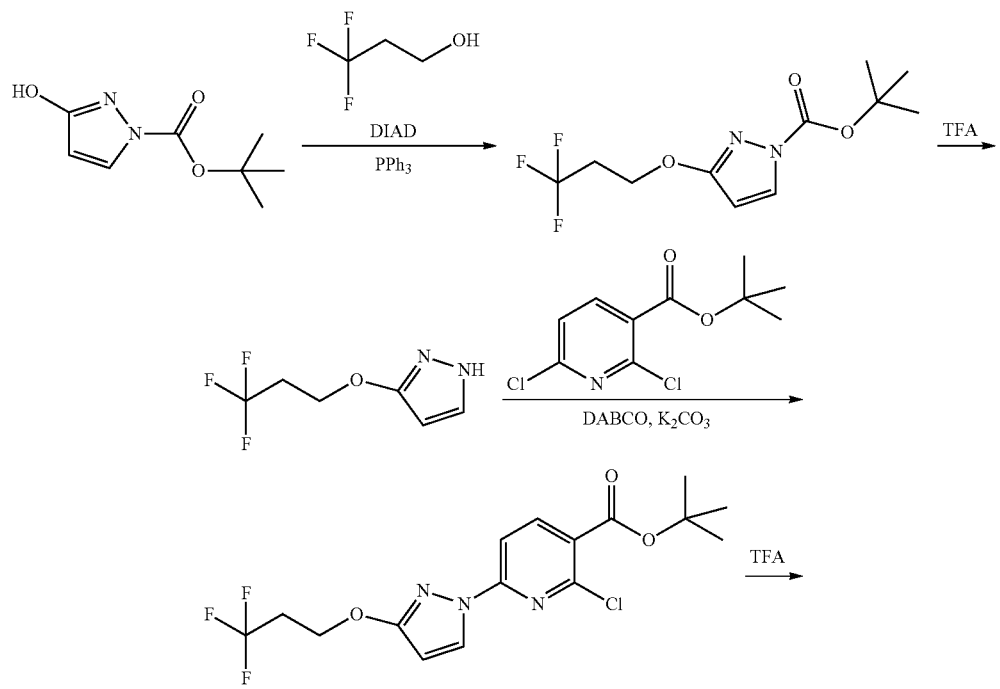

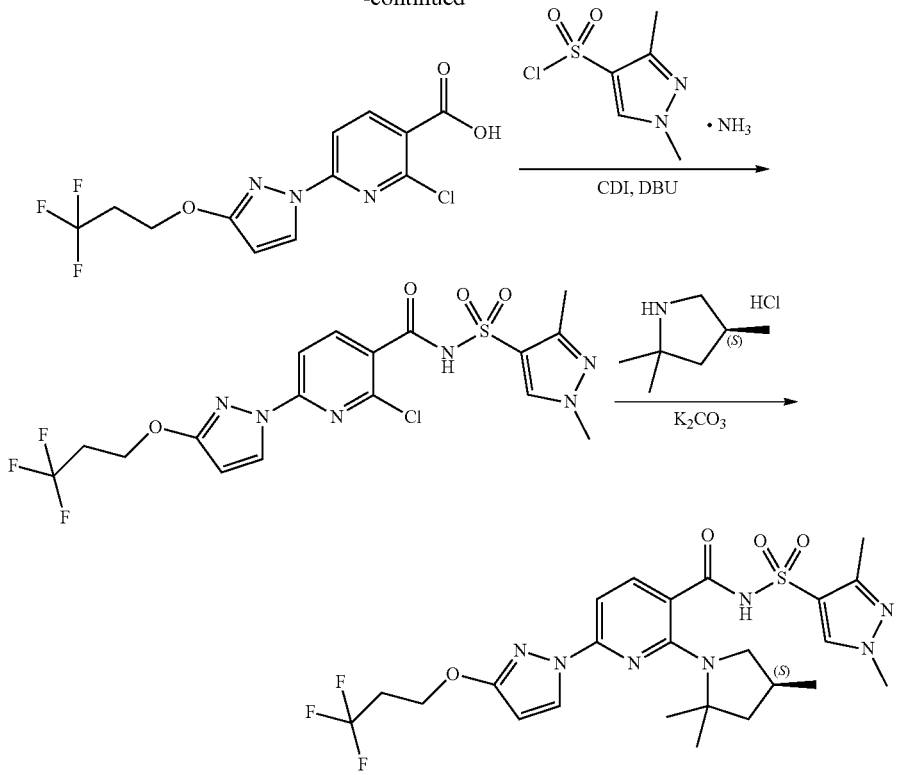

Step 1: tert-butyl 3-(3,3,3-trifluoropropoxy)pyrazole-1-carboxylate

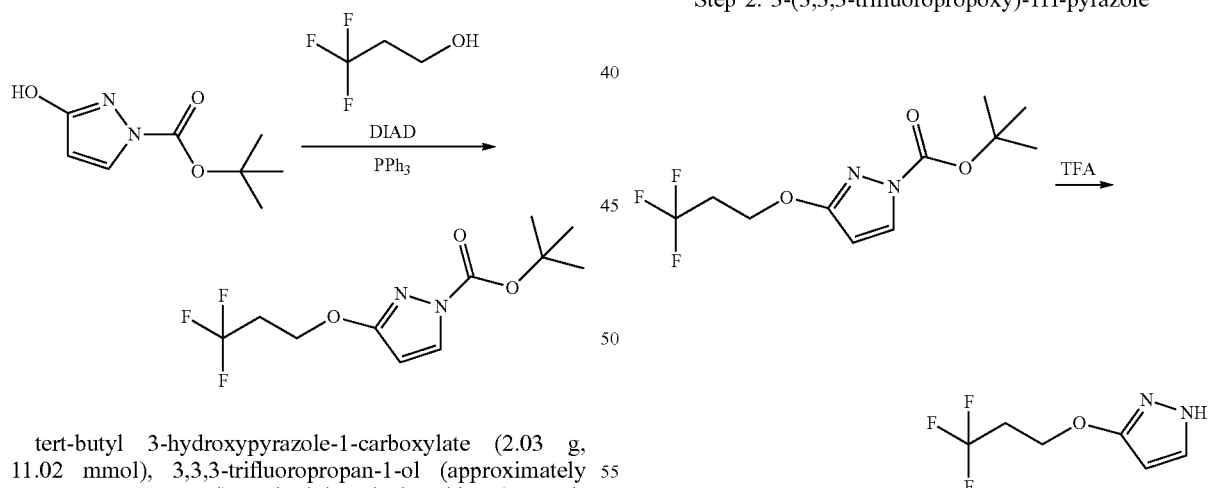

tert-butyl 3-hydroxypyrazole-1-carboxylate (2.03 g, 11.02 mmol), 3,3,3-trifluoropropan-1-ol (approximately 1.320 g, 11.57 mmol), and triphenyl phosphine (approximately 3.189 g, 2.817 mL, 12.16 mmol) were combined in THF (20.40 mL) and the reaction was cooled in an ice bath. To the mixture was added DIAD (approximately 2.507 g, 2.441 mL, 12.40 mmol) dropwise and the reaction was allowed to warm to room temperature for 16 h. The mixture was evaporated and the resulting material was partitioned between ethyl acetate (50 mL) and 1N sodium hydroxide (50 mL). The organics were separated, washed with brine (30 mL), dried over sodium sulfate and evaporated. The crude material was purified by silica gel chromatography eluting with 0-30% ethyl acetate in hexanes to give tert-butyl 3-(3,3,3-trifluoropropoxy)pyrazole-1-carboxylate (2.0 g, 65%) ESI-MS ink calc. 280.1035, found 281.1 (M+1)+; Retention time: 0.62 minutes.

Step 2: 3-(3,3,3-trifluoropropoxy)-1H-pyrazole tert-butyl 3-(3,3,3-trifluoropropoxy)pyrazole-1-carboxylate (2.0 g, 7.137 mmol) and TFA (approximately 8.138 g, 5.499 mL, 71.37 mmol) were dissolved in dichloromethane (20.00 mL) and stirred for 2 h and then evaporated to a solid. The solid was partitioned between ethyl acetate and a saturated sodium bicarbonate solution. The organics were separated, washed with brine, and dried over sodium sulfate. The organics were dried to give 3-(3,3,3-trifluoropropoxy)-1H-pyrazole (1.24 g, 96%) ESI-MS m/z calc. 180.05104, found 180.9 (M+1)+; Retention time: 0.37 minutes.

Step 3: tert-butyl 2-chloro-6-[3-(3,3,3-trifluoro-propoxy)pyrazol-1-yl]pyridine-3-carboxylate

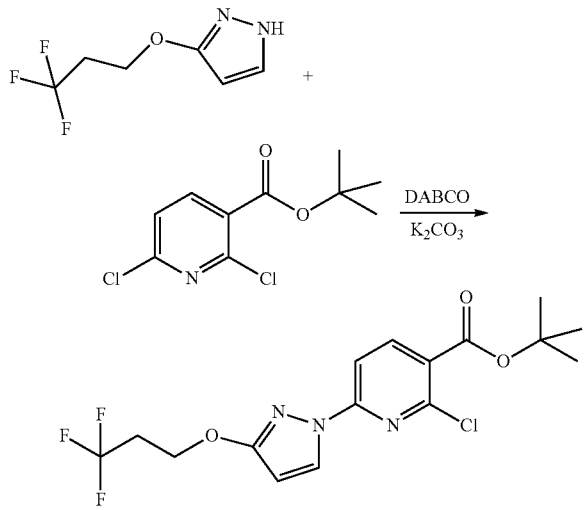

tert-butyl 2,6-dichloropyridine-3-carboxylate (approximately 1.433 g, 5.774 mmol), 3-(3,3,3-trifluoropropoxy)-1H-pyrazole (1.04 g, 5.774 mmol), and potassium carbonate (approximately 957.6 mg, 6.929 mmol) (freshly ground) were combined in anhydrous DMSO (28.66 mL). 1,4-diazabicyclo[2.2.2]octane (approximately 129.6 mg, 1.155 mmol) was added and the mixture was stirred at room temperature under nitrogen for 16 hours. The reaction mixture was diluted with water (20 mL) and stirred for 15 min. The resulting solid was collected and washed with water. The solid was dissolved in dichloromethane and the small amount of aqueous layer removed. The organics were dried over sodium sulfate and evaporated to give tert-butyl 2-chloro-6-[3-(3,3,3-trifluoropropoxy)pyrazol-1-yl]pyridine-3-carboxylate (1.81 g, 80%) ESI-MS m/z calc. 391.09106, found 392.2 (M+1)+; Retention time: 0.84 minutes.

Step 4: 2-Chloro-6-[3-[(1R,2S,4S)-norbornan-2-yl]oxypyrazol-1-yl]pyridine-3-carboxylic acid

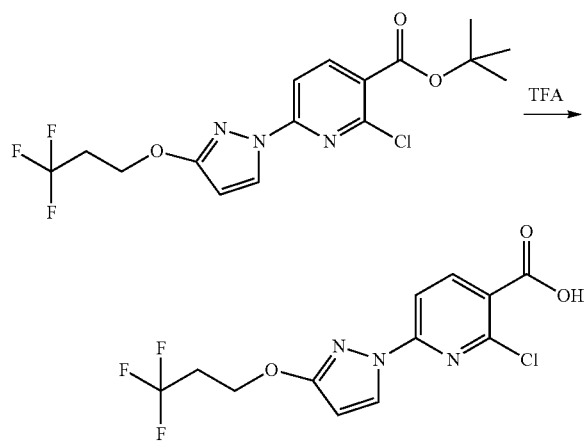

tert-butyl 2-chloro-6-[3-(3,3,3-trifluoropropoxy)pyrazol-1-yl]pyridine-3-carboxylate (1.81 g, 4.620 mmol) and TFA (3.6 mL, 47 mmol) were combined in methylene chloride (18 mL) and heated at 40° C. for 3 h. The reaction was evaporated to dryness and the resulting solid was re-evaporated from hexanes. The solid was further dried to give 2-chloro-6-[3-(3,3,3-trifluoropropoxy)pyrazol-1-yl]pyridine-3-carboxylic acid (1.55 g, 100%) ESI-MS m/z calc. 335.02844, found 336.0 (M+1)+; Retention time: 0.61 minutes.

Step 5: 2-chloro-N-(1,3-dimethylpyrazol-4-yl)sulfonyl-6-[3-(3,3,3-trifluoropropoxy)pyrazol-1-yl]pyridine-3-carboxamide

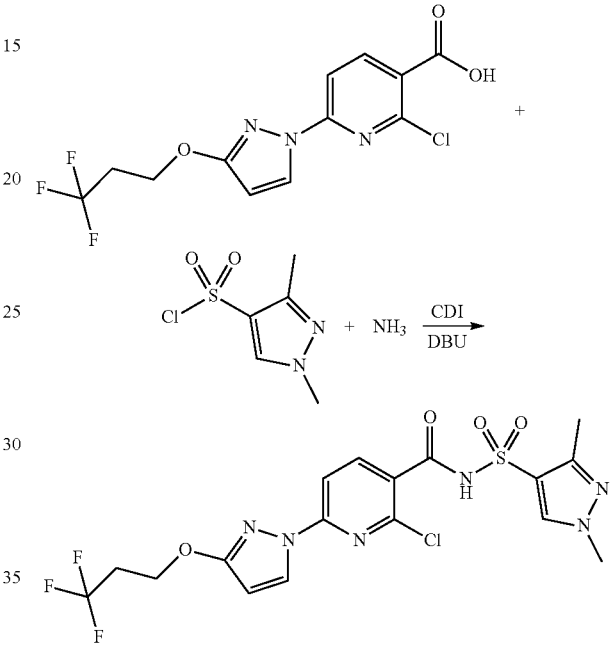

Step 1: Sulfonamide Formation 1,3-dimethylpyrazole-4-sulfonyl chloride (approximately 97.42 mg, 0.5005 mmol) was dissolved in ammonia in methanol (approximately 298.0 µL of 7 M, 2.086 mmol) and stirred at room temperature for 30 min. The mixture was evaporated to dryness and re-evaporated from dichloromethane. The solids were dissolved in THF (1 mL) and DBU (approximately 211.6 mg, 207.9 µL, 1.390 mmol) was added. The mixture was stirred at 70° C. for 30 min to liberate any remaining ammonia from the reaction.

Step 2

2-chloro-6-[3-(3,3,3-trifluoropropoxy)pyrazol-1-yl]pyridine-3-carboxylic acid (140 mg, 0.4171 mmol) and carbonyl diimidazole (approximately 85.36 mg, 0.5264 mmol) were combined in THF (1.250 mL) and stirred for 2 h. At this point, the mixture was added to the sulfonamide mixture from step 1. DBU (approximately 211.6 mg, 207.9 µL, 1.390 mmol) was added and the reaction was stirred for an additional 30 min at room temperature. The reaction was diluted with ethyl acetate and washed with a 1M citric acid solution, followed by brine. The organics were separated, dried over sodium sulfate, and evaporated to give 2-chloro-N-(1,3-dimethylpyrazol-4-yl)sulfonyl-6-[3-(3,3,3-trifluoropropoxy)pyrazol-1-yl]pyridine-3-carboxamide (196 mg, 95%) ESI-MS m/z calc. 492.05945, found 493.1 (M+1)+; Retention time: 0.61 minutes.

Step 6: N-(1,3-dimethylpyrazol-4-yl)sulfonyl-6-[3-(3,3,3-trifluoropropoxy)pyrazol-1-yl]-2-[(4S)-2,2,4-trimethylpyrrolidin-1-yl]pyridine-3-carboxamide

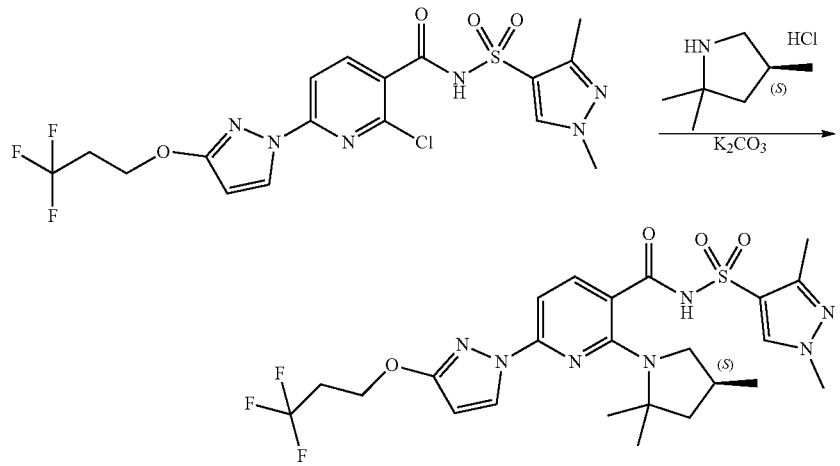

2-chloro-N-methylsulfonyl-6-[3-(3,3,3-trifluoropropoxy)pyrazol-1-yl]pyridine-3-carboxamide (approximately 100 mg, 0.2 mmol), (4S)-2,2,4-trimethylpyrrolidine (Hydrochloride salt) (approximately 91 mg, 0.60 mmol), and potassium carbonate (approximately 141 mg, 1.0 mmol) were combined in DMSO (500.0 µL) and heated at 130° C. for 16 h. The reaction was diluted with water (3 mL) and stirred for 20 min. A solid formed and the aqueous liquid was decanted. The solid was dissolved in ethyl acetate and washed with a 1M citric acid solution, then brine. The organics were dried over sodium sulfate and evaporated. The crude material was purified by silica gel chromatography eluting with 0-10% methanol in dichloromethane to give N-(1,3-dimethylpyrazol-4-yl)sulfonyl-6-[3-(3,3,3-trifluoropropoxy)pyrazol-1-yl]-2-[(4S)-2,2,4-trimethylpyrrolidin-1-yl]pyridine-3-carboxamide (29 mg, 25%) ESI-MS m/z calc. 569.20, found 570.3 (M+1)+; Retention time: 1.89 minutes.

$^1$H NMR (400 MHz, DMSO-d6) δ 12.36 (s, 1H), 8.37 (s, 1H), 8.22 (d, J=2.8 Hz, 1H), 7.74 (d, J=8.2 Hz, 1H), 6.92 (d, J=8.2 Hz, 1H), 6.15 (d, J=2.7 Hz, 1H), 4.44 (t, J=5.9 Hz, 2H), 3.81 (s, 3H), 2.83 (qt, J=11.5, 5.9 Hz, 2H), 2.59-2.53 (m, 1H), 2.46-2.37 (m, 1H), 2.32 (s, 3H), 2.26-2.10 (m, 1H), 1.88 (dd, J=11.9, 5.5 Hz, 1H), 1.55 (d, J=11.1 Hz, 6H), 1.42 (t, J=12.2 Hz, 1H), 0.81 (d, J=6.3 Hz, 3H).

Synthesis of N-(1,5-dimethylpyrazol-4-yl)sulfonyl-6-[3-(3,3,3-trifluoropropoxy)pyrazol-1-yl]-2-[(4S)-2,2,4-trimethylpyrrolidin-1-yl]pyridine-3-carboxamide (Compound 12)

Step 1: 2-chloro-N-(1,5-dimethylpyrazol-4-yl)sulfonyl-6-[3-(3,3,3-trifluoropropoxy)pyrazol-1-yl]pyridine-3-carboxamide

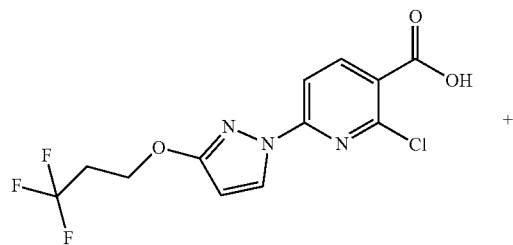

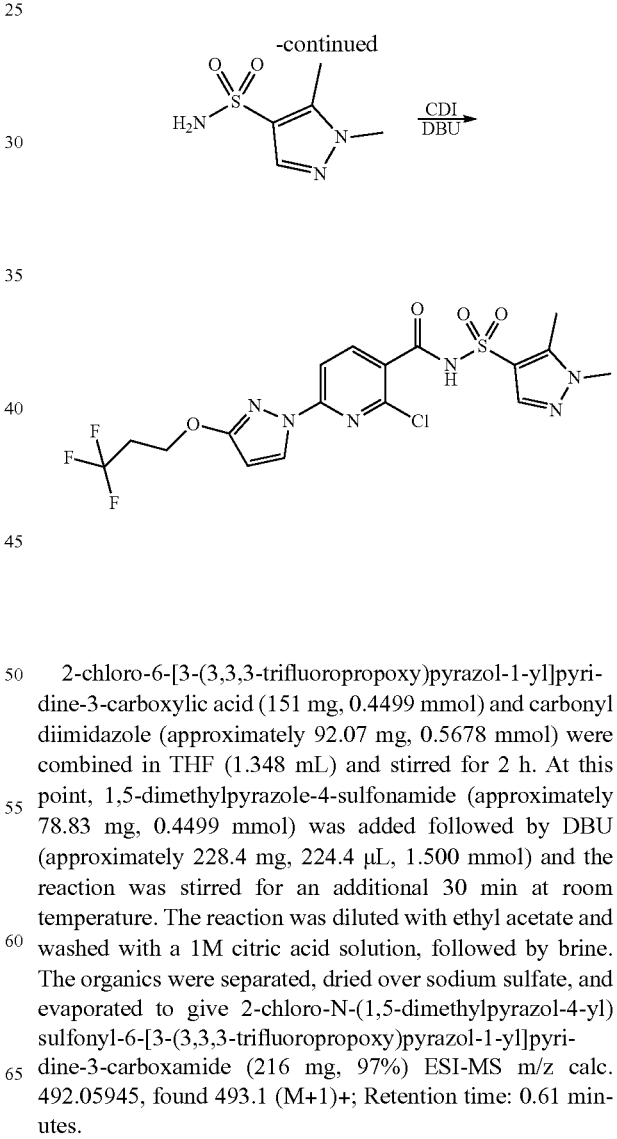

2-chloro-6-[3-(3,3,3-trifluoropropoxy)pyrazol-1-yl]pyridine-3-carboxylic acid (151 mg, 0.4499 mmol) and carbonyl diimidazole (approximately 92.07 mg, 0.5678 mmol) were combined in THF (1.348 mL) and stirred for 2 h. At this point, 1,5-dimethylpyrazole-4-sulfonamide (approximately 78.83 mg, 0.4499 mmol) was added followed by DBU (approximately 228.4 mg, 224.4 µL, 1.500 mmol) and the reaction was stirred for an additional 30 min at room temperature. The reaction was diluted with ethyl acetate and washed with a 1M citric acid solution, followed by brine. The organics were separated, dried over sodium sulfate, and evaporated to give 2-chloro-N-(1,5-dimethylpyrazol-4-yl)sulfonyl-6-[3-(3,3,3-trifluoropropoxy)pyrazol-1-yl]pyridine-3-carboxamide (216 mg, 97%) ESI-MS m/z calc. 492.05945, found 493.1 (M+1)+; Retention time: 0.61 minutes.

Step 2: N-(1,5-dimethylpyrazol-4-yl)sulfonyl-6-[3-(3,3,3-trifluoropropoxy)pyrazol-1-yl]-2-[(4S)-2,2,4-trimethylpyrrolidin-1-yl]pyridine-3-carboxamide

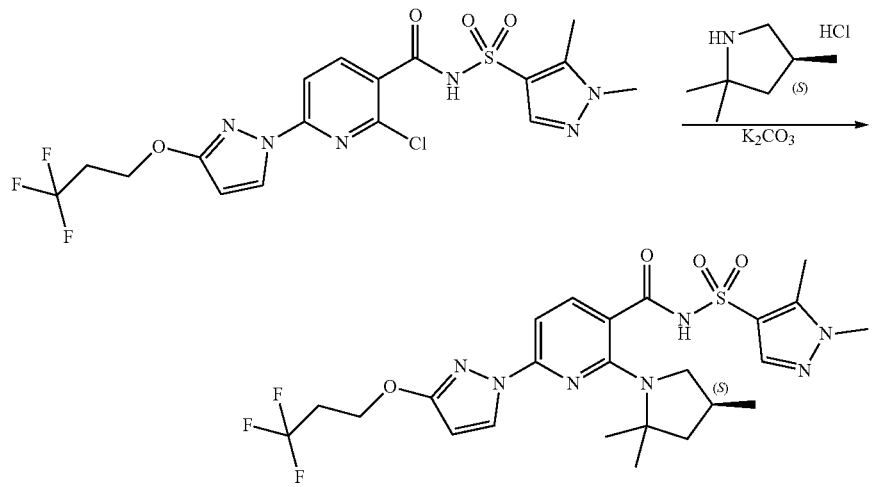

2-chloro-N-(1,5-dimethylpyrazol-4-yl)sulfonyl-6-[3-(3,3,3-trifluoropropoxy)pyrazol-1-yl]pyridine-3-carboxamide (approximately 100 mg, 0.2 mmol), (4S)-2,2,4-trimethylpyrrolidine (Hydrochloride salt) (approximately 91 mg, 0.60 mmol), and potassium carbonate (approximately 141 mg, 1.0 mmol) were combined in DMSO (500.0 µL) and heated at 130° C. for 16 h. The reaction was diluted with water (3 mL) and stirred for 20 min. A solid formed and the aqueous liquid was decanted. The solid was dissolved in ethyl acetate and washed with a 1M citric acid solution, then brine. The organics were dried over sodium sulfate and evaporated. The crude material was purified by silica gel chromatography eluting with 0-10% methanol in dichloromethane to give N-(1,5-dimethylpyrazol-4-yl)sulfonyl-6-[3-(3,3,3-trifluoropropoxy)pyrazol-1-yl]-2-[(4S)-2,2,4-trimethylpyrrolidin-1-yl]pyridine-3-carboxamide (51 mg, 44%) ESI-MS m/z calc. 569.20, found 570.3 (M+1)+; Retention time: 1.89 minutes.

$^1$H NMR (400 MHz, DMSO-$d_6$) δ 12.36 (s, 1H), 8.37 (s, 1H), 8.22 (d, J=2.8 Hz, 1H), 7.74 (d, J=8.2 Hz, 1H), 6.92 (d, J=8.2 Hz, 1H), 6.15 (d, J=2.7 Hz, 1H), 4.44 (t, J=5.9 Hz, 2H), 3.81 (s, 3H), 2.83 (qt, J=11.5, 5.9 Hz, 2H), 2.59-2.53 (m, 1H), 2.46-2.37 (m, 1H), 2.32 (s, 3H), 2.26-2.10 (m, 1H), 1.88 (dd, J=11.9, 5.5 Hz, 1H), 1.55 (d, J=11.1 Hz, 6H), 1.42 (t, J=12.2 Hz, 1H), 0.81 (d, J=6.3 Hz, 3H).

Synthesis of 6-[3-(Dicyclopropylmethoxy)pyrazol-1-yl]-N-(1,3-dimethylpyrazol-4-yl)sulfonyl-2-[(4S)-2,2,4-trimethylpyrrolidin-1-yl]pyridine-3-carboxamide (Compound 48)

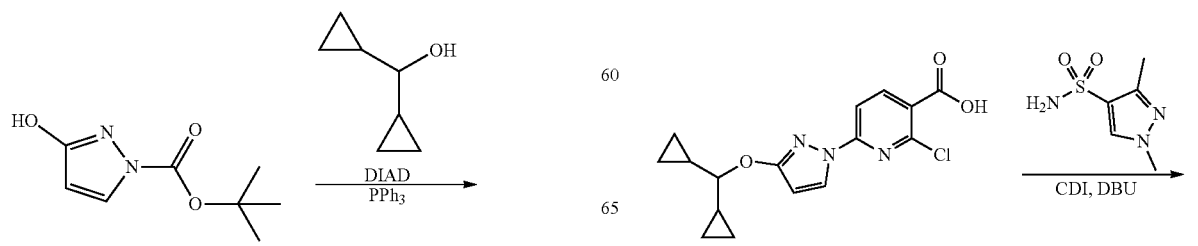

-continued

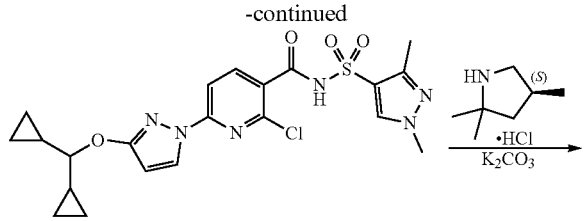

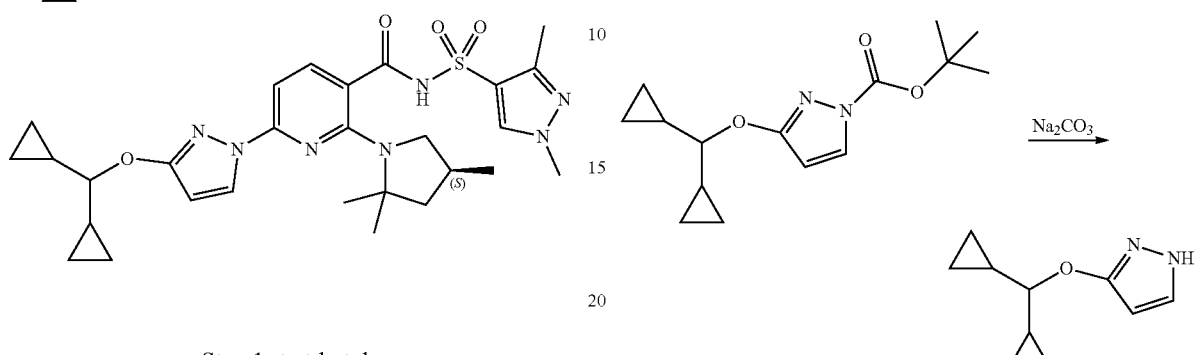

Step 1: tert-butyl 3-(dicyclopropylmethoxy)pyrazole-1-carboxylate

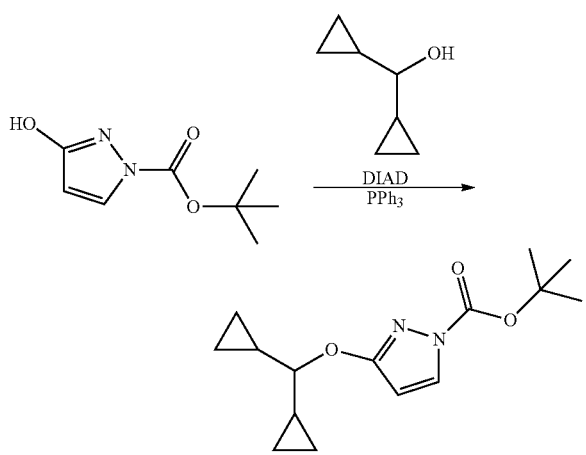

dicyclopropylmethanol (approximately 468.9 mg, 4.180 mmol), tert-butyl 3-hydroxypyrazole-1-carboxylate (700 mg, 3.800 mmol), and PPh3 (approximately 1.296 g, 4.940 mmol) were dissolved in THF (19.00 mL), and cooled to 0° C. in an ice bath. DIAD (approximately 998.9 mg, 956.8 µL, 4.940 mmol) was added dropwise by syringe, and the reaction mixture was allowed to slowly warm to room temperature over the course of an hour, and then stirred 16 hours at room temperature, and 2 hours at 60° C. Solvent was removed under reduced pressure. The remaining oil was then dissolved in 60 mL ethyl acetate, and washed with 50 mL 1N NaOH. The aqueous layer was further extracted with ethyl acetate (2×40 mL), and the combined organics were washed with brine, dried over sodium sulfate and concentrated. The crude material was then purified by silica gel chromatography, employing a 0-40% gradient of ethyl acetate in hexanes. The fractions containing the desired product were combined and concentrated to give tert-butyl 3-(dicyclopropylmethoxy)pyrazole-1-carboxylate (483 mg, 46%). ESI-MS m/z calc. 278.16306, found 279.3 (M+1)+; Retention time: 2.11 minutes.

$^1$H NMR (400 MHz, DMF) δ 8.02 (dd, J=3.1, 0.9 Hz, 1H), 6.07 (dd, J=3.1, 0.9 Hz, 1H), 3.80 (td, J=7.8, 1.0 Hz, 1H), 1.53 (d, J=1.0 Hz, 9H), 1.23-1.04 (m, 2H), 0.59-0.27 (m, 8H).

Step 2: 3-(dicyclopropylmethoxy)-1H-pyrazole

To tert-butyl 3-(dicyclopropylmethoxy)pyrazole-1-carboxylate (470 mg, 1.689 mmol) in 1,2-dimethoxyethane (5.875 mL) was added sodium carbonate (537 mg, 5.067 mmol) in water (2.5 mL), and the reaction mixture was heated to 90° C. for 16 hours in a screwcap vial. The reaction mixture was cooled to room temperature and diluted with water (50 mL) and ethyl acetate (50 mL). The organics were separated, and the aqueous layer was extracted 2×25 mL ethyl acetate. The combined organics were washed with brine, and dried over sodium sulfate, then concentrated to give a colorless oil, which was used in the next step without further purification. 3-(dicyclopropylmethoxy)-1H-pyrazole (230 mg, 76%) ESI-MS m/z calc. 178.11061, found 179.1 (M+1)+; Retention time: 1.32 minutes.

Step 3: ethyl 2-chloro-6-[3-(dicyclopropylmethoxy) pyrazol-1-yl]pyridine-3-carboxylate

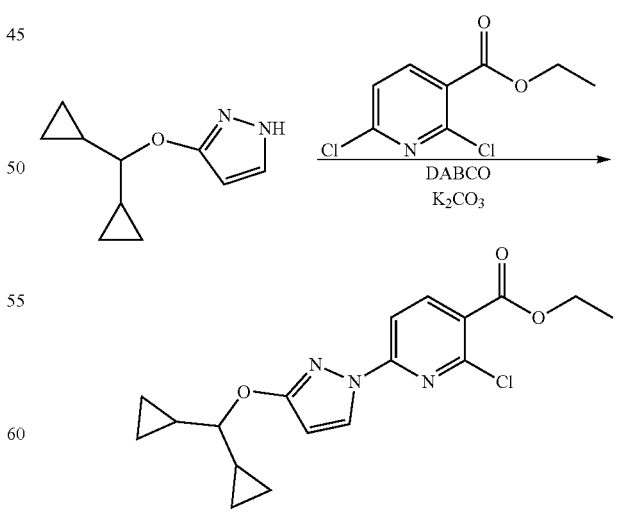

A round bottom flask was charged under nitrogen with 3-(dicyclopropylmethoxy)-1H-pyrazole (226 mg, 1.268 mmol), ethyl 2,6-dichloropyridine-3-carboxylate (280 mg, 1.272 mmol), K$_2$CO$_3$ (264 mg, 1.910 mmol) (freshly ground in a mortar) and anhydrous DMF (2.100 mL). DABCO (26 mg, 0.2318 mmol) was added and the mixture was stirred at room temperature under nitrogen for 16 hours. The reaction mixture was diluted with ethyl acetate (50 mL) and water (50 mL) and the two phases were separated. The aqueous phase was further extracted with ethyl acetate (2×30 mL), and the combined extracts were washed with brine and dried over sodium sulfate, after which the solvent was removed under reduced pressure. The material was subjected to flash chromatography on silica gel using a gradient of 0-30% ethyl acetate in hexanes. The pure fractions were combined and the solvents removed under reduced pressure to provide a white solid; ethyl 2-chloro-6-[3-(dicyclopropylmethoxy)pyrazol-1-yl]pyridine-3-carboxylate (210 mg, 46%). ESI-MS m/z calc. 361.11932, found 362.3 (M+1)+; Retention time: 0.82 minutes.

$^1$H NMR (400 MHz, DMSO) δ 8.48-8.31 (m, 2H), 7.69 (d, J=8.5 Hz, 1H), 6.19 (d, J 2.9 Hz, 1H), 4.34 (q, J=7.1 Hz, 2H), 3.88 (t, J=7.9 Hz, 1H), 1.33 (t, J=7.1 Hz, 3H), 1.27-1.14 (m, 2H), 0.60-0.35 (m, 8H).

Step 4: 2-chloro-6-[3-(dicyclopropylmethoxy)pyrazol-1-yl]pyridine-3-carboxylic acid

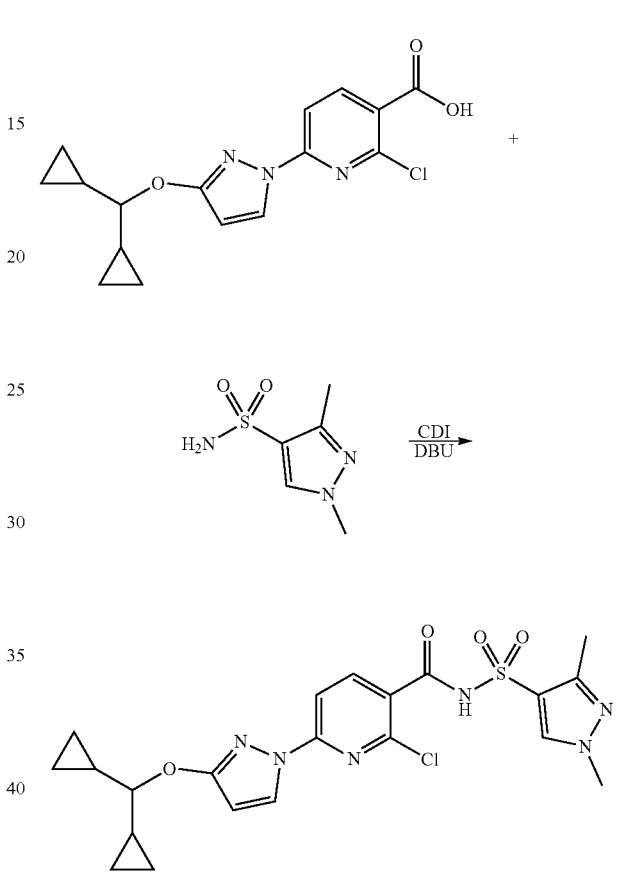

To a solution of ethyl 2-chloro-6-[3-(dicyclopropylmethoxy)pyrazol-1-yl]pyridine-3-carboxylate (5 g, 13.82 mmol) in THF (35.00 mL) and MeOH (15.00 mL) was added NaOH (approximately 13.82 mL of 2 M, 27.64 mmol). The mixture was stirred at ambient temperature for 45 min. The mixture was acidified with the slow addition of HCl (approximately 27.64 mL of 1 M, 27.64 mmol) and the mixture was extracted with EtOAc (125 mL). The aqueous phase was separated and the organic phase was washed with 75 mL of brine, dried over MgSO$_4$, filtered and concentrated in vacuo. The product was an off-white solid used without further purification. 2-chloro-6-[3-(dicyclopropylmethoxy)pyrazol-1-yl]pyridine-3-carboxylic acid (4.5 g, 98%). ESI-MS m/z calc. 333.088, found 334.0 (M+1)+; Retention time: 1.81 minutes.

$^1$H NMR (400 MHz, DMSO-d$_6$) δ 13.60 (s, 1H), 8.41-8.34 (m, 2H), 7.67 (d, J=8.4 Hz, 1H), 6.18 (d, J=2.9 Hz, 1H), 3.88 (t, J=7.9 Hz, 1H), 1.29-1.12 (m, 2H), 0.59-0.38 (m, 8H).

Step 5: 2-Chloro-6-[3-(dicyclopropylmethoxy)pyrazol-1-yl]-N-(1,3-dimethylpyrazol-4-yl)sulfonyl-pyridine-3-carboxamide

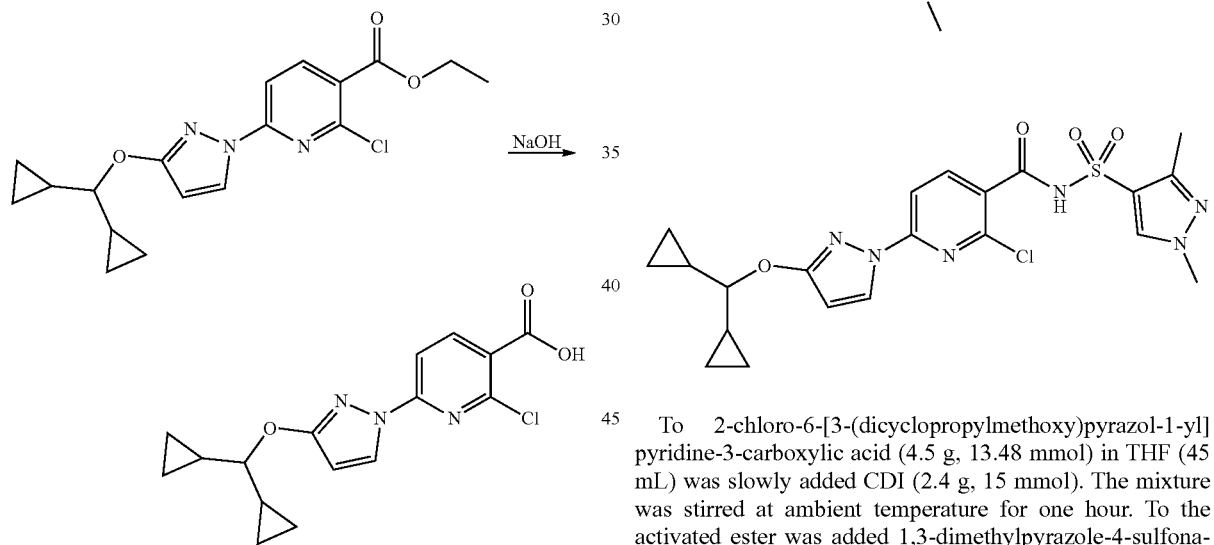

To 2-chloro-6-[3-(dicyclopropylmethoxy)pyrazol-1-yl]pyridine-3-carboxylic acid (4.5 g, 13.48 mmol) in THF (45 mL) was slowly added CDI (2.4 g, 15 mmol). The mixture was stirred at ambient temperature for one hour. To the activated ester was added 1,3-dimethylpyrazole-4-sulfonamide (2.6 g, 14.84 mmol) portionwise followed by DBU (2.4 mL, 16 mmol), and the mixture was stirred at ambient temperature for one hour. To the reaction mixture was slowly added citric acid (10.4 g, 54.1 mmol) in water (90 mL). The mixture was extracted with EtOAc (120 mL), and the organic phase washed with brine, dried over magnesium sulfate, filtered, and concentrated in vacuo. The crude product was chromatographed on a 120 g ISCO silica gel column eluting with 0-100% EtOAc/hexanes affording 2-chloro-6-[3-(dicyclopropylmethoxy)pyrazol-1-yl]-N-(1,3-dimethylpyrazol-4-yl)sulfonyl-pyridine-3-carboxamide (5.3 g, 80%). ESI-MS m/z calc. 490.119, found 491.1 (M+1)+; Retention time: 2.57 minutes.

$^1$H NMR (400 MHz, DMSO-d$_6$) δ 12.71 (s, 1H), 8.52-8.25 (m, 2H), 8.07 (d, J=8.4 Hz, 1H), 7.63 (d, J=8.3 Hz, 1H), 6.16 (d, J=2.9 Hz, 1H), 3.87 (t, J=8.0 Hz, 1H), 3.84 (s, 3H), 2.35 (s, 3H), 1.26-1.14 (m, 2H), 0.55-0.40 (m, 8H).

Step 6: 6-[3-(Dicyclopropylmethoxy)pyrazol-1-yl]-N-(1,3-dimethylpyrazol-4-yl)sulfonyl-2-[(4S)-2,2,4-trimethylpyrrolidin-1-yl]pyridine-3-carboxamide

Synthesis of 6-[3-(3-Bicyclo[1.1.1]pentanyl-methoxy)pyrazol-1-yl]-N-(1,5-dimethylpyrazol-4-yl)sulfonyl-2-[(4S)-2,2,4-trimethylpyrrolidin-1-yl]pyridine-3-carboxamide (Compound 23)

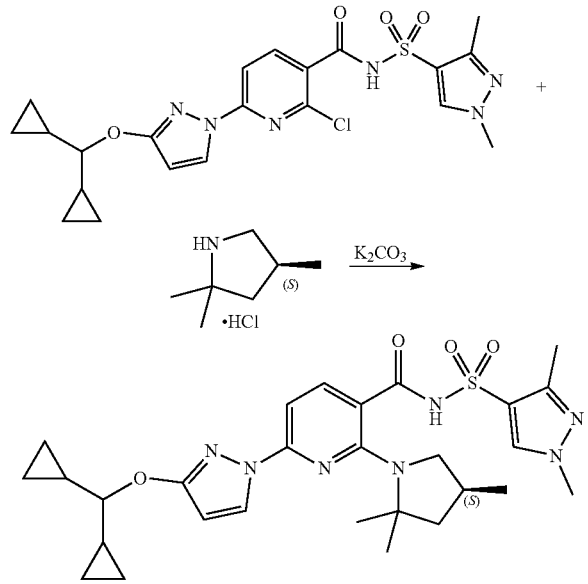

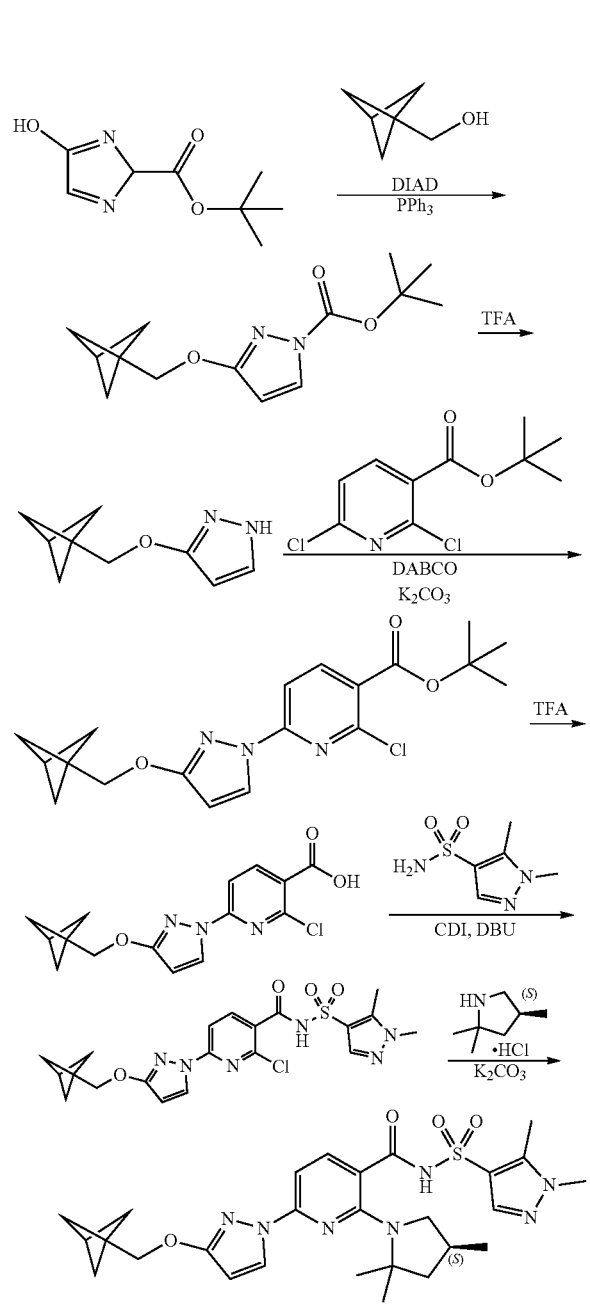

To a solution of 2-chloro-6-[3-(dicyclopropylmethoxy)pyrazol-1-yl]-N-(1,3-dimethylpyrazol-4-yl)sulfonyl-pyridine-3-carboxamide (5.2 g, 10.59 mmol) and (4S)-2,2,4-trimethylpyrrolidine (hydrochloride salt) (3.65 g, 24.39 mmol) in NMP (25 mL) and 1,2-diethoxyethane (5 mL) was added potassium carbonate (7.32 g, 53.0 mmol). The slurry was heated at 130° C. for 20 hours. The reaction suspension was cooled to ambient temperature and added slowly to a rapidly stirred solution of HCl (18 mL of 6 M, 108 mmol) in ice water (150 mL) affording an off-white slurry. The precipitate was collected and washed three times with 10 mL of water. The solid was air dried for one hour. The solid was dissolved in 150 mL of EtOAc and washed with 100 mL of 1 M HCl and 100 mL of brine. The organic phase was dried over magnesium sulfate, filtered, and concentrated in vacuo affording an off-white solid. The solid was dissolved in 20 mL of acetonitrile and chromatographed on a 415 g ISCO reverse-phase column eluting with 5-100% acetonitrile/water. Product fractions were collected and concentrated in vacuo. The product was re-chromatographed on an 80 g ISCO silica gel column eluting with 0-100% EtOAc/hexanes. Pure fractions were collected and concentrated in vacuo affording an off-white solid. The solid was dried under vacuum at 45° C. for four hours to give 6-[3-(dicyclopropylmethoxy)pyrazol-1-yl]-N-(1,3-dimethylpyrazol-4-yl)sulfonyl-2-[(4S)-2,2,4-trimethylpyrrolidin-1-yl]pyridine-3-carboxamide (4.1 g, 68%). ESI-MS m/z calc. 567.26276, found 567.0 (M+1)+; Retention time: 3.06 minutes.

$^1$H NMR (400 MHz, DMSO-d$_6$) δ 12.34 (s, 1H), 8.37 (s, 1H), 8.16 (d, J=2.8 Hz, 1H), 7.72 (d, J=8.2 Hz, 1H), 6.84 (d, J=8.2 Hz, 1H), 6.08 (d, J=2.7 Hz, 1H), 3.84 (t, J=7.8 Hz, 1H), 3.80 (s, 3H), 2.55 (d, J=10.5 Hz, 1H), 2.41 (t, J=8.6 Hz, 1H), 2.32 (s, 3H), 2.18 (dq, J=11.5, 6.1 Hz, 1H), 1.87 (dd, J=11.9, 5.6 Hz, 1H), 1.54 (d, J=10.8 Hz, 6H), 1.41 (t, J=12.1 Hz, 1H), 1.18 (dtd, J=12.9, 8.0, 5.1 Hz, 2H), 0.81 (d, J=6.2 Hz, 3H), 0.56-0.38 (m, 8H).

Step 1: tert-Butyl 3-(3-bicyclo[1.1.1]pentanyl-methoxy)pyrazole-1-carboxylate

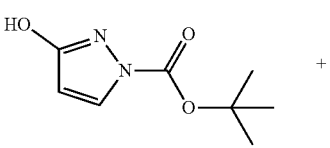

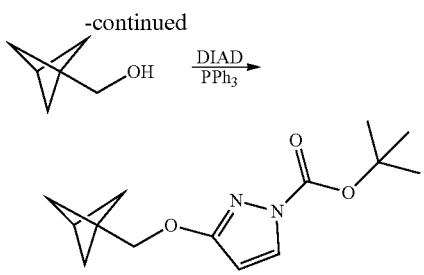

A solution of 3-bicyclo[1.1.1]pentanylmethanol (0.23 g, 2.3 mmol), Cert-butyl 3-hydroxypyrazole-1-carboxylate (0.42 g, 2.3 mmol), and triphenyl phosphine (0.66 g, 2.5 mmol) in THF (12 mL) was cooled in an ice bath, and isopropyl N-isopropoxycarbonyliminocarbamate (0.49 mL, 2.5 mmol) was slowly added. The reaction was allowed to slowly warm to room temperature and was stirred for three days. It was diluted with ethyl acetate, washed with saturated aqueous sodium bicarbonate, dried over sodium sulfate, and evaporated under vacuum. The residue was purified by silica gel chromatography with 0-40% ethyl acetate in hexanes to give tert-butyl 3-(3-bicyclo[1.1.1]pentanyl-methoxy)pyrazole-1-carboxylate as a colorless oil (0.40 g, 66%) ESI-MS m/z calc. 264.15, found 265.2 (M+1)+; Retention time: 0.79 minutes.

Step 2: 3-({Bicyclo[1.1.1]pentan-1-yl}methoxy)-1H-pyrazole

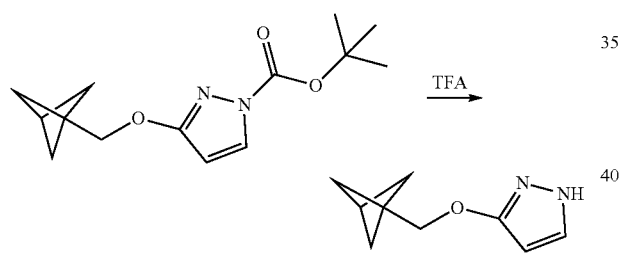

A solution of tert-butyl 3-(3-bicyclo[1.1.1]pentanyl-methoxy)pyrazole-1-carboxylate (0.40 g, 1.513 mmol) and trifluoroacetic acid (583 µL, 7.57 mmol) in dichloromethane (3 mL) was stirred for four hours. The volatiles were removed under vacuum, and the residue was basified with saturated aqueous sodium bicarbonate and extracted with ethyl acetate. The combined extracts were dried over sodium sulfate and evaporated to give 3-({bicyclo[1.1.1]pentan-1-yl}methoxy)-1H-pyrazole as a colorless oil (0.23 g, 93%) ESI-MS m/z calc. 164.09, found 165.1 (M+1)+; Retention time: 0.45 minutes.

Step 3: tert-Butyl 6-[3-(3-bicyclo[1.1.1]pentanyl-methoxy)pyrazol-1-yl]-2-chloro-pyridine-3-carboxylate

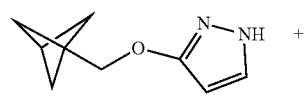 +

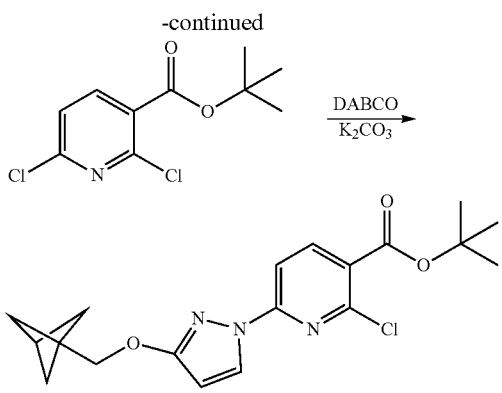

A mixture of 3-(3-bicyclo[1.1.1]pentanylmethoxy)-1H-pyrazole (0.23 g, 1.4 mmol), tert-butyl 2,6-dichloropyridine-3-carboxylate (0.35 g, 1.4 mmol), potassium carbonate (0.23 g, 1.7 mmol), and 1,4-diazabicyclo[2.2.2]octane (32 mg, 0.29 mmol) in DMSO (7 mL) was stirred at room temperature for 16 hours. The reaction was diluted with water and extracted with ethyl acetate. The combined extracts were washed with brine and water, dried over sodium sulfate, and evaporated. The residue was purified by silica gel chromatography with 0-5% methanol in dichloromethane to give tert-butyl 6-[3-(3-bicyclo[1.1.1]pentanylmethoxy)pyrazol-1-yl]-2-chloro-pyridine-3-carboxylate (0.45 g, 85%) ESI-MS m/z calc. 375.13, found 376.2 (M+1)+; Retention time: 0.93 minutes.

Step 4: 6-[3-(3-Bicyclo[1.1.1]pentanylmethoxy)pyrazol-1-yl]-2-chloro-pyridine-3-carboxylic acid

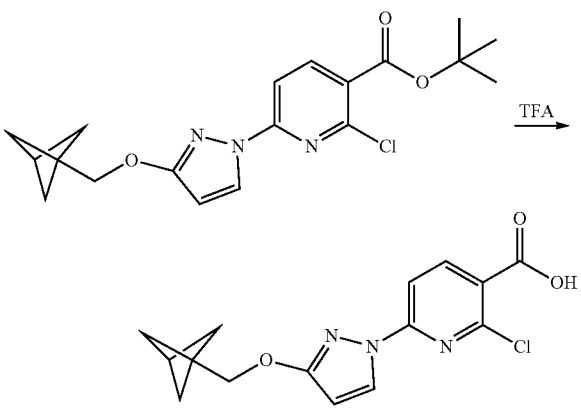

A solution of Cert-butyl 6-[3-(3-bicyclo[1.1.1]pentanyl-methoxy)pyrazol-1-yl]-2-chloro-pyridine-3-carboxylate (0.45 g, 1.2 mmol) and trifluoroacetic acid (0.95 mL, 12 mmol) in dichloromethane (6 mL) was stirred for four hours. The solvent was evaporated, and the residue was taken up in acetonitrile. The solvent was evaporated to give 6-[3-(3-bicyclo[1.1.1]pentanylmethoxy)pyrazol-1-yl]-2-chloro-pyridine-3-carboxylic acid as a colorless solid (0.38 g, 100%) ESI-MS m/z calc. 319.07, found 320.1 (M+1)+; Retention time: 0.69 minutes $^1$H NMR (400 MHz, DMSO-$d_6$) δ 8.50-8.34 (m, 2H), 7.72 (d, J=8.4 Hz, 1H), 6.21 (d, J=2.8 Hz, 1H), 4.19 (s, 2H), 2.54 (s, 1H), 1.81 (s, 6H).

Step 5: 6-[3-(3-Bicyclo[1.1.1]pentanylmethoxy)pyrazol-1-yl]-2-chloro-N-(1,5-dimethylpyrazol-4-yl)sulfonyl-pyridine-3-carboxamide

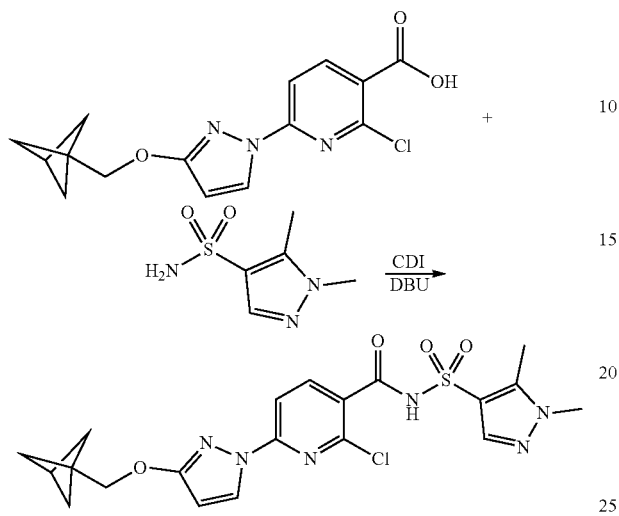

A solution of 6-[3-(3-bicyclo[1.1.1]pentanylmethoxy)pyrazol-1-yl]-2-chloro-pyridine-3-carboxylic acid (0.12 g, 0.3753 mmol) and carbonyl diimidazole (approximately 73 mg, 0.45 mmol) in THF (1.9 mL) was stirred for 30 minutes, and 1,5-dimethylpyrazole-4-sulfonamide (approximately 85 mg, 0.49 mmol) and diazabicyclo[5.4.0]undec-7-ene (approximately 68 mg, 67 μL, 0.45 mmol) were added. After 16 hours the reaction was diluted with 1 M aqueous citric acid and extracted with ethyl acetate. The combined extracts were washed with brine, dried over sodium sulfate and evaporated to give crude 6-[3-(3-bicyclo[1.1.1]pentanylmethoxy)pyrazol-1-yl]-2-chloro-N-(1,5-dimethylpyrazol-4-yl)sulfonyl-pyridine-3-carboxamide which was used in the next step as-is (0.19 g, 106%) ESI-MS m/z calc. 476.10, found 477.2 (M+1)+; Retention time: 0.68 minutes.

Step 6: 6-[3-(3-Bicyclo[1.1.1]pentanylmethoxy)pyrazol-1-yl]-N-(1,5-dimethylpyrazol-4-yl)sulfonyl-2-[(4S)-2,2,4-trimethylpyrrolidin-1-yl]pyridine-3-carboxamide

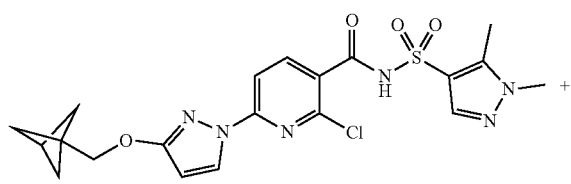

A mixture of 6-[3-(3-bicyclo[1.1.1]pentanylmethoxy)pyrazol-1-yl]-2-chloro-N-(1,5-dimethylpyrazol-4-yl)sulfonyl-pyridine-3-carboxamide (approximately 0.18 g, 0.38 mmol), (4S)-2,2,4-trimethylpyrrolidine (hydrochloride salt) (approximately 160 mg, 1.1 mmol), and potassium carbonate (approximately 320 mg, 2.3 mmol) in DMSO (1.9 mL) was stirred at 130° C. for 16 hours. The reaction was filtered and purified by reverse-phase HPLC-MS (30%-99% acetonitrile/water (5 mM HCl)) to give 6-[3-(3-bicyclo[1.1.1]pentanylmethoxy)pyrazol-1-yl]-N-(1,5-dimethylpyrazol-4-yl)sulfonyl-2-[(4S)-2,2,4-trimethylpyrrolidin-1-yl]pyridine-3-carboxamide (90 mg, 42%) ESI-MS m/z calc. 553.25, found 554.5 (M+1)+; Retention time: 2.11 minutes. $^1$H NMR (400 MHz, DMSO-d6) δ 8.19 (d, J=2.7 Hz, 1H), 7.78 (s, 1H), 7.72 (d, J=8.2 Hz, 1H), 6.89 (d, J=8.2 Hz, 1H), 6.12 (d, J=2.8 Hz, 1H), 4.15 (s, 2H), 3.78 (s, 3H), 2.62-2.52 (m, 5H), 2.40 (t, J=8.6 Hz, 1H), 2.27-2.11 (m, 1H), 1.87 (dd, J=11.9, 5.6 Hz, 1H), 1.80 (s, 6H), 1.55 (d, J=15.0 Hz, 6H), 1.43 (t, J=12.1 Hz, 1H), 0.80 (d, J=6.2 Hz, 3H)

Synthesis of N-(1,3-Dimethylpyrazol-4-yl)sulfonyl-6-[3-(2-dispiro[2.0.2.1]heptan-7-ylethoxy)pyrazol-1-yl]-2-[(4S)-2,2,4-trimethylpyrrolidin-1-yl]pyridine-3-carboxamide (Compound 56)

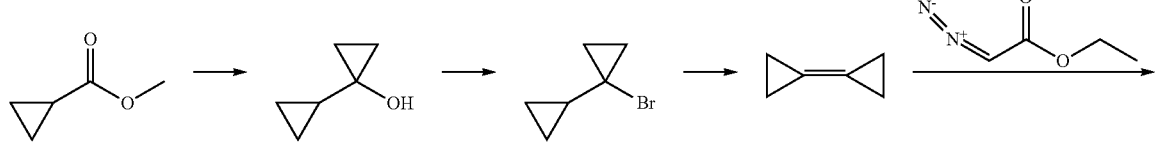

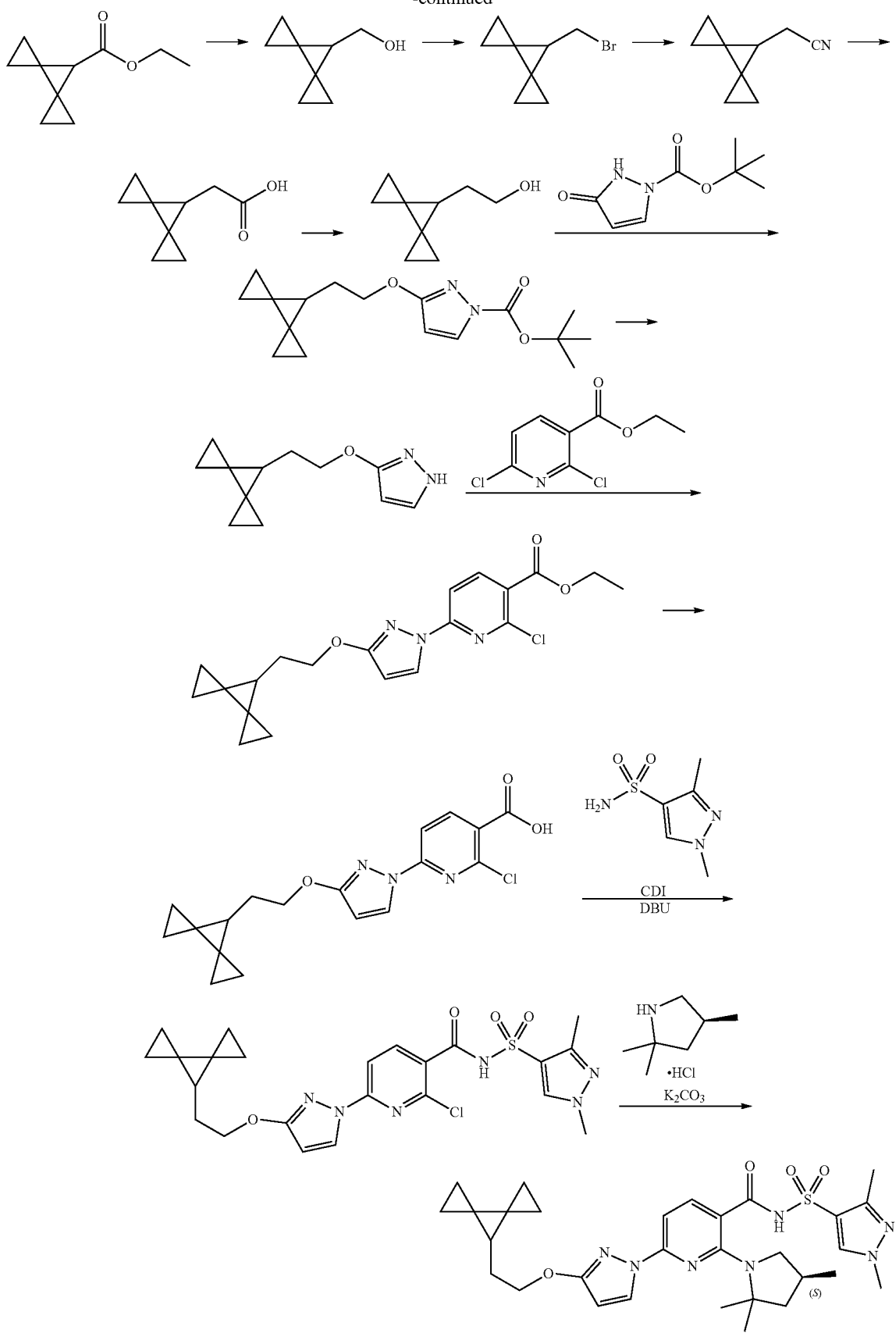

Step 1: 1-cyclopropylcyclopropanol

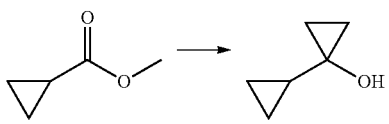

To a solution of methyl cyclopropanecarboxylate (75 g, 749.1 mmol) in ether (450 mL) was added titanium(IV) isopropoxide (55.3 mL, 187.4 mmol). To the mixture was slowly added ethyl magnesium bromide (1.6 L of 1 M, 1.60 mol) over 2 hr. The addition is exothermic and contolled with monitoring the addition rate and using a cooling bath. The reaction temperature was kept between 21-26° C. during addition. The mixture was stirred an additional 2 hr at ambient temperature. After 2 hours, the mixture was chilled to −5° C. using an acetone/dry ice bath and slowly quenched with sulfuric acid (970 g of 10% w/w, 990 mmol). The reaction mixture was cooled in a dry ice/acetone bath to keep the reaction vessel below 0° C. during the quench. As quench progresses, a grey/purple solid forms. Following complete addition of aqueous sulfuric acid, the solid never went into solution. The mixture was stirred at 0° C. for 1 hr. The precipitate was filtered through celite using a medium frit and the precipitate washed with diethyl ether (900 mL). The filtrate was transferred to a seperatory funnel and the organic phase was washed with brine (1 L), saturated sodium bicarbonate (1 L), and brine (1 L). The organic phase was dried over magnesium sulfate, filtered over celite, and the solvent was evaporated in vacuo at 100 torr and the water bath set at 20° C. The crude product was stored at −23° C. overnight and used without further purification. 1-cyclopropylcyclopropanol (61 g, 83%) was found to contain ~50% solvent (THF and iPrOH) and used as is in the next step.

$^1$H NMR (400 MHz, Chloroform-d) δ 1.32 (tt, J=8.2, 5.1 Hz, 1H), 0.71-0.61 (m, 2H), 0.51-0.43 (m, 2H), 0.43-0.33 (m, 2H), 0.23-0.14 (m, 2H).

Step 2: 1-bromo-1-cyclopropyl-cyclopropane

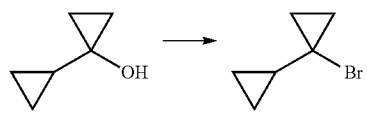

A solution of triphenylphosphine (56.1 g, 213.9 mmol) in DCM (200 mL) was cooled to −10° C. A solution of bromine (11.0 mL, 214 mmol) in DCM (40 mL) was added and the reaction was stirred at −10° C. for an additional 15 minutes. The reaction was then cooled to −30° C. and pyridine (3.3 mL, 41 mmol) was added. A solution of 1-cyclopropylcyclopropanol (20.0 g, 204 mmol), pyridine (17.3 mL, 214 mmol), and DCM (100 mL) was added dropwise while maintaining the temperature between −15° C. to −20° C. After 30 minutes, the addition was complete and the reaction was allowed to gradually warm to rt. $^1$H NMR analysis showed some product. The reaction was allowed to stir at 40° C. overnight. GCMS analysis showed 89% product. The reaction was cooled to rt and then quenched with water (100 mL). The reaction was stirred for 10 minutes and then the phases were separated. The organic phase successively washed with 1 M HCl (102 mL), sat. sodium bicarbonate (50 mL), dried over sodium sulfate, and concentrated (30° C./house vacuum ~300 torr) to remove most of the DCM. The crude reaction mixture was flash distilled (40° C./20 torr) to provide the product (approximately 50 g). The solid residue (Ph$_3$PO and product) was re-heated and distilled (50-60° C./20 torr) to afford 60.4 g. After combining all of the above and rinsing with DCM, concentration afforded 21.5 g (65% yield) of a turbid, colorless liquid. $^1$H NMR (400 MHz, Chloroform-d) δ 5.30 (s, 1H), 1.61 (tt, J=8.2, 5.0 Hz, 1H), 1.07-1.02 (m, 2H), 0.78-0.66 (m, 2H), 0.67-0.51 (m, 2H), 0.35-0.21 (m, 2H).

Step 3: cyclopropylidenecyclopropane

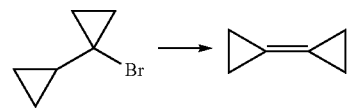 [SMILES: BrC1(C2CC2)CC1 ; C1CC1=C1CC1]

A solution of potassium tert-butoxide (16.7 g, 148.8 mmol) in DMSO (100 mL) was stirred at RT in a 3-neck 250-mL RB flask. 1-bromo-1-cyclopropyl-cyclopropane (20.0 g, 124.2 mmol) was added dropwise and the reaction immediately turned dark and then brown. The reaction was mildly exothermic (maintained temperature between 18° C. to 22° C. using an ice-water bath). After 10 minutes, the addition was completed. The ice-water bath was removed and the reaction was allowed to stir at RT. After 90 minutes, $^1$H NMR analysis showed that the reaction was nearly complete. The reaction mixture was vacuum distilled using a bulb-to-bulb distillation. The distillation took place from 60° C. to 80° C. between 40 and 100 torr. The distillate slowly collected in the receiver to afford 18.2 g (~95% for olefin/t-BuOH combined) of a colorless liquid which was analyzed by $^1$H NMR to contain (7.28 grams of olefin) along with t-BuOH.

The distillate was further washed with water (5×10 mL). DCM (10 mL) was added and the reaction phases were separated with each washing. The organic layers were dried over magnesium sulfate, filtered, and evaporated to afford 17.30 g (containing 7.30 g product; 73%) as a colorless liquid (solution). $^1$H NMR (400 MHz, Chloroform-d) δ 1.19 (s, 8H). The $^1$H NMR confirms the presence of DCM and a small amount of tert-butanol.

Step 4: ethyl dispiro[2.0.2.1]heptane-7-carboxylate

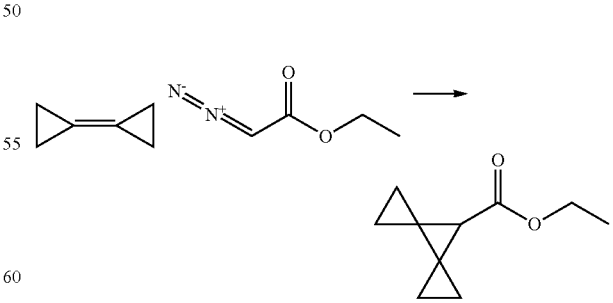

To a solution of cyclopropylidenecyclopropane (49.5 g, 617.8 mmol) in DCM (110 mL) at 0° C. under a nitrogen atmosphere was added rhodium(II) acetate (4.2 g, 9.503 mmol). To the mixture at 0° C. was added ethyl 2-diazoacetate (106.8 mL, 1.016 mol) using a syringe pump set at an addition rate of 0.02 mL/min (1.2 mL/hr). The addition was continuous for 89 hr. The crude reaction mixture was filtered through a plug of silica, washing 3X with 150 mL of DCM. The volatile materials were removed in vacuo affording a dark yellow oil, containing 20% DCM, diethyl (E)-but-2-enedioate and diethyl (Z)-but-2-enedioate as by-products. Ethyl dispiro[2.0.2.1]heptane-7-carboxylate (100 g, 97%), ¹H NMR (400 MHz, chloroform-d) δ 4.13 (q, J=7.1 Hz, 2H), 2.23 (s, 1H), 1.24 (t, J=7.1 Hz, 3H), 1.08-0.93 (m, 4H), 0.90-0.82 (m, 2H), 0.77 (ddd, J=8.2, 5.0, 3.5 Hz, 2H).

Step 5: dispiro[2.0.2.1]heptan-7-yl}methanol

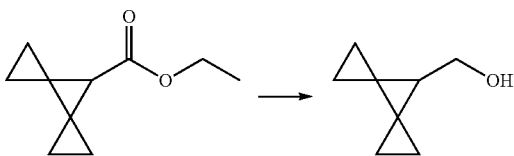

To a slurry of LiAlH₄ (7.8 g, 200.2 mmol) in diethyl ether (300 mL) chilled with an ice-bath was slowly added ethyl dispiro[2.0.2.1]heptane-7-carboxylate (10.77 g, 64.79 mmol). The mixture was allowed to warm to a gentle reflux during the addition and continued to stir at ambient temperature for 1 hr. By ¹H NMR, the reaction was complete. The reaction was chilled with an ice-bath and slowly quenched with the addition of water (8.0 mL, 440 mmol), followed by sodium hydroxide (8.0 mL of 2 M, 16 mmol) and then water (24.0 mL, 1.33 mol). The light yellow slurry was filtered over celite and washed 3× with 150 mL of MTBE. The filtrate was concentrated in vacuo affording 8.87 g of a clear oil. {dispiro[2.0.2.1]heptan-7-yl}methanol (8.87 g, 110%).

¹H NMR (400 MHz, Chloroform-d) δ 3.71 (dd, J=6.7, 5.5 Hz, 2H), 1.76-1.65 (m, 1H), 1.46 (t, J=5.6 Hz, 1H), 0.87 (q, J=1.9 Hz, 4H), 0.72-0.61 (m, 2H), 0.60-0.50 (m, 2H).

Step 6: 7-(bromomethyl)dispiro[2.0.2.1]heptane

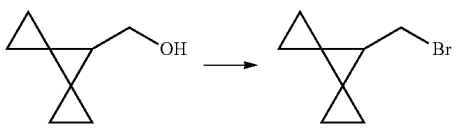

A 1000 mL 3 neck RB flask was fitted with a mechanical stirrer, a cooling bath, an addition funnel, a J-Kem temperature probe and a nitrogen inlet/outlet. The vessel was charged under a nitrogen atmosphere with triphenylphosphine (102.7 mL, 443.2 mmol) and dichloromethane (1 L) which provided a clear colorless solution. Stirring was commenced and the cooling bath was charged with acetone. Dry ice was added in portions until a pot temperature of −15° C. was obtained. The addition funnel was charged with a solution of bromine (22.82 mL, 443.0 mmol) in dichloromethane (220 mL, 10 mL/g) which was subsequently added dropwise over 1 hour. Dry ice was added in portions during the addition to maintain the pot temperature at −15° C. After the addition was completed, the pale yellow suspension was continued to stir at −15° C. for 15 minutes at which point the suspension was cooled to −30° C. The addition funnel was charged with a solution of dispiro[2.0.2.1]heptan-7-ylmethanol (50 g, 402.6 mmol), pyridine (35.82 mL, 442.9 mmol) and dichloromethane (250 mL, 5 mL/g). The clear pale yellow solution was then added dropwise over 1.5 hours maintaining the pot temperature at −30° C. The resulting clear light yellow reaction mixture was allowed to gradually warm to a pot temperature of −5° C. and then continue to stir at −5° C. for 1 hour. An aliquot was removed, diluted with hexane which resulted in the formation of a precipitate. The suspension was filtered through a plug of celite. The clear filtrate was concentrated under reduced pressure (water bath temperature at 20° C.) to provide a clear yellow oil. Analysis by ¹H NMR indicated no remaining starting material. Reaction completion was determined by disappearance of starting material doublet at 3.71 ppm and appearance of product doublet at 3.49 ppm. The reaction mixture was poured into hexane (2000 mL) which resulted in the formation of a precipitate. The suspension was stirred at room temperature for 30 minutes and then filtered through a glass frit Buchner funnel with a 20 mm layer of Celite. The clear filtrate was concentrated under reduced pressure (water bath temperature at 20° C.) to provide a yellow oil with some precipitates present. The oil was diluted with hexane, allowed to stand at room temperature for 15 minutes and then filtered through a glass fit Buchner funnel with a 20 mm layer of celite. The clear filtrate was concentrated under reduced pressure (water bath temperature at 20° C.) to provide 7-(bromomethyl)dispiro[2.0.24.13]heptane (70 g, 93%) ¹H NMR (400 MHz, Chloroform-d) δ 3.49 (d, J=7.5 Hz, 2H), 1.90 (t, J=7.5 Hz, 1H), 1.06-0.84 (m, 4H), 0.71 (ddd, J=9.1, 5.1, 4.0 Hz, 2H), 0.54 (dddd, J=8.6, 4.8, 3.8, 1.0 Hz, 2H). as a clear yellow oil (70 g, 0.374 mol, 93% yield).

Step 7: 2-dispiro[2.0.2.1]heptan-7-ylacetonitrile

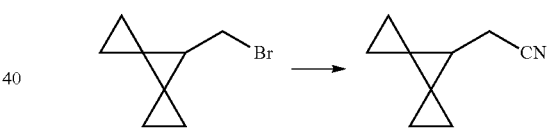

A 1000 mL 3 neck RB flask was fitted with a mechanical stirrer, a cooling bath used as secondary containment, a J-Kem temperature probe and a nitrogen inlet/outlet. The vessel was charged under a nitrogen atmosphere with 7-(bromomethyl)dispiro[2.0.2.1]heptane (35 g, 187.1 mmol) and dimethyl sulfoxide (245 mL) which provided a clear amber solution. Stirring was commenced and the pot temperature was recorded at 19° C. The vessel was then charged with sodium cyanide (11.46 g, 233.8 mmol) added as a solid in one portion which resulted in a dark solution and a gradual exotherm to 49° C. over 15 minutes. After a few minutes the pot temperature began to decrease and the mixture was continued to stir at room temperature overnight (about 15 hours). The dark reaction mixture was quenched with ice cold saturated sodium carbonate solution (500 mL) and then transferred to a separatory funnel and partitioned with diethyl ether (500 mL). The organic was removed and the residual aqueous was extracted with diethyl ether (2×250 mL). The combined organic was washed with water (500 mL), dried over sodium sulfate (200 g) and then filtered through a glass frit Buchner funnel. The clear amber filtrate was concentrated under reduced pressure (water bath temperature 20° C.) to provide 2-dispiro[2.0.2.1]heptan-7-ylacetonitrile (21 g, 84%) ¹H NMR (400 MHz, Chloroform-d) δ

2.42 (d, J=6.6 Hz, 2H), 1.69 (t, J=6.6 Hz, 1H), 1.02-0.88 (m, 4H), 0.79-0.70 (m, 2H), 0.66-0.55 (m, 2H) as a clear dark amber oil (21 g, 0.158 mol, 84% yield).

Step 8: 2-dispiro[2.0.2.1]heptan-7-ylacetic acid

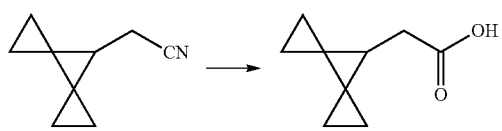 [SMILES: N#CCC1C2(CC2)C12CC2 ; O=C(O)CC1C2(CC2)C12CC2]

A 5000 mL 3 neck RB flask was fitted with a mechanical stirrer, a heating mantle, a J-Kem temperature probe/controller, a water cooled reflux condenser and a nitrogen inlet/outlet. The vessel was subsequently charged under a nitrogen atmosphere with 2-dispiro[2.0.2.1]heptan-7-ylacetonitrile (105 g, 788.3 mmol) and ethyl alcohol (1.05 L) which provided a clear amber solution. Stirring was commenced and the pot temperature was recorded at 19° C. The vessel was then charged with sodium hydroxide (525.5 mL of 6 M, 3.153 mol) added in one portion. The resulting clear amber solution was heated to a pot temperature of 70° C. and the condition was maintained for 24 hours. After cooling to room temperature, the reaction mixture was concentrated to remove the ethyl alcohol. The residual aqueous was diluted with water (500 ml) and then transferred to a separatory funnel and partitioned with diethyl ether (250 mL). The organic was removed and the residual aqueous was extracted with diethyl ether (250 mL). The aqueous was removed and the pH was adjusted to pH~1 with 6 Molar HCl solution. The resulting aqueous solution was transferred to a separatory funnel and partitioned with diethyl ether (500 ml). The organic was removed and the residual aqueous was extracted with diethyl ether (2×250 mL). The combined organic was dried over sodium sulfate (250 g) and then filtered through a glass frit Buchner funnel. The clear filtrate was concentrated under reduced pressure to provide the desired product 2-dispiro[2.0.2.1]heptan-7-ylacetic acid (103 g, 86%) $^1$H NMR (400 MHz, Chloroform-d) δ 2.44 (d, J=6.9 Hz, 2H), 1.67 (d, J=13.8 Hz, 1H), 0.91 (ddd, J=9.0, 5.2, 3.9 Hz, 2H), 0.81 (ddd, J=8.9, 5.2, 3.9 Hz, 2H), 0.68 (ddd, J=8.9, 5.2, 3.9 Hz, 2H), 0.50 (dddd, J=8.9, 5.0, 3.9, 0.9 Hz, 2H). (103 g, 0.676 mol, 86% yield) of a clear amber oil which solidified upon standing.

Step 9: 2-dispiro[2.0.2.1]heptan-7-ylethanol

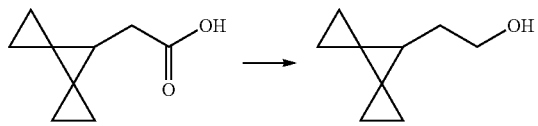 [SMILES: O=C(O)CC1C2(CC2)C12CC2 ; OCCC1C2(CC2)C12CC2]

A 1000 mL 3 neck RB flask was fitted with a mechanical stirrer, a cooling bath, an addition funnel, a J-Kem temperature probe, and a nitrogen inlet/outlet. The vessel was charged under a nitrogen atmosphere with lithium aluminum hydride (6.483 g, 170.8 mmol). The vessel was then charged under a nitrogen atmosphere with tetrahydrofuran (200 mL). Stirring was commenced and the pot temperature recorded at 20° C. The mixture was allowed to stir at room temperature for 0.5 hour to allow the pellets to dissolve. The pot temperature of the resulting grey suspension was recorded at 24° C. The cooling bath was then charged with crushed ice/water and the pot temperature was lowered to 0° C. The addition funnel was charged with a solution of 2-dispiro[2.0.2.1]heptan-7-ylacetic acid (20 g, 131.4 mmol) in tetrahydrofuran (60 mL, 3 mL/g) and the clear pale amber solution was added dropwise over 1 hour. After the completed addition, the pot temperature of the resulting greyish-brown suspension was recorded at 5° C. The mixture was allowed to slowly warm to room temperature and continue to stir at RT for 24 hours. The suspension was cooled to 0° C. with a crushed ice/water cooling bath and then quenched by the very slow dropwise addition of water (6.483 mL), followed by 15 wt % sodium hydroxide solution (6.483 mL) and then finally with water (19.45 mL). The pot temperature of the resulting white suspension was recorded at 5° C. The suspension was continued to stir at ~5° C. for 30 minutes and then filtered through a glass frit Buchner funnel with a 20 mm layer of celite. The filter cake was displacement washed with tetrahydrofuran (2×150 ml) and then dried under reduced pressure for 15 minutes. The filtrate was dried over sodium sulfate (250 g) and then filtered through a glass frit Buchner funnel. The filtrate was concentrated under reduced pressure to provide 2-dispiro[2.0.2.1]heptan-7-ylethanol (16.7 g, 92%) 1H NMR (400 MHz, Chloroform-d) δ 3.63 (t, J=6.8 Hz, 2H), 1.68 (q, J=6.7 Hz, 2H), 1.39 (t, J=6.6 Hz, 1H), 0.90-0.73 (m, 4H), 0.65 (ddd, J=8.0, 4.8, 3.5 Hz, 2H), 0.57-0.43 (m, 2H) as a clear pale amber oil. The proton NMR indicates 5 wt % of residual tetrahydrofuran (0.95) 17.6 g=16.7 g (92% yield)

Step 10: tert-butyl 3-(2-dispiro[2.0.2.1]heptan-7-ylethoxy)pyrazole-1-carboxylate

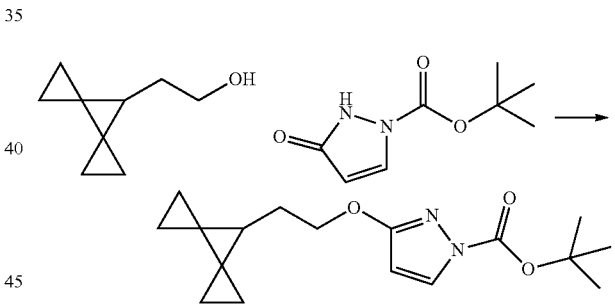

A 5000 mL 3 neck RB flask was fitted with a mechanical stirrer, a heating mantle, a J-Kem temperature probe/controller, an addition funnel, a water cooled reflux condenser and a nitrogen inlet/outlet. The vessel was charged under a nitrogen atmosphere with tert-butyl 5-oxo-1H-pyrazole-2-carboxylate (100 g, 542.9 mmol) and tetrahydrofuran (1,200 mL) which provided a clear pale yellow solution. Stirring was commenced and the pot temperature was recorded at 19° C. The vessel was then charged with 2-dispiro[2.0.2.1]heptan-7-ylethanol (82.54 g, 597.2 mmol) added neat in one portion followed by triphenylphosphine (156.6 g, 597.1 mmol) added as a solid in one portion. The resulting clear pale yellow solution was then treated with diisopropyl azodicarboxylate (120.8 g, 597.4 mmol) (clear reddish-orange liquid) added neat dropwise over 60 minutes which resulted in a gradual exotherm to 40° C. and a clear light amber solution. The reaction mixture was then heated to a pot temperature of 50° C. and the condition was maintained for 2 hours when analysis by LC/MS indicated complete consumption of the starting material. The clear amber reaction mixture was concentrated under reduced pressure and the resulting clear dark amber oil was suspended in toluene (800 mL) and stirred at room temperature for 1 hour during which time a solid (triphenylphosphine oxide) precipitated. The thick slurry was filtered through a glass frit Buchner funnel and the filter cake was displacement washed with toluene (2×500 mL) with vacuum pulled for an additional 30 minutes. The off-white solid filter cake was consistent by LC/MS for triphenylphosphine oxide. The clear amber filtrate was concentrated under reduced pressure to provide a clear pale amber oil (175 g). The material was purified by silica gel plug flash chromatography eluting with a gradient of 100% hexane to 20% ethyl acetate in hexane collecting 50 ml fractions. The product elutes around 5% ethyl acetate in hexane. The desired fractions were combined and concentrated under reduced pressure to provide tert-butyl 3-(2-dispiro[2.0.2.1]heptan-7-ylethoxy)pyrazole-1-carboxylate (124 g, 75%) $^1$H NMR (400 MHz, DMSO-$d_6$) δ 8.06 (d, J=2.9 Hz, 1H), 6.05 (d, J=2.9 Hz, 1H), 4.16 (t, J=6.7 Hz, 2H), 1.77 (q, J=6.7 Hz, 2H), 1.55 (s, 9H), 1.43 (t, J=6.5 Hz, 1H), 0.88-0.77 (m, 4H), 0.67-0.60 (m, 2H), 0.52-0.45 (m, 2H). ESI-MS m/z calc. 304.17868, found 305.0 (M+1)+; Retention time: 2.18 minutes as a clear pale yellow oil (124 g, 0.407 mol, 75% yield) which solidified upon standing.

Step 11: 3-(2-dispiro[2.0.2.1]heptan-7-ylethoxy)-1H-pyrazole

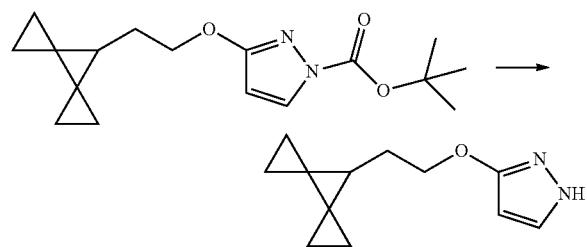

A 5000 mL 3 neck RB flask was fitted with a mechanical stirrer, a heating mantle, a J-Kem temperature probe/controller, a water cooled reflux condenser, an addition funnel, and a nitrogen inlet/outlet. The vessel was charged under a nitrogen atmosphere with tert-butyl 3-(2-dispiro[2.0.2.1]heptan-7-ylethoxy)pyrazole-1-carboxylate (123 g, 404.1 mmol), dichloromethane (492 mL) and methyl alcohol (492 mL) which provided a clear pale yellow solution. Stirring was commenced and the pot temperature was recorded at 19° C. The addition funnel was charged with hydrogen chloride in 1,4-dioxane (303 mL of 4 M, 1.212 mol), which was subsequently added dropwise over 2 hours which resulted in a gradual exotherm to 30° C. The resulting clear pale yellow solution was heated to a pot temperature of 45° C. and the condition was maintained for 1 hour when analysis by LC/MS indicated reaction completion. The reaction mixture was allowed to cool to room temperature and then concentrated under reduced pressure. The remaining white solid residue was dissolved in methyl tert-butyl ether (984 mL) and then transferred to a separatory funnel and partitioned with ice cold sodium hydroxide (606 mL of 2 M, 1.212 mol). The organic was removed and the residual aqueous was extracted with tert-butyl methyl ether (2×250 mL). The combined organic was washed with saturated sodium chloride solution (2×100 mL), dried over sodium sulfate (150 g) and then filtered through a glass frit Buchner funnel. The clear pale yellow filtrate was concentrated under reduced pressure to provide 3-(2-dispiro[2.0.2.1]heptan-7-ylethoxy)-$^1$H-pyrazole (77 g, 93%) ESI-MS m/z calc. 204.12627, found 205.1 (M+1)+; Retention time: 1.53 minutes as a clear light yellow oil (77 g, 0.377 mol, 93% yield).

Step 12: ethyl 2-chloro-6-[3-(2-dispiro[2.0.2.1]heptan-7-ylethoxy)pyrazol-1-yl]pyridine-3-carboxylate

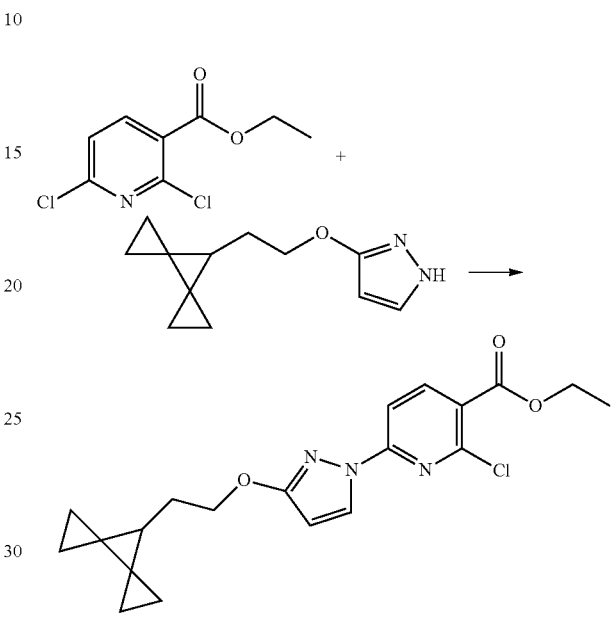

A 5000 mL 3 neck RB flask was fitted with a mechanical stirrer, a cooling bath used as secondary containment, a J-Kem temperature probe, a water cooled reflux condenser, an addition funnel, and a nitrogen inlet/outlet. The vessel was charged under a nitrogen atmosphere with 3-(2-dispiro [2.0.2.1]heptan-7-ylethoxy)-1H-pyrazole (64.98 g, 318.1 mmol) and N,N-dimethyl formamide (840 mL) which provided a clear pale yellow solution. Stirring was commenced and the pot temperature was recorded at 17° C. The vessel was then charged with ethyl 2,6-dichloropyridine-3-carboxylate (70 g, 318.1 mmol) added as a solid in one portion. The resulting clear pale yellow solution was then treated with potassium carbonate (57.15 g, 413.5 mmol) added as a solid in one portion followed by 1,4-diazabicyclo[2.2.2] octane (5.353 g, 47.72 mmol) added as a solid in one portion. The resulting pale yellow suspension was allowed to stir at RT for 24 hours. After 24 hours, a 5000 mL 3 neck RB flask was fitted with a mechanical stirrer, a cooling bath used as secondary containment, a J-Kem temperature probe and an addition funnel. The vessel was charged with ice cold water (2.800 L) and stirring was commenced. The pot temperature was recorded at 5° C. The addition funnel was charged with the reaction mixture, which was subsequently added over 1 hour resulting in the formation of a precipitate and an exotherm to 15° C. The resulting suspension was continued to stir at 15° C. for 30 minutes and then filtered through a glass frit Buchner funnel. The filter cake was displacement washed with water (3×500 mL) and then dried under reduced pressure in the Buchner funnel for 2 hours. The material was then dried under vacuum overnight to provide (137 g) of an off-white solid as the crude product. The material was purified by silica gel (15:1) plug flash chromatography in a glass frit Buchner funnel eluting with a gradient of 100% hexane to 10% ethyl acetate in hexane collecting 1000 mL fractions. The desired fractions were combined and concentrated under reduced pressure to provide ethyl 2-chloro-6-[3-(2-dispiro[2.0.2.1]heptan-7-ylethoxy)pyrazol-1-yl]pyridine-3-carboxylate (121 g, 98%) ESI-MS m/z calc. 387.13498, found 388.1 (M+1)+; Retention time: 3.57 minutes as a white solid.

Step 13: 2-chloro-6-[3-(2-dispiro[2.0.2.1]heptan-7-ylethoxy)pyrazol-1-yl]pyridine-3-carboxylic acid

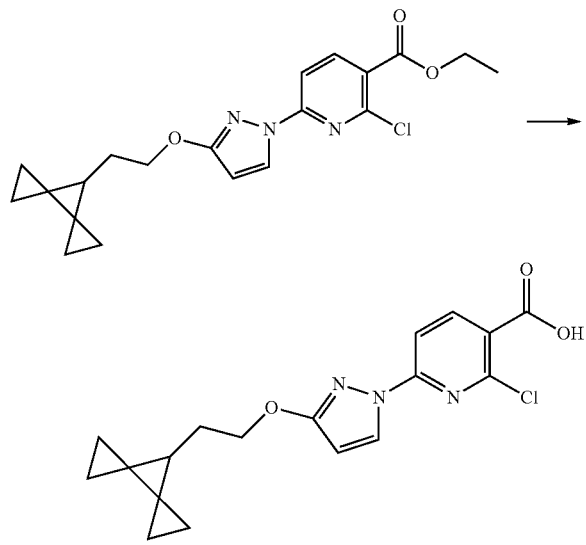

A 5000 mL 3 neck RB flask was fitted with a mechanical stirrer, a heating mantle, a J-Kem temperature probe/controller, an addition funnel, a water cooled reflux condenser, and a nitrogen inlet/outlet. The vessel was charged under a nitrogen atmosphere with ethyl 2-chloro-6-[3-(2-dispiro[2.0.2.1]heptan-7-ylethoxy)pyrazol-1-yl]pyridine-3-carboxylate (155 g, 399.6 mmol), tetrahydrofuran (1,240 mL) and methyl alcohol (1,240 mL) which provided a clear pale amber solution. Stirring was commenced and the pot temperature was recorded at 19° C. The addition funnel was charged with sodium hydroxide (399.6 mL of 2 M, 799.2 mmol) which was subsequently added over 15 minutes which resulted in a gradual exotherm to 27° C. The clear light amber reaction mixture was heated to a pot temperature of 40° C. for 30 minutes. Analysis by LC/MS indicated complete consumption of the starting material. The reaction mixture was concentrated under reduced pressure to remove most of the organic solvent. The remaining aqueous suspension was further diluted with water (1000 mL). The pH was then adjusted to pH-1 with ice cold 2 M HCl solution. The resulting very thick slurry was vacuum filtered through a glass fit Buchner funnel. The filter cake was displacement washed with water (2×250 mL) and then dried under reduced pressure for 45 minutes. The material was dissolved in dichloromethane (1000 mL) and transferred to a separatory funnel and partitioned with saturated sodium chloride solution (250 mL). The organic was removed and dried over sodium sulfate (250 g) and then filtered through a glass frit Buchner funnel. The clear filtrate was concentrated under reduced pressure to provide 2-chloro-6-[3-(2-dispiro[2.0.2.1]heptan-7-ylethoxy)pyrazol-1-yl]pyridine-3-carboxylic acid (143 g, 97%) ESI-MS m/z calc. 359.10367, found 360.1 (M+1)+; Retention time: 2.97 minutes of a white solid. HPLC analysis indicated 97.12 area %.

Actual yield: 0.9712 (143)=138.9 g (96% yield)

Recrystallization of 2-chloro-6-[3-(2-dispiro[2.0.2.1]heptan-7-ylethoxy)pyrazol-1-yl]pyridine-3-carboxylic acid 2-chloro-6-[3-(2-dispiro[2.0.2.1]heptan-7-ylethoxy)pyrazol-1-yl]pyridine-3-carboxylic acid (143 g, 397.4 mmol) was dissolved in dichloromethane (1000 mL) which provided a clear pale yellow solution. The solution was vacuum filtered through a Buchner funnel with Whatman paper to remove any solid impurities. The clear dichloromethane solution was concentrated under reduced pressure to provide a white solid. The solid was then concentrated under reduced pressure from toluene (1000 mL). The resulting solid was again concentrated under reduced pressure from toluene (1000 mL) which provided a white solid. A 5000 mL 3 neck RB flask was fitted with a mechanical stirrer, a heating mantle, a J-Kem temperature probe/controller, an addition funnel, a water cooled reflux condenser and a nitrogen inlet/outlet. The vessel was charged under a nitrogen atmosphere with 2-chloro-6-[3-(2-dispiro[2.0.2.1]heptan-7-ylethoxy)pyrazol-1-yl]pyridine-3-carboxylic acid (143 g, 0.3974 mol) and toluene (1430 mL) (10 mL/g) which provided a white suspension. Stirring was commenced (slow rotation) and the pot temperature was heated to (110° C.) reflux which provided a slightly cloudy pale yellow solution. The solution was maintained at reflux for 15 minutes and then allowed to cool very slowly to room temperature. The cooling process from 110° C. to room temperature was done over a 6 hour time period. A solid began to form when the pot temperature was recorded at 90° C. The material was collected by vacuum filtration in a Buchner funnel with Whatman paper. The filter cake was displacement washed with toluene (125 mL) and then pulled in the Buchner funnel for 1 hour to provide 2-chloro-6-[3-(2-dispiro[2.0.2.1]heptan-7-ylethoxy)pyrazol-1-yl]pyridine-3-carboxylic acid (113 g, 79%) 1H NMR (400 MHz, DMSO-d6) δ 13.59 (s, 1H), 8.56-8.33 (m, 2H), 7.71 (d, J=8.4 Hz, 1H), 6.17 (d, J=2.9 Hz, 1H), 4.24 (t, J=6.7 Hz, 2H), 1.82 (q, J=6.7 Hz, 2H), 1.47 (t, J=6.5 Hz, 1H), 0.95-0.75 (m, 4H), 0.72-0.58 (m, 2H), 0.60-0.44 (m, 2H). ESI-MS m/z calc. 359.10367, found 360.1 (M+1)+; Retention time: 2.98 minutes (113 g, 0.314 mol, 79% recovery) of a white solid. HPLC analysis indicated 99.45 area %.

Step 14: 2-Chloro-N-(1,3-dimethylpyrazol-4-yl)sulfonyl-6-[3-(2-dispiro[2.0.2.1]heptan-7-ylethoxy)pyrazol-1-yl]pyridine-3-carboxamide

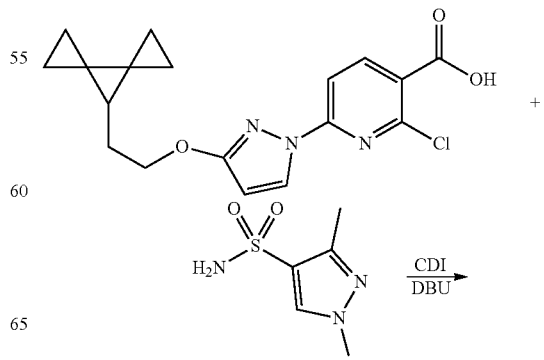

307

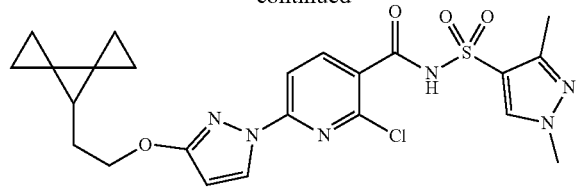

2-Chloro-6-[3-(2-dispiro[2.0.2.1]heptan-7-ylethoxy)pyrazol-1-yl]pyridine-3-carboxylic acid (20 mg, 0.05559 mmol) and carbonyl diimidazole (13.52 mg, 0.08338 mmol) were combined in THF (260 µL) and stirred at room temperature for one hour. 1,3-Dimethylpyrazole-4-sulfonamide (97.4 mg, 0.5559 mmol) was added followed by DBU (42.34 mg, 0.2781 mmol), and the reaction was stirred for an additional three hours. The reaction mixture was diluted with 1 M citric acid and extracted twice with ethyl acetate. The combined organics were washed with water and brine, dried over sodium sulfate, and concentrated to give 2-chloro-N-(1,3-dimethylpyrazol-4-yl)sulfonyl-6-[3-(2-dispiro[2.0.2.1]heptan-7-ylethoxy)pyrazol-1-yl]pyridine-3-carboxamide (28.74 mg, 100%) ESI-MS m/z calc. 516.13464, found 517.0 (M+1)+; Retention time: 0.77 minutes as a white solid, which was used in the next step without further purification.

Step 15: N-(1,3-Dimethylpyrazol-4-yl)sulfonyl-6-[3-(2-dispiro[2.0.2.1]heptan-7-ylethoxy)pyrazol-1-yl]-2-[(4S)-2,2,4-trimethylpyrrolidin-1-yl]pyridine-3-carboxamide

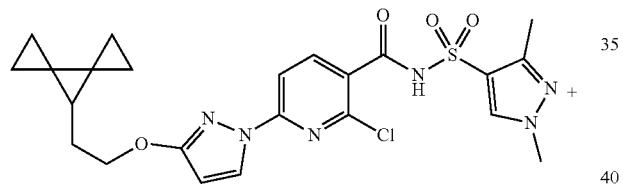

308

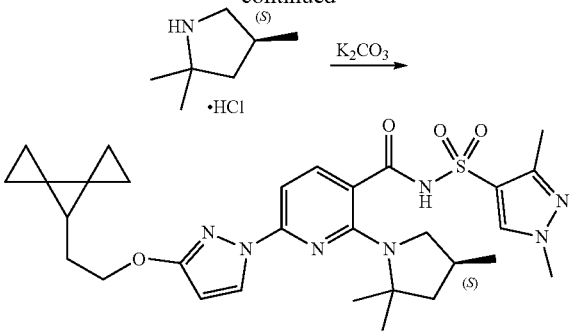

2-Chloro-N-(1,3-dimethylpyrazol-4-yl)sulfonyl-6-[3-(2-dispiro[2.0.2.1]heptan-7-ylethoxy)pyrazol-1-yl]pyridine-3-carboxamide (28.74 mg, 0.05559 mmol), (4S)-2,2,4-trimethylpyrrolidine (hydrochloride salt) (81.79 mg, 0.5465 mmol), three angstrom molecular sieves (1 bead), and potassium carbonate (150.1 mg, 1.086 mmol) were combined in DMSO (492.6 µL) and heated at 165° C. for 16 hours. The crude reaction mixture was cooled to room temperature, filtered and then was purified directly by reverse-phase preparative chromatography utilizing a C18 column and method HPLC 50-99 (acetonitrile—(water+5 mmol HCl)) over 15 minutes to afford white solid of N-(1,3-dimethylpyrazol-4-yl)sulfonyl-6-[3-(2-dispiro[2.0.2.1]heptan-7-ylethoxy)pyrazol-1-yl]-2-[(4S)-2,2,4-trimethylpyrrolidin-1-yl]pyridine-3-carboxamide (13 mg, 39%) ESI-MS m/z calc. 593.27844, found 594.2 (M+1)+; Retention time: 2.38 minutes.

Synthesis of 6-[3-[(2,2-Difluoro-1-methyl-cyclopropyl)methoxy]pyrazol-1-yl]-N-(1,5-dimethylpyrazol-4-yl)sulfonyl-2-[(4S)-2,2,4-trimethylpyrrolidin-1-yl]pyridine-3-carboxamide (Compound 24)

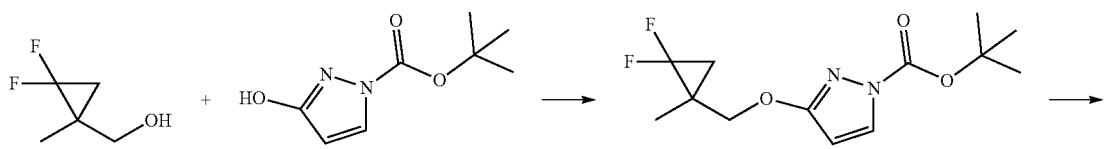

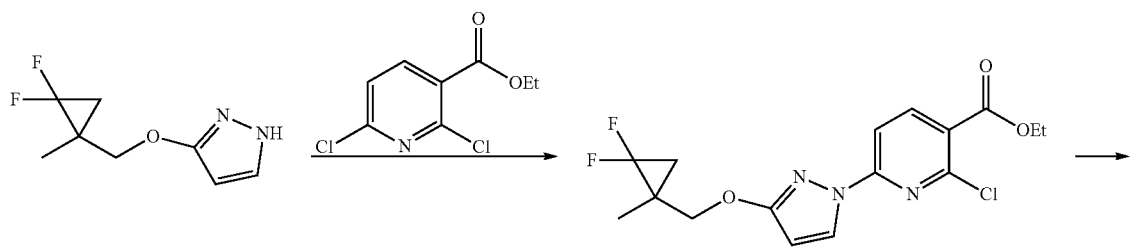

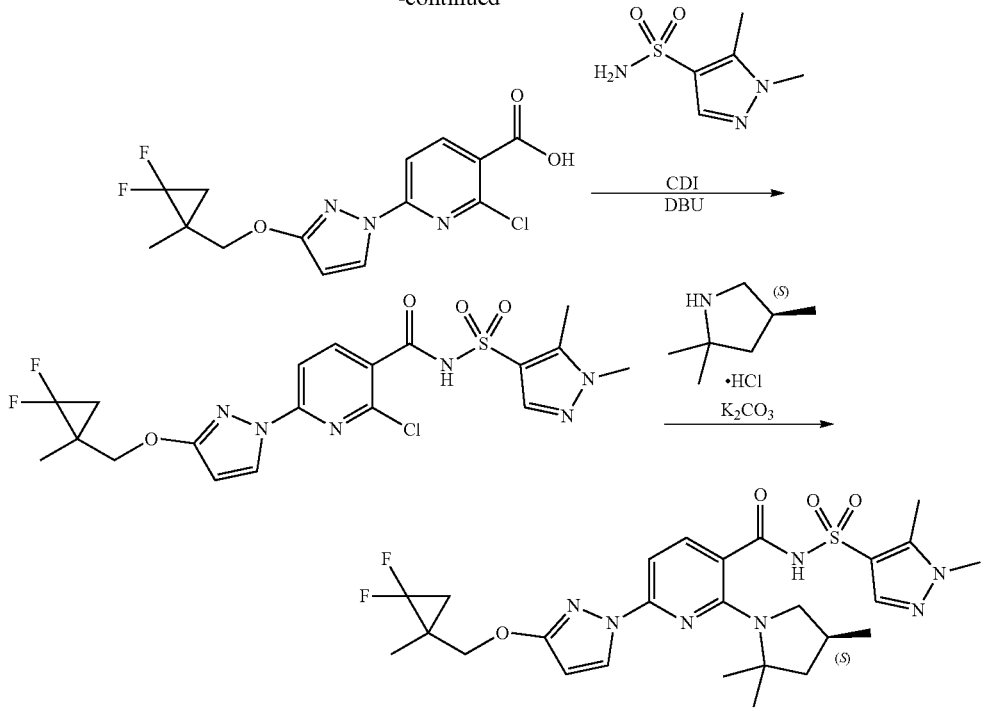

Step 1: tert-Butyl 3-[(2,2-difluoro-1-methyl-cyclopropyl)methoxy]pyrazole-1-carboxylate

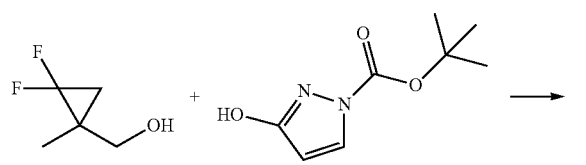

tert-Butyl 3-hydroxypyrazole-1-carboxylate (1.00 g, 5.429 mmol), (2,2-difluoro-1-methyl-cyclopropyl)methanol (approximately 729.3 mg, 5.972 mmol), and triphenylphosphine (approximately 1.994 g, 1.761 mL, 7.601 mmol) were combined and dissolved in THF (10 mL). The resulting solution was cooled to 0° C., and DIAD (approximately 1.537 g, 1.472 mL, 7.601 mmol) was added dropwise. The reaction mixture was allowed to slowly warm to room temperature and was stirred overnight. Volatiles were evaporated under reduced pressure. The remaining residue was dissolved in ethyl acetate (50 mL) and washed with saturated aqueous sodium bicarbonate (2×50 mL) and brine (2×50 mL). The organic layer was dried over sodium sulfate, filtered, and concentrated under reduced pressure. The crude product was purified by silica gel column chromatography eluting with a 0-25% EtOAc/hexane gradient on a 80 gram silica gel column. tert-Butyl 3-[(2,2-difluoro-1-methyl-cyclopropyl)methoxy]pyrazole-1-carboxylate (1.27 g, 75%) was obtained as a clear colorless oil. ESI-MS m/z calc. 288.12854, found 289.2 (M+1)+; Retention time: 1.75 minutes.

$^1$H NMR (400 MHz, DMSO-d6) δ 8.10 (d, J=2.9 Hz, 1H), 6.15 (d, J=2.9 Hz, 1H), 4.32 (dt, J=10.8, 2.4 Hz, 1H), 4.08 (d, J=10.9 Hz, 1H), 1.66 (dt, J=11.4, 7.8 Hz, 1H), 1.55 (s, 9H), 1.39 (dt, J=10.2, 7.5 Hz, 1H), 1.30 (d, J=2.3 Hz, 3H).

Step 2: 3-[(2,2-Difluoro-1-methyl-cyclopropyl)methoxy]-1H-pyrazole

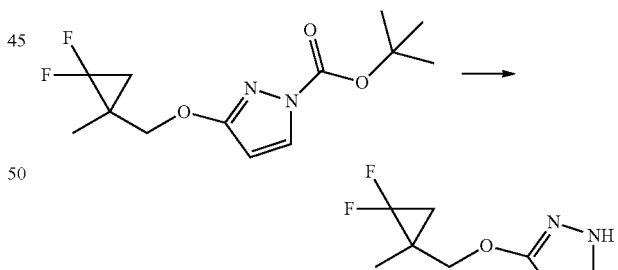

tert-Butyl 3-[(2,2-difluoro-1-methyl-cyclopropyl)methoxy]pyrazole-1-carboxylate (1.27 g, 4.405 mmol) was dissolved in 1,2-dimethoxyethane (15.88 mL). A solution of sodium carbonate (approximately 750.7 mg, 7.083 mmol) in water (4.762 mL) was added. The reaction vial was sealed and heated overnight at 90° C. and then 100° C. for one day. The reaction mixture was cooled to room temperature and diluted with water (50 mL) and ethyl acetate (50 mL). The organic layer was isolated, and the aqueous layer was extracted with ethyl acetate (2×50 mL). The combined organics were washed with brine, dried over sodium sulfate, and concentrated. The product was purified by silica gel column chromatography eluting with a 0-100% EtOAc/hexane gradient on an 80 gram silica gel column. 3-[(2,2-Difluoro-1-methyl-cyclopropyl)methoxy]-1H-pyrazole (490 mg, 59%) was obtained as a clear slightly yellow oil. ESI-MS m/z calc. 188.07613, found 189.0 (M+1)+; Retention time: 1.01 minutes.

Step 3: Ethyl 2-chloro-6-[3-[(2,2-difluoro-1-methyl-cyclopropyl)methoxy]pyrazol-1-yl]pyridine-3-carboxylate

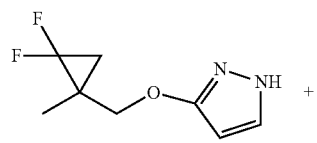

+

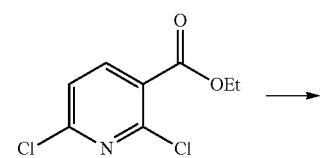

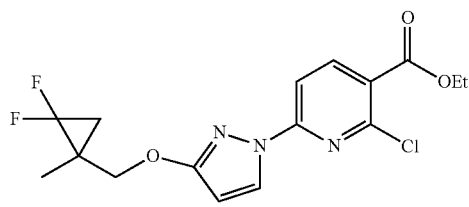

3-[(2,2-Difluoro-1-methyl-cyclopropyl)methoxy]-1H-pyrazole (490 mg, 2.604 mmol) was dissolved in DMF (5 mL). Ethyl 2,6-dichloropyridine-3-carboxylate (approximately 573.0 mg, 2.604 mmol) was added followed by 1,4-diazabicyclo[2.2.2]octane (approximately 58.42 mg, 0.5208 mmol) and finely ground potassium carbonate (approximately 539.8 mg, 3.906 mmol). The reaction mixture was allowed to stir overnight at room temperature. The reaction mixture was diluted with water (50 mL) and extracted with EtOAc (2×50 mL). The combined organic layers were then washed with brine (1x 75 mL), dried over sodium sulfate, filtered, and concentrated under reduced pressure. The crude product was isolated by silica gel column chromatography eluting with a 0-20% EtOAc/hexane gradient on a 40 gram silica gel column. Ethyl 2-chloro-6-[3-[(2,2-difluoro-1-methyl-cyclopropyl)methoxy]pyrazol-1-yl]pyridine-3-carboxylate (797 mg, 82%) was obtained as a white solid. $^1$H NMR (400 MHz, DMSO-$d_6$) δ 8.46 (dd, J=2.8, 0.9 Hz, 1H), 8.41 (dd, J=8.4, 0.9 Hz, 1H), 7.75 (dd, J=8.5, 0.9 Hz, 1H), 6.27 (dd, J=2.9, 0.9 Hz, 1H), 4.44-4.37 (m, 1H), 4.37-4.31 (m, 2H), 4.17 (d, J=10.8 Hz, 1H), 1.67 (q, J=8.9 Hz, 1H), 1.42 (q, J=8.4 Hz, 1H), 1.38-1.30 (m, 6H). ESI-MS m/z calc. 371.08484, found 372.0 (M+1)+; Retention time: 2.09 minutes.

Step 4: 2-Chloro-6-[3-[(2,2-difluoro-1-methyl-cyclopropyl)methoxy]pyrazol-1-yl]pyridine-3-carboxylic acid

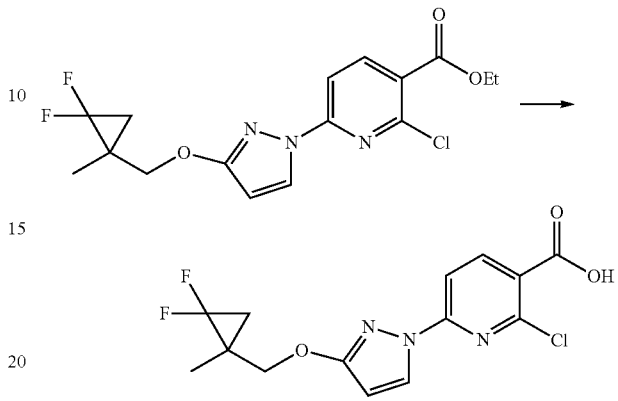

A solution of sodium hydroxide (approximately 428.8 mg, 10.72 mmol) in water (3.985 mL) was added to a solution of ethyl 2-chloro-6-[3-[(2,2-difluoro-1-methyl-cyclopropyl)methoxy]pyrazol-1-yl]pyridine-3-carboxylate (797 mg, 2.144 mmol) in isopropanol (3.985 mL) stirring at 90° C. The reaction mixture was allowed to stir at 85° C. for 30 minutes. After cooling to room temperature, the reaction mixture was diluted with EtOAc (50 mL) and extracted with aqueous NaOH (1 N, 2×50 mL). The aqueous layers were combined, cooled to 0° C., and acidified to pH 1 with the addition of 6 N HCl. Solids were collected by filtration. The solids obtained from the aqueous layer were dissolved in EtOAc and added to the organic layer. It was then dried over sodium sulfate, filtered and concentrated under reduced pressure. 2-chloro-6-[3-[(2,2-difluoro-1-methyl-cyclopropyl)methoxy]pyrazol-1-yl]pyridine-3-carboxylic acid (950 mg, 129%) was obtained as a white solid. $^{1H}$ NMR (400 MHz, DMSO-d6) δ 8.34 (d, J=2.8 Hz, 1H), 7.93 (dd, J=8.2, 1.8 Hz, 1H), 7.55 (d, J=8.1 Hz, 1H), 6.13 (d, J=2.7 Hz, 1H), 4.37 (dt, J=10.8, 2.3 Hz, 1H), 4.14 (d, J=10.8 Hz, 1H), 1.64 (dd, J=10.4, 7.9 Hz, 1H), 1.40 (q, J=8.1 Hz, 1H), 1.33 (d, J=2.1 Hz, 3H). ESI-MS m/z calc. 343.05353, found 344.2 (M+1)+; Retention time: 0.63 minutes.

Step 5: 2-Chloro-6-[3-[(2,2-difluoro-1-methyl-cyclopropyl)methoxy]pyrazol-1-yl]-N-(1,5-dimethylpyrazol-4-yl)sulfonyl-pyridine-3-carboxamide

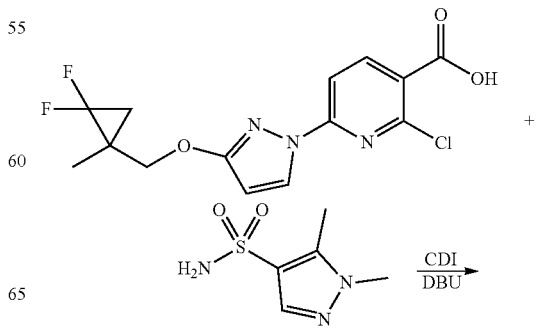

313
-continued

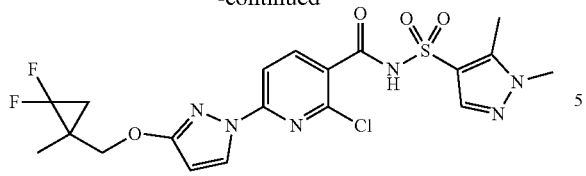

Carbonyl diimidazole (approximately 28.31 mg, 0.1746 mmol) was added to a solution of 2-chloro-6-[3-[(2,2-difluoro-1-methyl-cyclopropyl)methoxy]pyrazol-1-yl]pyridine-3-carboxylic acid (50 mg, 0.1455 mmol) in THF (2 mL). The solution was allowed to stir at room temperature for 1 hour. 1,5-dimethylpyrazole-4-sulfonamide (approximately 33.15 mg, 0.1891 mmol) was added followed by DBU (approximately 26.58 mg, 26.11 µL, 0.1746 mmol). The final reaction mixture was then allowed to stir overnight at room temperature. Volatiles were removed by evaporation. The remaining residue was diluted with ethyl acetate (2 mL) and washed with aqueous citric acid (1 M, 2×2 mL) and brine (1×2 mL). The organic layer was dried over sodium sulfate, filtered, and concentrated under reduced pressure. The product was used in the next step without further purification. 2-Chloro-6-[3-[(2,2-difluoro-1-methyl-cyclopropyl)methoxy]pyrazol-1-yl]-N-(1,5-dimethylpyrazol-4-yl)sulfonyl-pyridine-3-carboxamide (61 mg, 83.70%) was obtained. ESI-MS m/z calc. 500.0845, found 501.0 (M+1)+; Retention time: 1.67 minutes.

Step 6: 6-[3-[(2,2-Difluoro-1-methyl-cyclopropyl)methoxy]pyrazol-1-yl]-N-(1,5-dimethylpyrazol-4-yl)sulfonyl-2-[(4S)-2,2,4-trimethylpyrrolidin-1-yl]pyridine-3-carboxamide

314
-continued

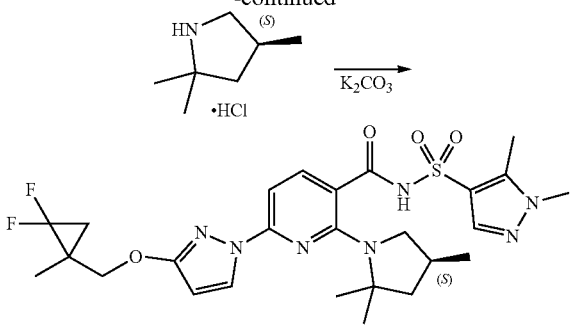

2-Chloro-6-[3-[(2,2-difluoro-1-methyl-cyclopropyl)methoxy]pyrazol-1-yl]-N-(1,5-dimethylpyrazol-4-yl)sulfonyl-pyridine-3-carboxamide (61 mg, 0.1218 mmol) was dissolved in DMSO (2 mL). (4S)-2,2,4-trimethylpyrrolidine (hydrochloride salt) (approximately 54.69 mg, 0.3654 mmol) was added followed by finely ground potassium carbonate (approximately 101.0 mg, 0.7308 mmol). The reaction vial was sealed and allowed to stir overnight at 130° C. The reaction mixture was diluted with ethyl acetate (50 mL) and washed with aqueous citric acid (1 N, 2×50 mL) and brine (1×50 mL). The organic layer was dried over sodium sulfate, filtered and concentrated under reduced pressure. The product was isolate by silica gel column chromatography eluting with a 0-5% MeOH/DCM gradient on a 24 gram silica gel column to give 6-[3-[(2,2-difluoro-1-methyl-cyclopropyl)methoxy]pyrazol-1-yl]-N-(1,5-dimethylpyrazol-4-yl)sulfonyl-2-[(4S)-2,2,4-trimethylpyrrolidin-1-yl]pyridine-3-carboxamide (20.3 mg, 28.85%) ESI-MS m/z calc. 577.2283, found 578.5 (M+1)+; Retention time: 1.99 minutes.

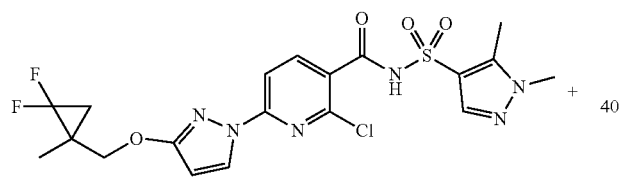

Synthesis of N-(1,3-dimethylpyrazol-4-yl)sulfonyl-6-[3-[3,3,3-trifluoro-2-(hydroxymethyl)-2-methylpropoxy]pyrazol-1-yl]-2-[(4S)-2,2,4-trimethylpyrrolidin-1-yl]pyridine-3-carboxamide (Compound 45)

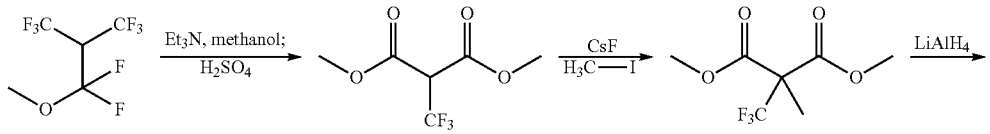

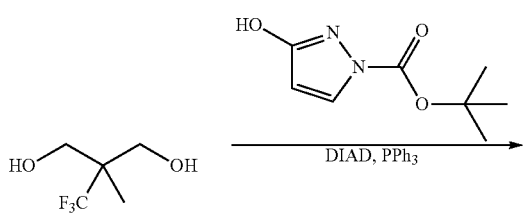

-continued
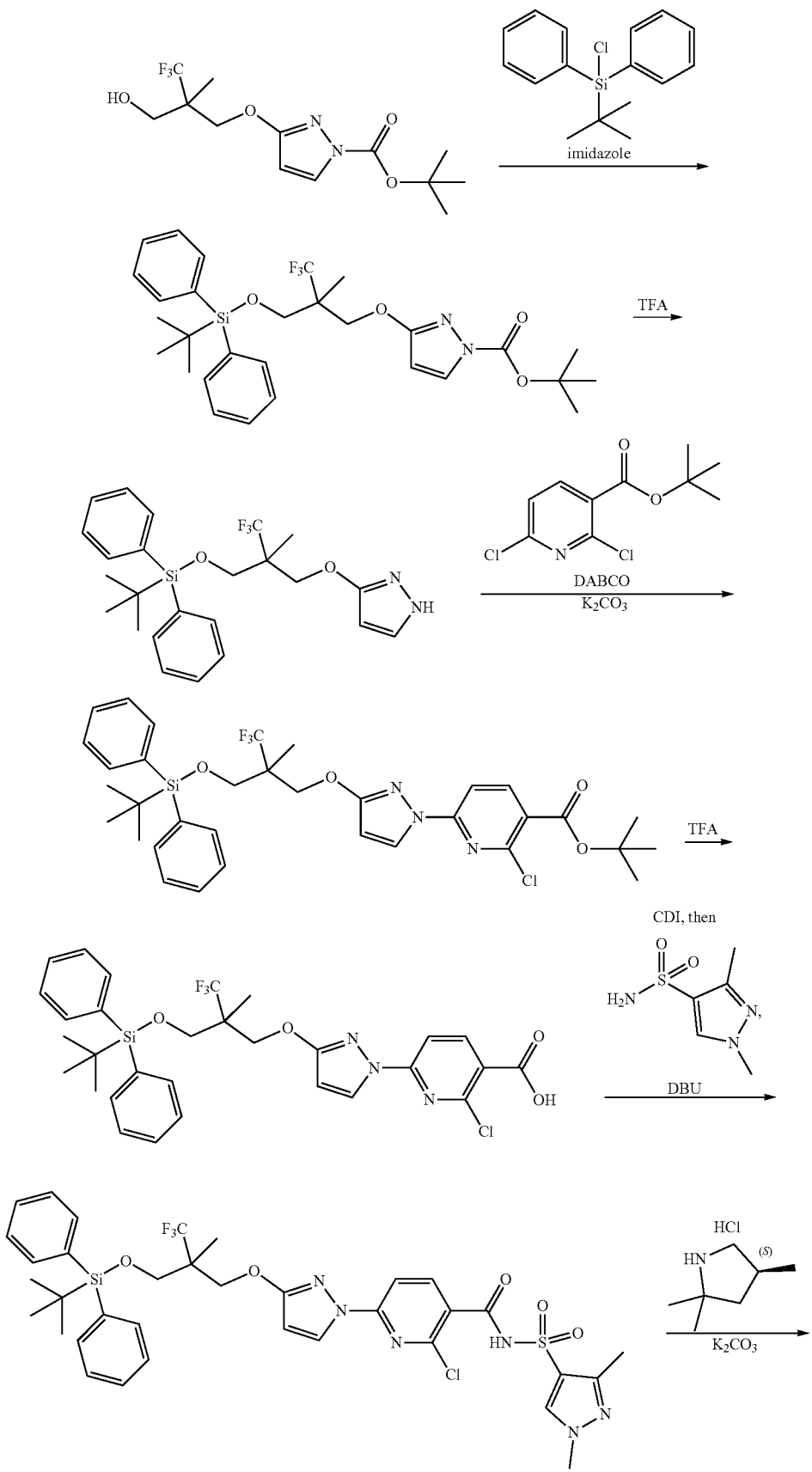

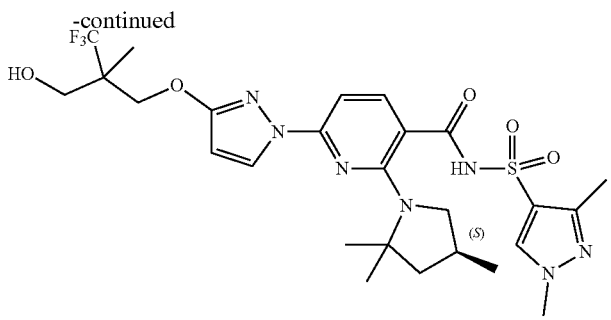

Step 1: Dimethyl 2-(trifluoromethyl)propanedioate

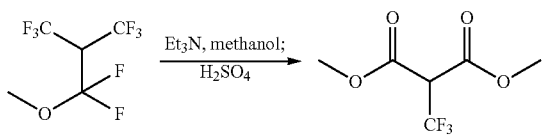

2-[difluoro(methoxy)methyl]-1,1,1,3,3,3-hexafluoro-propane (4.64 g, 19.99 mmol) was dissolved in anhydrous DMF (4 mL) and cooled in an ice bath. Triethylamine (5.6 mL, 40.18 mmol) was added dropwise by syringe, followed by dropwise addition of methanol (4 mL, 98.75 mmol) and continued stirring at 0° C. for 90 minutes. The reaction mixture was poured into a separatory funnel with 70 mL water, and the resulting organic layer was separated. The aqueous layer was further extracted 2×40 mL diethyl ether, and the organics were combined, washed with brine, dried over sodium sulfate and concentrated. Sulfuric acid (0.5 mL, 9.380 mmol) was then added to the resulting oil, and the reaction was stirred at room temperature for 16 hours. The reaction mixture was then poured into 40 mL chilled water and extracted 3×20 mL diethyl ether. The combined organics were washed with brine, dried over sodium sulfate, and concentrated. The crude material was then purified by silica chromatography using a gradient of 0-90% ethyl acetate in hexanes to give a colorless oil, with some solvent remaining, but used in the next step without additional purification. dimethyl 2-(trifluoromethyl)propanedioate (1.79 g, 45%). $^1$H NMR (400 MHz, DMSO) δ 5.39 (q, J=8.7 Hz, 1H), 3.78 (s, 6H).

Step 2: Dimethyl 2-methyl-2-(trifluoromethyl)propanedioate

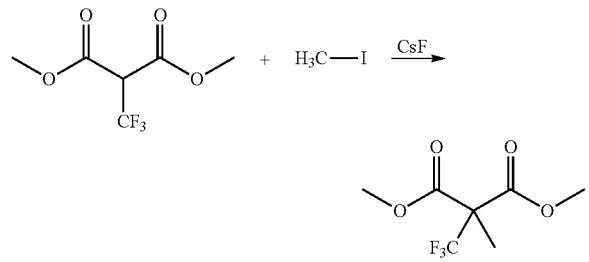

Dimethyl 2-(trifluoromethyl)propanedioate (1.79 g, 8.945 mmol) and iodomethane (640 µL, 10.28 mmol) were combined in diglyme (18 mL), and cesium fluoride (4.1 g, 26.99 mmol) was added in one portion. The reaction mixture was then stirred for 16 hours at room temperature. After this time the reaction mixture was diluted with 100 mL water and 100 mL diethyl ether, and the organics were separated. The aqueous layer was extracted with an additional 50 mL diethyl ether and the organics were combined and washed with 50 mL water, then with brine, and dried over sodium sulfate. After filtering, the reaction mixture was concentrated to give 6 g of a crude oil. The crude material was subjected to column chromatography on silica using a gradient of 0-100% ethyl acetate in hexanes. The fractions were combined and concentrated. The resulting oil was then diluted with 250 mL diethyl ether and washed 10×50 mL water and 1×50 mL brine to remove diglyme that remained after chromatography. The organics were concentrated and dried over sodium sulfate to give a slightly yellow oil (some residual solvents remaining). The material was used in the next step without additional purification. dimethyl 2-methyl-2-(trifluoromethyl)propanedioate (880 mg, 46%). $^1$H NMR (400 MHz, DMSO) δ 3.79 (s, 6H), 1.65 (q, J=0.8 Hz, 3H).

Step 3: 2-methyl-2-(trifluoromethyl)propane-1,3-diol

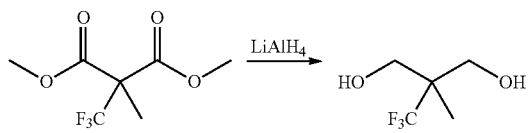

Dimethyl 2-methyl-2-(trifluoromethyl)propanedioate (880 mg, 4.109 mmol), dissolved in anhydrous THF (8.218 mL), was added dropwise to a solution of lithium aluminum hydride (8 mL of 2 M, 16.00 mmol) (in THF) at 0° C. After 20 minutes, the reaction mixture was allowed to warm to room temperature, and stirred for an additional 5 hours. The reaction mixture was then cooled again to 0° C., and carefully quenched with 2 mL water, and 2 mL 1M NaOH. After stirring for 20 minutes at room temperature, the reaction mixture was diluted with diethyl ether, filtered through celite, then dried thoroughly over sodium sulfate and concentrated. This crude material was then purified by silica gel chromatography using a gradient of 0-100% ethyl acetate in hexanes, giving a colorless solid. 2-methyl-2-(trifluoromethyl)propane-1,3-diol (280 mg, 43%). $^1$H NMR (400 MHz, DMSO) δ 4.87 (t, J=5.6 Hz, 2H), 3.54-3.43 (m, 4H), 0.97 (d, J=0.7 Hz, 3H).

Step 4: tert-butyl 3-[3,3,3-trifluoro-2-(hydroxymethyl)-2-methyl-propoxy]pyrazole-1-carboxylate

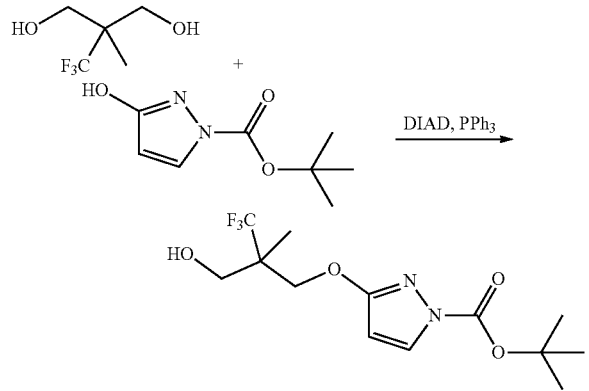

2-Methyl-2-(trifluoromethyl)propane-1,3-diol (278 mg, 1.758 mmol), tert-butyl 3-hydroxypyrazole-1-carboxylate (324 mg, 1.759 mmol), and PPh3 (507 mg, 1.933 mmol) were dissolved in THF (11.72 mL), and cooled to 0° C. in an ice bath. DIAD (358 µL, 1.848 mmol) was added dropwise by syringe, and the reaction mixture was allowed to slowly warm to room temperature and was stirred for 16 h. UPLC/LCMS showed very low conversion to the desired product, and the reaction temperature was increased to 60° C. Conversion to product increased, then stalled after 7 hours. The reaction was removed from heat, and solvent was removed under reduced pressure. The remaining oil was then dissolved in 60 mL ethyl acetate, and washed with 50 mL 1N NaOH. The aqueous layer was further extracted 2×40 mL ethyl acetate, and the combined organics were washed with brine, dried over sodium sulfate and concentrated. The crude material was then purified by silica gel chromatography, employing a 0-100% gradient of ethyl acetate in hexanes. The pure fractions were combined and concentrated to give tert-butyl 3-[3,3,3-trifluoro-2-(hydroxymethyl)-2-methyl-propoxy]pyrazole-1-carboxylate (115 mg, 20%) ESI-MS m/z calc. 324.1297, found 325.3 (M+1)+; Retention time: 0.58 minutes. $^1$H NMR (400 MHz, DMSO) δ 8.11 (d, J=2.9 Hz, 1H), 6.14 (d, J=3.0 Hz, 1H), 5.22 (t, J=5.6 Hz, 1H), 4.34-4.19 (m, 2H), 3.65 (dd, J=11.2, 5.7 Hz, 1H), 3.53 (dd, J=11.2, 5.6 Hz, 1H), 1.55 (s, 9H), 1.14 (s, 3H).

Step 5: tert-butyl 3-[2-[[tert-butyl(diphenyl)silyl]oxymethyl]-3,3,3-trifluoro-2-methyl-propoxy]pyrazole-1-carboxylate

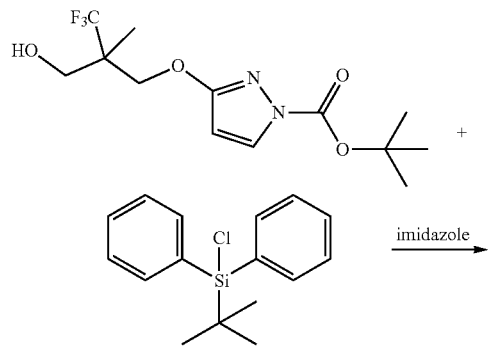

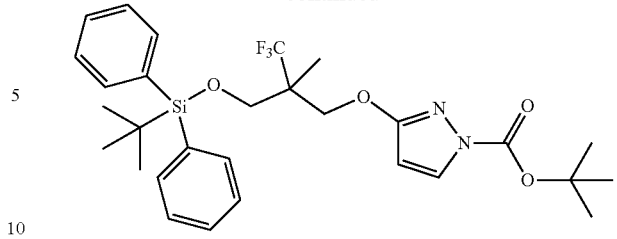

tert-Butyl 3-[3,3,3-trifluoro-2-(hydroxymethyl)-2-methyl-propoxy]pyrazole-1-carboxylate (113 mg, 0.3484 mmol) and imidazole (47 mg, 0.6904 mmol) were dissolved in DMF (696.8 µL) and cooled in an ice bath. tert-Butyl-chloro-diphenyl-silane (110 µL, 0.4230 mmol) was then added in a single portion, and after 15 minutes the ice bath was removed and the reaction mixture was allowed to stir 16 hours at room temperature. 2 mL saturated aqueous ammonium chloride was added and the reaction was stirred for 10 minutes, then further diluted with diethyl ether (50 mL) and additional saturated ammonium chloride (10 mL) and water (30 mL). The layers were separated, and the aqueous portion was extracted two additional times with ether, then the combined organics were washed with brine, dried over sodium sulfate, and concentrated. The resulting oil was purified by silica gel chromatography using a 0-20% gradient of ethyl acetate in hexanes, to give a colorless oil, (unidentified impurity present but used in the next step without additional purification) tert-butyl 3-[2-[[tert-butyl (diphenyl)silyl]oxymethyl]-3,3,3-trifluoro-2-methyl-propoxy]pyrazole-1-carboxylate (195 mg, 99%). ESI-MS m/z calc. 562.2475, found 563.4 (M+1)+; Retention time: 0.97 minutes.

Step 6: tert-butyl-diphenyl-[3,3,3-trifluoro-2-methyl-2-(1H-pyrazol-3-yloxymethyl)propoxy]silane

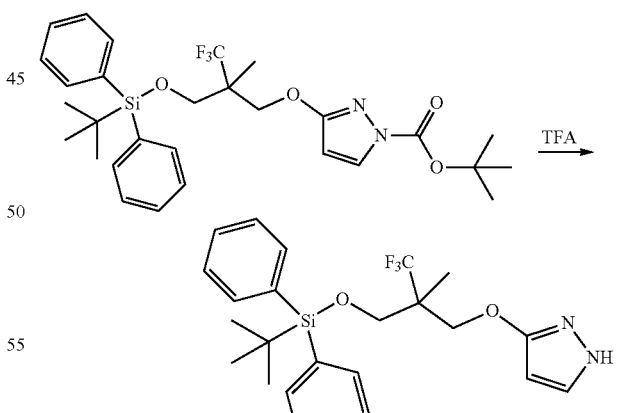

tert-Butyl 3-[2-[[tert-butyl(diphenyl)silyl]oxymethyl]-3,3,3-trifluoro-2-methyl-propoxy]pyrazole-1-carboxylate (195 mg, 0.3465 mmol) was dissolved in DCM (4.062 mL) with TFA (3504, 4.543 mmol) and the reaction was stirred at room temperature for 60 minutes. Hexanes (1 mL) were added, and the reaction was evaporated. The resulting oil was partitioned between ethyl acetate (10 mL) and a saturated sodium bicarbonate solution (10 mL). The organics were separated, and the aqueous layer was extracted an additional 2×10 mL ethyl acetate. The combined organics were washed with brine, dried over sodium sulfate and evaporated to give a colorless oil (with an unidentified impurity present, but used in the next step without further purification) tert-butyl-diphenyl-[3,3,3-trifluoro-2-methyl-2-(1H-pyrazol-3-yloxymethyl)propoxy]silane (159 mg, 99%) ESI-MS m/z calc. 462.19504, found 463.4 (M+1)+; Retention time: 0.86 minutes.

Step 7: tert-Butyl 6-[3-[2-[[tert-butyl(diphenyl)silyl]oxymethyl]-3,3,3-trifluoro-2-methyl-propoxy]pyrazol-1-yl]-2-chloro-pyridine-3-carboxylate

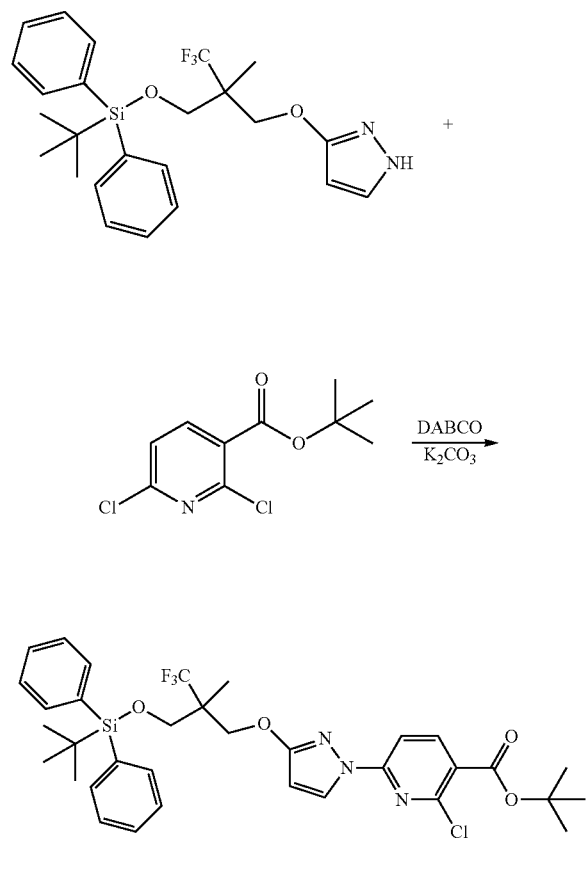

A nitrogen-purged vial was charged with tert-butyl-diphenyl-[3,3,3-trifluoro-2-methyl-2-(1H-pyrazol-3-yloxymethyl)propoxy]silane (159 mg, 0.3437 mmol), tert-butyl 2,6-dichloropyridine-3-carboxylate (110 mg, 0.4434 mmol), $K_2CO_3$ (76 mg, 0.5499 mmol) (freshly ground in a mortar) and anhydrous DMF (572.8 µL). DABCO (7 mg, 0.06240 mmol) was added and the mixture was stirred at room temperature under nitrogen for 16 hours. The reaction mixture was diluted with ethyl acetate (50 mL) and water (50 mL) and the two phases were separated. The aqueous phase was further extracted with ethyl acetate (2×30 mL). The combined extracts were washed with brine and dried over sodium sulfate, and the solvent was removed under reduced pressure. The material was subjected to flash chromatography on silica gel using a gradient of ethyl acetate (0-5%) in hexanes. The pure fractions were combined and the solvents removed under reduced pressure to provide tert-butyl 6-[3-[2-[[tert-butyl(diphenyl)silyl]oxymethyl]-3,3,3-trifluoro-2-methyl-propoxy]pyrazol-1-yl]-2-chloro-pyridine-3-carboxylate (170 mg, 73%) ESI-MS m/z calc. 673.23505, found 674.5 (M+1)+; Retention time: 0.87 minutes. $^1$H NMR (400 MHz, DMSO) δ 8.46 (d, J=2.9 Hz, 1H), 8.33 (d, J=8.4 Hz, 1H), 7.73 (d, J=8.4 Hz, 1H), 7.59 (dt, J=8.1, 1.8 Hz, 4H), 7.50-7.40 (m, 6H), 6.25 (d, J=2.9 Hz, 1H), 4.55 (d, J=10.4 Hz, 1H), 4.45 (d, J=10.5 Hz, 1H), 3.87 (d, J=10.4 Hz, 1H), 3.76 (d, J=10.5 Hz, 1H), 1.57 (s, 9H), 1.23 (s, 3H), 0.96 (s, 9H).

Step 8: 6-[3-[2-[[tert-butyl(diphenyl)silyl]oxymethyl]-3,3,3-trifluoro-2-methyl-propoxy]pyrazol-1-yl]-2-chloro-pyridine-3-carboxylic acid

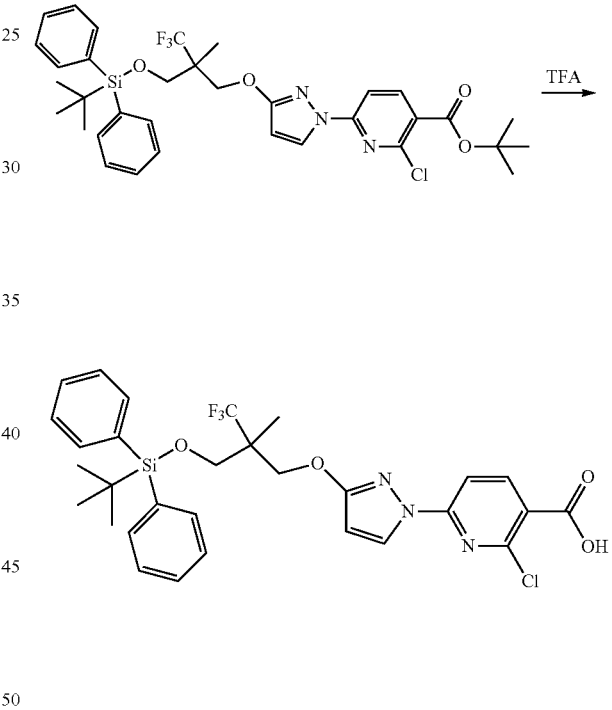

tert-butyl 6-[3-[2-[[tert-butyl(diphenyl)silyl]oxymethyl]-3,3,3-trifluoro-2-methyl-propoxy]pyrazol-1-yl]-2-chloro-pyridine-3-carboxylate (170 mg, 0.2521 mmol) and TFA (450 µL, 5.841 mmol) were combined in dichloromethane (1.703 mL) and and stirred at room temperature for 4 hours. The reaction was evaporated. Hexanes were added and the mixture evaporated again to give a white solid 6-[3-[2-[[tert-butyl(diphenyl)silyl]oxymethyl]-3,3,3-trifluoro-2-methyl-propoxy]pyrazol-1-yl]-2-chloro-pyridine-3-carboxylic acid (117 mg, 75%) ESI-MS m/z calc. 617.1724, found 618.5 (M+1)$^+$; Retention time: 0.63 minutes.

Step 9: 6-[3-[2-[[tert-butyl(diphenyl)silyl]oxymethyl]-3,3,3-trifluoro-2-methyl-propoxy]pyrazol-1-yl]-2-chloro-N-(1,3-dimethylpyrazol-4-yl)sulfonyl-pyridine-3-carboxamide

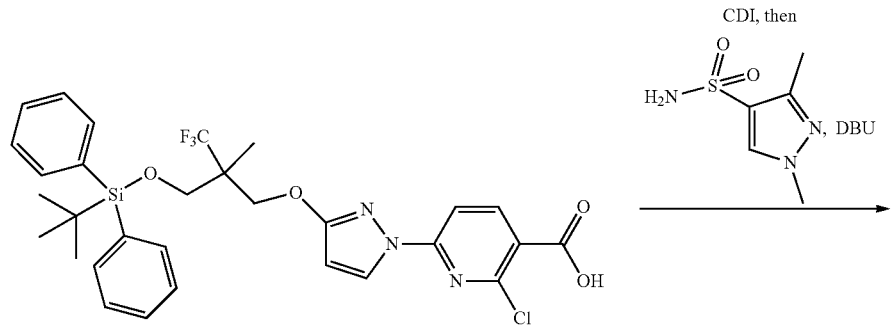

6-[3-[2-[[tert-butyl(diphenyl)silyl]oxymethyl]-3,3,3-trifluoro-2-methyl-propoxy]pyrazol-1-yl]-2-chloro-pyridine-3-carboxylic acid (40 mg, 0.06471 mmol) and CDI (14 mg, 0.08634 mmol) were combined in THF (200 μL) and stirred at room temperature for 2 hours. 1,3-dimethylpyrazole-4-sulfonamide (14 mg, 0.07990 mmol) was added followed by DBU (13 μL, 0.08693 mmol) and the reaction was stirred for an additional 2 h at room temperature. The reaction mixture was diluted with 10 mL 1 M citric acid, and extracted 3×10 mL ethyl acetate. The combined organics were washed with water, brine, dried over sodium sulfate, and concentrated to give a white solid, which was used in the next step without further purification (some starting material remaining). 6-[3-[2-[[tert-butyl(diphenyl)silyl]oxymethyl]-3,3,3-trifluoro-2-methyl-propoxy]pyrazol-1-yl]-2-chloro-N-(1,3-dimethylpyrazol-4-yl)sulfonyl-pyridine-3-carboxamide (48 mg, 96%) ESI-MS m/z calc. 774.2034, found 775.5 (M+1)+; Retention time: 0.6 minutes.

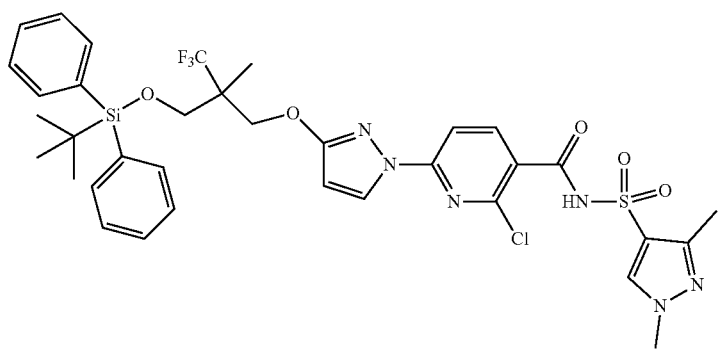

Step 10: N-(1,3-dimethylpyrazol-4-yl)sulfonyl-6-[3-[3,3,3-trifluoro-2-(hydroxymethyl)-2-methyl-propoxy]pyrazol-1-yl]-2-[(4S)-2,2,4-trimethylpyrrolidin-1-yl]pyridine-3-carboxamide

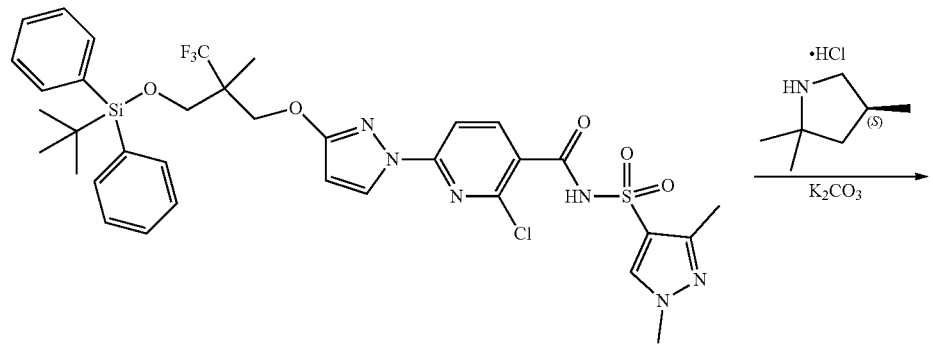

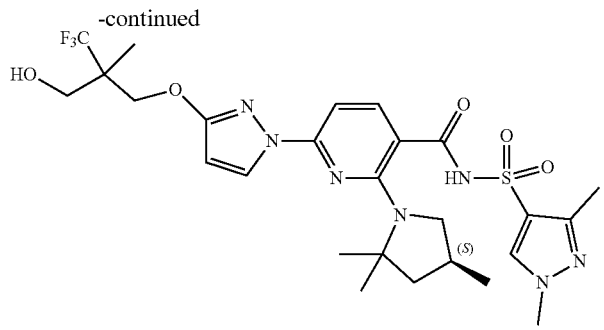

6-[3-[2-[[tert-Butyl(diphenyl)silyl]oxymethyl]-3,3,3-trifluoro-2-methyl-propoxy]pyrazol-1-yl]-2-chloro-N-(1,3-dimethylpyrazol-4-yl)sulfonyl-pyridine-3-carboxamide (48 mg, 0.06191 mmol), (4S)-2,2,4-trimethylpyrrolidine (hydrochloride salt) (56 mg, 0.3742 mmol), and potassium carbonate (103 mg, 0.7453 mmol) were combined in DMSO (154.8 µL) and heated at 130° C. for 9 hours. The reaction was cooled to room temperature and diluted with 15 mL 1M citric acid and 20 mL ethyl acetate. The aqueous and organic layers were separated, and the aqueous layer was extracted two additional times with 15 mL ethyl acetate. The organics were combined, washed with brine, dried over sodium sulfate and concentrated. The reaction mixture was the purified by chromatography on silica gel (eluting with 0-10% methanol in DCM), and a portion of the product that had desilylated under the reaction conditions was isolated.

This material was further purified by prep HPLC (1-99ACN) HCl modifier, to give, after extraction with ethyl acetate and concentration under reduced pressure, N-(1,3-dimethylpyrazol-4-yl)sulfonyl-6-[3-[3,3,3-trifluoro-2-(hydroxymethyl)-2-methyl-propoxy]pyrazol-1-yl]-2-[(4S)-2,2,4-trimethylpyrrolidin-1-yl]pyridine-3-carboxamide (8 mg, 21%) ESI-MS m/z calc. 613.22943, found 614.4 (M+1)+; Retention time: 1.81 minutes. $^1$H NMR (400 MHz, DMSO) δ 12.36 (s, 1H), 8.37 (s, 1H), 2.71-2.62 (m, 1H), 8.21 (d, J=2.8 Hz, 1H), 7.74 (d, J=8.2 Hz, 1H), 6.93 (d, J=8.1 Hz, 1H), 6.16 (d, J=2.8 Hz, 1H), 5.27-5.18 (m, 1H), 4.38-4.25 (m, 2H), 3.80 (s, 3H), 3.67 (dd, J=11.1, 5.7 Hz, 1H), 3.56 (dd, J=11.2, 5.6 Hz, 1H), 2.41 (s, 1H), 2.32 (s, 3H), 2.17 (d, J=10.5 Hz, 1H), 1.87 (dd, J=12.0, 5.6 Hz, 1H), 1.55 (d, J=11.3 Hz, 6H), 1.43 (d, J=12.2 Hz, 1H), 1.16 (s, 3H), 0.81 (d, J=6.2 Hz, 3H).

N-((1,3-dimethyl-1H-pyrazol-4-yl)sulfonyl)-2-((S)-2,2-dimethyl-4-(methyl-d3)pyrrolidin-1-yl-3,3-d2)-6-(3-(3,3,3-trifluoro-2-(hydroxymethyl)-2-methyl-propoxy)-1H-pyrazol-1-yl)nicotinamide (Compound 4)

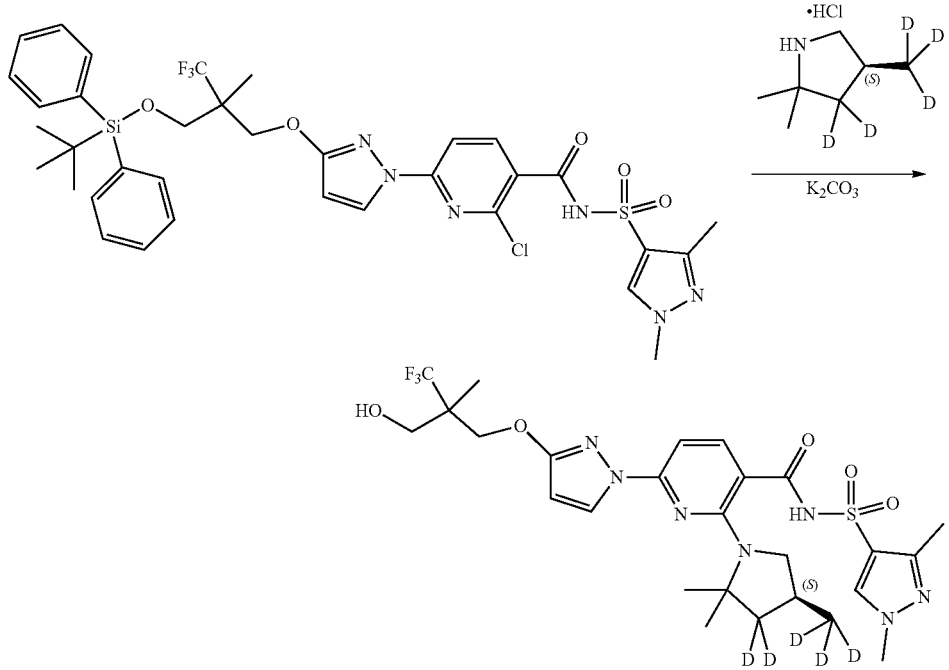

6-[3-[2-[[tert-Butyl(diphenyl)silyl]oxymethyl]-3,3,3-trifluoro-2-methyl-propoxy]pyrazol-1-yl]-2-chloro-N-(1,3-dimethylpyrazol-4-yl)sulfonyl-pyridine-3-carboxamide (900 mg, 1.16 mmol), (4S)-3,3-dideuterio-2,2-dimethyl-4-(trideuteriomethyl)pyrrolidine (Hydrochloride salt) (1.8 g, 12 mmol), and potassium carbonate (3.2 g, 23 mmol) were combined in DMSO (3 mL) and dimethoxyethane (0.5 mL)

and heated at 130° C. for 2 days. The reaction was cooled to room temperature and diluted with 20 mL 1M citric acid and 40 mL ethyl acetate. The aqueous and organic layers were separated, and the aqueous layer was extracted two additional times with 50 mL ethyl acetate. The organics were combined, washed with brine, dried over sodium sulfate and concentrated. The reaction mixture was the purified by chromatography on silica gel to give the free alcohol N-((1,3-dimethyl-1H-pyrazol-4-yl)sulfonyl)-2-((S)-2,2-dimethyl-4-(methyl-d3)pyrrolidin-1-yl-3,3-d2)-6-(3-(3,3,3-trifluoro-2-(hydroxymethyl)-2-methylpropoxy)-1H-pyrazol-1-yl) nicotinamide (0.7 g, 98%) ESI-MS m/z calc. 618.26, found 619.7 (M+1)$^+$; Retention time: 5.06 minutes (17 minute run).

Synthesis of N-(1,3-dimethylpyrazol-4-yl)sulfonyl-6-[3-(norbornan-7-ylmethoxy)pyrazol-1-yl]-2-[(4S)-2,2,4-trimethylpyrrolidin-1-yl]pyridine-3-carboxamide (Compound 52)

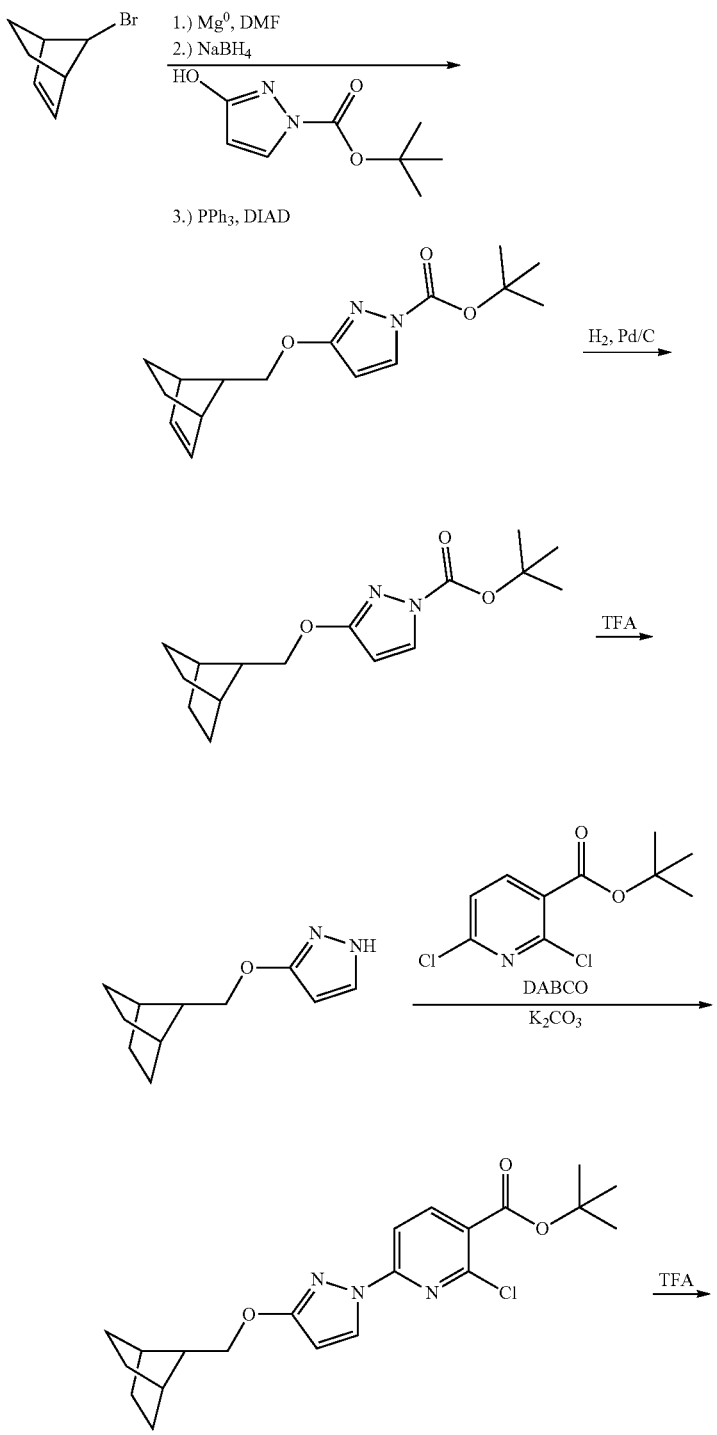

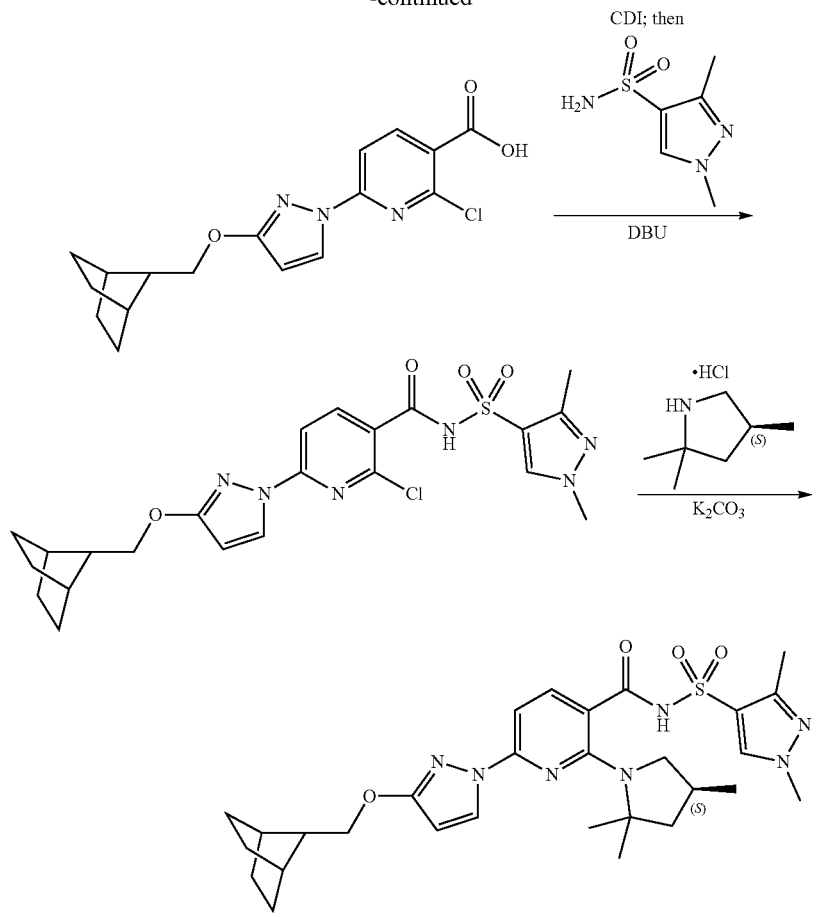

Steps 1-3: tert-Butyl 3-(7-bicyclo[2.2.1]hept-2-enyl-methoxy)pyrazole-1-carboxylate

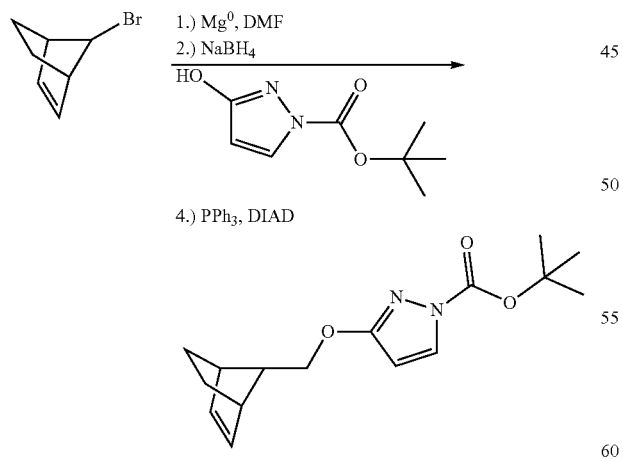

Step 1: bicyclo[2.2.1]hept-2-ene-7-carbaldehyde 7-bromobicyclo[2.2.1]hept-2-ene (400 mg, 2.311 mmol) and magnesium (67 mg, 2.757 mmol) (surface scratched) were combined in a vial in anhydrous diethyl ether (4 mL), and heated to 40° C. for 2 hours, at which time the magnesium was mostly, but not completely consumed. The reaction mixture was then cooled to 0° C., and DMF (220 µL, 2.841 mmol) was added dropwise, resulting in the formation of a solid white precipitate. The reaction mixture was returned to 40° C. for an additional 2 hours, then cooled to room temperature and quenched with 3 mL 0.1 M HCl. After diluting with 25 mL water and 25 mL diethyl ether the layers were separated, and the aqueous layer was extracted with an additional 3x 20 mL diethyl ether. The combined organics were washed with brine and dried over sodium sulfate, then partially concentrated to a volume under 1 mL, then used in the next step without isolation.

Step 2: 7-bicyclo[2.2.1]hept-2-enylmethanol

The mixture from the previous step was diluted with methanol (3 mL) and cooled to 0° C. in an ice bath. Sodium Borohydride (262 mg, 6.925 mmol) was added, and the reaction mixture was stirred for 2 hours, during which time the ice mostly melted. The reaction mixture was quenched with 3 mL saturated ammonium chloride, then diluted with 20 mL water and 20 mL ethyl acetate. The organics were separated, and the aqueous layer was extracted an additional 4x20 mL ethyl acetate. The combined organics were washed with brine and dried over sodium sulfate, then concentrated to an oil. The resulting crude mixture was used in the next step without further purification.

Step 3

The crude material from step 2 was combined with PPh3 (606 mg, 2.310 mmol), and tert-butyl 3-hydroxypyrazole-1-carboxylate (426 mg, 2.313 mmol) in THF (6 mL), then cooled to 0° C., at which point DIAD (448 μL, 2.313 mmol) was added dropwise. After 30 minutes the reaction mixture was allowed to warm to room temperature and stirred for 1 hour. The reaction temperature was then increased to 50° C. for 1 hour, but appeared to rapidly become messier and was returned to room temperature for an additional 16 hours. The reaction mixture was then diluted with 100 mL ethyl acetate, and washed with 50 mL aqueous 1M NaOH, and the aqueous layer was extracted with an additional 50 mL ethyl acetate. The combined organics were then washed with brine, dried over sodium sulfate and concentrated. The resulting material was purified by flash chromatography on silica gel to give tert-butyl 3-(7-bicyclo[2.2.1]hept-2-enyl-methoxy)pyrazole-1-carboxylate (20 mg, 2%) ESI-MS m/z calc. 290.16306, found 291.3 (M+1)+; Retention time: 0.74 minutes with a significant impurity unidentified.

Step 4: tert-butyl 3-(norbornan-7-ylmethoxy)pyrazole-1-carboxylate

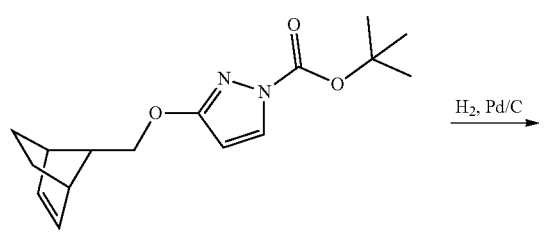

tert-butyl 3-(7-bicyclo[2.2.1]hept-2-enylmethoxy)pyrazole-1-carboxylate (20 mg, 0.04959 mmol) was combined with 10% palladium on carbon (20 mg, 0.01879 mmol) in ethanol (500 μL) and hydrogen gas was bubbled through the reaction mixture from a balloon for 15 minutes, and the reaction was stirred for a further 6 hours with the hydrogen balloon in place above the solvent level. The reaction mixture was then filtered and concentrated to give tert-butyl 3-(norbornan-7-ylmethoxy)pyrazole-1-carboxylate (17 mg, 84%) ESI-MS m/z calc. 292.17868, found 293.3 (M+1)+; Retention time: 0.83 minutes.

Step 5: 3-(norbornan-7-ylmethoxy)-1H-pyrazole

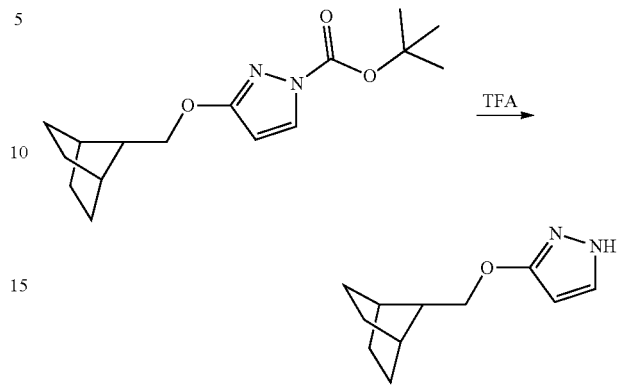

tert-butyl 3-(norbornan-7-ylmethoxy)pyrazole-1-carboxylate (17 mg, 0.0412 mmol) was dissolved in dichloromethane (1 mL) with TFA (approximately 84.81 mg, 57.30 μL, 0.7438 mmol), and was stirred for 1 hour at room temperature. The reaction mixture was then concentrated under reduced pressure. Hexanes were added and the reaction mixture was reconcentrated to give 3-(norbornan-7-ylmethoxy)-1H-pyrazole (11 mg, 83%) ESI-MS m/z calc. 192.12627, found 193.1 (M+1)+; Retention time: 0.56 minutes.

Step 6: tert-butyl 2-chloro-6-[3-(norbornan-7-ylmethoxy)pyrazol-1-yl]pyridine-3-carboxylate

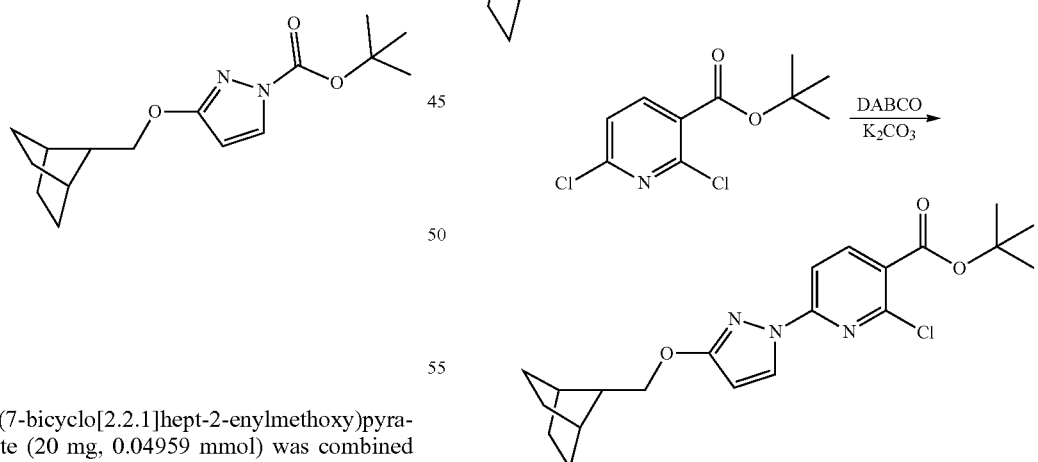

A reaction vial was charged under nitrogen with tert-butyl 2,6-dichloropyridine-3-carboxylate (14 mg, 0.05643 mmol), 3-(norbornan-7-ylmethoxy)-1H-pyrazole (11 mg, 0.04119 mmol), and K₂CO₃ (10 mg, 0.07236 mmol) (freshly ground in a mortar) and anhydrous DMF (200 μL). DABCO (1 mg, 0.008915 mmol) was added and the mixture was stirred at room temperature under nitrogen for 8 hours. The reaction mixture was diluted with ethyl acetate (10 mL) and water (10 mL) and the two phases were separated. The aqueous phase was further extracted with ethyl acetate (2×10 mL). The combined extracts were washed with brine, dried over sodium sulfate, and the solvent removed under reduced pressure. The material was subjected to flash chromatography on silica gel using a gradient of ethyl acetate (0 to 20%) in hexanes. The pure fractions were combined and the solvent removed under reduced pressure to provide tert-butyl 2-chloro-6-[3-(norbornan-7-ylmethoxy)pyrazol-1-yl]pyridine-3-carboxylate (9 mg, 39%) ESI-MS m/z calc. 403.16626, found 404.3 (M+1)+; Retention time: 0.95 minutes.

Step 7: 2-Chloro-6-[3-(norbornan-7-ylmethoxy) pyrazol-1-yl]pyridine-3-carboxylic acid tert-butyl 2-chloro-6-[3-(norbornan-7-ylmethoxy)pyrazol-1-yl]pyridine-3-carboxylate (9 mg, 0.02228 mmol) and TFA (30 μL, 0.3894 mmol) were combined in dichloromethane (90.00 μL) and heated at 40° C. for 2 h. Solvent was evaporated under reduced pressure, then hexanes were added and the mixture was evaporated again to give a white solid 2-chloro-6-[3-(norbornan-7-ylmethoxy)pyrazol-1-yl]pyridine-3-carboxylic acid (7 mg, 90%) ESI-MS m/z calc. 347.10367, found 348.2 (M+1)+; Retention time: 0.76 minutes.

Step 8: 2-Chloro-N-(1,3-dimethylpyrazol-4-yl)sulfonyl-6-[3-(norbornan-7-ylmethoxy)pyrazol-1-yl]pyridine-3-carboxamide

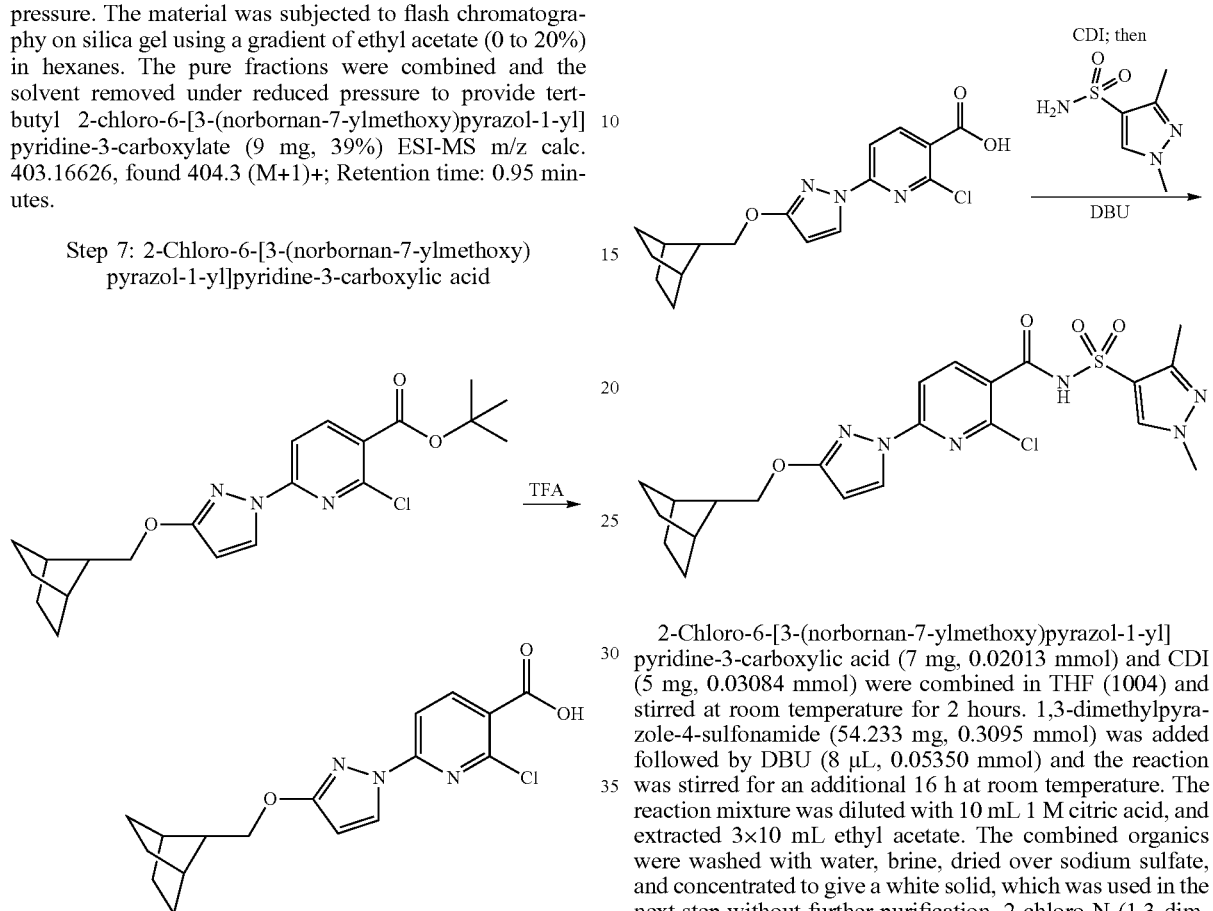

2-Chloro-6-[3-(norbornan-7-ylmethoxy)pyrazol-1-yl]pyridine-3-carboxylic acid (7 mg, 0.02013 mmol) and CDI (5 mg, 0.03084 mmol) were combined in THF (1004) and stirred at room temperature for 2 hours. 1,3-dimethylpyrazole-4-sulfonamide (54.233 mg, 0.3095 mmol) was added followed by DBU (8 μL, 0.05350 mmol) and the reaction was stirred for an additional 16 h at room temperature. The reaction mixture was diluted with 10 mL 1 M citric acid, and extracted 3×10 mL ethyl acetate. The combined organics were washed with water, brine, dried over sodium sulfate, and concentrated to give a white solid, which was used in the next step without further purification. 2-chloro-N-(1,3-dimethylpyrazol-4-yl)sulfonyl-6-[3-(norbornan-7-ylmethoxy)pyrazol-1-yl]pyridine-3-carboxamide (10 mg, 98%) ESI-MS m/z calc. 504.13464, found 505.3 (M+1)+; Retention time: 0.74 minutes.

Step 9: N-(1,3-Dimethylpyrazol-4-yl)sulfonyl-6-[3-(norbornan-7-ylmethoxy)pyrazol-1-yl]-2-[(4S)-2,2,4-trimethylpyrrolidin-1-yl]pyridine-3-carboxamide

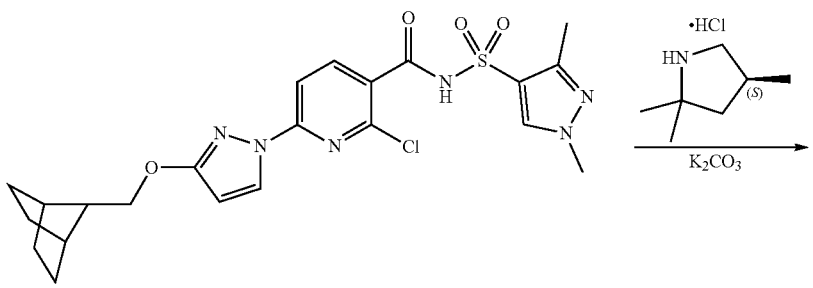

-continued

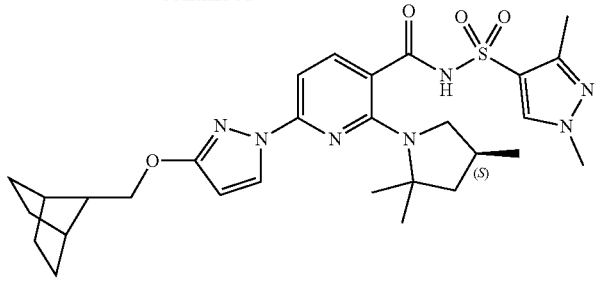

2-Chloro-N-(1,3-dimethylpyrazol-4-yl)sulfonyl-6-[3-(norbornan-7-ylmethoxy)pyrazol-1-yl]pyridine-3-carboxamide (10 mg, 0.01980 mmol), (4S)-2,2,4-trimethylpyrrolidine (Hydrochloride salt) (15 mg, 0.1002 mmol), and potassium carbonate (27 mg, 0.1954 mmol) were combined in DMSO (150 μL) and heated at 130° C. for 16 h. The reaction was cooled to room temperature and diluted with 15 mL ethyl acetate and 15 mL 1M citric acid. The aqueous and organic layers were separated, and the aqueous layer was extracted two additional times with 15 mL ethyl acetate. The organics were combined, washed with brine, dried over sodium sulfate and concentrated. The resulting crude was purified by prep HPLC (1-99ACN) with HCl modifier, 30 minute run. The fractions containing product were concentrated and dried under vacuum to give N-(1,3-dimethylpyrazol-4-yl)sulfonyl-6-[3-(norbornan-7-ylmethoxy)pyrazol-1-yl]-2-[(4S)-2,2,4-trimethylpyrrolidin-1-yl]pyridine-3-carboxamide (2 mg, 17%) ESI-MS m/z calc. 581.27844, found 582.5 (M+1)+; Retention time: 2.32 minutes.

Synthesis of (7S)-6-((1,3-dimethyl-1H-pyrazol-4-yl)sulfonyl)-7,9,9-trimethyl-2-(3-(3,3,3-trifluoro-2,2-dimethylpropoxy)-1H-pyrazol-1-yl)-6a,7,8,9-tetrahydropyrido[3,2-e]pyrrolo[1,2-a]pyrimidin-5(6H)-one (Compound 36)

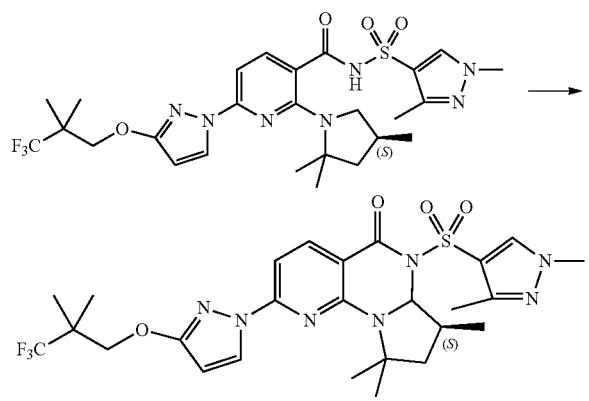

N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (50.5 mg, 0.08450 mmol), NaOAc (13.86 mg, 0.1690 mmol), water (15.22 mg, 15.22 μL, 0.8450 mmol), and [Ir{dF(CF3)ppy}2(dtbpy)]PF6 (94.80 mg, 0.08450 mmol) were combined in DMA (880.7 μL) and the reaction mixture was placed next to a 23 WCFL light source for 1.5 h. The reaction was injected directly onto a silica gel column without any workup. The crude mixture was purified by silica gel chromatography eluting with 0-100% ethyl acetate in hexanes. The product was contaminated with DMA so the product was re-purified by silica gel chromatography eluting with 0-100% ethyl acetate in hexanes to give C26H32F3N7O4S (10.4 mg, 21%) ESI-MS m/z calc. 595.2189, found 596.4 (M+1)+; Retention time: 2.4 minutes.

Preparations of Spray Dried Dispersions (SDDs) of Compound 1

A spray dried dispersion of Compound 1 was prepared using Buchi Mini Spray Dryer B290. HPMCAS-HG (6.0 grams) was dissolved in 200 mL of MeOH (methanol)/DCM (dichloromethane) (1/3), and Compound 1 (15.0 grams) was added and stirred for 30 minutes forming a clear solution. The resulting solution was spray dried under the following conditions resulting in a 50 wt % Compound 1/50 wt % HPMCAS-HG spray dried dispersion (Yield: 70%, Solid load: 13%).

| | Conditions |
|---|---|
| Inlet Temperature (° C.) | 80 |
| Outlet Temperature (° C.) | 39 |
| Nitrogen Pressure (PSI) | 95 |
| Aspirator (%) | 100 |
| Pump (%) | 25 |
| Rotameter (mm) | 60 |
| Filter Pressure (mBar) | −50 |
| Condenser Temperature (° C.) | −10 |

Additional SDDs of Compound 1 were prepared as follows: 400 mg of Compound 1 was added to 100 mg of one of the following polymers: HPMC E15, HPC, HPMCAS-HF, and PVP VA64. Each of the four resulting mixtures was dissolved in 40 mL of t-butanol by stirring overnight and the solutions were then flash frozen in an acetone/dry ice bath. Frozen samples were lyophilized (0.01 mbar vacuum, −55C collector) over 72 hours. The lyophized samples were determined to be amorphous by XRPD.

Assays for Detecting and Measuring F508del-CFTR Modulator Properties of Compounds Membrane Potential Optical Methods for Assaying Properties of F508del-CFTR Modulators The assay utilizes fluorescent voltage sensing dyes to measure changes in membrane potential using a fluorescent plate reader (e.g., FLIPR III, Molecular Devices, Inc.) as a readout for increase in functional F508del in NIH 3T3 cells. The driving force for the response is the creation of a chloride ion gradient in conjunction with channel activation and concurrent with compound treatment by a single liquid addition step after the cells have previously been loaded with a voltage sensing dye.

A1. Identification of F508del-CFTR Modulators

To identify modulators of F508del, a fluorescence based HTS assay format was developed. This HTS assay utilizes fluorescent voltage sensing dyes to measure changes in membrane potential on the FLIPR III as a measurement for increase in gating (conductance) of F508del NIH 3T3 cells. The driving force for the response is the creation of a chloride ion gradient in conjunction with channel activation and concurrent with compound treatment by a single liquid addition step after the cells have previously been loaded with a voltage sensing dye. Data for Compounds 1-65 that were obtained using the assay described here are summarized in Table 9 below. For example, using this method, Compound 1 had an $EC_{50}$ of less than 3 µM and a % Efficacy of ≥100% relative to Compound II.

Solutions

Bath Solution #1: (in mM) NaCl 160, KCl 4.5, $CaCl_2$ 2, $MgCl_2$ 1, HEPES 10, pH 7.4 with NaOH, Glucose 10.

Chloride-free bath solution: Chloride salts in Bath Solution #1 (above) are substituted with gluconate salts.

Cell Culture

NIH3T3 mouse fibroblasts stably expressing F508del were used for optical measurements of membrane potential. The cells were maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 cm² culture flasks. For all optical assays, the cells were seeded at 12,000 cells/well in 384-well matrigel-coated plates and cultured for 18-24 hrs at 37° C. for the potentiator assay. For the correction assay, the cells were cultured at 37° C. with and without compounds for 18-24 hours.

Electrophysiological Assays for Assaying F508delModulation Properties of Compounds.

Ussing Chamber Assay

Ussing chamber experiments were performed on polarized airway epithelial cells expressing F508del to further characterize the F508del modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) In Vitro Cell. Dev. Biol. 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for F508del or compound heterozygous for F508del with an different disease causing mutation on the other allele.

HBE grown on Costar® Snapwell™ cell culture inserts were mounted in an Ussing chamber (Physiologic Instruments, Inc., San Diego, Calif.), and the transepithelial resistance and short-circuit current in the presence of a basolateral to apical Cl⁻ gradient ($I_{SC}$) were measured using a voltage-clamp system (Department of Bioengineering, University of Iowa, Iowa). Briefly, HBE were examined under voltage-clamp recording conditions ($V_{hold}$=0 mV) at 37° C. The basolateral solution contained (in mM) 145 NaCl, 0.83 $K_2HPO_4$, 3.3 $KH_2PO_4$, 1.2 $MgCl_2$, 1.2 $CaCl_2$), 10 Glucose, 10 HEPES (pH adjusted to 7.35 with NaOH) and the apical solution contained (in mM) 145 NaGluconate, 1.2 $MgCl_2$, 1.2 $CaCl_2$), 10 glucose, 10 HEPES (pH adjusted to 7.35 with NaOH).

A2. Identification of F508del-CFTR Modulators

Typical protocol utilized a basolateral to apical membrane Cl⁻ concentration gradient. To set up this gradient, normal ringers was used on the basolateral membrane, whereas apical NaCl was replaced by equimolar sodium gluconate (titrated to pH 7.4 with NaOH) to give a large Cl⁻ concentration gradient across the epithelium. Modulators were added either to the basolateral side 18-24 prior to assay or to the apical side during the assay. Forskolin (10 µM) was added to the apical side during the assay to stimulate CFTR-mediated Cl⁻ transport.

Patch-Clamp Recordings

Total Cl⁻ current in F508del-NIH3T3 cells was monitored using the perforated-patch recording configuration as previously described (Rae, J., Cooper, K., Gates, P., & Watsky, M. (1991) *J. Neurosci. Methods* 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 $MgCl_2$, 2 $CaCl_2$, 10 EGTA, 10 HEPES, and 240 µg/mL amphotericin-B (pH adjusted to 7.35 with HCl). The extracellular medium contained (in mM) 150 NMDG-Cl, 2 $MgCl_2$, 2 $CaCl_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate F508del, 10 µM forskolin and 20 µM genistein were added to the bath and the current-voltage relation was monitored every 30 sec.

A3. Identification of F508del-CFTR Modulators

The ability of F508del-CFTR modulators to increase the macroscopic F508delCl⁻ current ($I_{F508del}$) in NIH3T3 cells stably expressing F508delwas also investigated using per-forated-patch-recording techniques. Modulators identified from the optical assays evoked a dose-dependent increase in $IA_{F508}$ with similar potency and efficacy observed in the optical assays.

Cell Culture

NIH3T3 mouse fibroblasts stably expressing F508del are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 18-24 hrs in the presence or absence of modulators 37° C.

Single-Channel Recordings

Gating activity of F508del-CFTR expressed in NIH3T3 cells following modulator treatment was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) *Nature* 354, 526-528) using an Axopatch 200B patch-clamp amplifier (Axon Instruments Inc.). The pipette contained (in mM): 150 NMDG, 150 aspartic acid, 5 $CaCl_2$, 2 $MgCl_2$, and 10 HEPES (pH adjusted to 7.35 with Tris base). The bath contained (in mM): 150 NMDG-Cl, 2 $MgCl_2$, 5 EGTA, 10 TES, and 14 Tris base (pH adjusted to 7.35 with HCl). After excision, both wt- and F508delwere activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing 2 active channels. The maximum number of simultaneous openings determined the number of active channels during the course of an experiment. To determine the single-channel current amplitude, the data recorded from 120 sec of F508del activity was filtered "off-line" at 100 Hz and then used to construct all-point amplitude histograms that were fitted with multigaussian functions using Bio-Patch Analysis software (Bio-Logic Comp. France). The total microscopic current and open probability (Po) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing F508del are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1λNEAA, β-ME, 1× pen/strep, and 25 mM HEPES in 175 cm² culture flasks. For single channel recordings, 2,500-5,000 cells were seeded on poly-L-lysine-coated glass coverslips and cultured for 18-24 hrs in the presence or absence of modulators at 37° C.

B. Chromatographic Determination of Human Serum Albumin (HSA) Assay

Chromatographic determination of Human Serum Albumin (HSA) values was performed on a UPLC-MS system using a ChiralPak® HSA column (p/n: 58469AST) from Sigma Aldrich. Mobile phase A consisted of 50 mM ammonium acetate buffer in water adjusted to pH=7.4, and mobile phase B was 2-propanol. The column compartment was kept at constant temperature of 30° C. Determination of retention time on the HSA column was performed by injecting 3 mL of 0.5 mM of compound (in DMSO) using a linear gradient from 0%-30% B in 2.5 minutes, followed by a hold at 30% B for 2 minutes, and the final equilibration step from 30%-0% B in 1.5 minutes, for a total run time of 6 minutes. Flow rate was kept constant throughout the gradient and set to 1.8 mL/min. Compound retention time on the HSA column was converted to % HSA values according to a previously published protocol (Valko, et. al, 2003) correlating column retention times to standard plasma protein binding (PPB) values obtained from dialysis experiments. HSA data for certain compounds are summarized below in Table 9 below.

Valko, K., Nunhuck, S., Bevan, C., Abraham, M. H., Reynolds, D. P. Fast Gradient HPLC Method to Determine Compounds Binding to Human Serum Albumin. Relationships with Octanol/Water and Immobilized Artificial Membrane Lipophilicity. *J. of Pharm. Sci.* 2003, 92, 2236-2248.

C. Experimental Protocol for Rat IV and PO PK Studies

The tested compound was administered to male Sprague-Dawley rats as a single nominal intravenous dose of 3.0 mg/kg as a solution in 10% NMP, 10% solutol, 15% EtOH, 35% PEG400 and 30% D5W. The tested compound was also administered to male Sprague-Dawley rats at single nominal oral dose of 3 mg/kg as a solution in 5% NMP, 30% PEG400, 10% TPGS, 5% PVP-K30 at 5 mL/kg dose volume. Analyses of plasma and dose preparations were performed using LC/MS/MS.

Plasma concentration-time profiles of the tested compound in Sprague-Dawley rats at scheduled (nominal) sampling times were analyzed by noncompartmental pharmacokinetic methods using PK function within Watson LIMS software, Version 7.4.2 (Thermo Scientific Inc, Waltham, Mass.). AUC values were calculated using the linear trapezoidal rule.

D. Experimental Protocol for PXR Assay

The propensity for PXR mediated CYP3A4 induction is assessed using the DPX-2 cell line in vitro. This cell line, which has been licensed from Puracyp Inc. was derived from HepG2 cells and has been stably transfected with genes encoding human PXR as well as a modified luciferase reporter linked to the CYP3A4 promoter region and related distal and proximal enhancers.

The assay is run in 384 well format and each test article is administered in 11 doses ranging from 0.1 to 60 μM. On day 1, DPX-2 cells which have previously been expanded in-house and cryopreserved are thawed and seeded in tissue culture plates. The following day, media is changed and cells are cultured in media containing test article, vehicle control or the positive control compound, the clinically validated CYP3A4 inducer rifampicin. Cells are cultured in the presence of test article for 48 hours and then cell viability is assessed using fluorescence based assay (Cell Titer-Fluor, Promega) with an EnVision Plate Reader (PerkinElmer). Subsequently, CYP3A4 transactivation, which is proportional to luciferase activity, is measured by reading luminescense using the Promega One-Glo reagent system using the same plate reader.

Data processing within the Genedata software package allows reporting of max fold induction compared to vehicle control, an $EC_{50}$ value for CYP3A4 inducers and an 11 point-dose response curve. Wells with cell viability less than 70% are not used for the analysis and plates where the rifampicin positive control response falls outside of the expected range, either in potency or max fold induction, are not reported.

E. CFTR Data of Compounds

The compounds of formula (I) are useful as modulators of CFTR activity. The Table 9 below illustrates the EC50 of the compounds of Table 9 using procedures described above (assay described above in A1). Table 9 below also summarizes CFTR activity (CFTR dF508 EC50), PXR Max induction, Rat IV clearance, Rat PO AUC, and Rat PO data for certain compounds described above.

TABLE 9

CFTR Activity and HAS Data

| Comp. No. | Molecule | CFTRdF50 8 Cor 3T3 FLIPR 384 CFTRdF50 8 MP 3T3 770 EC50(uM) | CYP3A4 Induction-PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
|---|---|---|---|---|---|---|---|---|
| 1 | | 0.07 | 2 | 4.5 | 66 | 1.6 | 83 | 23.5 |
| 2 | | | | | | | | |
| 3 | | | | | | | | |
| 4 | | | | | | | | |

TABLE 9-continued

| Comp. No. | Molecule | CFTR Activity and HAS Data ||||||| 
| | | CFTRdF50 8 Cor 3T3 FLIPR 384 CFTRdF50 8 MP 3T3 770 EC50(uM) | CYP3A4 Induction-PXR human PXR internal Max % Activity (%) | MDCK-Wild Type-Permeability 96 well + 0.1% BS A Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
|---|---|---|---|---|---|---|---|---|
| 5 | | 1.3 | 0 | 0.3 | 33 | | | |
| 6 | | 0.3 | 9 | 2.1 | 53 | | | |
| 7 | | 0.65 | 4 | 3.1 | | | | |
| 8 | | 0.4 | 10 | 3.2 | 62 | | | |

TABLE 9-continued

CFTR Activity and HAS Data

| Comp. No. | Molecule | CFTRdF50 8 Cor 3T3 FLIPR 384 CFTRdF50 8 MP 3T3 770 EC50(uM) | CYP3A4 Induction-PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
|---|---|---|---|---|---|---|---|---|
| 9 | | 0.42 | 7 | 6.1 | 30 | 1.7 | 99 | 23.4 |
| 10 | | 0.22 | 4 | 7.1 | | | | |
| 11 | | 0.41 | 18 | | | | | |
| 12 | | 0.86 | 33.5 | | | | | |

TABLE 9-continued

| Comp. No. | Molecule | CFTR Activity and HAS Data ||||||||
|---|---|---|---|---|---|---|---|---|
| | | CFTRdF50 8 Cor 3T3 FLIPR 384 CFTRdF50 8 MP 3T3 770 EC50(uM) | CYP3A4 Induction-human PXR internal PXR Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
| 13 | | 0.13 | 4 | 11.7 | 117 | 3 | 65 | 13.4 |
| 14 | | 0.28 | 2 | 2.8 | 50 | 3.9 | 61 | 10.5 |
| 15 | | 0.13 | 3 | 2.7 | 97 | 2.5 | 66 | 16.3 |
| 16 | | 0.4 | 13 | 3.9 | 10 | | | |

TABLE 9-continued
| Comp. No. | Molecule | CFTRdF50 8 Cor 3T3 FLIPR 384 CFTRdF50 8 MP 3T3 770 EC50(uM) | CYP3A4 Induction-PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
|---|---|---|---|---|---|---|---|---|
| 17 | 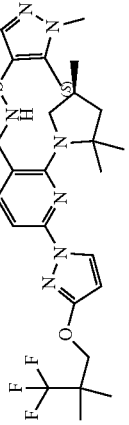 | 0.17 | 3 | 3.8 | 19 | | | |
| 18 | 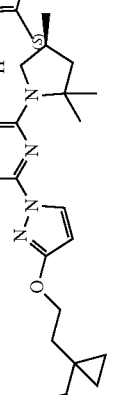 | 0.17 | 5 | 8 | 0 | | | |
| 19 |  | 0.09 | 1 | 8.8 | | | | |
| 20 | 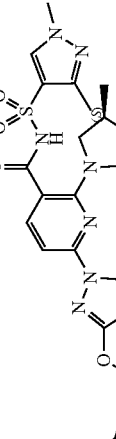 | 0.17 | 4 | 1.4 | 13 | 4.9 | 21 | 3 |

TABLE 9-continued

CFTR Activity and HAS Data

| Comp. No. | Molecule | CFTRdF50 8 Cor 3T3 FLIPR 384 CFTRdF50 8 MP 3T3 770 EC50(uM) | CYP3A4 Induction-PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
|---|---|---|---|---|---|---|---|---|
| 21 | | 0.52 | 1 | 3 | 0 | 6.7 | 47 | 3.9 |
| 22 | | 2.1 | | | | | | |
| 23 | | 0.54 | 4 | | | | | |
| 24 | | 0.71 | 6 | | | | | |

TABLE 9-continued

CFTR Activity and HAS Data

| Comp. No. | Molecule | CFTRdF50 8 Cor 3T3 FLIPR 384 CFTRdF50 8 MP 3T3 770 EC50(uM) | CYP3A4 Induction-PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg PO% F_drg (%) | RAT PLASMA-RAW PO AUC(0-inf)_drg(ug*h/mL) |
|---|---|---|---|---|---|---|---|---|
| 25 | | 0.44 | 6 | 1.3 | | | | |
| 26 | | 1 | 6 | 2.3 | | | | |
| 27 | | 1.4 | | | | | | |

TABLE 9-continued

| Comp. No. | Molecule | CFTR Activity and HAS Data ||||||||
|---|---|---|---|---|---|---|---|---|
| | | CFTRdF50 8 Cor 3T3 FLIPR 384 CFTRdF50 8 MP 3T3 770 EC50(uM) | CYP3A4 Induction-PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
| 28 | | 0.09 | 4 | 2.2 | 41 | 1.8 | 80 | 7.1 |
| 29 | | 0.11 | | | | | | |
| 30 | | 0.95 | 4 | 0.6 | 39 | | | |

TABLE 9-continued

CFTR Activity and HAS Data

| Comp. No. | Molecule | CFTRdF50 8 Cor 3T3 FLIPR 384 CFTRdF50 8 MP 3T3 770 EC50(uM) | CYP3A4 Induction-PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
|---|---|---|---|---|---|---|---|---|
| 31 | | 0.41 | 1 | 1.1 | 30 | | | |
| 32 | | 0.2 | 5 | 3.8 | | | | |
| 33 | | 0.37 | 5 | | | | | |
| 34 | | 0.61 | 6 | 7.5 | 39 | | | |

TABLE 9-continued

CFTR Activity and HAS Data

| Comp. No. | Molecule | CFTRdF50 8 Cor 3T3 FLIPR 384 CFTRdF50 8 MP 3T3 770 EC50(uM) | CYP3A4 Induction-PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
|---|---|---|---|---|---|---|---|---|
| 35 | | 1.4 | 21 | 5.5 | 54 | | | |
| 36 | | 0.29 | 7 | 5.1 | | | | |
| 37 | | 0.11 | 2 | 1 | 56 | | | |
| 38 | | 0.46 | 1 | | 39 | | | |

TABLE 9-continued

| Comp. No. | Molecule | CFTR Activity and HAS Data ||||||||
|---|---|---|---|---|---|---|---|---|
| | | CFTRdF50 8 Cor 3T3 FLIPR 384 CFTRdF50 8 MP 3T3 770 EC50(uM) | CYP3A4 Induction-PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
| 40 | | 0.08 | 13 | | | | | |
| 41 | | 0.12 | 4 | | | | | |
| 42 | | 0.61 | 16 | | | | | |

TABLE 9-continued

CFTR Activity and HAS Data

| Comp. No. | Molecule | CFTRdF50 8 Cor 3T3 FLIPR 384 CFTRdF50 8 MP 3T3 770 EC50(uM) | CYP3A4 Induction- PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
|---|---|---|---|---|---|---|---|---|
| 43 | | 0.22 | 4 | | | | | |
| 44 | | 0.39 | 9 | 1.2 | 49 | | | |
| 45 | | 0.56 | | | | | | |

TABLE 9-continued

| | | CFTR Activity and HAS Data | | | | | | |
|---|---|---|---|---|---|---|---|---|
| Comp. No. | Molecule | CFTRdF50 8 Cor 3T3 FLIPR 384 CFTRdF50 8 MP 3T3 770 EC50(uM) | CYP3A4 Induction- PXR human PXR internal Max % Activity (%) | MDCK-Wild Type-Permeability 96 well + 0.1% BS A Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
| 46 | | 0.39 | | | | | | |
| 47 | | 0.06 | | | | | | |
| 48 | | 1 | 8 | 4.6 | | | | |

TABLE 9-continued

CFTR Activity and HAS Data

| Comp. No. | Molecule | CFTRdF50 8 Cor 3T3 FLIPR 384 CFTRdF50 8 MP 3T3 770 EC50(uM) | CYP3A4 Induction- PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA- RAW IV-bolus CL_drg (mL/min/kg) | RAT PLASMA-RAW PO% F_drg PO% F_drg (%) | RAT PLASMA-RAW PO AUC(0-inf)_drg(ug*h/mL) |
|---|---|---|---|---|---|---|---|---|
| 49 | | 0.19 | | | | | | |
| 50 | | 0.08 | 4 | 13 | 20 | | | |
| 51 | | 0.15 | 6 | 2.9 | 29 | | | |
| 52 | | 0.17 | 2 | 2 | 18 | | | |

TABLE 9-continued

| | CFTR Activity and HAS Data | | | | | | |
|---|---|---|---|---|---|---|---|
| Comp. No. | Molecule | CFTRdF50 8 Cor 3T3 FLIPR 384 CFTRdF50 8 MP 3T3 770 EC50(uM) | CYP3A4 Induction- PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA- RAW IV-bolus CL_drg (mL/min/kg) | RAT PLASMA-RAW PO% F_drg (%) | RAT PLASMA-RAW PO AUC(0-inf)_drg(ug*h/mL) |
| 53 | | 0.39 | 7 | | | | |
| 54 | | 0.05 | 5 | 1.1 | 30 | | |
| 55 | | 0.1 | 9 | | | | |

TABLE 9-continued

| Comp. No. | Molecule | CFTR Activity and HAS Data ||||||||
|---|---|---|---|---|---|---|---|---|
| | | CFTRdF50 8 Cor 3T3 FLIPR 384 CFTRdF50 8 MP 3T3 770 EC50(uM) | CYP3A4 Induction-PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
| 56 | | | 11 | | | | | |
| 57 | | 30 | 13 | 2.6 | 35 | | | |
| A | | 0.06 | 2 | 2.6 | 13 | 17.8 | 28 | 2.7 |
| B | | 0.26 | 3 | 0.4 | 13 | | | |

TABLE 9-continued

| Comp. No. | Molecule | CFTR Activity and HAS Data ||||||| 
| | | CFTRdF50 8 Cor 3T3 FLIPR 384 CFTRdF50 8 MP 3T3 770 EC50(uM) | CYP3A4 Induction-PXR human PXR internal Max % Activity (%) | MDCK-Wild Type-Permeability 96 well + 0.1% BSA Papp compound (A-B) (10E-6 cm/s) | Hepatocyte clearance-Rat Rat hepatocytes CL pct_unchanged (%) | RAT PLASMA-RAW IV-bolus CL_drg (mL/min/kg) | RAT PLASMA-RAW PO% F_drg (%) | RAT PLASMA-RAW PO AUC(0-inf)_drg(ug*h/mL) |
|---|---|---|---|---|---|---|---|---|
| C | *(structure)* | 0.12 | 9 | 1.5 | 6 | 29.2 | | |
| D | *(structure)* | 0.21 | 10 | | 19 | | | |

F. Metabolites

It has been determined that Compound 1 is metabolized both in vitro and in vivo, mostly by oxidative metabolism. Compounds 30, 31, 36, 39, 45, and 57 are metabolites of Compound 1.

Example G: Chloride Transport Experiments

In one Ussing Chamber experiment with F508del/F508del-HBE cells, Compound 1 enhanced chloride transport. The effect of Compound 1 on chloride transport was additive to the effect of Compound II. In addition, F508del-CFTR delivered to the cell surface by either Compound 1 alone or in combination with Compound II was potentiated by Compound III. The triple combination of Compound 1/Compound II/Compound III provided a superior increase in chloride transport compared to the 3 dual regimens under most conditions tested.

Example G2: F508del-CFTR Processing and Trafficking In Vitro Experiments

The combination of Compound 1 and Compound II resulted in more than additive improvement in CFTR processing and trafficking compared to either CFTR corrector alone, suggesting that the two CFTR correctors act through different mechanisms of action, which act synergistically to increase the amount of F508del-CFTR delivered to the cell surface.

In addition, the more than additive effect of the combination of Compound 1 and Compound II on the processing and trafficking of CFTR suggests that the two CFTR correctors act through different mechanisms to result in the delivery of more CFTR protein to the cell surface compared to either CFTR corrector alone.

Other Embodiments

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:

1. Crystalline Form A of Compound 1:

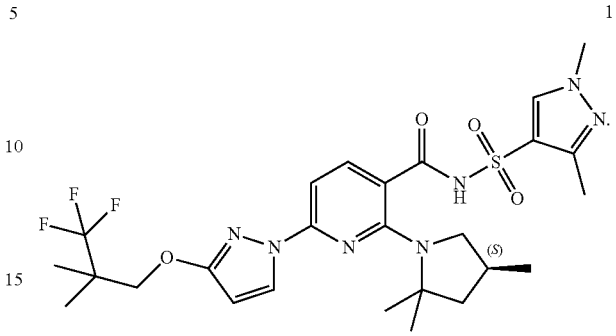

2. Crystalline Form A according to claim 1 in substantially pure form.

3. Crystalline Form A according to claim 1, characterized by an X-ray powder diffractogram having a signal at at least three two-theta values chosen from 6.6±0.2, 7.6±0.2, 9.6±0.2, 12.4±0.2, 13.1±0.2, 15.2±0.2, 16.4±0.2, 18.2±0.2, and 18.6±0.2.

4. Crystalline Form A according to claim 1, characterized by an X-ray powder diffractogram having a signal at at least three two-theta values chosen from 6.6±0.2, 9.6±0.2, 13.1±0.2, 15.2±0.2, 18.2±0.2, and 18.6±0.2.

5. Crystalline Form A according to claim 1, characterized by an X-ray powder diffractogram having a signal at three two-theta values of 6.6±0.2, 13.1±0.2, 18.2±0.2.

6. Crystalline Form A according to claim 1, characterized by an X-ray powder diffractogram having a signal at six two-theta values of 6.6±0.2, 9.6±0.2, 13.1±0.2, 15.2±0.2, 18.2±0.2, and 18.6±0.2.

7. Crystalline Form A according to claim 1, characterized by an X-ray powder diffractogram substantially similar to that in FIG. 2.

8. A pharmaceutical formulation comprising at least one crystalline form according to claim 1 and a pharmaceutically acceptable carrier.

* * * * *